United States Patent
Brizgys et al.

(10) Patent No.: US 12,404,262 B2
(45) Date of Patent: Sep. 2, 2025

(54) THERAPEUTIC COMPOUNDS FOR HIV VIRUS INFECTION

(71) Applicant: Gilead Sciences, Inc., Foster City, CA (US)

(72) Inventors: Gediminas J. Brizgys, San Carlos, CA (US); Chienhung Chou, Dublin, CA (US); Hang Chu, San Mateo, CA (US); Julie Farand, San Mateo, CA (US); Michael Graupe, Pacifica, CA (US); Tezcan Guney, Foster City, CA (US); Darryl Kato, San Francisco, CA (US); Jiayao Li, Foster City, CA (US); John O. Link, San Francisco, CA (US); James B. C. Mack, San Mateo, CA (US); Dong Min Mun, Newark, CA (US); Scott D. Schroeder, Union City, CA (US); William J. Watkins, Saratoga, CA (US); Qiaoyin Wu, Foster City, CA (US); Jennifer R. Zhang, Union City, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 18/061,150

(22) Filed: Dec. 2, 2022

(65) Prior Publication Data
US 2023/0212148 A1    Jul. 6, 2023

Related U.S. Application Data

(60) Provisional application No. 63/285,745, filed on Dec. 3, 2021.

(51) Int. Cl.
*C07D 401/14* (2006.01)
*A61K 45/06* (2006.01)
*C07F 9/6558* (2006.01)

(52) U.S. Cl.
CPC ............ *C07D 401/14* (2013.01); *A61K 45/06* (2013.01); *C07F 9/65583* (2013.01)

(58) Field of Classification Search
CPC ... C07D 401/14; A61K 45/06; C07F 9/65583; A61P 31/18
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 4,816,570 A | 3/1989 | Farquhar | |
| 4,902,514 A | 2/1990 | Barclay et al. | |
| 4,968,788 A | 11/1990 | Farquhar | |
| 4,992,445 A | 2/1991 | Lawter et al. | |
| 5,001,139 A | 3/1991 | Lawter et al. | |
| 5,023,252 A | 6/1991 | Hseih | |
| 5,616,345 A | 4/1997 | Geoghegan et al. | |
| 5,663,159 A | 9/1997 | Starrett, Jr. et al. | |
| 5,792,756 A | 8/1998 | Starrett, Jr. et al. | |
| 5,922,695 A | 7/1999 | Arimilli et al. | |
| 5,935,946 A | 8/1999 | Munger, Jr. et al. | |
| 5,977,089 A | 11/1999 | Arimilli et al. | |
| 7,390,791 B2 | 6/2008 | Becker et al. | |
| 7,803,788 B2 | 9/2010 | Becker et al. | |
| 8,193,225 B2 | 6/2012 | Schneider et al. | |
| 8,263,627 B2 | 9/2012 | Barrow et al. | |
| 8,435,968 B2 | 5/2013 | Greig et al. | |
| 8,748,412 B2 | 6/2014 | Liao et al. | |
| 8,754,065 B2 | 6/2014 | Liu et al. | |
| 8,835,488 B2 | 9/2014 | Yamashita et al. | |
| 9,012,441 B2 | 4/2015 | Bondy et al. | |
| 9,050,344 B2 | 6/2015 | Brizgys et al. | |
| 9,216,996 B2 | 12/2015 | Jin et al. | |
| 9,220,710 B2 | 12/2015 | Bondy et al. | |
| 9,540,343 B2 | 1/2017 | Bondy et al. | |
| 9,670,205 B2 | 6/2017 | Aktoudianakis et al. | |
| 9,730,936 B2 | 8/2017 | Baszcynski et al. | |
| 9,789,089 B2 | 10/2017 | Bondy et al. | |
| 9,873,680 B2 | 1/2018 | Brizgys et al. | |
| 9,944,619 B2 | 4/2018 | Bondy et al. | |
| 9,951,043 B2 | 4/2018 | Brizgys et al. | |
| 10,071,885 B2 | 9/2018 | O'Brien et al. | |
| 10,071,985 B2 | 9/2018 | Graupe et al. | |
| 10,294,234 B2 | 5/2019 | Bacon et al. | |

(Continued)

FOREIGN PATENT DOCUMENTS

| | | |
|---|---|---|
| CN | 101910133 | 12/2010 |
| CN | 107207498 | 9/2017 |

(Continued)

OTHER PUBLICATIONS

Patani, G. A et al. "Bioisosterism: A Rational Approach in Drug Design." Chemical reviews 1996, vol. 96, 8: 3147-3176. (Year: 1996).*

(Continued)

*Primary Examiner* — Amy L Clark
*Assistant Examiner* — Chihyi Lee
(74) *Attorney, Agent, or Firm* — Fish & Richardson P.C.

(57) ABSTRACT

The present disclosure relates generally to certain compounds, pharmaceutical compositions comprising said compounds, and methods of making and using said compounds and pharmaceutical compositions. The compounds and compositions provided herein may be used for the treatment or prevention of a Retroviridae infection, including an HIV infection.

22 Claims, No Drawings

(56) References Cited

U.S. PATENT DOCUMENTS

| | | |
|---|---|---|
| 10,370,342 B2 | 8/2019 | Chin et al. |
| 10,370,358 B2 | 8/2019 | Bondy et al. |
| 10,640,499 B2 | 5/2020 | Chin et al. |
| 10,654,827 B2 | 5/2020 | Graupe et al. |
| 10,696,657 B2 | 6/2020 | Vandehey |
| 10,836,746 B2 | 11/2020 | Brizgys et al. |
| 10,849,892 B2 | 12/2020 | Houston et al. |
| 11,034,668 B2 | 6/2021 | Bondy et al. |
| 11,078,208 B1 | 8/2021 | Bacon et al. |
| 11,084,832 B2 | 8/2021 | Chu et al. |
| 11,117,886 B2 | 9/2021 | Vandebey et al. |
| 11,266,638 B2 | 3/2022 | Houston et al. |
| 11,267,799 B2 | 3/2022 | Shi |
| 11,267,801 B2 | 3/2022 | Brizgy et al. |
| 11,680,064 B2 | 6/2023 | Chou et al. |
| 11,753,399 B2 | 9/2023 | Brizgy et al. |
| 11,757,825 B2 | 9/2023 | Farand et al. |
| 11,807,625 B2 | 11/2023 | Bekerman et al. |
| 2005/0282805 A1 | 12/2005 | Hangeland et al. |
| 2007/0083045 A1 | 4/2007 | Di Francesco et al. |
| 2008/0234251 A1 | 9/2008 | Doherty et al. |
| 2008/0306050 A1 | 12/2008 | Doherty et al. |
| 2010/0029585 A1 | 2/2010 | Dietsch et al. |
| 2010/0129306 A1 | 5/2010 | Julien et al. |
| 2010/0143301 A1 | 6/2010 | Desai et al. |
| 2010/0189796 A1 | 7/2010 | Stokbroekx |
| 2010/0249176 A1 | 9/2010 | Barrow et al. |
| 2011/0092485 A1 | 4/2011 | Burgess et al. |
| 2011/0118235 A1 | 5/2011 | Burgess et al. |
| 2012/0045761 A1 | 2/2012 | Jagannath et al. |
| 2012/0082658 A1 | 4/2012 | Hershberg |
| 2012/0219615 A1 | 8/2012 | Coukos et al. |
| 2013/0165489 A1 | 6/2013 | Cocklin et al. |
| 2013/0251673 A1 | 9/2013 | Flores et al. |
| 2014/0045849 A1 | 2/2014 | McGowan et al. |
| 2014/0066432 A1 | 3/2014 | Burgess et al. |
| 2014/0073642 A1 | 3/2014 | Embrechts et al. |
| 2014/0088085 A1 | 3/2014 | Burgess et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0221417 A1 | 8/2014 | Halcomb et al. |
| 2014/0221421 A1 | 8/2014 | Bondy et al. |
| 2014/0275167 A1 | 9/2014 | Hartman |
| 2014/0296266 A1 | 10/2014 | Hu et al. |
| 2014/0303164 A1 | 10/2014 | Brizgys et al. |
| 2014/0350031 A1 | 11/2014 | McGowan et al. |
| 2015/0104511 A1 | 4/2015 | Malhotra et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0250215 A1 | 9/2016 | Baszcynski et al. |
| 2016/0289229 A1 | 10/2016 | Aktoudianakis et al. |
| 2016/0368881 A1 | 12/2016 | Bondy et al. |
| 2017/0137405 A1 | 5/2017 | Bondy et al. |
| 2018/0051005 A1* | 2/2018 | Graupe ............. A61K 31/4439 |
| 2018/0194746 A1 | 7/2018 | Bondy et al. |
| 2018/0258097 A1 | 9/2018 | Bacon et al. |
| 2018/0273508 A1 | 9/2018 | Brizgys et al. |
| 2018/0370950 A1 | 12/2018 | Graupe et al. |
| 2019/0014787 A1 | 1/2019 | Greenshields et al. |
| 2019/0083478 A1 | 3/2019 | Houston et al. |
| 2019/0084963 A1 | 3/2019 | Shi |
| 2019/0125747 A1 | 5/2019 | Rezaei et al. |
| 2019/0300505 A1 | 10/2019 | Allan et al. |
| 2019/0345136 A1 | 11/2019 | Brizgys et al. |
| 2019/0375726 A1 | 12/2019 | Bondy et al. |
| 2020/0038389 A1 | 2/2020 | Bauer |
| 2020/0262815 A1 | 8/2020 | Graupe et al. |
| 2020/0369647 A1 | 11/2020 | Allan et al. |
| 2020/0397772 A1 | 12/2020 | Houston et al. |
| 2021/0009555 A1 | 1/2021 | Brizgys et al. |
| 2021/0188815 A1 | 6/2021 | Bekerman et al. |
| 2022/0009904 A1 | 1/2022 | Allan et al. |
| 2022/0249460 A1 | 8/2022 | Houston et al. |
| 2022/0251069 A1 | 8/2022 | Shi |
| 2022/0267302 A1 | 8/2022 | Brizgys et al. |
| 2023/0012449 A1 | 1/2023 | Bondy et al. |
| 2023/0038823 A1 | 2/2023 | Chou et al. |
| 2023/0203069 A1 | 6/2023 | Nair et al. |
| 2023/0312567 A1 | 10/2023 | Chou et al. |
| 2024/0376077 A1 | 11/2024 | Graupe et al. |

FOREIGN PATENT DOCUMENTS

| | | |
|---|---|---|
| JP | 2013515007 | 5/2013 |
| JP | 2013533306 | 8/2013 |
| WO | WO 1991019721 | 12/1991 |
| WO | WO 2003002530 | 1/2003 |
| WO | WO 2003002553 | 1/2003 |
| WO | WO 2004050643 | 6/2004 |
| WO | WO 2004071448 | 8/2004 |
| WO | WO 2004096286 | 11/2004 |
| WO | WO 2005087725 | 9/2005 |
| WO | WO 2005123680 | 12/2005 |
| WO | WO 2006015261 | 2/2006 |
| WO | WO 2006110157 | 10/2006 |
| WO | WO 2007070826 | 8/2007 |
| WO | WO 2008013622 | 1/2008 |
| WO | WO 2008118849 | 10/2008 |
| WO | WO 2009005677 | 1/2009 |
| WO | WO 2009010804 | 1/2009 |
| WO | WO 2009062285 | 5/2009 |
| WO | WO 2009114677 | 9/2009 |
| WO | WO 2010130034 | 11/2010 |
| WO | WO 2011059887 | 5/2011 |
| WO | WO 2011084733 | 7/2011 |
| WO | WO 2011143772 | 11/2011 |
| WO | WO 2011144666 A1 | 11/2011 |
| WO | WO 2012003497 | 1/2012 |
| WO | WO 2012003498 | 1/2012 |
| WO | WO 2012020301 | 2/2012 |
| WO | WO 2012065062 | 5/2012 |
| WO | WO 2012145728 | 10/2012 |
| WO | WO 2013006738 | 1/2013 |
| WO | WO 2013006792 | 1/2013 |
| WO | WO 2013091096 | 6/2013 |
| WO | WO 2013159064 | 10/2013 |
| WO | WO 2014016358 | 1/2014 |
| WO | WO 2014023813 | 2/2014 |
| WO | WO 2014028931 | 2/2014 |
| WO | WO 2014056953 | 4/2014 |
| WO | WO 2014076221 | 5/2014 |
| WO | WO 2014100323 | 6/2014 |
| WO | WO 2014110297 | 7/2014 |
| WO | WO 2014110298 | 7/2014 |
| WO | WO 2014110323 | 7/2014 |
| WO | WO 2014128189 | 8/2014 |
| WO | WO 2014128213 | 8/2014 |
| WO | WO 2014134566 | 9/2014 |
| WO | WO 2015008097 | 1/2015 |
| WO | WO 2015061518 | 4/2015 |
| WO | WO 2015130966 | 9/2015 |
| WO | WO 2016033243 | 3/2016 |
| WO | WO 2016040084 | 3/2016 |
| WO | WO 2016172424 | 10/2016 |
| WO | WO 2016172425 | 10/2016 |
| WO | WO 2017007689 | 1/2017 |
| WO | WO 2018035359 | 2/2018 |
| WO | WO 2018145021 | 8/2018 |
| WO | WO 2018203235 | 11/2018 |
| WO | WO 2019035904 | 2/2019 |
| WO | WO 2019035973 | 2/2019 |
| WO | WO 2020018459 | 1/2020 |
| WO | WO 2024220624 A1 | 10/2024 |

OTHER PUBLICATIONS

[No Author Listed], "2-[9-(Difluoromethyl)-5,5-difluoro-7,8-diazatricylo[4.4.0.02,4]nona-1(6),8-dien-7-yl]acetic acid," PubChem CID 71186949, Mar. 21, 2013, 18 pages.

(56) References Cited

OTHER PUBLICATIONS

[No Author Listed], "3-Methyl-3-methylsulfonylbut-1-yne," PubChem CID 14241469, Feb. 9, 2002, 16 pages.
[No Author Listed], CAS registry No. 1620056-83-8, Aug. 6, 2014, 1 page.
Bastin et al., "Salt Selection and Optimisation Procedures for Pharmaceutical New Chemical Entities," Organic Process Research & Development, Jul. 2000, 4(5): 427-435.
Benzaria et al., "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem., Dec. 1996, 39(25):4958-4965.
Berge et al., "Pharmaceutical Salts," J. Pharma. Sci., 1977, 66(1): 1-19.
Blair et al., "HIV Capsid is a Tractable Target for Small Molecule Therapeutic Intervention," PLoS Pathog., 2010, 6(12): e1001220, 10 pages.
Briggs et al., "Structural Organization of Authentic, Mature HIV-1 Virions and Cores," The EMBO Journal, 2003, 22(7): 1707-1715.
Brown et al., "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew. Chem. Int. Ed. Engl., 2005, 44(33):5306-5310.
Bundgaard, "Design and Application of Prodrugs," Chapter 5 in A Textbook of Drug Design and Development, Krogsgaard-Larsen, P. et al. eds., Harwood Academic Publishers, Chur, Switzerland, 1991, pp. 113-191.
Campbell et al., "HIV-1 Capsid: The Multifaceted Key Player in HIV-1 Infection," Nat Rev Microbial., 2015, 13(8): 471-483.
Carnes et al., "Inhibitors of the HIV-1 Capsid, A Target of Opportunity," Curr. Opin. HIV AIDS, 2018, 13(4):359-365.
Chin et al., "Direct Visualization of HIV-1 Replication Intermediates Shows That Capsid and CPSF6 Modulate HIV-1 Intra-Nuclear Invasion and Integration", Cell Repotis, 2015, 13:1717-1731.
Choy et al., "Synthesis of irreversible HIV-1 protease inhibitors containing sulfonamide and sulfone as amide bond isosteres," Bioorganic & Medicinal Chemistry Letters, Oct. 1997, 7(20):2635-38.
Cos et al., "Structure-Activity Relationship and Classification of Flavonoids as Inhibitors of Xanthine Oxidase and Su peroxide Scavengers," J. Natl. Prod., 1998, 61:71-76.
Cossy et al., "Ring Opening of Cyclopropylketones Induced by Photochemical Electron Transfer," Tetrahedron, Oct. 1995, 51 (43):11751-11764.
Curreli et al., "Virtual Screening Based Identification of Novel Small-molecule Inhibitors Targeted to the HIV-1 Capsid," Bioorganic & Medicinal Chemistry, 2011, 19:77-90.
De Lombaert et al., "N-Phosphonomethyl Dipeptides and Their Phosphonate Prodrugs, A New Generation of Neutral Endopeptidase (NEP, EC 3.4.24.11) Inhibitors," J. Med. Chem., Feb. 1994, 37(4):498-511.
Fader et al., "Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety," Bioorganic & Medicinal Chemistry Letters, 2013, 23(11):3396-3400.
Farquhar et al., "Biologically Reversible Phosphate-Protective Groups," J. Pharm. Sci., Mar. 1983, 72(3):324-325.
Fields, "Methods for Removing the Fmoc Group," Methods in Molecular Biology, 1994, 35:17-27.
Fontes Ferreira da Cunha et al., "4D-QSAR Models of HOE/BAY-793 Analogues as HIV-1 Protease Inhibitors," QSAR & Combinatorial Science, 2005, 24(2): 240-253.
Forshey et al., "Formation of a Human Immunodeficiency Virus Type 1 Core of Optimal Stability Is Crucial for Viral Replication," J. Virology, 2002, 76(11) p. 5667-5677.
Foster, "Deuterium Isotope Effects in Studies of Drug Metabolism," Trends Pharmacol. Sci., 1984, 5(12):524-527.
Ganser et al., "Assembly and Analysis of Conical Models for the HIV-1 Core," Science, 1999, 283: 80-82.
Ganser-Pornillos et al., "Structure of Full-Length HIV-1 CA: A Model for the Mature Capsid Lattice," Cell, 2007, 131(1):70-9, 29 pages.
Hagmann, "The many roles for fluorine in medicinal chemistry," J. Med. Chem., 2008, 51(15):4359-4369.
Hammer et al., "Antiretroviral Treatment of Adult HIV Infection. 2008 Recommendations of the International AIDS Society: USA Panel," JAMA, Aug. 2008, 300(5):555-570.
Hanack et al., "cis—und trans bicyclo [3.1.0] hexano-(2)," Chemische Berichte, 1964, 97(6):1669-1672, XP055573746 (with English translation).
Hodgson et al. "Intramolecular Cyclopropanation of Unsaturated Terminal Epoxides," J. Am. Chem. Soc., 2004, 126(28):8664-8665.
Hodgson et al., "Intramolecular Cyclopropanation of Unsaturated Terminal Epoxides and Chlorohydrins," J. Am. Chem. Soc., 2007, 129(14):4456-4462.
Hung et al., "Large-Scale Functional Purification of Recombinant HIV-1 Capsid," PLOS One, 2013, 8(3):e58035, 11 pages.
Ishiyama et al., "Palladium(0)-Catalyzed Cross-Coupling Reaction of Alkoxydiboron with Haloarenes: A Direct Procedure for Arylboronic Esters," J. Org. Chem., 1995, 60(23):7508-7510.
Jarvis et al., "Conquering HIV's capsid", C&EN Chicago, Jul. 2017, 95(31): 23-25.
Jeong, "Synthesis of Tetrasubstituted Pyrazones and Pyrazone N-Oxides," Tetrahedron Letters, 2010, 51 (6):974-976.
Jin et al., "SAR and Molecular Mechanism Study of Novel Acylhydrazone Compounds Targeting HIV-1 CA," Bioorganic & Medicinal Chemistry, 2010, 18: 2135-2140.
Jouvenet et al., "Plasma Membrane Is the Site of Productive HIV-1 Particle Assembly," PLoS Biol., 2006, 4(12):e435, 15 pages.
Kashima et al., "New Peptide Synthesis Using the Ozonolysate of 2-(1-Phthalimido)alkyl-5-Phenyloxazoles," J. Heterocyclic Chem., 1991, 28: 1241-1244.
Kelly et al., "Structure of the Antiviral Assembly Inhibitor CAP-1 Complex with the HIV-1 CA Protein," Journal of Molecular Biology, 2007, 373(2):355-66.
Khamnei et al., "Neighboring Group Catalysis in the Design of Nucleotide Prodrugs," J. Med. Chem., 1996, 39(20):4109-4115.
Kim et al., "Discovery of a New HIV-1 Inhibitor Scaffold and Synthesis of Potential Prodrugs of Indazoles," Bioorganic & Medicinal Chemistry Letters, 2013, 23(10):2888-2892.
Kocienski, "Carbonyl Protecting Groups," Chapter 5 in Protecting Groups, Thieme Publishing Group: New York, NY, May 1994, pp. 155-184.
Kocienski, "Carboxyl Protecting Groups," Chapter 4 in Protecting Groups, Thieme Publishing Group: New York, NY, May 1994, pp. 118-154.
Kocienski, "Diol Protecting Groups," Chapter 3 in Protecting Groups, Thieme Publishing Group: New York, NY, May 1994, pp. 95-117.
Kocienski, "Hydroxyl Protecting Groups," Chapter 2 in Protecting Groups, Thieme Publishing Group: New York, NY, May 1994, pp. 21-94.
Kocienski, "Protecting Groups: An Overview," Chapter 1 in Protecting Groups, Thieme Publishing Group: New York, NY, May 1994, pp. 1-20.
Lad et al., "Functional Label-Free Assays for Characterizing the in Vitro Mechanism of Action of Small Molecule Modulators of Capsid Assembly" Biochemistry, 2015, 54: 2240-2248.
Lamorte et al., "Discovery of Novel Small-Molecule HIV-1 Replication Inhibitors That Stabilize Capsid Complexes" Antimicrobial Agents and Chemotherapy, 2015, 57(10): 4622-4631.
Lazerwith et al., "New Antiretrovirals for HIV and Antivirals for HBV," in Comprehensive Medicinal Chemistry, 3rd Edition, 2017, pp. 1-36.
Lee et al., "Flexible Use of Nuclear Import Pathways by HIV-1," Cell Host & Microbe, 2010, 7:221-233.
Lemke et al., "Distinct Effects of Two HIV-1 Capsid Assembly Inhibitor Families That Bind the Same Site Within the N-Terminal Domain of the Viral CA Protein," J. Virol., Jun. 2012, 86(12):6643-6655.

(56) References Cited

OTHER PUBLICATIONS

Macmillan et al., "Evaluation of alternative solvent in common amide coupling reactions: replacement of dicloromethane and N,N-dimethiformamide," Green Chem, 2013, 15: 596-600.
Matreyek et al., "Nucleoporin NUP153 Phenylalanine-Glycine Motifs Engage a Common Binding Pocket within the HIV-1 Capsid Protein to Mediate Lentiviral Infectivity" PLOS Pathogens, 2013, 9(10): e1003693. 21 pages.
Mitchell et al., "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, 1992, pp. 2345-2353.
Miyaura et al., "Palladium-Catalyzed Cross-Coupling Reactions of Oganoboron Compounds," Chem Rev, 1995, 95:2457-2483.
Molina et al., "On-Demand Preexposure Prophylaxis in Men at High Risk for HIV-1 Infection", The New England Journal of Medicine, Dec. 2015, 353:2237-2246.
Montalbetti et al., "Amide bond formation and peptide coupling," Tetrahedon, 2005, 61:10827-10852.
Morissette et al., "High-throughput crystallization: polymorphs, salts, co-crystals and solvates of pharmaceutical solids," Advanced Drug Delivery Reviews, Feb. 2004, 56(3):275-300.
Nicolaou et al., "Palladium-Catalyzed Cross-Coupling Reactions in Total Synthesis," Angew Chem Int Ed, 2005, 44:4442-4489.
Ovais et al. "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 2013, 67:352-358.
Owen et al., "Strengths, weaknesses, opportunities and challenges for long acting injectable therapies: Insights for applications in HIV therapy," Advances Drug Delivery Reviews, 2016, 103:144-156.
Palella et al., "Declining morbidity and mortality among patients with advanced human immunodeficiency virus infection," N Engl. J Med., 1998, 338:853-860.
Patel et al., "Poloxamers: a pharmaceutical excipients with therapeutic behaviors," International Journal of Pharm Tech Research, 2009, 1(2):299-303.
Pornillos et al., "Atomic level modeling of the HIV capsid," Nature, Jan. 2011, 469(7330):424-427.
Pornillos et al., "X-ray Structures of the Hexameric Building Block of the HIV Capsid" Cell, 2009, 137(7): 1282-1292.
Powers et al., "Synthesis of Methyl-, Fluoro-, and Chloro-substituted 6-Hydroxyisoindolin-1-1-Ones," Tetrahedron Letters, 2009, 50(12):1267-1269.
Price et al., "CPSF6 Defines a Conserved Capsid Interface That Modulates HIV-1 Replication," PLOS Pathogens, 2012, 8(8):e1002896, 14 pages.
Puech et al., "Intracellular Delivery of Nucleoside Monophosphates Through a Reductase-Mediated Activation Process," Antiviral Res., Oct. 1993, 22(2-3):155-174.
Pungpo et al., "Computer-aided molecular design of highly potent HIV-1 RT inhibitors: 3D QSAR and molecular docking studies of efavirenz derivatives," SAR and QSAR in Environmental Research, 2006, 17(4):353-370.
Registry (STN) [online], Mar. 22, 2010 [date of retrieval: Nov. 12, 2018], CAS registry No. 1213065-84-9.
Registry (STN) [online], Mar. 23, 2010 [date of retrieval: Nov. 12, 2018], CAS registry No. 1213495-28-3.
Registry (STN)[online], Nov. 15, 1991, STN Registry No. 137349-29-2, 1 page.
Rihn et al., "Extreme Genetic Fragility of the HIV-1 Capsid," PLOS One, 2013, 9(6):e1003461, 25 pages.
Shi et al., "Small-Molecule Inhibition of Human Immunodeficiency Virus Type 1 Capsid Destabilization," Journal of Virology, 2011, 85(1): 542-549.
Siddiqui et al., "The Presence of Substituents on the Aryl Moiety of the Aryl Phosphoramidate Derivative of d4T Enhances Anti-HIV Efficacy in Cell Culture: A Structure-Activity Relationship," J. Med. Chem., 1999, 42:393-399.
Silverman, "The Organic Chemistry of Drug Design and Drug Action," Elsevier, 2004, pp. 121-169.
Silvestri et al., "Novel Indolyl Aryl Sulfones Active against HIV-1 Carrying NNRTI Resistance Mutations: Synthesis and SAR Studies," Journal of Medical Chemistry, 2003, 46(12): 2482-2493.
Smith et al., "Evolutionary Dynamics of Complex Networks of HIV Drug-Resistant Strains: The Case of San Francisco," Science, 2010, 327(5966):697-701.
Sticht et al., "A peptide inhibitor of HIV-1 assembly in vitro," Nature Structural & Molecular Biology, 2005, 12(8): 671-677.
Sublocade Product Label, issued: Nov. 2017, 43 pages.
Taiwo, "Understanding Transmitted HIV Resistance Through the Experience in the USA," International Journal of Infectious Diseases, 2009, 13(5):552-559.
Talele, "The 'Cyclopropyl Fragment' is a Versatile Player that Frequently Appears in Preclinical/Clinical Drug Molecules," Journal of Medicinal Chemistry, 2016, 59(19):8712-8756.
Tanaka et al., "One-Pot Synthesis of Metalated Pyridines from Two Acetylenes, a Nitrile, and a Titanium(II) Alkoxide," J. Am. Chem. Soc., 2005, 127(21):7774-7780.
Tang et al., "Antiviral Inhibition of the HIV-1 Capsid Protein," J. Mol. Biol., 2003, 327: 1013-1020.
Thenin-Houssier et al., "HIV-1 capsid inhibitors as antiretroviral agents," Curr. HIV Res., 2016, 14(3):270-282.
Tse et al., "Discovery of Novel Potent HIV Capsid Inhibitors with Long-Acting Potential," Abstract for Oral Presentation at the Conference on Retroviruses and Opportunistic Infections (CROI), Seattle, WA, 2017, 18 pages.
Tsiang et al., "A Trimer of Dimers Is the Basic Building Block for Human Immunodeficiency Virus-1 Capsid Assembly," Biochemistry, 2012, 51: 4416-4428.
Wu et al., "Selective Inhibitors of Tumor Progression Loci-2(Tpl2) Kinase with Potent Inhibition of TNF-Alpha Production in Human Whole Blood," Bioorg. Med. Chem. Lett., 2009, 19(13):3485-3488.
Xianghui et al., "In Silico Virtual Screening," Biotechnology in the Post-Genome Era, 2003, 16 pages.
Yadav et al., "Co-crystals: a novel approach to modify physicochemical properties of active pharmaceutical ingredients," Indian J. Pharm. Sci., 2009, 71(4):359-370.
Yale, "The trifluoromethyl group in medicinal chemistry," J. Med. Chem., 1958, 1(2):121-133.
Zhou et al. "HIV-1 Resistance to the Capsid-Targeting Inhibitor PF74 Results in Altered Dependence on Host Factors Required for Virus Nuclear Entry," Journal of Virology, 2015, 89(17): 9068-9079.
Jindal et al., "Nevirapine loaded Poloxamer 407/Pluronic P123 mixed micelles: Optimization of formulation and in vitro evaluation," Colloids and Surfaces B: Biointerfaces, May 2015, 129:100-106.
Klooster et al., "Pharmacokinetics and Disposition of Rilpivirine (TMC278) Nanosuspension as a Long-Acting Injectable Antiretroviral Formulation," Antimicrobial Agents and Chemotherapy, May 2010, 54(5):2042-2050.
Landovitz et al., "The promise and pitfalls of long acting injectable agents for HIV prevention," Current Opinion in HIV and AIDS, Jan. 2016, (1):122-128.
Magiorakos et al., "Multidrug-resistant, extensively drug-resistant and pandrug-resistant bacteria: an international expert proposal for interim standard definitions for acquired resistance," Clinical Microbiology and Infection, Mar. 2012, 18(3): 268-281.
Palombo et al., "Prodrug and conjugate drug delivery strategies for improving HIV/ADS therapy," Journal of drug delivery science and technology, Jan. 2009, 19(1): 31 pages.
Seremeta et al., "Poly(ϵ-caprolactone), Eudragit® RS 100 and poly(ϵ-caprolactone)/Eudragit® RS 100 blend submicron particles for the sustained release of the antiretroviral efavirenz," Colloids and Surfaces B: Biointerfaces, Feb. 2013, 102: 441-449.
Spreen et al., "Long-acting injectable antiretrovirals for HIV treatment and prevention," Current Opinion in HIV and AIDS, Nov. 8, 2013, 8(6):565-571.
PCT International Search Report and Written Opinion in International Appln. No. PCT/US2020080813, dated Mar. 9, 2023, 13 pages.

(56) References Cited

OTHER PUBLICATIONS

Bhattacharya et al., Structural Basis of HIV-1 Capsid Recognition by PF74 and CPSF6, PNAS, 2014, 111(52):18625-18630.

Brittain, "Polymorphism in pharmaceutical solids," Marcel Dekker, Inc., 1999, 235-238.

Jornada et al., "The Prodrug Approach: A Successful Tool for Improving Drug Solubility," Molecules, Dec. 29, 2015, 21(1):42, 31 pages.

Yang et al., "Design, synthesis and anti-HIV-1 evaluation of hydrazide-based peptidomimetics as selective gelatinase inhibitors," Bioorganic & Medicinal Chemistry, May 2016, 24(9):2125-2136.

Yant et al., "PF74 Inhibits Multiple HIV Capsid Functions Independently of Host Cyclophilin A and CPSF6," Abstract for Poster Presented at the Conference on Retroviruses and Opportunistic Infections (CROI), Boston, Massachusetts, 2014, 1 page.

Office Action in Taiwanese Appln. No. 111146361, mailed on Nov. 28, 2023, 8 pages (with English translation).

[No. Author], "Sunlenca; Annex I: Summary of Product Characteristics," Jun. 27, 2023, retrieved on Feb. 8, 2024, retrieved from URL<https://www.ema.europa.eu/en/documents/product-information/sunlenca-epar-product-information_en.pdf>, 63 pages.

ClinicalTrials.gov [online], "Study Evaluating the Safety and Efficacy of Islatravir in Combination With Lenacapavir in Virologically Suppressed People with HIV," NCT05052996, last updated on Jan. 19, 2024, retrieved on Feb. 8, 2024, retrieved from URL<https://clinicaltrials.gov/study/NCT05052996?intr-lenacapavir&term=NCT05052996&rank=1&tab=history&a=11>, 14 pages.

Wong et al., "SPR Assay Development to Characterize Capsid Inhibitors Binding & MOA," Poster Presented at the Developments in Protein Interaction (DiPIA), La Jolla, CA, 2014, 8 pages.

Yant et al., "An Improved PF74 Analog Inhibits Multiple HIV Capsid Functions Independently of Host Cyclophilin A and CPSF6," Poster Presented at the Conference on Retroviruses and Opportunistic Infections (CROI), Boston, Massachusetts, 2014, 1 page.

Zheng et al. "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, 22 pages.

Office Action in Taiwanese Appln. No. 111146361, mailed on Mar. 27, 2024, 5 pages (with English translation).

PCT International Preliminary Report on Patentability in International Appln. No. PCT/US2020080813, dated Jun. 13, 2024, 8 pages.

Office Action for Japanese Appln. No. 2024-532836, mailed Apr. 22, 2025, 7 pages (with English translation).

Lopes et al., "Acyloxymethyl as a drug protecting group. Part 6: N-acyloxymethyl- and N-[(aminocarbonyloxy) methyl] sulfonamides as prodrugs of agents containing a secondary sulfonamide group," Bioorganic & medicinal chemistry, Apr. 1, 2000, 8(4):707-16.

\* cited by examiner

THERAPEUTIC COMPOUNDS FOR HIV VIRUS INFECTION

CROSS REFERENCE TO RELATED APPLICATIONS

This application claims the benefit of U.S. Provisional Application No. 63/285,745, filed on Dec. 3, 2021, the entire content of which is hereby incorporated by reference in its entirety.

FIELD

This disclosure relates generally to novel compounds and pharmaceutical compositions comprising said compounds for use in the prevention or treatment of a Retroviridae viral infection, including an infection caused by the human immunodeficiency virus (HIV). This disclosure also relates to methods of making said compounds and of said compounds.

BACKGROUND

Positive-single stranded RNA viruses comprising the Retroviridae family include those of the subfamily Orthoretrovirinae and genera Alpharetrovirus, Betaretrovirus, Gammaretrovirus, Deltaretrovirus, Epsilonretrovirus, Lentivirus, and Spumavirus which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants.

Also of interest in the area of HIV therapies and treatments is providing regimens to patients with improved pharmacokinetic properties, including, for example, increased potency, long-acting pharmacokinetics, low solubility, low clearance, and/or other properties. While current regimens for treating HIV have progressed enough that patients no longer have to take multiple pills multiple times a day, patients today still are required to take a pill every day for the foreseeable span of their life. Thus, it would be beneficial to have HIV therapies that require patients take medication less than once a day (e.g. once every couple of days, once a week, once every other week, once a month, and so forth) or take a smaller effective dose of the medication(s) on a daily, weekly, monthly, or longer basis.

SUMMARY

In one embodiment, provided herein is a compound of Formula I,

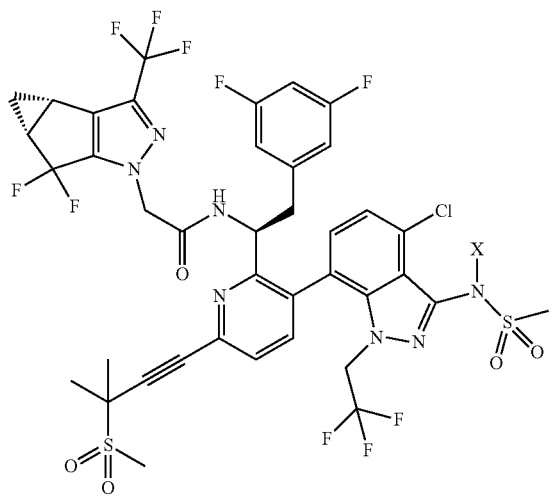

Formula I or a pharmaceutically acceptable salt thereof,
wherein
X is —C(O)C(O)NR$^1$R$^1$, —C(O)C(O)OR$^2$, —(C$_{1-6}$ alkyl)OR$^3$, —C(O)NR$^4$R$^5$, —C(O)OR$^6$, or —C(O)C$_{1-10}$ alkyl,
  wherein the C$_{1-10}$ alkyl is optionally substituted with one 4-7 membered monocyclic heterocyclyl,
    wherein the 4-7 membered monocyclic heterocyclyl is optionally substituted with 1-3 groups independently selected from —CN, halogen, R$^a$, R$^b$, and R$^c$;
each R$^1$ independently is H or C$_{1-6}$ alkyl, wherein the C$_{1-6}$ alkyl is optionally substituted with 1-3 groups independently selected from —CN, halogen, R$^a$, R$^b$, and R$^c$;
R$^2$ is H or C$_{1-6}$ alkyl, wherein the C$_{1-6}$ alkyl is optionally substituted with 1-3 groups independently selected from —CN, halogen, R$^a$, R$^b$, and R$^c$;
R$^3$ is —P(O)(OH)$_2$, —C(O)R$^{3a}$, —C(O)OR$^{3a}$, —C(O)NR$^{3b}$R$^{3b}$, —C(O)C(O)OR$^{3a}$, —S(O)$_2$R$^{3a}$, —S(O)$_2$NR$^{3b}$R$^{3b}$, or —S(O)$_2$OR$^{3a}$;
R$^{3a}$ is H or C$_{1-6}$ alkyl, wherein the C$_{1-6}$ alkyl is substituted with 1-3 groups independently selected from —CN, R$^a$, R$^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$;
each R$^{3b}$ independently is R$^d$ or C$_{1-6}$ alkyl, wherein the C$_{1-6}$ alkyl is substituted with 1-3 groups independently selected from —CN, R$^a$, R$^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$;
R$^4$ is H or C$_{1-6}$ alkyl, wherein the C$_{1-6}$ alkyl is optionally substituted with 1-3 groups independently selected from —B(OH)$_2$, —CN, halogen, R$^a$, R$^b$, and R$^c$;
R$^5$ is H, C$_{1-6}$ alkyl, or 8-10 membered fused bicyclic heteroaryl,
  wherein the C$_{1-6}$ alkyl is optionally substituted with 1-3 groups independently selected from —B(OH)$_2$, —CN, halogen, R$^a$, R$^b$, R$^c$, and R$^{5a}$, wherein the 8-10 membered fused bicyclic heteroaryl is optionally substituted with 1-3 groups independently selected from —CN, halogen, $R^a$, $R^b$, $R^1$ and $R^{5b}$.

each $R^{5a}$ independently is 4-7 membered monocyclic heterocyclyl, phenyl, naphthalenyl, 5-6 membered monocyclic heteroaryl, or 8-10 membered fused bicyclic heteroaryl, wherein the 4-7 membered monocyclic heterocyclyl, phenyl, naphthalenyl, 5-6 membered monocyclic heteroaryl, and 8-10 membered fused bicyclic heteroaryl are each independently optionally substituted with 1-3 groups independently selected from —CN, halogen, $R^a$, $R^b$, and $R^c$;

each $R^{5b}$ independently is $C_{1-6}$ alkyl, wherein the $C_{1-6}$ alkyl is optionally substituted with 1-3 groups independently selected from —CN, halogen, $R^a$, $R^b$, and $R^c$;

$R^6$ is $C_{1-10}$ alkyl or $C_{3-7}$ monocyclic cycloalkyl, wherein the $C_{1-10}$ alkyl is optionally substituted with 1-3 groups independently selected from —CN, halogen, $R^a$, $R^b$, $R^c$, and —OC(O)($C_{2-6}$ alkenylene)C(O)OR$^9$, 4-7 membered monocyclic heterocyclyl, phenyl, naphthalenyl, 5-6 membered monocyclic heteroaryl, and 8-10 membered fused bicyclic heteroaryl, wherein the $C_{3-7}$ monocyclic cycloalkyl is optionally substituted with 1-3 groups independently selected from —CN, halogen, $R^a$, $R^b$, and $R^c$;

each $R^a$ independently is —P(O)(OH)$_2$ or —OP(O)(OH)$_2$;

each $R^b$ independently is —C(O)R$^7$, —C(O)OR$^7$, —C(O)NR$^8$R$^8$, —C(O)C(O)OR$^7$, —C(=NR$^{8a}$)(NR$^8$R$^8$), —S(O)$_2$R$^7$, —S(O)$_2$NR$^8$R$^8$, or —S(O)$_2$OR$^7$;

each $R^c$ independently is —OR$^7$, —OC(O)R$^7$, —OC(O)C(O)OR$^7$, —(O($C_{1-4}$ alkyl))$_n$OR$^{7a}$, —NR$^8$R$^8$, —N$^+$R$^8$R$^8$R$^{8a}$, —NR$^8$C(O)R$^7$, —NR$^8$C(O)NR$^8$R$^8$, —NR$^8$C(O)OR$^7$, —NR$^8$C(O)C(O)OR$^7$, —NR$^8$C(=NR$^{8a}$)NR$^8$R$^8$, or —NR$^8$S(O)$_2$R$^7$;

each $R^7$ independently is H or $C_{1-6}$ alkyl, wherein the $C_{1-6}$ alkyl is optionally substituted with 1-3 groups independently selected from —CN, halogen, $R^a$, $R^d$, and $R^e$;

each $R^{7a}$ independently is H, —P(O)(OH)$_2$, or $C_{1-6}$ alkyl, wherein the $C_{1-6}$ alkyl is optionally substituted with 1-3 groups independently selected from —CN, halogen, $R^a$, $R^d$, and $R^e$;

each $R^8$ independently is H, $R^d$, or $C_{1-6}$ alkyl, wherein the $C_{1-6}$ alkyl is optionally substituted with 1-3 groups independently selected from —CN, halogen, $R^a$, $R^d$, and $R^e$;

each $R^{8a}$ independently is H or $C_{1-3}$ alkyl;

each $R^d$ independently is —C(O)R$^9$, —C(O)OR$^9$, —C(O)NR$^{10}$R$^{10}$, —C(O)C(O)OR$^9$, —C(=NR$^{10a}$)(NR$^{10}$R$^{10}$), —S(O)$_2$R$^9$, —S(O)$_2$NR$^{10}$R$^{10}$, or —S(O)$_2$OR$^9$;

each $R^e$ independently is —OR$^9$, —OC(O)R$^9$, —OC(O)C(O)OR$^9$, —NR$^{10}$R$^{10}$, —N$^+$R$^{10}$R$^{10}$R$^{10a}$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, or —NR$^{10}$S(O)$_2$R$^9$;

each $R^9$ independently is H or $C_{1-6}$ alkyl, wherein the $C_{1-6}$ alkyl is optionally substituted with 1-3 groups independently selected from CN, halogen, $R^a$, $R^f$, and $R^g$;

each $R^{10}$ independently is H, $R^f$, or $C_{1-6}$ alkyl, wherein the $C_{1-6}$ alkyl is optionally substituted with 1-3 groups independently selected from —CN, halogen, $R^a$, $R^f$, and $R^g$;

each $R^{10a}$ independently is H or $C_{1-3}$ alkyl;

each $R^f$ independently is —C(O)R$^{11}$, —C(O)OR$^{11}$, —C(O)NR$^{11}$R$^{11}$, —C(O)C(O)OR$^{11}$, —C(=NR$^{11a}$)(NR$^{11}$R$^{11}$), —S(O)$_2$R$^{11}$, —S(O)$_2$NR$^{11}$R$^{11}$, or —S(O)$_2$OR$^{11}$;

each $R^g$ independently is —OR$^{11}$, —OC(O)R$^{11}$, —OC(O)C(O)OR$^{11}$, —NR$^{11}$R$^{11}$, —N$^+$R$^{11}$R$^{11}$R$^{11a}$, —NR$^{11}$C(O)R$^{11}$, —NR$^{11}$C(O)NR$^{11}$R$^{11}$, —NR$^{11}$C(O)OR$^{11}$, —NR$^{11}$C(O)C(O)OR$^{11}$, —NR$^{11}$C(=NR$^{11a}$)NR$^{11}$R$^{11}$, or —NR$^{11}$S(O)$_2$R$^{11}$;

each $R^{11}$ independently is H or $C_{1-6}$ alkyl, wherein the $C_{1-6}$ alkyl is optionally substituted with 1-3 groups independently selected from —OH, CN, halogen, —COOH, and $R^a$; each $R^{11a}$ independently is H or $C_{1-3}$ alkyl;

n is 1, 2, 3, 4, or 5;

wherein each 4 membered monocyclic heterocyclyl has 1 ring heteroatom selected from N, O, and S;

wherein each 5-7 membered monocyclic heterocyclyl has 1-2 ring heteroatoms independently selected from N, O, and S; and wherein each 5-6 membered monocyclic heteroaryl and 8-10 membered fused bicyclic heteroaryl independently have 1-4 ring heteroatoms independently selected from N, O, and S.

In one embodiment, provided herein is a pharmaceutical composition comprising a therapeutically effective amount of a compound provided herein, or a pharmaceutically acceptable salt thereof, and a pharmaceutically acceptable excipient.

In one embodiment, provided herein is a method of treating or preventing a human immunodeficiency virus (HIV) infection in a patient in need thereof comprising administering to the patient a therapeutically effective amount of a compound provided herein, or a pharmaceutically acceptable salt thereof, or a pharmaceutical composition provided herein.

In one embodiment, provided herein is a method of treating a human immunodeficiency virus (HIV) infection in a heavily treatment-experienced patient, the method comprising administering to the patient a therapeutically effective amount of a compound provided herein, or a pharmaceutically acceptable salt thereof, or a pharmaceutical composition provided herein.

In one embodiment, provided herein is a therapeutically effective amount of a compound provided herein, or a pharmaceutically acceptable salt thereof, or a pharmaceutical composition provided herein for use in therapy.

In one embodiment, provided herein is a compound provided herein, or a pharmaceutically acceptable salt thereof, or a pharmaceutical composition provided herein for use in a method of treating or preventing a human immunodeficiency virus (HIV) infection in a patient in need thereof, the method comprising administering to the patient a therapeutically effective amount of the compound, or a pharmaceutically acceptable salt thereof, or the pharmaceutical composition.

In one embodiment, provided herein is a compound provided herein, or a pharmaceutically acceptable salt thereof, or a pharmaceutical composition provided herein for use in a method of treating a human immunodeficiency virus (HIV) infection in a heavily treatment-experienced patient, the method comprising administering to the patient a therapeutically effective amount of the compound, or a pharmaceutically acceptable salt thereof, or the pharmaceutical composition.

DETAILED DESCRIPTION

I. Definitions

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present disclosure, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring (including a fused, bridged or spirocyclic ring system) indicates that the point of attachment for a substituent on the ring can be at any ring atom. For example, $R^{aa}$ in the below structure can be attached to any of the five carbon ring atoms or $R^{aa}$ can replace the hydrogen attached to the nitrogen ring atom:

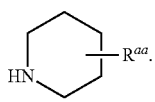

As another example, $R^{aa}$ in the below structure:

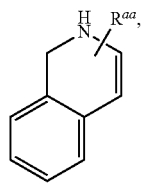

$R^{aa}$ can be attached to any of the numbered positions shown below:

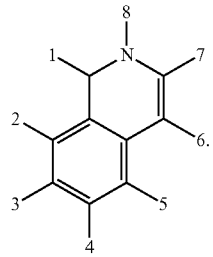

A solid line coming out of the center of a ring (including a fused, bridged, or spirocyclic ring system) indicates that the point of attachment for the ring system to the rest of the compound can be at any ring atom of the fused, bridged, or spirocyclic ring system. For example, in the below structure:

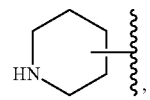

the monocyclic heterocyclyl can be attached to the rest of the compound at any of the numbered positions shown below:

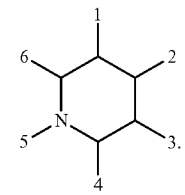

As another example, in the below fused bicyclic heterocyclic structure,

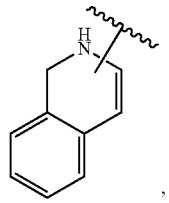

the fused bicyclic heterocyclyl can be attached to the rest of the compound at any of the eight numbered positions shown below:

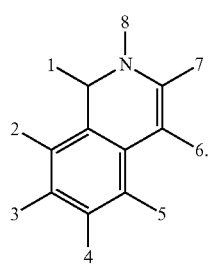

The prefix "$C_{u-v}$" indicates that the following group has from u to v carbon atoms. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (i.e., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula I. Also included are the specific compounds of Examples 1 to 137.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, the term "about X" includes description of "X".

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), 1 to 3 carbon atoms (i.e., $C_{1-3}$ alkyl), or 1 to 2 carbon atoms (i.e., $C_{1-2}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —$(CH_2)_3CH_3$), sec-butyl (i.e. —$CH(CH_3)CH_2CH_3$), isobutyl (i.e. —$CH_2CH(CH_3)_2$) and tert-butyl (i.e. —$C(CH_3)_3$); and "propyl" includes n-propyl (i.e. —$(CH_2)_2CH_3$) and isopropyl (i.e. —$CH(CH_3)_2$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkylene" refers to a divalent and unbranched saturated hydrocarbon chain. As used herein, alkylene has 1 to 20 carbon atoms (i.e., $C_{1-20}$ alkylene), 1 to 12 carbon atoms (i.e., $C_{1-12}$ alkylene), 1 to 8 carbon atoms (i.e., $C_{1-8}$ alkylene), 1 to 6 carbon atoms (i.e., $C_{1-6}$ alkylene), 1 to 4 carbon atoms (i.e., $C_{1-4}$ alkylene), 1 to 3 carbon atoms (i.e., $C_{1-3}$ alkylene), or 1 to 2 carbon atoms (i.e., $C_{1-2}$ alkylene). Examples of alkylene groups include methylene, ethylene, propylene, butylene, pentylene, and hexylene. In some embodiments, an alkylene is optionally substituted with an alkyl group. Examples of substituted alkylene groups include —$CH(CH_3)CH_2$—, —$CH_2CH(CH_3)$—, —$CH_2CH(CH_2CH_3)$—, —$CH_2C(CH_3)_2$—, —$C(CH_3)_2CH_2$—, —$CH(CH_3)CH(CH_3)$—, —$CH_2C(CH_2CH_3)(CH_3)$—, and —$CH_2C(CH_2CH_3)_2$.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)NR$^Y$R$^z$ and an "N-amido" group which refers to the group —NR$^Y$C(=O)R$^z$, wherein R$^y$ and R$^z$ are independently selected from the group consisting of hydrogen, alkyl, aryl, haloalkyl, heteroaryl, cycloalkyl, or heterocyclyl; each of which may be optionally substituted.

"Amino" refers to the group —NR$^Y$R$^z$ wherein R$^y$ and R$^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Bridged" refers to a ring fusion wherein non-adjacent atoms on a ring are joined by a divalent substituent, such as an alkylenyl group, an alkylenyl group containing one or two heteroatoms, or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkylene" refers to a divalent and unbranched saturated hydrocarbon chain having one, two, or three heteroatoms selected from NH, O, or S. As used herein, a heteroalkylene has 1 to 20 carbon atoms and one, two, or three heteroatoms selected from NH, O, and S (i.e., $C_{1-20}$ heteroalkylene); 1 to 8 carbon atoms and one, two, or three heteroatoms selected from NH, O, and S (i.e., $C_{1-8}$ heteroalkylene); 1 to 6 carbon atoms and one, two, or three heteroatoms selected from NH, O, and S S (i.e., $C_{1-6}$ heteroalkylene); 1 to 4 carbon atoms and one, two, or three heteroatoms selected from NH, O, and S (i.e., $C_{1-4}$ heteroalkylene); 1 to 3 carbon atoms and one, two, or three heteroatoms selected from NH, O, and S (i.e., $C_{1-3}$ heteroalkylene); or 1 to 2 carbon atoms and one, two, or three heteroatoms selected from NH, O, and S (i.e., $C_{1-3}$ heteroalkylene). For example, —CH$_2$O— is a $C_1$ heteroalkylene and —CH$_2$SCH$_2$— is a $C_2$ heteroalkylene. Examples of heteroalkylene groups include —CH$_2$CH$_2$OCH$_2$—, —CH$_2$SCH$_2$OCH$_2$—, —CH$_2$O—, and —CH$_2$NHCH$_2$—. In some embodiments, a heteroalkylene is optionally substituted with an alkyl group. Examples of substituted heteroalkylene groups include —CH(CH$_3$)N(CH$_3$)CH$_2$—, —CH$_2$OCH(CH$_3$)—, —CH$_2$CH(CH$_2$CH$_3$)S—, —CH$_2$NHC(CH$_3$)$_2$—, —C(CH$_3$)$_2$SCH$_2$—, —CH(CH$_3$)N(CH$_3$)CH(CH$_3$)O—, —CH$_2$SC(CH$_2$CH$_3$)(CH$_3$)—, and —CH$_2$C(CH$_2$CH$_3$)$_2$NH—.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., $C_{1-20}$ heteroaryl), 3 to 12 carbon ring atoms (i.e., $C_{3-12}$ heteroaryl), or 3 to 8 carbon ring atoms (i.e., $C_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5] nonanyl, 2-oxa-6-azaspiro[3.4]octanyl, and 6-oxa-1-azaspiro[3.3]heptanyl. As used herein, the terms "heterocycle", "heterocyclyl", and "heterocyclic ring" are used interchangeably. In some embodiments, a heterocyclyl is substituted with an oxo group.

"Hydroxy" or "hydroxyl" refers to the group —OH.

"Oxo" refers to the group (=O) or (O).

"Sulfonyl" refers to the group —S(O)$_2$R$^{bb}$, where R$^{bb}$ is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

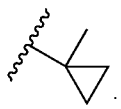

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

A "tautomer" refers to a proton shift from one atom of a molecule to another atom of the same molecule. The present disclosure includes tautomers of any compounds provided herein.

Some of the compounds provided herein exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

A "solvate" is formed by the interaction of a solvent and a compound. Solvates of salts of the compounds provided herein are also provided. Hydrates of the compounds provided herein are also provided.

Any formula or structure provided herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}P$, $^{36}Cl$ and $^{125}I$. Various isotopically labeled compounds of the present disclosure, for example those into which radioactive isotopes such as $^2H$, $^3H$, $^{13}C$ and $^{14}C$ are incorporated, are also provided herein. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The present disclosure also includes compounds of Formula I, in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the present disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example, increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure, any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, and the like. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (i.e., decreasing one or more symptoms resulting from the disease or condition, and/or diminishing the extent of the disease or condition); b) slowing or arresting the development of one or more clinical symptoms associated with the disease or condition (i.e., stabilizing the disease or condition, preventing or delaying the worsening or progression of the disease or condition, and/or preventing or delaying the spread (i.e., metastasis) of the disease or condition); and/or c) relieving the disease, that is, causing the regression of clinical symptoms (i.e., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to improve a symptom of a Retroviridae viral infection, including but not limited to HIV infection. The therapeutically effective amount may vary depending on the subject, and the disease or condition being treated, the weight and age of the subject, the severity of the disease or condition, and the manner of administering, which can readily be determined by one of ordinary skill in the art.

II. Compounds

In one embodiment, provided herein is a compound of Formula I,

Formula I

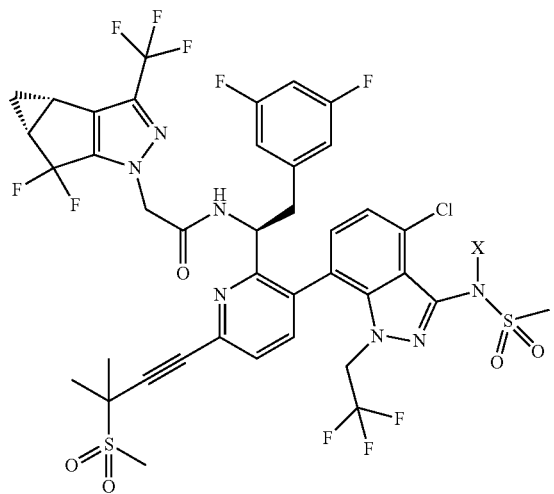

or a pharmaceutically acceptable salt thereof,
wherein
- X is —C(O)C(O)NR$^1$R$^1$, —C(O)C(O)OR$^2$, —(C$_{1-6}$ alkyl)OR$^3$, —C(O)NR$^4$R$^5$, —C(O)OR$^6$, or —C(O)C$_{1-10}$ alkyl, wherein the C$_{1-10}$ alkyl is optionally substituted with one 4-7 membered monocyclic heterocyclyl,
  - wherein the 4-7 membered monocyclic heterocyclyl is optionally substituted with 1-3 groups independently selected from —CN, halogen, R$^a$, R$^b$, and R$^c$;
- each R$^1$ independently is H or C$_{1-6}$ alkyl, wherein the C$_{1-6}$ alkyl is optionally substituted with 1-3 groups independently selected from —CN, halogen, R$^a$, R$^b$, and R$^c$;
- R$^2$ is H or C$_{1-6}$ alkyl, wherein the C$_{1-6}$ alkyl is optionally substituted with 1-3 groups independently selected from —CN, halogen, R$^a$, R$^b$, and R$^c$;
- R$^3$ is —P(O)(OH)$_2$, —C(O)R$^{3a}$, —C(O)OR$^{3a}$, —C(O)NR$^{3b}$R$^{3b}$, —C(O)C(O)OR$^{3a}$, —S(O)$_2$R$^{3a}$, —S(O)$_2$NR$^{3b}$R$^{3b}$, or —S(O)$_2$OR$^{3a}$;
- each R$^{3a}$ independently is H or C$_{1-6}$ alkyl, wherein the C$_{1-6}$ alkyl is substituted with 1-3 groups independently selected from —CN, R$^a$, R$^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$;
- each R$^{3b}$ independently is R$^d$ or C$_{1-6}$ alkyl, wherein the C$_{1-6}$ alkyl is substituted with 1-3 groups independently selected from —CN, R$^a$, R$^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$;
- R$^4$ is H or C$_{1-6}$ alkyl, wherein the C$_{1-6}$ alkyl is optionally substituted with 1-3 groups independently selected from —B(OH)$_2$, —CN, halogen, R$^a$, R$^b$, and R$^c$;
- R$^5$ is H, C$_{1-6}$ alkyl, or 8-10 membered fused bicyclic heteroaryl,
  - wherein the C$_{1-6}$ alkyl is optionally substituted with 1-3 groups independently selected from —B(OH)$_2$, —CN, halogen, R$^a$, R$^b$, R$^c$, and R$^{5a}$,
  - wherein the 8-10 membered fused bicyclic heteroaryl are each independently optionally substituted with 1-3 groups independently selected from —CN, halogen, R$^a$, R$^b$, R$^c$ and R$^{5b}$;
- each R$^{5a}$ independently is 4-7 membered monocyclic heterocyclyl, phenyl, naphthalenyl, 5-6 membered monocyclic heteroaryl, or 8-10 membered fused bicyclic heteroaryl,
  - wherein the 4-7 membered monocyclic heterocyclyl, phenyl, naphthalenyl, 5-6 membered monocyclic heteroaryl, and 8-10 membered fused bicyclic heteroaryl are each independently optionally substituted with 1-3 groups independently selected from —CN, halogen, R$^a$, R$^b$, and R$^c$;
- each R$^{5b}$ independently is C$_{1-6}$ alkyl, wherein the C$_{1-6}$ alkyl is optionally substituted with 1-3 groups independently selected from —CN, halogen, R$^a$, R$^b$, and R$^c$;
- R$^6$ is C$_{1-10}$ alkyl or C$_{3-7}$ monocyclic cycloalkyl, wherein the C$_{1-10}$ alkyl is optionally substituted with 1-3 groups independently selected from —CN, halogen, R$^a$, R$^b$, R$^c$, and —OC(O)(C$_{2-6}$ alkenylene)C(O)OR$^9$, 4-7 membered monocyclic heterocyclyl, phenyl, naphthalenyl, 5-6 membered monocyclic heteroaryl, and 8-10 membered fused bicyclic heteroaryl,
  - wherein the C$_{3-7}$ monocyclic cycloalkyl is optionally substituted with 1-3 groups independently selected from —CN, halogen, R$^a$, R$^b$, and R$^c$;
- each R$^a$ independently is —P(O)(OH)$_2$ or —OP(O)(OH)$_2$;
- each R$^b$ independently is —C(O)R$^7$, —C(O)OR$^7$, —C(O)NR$^8$R$^8$, —C(O)C(O)OR$^7$, —C(=NR$^{8a}$)(NR$^8$R$^8$), —S(O)$_2$R$^7$, —S(O)$_2$NR$^8$R$^8$, or —S(O)$_2$OR$^7$;
- each R$^c$ independently is —OR$^7$, —OC(O)R$^7$, —OC(O)C(O)OR$^7$, —(O(C$_{1-4}$ alkyl))$_n$OR$^{7a}$, —NR$^8$R$^8$, —N$^+$R$^8$R$^8$R$^{8a}$, —NR$^8$C(O)R$^7$, —NR$^8$C(O)NR$^8$R$^8$, —NR$^8$C(O)OR$^7$, —NR$^8$C(O)C(O)OR$^7$, —NR$^8$C(=NR$^{8a}$)NR$^8$R$^8$, or —NR$^8$S(O)$_2$R$^7$;
- each R$^7$ independently is H or C$_{1-6}$ alkyl, wherein the C$_{1-6}$ alkyl is optionally substituted with 1-3 groups independently selected from —CN, halogen, R$^a$, R$^d$, and R$^e$;
- each R$^{7a}$ independently is H, —P(O)(OH)$_2$, or C$_{1-6}$ alkyl, wherein the C$_{1-6}$ alkyl is optionally substituted with 1-3 groups independently selected from —CN, halogen, R$^a$, R$^d$, and R$^e$;
- each R$^8$ independently is H, R$^d$, or C$_{1-6}$ alkyl, wherein the C$_{1-6}$ alkyl is optionally substituted with 1-3 groups independently selected from —CN, halogen, R$^a$, R$^d$, and R$^e$;
- each R$^{8a}$ independently is H or C$_{1-3}$ alkyl;
- each R$^d$ independently is —C(O)R$^9$, —C(O)OR$^9$, —C(O)NR$^{10}$R$^{10}$, —C(O)C(O)OR$^9$, —C(=NR$^{10a}$)(NR$^{10}$R$^{10}$), —S(O)$_2$R$^9$, —S(O)$_2$NR$^{10}$R$^{10}$, or —S(O)$_2$OR$^9$;
- each R$^e$ independently is —OR$^9$, —OC(O)R$^9$, —OC(O)C(O)OR$^9$, —NR$^{10}$R$^{10}$, —N$^+$R$^{10}$R$^{10}$R$^{10a}$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, or —NR$^{10}$S(O)$_2$R$^9$;
- each R$^9$ independently is H or C$_{1-6}$ alkyl, wherein the C$_{1-6}$ alkyl is optionally substituted with 1-3 groups independently selected from CN, halogen, R$^a$, R$^f$, and R$^g$;
- each R$^{10}$ independently is H, R$^f$, or C$_{1-6}$ alkyl, wherein the C$_{1-6}$ alkyl is optionally substituted with 1-3 groups independently selected from —CN, halogen, R$^a$, R$^f$, and R$^g$;

17 each $R^{10a}$ independently is H or $C_{1-3}$ alkyl;
each $R^f$ independently is —C(O)$R^{11}$, —C(O)O$R^{11}$, —C(O)N$R^{11}R^{11}$, —C(O)C(O)O$R^{11}$, —C(=N$R^{11a}$)(N$R^{11}R^{11}$), —S(O)$_2R^{11}$, —S(O)$_2$N$R^{11}R^{11}$, or —S(O)$_2$O$R^{11}$;
each $R^g$ independently is —O$R^{11}$, —OC(O)$R^{11}$, —OC(O)C(O)O$R^{11}$, —N$R^{11}R^{11}$, —N$^+R^{11}R^{11}R^{11a}$, —N$R^{11}$C(O)$R^{11}$, —N$R^{11}$C(O)N$R^{11}R^{11}$, —N$R^{11}$C(O)O$R^{11}$, —N$R^{11}$C(O)C(O)O$R^{11}$, —N$R^{11}$C(=N$R^{11a}$)N$R^{11}R^{11}$, or —N$R^{11}$S(O)$_2R^{11}$;
each $R^{11}$ independently is H or $C_{1-6}$ alkyl, wherein the $C_{1-6}$ alkyl is optionally substituted with 1-3 groups independently selected from —OH, CN, halogen, —COOH, and $R^a$; each $R^{11a}$ independently is H or $C_{1-3}$ alkyl;
n is 1, 2, 3, 4, or 5;
wherein each 4 membered monocyclic heterocyclyl has 1 ring heteroatom selected from N, O, and S;
wherein each 5-7 membered monocyclic heterocyclyl has 1-2 ring heteroatoms independently selected from N, O, and S; and
wherein each 5-6 membered monocyclic heteroaryl and 8-10 membered fused bicyclic heteroaryl independently have 1-4 ring heteroatoms independently selected from N, O, and S.

In some embodiments of the compound of Formula I, or a pharmaceutically acceptable salt thereof, X is —C(O)C(O)N$R^1R^1$, —C(O)C(O)O$R^2$, —(C$_{1-6}$ alkyl)O$R^3$, —C(O)N$R^4R^5$, —C(O)O$R^6$, or —C(O)C$_{1-10}$ alkyl,
    wherein the $C_{1-10}$ alkyl is optionally substituted with one 4-7 membered monocyclic heterocyclyl,
        wherein the 4-7 membered monocyclic heterocyclyl is optionally substituted with 1-3 groups independently selected from —CN, halogen, $R^a$, $R^b$, and $R^c$;
each $R^1$ independently is H or $C_{1-6}$ alkyl, wherein the $C_{1-6}$ alkyl is optionally substituted with 1-3 groups independently selected from —OH, —CN, halogen, —C(O)OH, and $R^a$;
$R^2$ is H or $C_{1-6}$ alkyl, wherein the $C_{1-6}$ alkyl is optionally substituted with 1-3 groups independently selected from —OH, —CN, halogen, —C(O)OH, and $R^a$;
$R^3$ is —C(O)$R^{3a}$, —C(O)C(O)O$R^{3a}$, or —P(O)(OH)$_2$;
each $R^{3a}$ independently is H or $C_{1-6}$ alkyl, wherein the $C_{1-6}$ alkyl is substituted with 1-3 groups independently selected from —CN, $R^a$, $R^d$, —OC(O)$R^9$, —OC(O)C(O)O$R^9$, —N$R^{10}$C(O)$R^9$, —N$R^{10}$C(O)N$R^{10}R^{10}$, —N$R^{10}$C(O)O$R^9$, —N$R^{10}$C(O)C(O)O$R^9$, —N$R^{10}$C(=N$R^{10a}$)N$R^{10}R^{10}$, and —N$R^{10}$S(O)$_2R^9$;
$R^4$ is H or $C_{1-6}$ alkyl, wherein the $C_{1-6}$ alkyl is optionally substituted with 1-3 groups independently selected from —B(OH)$_2$, —CN, halogen, $R^a$, $R^b$, and $R^c$;
$R^5$ is H, or $C_{1-6}$ alkyl, wherein the $C_{1-6}$ alkyl is optionally substituted with 1-3 groups independently selected from —CN, halogen, $R^a$, $R^b$, $R^c$, and $R^{5a}$;
each $R^{5a}$ independently is 4-7 membered monocyclic heterocyclyl or phenyl,
    wherein the 4-7 membered monocyclic heterocyclyl and phenyl are each independently optionally substituted with 1-3 groups independently selected from —CN, halogen, $R^a$, $R^b$, and $R^c$;
$R^6$ is $C_{1-10}$ alkyl or $C_{3-7}$ monocyclic cycloalkyl,
    wherein the $C_{1-10}$ alkyl is optionally substituted with 1-3 groups independently selected from —CN, halogen, $R^a$, $R^b$, $R^c$, and —OC(O)(C$_{2-6}$ alkenylene)C(O)O$R^9$, 4-7 membered monocyclic heterocyclyl, and 5-6 membered monocyclic heteroaryl,
        wherein the $C_{3-7}$ monocyclic cycloalkyl is optionally substituted with 1-3 groups independently selected from —OH, —CN, halogen, —C(O)OH, —N$R^8R^8$, and $R^a$;
each $R^a$ independently is —P(O)(OH)$_2$ or —OP(O)(OH)$_2$;
each $R^b$ independently is —C(O)$R^7$, —C(O)O$R^7$, —C(O)N$R^8R^8$, —C(O)C(O)O$R^7$, —C(=N$R^{8a}$)(N$R^8R^8$), —S(O)$_2R^7$, —S(O)$_2$N$R^8R^8$, or —S(O)$_2$O$R^7$;
each $R^c$ independently is —O$R^7$, —OC(O)$R^7$, —OC(O)C(O)O$R^7$, —(O(C$_{1-4}$ alkyl))$_n$O$R^{7a}$, —N$R^8R^8$, —N$^+R^8R^8R^{8a}$, —N$R^8$C(O)$R^7$, —N$R^8$C(O)N$R^8R^8$, —N$R^8$C(O)O$R^7$, —N$R^8$C(O)C(O)O$R^8$, —N$R^8$C(=N$R^{8a}$)N$R^8R^8$, or —N$R^8$S(O)$_2R^7$;
each $R^7$ independently is H or $C_{1-6}$ alkyl, wherein the $C_{1-6}$ alkyl is optionally substituted with 1-3 groups independently selected from —CN, halogen, $R^a$, $R^d$, and $R^e$;
each $R^{7a}$ independently is H or —P(O)(OH)$_2$;
each $R^8$ independently is H or $C_{1-6}$ alkyl, wherein the $C_{1-6}$ alkyl is optionally substituted with 1-3 groups independently selected from —CN, halogen, $R^a$, $R^d$, and $R^e$;
each $R^{8a}$ independently is H or $C_{1-3}$ alkyl;
each $R^d$ independently is —C(O)$R^9$, —C(O)O$R^9$, —C(O)N$R^{10}R^{10}$, —C(O)C(O)O$R^9$, —C(=N$R^{10a}$)(N$R^{10}R^{10}$), —S(O)$_2R^9$, —S(O)$_2$N$R^{10}R^{10}$, or —S(O)$_2$O$R^9$;
each $R^e$ independently is —O$R^9$, —OC(O)$R^9$, —OC(O)C(O)O$R^9$, —N$R^{10}R^{10}$, —N$^+R^{10}R^{10}R^{10a}$, —N$R^{10}$C(O)$R^9$, —N$R^{10}$C(O)N$R^{10}R^{10}$, —N$R^{10}$C(O)O$R^9$, —N$R^{10}$C(O)C(O)O$R^9$, —N$R^{10}$C(=N$R^{10a}$)N$R^{10}R^{10}$, or —N$R^{10}$S(O)$_2R^9$;
each $R^9$ independently is H or $C_{1-6}$ alkyl, wherein the $C_{1-6}$ alkyl is optionally substituted with 1-3 groups independently selected from —OH, CN, halogen, —C(O)OH, and $R^a$;
each $R^{10}$ independently is H or $C_{1-6}$ alkyl, wherein the $C_{1-6}$ alkyl is optionally substituted with 1-3 groups independently selected from —OH, —CN, halogen, —C(O)OH, and $R^a$;
each $R^{10a}$ independently is H or $C_{1-3}$ alkyl;
n is 1, 2, 3, 4, or 5;
wherein each 4 membered monocyclic heterocyclyl has 1 ring heteroatom selected from N, O, and S;
wherein each 5-7 membered monocyclic heterocyclyl has 1-2 ring heteroatoms independently selected from N, O, and S; and
wherein each 5-6 membered monocyclic heteroaryl and 8-10 membered fused bicyclic heteroaryl independently have 1-4 ring heteroatoms independently selected from N, O, and S.

In some embodiments of the compound of Formula I, or a pharmaceutically acceptable salt thereof, X is —C(O)C(O)N$R^1R^1$, —C(O)C(O)O$R^2$, —(C$_{1-6}$ alkyl)O$R^3$, —C(O)N$R^4R^5$, —C(O)O$R^6$, or —C(O)C$_{1-10}$ alkyl,
    wherein the $C_{1-10}$ alkyl is optionally substituted with one 4-7 membered monocyclic heterocyclyl,
        wherein the 4-7 membered monocyclic heterocyclyl is optionally substituted with 1-3 groups independently selected from —OH, —CN, halogen, —C(O)OH, —C(=N$R^{8a}$)(N$R^8R^8$), and $R^a$;
each $R^1$ independently is H or $C_{1-6}$ alkyl, wherein the $C_{1-6}$ alkyl is optionally substituted with 1-3 groups independently selected from —OH, —CN, halogen, —C(O)OH, and $R^a$;

R$^2$ is H or C$_{1-6}$ alkyl, wherein the C$_{1-6}$ alkyl is optionally substituted with 1-3 groups independently selected from —OH, —CN, halogen, —C(O)OH, and R$^a$;

R$^3$ is —C(O)R$^{3a}$, —C(O)C(O)OR$^{3a}$, or —P(O)(OH)$_2$;

each R$^{3a}$ independently is H or C$_{1-6}$ alkyl, wherein the C$_{1-6}$ alkyl is substituted with 1-3 groups independently selected from —CN, —C(O)OR$^9$, and R$^a$;

R$^4$ is H or C$_{1-6}$ alkyl, wherein the C$_{1-6}$ alkyl is optionally substituted with 1-3 groups independently selected from —OH, —CN, halogen, —C(O)OH, and R$^a$;

R$^5$ is H or C$_{1-6}$ alkyl, wherein the C$_{1-6}$ alkyl is optionally substituted with 1-3 groups independently selected from —OH, —CN, halogen, —C(O)OR$^7$, —OC(O)C(O)OR$^7$, —NR$^8$R$^8$, —N$^+$R$^8$R$^8$R$^{5a}$, —NR$^8$C(O)OR$^7$, —NR$^8$C(O)C(O)OR$^8$, —NR$^8$C(=NR$^{8a}$)NR$^8$R$^8$, R$^a$, and R$^{5a}$;

each R$^{5a}$ independently is 4-7 membered monocyclic heterocyclyl or phenyl,
wherein the 4-7 membered monocyclic heterocyclyl and phenyl are each independently optionally substituted with 1-3 groups independently selected from —OH, —CN, halogen, —C(O)OH, —C(=NR$^{8a}$)(NR$^8$R$^8$), and R$^a$;

R$^6$ is C$_{1-10}$ alkyl or C$_{3-5}$ monocyclic cycloalkyl,
wherein the C$_{1-10}$ alkyl is optionally substituted with 1-3 groups independently selected from —OH, —CN, halogen, —C(O)OR$^7$, —S(O)$_2$OR$^7$, —(O(C$_{1-4}$ alkyl))$_n$OR$^{7a}$, —NR$^8$R$^8$, R$^a$, —OC(O)(C$_{2-6}$ alkenylene)C(O)OR$^9$, 4-7 membered monocyclic heterocyclyl, and 5-6 membered monocyclic heteroaryl,
wherein the C$_{3-5}$ monocyclic cycloalkyl is optionally substituted with 1-3 groups independently selected from —OH, —CN, halogen, —C(O)OH, —NR$^8$R$^8$, and R$^a$;

each R$^a$ independently is —P(O)(OH)$_2$ or —OP(O)(OH)$_2$;

each R$^7$ independently is H or C$_{1-6}$ alkyl, wherein the C$_{1-6}$ alkyl is optionally substituted with 1-3 groups independently selected from —OH, —CN, halogen, —C(O)OR$^9$, —NR$^{10}$R$^{10}$, and R$^a$;

each R$^{7a}$ independently is H or —P(O)(OH)$_2$;

each R$^8$ independently is H, —C(O)OR$^9$, —C(O)C(O)OR$^9$, —C(=NR$^{10a}$)(NR$^{10}$R$^{10}$), or C$_{1-6}$ alkyl, wherein the C$_{1-6}$ alkyl is optionally substituted with 1-3 groups independently selected from —OH, —CN, halogen, —C(O)OR$^9$, and R$^a$;

each R$^{8a}$ independently is H or C$_{1-3}$ alkyl;

each R$^9$ independently is H or C$_{1-3}$ alkyl, wherein the C$_{1-3}$ alkyl is optionally substituted with 1-3 groups independently selected from —OH, CN, halogen, —C(O)OH, and R$^a$;

each R$^{10}$ independently is H or C$_{1-4}$ alkyl, wherein the C$_{1-4}$ alkyl is optionally substituted with 1-3 groups independently selected from —OH, —CN, halogen, —C(O)OH, and R$^a$;

each R$^{10a}$ independently is H or C$_{1-3}$ alkyl;

n is 1, 2, 3, 4, or 5;

wherein each 4 membered monocyclic heterocyclyl has 1 ring heteroatom selected from N, O, and S;

wherein each 5-7 membered monocyclic heterocyclyl has 1-2 ring heteroatoms independently selected from N, O, and S; and wherein each 5-6 membered monocyclic heteroaryl and 8-10 membered fused bicyclic heteroaryl independently have 1-4 ring heteroatoms independently selected from N, O, and S.

As used herein, a 4 membered monocyclic heterocyclyl has 1 ring heteroatom selected from N, O, and S. As used herein, a 5-7 membered monocyclic heterocyclyl has 1-2 ring heteroatoms independently selected from N, O, and S. As used herein, a 5-6 membered monocyclic heteroaryl has 1-4 ring heteroatoms independently selected from N, O, and S. As used herein, a 8-10 membered fused bicyclic heteroaryl has 1-4 ring heteroatoms independently selected from N, O, and S.

In some embodiments of the compound of Formula I, or a pharmaceutically acceptable salt thereof, X is —C(O)C(O)NR$^1$R$^1$, —C(O)C(O)OR$^2$, —(C$_{1-6}$ alkyl)OR$^3$, —C(O)NR$^4$R$^5$, —C(O)OR$^6$, or —C(O)C$_{1-10}$ alkyl, wherein the C$_{1-10}$ alkyl is optionally substituted with one 4-7 membered monocyclic heterocyclyl,
wherein the 4-7 membered monocyclic heterocyclyl is optionally substituted with 1-3 groups independently selected from —CN, halogen, R$^a$, R$^b$, and R$^c$.

In some embodiments of the compound of Formula I, or a pharmaceutically acceptable salt thereof, X is —C(O)C(O)NR$^1$R$^1$, —C(O)C(O)OR$^2$, —(C$_{1-6}$ alkyl)OR$^3$, —C(O)NR$^4$R$^5$, —C(O)OR$^6$, or —C(O)C$_{1-10}$ alkyl, wherein the C$_{1-10}$ alkyl is optionally substituted with one 4-7 membered monocyclic heterocyclyl,
wherein the 4-7 membered monocyclic heterocyclyl is optionally substituted with 1-3 groups independently selected from —OH, —CN, halogen, —C(O)OH, —C(=NR$^{8a}$)(NR$^8$R$^8$), and R$^a$.

In some embodiments of the compound of Formula I, or a pharmaceutically acceptable salt thereof, X is —C(O)C(O)NR$^1$R$^1$.

In some embodiments of the compound of Formula I, or a pharmaceutically acceptable salt thereof, each R$^1$ independently is H or C$_{1-6}$ alkyl, wherein the C$_{1-6}$ alkyl is optionally substituted with 1-3 groups independently selected from —CN, halogen, R$^a$, R$^b$, and R$^c$. In some embodiments of the compound of Formula I, or a pharmaceutically acceptable salt thereof, each R$^1$ independently is H or C$_{1-6}$ alkyl, wherein the C$_{1-6}$ alkyl is optionally substituted with 1-3 groups independently selected from —OH, —CN, halogen, —C(O)OH, and R$^a$. In some embodiments of the compound of Formula I, or a pharmaceutically acceptable salt thereof, each R$^1$ independently is H or C$_{1-6}$ alkyl, wherein the C$_{1-6}$ alkyl is optionally substituted with 1-3 groups independently selected from —C(O)OH and R$^a$.

In some embodiments of the compound of Formula I, or a pharmaceutically acceptable salt thereof, one or both R$^1$ is H. In some embodiments of the compound of Formula I, or a pharmaceutically acceptable salt thereof, one or both R$^1$ is C$_{1-6}$ alkyl, wherein the C$_{1-6}$ alkyl is optionally substituted with 1-3 groups independently selected from —CN, halogen, R$^a$, R$^b$, and R$^c$. In some embodiments of the compound of Formula I, or a pharmaceutically acceptable salt thereof, one or both R$^1$ is C$_{1-6}$ alkyl, wherein the C$_{1-6}$ alkyl is optionally substituted with 1-3 groups independently selected from —OH, —CN, halogen, —C(O)OH, and R$^a$. In some embodiments of the compound of Formula I, or a pharmaceutically acceptable salt thereof, one or both R$^1$ is C$_{1-6}$ alkyl, wherein the C$_{1-6}$ alkyl is optionally substituted with 1-3 groups independently selected from —C(O)OH and R$^a$. In some embodiments of the compound of Formula I, or a pharmaceutically acceptable salt thereof, one or both R$^1$ is C$_{1-6}$ alkyl, wherein the C$_{1-6}$ alkyl is substituted with 1-3 groups independently selected from —CN, halogen, R$^a$, R$^b$, and R$^c$. In some embodiments of the compound of Formula I, or a pharmaceutically acceptable salt thereof, one or both R$^1$ is C$_{1-6}$ alkyl, wherein the C$_{1-6}$ alkyl is substituted with 1-3 groups independently selected from —OH, —CN, halogen, —C(O)OH, and $R^a$. In some embodiments of the compound of Formula I, or a pharmaceutically acceptable salt thereof, one or both $R^1$ is $C_{1-6}$ alkyl, wherein the $C_{1-6}$ alkyl is substituted with 1-3 groups independently selected from —C(O)OH and $R^a$. In some embodiments of the compound of Formula I, or a pharmaceutically acceptable salt thereof, one or both $R^1$ is $C_{1-6}$ alkyl.

In some embodiments of the compound of Formula I, or a pharmaceutically acceptable salt thereof, one $R^1$ is H and one $R^1$ is $C_{1-6}$ alkyl, wherein the $C_{1-6}$ alkyl is substituted with 1-3 groups independently selected from —C(O)OH and $R^a$.

In some embodiments of the compound of Formula I, or a pharmaceutically acceptable salt thereof, X is —C(O)C(O)OR$^2$.

In some embodiments of the compound of Formula I, or a pharmaceutically acceptable salt thereof, $R^2$ is H or $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, $R^2$ is H or $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, $R^2$ is H or $C_{1-3}$ alkyl, wherein the $C_{1-3}$ alkyl is optionally substituted with 1-3 groups independently selected from —C(O)OH and $R^a$. In some embodiments of the compound of Formula I, or a pharmaceutically acceptable salt thereof, $R^2$ is H, methyl, or ethyl.

In some embodiments of the compound of Formula I, or a pharmaceutically acceptable salt thereof, $R^2$ is H. In some embodiments of the compound of Formula I, or a pharmaceutically acceptable salt thereof, $R^2$ is $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, $R^2$ is $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, $R^2$ is $C_{1-3}$ alkyl, wherein the $C_{1-3}$ alkyl is optionally substituted with 1-3 groups independently selected from —C(O)OH and $R^a$. In some embodiments of the compound of Formula I, or a pharmaceutically acceptable salt thereof, $R^2$ is $C_{1-6}$ alkyl, wherein the $C_{1-6}$ alkyl is substituted with 1-3 groups independently selected from —CN, halogen, $R^a$, $R^b$, and $R^c$. In some embodiments of the compound of Formula I, or a pharmaceutically acceptable salt thereof, $R^2$ is $C_{1-6}$ alkyl, wherein the $C_{1-6}$ alkyl is substituted with 1-3 groups independently selected from —OH, —CN, halogen, —C(O)OH, and $R^a$. In some embodiments of the compound of Formula I, or a pharmaceutically acceptable salt thereof, $R^2$ is $C_{1-3}$ alkyl, wherein the $C_{1-3}$ alkyl is substituted with 1-3 groups independently selected from —C(O)OH and $R^a$. In some embodiments of the compound of Formula I, or a pharmaceutically acceptable salt thereof, $R^2$ is $C_{1-6}$ alkyl. In some embodiments of the compound of Formula I, or a pharmaceutically acceptable salt thereof, $R^2$ is $C_{1-3}$ alkyl. In some embodiments of the compound of Formula I, or a pharmaceutically acceptable salt thereof, $R^2$ is H. In some embodiments of the compound of Formula I, or a pharmaceutically acceptable salt thereof, $R^2$ is methyl. In some embodiments of the compound of Formula I, or a pharmaceutically acceptable salt thereof, $R^2$ is ethyl.

In some embodiments of the compound of Formula I, or a pharmaceutically acceptable salt thereof, X is —($C_{1-6}$ alkyl)OR$^3$. In some embodiments of the compound of Formula I, or a pharmaceutically acceptable salt thereof, X is —($C_{1-4}$ alkyl)OR$^3$. In some embodiments of the compound of Formula I, or a pharmaceutically acceptable salt thereof, X is —CH$_2$OR$^3$ or —CH$_2$CH$_2$OR$^3$.

In some embodiments of the compound of Formula I, or a pharmaceutically acceptable salt thereof, $R^3$ is —P(O)(OH)$_2$, —C(O)R$^{3a}$, —C(O)OR$^{3a}$, —C(O)NR$^{3b}$R$^{3b}$, —C(O)C(O)OR$^{3a}$, —S(O)$_2$R$^{3a}$, —S(O)$_2$NR$^{3b}$R$^{3b}$, or —S(O)$_2$OR$^{3a}$. In some embodiments of the compound of Formula I, or a pharmaceutically acceptable salt thereof, $R^3$ is —C(O)R$^{3a}$, —C(O)C(O)OR$^{3a}$, or —P(O)(OH)$_2$. In some embodiments of the compound of Formula I, or a pharmaceutically acceptable salt thereof, $R^3$ is —C(O)R$^{3a}$ or —C(O)C(O)OR$^{3a}$.

In some embodiments of the compound of Formula I, or a pharmaceutically acceptable salt thereof, $R^3$ is —P(O)(OH)$_2$. In some embodiments of the compound of Formula I, or a pharmaceutically acceptable salt thereof, $R^3$ is —C(O)R$^{3a}$. In some embodiments of the compound of Formula I, or a pharmaceutically acceptable salt thereof, $R^3$ is —C(O)OR$^{3a}$. In some embodiments of the compound of Formula I, or a pharmaceutically acceptable salt thereof, $R^3$ is —C(O)NR$^{3b}$R$^{3b}$. In some embodiments of the compound of Formula I, or a pharmaceutically acceptable salt thereof, $R^3$ is —C(O)C(O)OR$^{3a}$. In some embodiments of the compound of Formula I, or a pharmaceutically acceptable salt thereof, $R^3$ is —S(O)$_2$R$^{3a}$. In some embodiments of the compound of Formula I, or a pharmaceutically acceptable salt thereof, $R^3$ is —S(O)$_2$NR$^{3b}$R$^{3b}$. In some embodiments of the compound of Formula I, or a pharmaceutically acceptable salt thereof, $R^3$ is —S(O)$_2$OR$^{3a}$.

In some embodiments of the compound of Formula I, or a pharmaceutically acceptable salt thereof, $R^{3a}$ is H or $C_{1-6}$ alkyl, wherein the $C_{1-6}$ alkyl is substituted with 1-3 groups independently selected from —CN, $R^a$, $R^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$. In some embodiments of the compound of Formula I, or a pharmaceutically acceptable salt thereof, $R^{3a}$ is H or $C_{1-6}$ alkyl, wherein the $C_{1-6}$ alkyl is substituted with 1-3 groups independently selected from —CN, —C(O)OR$^9$, and $R^a$.

In some embodiments of the compound of Formula I, or a pharmaceutically acceptable salt thereof, $R^{3a}$ is H. In some embodiments of the compound of Formula I, or a pharmaceutically acceptable salt thereof, $R^{3a}$ is $C_{1-6}$ alkyl, wherein the $C_{1-6}$ alkyl is substituted with 1-3 groups independently selected from —CN, $R^a$, $R^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$. In some embodiments of the compound of Formula I, or a pharmaceutically acceptable salt thereof, $R^{3a}$ is $C_{1-6}$ alkyl, wherein the $C_{1-6}$ alkyl is substituted with 1-3 groups independently selected from —CN, —C(O)OR$^9$, and $R^a$.

In some embodiments of the compound of Formula I, or a pharmaceutically acceptable salt thereof, each $R^{3b}$ independently is $R^d$ or $C_{1-6}$ alkyl, wherein the $C_{1-6}$ alkyl is substituted with 1-3 groups independently selected from —CN, $R^a$, $R^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S (O)$_2$R$^9$. In some embodiments of the compound of Formula I, or a pharmaceutically acceptable salt thereof, one or both R$^{3b}$ is R$^d$. In some embodiments of the compound of Formula I, or a pharmaceutically acceptable salt thereof, one or both R$^{3b}$ is C$_{1-6}$ alkyl, wherein the C$_{1-6}$ alkyl is substituted with 1-3 groups independently selected from —CN, R$^a$, R$^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$.

In some embodiments of the compound of Formula I, or a pharmaceutically acceptable salt thereof, R$^3$ is —P(O)(OH)$_2$,

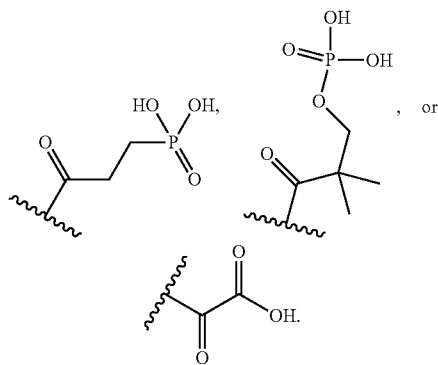

, or

In some embodiments of the compound of Formula I, or a pharmaceutically acceptable salt thereof, X is —C(O)NR$^4$R$^5$.

In some embodiments of the compound of Formula I, or a pharmaceutically acceptable salt thereof, R$^4$ is H or C$_{1-6}$ alkyl, wherein the C$_{1-6}$ alkyl is optionally substituted with 1-3 groups independently selected from —B(OH)$_2$, —CN, halogen, R$^a$, R$^b$, and R$^c$. In some embodiments of the compound of Formula I, or a pharmaceutically acceptable salt thereof, R$^4$ is H or C$_{1-6}$ alkyl, wherein the C$_{1-6}$ alkyl is optionally substituted with 1-3 groups independently selected from —OH, —CN, halogen, —C(O)OH, and R$^a$. In some embodiments of the compound of Formula I, or a pharmaceutically acceptable salt thereof, R$^4$ is H or C$_{1-6}$ alkyl, wherein the C$_{1-6}$ alkyl is optionally substituted with 1-3 groups independently selected from —B(OH)$_2$, —C(O)OR$^7$, —C(O)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, and R$^a$. In some embodiments of the compound of Formula I, or a pharmaceutically acceptable salt thereof, R$^4$ is H or C$_{1-6}$ alkyl, wherein the C$_{1-6}$ alkyl is optionally substituted with 1-2 groups independently selected from —C(O)OH and R$^a$. In some embodiments of the compound of Formula I, or a pharmaceutically acceptable salt thereof, R$^4$ is H or methyl.

In some embodiments of the compound of Formula I, or a pharmaceutically acceptable salt thereof, R$^4$ is H. In some embodiments of the compound of Formula I, or a pharmaceutically acceptable salt thereof, R$^4$ is C$_{1-6}$ alkyl, wherein the C$_{1-6}$ alkyl is optionally substituted with 1-3 groups independently selected from —B(OH)$_2$, —CN, halogen, R$^a$, R$^b$, and R$^c$. In some embodiments of the compound of Formula I, or a pharmaceutically acceptable salt thereof, R$^4$ is C$_{1-6}$ alkyl, wherein the C$_{1-6}$ alkyl is optionally substituted with 1-3 groups independently selected from —OH, —CN, halogen, —C(O)OH, and R$^a$. In some embodiments of the compound of Formula I, or a pharmaceutically acceptable salt thereof, R$^4$ is C$_{1-6}$ alkyl, wherein the C$_{1-6}$ alkyl is optionally substituted with 1-3 groups independently selected from —B(OH)$_2$, —C(O)OR$^7$, —C(O)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, and R$^a$. In some embodiments of the compound of Formula I, or a pharmaceutically acceptable salt thereof, R$^4$ is C$_{1-6}$ alkyl, wherein the C$_{1-6}$ alkyl is optionally substituted with 1-2 groups independently selected from —C(O)OH and R$^a$. In some embodiments of the compound of Formula I, or a pharmaceutically acceptable salt thereof, R$^4$ is C$_{1-6}$ alkyl, wherein the C$_{1-6}$ alkyl is substituted with 1-3 groups independently selected from —B(OH)$_2$, —CN, halogen, R$^a$, R$^b$, and R$^c$. In some embodiments of the compound of Formula I, or a pharmaceutically acceptable salt thereof, R$^4$ is C$_{1-6}$ alkyl, wherein the C$_{1-6}$ alkyl is substituted with 1-3 groups independently selected from —OH, —CN, halogen, —C(O)OH, and R$^a$. In some embodiments of the compound of Formula I, or a pharmaceutically acceptable salt thereof, R$^4$ is C$_{1-6}$ alkyl, wherein the C$_{1-6}$ alkyl is substituted with 1-3 groups independently selected from —B(OH)$_2$, —C(O)OR$^7$, —C(O)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, and R$^a$. In some embodiments of the compound of Formula I, or a pharmaceutically acceptable salt thereof, R$^4$ is C$_{1-6}$ alkyl, wherein the C$_{1-6}$ alkyl is substituted with 1-2 groups independently selected from —C(O)OH and R$^a$. In some embodiments of the compound of Formula I, or a pharmaceutically acceptable salt thereof, R$^4$ is C$_{1-6}$ alkyl. In some embodiments of the compound of Formula I, or a pharmaceutically acceptable salt thereof, R$^4$ is methyl.

In some embodiments of the compound of Formula I, or a pharmaceutically acceptable salt thereof, R$^5$ is H, C$_{1-6}$ alkyl, or 8-10 membered fused bicyclic heteroaryl,
  wherein the C$_{1-6}$ alkyl is optionally substituted with 1-3 groups independently selected from —B(OH)$_2$, —CN, halogen, R$^a$, R$^b$, R$^c$, and R$^{5a}$,
  wherein the 8-10 membered fused bicyclic heteroaryl is optionally substituted with 1-3 groups independently selected from —CN, halogen, R$^a$, R$^b$, R$^c$, and R$^{5b}$.

In some embodiments of the compound of Formula I, or a pharmaceutically acceptable salt thereof, R$^5$ is H or C$_{1-6}$ alkyl, wherein the C$_{1-6}$ alkyl is optionally substituted with 1-3 groups independently selected from —CN, halogen, R$^a$, R$^b$, R$^c$, and R$^{8a}$. In some embodiments of the compound of Formula I, or a pharmaceutically acceptable salt thereof, R$^5$ is H or C$_{1-6}$ alkyl, wherein the C$_{1-6}$ alkyl is optionally substituted with 1-3 groups independently selected from —B(OH)$_2$, —C(O)OR$^7$, —C(O)NR$^8$R$^8$, —OC(O)C(O)OR$^7$, —NR$^8$R$^8$, —N+R$^8$R$^8$R$^{8a}$, —NR$^8$C(O)OR$^7$, —NR$^8$C(O)C(O)OR$^8$, —NR$^8$C(=NR$^{8a}$)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, R$^a$, and R$^{8a}$. In some embodiments of the compound of Formula I, or a pharmaceutically acceptable salt thereof, R$^5$ is H or C$_{1-6}$ alkyl, wherein the C$_{1-6}$ alkyl is optionally substituted with 1-3 groups independently selected from —OH, —CN, halogen, —C(O)OR$^7$, —OC(O)C(O)OR$^7$, —NR$^8$R$^8$, —N+R$^8$R$^8$R$^{8a}$, —NR$^8$C(O)OR$^7$, —NR$^8$C(O)C(O)OR$^8$, —NR$^8$C(=NR$^{8a}$)NR$^8$R$^8$, R$^a$, and R$^{8a}$. In some embodiments of the compound of Formula I, or a pharmaceutically acceptable salt thereof, R$^5$ is H or C$_{1-6}$ alkyl, wherein the C$_{1-6}$ alkyl is
  i) substituted with —NR$^8$C(O)R$^7$, and
  ii) optionally substituted with 1-2 groups independently selected from —B(OH)$_2$, —C(O)OR$^7$, —C(O)NR$^8$R$^8$, —OC(O)C(O)OR$^7$, —NR$^8$R$^8$, —N+R$^8$R$^8$R$^{5a}$, —NR$^8$C(O)OR$^7$, —NR$^8$C(O)C(O)OR$^8$, —NR$^8$C(=NR$^{8a}$)

NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, R$^a$, and R$^{5a}$.

In some embodiments of the compound of Formula I, or a pharmaceutically acceptable salt thereof, R$^5$ is H.

In some embodiments of the compound of Formula I, or a pharmaceutically acceptable salt thereof, R$^5$ is C$_{1-6}$ alkyl, wherein the C$_{1-6}$ alkyl is optionally substituted with 1-3 groups independently selected from —B(OH)$_2$, —CN, halogen, R$^a$, R$^b$, R$^c$, and R$^{8a}$. In some embodiments of the compound of Formula I, or a pharmaceutically acceptable salt thereof, R$^5$ is C$_{1-6}$ alkyl, wherein the C$_{1-6}$ alkyl is optionally substituted with 1-3 groups independently selected from —CN, halogen, R$^a$, R$^b$, R$^c$, and R$^{8a}$. In some embodiments of the compound of Formula I, or a pharmaceutically acceptable salt thereof, R$^5$ is C$_{1-6}$ alkyl, wherein the C$_{1-6}$ alkyl is optionally substituted with 1-3 groups independently selected from —B(OH)$_2$, —C(O)OR$^7$, —C(O)NR$^8$R$^8$, —OC(O)C(O)OR$^7$, —NR$^8$R$^8$, —N$^+$R$^8$R$^8$R$^{5a}$, —NR$^8$C(O)OR$^7$, —NR$^8$C(O)C(O)OR$^8$, —NR$^8$C(=NR$^{8a}$)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, R$^a$, and R$^{5a}$. In some embodiments of the compound of Formula I, or a pharmaceutically acceptable salt thereof, R$^5$ is C$_{1-6}$ alkyl, wherein the C$_{1-6}$ alkyl is optionally substituted with 1-3 groups independently selected from —OH, —CN, halogen, —C(O)OR$^7$, —OC(O)C(O)OR$^7$, —NR$^8$R$^8$, —N$^+$R$^8$R$^8$R$^{5a}$, —NR$^8$C(O)OR$^7$, —NR$^8$C(O)C(O)OR$^8$, —NR$^8$C(=NR$^{8a}$)NR$^8$R$^8$, R$^a$, and R$^{5a}$. In some embodiments of the compound of Formula I, or a pharmaceutically acceptable salt thereof, R$^5$ is C$_{1-6}$ alkyl, wherein the C$_{1-6}$ alkyl is optionally substituted with 1-3 groups independently selected from —OH, —C(O)OR$^7$, —OC(O)C(O)OR$^7$, —NR$^8$R$^8$, —N$^+$R$^8$R$^8$R$^{8a}$, —NR$^8$C(O)OR$^7$, —NR$^8$C(O)C(O)OR$^8$, —NR$^8$C(=NR$^{8a}$)NR$^8$R$^8$, R$^a$, and R$^{5a}$. In some embodiments of the compound of Formula I, or a pharmaceutically acceptable salt thereof, R$^5$ is C$_{1-6}$ alkyl, wherein the C$_{1-6}$ alkyl is
  i) substituted with —NR$^8$C(O)R$^7$, and
  ii) optionally substituted with 1-2 groups independently selected from —B(OH)$_2$, —C(O)OR$^7$, —C(O)NR$^8$R$^8$, —OC(O)C(O)OR$^7$, —NR$^8$R$^8$, —N$^+$R$^8$R$^8$R$^{8a}$, —NR$^8$C(O)OR$^7$, —NR$^8$C(O)C(O)OR$^8$, —NR$^8$C(=NR$^{8a}$)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, R$^a$, and R$^{5a}$.

In some embodiments of the compound of Formula I, or a pharmaceutically acceptable salt thereof, R$^5$ is C$_{1-6}$ alkyl, wherein the C$_{1-6}$ alkyl is substituted with 1-3 groups independently selected from —B(OH)$_2$, —CN, halogen, R$^a$, R$^b$, R$^c$, and R$^{5a}$. In some embodiments of the compound of Formula I, or a pharmaceutically acceptable salt thereof, R$^5$ is C$_{1-6}$ alkyl, wherein the C$_{1-6}$ alkyl is substituted with 1-3 groups independently selected from —CN, halogen, R$^a$, R$^b$, R$^c$, and R$^{5a}$. In some embodiments of the compound of Formula I, or a pharmaceutically acceptable salt thereof, R$^5$ is C$_{1-6}$ alkyl, wherein the C$_{1-6}$ alkyl is substituted with 1-3 groups independently selected from —B(OH)$_2$, —C(O)OR$^7$, —C(O)NR$^8$R$^8$, —OC(O)C(O)OR$^7$, —NR$^8$R$^8$, —N$^+$R$^8$R$^8$R$^{8a}$, —NR$^8$C(O)OR$^7$, —NR$^8$C(O)C(O)OR$^8$, —NR$^8$C(=NR$^{8a}$)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, R$^a$, and R$^{5a}$. In some embodiments of the compound of Formula I, or a pharmaceutically acceptable salt thereof, R$^5$ is C$_{1-6}$ alkyl, wherein the C$_{1-6}$ alkyl is substituted with 1-3 groups independently selected from —OH, —CN, halogen, —C(O)OR$^7$, —OC(O)C(O)OR$^7$, —NR$^8$R$^8$, —N$^+$R$^8$R$^8$R$^{8a}$, —NR$^8$C(O)OR$^7$, —NR$^8$C(O)C(O)OR$^8$, —NR$^8$C(=NR$^{8a}$)NR$^8$R$^8$, R$^a$, and R$^{5a}$. In some embodiments of the compound of Formula I, or a pharmaceutically acceptable salt thereof, R$^5$ is C$_{1-6}$ alkyl, wherein the C$_{1-6}$ alkyl is substituted with 1-3 groups independently selected from —OH, —C(O)OR$^7$, —OC(O)C(O)OR$^7$, —NR$^8$R$^8$, —N$^+$R$^8$R$^8$R$^{8a}$, —NR$^8$C(O)OR$^7$, —NR$^8$C(O)C(O)OR$^8$, —NR$^8$C(=NR$^{8a}$)NR$^8$R$^8$, R$^a$, and R$^{5a}$. In some embodiments of the compound of Formula I, or a pharmaceutically acceptable salt thereof, R$^5$ is C$_{1-6}$ alkyl, wherein the C$_{1-6}$ alkyl is
  i) substituted with —NR$^8$C(O)R$^7$, and
  ii) substituted with 1-2 groups independently selected from —B(OH)$_2$, —C(O)OR$^7$, —C(O)NR$^8$R$^8$, —OC(O)C(O)OR$^7$, —NR$^8$R$^8$, —N$^+$R$^8$R$^8$R$^{5a}$, —NR$^8$C(O)OR$^7$, —NR$^8$C(O)C(O)OR$^8$, —NR$^8$C(=NR$^{8a}$)NR$^8$R$^8$, —S(O)$_2$R$^7$, —S(O)$_2$NR$^8$R$^8$, —S(O)$_2$OR$^7$, —NR$^8$C(O)R$^7$, —NR$^8$C(O)NR$^8$R$^8$, —NR$^8$S(O)$_2$R$^7$, R$^a$, and R$^{5a}$.

In some embodiments of the compound of Formula I, or a pharmaceutically acceptable salt thereof, each R$^{5a}$ independently is 4-7 membered monocyclic heterocyclyl, phenyl, naphthalenyl, 5-6 membered monocyclic heteroaryl, or 8-10 membered fused bicyclic heteroaryl,
  wherein the 4-7 membered monocyclic heterocyclyl, phenyl, naphthalenyl, 5-6 membered monocyclic heteroaryl, and 8-10 membered fused bicyclic heteroaryl are each independently optionally substituted with 1-3 groups independently selected from —CN, halogen, R$^a$, R$^b$, and R$^c$.

In some embodiments of the compound of Formula I, or a pharmaceutically acceptable salt thereof, each R$^{5a}$ independently is 4-7 membered monocyclic heterocyclyl or phenyl, wherein the 4-7 membered monocyclic heterocyclyl and phenyl are each independently optionally substituted with 1-3 groups independently selected from —CN, halogen, R$^a$, R$^b$, and R$^c$.

In some embodiments of the compound of Formula I, or a pharmaceutically acceptable salt thereof, each R$^{5a}$ independently is 4-7 membered monocyclic heterocyclyl or phenyl, wherein the 4-7 membered monocyclic heterocyclyl and phenyl are each independently optionally substituted with 1-3 groups independently selected from —OH, —CN, halogen, —C(O)OH, —C(=NR$^{8a}$)(NR$^8$R$^8$), and R$^a$.

In some embodiments of the compound of Formula I, or a pharmaceutically acceptable salt thereof, one or more R$^{5a}$ is 4-7 membered monocyclic heterocyclyl, wherein the 4-7 membered monocyclic heterocyclyl is optionally substituted with 1-3 groups independently selected from —CN, halogen, R$^a$, R$^b$, and R$^c$. In some embodiments of the compound of Formula I, or a pharmaceutically acceptable salt thereof, one or more R$^{5a}$ is 4-7 membered monocyclic heterocyclyl, wherein the 4-7 membered monocyclic heterocyclyl is optionally substituted with 1-3 groups independently selected from —OH, —CN, halogen, —C(O)OH, —C(=NR$^{8a}$)(NR$^8$R$^8$), and R$^a$. In some embodiments of the compound of Formula I, or a pharmaceutically acceptable salt thereof, one or more R$^{5a}$ is 4-7 membered monocyclic heterocyclyl, wherein the 4-7 membered monocyclic heterocyclyl is substituted with 1-3 groups independently selected from —CN, halogen, R$^a$, R$^b$, and R$^c$. In some embodiments of the compound of Formula I, or a pharmaceutically acceptable salt thereof, one or more R$^{5a}$ is 4-7 membered monocyclic heterocyclyl, wherein the 4-7 membered monocyclic heterocyclyl is substituted with 1-3 groups independently selected from —OH, —CN, halogen, —C(O)OH, —C(=NR$^{8a}$)(NR$^8$R$^8$), and R$^a$. In some embodiments of the compound of Formula I, or a pharmaceutically acceptable salt thereof, one or more $R^{5a}$ is 4-7 membered monocyclic heterocyclyl.

In some embodiments of the compound of Formula I, or a pharmaceutically acceptable salt thereof, one or more $R^{5a}$ is phenyl, wherein the phenyl is optionally substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is phenyl, wherein the phenyl is optionally substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is phenyl, wherein the phenyl is substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is phenyl, wherein the phenyl is substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is phenyl.

In some embodiments of the compound of Formula I, or a pharmaceutically acceptable salt thereof, one or more $R^{5a}$ is naphthalenyl, wherein the naphthalenyl is optionally substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is naphthalenyl, wherein the naphthalenyl is optionally substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is naphthalenyl, wherein the naphthalenyl is substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is naphthalenyl, wherein the naphthalenyl is substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is naphthalenyl.

In some embodiments of the compound of Formula I, or a pharmaceutically acceptable salt thereof, one or more $R^{5a}$ is 5-6 membered monocyclic heteroaryl, wherein the 5-6 membered monocyclic heteroaryl is optionally substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is 5-6 membered monocyclic heteroaryl, wherein the 5-6 membered monocyclic heteroaryl is optionally substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is 5-6 membered monocyclic heteroaryl, wherein the 5-6 membered monocyclic heteroaryl is substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is 5-6 membered monocyclic heteroaryl, wherein the 5-6 membered monocyclic heteroaryl is substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is 5-6 membered monocyclic heteroaryl.

In some embodiments of the compound of Formula I, or a pharmaceutically acceptable salt thereof, one or more $R^{5a}$ is 8-10 membered fused bicyclic heteroaryl, wherein the 8-10 membered fused bicyclic heteroaryl is optionally substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is 8-10 membered fused bicyclic heteroaryl, wherein the 8-10 membered fused bicyclic heteroaryl is optionally substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is 8-10 membered fused bicyclic heteroaryl, wherein the 8-10 membered fused bicyclic heteroaryl is substituted with 1-3 groups independently selected from —CN, halogen, $R^a$, $R^b$, and $R^c$. In some embodiments of the compound of Formula I, or a pharmaceutically acceptable salt thereof, one or more $R^{5a}$ is 8-10 membered fused bicyclic heteroaryl, wherein the 8-10 membered fused bicyclic heteroaryl is substituted with 1-3 groups independently selected from —OH, —CN, halogen, —C(O)OH, —C(=NR$^{8a}$)(NR$^8$R$^8$), and $R^a$. In some embodiments of the compound of Formula I, or a pharmaceutically acceptable salt thereof, one or more $R^{5a}$ is 8-10 membered fused bicyclic heteroaryl.

In some embodiments of the compound of Formula I, or a pharmaceutically acceptable salt thereof, $R^5$ is $C_{1-4}$ alkyl, wherein the $C_{1-4}$ alkyl is substituted with a 6-membered monocyclic heterocyclyl or phenyl, wherein the 6-membered monocyclic heterocyclyl and phenyl are each independently optionally substituted with 1-2 groups independently selected from —NR$^8$C(=NR$^{8a}$)NR$^8$R$^8$ and $R^a$. In some embodiments of the compound of Formula I, or a pharmaceutically acceptable salt thereof, $R^5$ is $C_{1-4}$ alkyl, wherein the $C_{1-4}$ alkyl is substituted with morpholinyl, piperazinyl, or phenyl, each of which is optionally substituted with one group selected from —NHC(=NH)NH$_2$ and $R^a$.

In some embodiments of the compound of Formula I, or a pharmaceutically acceptable salt thereof, $R^5$ is $C_{1-6}$ alkyl.

In some embodiments of the compound of Formula I, or a pharmaceutically acceptable salt thereof, $R^5$ is methyl,

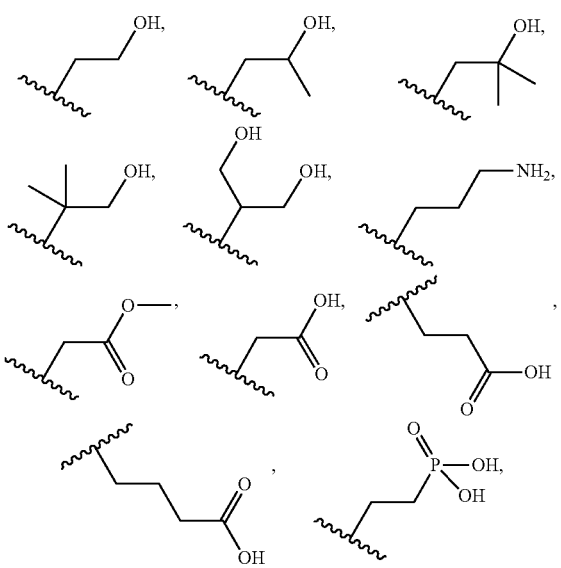

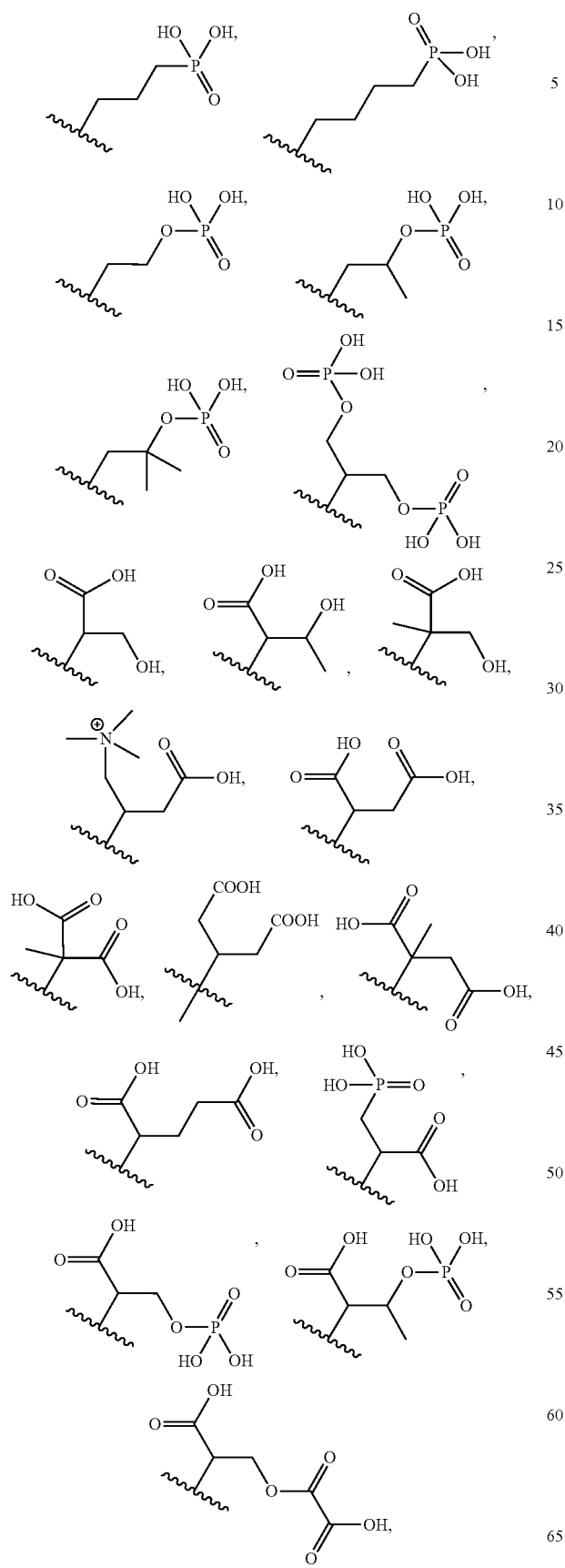
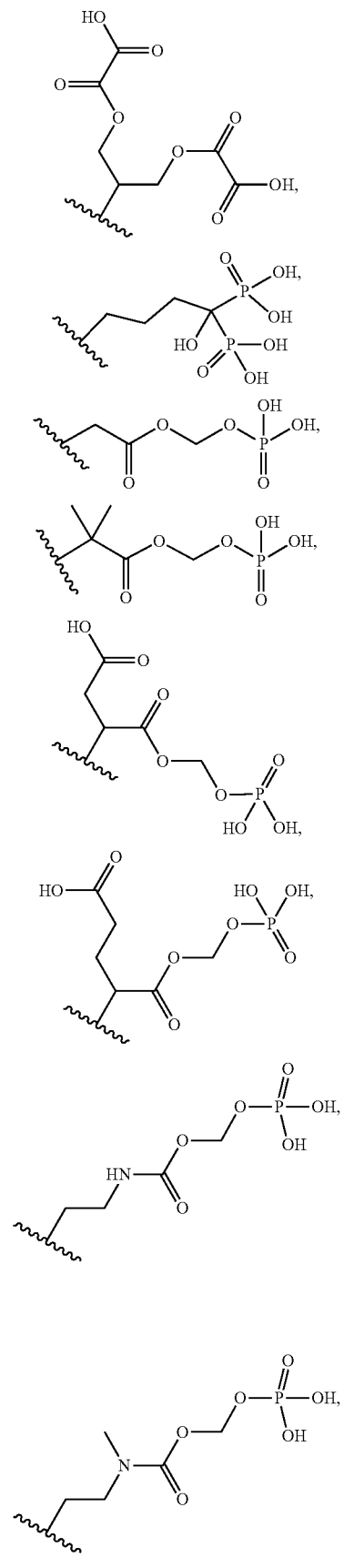

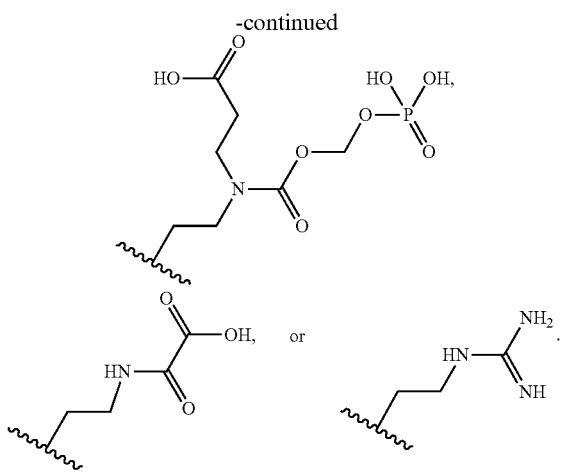

In some embodiments of the compound of Formula I, or a pharmaceutically acceptable salt thereof, $R^5$ is 8-10 membered fused bicyclic heteroaryl, wherein the 8-10 membered fused bicyclic heteroaryl is optionally substituted with 1-3 groups independently selected from —CN, halogen, $R^a$, $R^b$, $R^c$, and $R^{5b}$. In some embodiments of the compound of Formula I, or a pharmaceutically acceptable salt thereof, $R^5$ is 8-10 membered fused bicyclic heteroaryl, wherein the 8-10 membered fused bicyclic heteroaryl is substituted with 1-3 groups independently selected from —CN, halogen, $R^a$, $R^b$, $R^c$, and $R^{5b}$. In some embodiments of the compound of Formula I, or a pharmaceutically acceptable salt thereof, $R^5$ is 8-10 membered fused bicyclic heteroaryl.

In some embodiments of the compound of Formula I, or a pharmaceutically acceptable salt thereof, each $R^{5b}$ independently is $C_{1-6}$ alkyl, wherein the $C_{1-6}$ alkyl is optionally substituted with 1-3 groups independently selected from —CN, halogen, $R^a$, $R^b$, and $R^c$. In some embodiments of the compound of Formula I, or a pharmaceutically acceptable salt thereof, each $R^{5b}$ independently is $C_{1-6}$ alkyl, wherein the $C_{1-6}$ alkyl is substituted with 1-3 groups independently selected from —CN, halogen, $R^a$, $R^b$, and $R^c$. In some embodiments of the compound of Formula I, or a pharmaceutically acceptable salt thereof, each $R^{5b}$ independently is $C_{1-6}$ alkyl.

In some embodiments of the compound of Formula I, or a pharmaceutically acceptable salt thereof, X is —C(O)$OR^6$.

In some embodiments of the compound of Formula I, or a pharmaceutically acceptable salt thereof, $R^6$ is $C_{1-10}$ alkyl or $C_{3-7}$ monocyclic cycloalkyl,
wherein the $C_{1-10}$ alkyl is optionally substituted with 1-3 groups independently selected from —CN, halogen, $R^a$, $R^b$, $R^c$, and —OC(O)($C_{2-6}$ alkenylene)C(O)$OR^9$, 4-7 membered monocyclic heterocyclyl, phenyl, naphthalenyl, 5-6 membered monocyclic heteroaryl, and 8-10 membered fused bicyclic heteroaryl,
wherein the $C_{3-7}$ monocyclic cycloalkyl is optionally substituted with 1-3 groups independently selected from —CN, halogen, $R^a$, $R^b$, and $R^c$.

In some embodiments of the compound of Formula I, or a pharmaceutically acceptable salt thereof, $R^6$ is $C_{1-10}$ alkyl or $C_{3-7}$ monocyclic cycloalkyl,
wherein the $C_{1-10}$ alkyl is optionally substituted with 1-3 groups independently selected from —CN, halogen, $R^a$, $R^b$, $R^c$, and —OC(O)($C_{2-6}$ alkenylene)C(O)$OR^9$, 4-7 membered monocyclic heterocyclyl, and 5-6 membered monocyclic heteroaryl,
wherein the $C_{3-7}$ monocyclic cycloalkyl is optionally substituted with 1-3 groups independently selected from —OH, —CN, halogen, —C(O)OH, —$NR^8R^8$, and $R^a$.

In some embodiments of the compound of Formula I, or a pharmaceutically acceptable salt thereof, $R^6$ is $C_{1-10}$ alkyl or $C_{3-5}$ monocyclic cycloalkyl, wherein the $C_{1-10}$ alkyl is optionally substituted with 1-3 groups independently selected from —OH, —CN, halogen, —C(O)$OR^7$, —S(O)$_2OR^7$, —(O($C_{1-4}$ alkyl))$_n OR^{7a}$, —$NR^8R^8$, $R^a$, —OC(O)($C_{2-6}$ alkenylene)C(O)$OR^9$, 4-7 membered monocyclic heterocyclyl, and 5-6 membered monocyclic heteroaryl, wherein the $C_{3-5}$ monocyclic cycloalkyl is optionally substituted with 1-3 groups independently selected from —OH, —CN, halogen, —C(O)OH, —$NR^8R^8$, and $R^a$.

In some embodiments of the compound of Formula I, or a pharmaceutically acceptable salt thereof, $R^6$ is $C_{1-10}$ alkyl, wherein the $C_{1-10}$ alkyl is optionally substituted with 1-3 groups independently selected from —CN, halogen, $R^a$, $R^b$, $R^c$, and —OC(O)($C_{2-6}$ alkenylene)C(O)$OR^9$, 4-7 membered monocyclic heterocyclyl, phenyl, naphthalenyl, 5-6 membered monocyclic heteroaryl, and 8-10 membered fused bicyclic heteroaryl. In some embodiments of the compound of Formula I, or a pharmaceutically acceptable salt thereof, $R^6$ is $C_{1-10}$ alkyl, wherein the $C_{1-10}$ alkyl is optionally substituted with 1-3 groups independently selected from —CN, halogen, $R^a$, $R^b$, $R^c$, and —OC(O)($C_{2-6}$ alkenylene)C(O)$OR^9$, 4-7 membered monocyclic heterocyclyl, and 5-6 membered monocyclic heteroaryl. In some embodiments of the compound of Formula I, or a pharmaceutically acceptable salt thereof, $R^6$ is $C_{1-10}$ alkyl, wherein the $C_{1-10}$ alkyl is optionally substituted with 1-3 groups independently selected from —OH, —CN, halogen, —C(O)$OR^7$, —S(O)$_2OR^7$, —(O($C_{1-4}$ alkyl))$_n OR^{7a}$, —$NR^8R^8$, $R^a$, —OC(O)($C_{2-6}$ alkenylene)C(O)$OR^9$, 4-7 membered monocyclic heterocyclyl, and 5-6 membered monocyclic heteroaryl. In some embodiments of the compound of Formula I, or a pharmaceutically acceptable salt thereof, $R^6$ is $C_{1-10}$ alkyl, wherein the $C_{1-10}$ alkyl is optionally substituted with 1-3 groups independently selected from —OH, —CN, halogen, —C(O)$OR^7$, —S(O)$_2OR^7$, —(O($C_{1-4}$ alkyl))$_n OR^{7a}$, —$NR^8R^8$, $R^a$, —OC(O)($C_{2-6}$ alkenylene)C(O)$OR^9$, 5-6 membered monocyclic heterocyclyl, and 6 membered monocyclic heteroaryl. In some embodiments of the compound of Formula I, or a pharmaceutically acceptable salt thereof, $R^6$ is $C_{1-10}$ alkyl, wherein the $C_{1-10}$ alkyl is substituted with 1-3 groups independently selected from —CN, halogen, $R^a$, $R^b$, $R^c$, and —OC(O)($C_{2-6}$ alkenylene)C(O)$OR^9$, 4-7 membered monocyclic heterocyclyl, phenyl, naphthalenyl, 5-6 membered monocyclic heteroaryl, and 8-10 membered fused bicyclic heteroaryl. In some embodiments of the compound of Formula I, or a pharmaceutically acceptable salt thereof, $R^6$ is $C_{1-10}$ alkyl, wherein the $C_{1-10}$ alkyl is substituted with 1-3 groups independently selected from —CN, halogen, $R^a$, $R^b$, $R^c$, and —OC(O)($C_{2-6}$ alkenylene)C(O)$OR^9$, 4-7 membered monocyclic heterocyclyl, and 5-6 membered monocyclic heteroaryl. In some embodiments of the compound of Formula I, or a pharmaceutically acceptable salt thereof, $R^6$ is $C_{1-10}$ alkyl, wherein the $C_{1-10}$ alkyl is substituted with 1-3 groups independently selected from —OH, —CN, halogen, —C(O)$OR^7$, —S(O)$_2OR^7$, —(O($C_{1-4}$ alkyl))$_n OR^{7a}$, —$NR^8R^8$, $R^a$, —OC(O)($C_{2-6}$ alkenylene)C(O)$OR^9$, 4-7 membered monocyclic heterocyclyl, and 5-6 membered monocyclic heteroaryl. In some embodiments of the compound of Formula I, or a pharmaceutically acceptable salt thereof, $R^6$ is $C_{1-10}$ alkyl, wherein the $C_{1-10}$ alkyl is substituted with 1-3 groups independently selected from —OH, —CN, halogen, —C(O)OR$^7$, —S(O)$_2$OR$^7$, —(O(C$_{1-4}$ alkyl))$_n$OR$^{7a}$, —NR$^8$R$^8$, R$^a$, —OC(O)(C$_{2-6}$ alkenylene)C(O)OR$^9$, 5-6 membered monocyclic heterocyclyl, and 6 membered monocyclic heteroaryl. In some embodiments of the compound of Formula I, or a pharmaceutically acceptable salt thereof, R$^6$ is C$_{1-5}$ alkyl, wherein the C$_{1-5}$ alkyl is substituted with one —(O(C$_{1-4}$ alkyl))$_n$OR$^{7a}$. In some embodiments of the compound of Formula I, or a pharmaceutically acceptable salt thereof, R$^6$ is C$_{1-10}$ alkyl.

In some embodiments of the compound of Formula I, or a pharmaceutically acceptable salt thereof, n is 1, 2, 3, 4, or 5. In some embodiments of the compound of Formula I, or a pharmaceutically acceptable salt thereof, n is 1. In some embodiments of the compound of Formula I, or a pharmaceutically acceptable salt thereof, n is 2. In some embodiments of the compound of Formula I, or a pharmaceutically acceptable salt thereof, n is 3. In some embodiments of the compound of Formula I, or a pharmaceutically acceptable salt thereof, n is 4. In some embodiments of the compound of Formula I, or a pharmaceutically acceptable salt thereof, n is 5.

In some embodiments of the compound of Formula I, or a pharmaceutically acceptable salt thereof, R$^6$ is methyl,

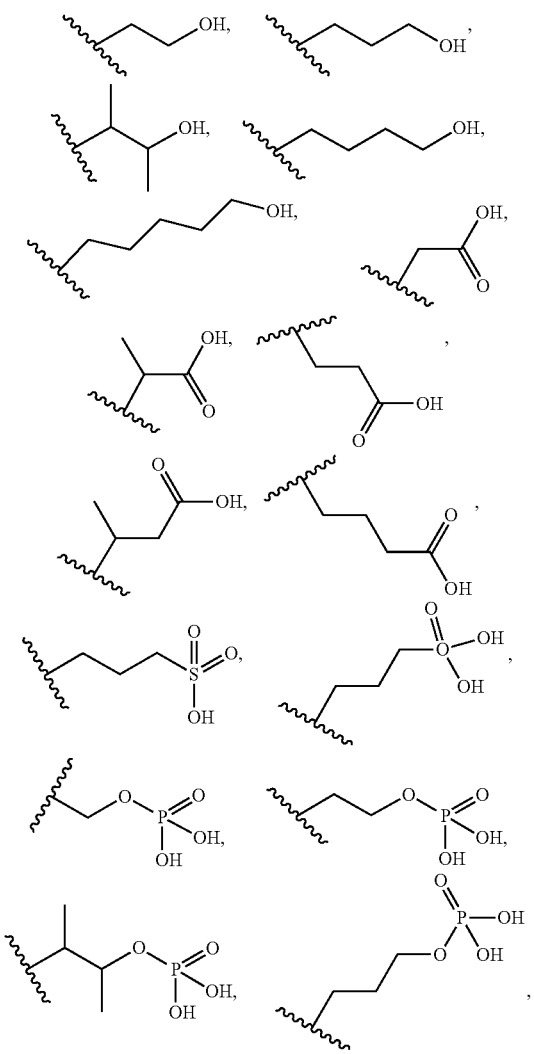

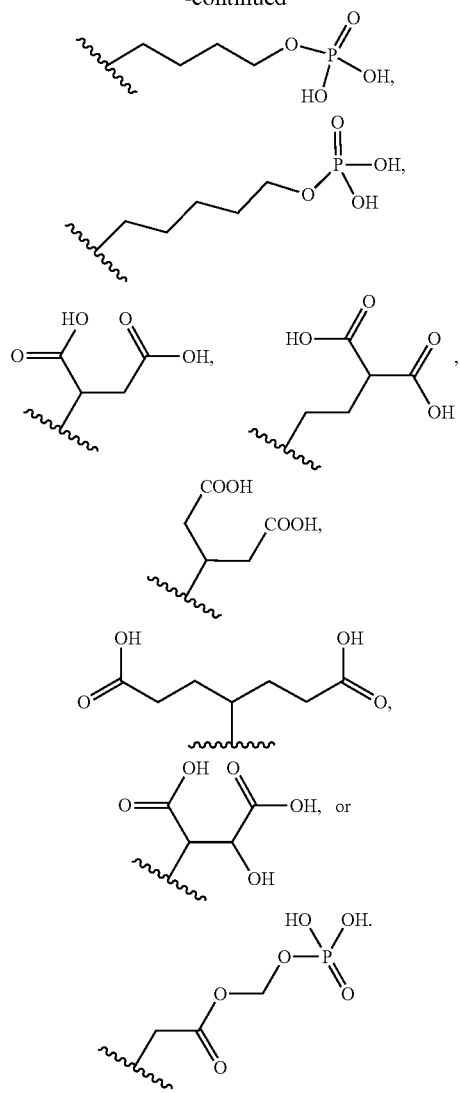

In some embodiments of the compound of Formula I, or a pharmaceutically acceptable salt thereof, R$^6$ is C$_{1-5}$ alkyl, wherein the C$_{1-5}$ alkyl is substituted with one —(O(C$_{1-4}$ alkyl))$_n$OR$^{7a}$ and wherein n is 1, 2, or 3.

In some embodiments of the compound of Formula I, or a pharmaceutically acceptable salt thereof, R$^6$ is

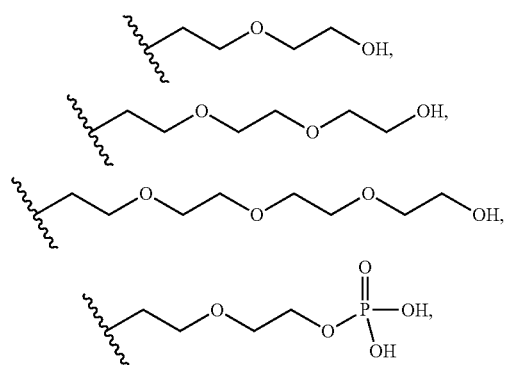

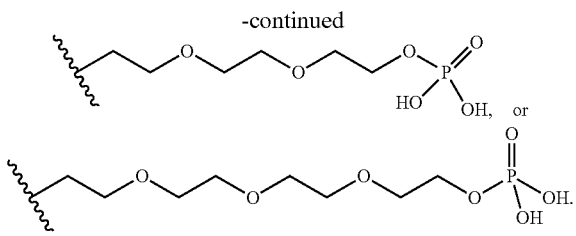

In some embodiments of the compound of Formula I, or a pharmaceutically acceptable salt thereof, $R^6$ is —($C_{1-4}$ alkylene)$NR^8R^8$,

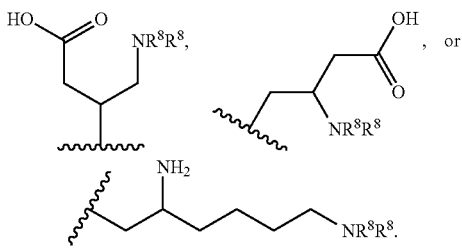

In some embodiments of the compound of Formula I, or a pharmaceutically acceptable salt thereof, $R^6$ is methyl, wherein the methyl is substituted with —OC(O)(CH=CH)C(O)OH or —OC(O)(CH=CH)C(O)OCH$_3$.

In some embodiments of the compound of Formula I, or a pharmaceutically acceptable salt thereof, $R^6$ is $C_{1-4}$ alkyl, wherein the $C_{1-4}$ alkyl is substituted with pyridinyl or morpholinyl.

In some embodiments of the compound of Formula I, or a pharmaceutically acceptable salt thereof, $R^6$ is $C_{3-7}$ monocyclic cycloalkyl, wherein the $C_{3-7}$ monocyclic cycloalkyl is optionally substituted with 1-3 groups independently selected from —CN, halogen, $R^a$, $R^b$, and $R^c$. In some embodiments of the compound of Formula I, or a pharmaceutically acceptable salt thereof, $R^6$ is $C_{3-7}$ monocyclic cycloalkyl, wherein the $C_{3-7}$ monocyclic cycloalkyl is optionally substituted with 1-3 groups independently selected from —OH, —CN, halogen, —C(O)OH, —$NR^8R^8$, and $R^a$. In some embodiments of the compound of Formula I, or a pharmaceutically acceptable salt thereof, $R^6$ is $C_{3-5}$ monocyclic cycloalkyl, wherein the $C_{3-5}$ monocyclic cycloalkyl is optionally substituted with 1-3 groups independently selected from —OH, —CN, halogen, —C(O)OH, —$NR^8R^8$, and $R^a$. In some embodiments of the compound of Formula I, or a pharmaceutically acceptable salt thereof, $R^6$ is $C_{3-7}$ monocyclic cycloalkyl, wherein the $C_{3-7}$ monocyclic cycloalkyl is substituted with 1-3 groups independently selected from —CN, halogen, $R^a$, $R^b$, and $R^c$. In some embodiments of the compound of Formula I, or a pharmaceutically acceptable salt thereof, $R^6$ is $C_{3-7}$ monocyclic cycloalkyl, wherein the $C_{3-7}$ monocyclic cycloalkyl is substituted with 1-3 groups independently selected from —OH, —CN, halogen, —C(O)OH, —$NR^8R^8$, and $R^a$. In some embodiments of the compound of Formula I, or a pharmaceutically acceptable salt thereof, $R^6$ is $C_{3-5}$ monocyclic cycloalkyl, wherein the $C_{3-5}$ monocyclic cycloalkyl is substituted with 1-3 groups independently selected from —OH, —CN, halogen, —C(O)OH, —$NR^8R^8$, and $R^a$. In some embodiments of the compound of Formula I, or a pharmaceutically acceptable salt thereof, $R^6$ is $C_{3-7}$ monocyclic cycloalkyl.

In some embodiments of the compound of Formula I, or a pharmaceutically acceptable salt thereof, $R^6$ is $C_{3-5}$ monocyclic cycloalkyl, wherein the $C_{3-5}$ monocyclic cycloalkyl is substituted with 1-2 groups independently selected from —C(O)OH, —$NR^8R^8$, and $R^a$.

In some embodiments of the compound of Formula I, or a pharmaceutically acceptable salt thereof, $R^6$ is cyclobutyl, wherein the cyclobutyl is substituted with one —$NR^8R^8$.

In some embodiments of the compound of Formula I, or a pharmaceutically acceptable salt thereof, X is —C(O)$C_{1-10}$ alkyl, wherein the $C_{1-10}$ alkyl is optionally substituted with one 4-7 membered monocyclic heterocyclyl, wherein the 4-7 membered monocyclic heterocyclyl is optionally substituted with 1-3 groups independently selected from —CN, halogen, $R^a$, $R^b$, and $R^c$. In some embodiments of the compound of Formula I, or a pharmaceutically acceptable salt thereof, X is —C(O)$C_{1-10}$ alkyl, wherein the $C_{1-10}$ alkyl is optionally substituted with one 4-7 membered monocyclic heterocyclyl, wherein the 4-7 membered monocyclic heterocyclyl is optionally substituted with 1-3 groups independently selected from —OH, —CN, halogen, —C(O)OH, —C(=$NR^{8a}$)($NR^8R^8$), and $R^a$. In some embodiments of the compound of Formula I, or a pharmaceutically acceptable salt thereof, X is —C(O)$C_{1-10}$ alkyl, wherein the $C_{1-10}$ alkyl is optionally substituted with one 4-7 membered monocyclic heterocyclyl, wherein the 4-7 membered monocyclic heterocyclyl is optionally substituted with 1-3 groups independently selected from —OH, —C(O)OH, —C(=$NR^{8a}$)($NR^8R^8$), and $R^a$.

In some embodiments of the compound of Formula I, or a pharmaceutically acceptable salt thereof, X is —C(O)$C_{1-10}$ alkyl, wherein the $C_{1-10}$ alkyl is substituted with one 4-7 membered monocyclic heterocyclyl, wherein the 4-7 membered monocyclic heterocyclyl is optionally substituted with 1-3 groups independently selected from —CN, halogen, $R^a$, $R^b$, and $R^c$. In some embodiments of the compound of Formula I, or a pharmaceutically acceptable salt thereof, X is —C(O)$C_{1-10}$ alkyl, wherein the $C_{1-10}$ alkyl is substituted with one 4-7 membered monocyclic heterocyclyl, wherein the 4-7 membered monocyclic heterocyclyl is optionally substituted with 1-3 groups independently selected from —OH, —CN, halogen, —C(O)OH, —C(=$NR^{8a}$)($NR^8R^8$), and $R^a$. In some embodiments of the compound of Formula I, or a pharmaceutically acceptable salt thereof, X is —C(O)$C_{1-10}$ alkyl, wherein the $C_{1-10}$ alkyl is substituted with one 4-7 membered monocyclic heterocyclyl, wherein the 4-7 membered monocyclic heterocyclyl is optionally substituted with 1-3 groups independently selected from —OH, —C(O)OH, —C(=$NR^{8a}$)($NR^8R^8$), and $R^a$.

In some embodiments of the compound of Formula I, or a pharmaceutically acceptable salt thereof, X is —C(O)$C_{1-6}$ alkyl, wherein the $C_{1-6}$ alkyl is substituted with a 5-6 membered monocyclic heterocyclyl, wherein the 5-6 membered monocyclic heterocyclyl is optionally substituted with 1-3 groups independently selected from —OH, —C(O)OH, —C(=$NR^{8a}$)($NR^8R^8$), and $R^a$.

In some embodiments of the compound of Formula I, or a pharmaceutically acceptable salt thereof, X is —C(O)$C_{1-6}$ alkyl, wherein the $C_{1-6}$ alkyl is substituted with morpholinyl or piperazinyl, each of which is optionally substituted with one —C(=$NR^{8a}$)($NR^8R^8$).

In some embodiments of the compound of Formula I, or a pharmaceutically acceptable salt thereof, X is —C(O)$C_{1-10}$ alkyl.

In some embodiments of the compound of Formula I, or a pharmaceutically acceptable salt thereof, each $R^a$ independently is —P(O)(OH)$_2$ or —OP(O)(OH)$_2$. In some embodiments of the compound of Formula I, or a pharmaceutically acceptable salt thereof, one or more $R^a$ is —P(O)(OH)$_2$. In some embodiments of the compound of Formula I, or a pharmaceutically acceptable salt thereof, one or more $R^a$ is —OP(O)(OH)$_2$.

In some embodiments of the compound of Formula I, or a pharmaceutically acceptable salt thereof, each $R^b$ independently is —C(O)R$^7$, —C(O)OR$^7$, —C(O)NR$^8$R$^8$, —C(O)C(O)OR$^7$, —C(=NR$^{8a}$)(NR$^8$R$^8$), —S(O)$_2$R$^7$, —S(O)$_2$NR$^8$R$^8$, or —S(O)$_2$OR$^7$. In some embodiments of the compound of Formula I, or a pharmaceutically acceptable salt thereof, one or more $R^b$ is —C(O)R$^7$. In some embodiments of the compound of Formula I, or a pharmaceutically acceptable salt thereof, one or more $R^b$ is —C(O)OR$^7$. In some embodiments of the compound of Formula I, or a pharmaceutically acceptable salt thereof, one or more $R^b$ is —C(O)NR$^8$R$^8$. In some embodiments of the compound of Formula I, or a pharmaceutically acceptable salt thereof, one or more $R^b$ is —C(O)C(O)OR$^7$. In some embodiments of the compound of Formula I, or a pharmaceutically acceptable salt thereof, one or more $R^b$ is —C(=NR$^{8a}$)(NR$^8$R$^8$). In some embodiments of the compound of Formula I, or a pharmaceutically acceptable salt thereof, one or more $R^b$ is —S(O)$_2$R$^7$. In some embodiments of the compound of Formula I, or a pharmaceutically acceptable salt thereof, one or more $R^b$ is —S(O)$_2$NR$^8$R$^8$. In some embodiments of the compound of Formula I, or a pharmaceutically acceptable salt thereof, one or more $R^b$ is —S(O)$_2$OR$^7$.

In some embodiments of the compound of Formula I, or a pharmaceutically acceptable salt thereof, each $R^c$ independently is —OR$^7$, —OC(O)R$^7$, —OC(O)C(O)OR$^7$, —(O(C$_{1-4}$ alkyl))$_n$OR$^{7a}$, —NR$^8$R$^8$, —N$^+$R$^8$R$^8$R$^{5a}$, —NR$^8$C(O)R$^7$, —NR$^8$C(O)NR$^8$R$^8$, —NR$^8$C(O)OR$^7$, —NR$^8$C(O)C(O)OR$^7$, —NR$^8$C(=NR$^{8a}$)NR$^8$R$^8$, or —NR$^8$S(O)$_2$R$^7$. In some embodiments of the compound of Formula I, or a pharmaceutically acceptable salt thereof, one or more $R^c$ is —OR$^7$. In some embodiments of the compound of Formula I, or a pharmaceutically acceptable salt thereof, one or more $R^c$ is —OC(O)R$^7$. In some embodiments of the compound of Formula I, or a pharmaceutically acceptable salt thereof, one or more $R^c$ is —OC(O)C(O)OR$^7$. In some embodiments of the compound of Formula I, or a pharmaceutically acceptable salt thereof, one or more $R^c$ is —(O(C$_{1-4}$ alkyl))$_n$OR$^{7a}$. In some embodiments of the compound of Formula I, or a pharmaceutically acceptable salt thereof, one or more $R^c$ is —NR$^8$R$^8$. In some embodiments of the compound of Formula I, or a pharmaceutically acceptable salt thereof, one or more $R^c$ is —N$^+$R$^8$R$^8$R$^{8a}$. In some embodiments of the compound of Formula I, or a pharmaceutically acceptable salt thereof, one or more $R^c$ is —NR$^8$C(O)R$^7$. In some embodiments of the compound of Formula I, or a pharmaceutically acceptable salt thereof, one or more $R^c$ is —NR$^8$C(O)NR$^8$R$^8$. In some embodiments of the compound of Formula I, or a pharmaceutically acceptable salt thereof, one or more $R^c$ is —NR$^8$C(O)OR$^7$. In some embodiments of the compound of Formula I, or a pharmaceutically acceptable salt thereof, one or more $R^c$ is —NR$^8$C(O)C(O)OR$^7$. In some embodiments of the compound of Formula I, or a pharmaceutically acceptable salt thereof, one or more $R^c$ is —NR$^8$C(=NR$^{8a}$)NR$^8$R$^8$. In some embodiments of the compound of Formula I, or a pharmaceutically acceptable salt thereof, one or more $R^c$ is —NR$^8$S(O)$_2$R$^7$.

In some embodiments of the compound of Formula I, or a pharmaceutically acceptable salt thereof, each $R^7$ independently is H or C$_{1-6}$ alkyl, wherein the C$_{1-6}$ alkyl is optionally substituted with 1-3 groups independently selected from —CN, halogen, R$^a$, R$^d$, and R$^{10}$. In some embodiments of the compound of Formula I, or a pharmaceutically acceptable salt thereof, each $R^7$ independently is H or C$_{1-6}$ alkyl, wherein the C$_{1-6}$ alkyl is optionally substituted with 1-3 groups independently selected from —OH, —CN, halogen, —C(O)OR$^9$, —NR$^{10}$R$^{10}$, and R$^a$. In some embodiments of the compound of Formula I, or a pharmaceutically acceptable salt thereof, each $R^7$ independently is H or C$_{1-6}$ alkyl, wherein the C$_{1-6}$ alkyl is optionally substituted with 1-3 groups independently selected from —OH, —NR$^{10}$R$^{10}$, and R$^a$.

In some embodiments of the compound of Formula I, or a pharmaceutically acceptable salt thereof, one or more $R^7$ is H. In some embodiments of the compound of Formula I, or a pharmaceutically acceptable salt thereof, one or more $R^7$ is C$_{1-6}$ alkyl, wherein the C$_{1-6}$ alkyl is optionally substituted with 1-3 groups independently selected from —CN, halogen, R$^a$, R$^d$, and R$^{10}$. In some embodiments of the compound of Formula I, or a pharmaceutically acceptable salt thereof, one or more $R^7$ is C$_{1-6}$ alkyl, wherein the C$_{1-6}$ alkyl is optionally substituted with 1-3 groups independently selected from —OH, —CN, halogen, —C(O)OR$^9$, —NR$^{10}$R$^{10}$, and R$^a$. In some embodiments of the compound of Formula I, or a pharmaceutically acceptable salt thereof, one or more $R^7$ is C$_{1-6}$ alkyl, wherein the C$_{1-6}$ alkyl is optionally substituted with 1-3 groups independently selected from —OH, —NR$^{10}$R$^{10}$, and R$^a$. In some embodiments of the compound of Formula I, or a pharmaceutically acceptable salt thereof, one or more $R^7$ is C$_{1-6}$ alkyl, wherein the C$_{1-6}$ alkyl is substituted with 1-3 groups independently selected from —CN, halogen, R$^a$, R$^d$, and R$^{10}$. In some embodiments of the compound of Formula I, or a pharmaceutically acceptable salt thereof, one or more $R^7$ is C$_{1-6}$ alkyl, wherein the C$_{1-6}$ alkyl is substituted with 1-3 groups independently selected from —OH, —CN, halogen, —C(O)OR$^9$, —NR$^{10}$R$^{10}$, and R$^a$. In some embodiments of the compound of Formula I, or a pharmaceutically acceptable salt thereof, one or more $R^7$ is C$_{1-6}$ alkyl, wherein the C$_{1-6}$ alkyl is substituted with 1-3 groups independently selected from —OH, —NR$^{10}$R$^{10}$, and R$^a$. In some embodiments of the compound of Formula I, or a pharmaceutically acceptable salt thereof, one or more $R^7$ is C$_{1-6}$ alkyl.

In some embodiments of the compound of Formula I, or a pharmaceutically acceptable salt thereof, each $R^{7a}$ independently is H, —P(O)(OH)$_2$, or C$_{1-6}$ alkyl, wherein the C$_{1-6}$ alkyl is optionally substituted with 1-3 groups independently selected from —CN, halogen, R$^a$, R$^d$, and R$^{10}$. In some embodiments of the compound of Formula I, or a pharmaceutically acceptable salt thereof, each $R^{7a}$ independently is H or —P(O)(OH)$_2$.

In some embodiments of the compound of Formula I, or a pharmaceutically acceptable salt thereof, one or more $R^{7a}$ is H. In some embodiments of the compound of Formula I, or a pharmaceutically acceptable salt thereof, one or more $R^{7a}$ is —P(O)(OH)$_2$. In some embodiments of the compound of Formula I, or a pharmaceutically acceptable salt thereof, one or more $R^{7a}$ is $C_{1-6}$ alkyl, wherein the $C_{1-6}$ alkyl is optionally substituted with 1-3 groups independently selected from —CN, halogen, $R^a$, $R^d$, and $R^{10}$. In some embodiments of the compound of Formula I, or a pharmaceutically acceptable salt thereof, one or more $R^{7a}$ is $C_{1-6}$ alkyl, wherein the $C_{1-6}$ alkyl is substituted with 1-3 groups independently selected from —CN, halogen, $R^a$, $R^d$, and $R^{10}$. In some embodiments of the compound of Formula I, or a pharmaceutically acceptable salt thereof, one or more $R^{7a}$ is $C_{1-6}$ alkyl.

In some embodiments of the compound of Formula I, or a pharmaceutically acceptable salt thereof, each $R^8$ independently is H, $R^d$, or $C_{1-6}$ alkyl, wherein the $C_{1-6}$ alkyl is optionally substituted with 1-3 groups independently selected from —CN, halogen, $R^a$, $R^d$, and $R^{10}$. In some embodiments of the compound of Formula I, or a pharmaceutically acceptable salt thereof, each $R^8$ independently is H or $C_{1-6}$ alkyl, wherein the $C_{1-6}$ alkyl is optionally substituted with 1-3 groups independently selected from —CN, halogen, $R^a$, $R^d$, and $R^{10}$. In some embodiments of the compound of Formula I, or a pharmaceutically acceptable salt thereof, each $R^8$ independently is H, —C(O)OR$^9$, —C(O)C(O)OR$^9$, —C(=NR$^{10a}$)(NR$^{10}$R$^{10}$), or $C_{1-6}$ alkyl, wherein the $C_{1-6}$ alkyl is optionally substituted with 1-3 groups independently selected from —OH, —CN, halogen, —C(O)OR$^9$, and $R^a$. In some embodiments of the compound of Formula I, or a pharmaceutically acceptable salt thereof, each $R^8$ independently is H, —C(O)OR$^9$, —C(O)C(O)OH, —C(=NH)NH$_2$, or $C_{1-6}$ alkyl, wherein the $C_{1-6}$ alkyl is optionally substituted with 1-3 groups independently selected from —OH, C(O)OH, and $R^a$.

In some embodiments of the compound of Formula I, or a pharmaceutically acceptable salt thereof, one or more $R^8$ is H. In some embodiments of the compound of Formula I, or a pharmaceutically acceptable salt thereof, one or more $R^8$ is $R^d$. In some embodiments of the compound of Formula I, or a pharmaceutically acceptable salt thereof, one or more $R^8$ is —C(O)OR$^9$. In some embodiments of the compound of Formula I, or a pharmaceutically acceptable salt thereof, one or more $R^8$ is —C(O)C(O)OR$^9$. In some embodiments of the compound of Formula I, or a pharmaceutically acceptable salt thereof, one or more $R^8$ is —C(O)C(O)OH. In some embodiments of the compound of Formula I, or a pharmaceutically acceptable salt thereof, one or more $R^8$ is —C(=NR$^{10a}$)(NR$^{10}$R$^{10}$). In some embodiments of the compound of Formula I, or a pharmaceutically acceptable salt thereof, one or more $R^8$ is —C(=NH)NH$_2$.

In some embodiments of the compound of Formula I, or a pharmaceutically acceptable salt thereof, one or more $R^8$ is $C_{1-6}$ alkyl, wherein the $C_{1-6}$ alkyl is optionally substituted with 1-3 groups independently selected from —CN, halogen, $R^a$, $R^d$, and $R^{10}$. In some embodiments of the compound of Formula I, or a pharmaceutically acceptable salt thereof, one or more $R^8$ is $C_{1-6}$ alkyl, wherein the $C_{1-6}$ alkyl is optionally substituted with 1-3 groups independently selected from —CN, halogen, $R^a$, $R^d$, and $R^{10}$. In some embodiments of the compound of Formula I, or a pharmaceutically acceptable salt thereof, one or more $R^8$ is $C_{1-6}$ alkyl, wherein the $C_{1-6}$ alkyl is optionally substituted with 1-3 groups independently selected from —OH, —CN, halogen, —C(O)OR$^9$, and $R^a$. In some embodiments of the compound of Formula I, or a pharmaceutically acceptable salt thereof, one or more $R^8$ is $C_{1-6}$ alkyl, wherein the $C_{1-6}$ alkyl is optionally substituted with 1-3 groups independently selected from —OH, C(O)OH, and $R^a$. In some embodiments of the compound of Formula I, or a pharmaceutically acceptable salt thereof, one or more $R^8$ is $C_{1-6}$ alkyl, wherein the $C_{1-6}$ alkyl is substituted with 1-3 groups independently selected from —CN, halogen, $R^a$, $R^d$, and $R^{10}$. In some embodiments of the compound of Formula I, or a pharmaceutically acceptable salt thereof, one or more $R^8$ is $C_{1-6}$ alkyl, wherein the $C_{1-6}$ alkyl is substituted with 1-3 groups independently selected from —CN, halogen, $R^a$, $R^d$, and $R^{10}$. In some embodiments of the compound of Formula I, or a pharmaceutically acceptable salt thereof, one or more $R^8$ is $C_{1-6}$ alkyl, wherein the $C_{1-6}$ alkyl is substituted with 1-3 groups independently selected from —OH, —CN, halogen, —C(O)OR$^9$, and $R^a$. In some embodiments of the compound of Formula I, or a pharmaceutically acceptable salt thereof, one or more $R^8$ is $C_{1-6}$ alkyl, wherein the $C_{1-6}$ alkyl is substituted with 1-3 groups independently selected from —OH, C(O)OH, and $R^a$. In some embodiments of the compound of Formula I, or a pharmaceutically acceptable salt thereof, one or more $R^8$ is $C_{1-6}$ alkyl.

In some embodiments of the compound of Formula I, or a pharmaceutically acceptable salt thereof, In some embodiments of the compound of Formula I, or a pharmaceutically acceptable salt thereof, one $R^8$ is H or In some embodiments of the compound of Formula I, or a pharmaceutically acceptable salt thereof, one $R^8$ is In some embodiments of the compound of Formula I, or a pharmaceutically acceptable salt thereof, each $R^{8a}$ independently is H or $C_{1-3}$ alkyl. In some embodiments of the compound of Formula I, or a pharmaceutically acceptable salt thereof, each $R^{8a}$ independently is H or methyl. In some embodiments of the compound of Formula I, or a pharmaceutically acceptable salt thereof, one or more $R^{8a}$ is H. In some embodiments of the compound of Formula I, or a pharmaceutically acceptable salt thereof, one or more $R^{8a}$ is $C_{1-3}$ alkyl. In some embodiments of the compound of Formula I, or a pharmaceutically acceptable salt thereof, one or more $R^{8a}$ is methyl.

In some embodiments of the compound of Formula I, or a pharmaceutically acceptable salt thereof, each $R^d$ independently is —C(O)R$^9$, —C(O)OR$^9$, —C(O)NR$^{10}$R$^{10}$, —C(O)C(O)OR$^9$, —C(=NR$^{10a}$)(NR$^{10}$R$^{10}$), —S(O)$_2$R$^9$, —S(O)$_2$NR$^{10}$R$^{10}$, or —S(O)$_2$OR$^9$. In some embodiments of the compound of Formula I, or a pharmaceutically acceptable salt thereof, one or more $R^d$ is —C(O)$R^9$. In some embodiments of the compound of Formula I, or a pharmaceutically acceptable salt thereof, one or more $R^d$ is —C(O)O$R^9$. In some embodiments of the compound of Formula I, or a pharmaceutically acceptable salt thereof, one or more $R^d$ is —C(O)N$R^{10}R^{10}$. In some embodiments of the compound of Formula I, or a pharmaceutically acceptable salt thereof, one or more $R^d$ is —C(O)C(O)O$R^9$. In some embodiments of the compound of Formula I, or a pharmaceutically acceptable salt thereof, one or more $R^d$ is —C(=N$R^{10a}$)(N$R^{10}R^{10}$). In some embodiments of the compound of Formula I, or a pharmaceutically acceptable salt thereof, one or more $R^d$ is —S(O)$_2R^9$. In some embodiments of the compound of Formula I, or a pharmaceutically acceptable salt thereof, one or more $R^d$ is —S(O)$_2$N$R^{10}R^{10}$. In some embodiments of the compound of Formula I, or a pharmaceutically acceptable salt thereof, one or more $R^d$ is —S(O)$_2$O$R^9$.

In some embodiments of the compound of Formula I, or a pharmaceutically acceptable salt thereof, each $R^e$ independently is —O$R^9$, —OC(O)$R^9$, —OC(O)C(O)O$R^9$, —N$R^{10}R^{10}$, —N$^+R^{10}R^{10}R^{10a}$, —N$R^{10}$C(O)$R^9$, —N$R^{10}$C(O)N$R^{10}R^{10}$, —N$R^{10}$C(O)O$R^9$, —N$R^{10}$C(O)C(O)O$R^9$, —N$R^{10}$C(=N$R^{10a}$)N$R^{10}R^{10}$, or —N$R^{10}$S(O)$_2R^9$. In some embodiments of the compound of Formula I, or a pharmaceutically acceptable salt thereof, one or more $R^e$ is —O$R^9$. In some embodiments of the compound of Formula I, or a pharmaceutically acceptable salt thereof, one or more $R^e$ is —OC(O)$R^9$. In some embodiments of the compound of Formula I, or a pharmaceutically acceptable salt thereof, one or more $R^e$ is —OC(O)C(O)O$R^9$. In some embodiments of the compound of Formula I, or a pharmaceutically acceptable salt thereof, one or more $R^e$ is —N$R^{10}R^{10}$. In some embodiments of the compound of Formula I, or a pharmaceutically acceptable salt thereof, one or more $R^e$ is —N$^+R^{10}R^{10}R^{10a}$. In some embodiments of the compound of Formula I, or a pharmaceutically acceptable salt thereof, one or more $R^e$ is —N$R^{10}$C(O)$R^9$. In some embodiments of the compound of Formula I, or a pharmaceutically acceptable salt thereof, one or more $R^e$ is —N$R^{10}$C(O)N$R^{10}R^{10}$. In some embodiments of the compound of Formula I, or a pharmaceutically acceptable salt thereof, one or more $R^e$ is —N$R^{10}$C(O)O$R^9$. In some embodiments of the compound of Formula I, or a pharmaceutically acceptable salt thereof, one or more $R^e$ is —N$R^{10}$C(O)C(O)O$R^9$. In some embodiments of the compound of Formula I, or a pharmaceutically acceptable salt thereof, one or more $R^e$ is —N$R^{10}$C(=N$R^{10a}$)N$R^{10}R^{10}$. In some embodiments of the compound of Formula I, or a pharmaceutically acceptable salt thereof, one or more $R^e$ is —N$R^{10}$S(O)$_2R^9$.

In some embodiments of the compound of Formula I, or a pharmaceutically acceptable salt thereof, each $R^9$ independently is H or $C_{1-6}$ alkyl, wherein the $C_{1-6}$ alkyl is optionally substituted with 1-3 groups independently selected from CN, halogen, $R^a$, $R^f$, and $R^g$. In some embodiments of the compound of Formula I, or a pharmaceutically acceptable salt thereof, each $R^9$ independently is H or $C_{1-6}$ alkyl, wherein the $C_{1-6}$ alkyl is optionally substituted with 1-3 groups independently selected from —OH, CN, halogen, —C(O)OH, and $R^a$. In some embodiments of the compound of Formula I, or a pharmaceutically acceptable salt thereof, each $R^9$ independently is H or $C_{1-3}$ alkyl, wherein the $C_{1-3}$ alkyl is optionally substituted with 1-3 groups independently selected from —OH, CN, halogen, —C(O)OH, and $R^a$. In some embodiments of the compound of Formula I, or a pharmaceutically acceptable salt thereof, each $R^9$ independently is H or $C_{1-3}$ alkyl.

In some embodiments of the compound of Formula I, or a pharmaceutically acceptable salt thereof, one or more $R^9$ is H. In some embodiments of the compound of Formula I, or a pharmaceutically acceptable salt thereof, one or more $R^9$ is $C_{1-6}$ alkyl, wherein the $C_{1-6}$ alkyl is optionally substituted with 1-3 groups independently selected from CN, halogen, $R^a$, $R^f$, and $R^g$. In some embodiments of the compound of Formula I, or a pharmaceutically acceptable salt thereof, one or more $R^9$ is $C_{1-6}$ alkyl, wherein the $C_{1-6}$ alkyl is optionally substituted with 1-3 groups independently selected from —OH, CN, halogen, —C(O)OH, and $R^a$. In some embodiments of the compound of Formula I, or a pharmaceutically acceptable salt thereof, one or more $R^9$ is $C_{1-3}$ alkyl, wherein the $C_{1-3}$ alkyl is optionally substituted with 1-3 groups independently selected from —OH, CN, halogen, —C(O)OH, and $R^a$. In some embodiments of the compound of Formula I, or a pharmaceutically acceptable salt thereof, one or more $R^9$ is $C_{1-6}$ alkyl, wherein the $C_{1-6}$ alkyl is substituted with 1-3 groups independently selected from CN, halogen, $R^a$, $R^f$, and $R^g$. In some embodiments of the compound of Formula I, or a pharmaceutically acceptable salt thereof, one or more $R^9$ is $C_{1-6}$ alkyl, wherein the $C_{1-6}$ alkyl is substituted with 1-3 groups independently selected from —OH, CN, halogen, —C(O)OH, and $R^a$. In some embodiments of the compound of Formula I, or a pharmaceutically acceptable salt thereof, one or more $R^9$ is $C_{1-3}$ alkyl, wherein the $C_{1-3}$ alkyl is substituted with 1-3 groups independently selected from —OH, CN, halogen, —C(O)OH, and $R^a$. In some embodiments of the compound of Formula I, or a pharmaceutically acceptable salt thereof, one or more $R^9$ is $C_{1-6}$ alkyl. In some embodiments of the compound of Formula I, or a pharmaceutically acceptable salt thereof, one or more $R^9$ is $C_{1-3}$ alkyl.

In some embodiments of the compound of Formula I, or a pharmaceutically acceptable salt thereof, each $R^{10}$ independently is H, $R^f$, or $C_{1-6}$ alkyl, wherein the $C_{1-6}$ alkyl is optionally substituted with 1-3 groups independently selected from —CN, halogen, $R^a$, $R^f$, and $R^g$. In some embodiments of the compound of Formula I, or a pharmaceutically acceptable salt thereof, each $R^{10}$ independently is H or $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, each $R^{10}$ independently is H or $C_{1-4}$ alkyl, wherein the $C_{1-4}$ alkyl is optionally substituted with 1-3 groups independently selected from —OH, —CN, halogen, —C(O)OH, and $R^a$. In some embodiments of the compound of Formula I, or a pharmaceutically acceptable salt thereof, each $R^{10}$ independently is H or $C_{1-3}$ alkyl.

In some embodiments of the compound of Formula I, or a pharmaceutically acceptable salt thereof, one or more $R^{10}$ is H. In some embodiments of the compound of Formula I, or a pharmaceutically acceptable salt thereof, one or more $R^{10}$ is $R^f$. In some embodiments of the compound of Formula I, or a pharmaceutically acceptable salt thereof, one or more $R^{10}$ is $C_{1-6}$ alkyl, wherein the $C_{1-6}$ alkyl is optionally substituted with 1-3 groups independently selected from —CN, halogen, $R^a$, $R^f$, and $R^g$. In some embodiments of the compound of Formula I, or a pharmaceutically acceptable salt thereof, one or more $R^{10}$ is $C_{1-6}$ alkyl, wherein the $C_{1-6}$ alkyl is optionally substituted with 1-3 groups independently selected from —OH, —CN, halogen, —C(O)OH, and $R^a$. In some embodiments of the compound of Formula I, or a pharmaceutically acceptable salt thereof, one or more $R^{10}$ is $C_{1-4}$ alkyl, wherein the $C_{1-4}$ alkyl is optionally substituted with 1-3 groups independently selected from —OH, —CN, halogen, —C(O)OH, and $R^a$. In some embodiments of the compound of Formula I, or a pharmaceutically acceptable salt thereof, one or more $R^{10}$ is $C_{1-6}$ alkyl, wherein the $C_{1-6}$ alkyl is substituted with 1-3 groups independently selected from —CN, halogen, $R^a$, $R^f$, and $R^g$. In some embodiments of the compound of Formula I, or a pharmaceutically acceptable salt thereof, one or more $R^{10}$ is $C_{1-6}$ alkyl, wherein the $C_{1-6}$ alkyl is substituted with 1-3 groups independently selected from —OH, —CN, halogen, —C(O)OH, and $R^a$. In some embodiments of the compound of Formula I, or a pharmaceutically acceptable salt thereof, one or more $R^{10}$ is $C_{1-4}$ alkyl, wherein the $C_{1-4}$ alkyl is substituted with 1-3 groups independently selected from —OH, —CN, halogen, —C(O)OH, and $R^a$. In some embodiments of the compound of Formula I, or a pharmaceutically acceptable salt thereof, one or more $R^{10}$ is $C_{1-6}$ alkyl. In some embodiments of the compound of Formula I, or a pharmaceutically acceptable salt thereof, one or more $R^{10}$ is $C_{1-4}$ alkyl. In some embodiments of the compound of Formula I, or a pharmaceutically acceptable salt thereof, one or more $R^{10}$ is $C_{1-3}$ alkyl.

In some embodiments of the compound of Formula I, or a pharmaceutically acceptable salt thereof, each $R^{10a}$ independently is H or $C_{1-3}$ alkyl. In some embodiments of the compound of Formula I, or a pharmaceutically acceptable salt thereof, each $R^{10a}$ independently is H or methyl. In some embodiments of the compound of Formula I, or a pharmaceutically acceptable salt thereof, one or more $R^{10a}$ is H. In some embodiments of the compound of Formula I, or a pharmaceutically acceptable salt thereof, one or more $R^{10a}$ is $C_{1-3}$ alkyl. In some embodiments of the compound of Formula I, or a pharmaceutically acceptable salt thereof, one or more $R^{10a}$ is methyl.

In some embodiments of the compound of Formula I, or a pharmaceutically acceptable salt thereof, each $R^f$ independently is —C(O)$R^{11}$, —C(O)O$R^{11}$, —C(O)N$R^{11}R^{11}$, —C(O)C(O)O$R^{11}$, —C(=N$R^{11a}$)(N$R^{11}R^{11}$), —S(O)$_2R^{11}$, —S(O)$_2$N$R^{11}R^{11}$, or —S(O)$_2$O$R^{11}$. In some embodiments of the compound of Formula I, or a pharmaceutically acceptable salt thereof, one or more $R^f$ is —C(O)$R^{11}$. In some embodiments of the compound of Formula I, or a pharmaceutically acceptable salt thereof, one or more $R^f$ is —C(O)O$R^{11}$. In some embodiments of the compound of Formula I, or a pharmaceutically acceptable salt thereof, one or more $R^f$ is —C(O)N$R^{11}R^{11}$. In some embodiments of the compound of Formula I, or a pharmaceutically acceptable salt thereof, one or more $R^f$ is —C(O)C(O)O$R^{11}$. In some embodiments of the compound of Formula I, or a pharmaceutically acceptable salt thereof, one or more $R^f$ is —C(=N$R^{11a}$)(N$R^{11}R^{11}$). In some embodiments of the compound of Formula I, or a pharmaceutically acceptable salt thereof, one or more $R^f$ is —S(O)$_2R^{11}$. In some embodiments of the compound of Formula I, or a pharmaceutically acceptable salt thereof, one or more $R^f$ is —S(O)$_2$N$R^{11}R^{11}$. In some embodiments of the compound of Formula I, or a pharmaceutically acceptable salt thereof, one or more $R^f$ is —S(O)$_2$O$R^{11}$.

In some embodiments of the compound of Formula I, or a pharmaceutically acceptable salt thereof, each $R^g$ independently is —O$R^{11}$, —OC(O)$R^{11}$, —OC(O)C(O)O$R^{11}$, —N$R^{11}R^{11}$, —N$^+R^{11}R^{11}R^{11a}$, —N$R^{11}$C(O)$R^{11}$, —N$R^{11}$C(O)N$R^{11}R^{11}$, —N$R^{11}$C(O)O$R^{11}$, —N$R^{11}$C(O)C(O)O$R^{11}$, —N$R^{11}$C(=N$R^{11a}$)N$R^{11}R^{11}$, or —N$R^{11}$S(O)$_2R^{11}$. In some embodiments of the compound of Formula I, or a pharmaceutically acceptable salt thereof, one or more $R^g$ is —O$R^{11}$. In some embodiments of the compound of Formula I, or a pharmaceutically acceptable salt thereof, one or more $R^g$ is —OC(O)$R^{11}$. In some embodiments of the compound of Formula I, or a pharmaceutically acceptable salt thereof, one or more $R^g$ is —OC(O)C(O)O$R^{11}$. In some embodiments of the compound of Formula I, or a pharmaceutically acceptable salt thereof, one or more $R^g$ is —N$R^{11}R^{11}$. In some embodiments of the compound of Formula I, or a pharmaceutically acceptable salt thereof, one or more $R^g$ is —N$^+R^{11}R^{11}R^{11a}$. In some embodiments of the compound of Formula I, or a pharmaceutically acceptable salt thereof, one or more $R^g$ is —N$R^{11}$C(O)$R^{11}$. In some embodiments of the compound of Formula I, or a pharmaceutically acceptable salt thereof, one or more $R^g$ is —N$R^{11}$C(O)N$R^{11}R^{11}$. In some embodiments of the compound of Formula I, or a pharmaceutically acceptable salt thereof, one or more $R^g$ is —N$R^{11}$C(O)O$R^{11}$. In some embodiments of the compound of Formula I, or a pharmaceutically acceptable salt thereof, one or more $R^g$ is —N$R^{11}$C(O)C(O)O$R^{11}$. In some embodiments of the compound of Formula I, or a pharmaceutically acceptable salt thereof, one or more $R^g$ is —N$R^{11}$C(=N$R^{11a}$)N$R^{11}R^{11}$. In some embodiments of the compound of Formula I, or a pharmaceutically acceptable salt thereof, one or more $R^g$ is —N$R^{11}$S(O)$_2R^{11}$.

In some embodiments of the compound of Formula I, or a pharmaceutically acceptable salt thereof, each $R^{11}$ independently is H or $C_{1-6}$ alkyl, wherein the $C_{1-6}$ alkyl is optionally substituted with 1-3 groups independently selected from —OH, CN, halogen, —COOH, and $R^a$. In some embodiments of the compound of Formula I, or a pharmaceutically acceptable salt thereof, one or more $R^{11}$ is H. In some embodiments of the compound of Formula I, or a pharmaceutically acceptable salt thereof, one or more $R^{11}$ is $C_{1-6}$ alkyl, wherein the $C_{1-6}$ alkyl is optionally substituted with 1-3 groups independently selected from —OH, CN, halogen, —COOH, and $R^a$. In some embodiments of the compound of Formula I, or a pharmaceutically acceptable salt thereof, one or more $R^{11}$ is $C_{1-6}$ alkyl, wherein the $C_{1-6}$ alkyl is substituted with 1-3 groups independently selected from —OH, CN, halogen, —COOH, and $R^a$. In some embodiments of the compound of Formula I, or a pharmaceutically acceptable salt thereof, one or more $R^{11}$ is $C_{1-6}$ alkyl.

In some embodiments of the compound of Formula I, or a pharmaceutically acceptable salt thereof, each $R^{11a}$ independently is H or $C_{1-3}$ alkyl. In some embodiments of the compound of Formula I, or a pharmaceutically acceptable salt thereof, each $R^{11a}$ independently is H or methyl. In some embodiments of the compound of Formula I, or a pharmaceutically acceptable salt thereof, one or more $R^{11a}$ is H. In some embodiments of the compound of Formula I, or a pharmaceutically acceptable salt thereof, one or more $R^{11a}$ is $C_{1-3}$ alkyl. In some embodiments of the compound of Formula I, or a pharmaceutically acceptable salt thereof, one or more $R^{11a}$ is methyl.

In some embodiments of the compound of Formula I, provided herein is a compound selected from the group consisting of:
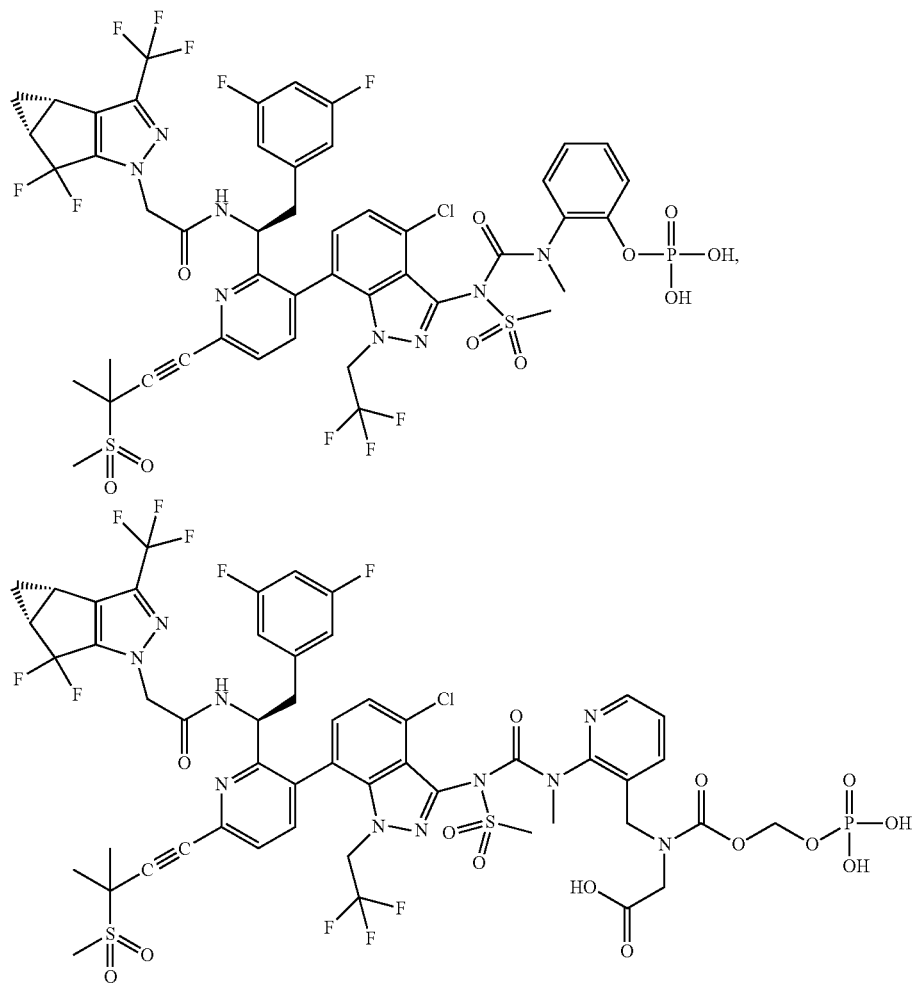
or a pharmaceutically acceptable salt thereof.
In some embodiments of the compound of Formula I, provided herein is a compound selected from the group consisting of:
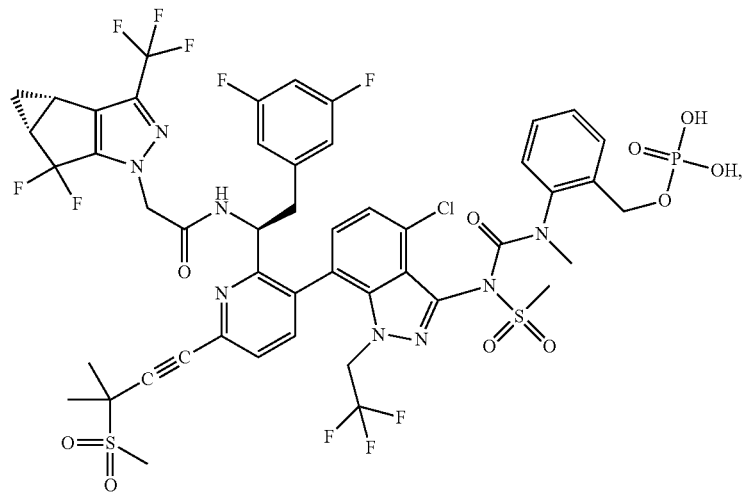

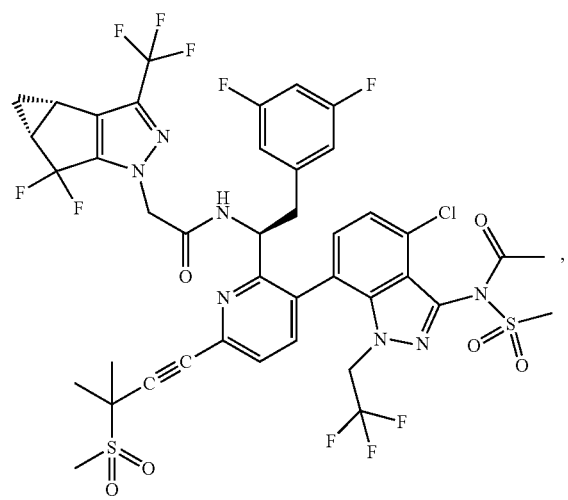
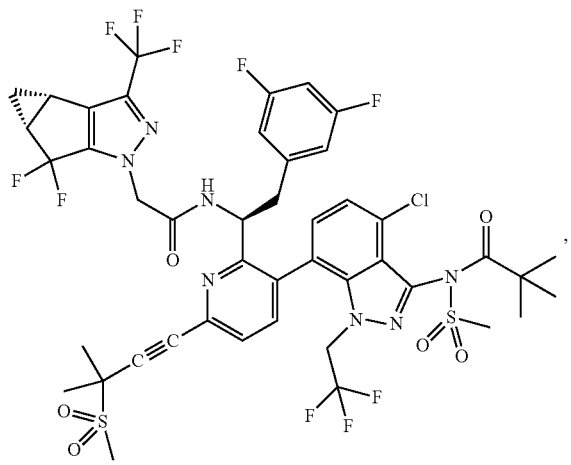
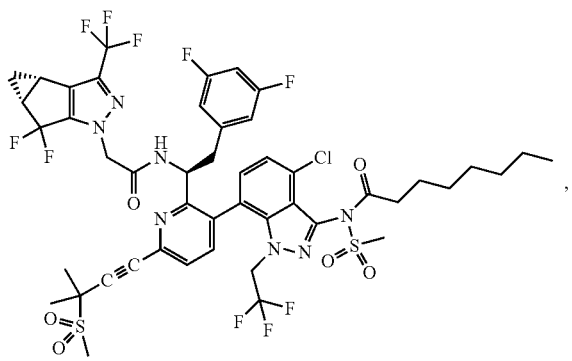
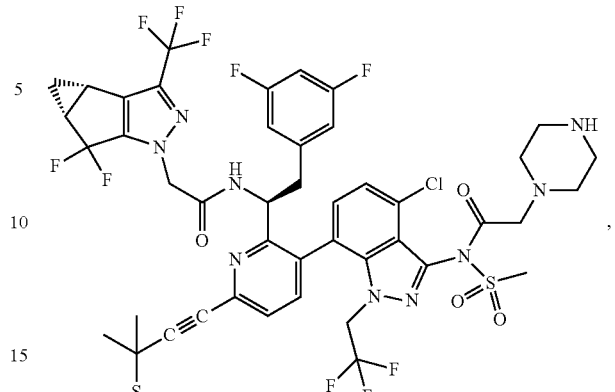
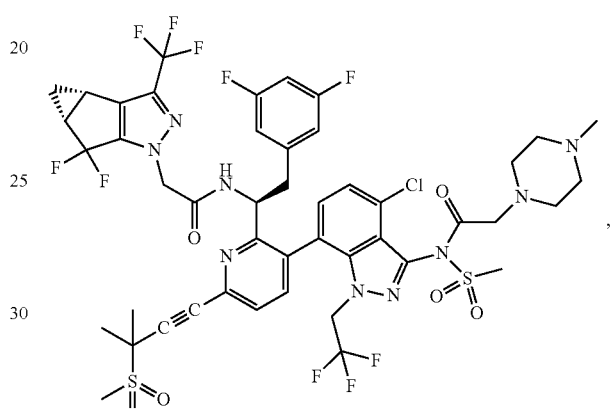
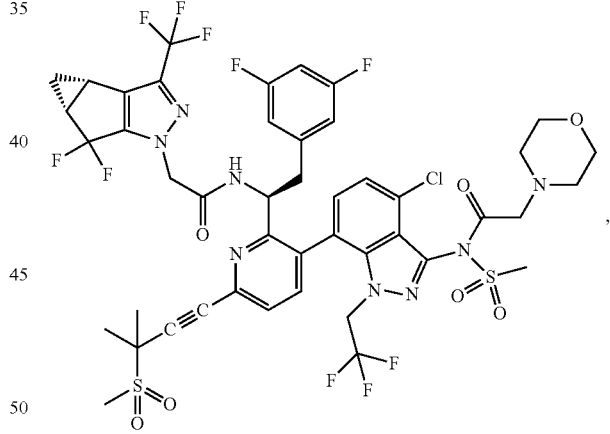
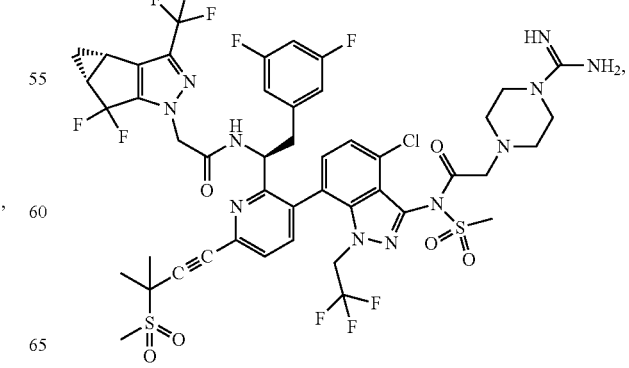

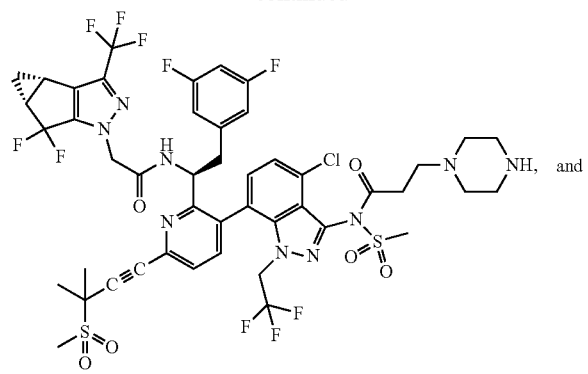
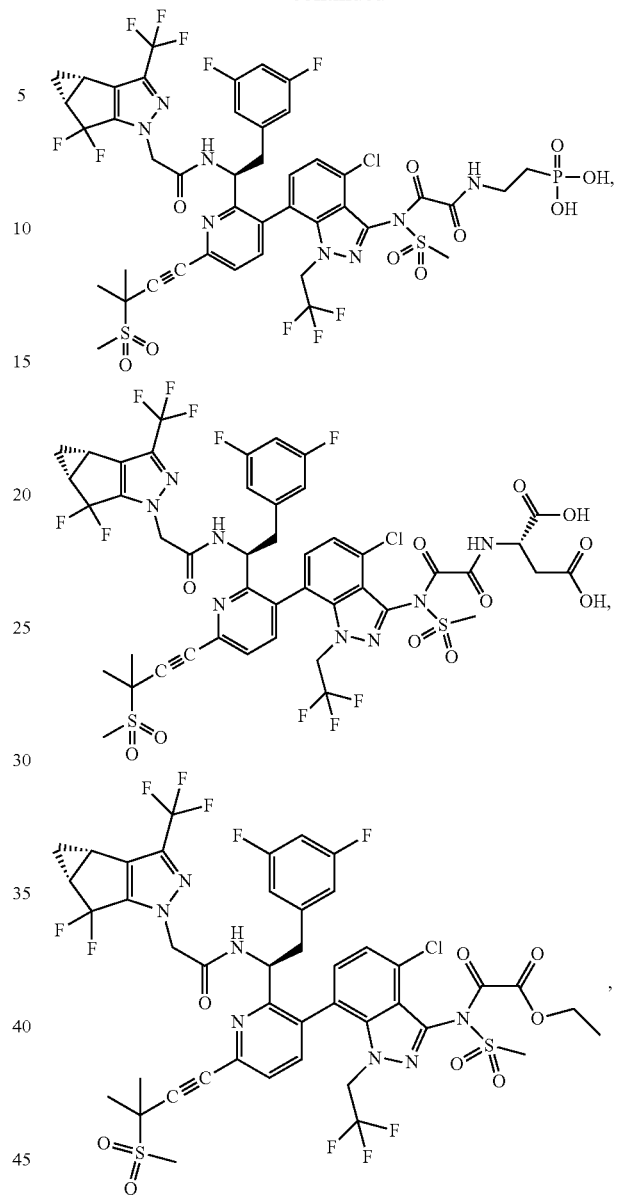
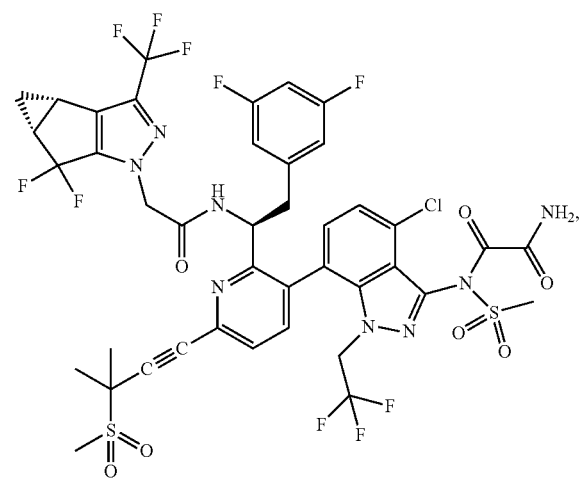
or a pharmaceutically acceptable salt thereof.
In some embodiments of the compound of Formula I, provided herein is a compound selected from the group consisting of:
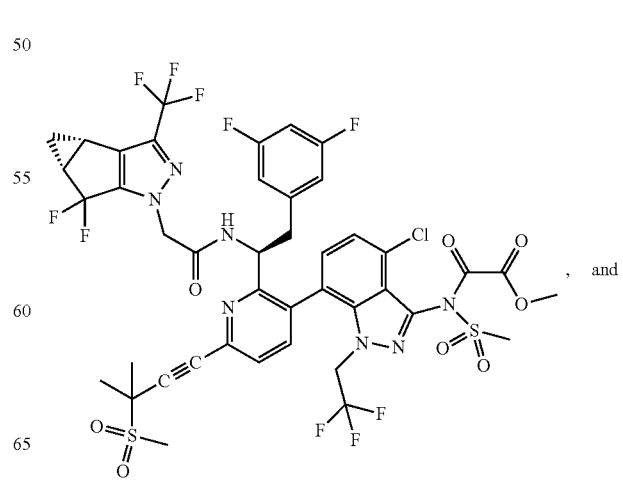

51
-continued
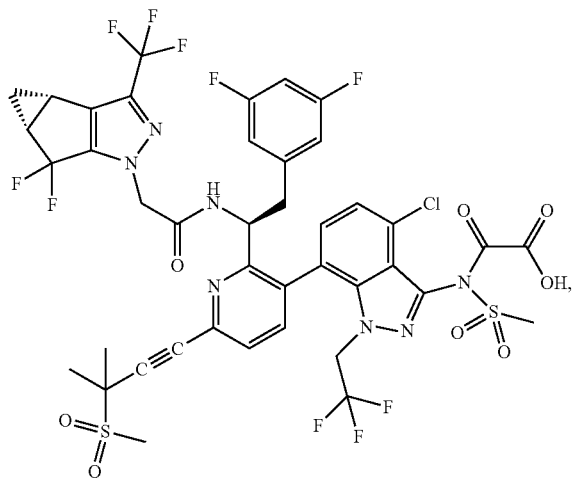
or a pharmaceutically acceptable salt thereof.
In some embodiments of the compound of Formula I, provided herein is a compound selected from the group consisting of:
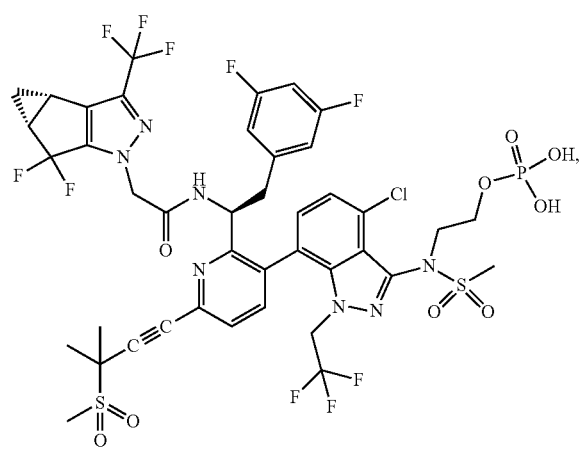
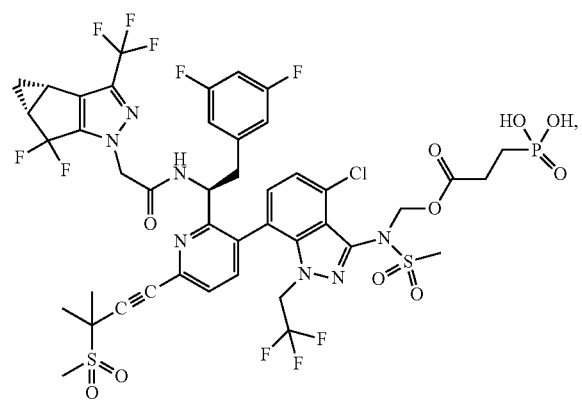
52
-continued
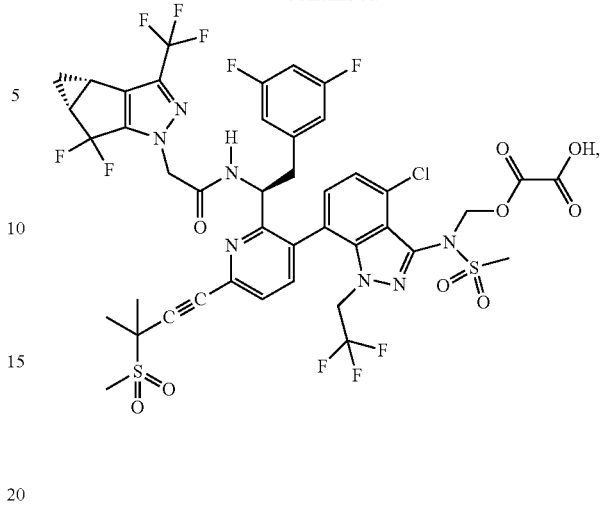
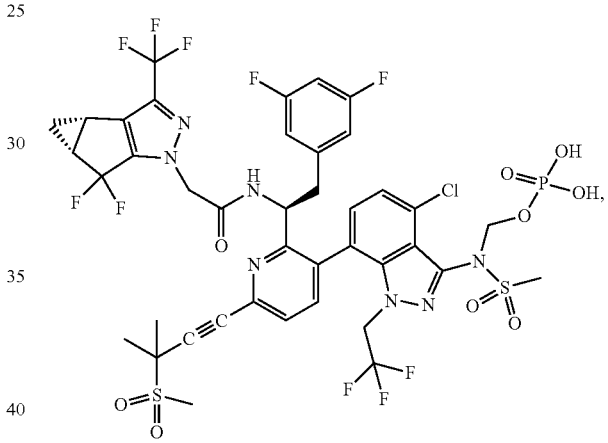
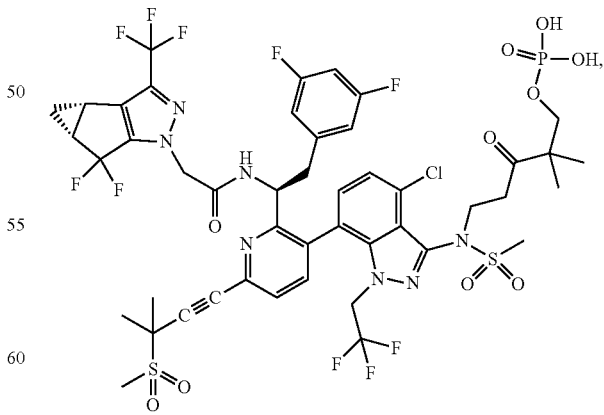
or a pharmaceutically acceptable salt thereof.
In some embodiments of the compound of Formula I, provided herein is a compound selected from the group consisting of:

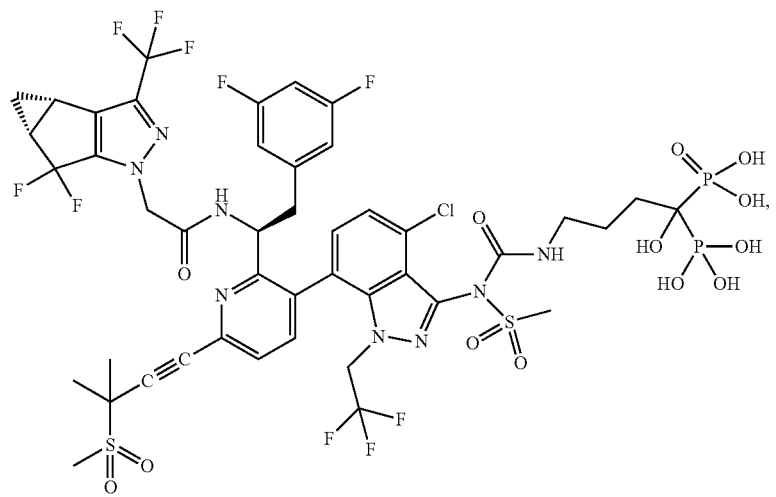
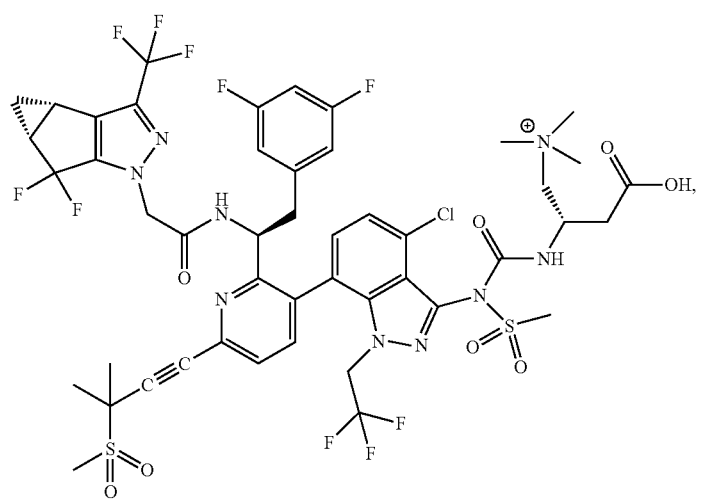
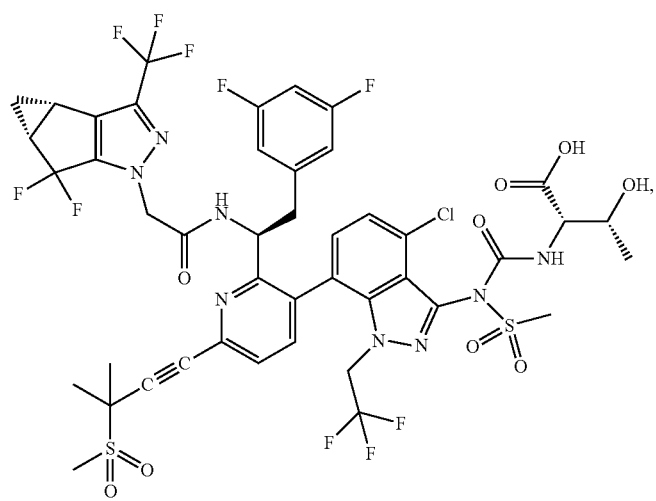

-continued
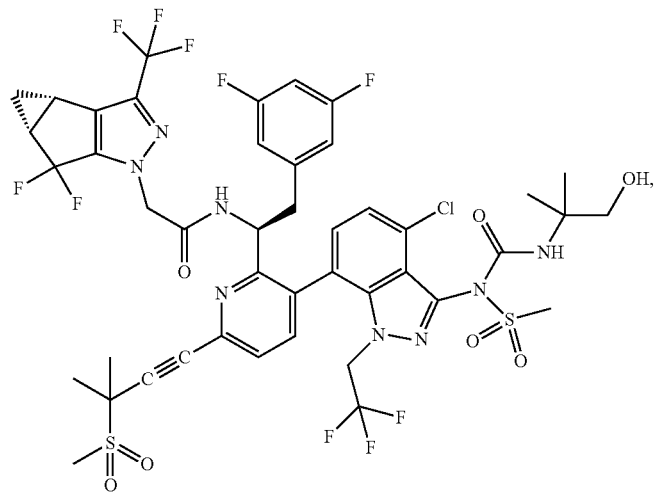
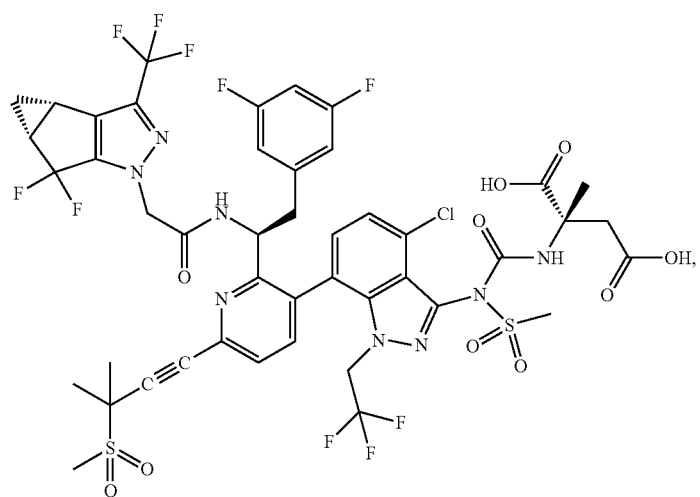
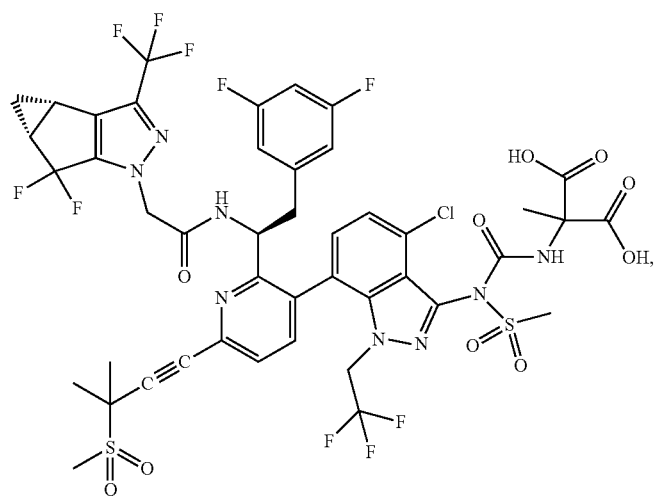

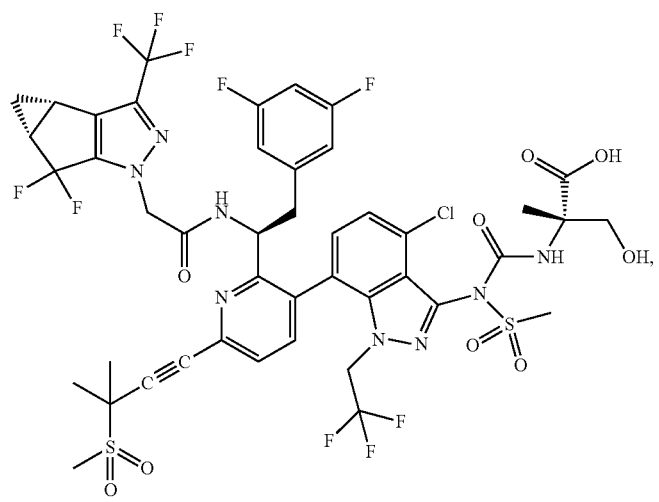
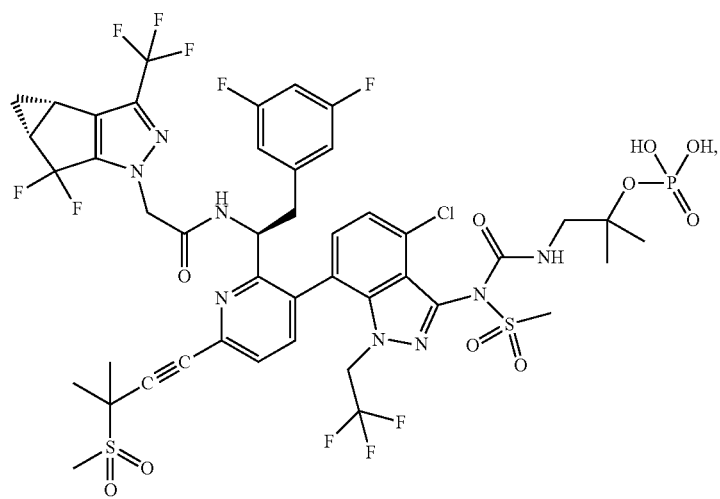

-continued
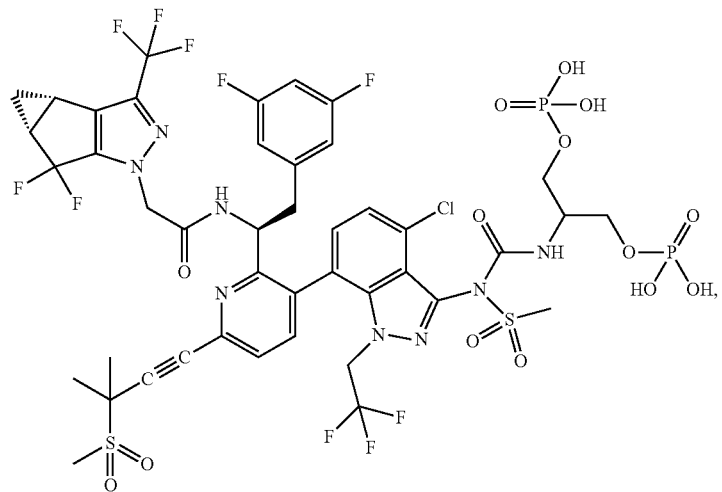
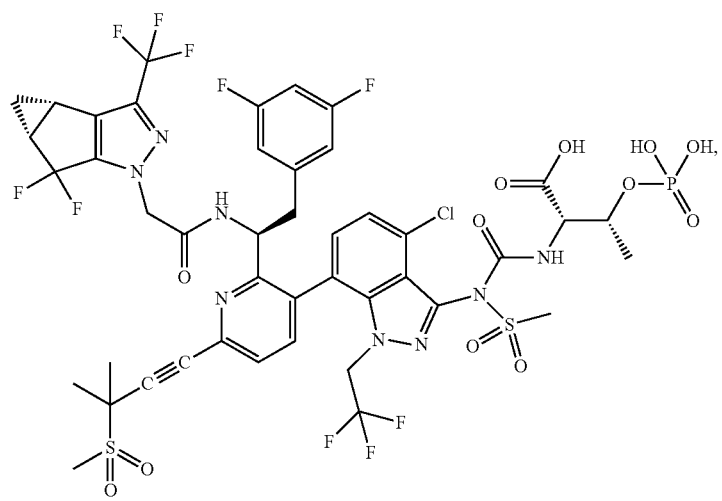
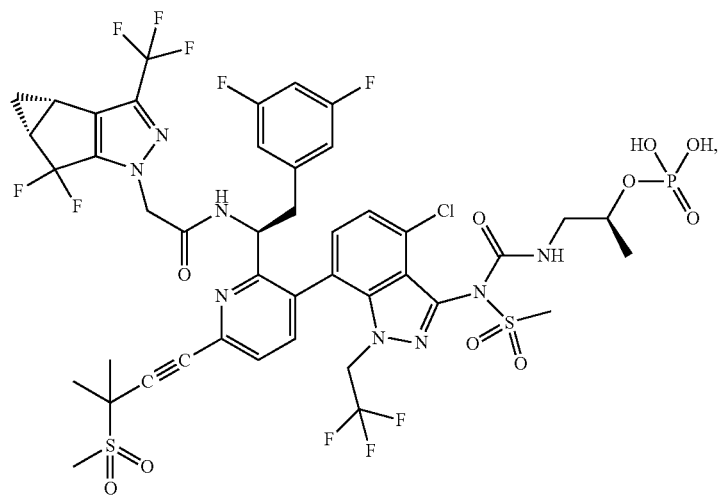

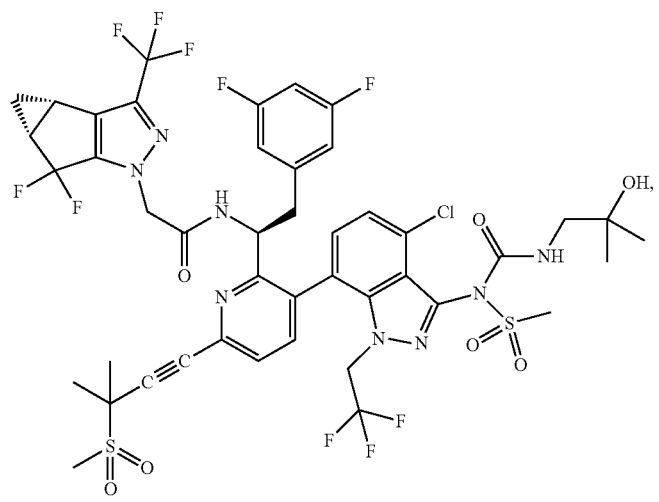
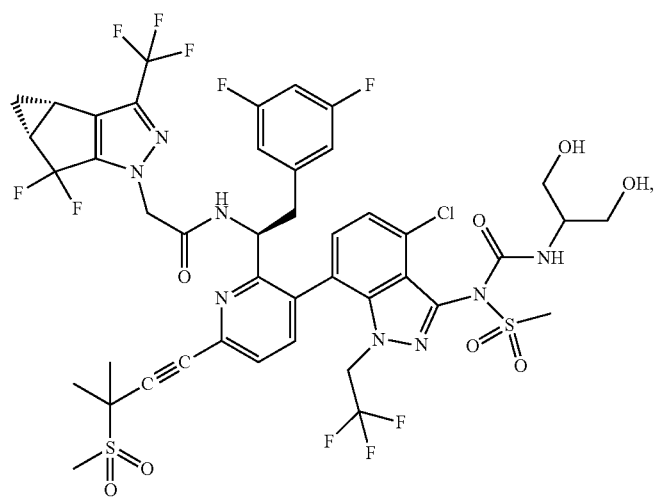
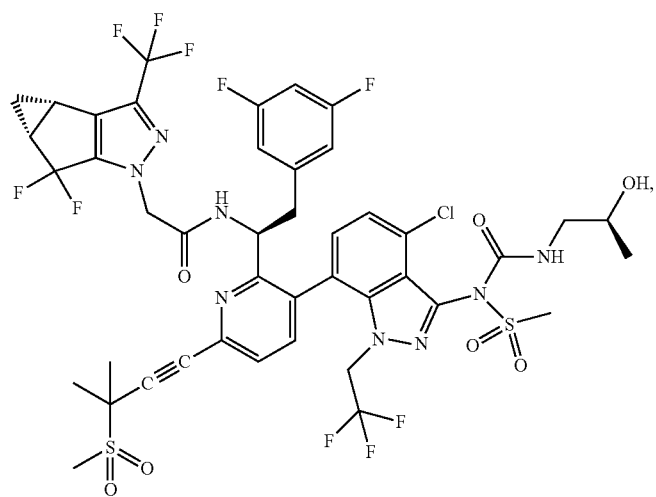

-continued
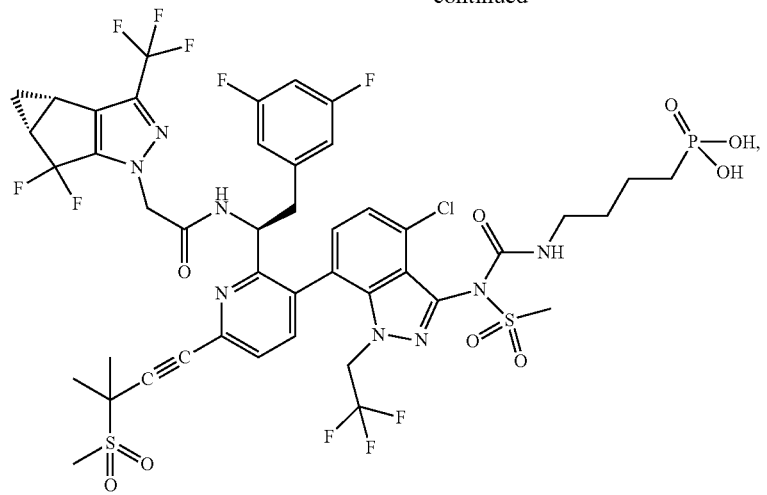
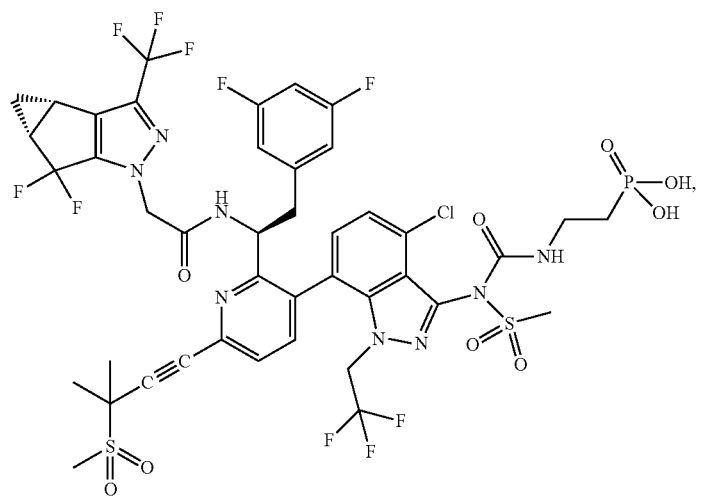
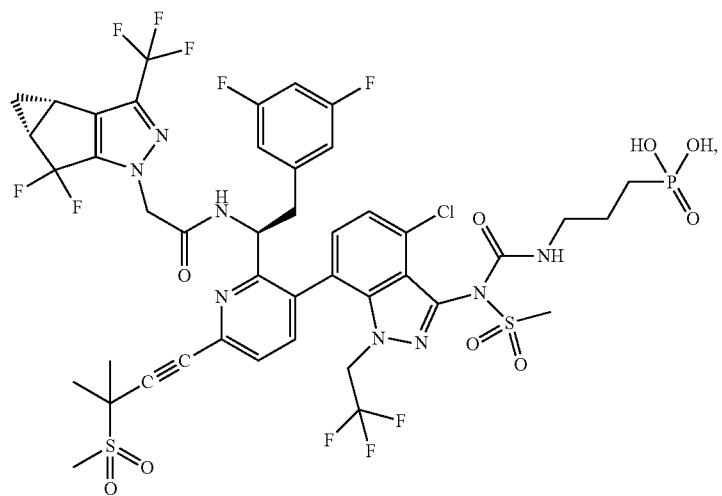

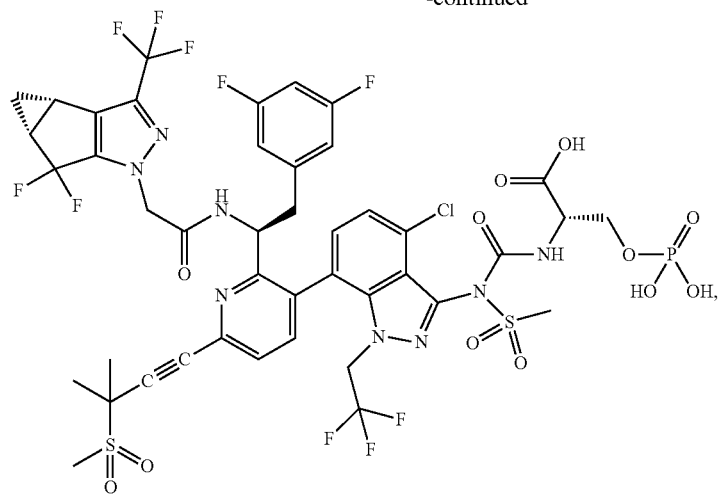
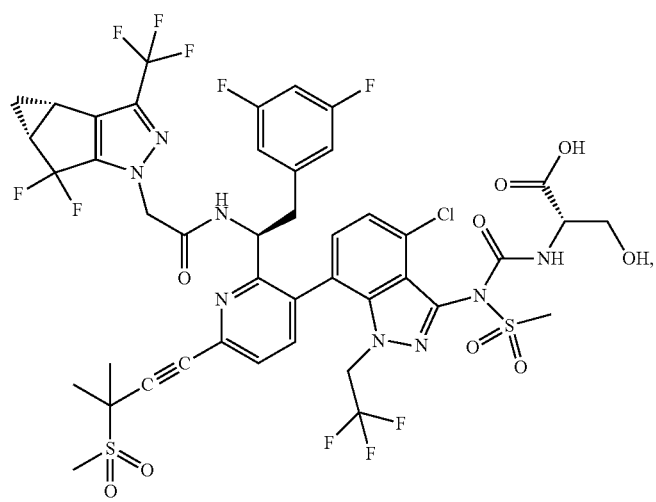
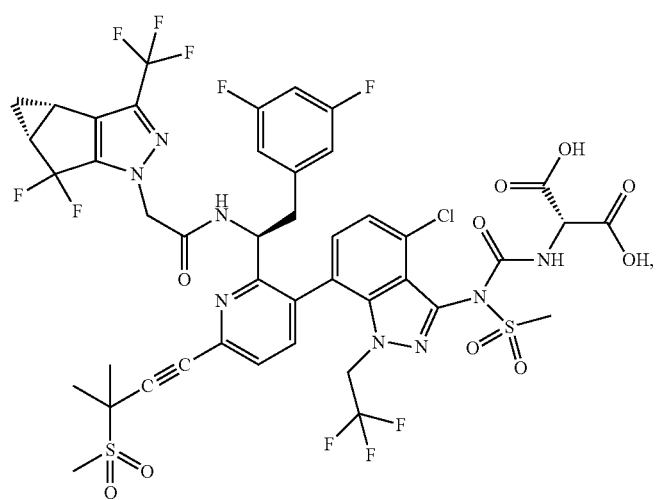

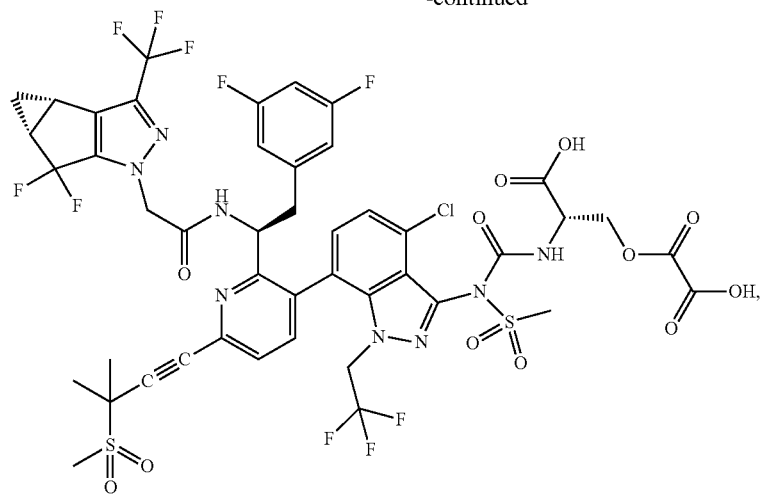
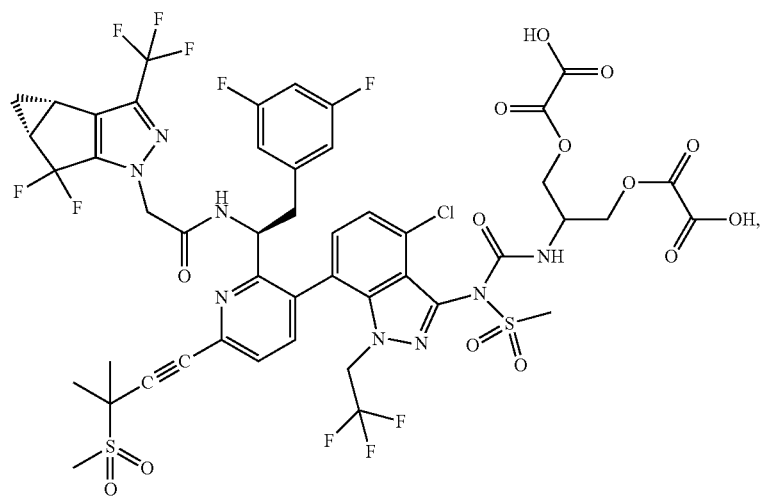
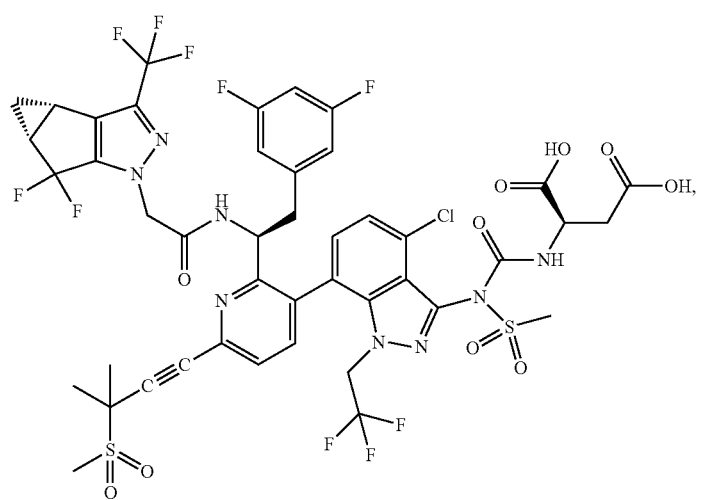

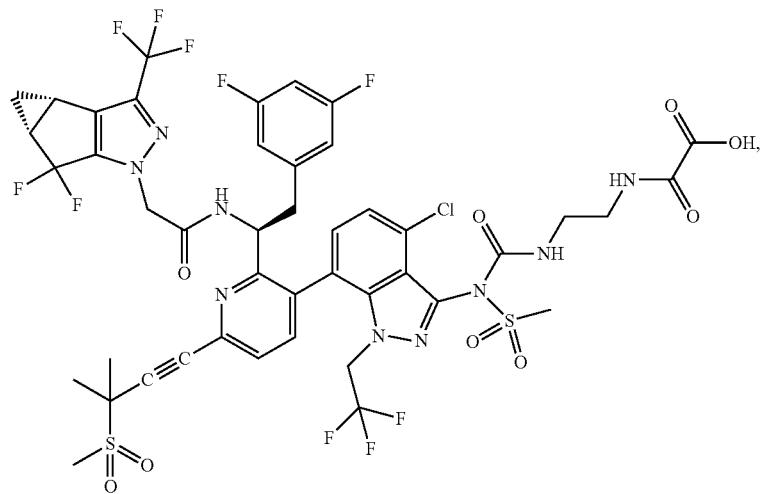
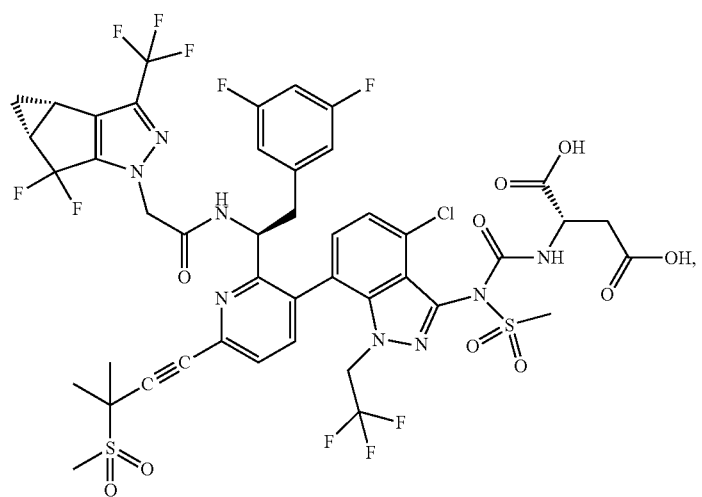
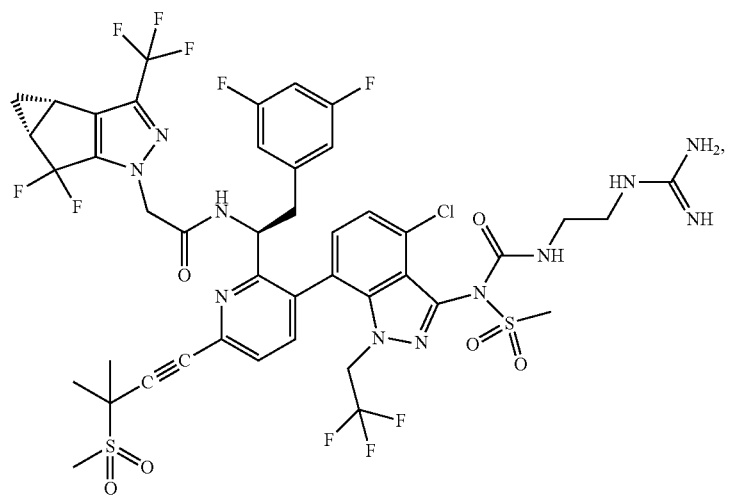

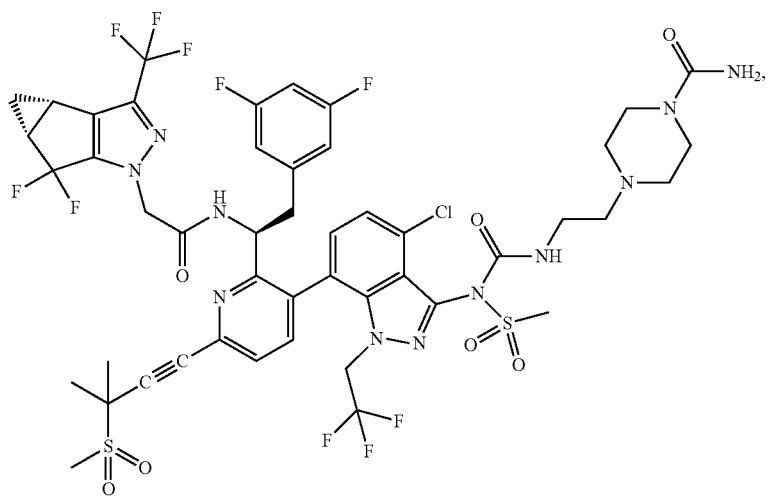
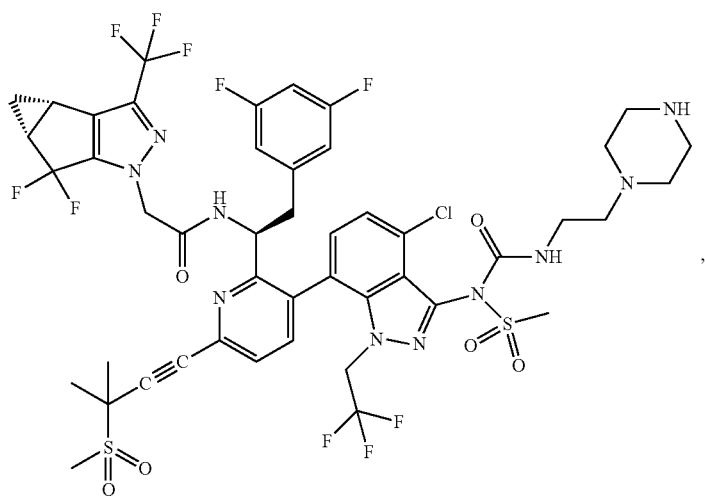
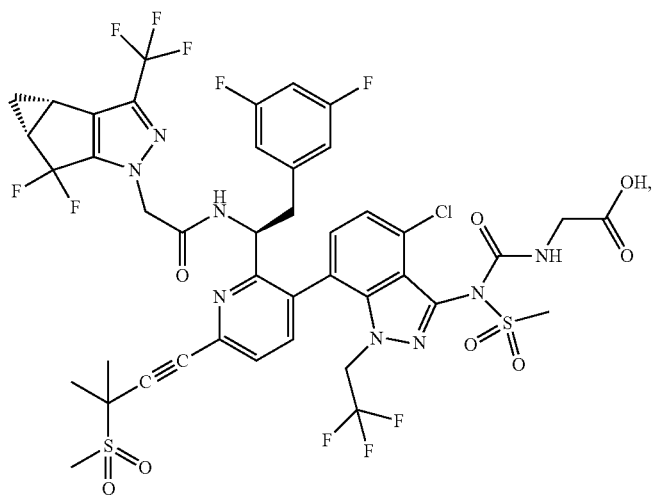

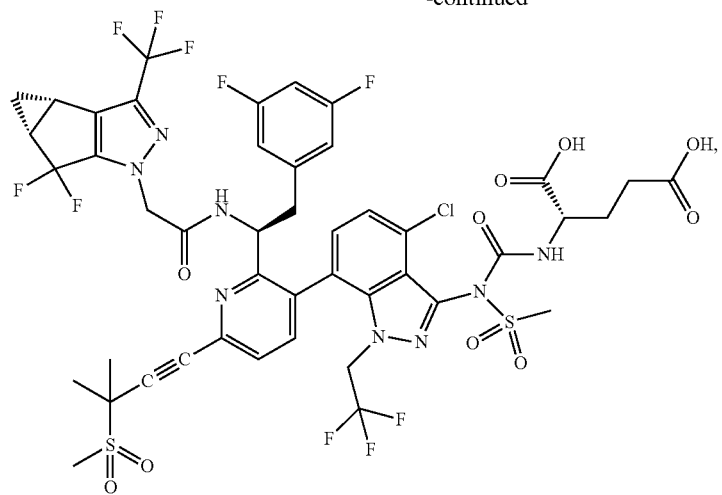
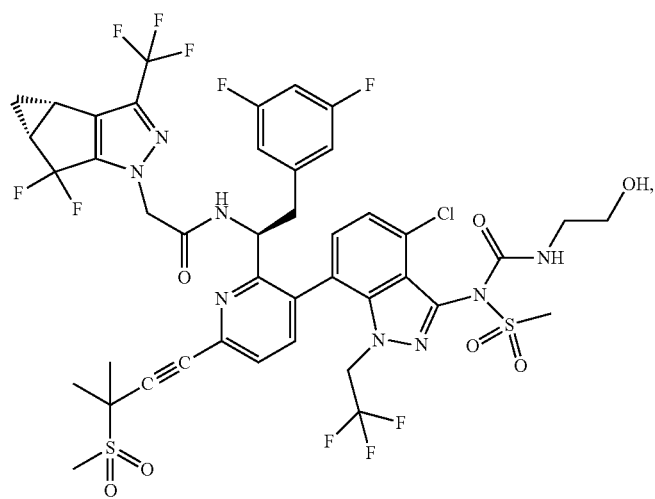
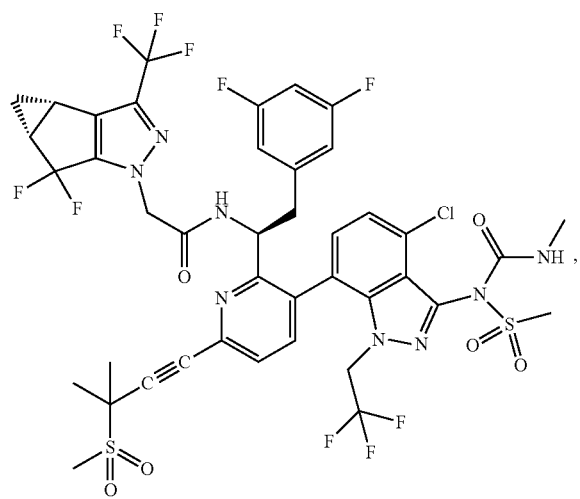

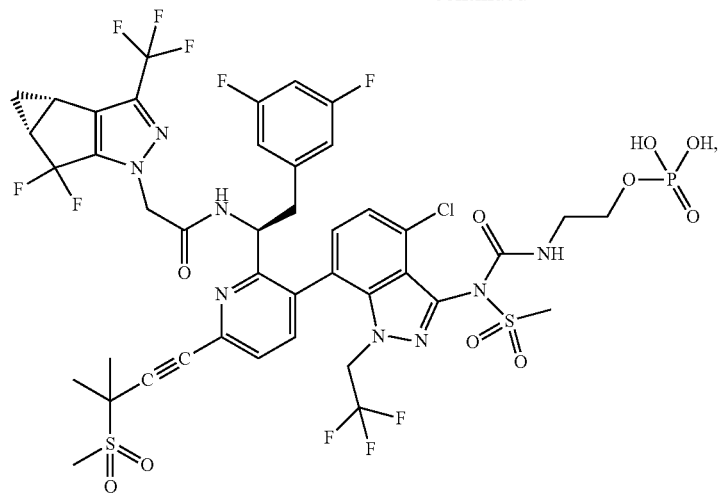
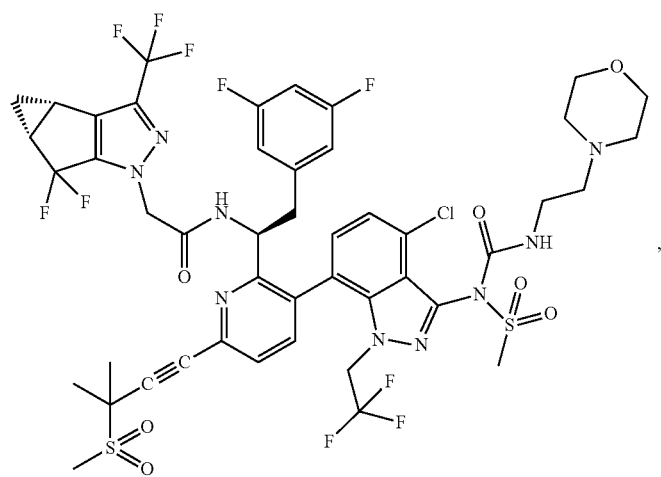
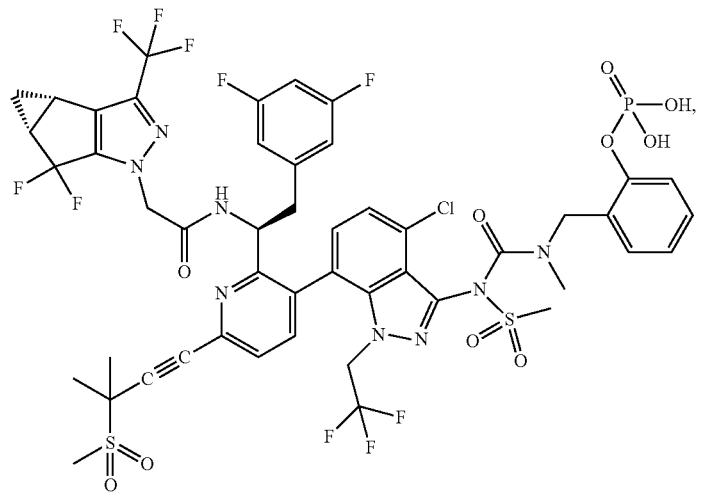

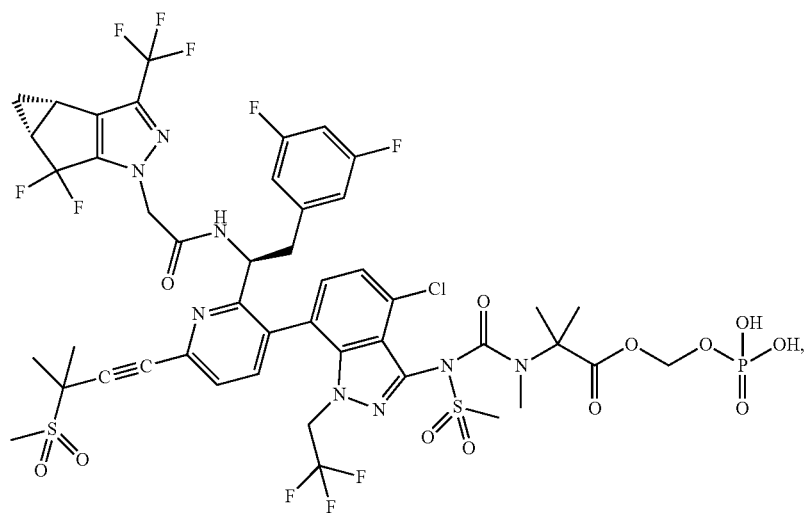
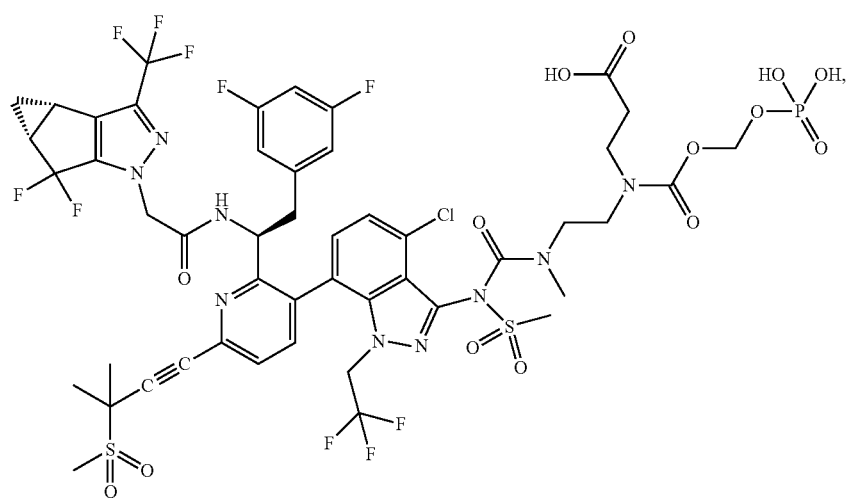
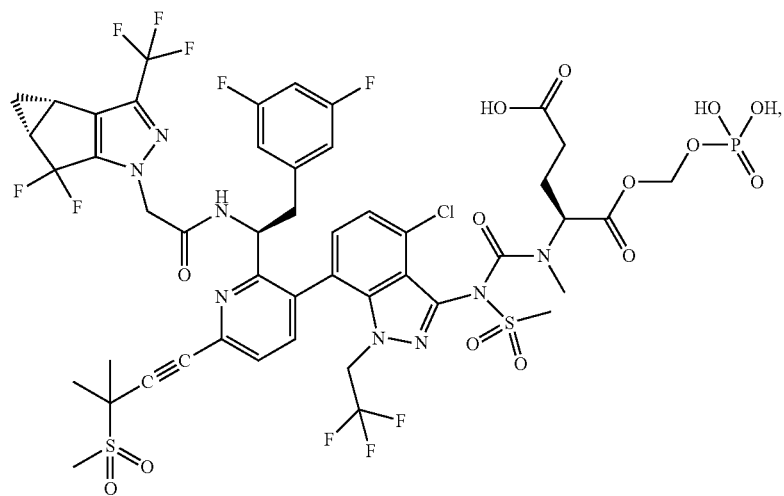

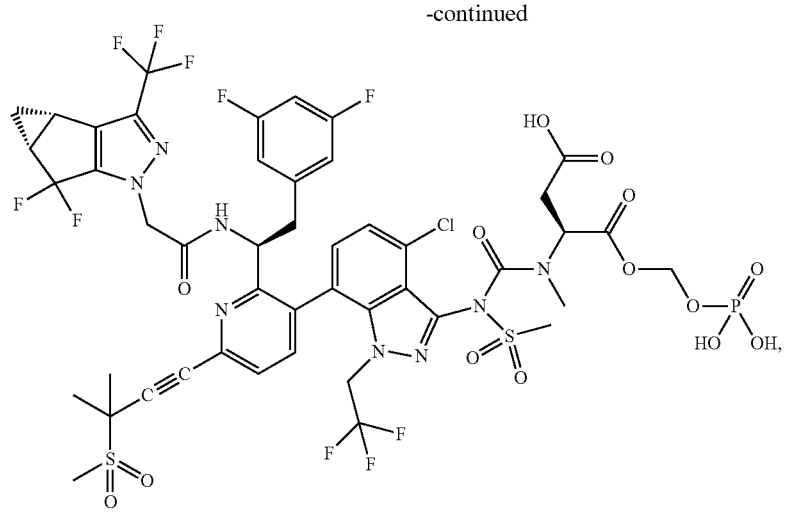
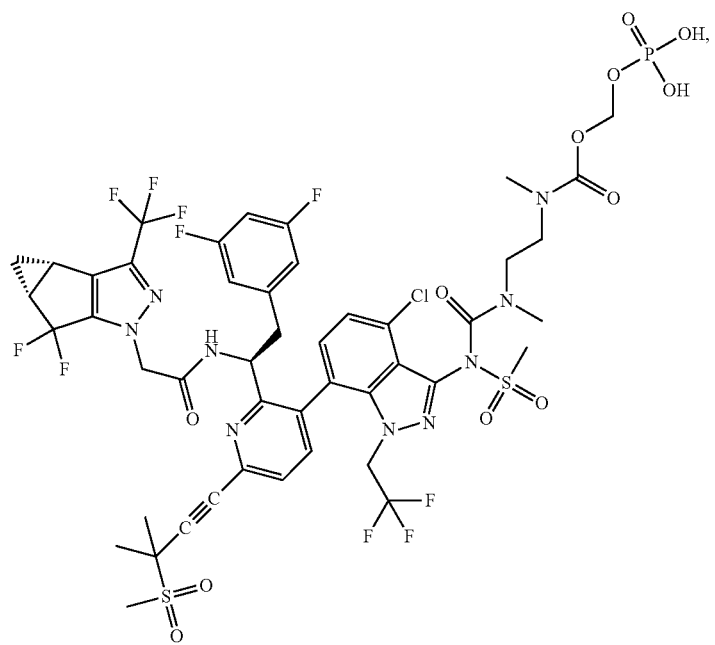
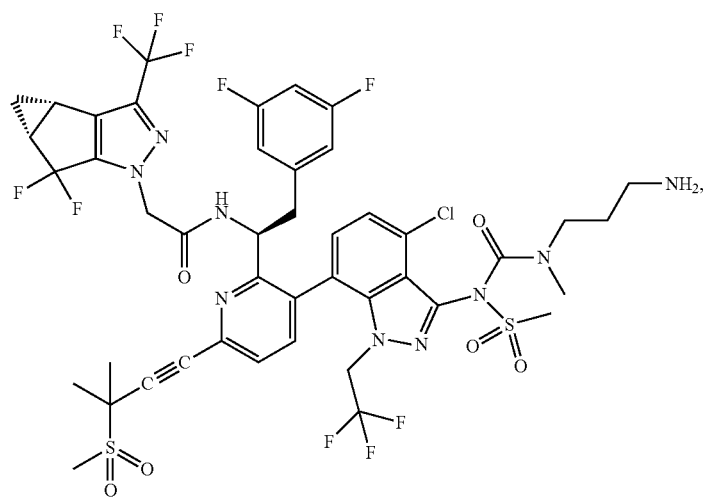

-continued
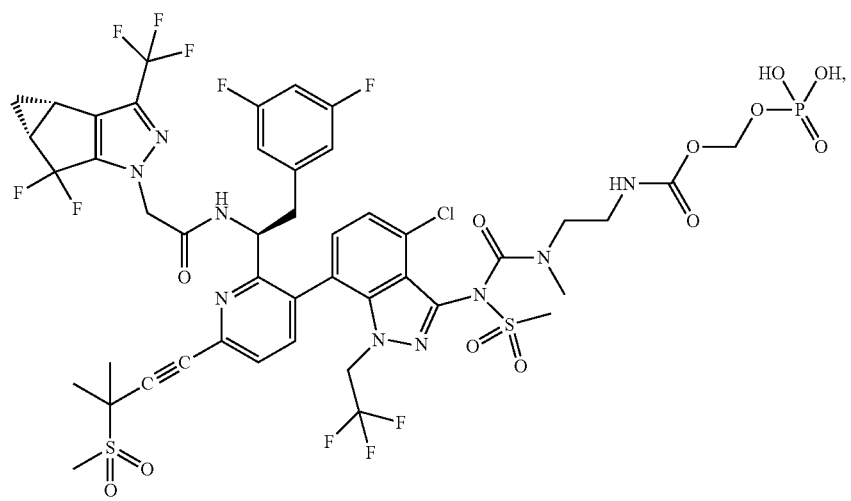
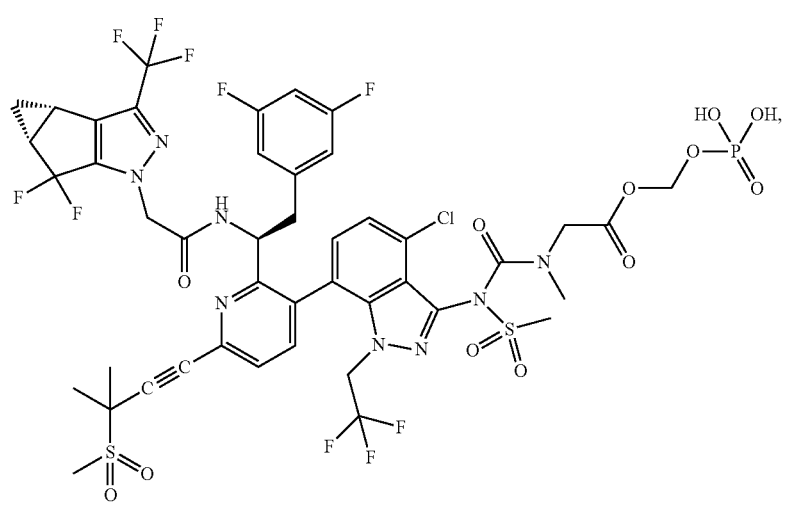
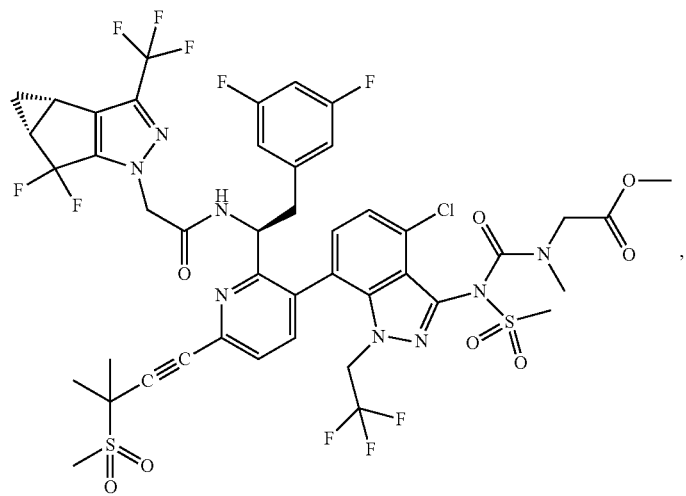

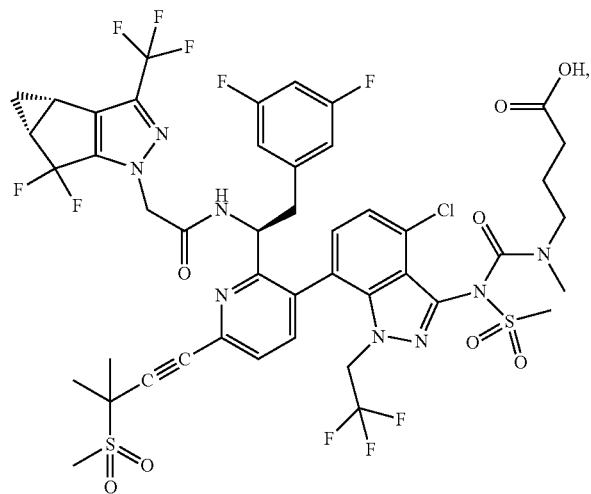
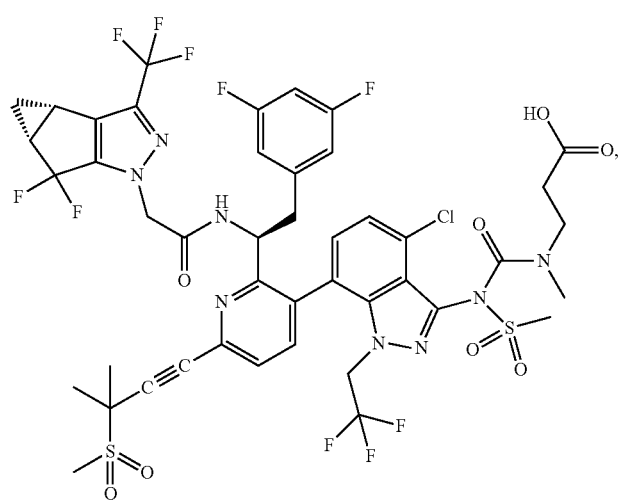
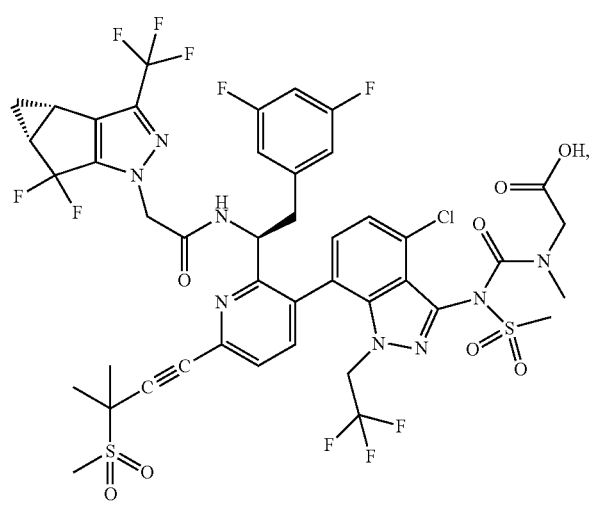

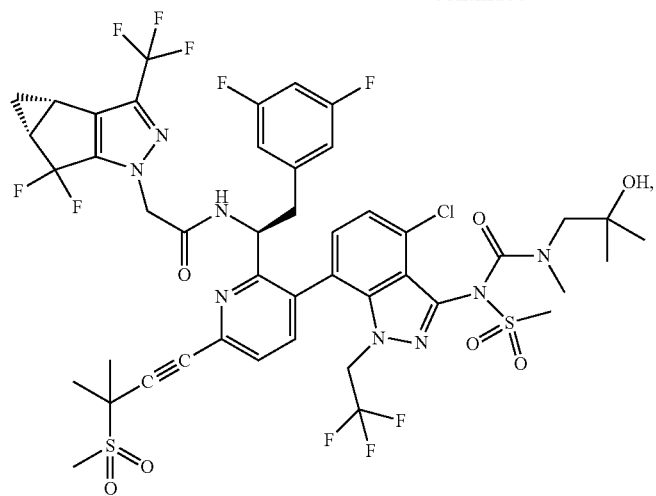
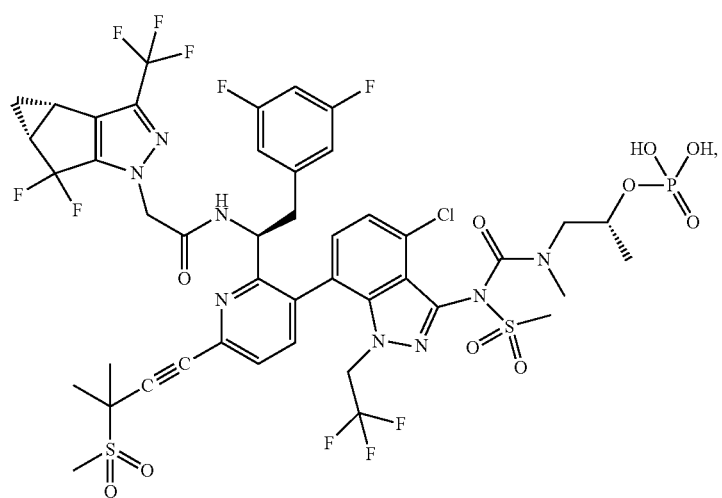
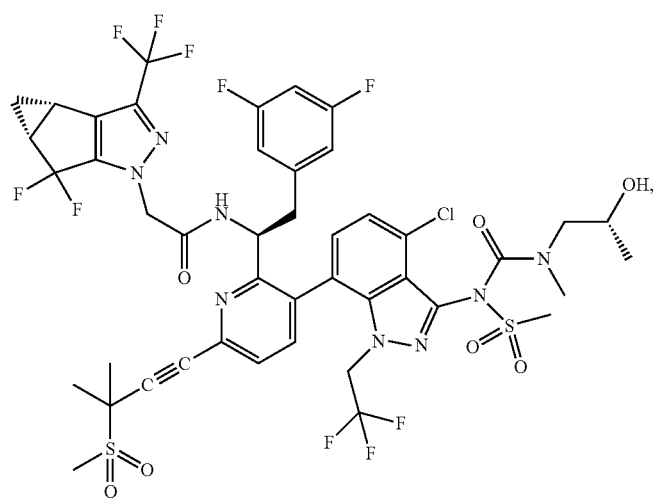

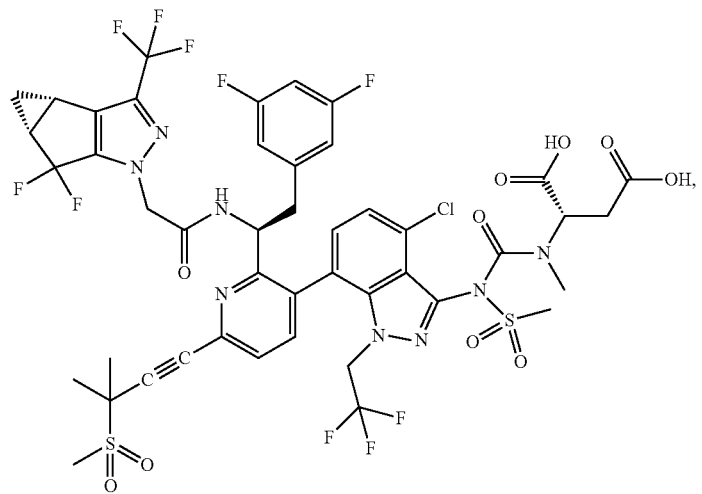
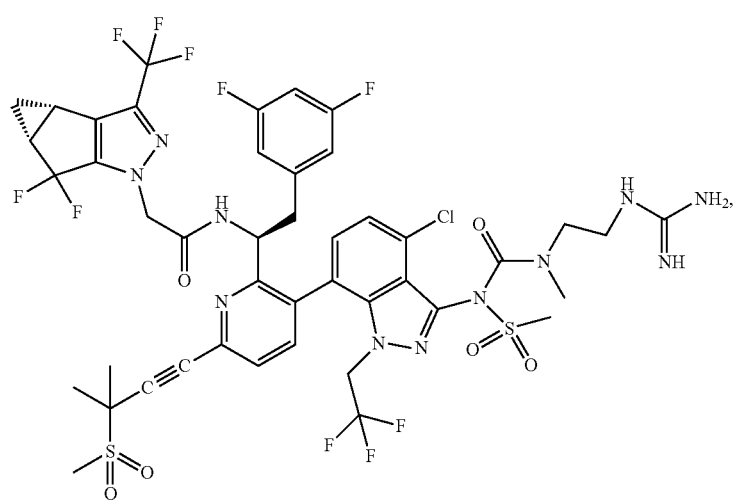
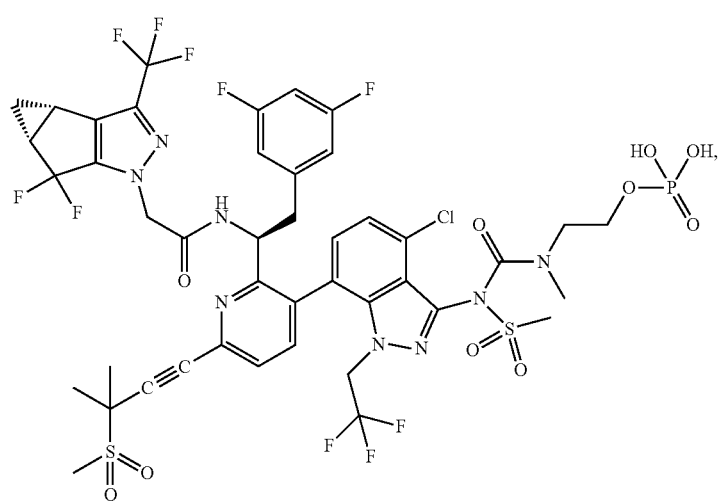

-continued
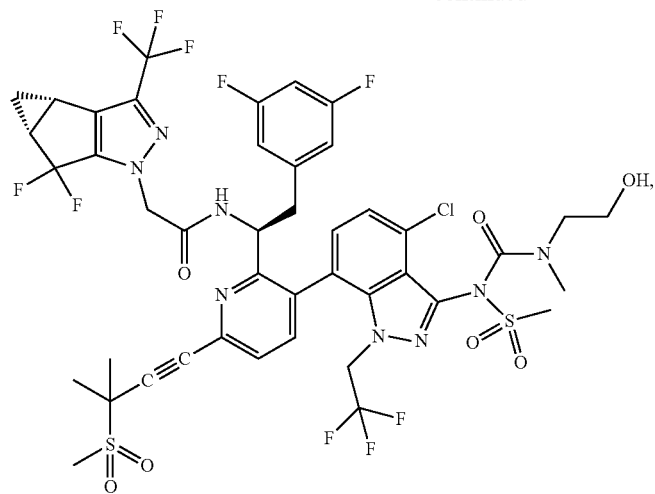
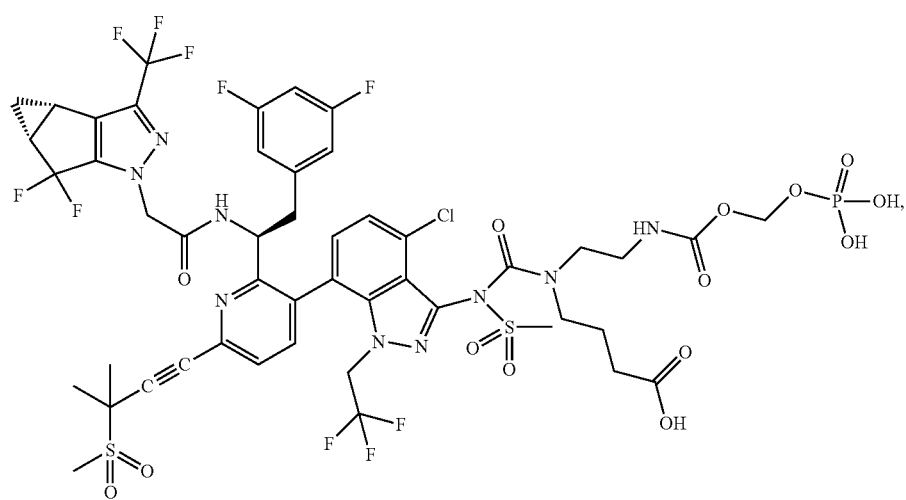
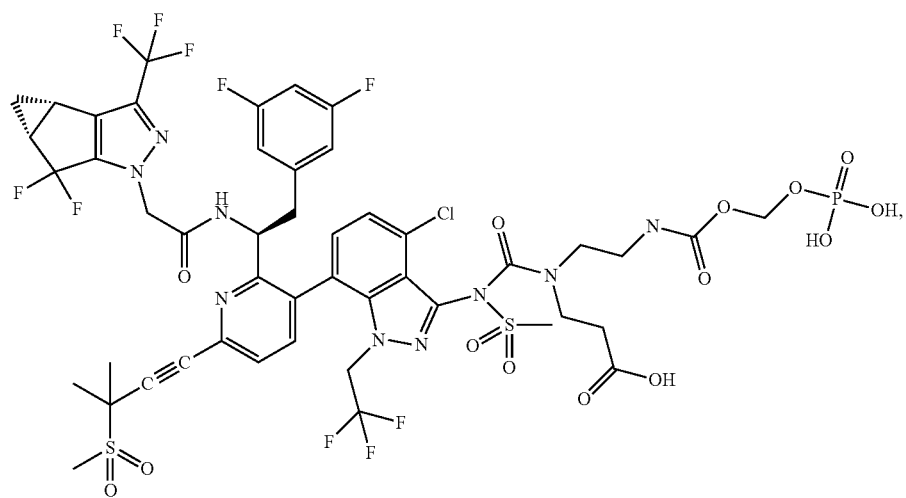

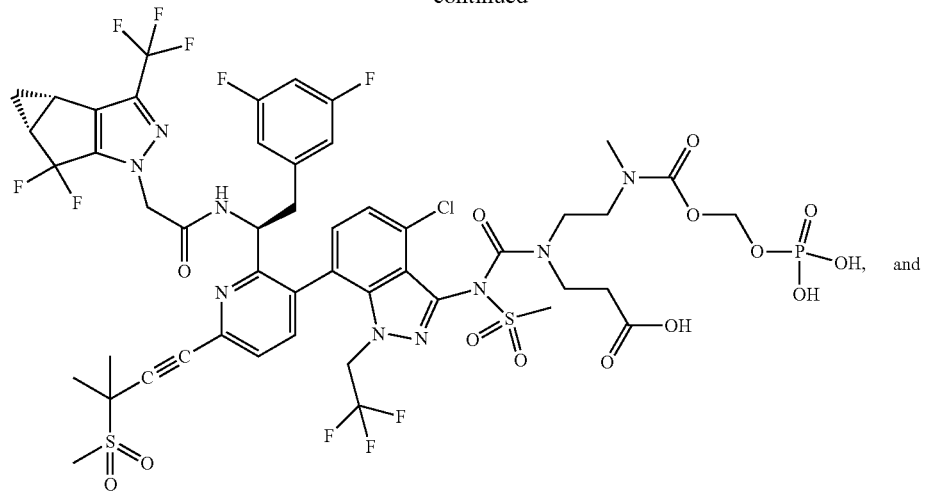
and
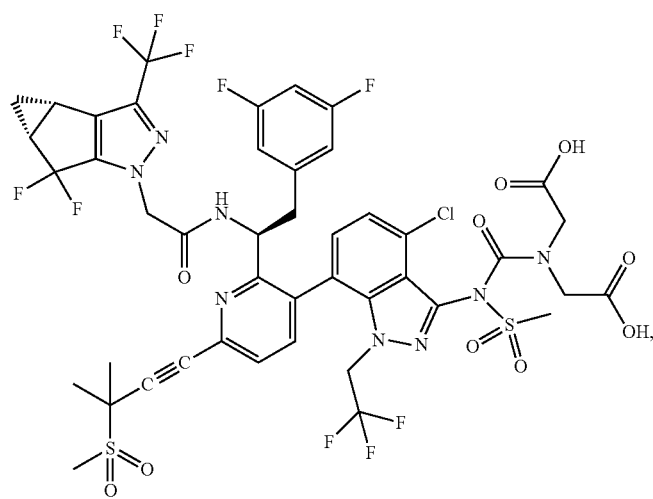
or a pharmaceutically acceptable salt thereof.
In some embodiments of the compound of Formula I, provided herein is a compound selected from the group consisting of:
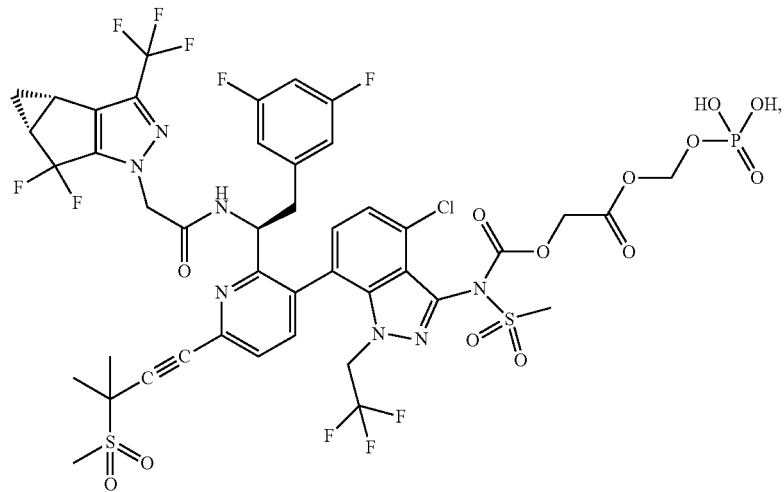

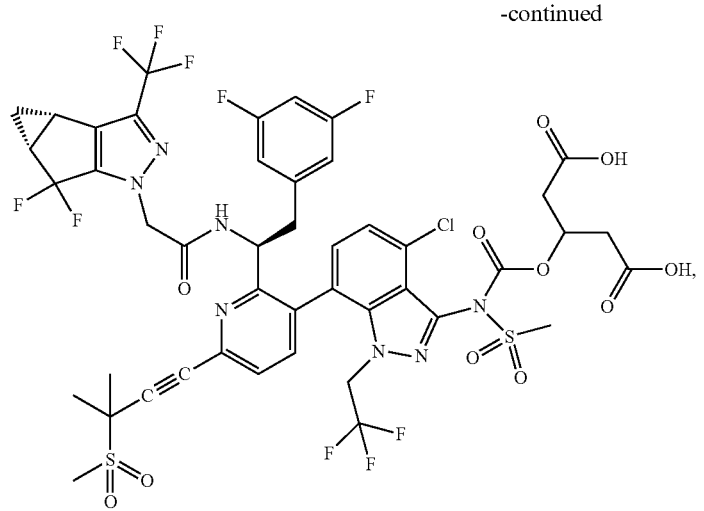
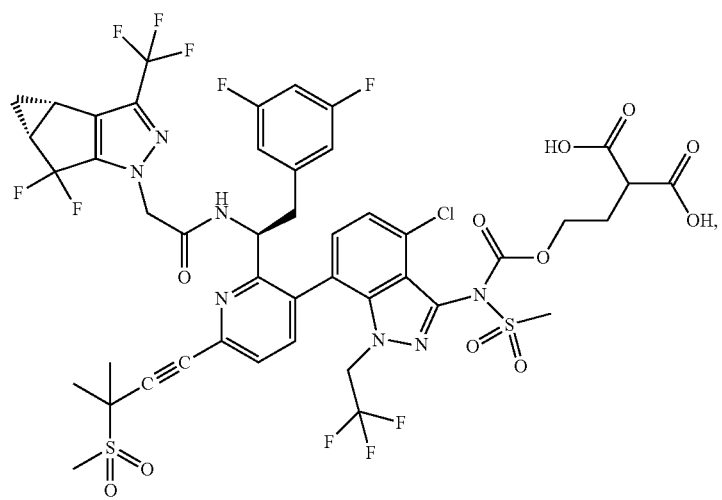
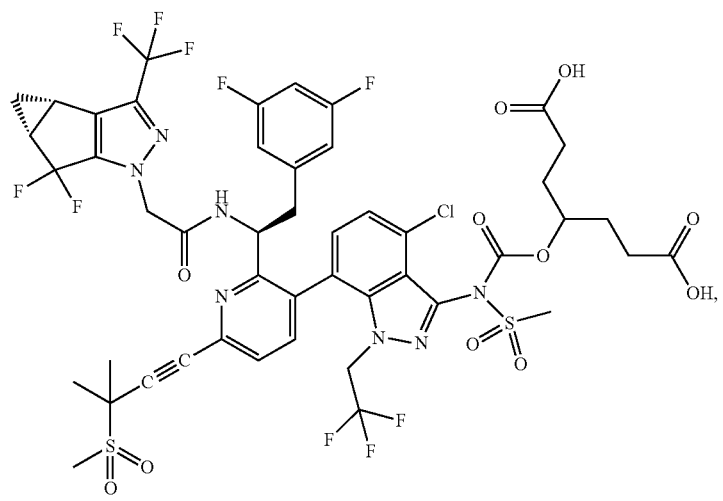

-continued
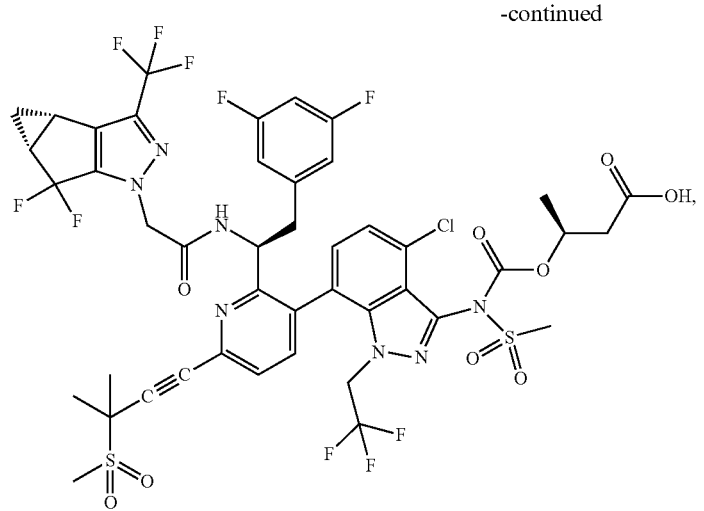
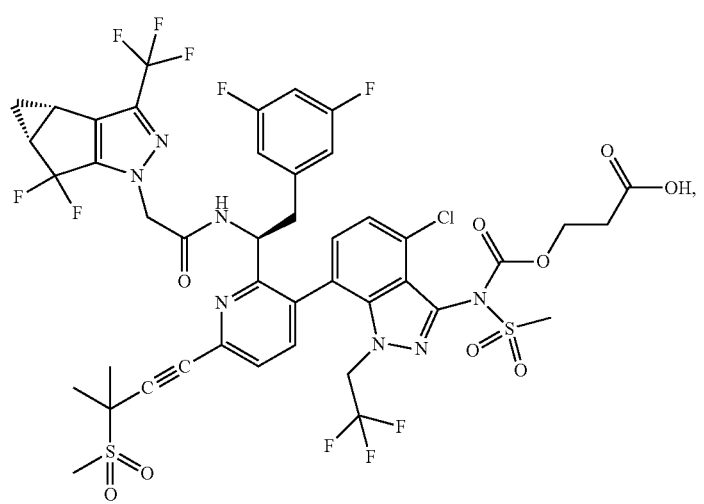
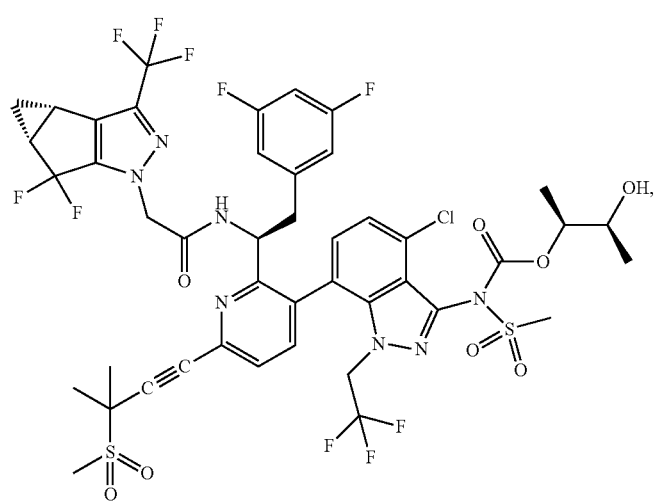

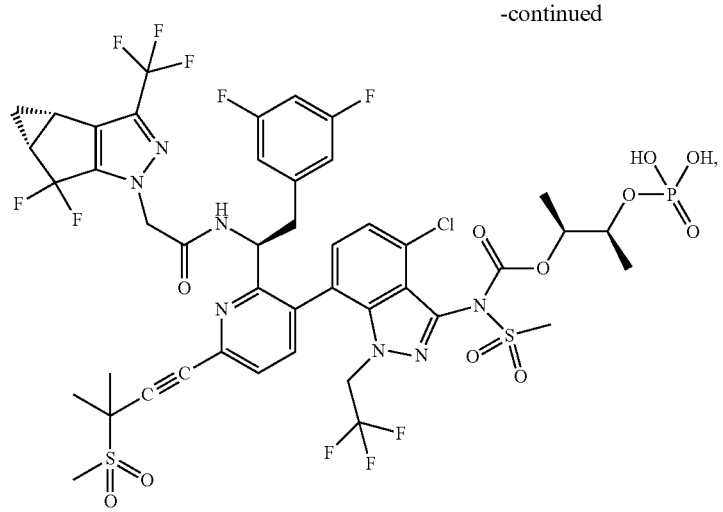
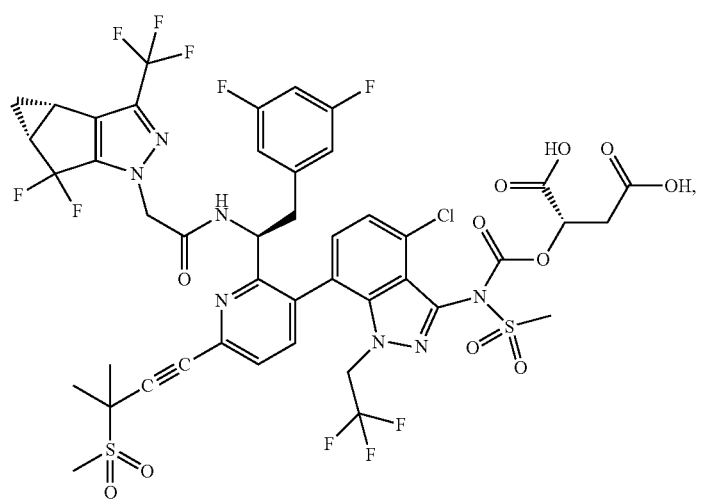
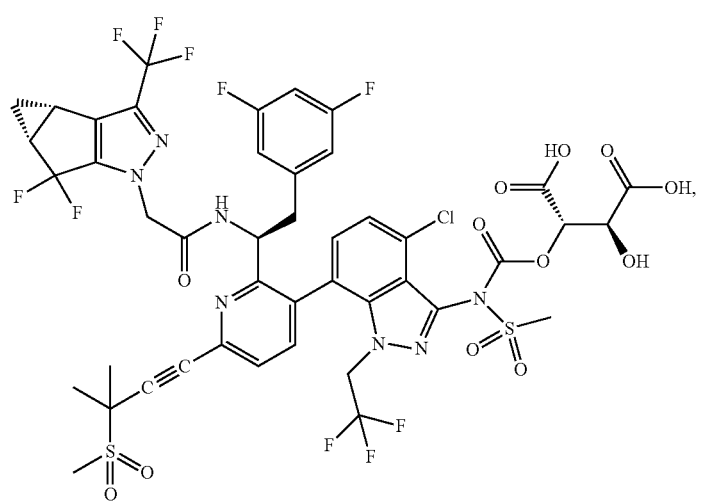

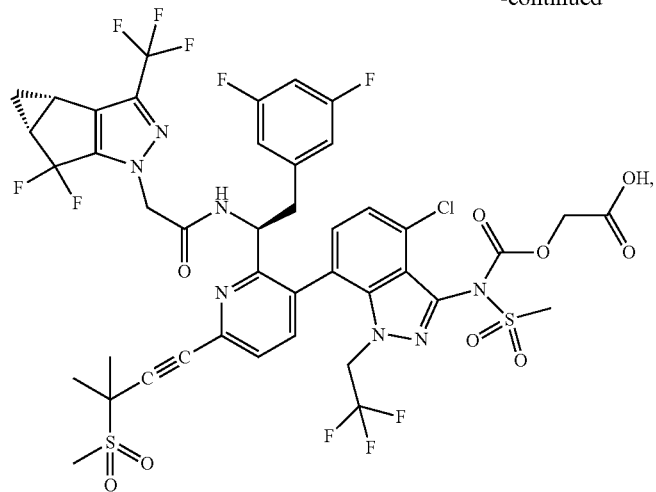
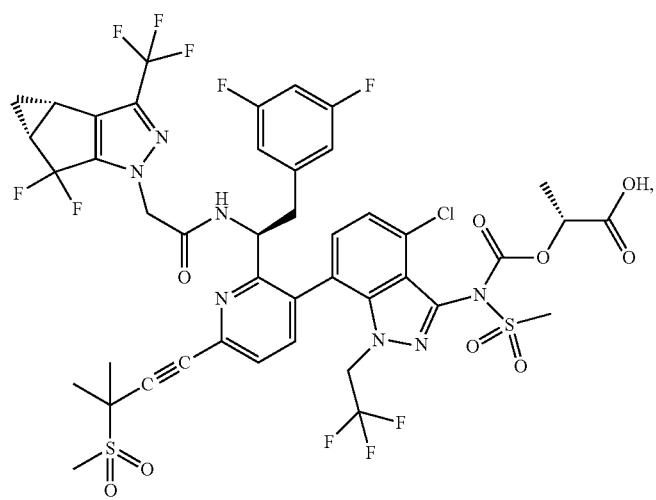
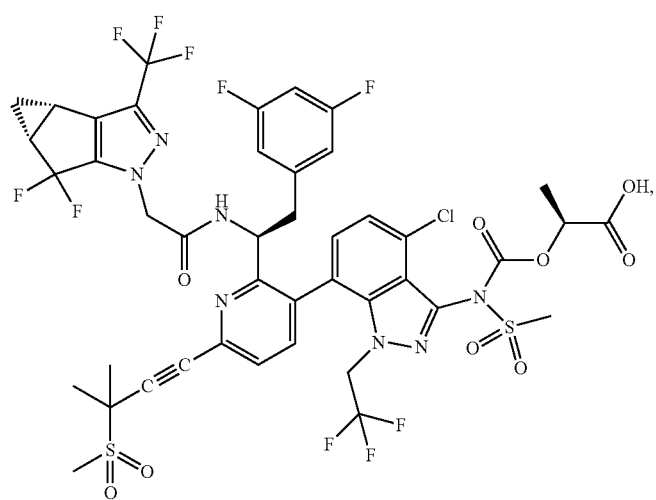

-continued
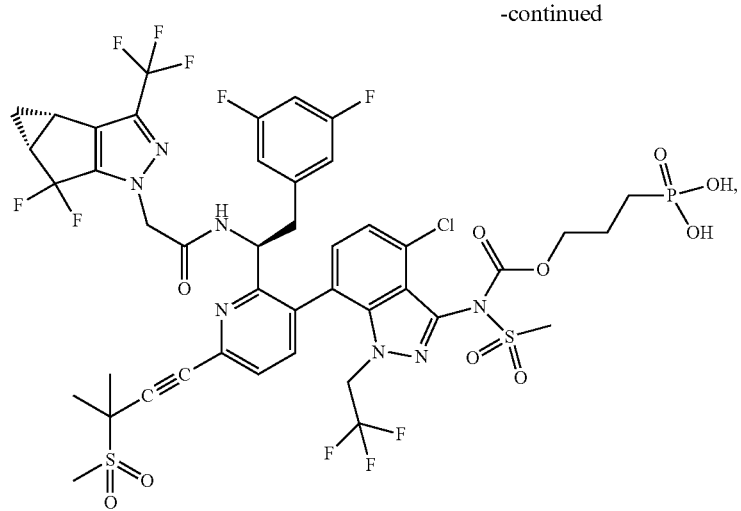
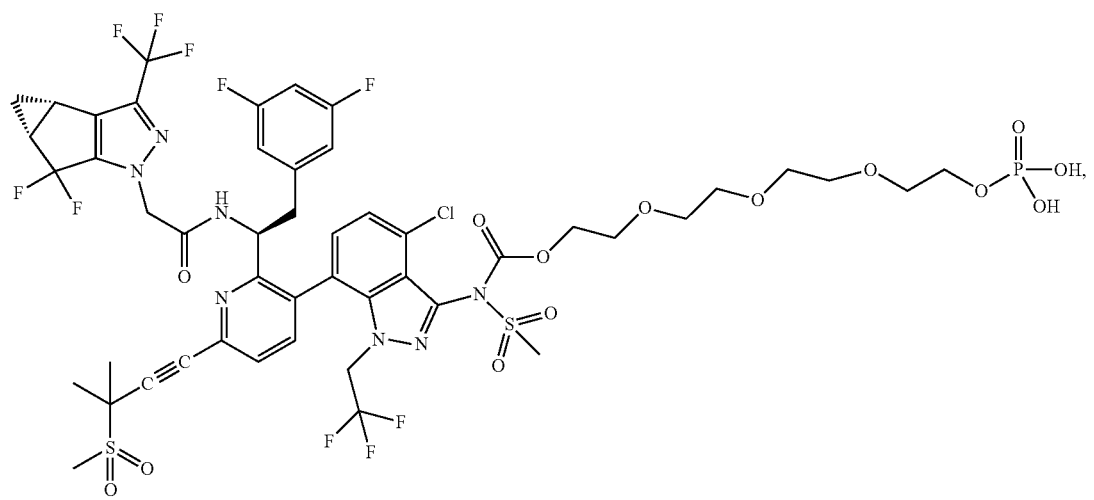
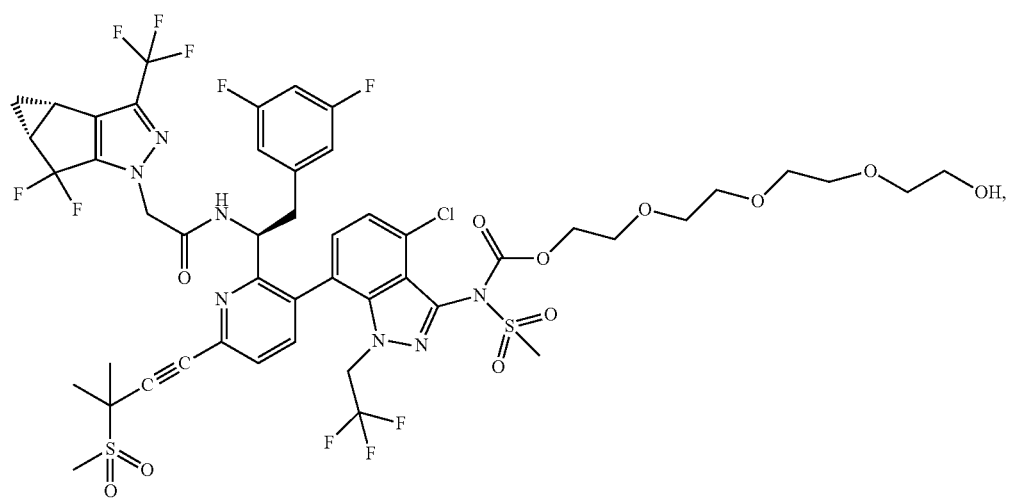

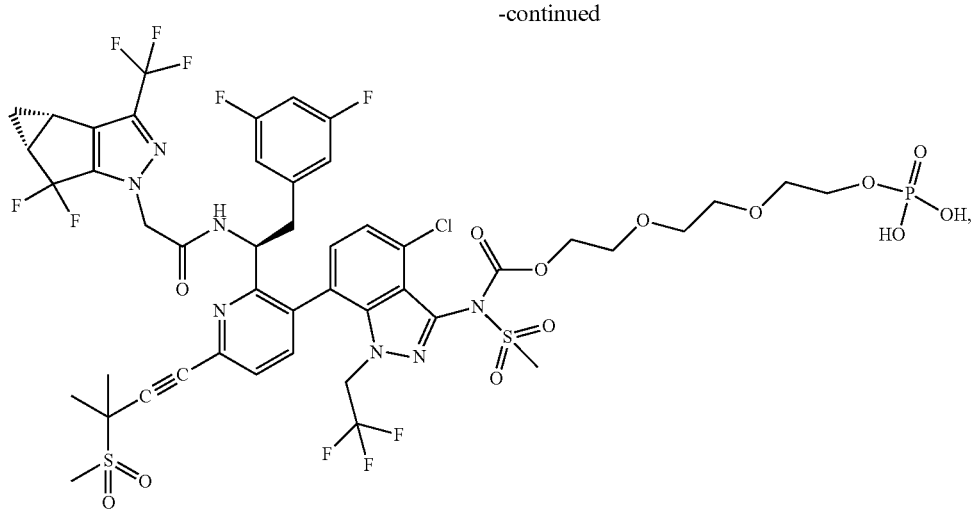
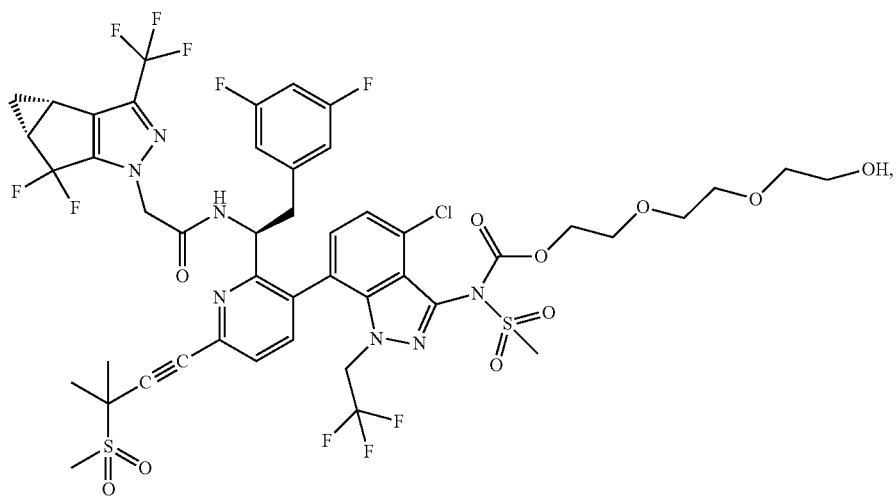
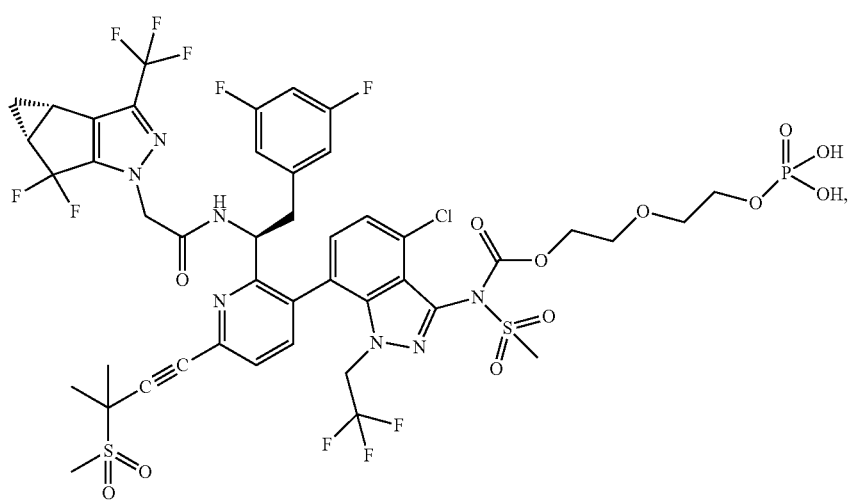

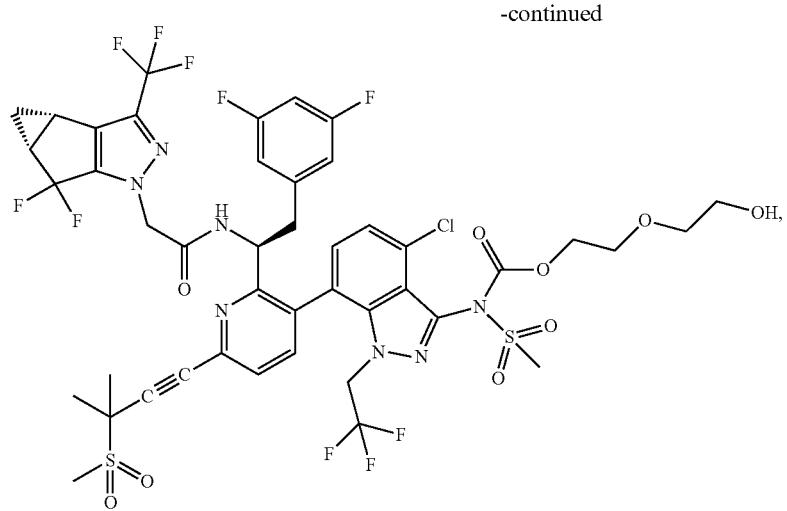
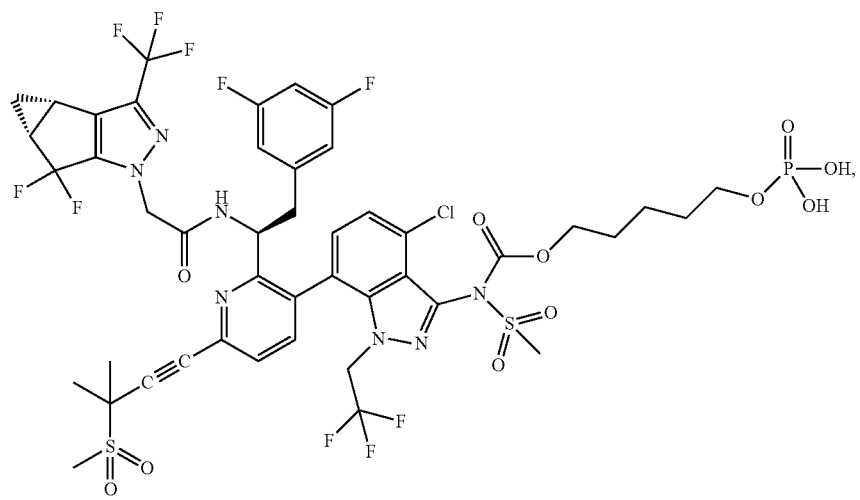
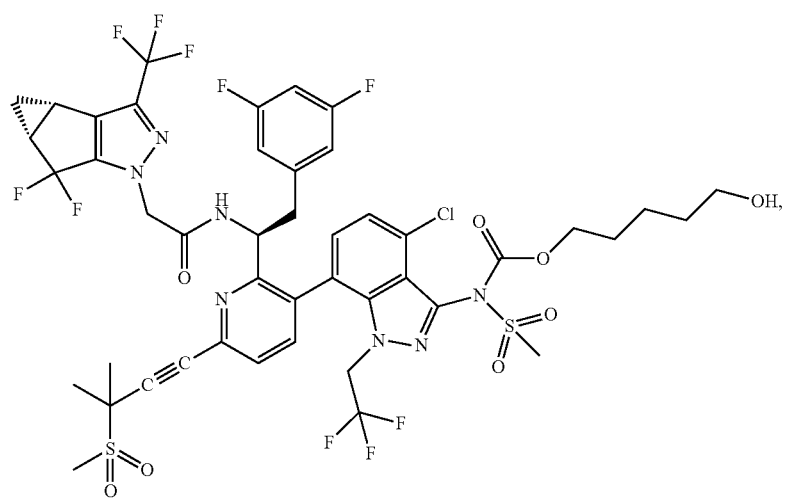

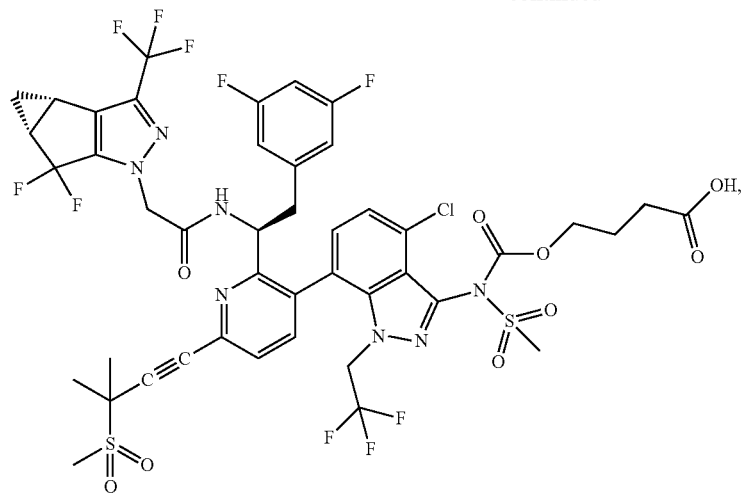
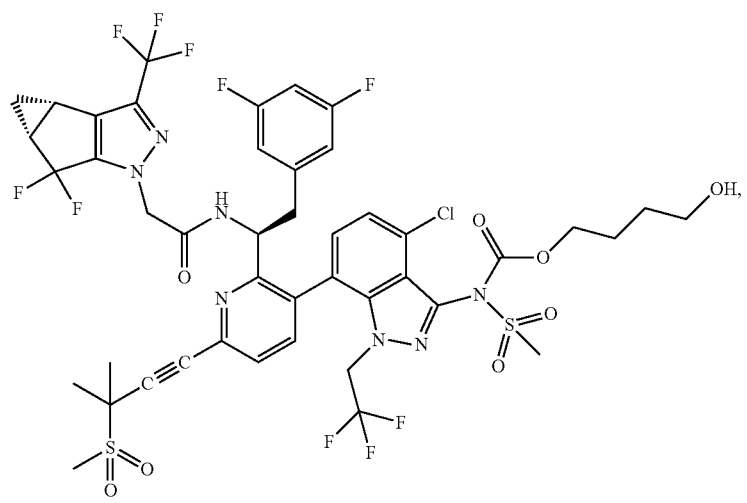
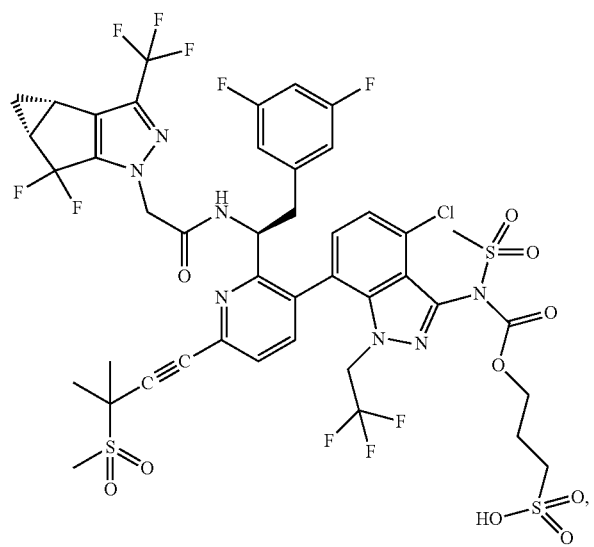

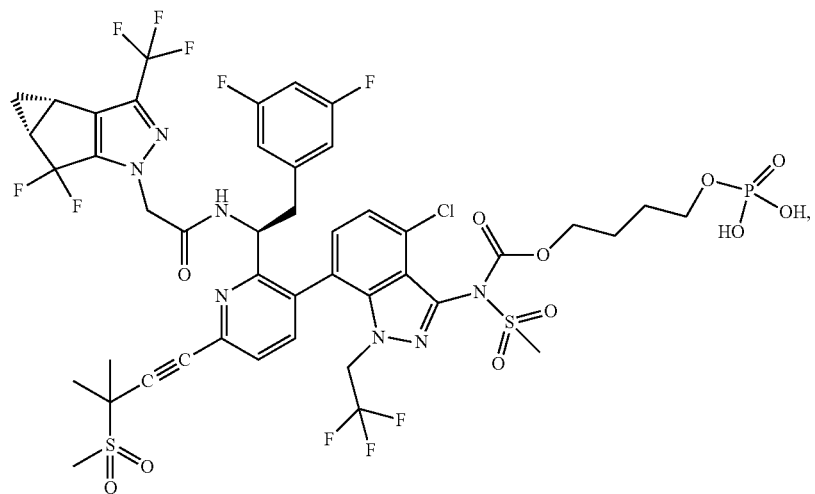
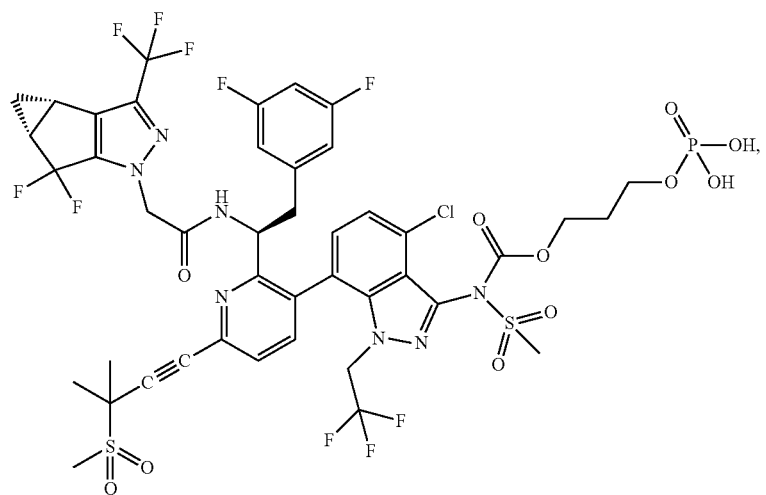
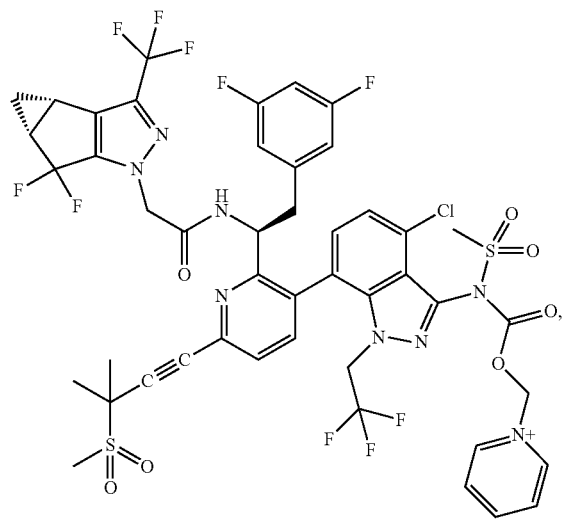

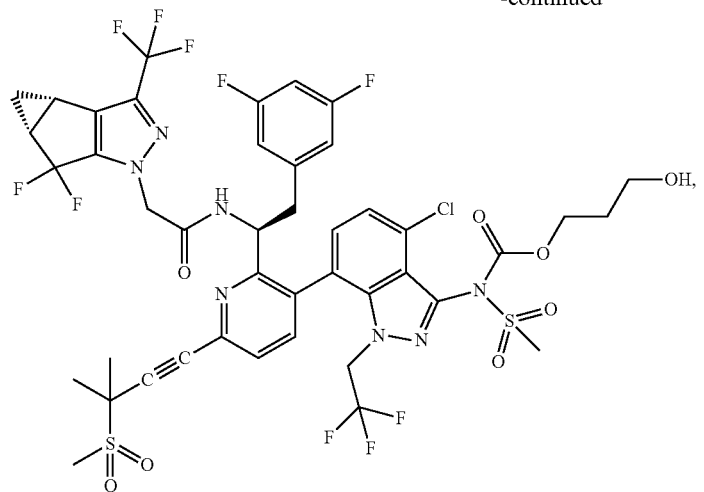
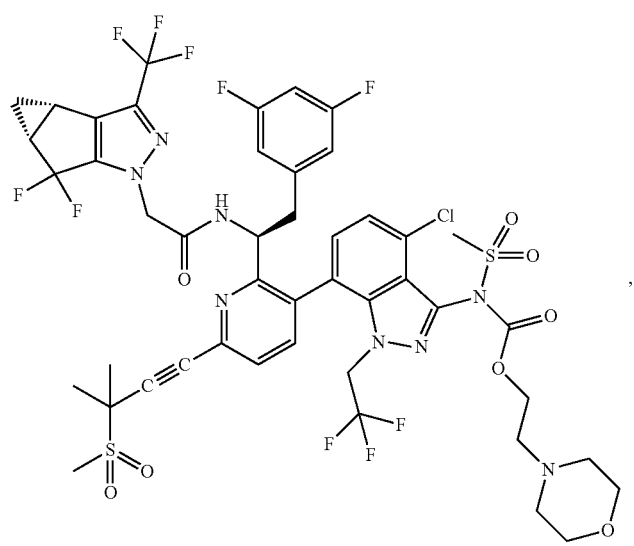
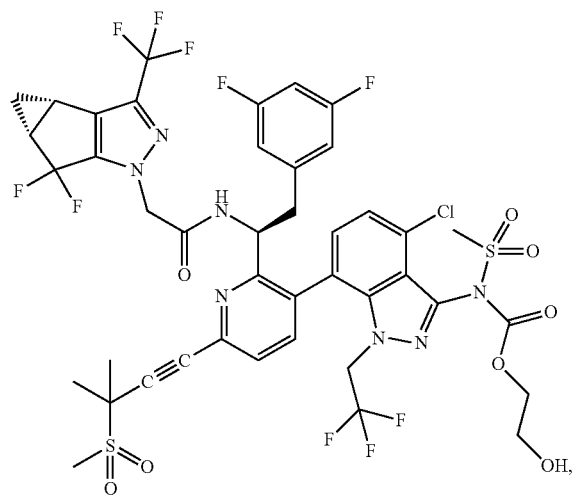

-continued
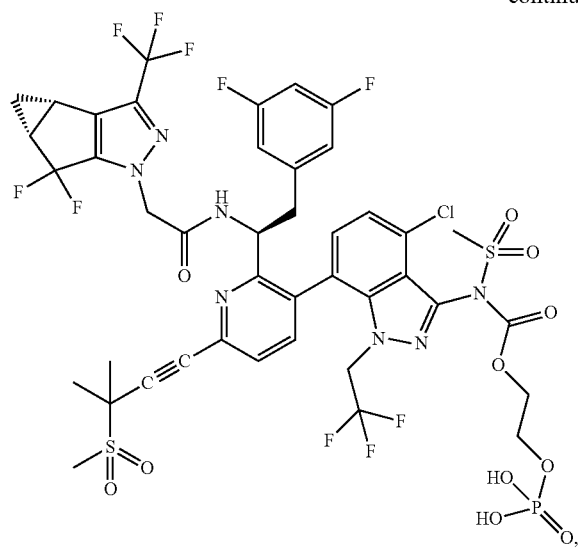
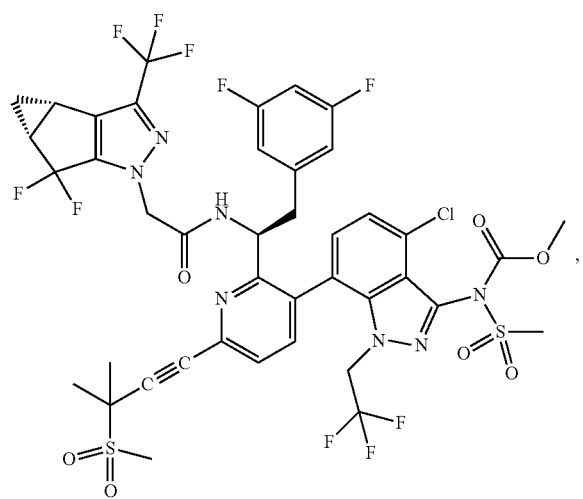
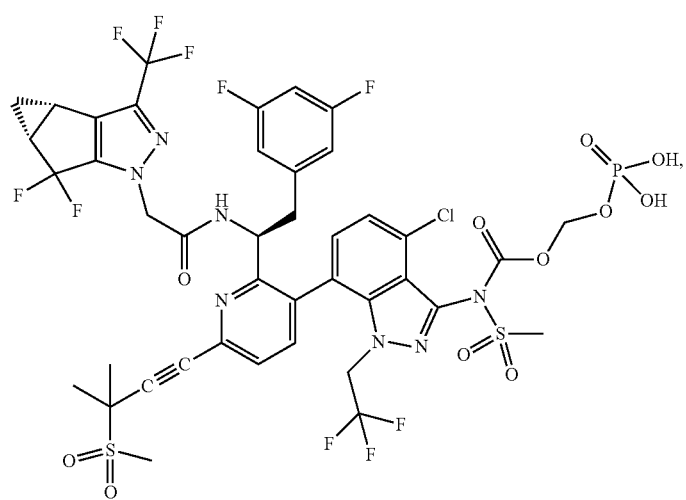

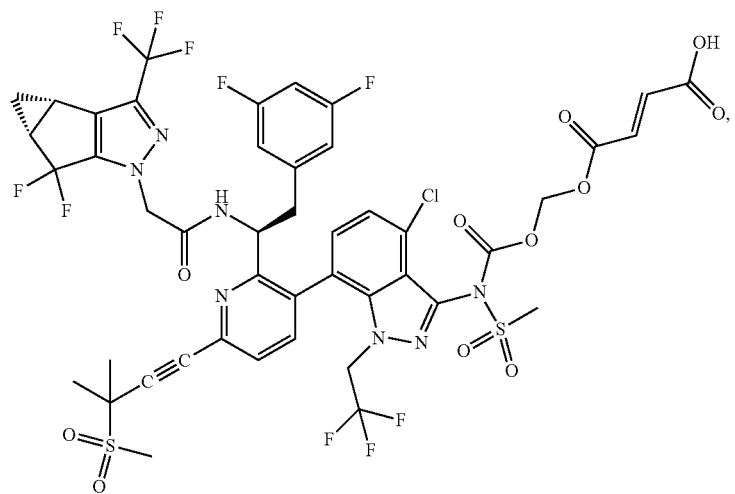
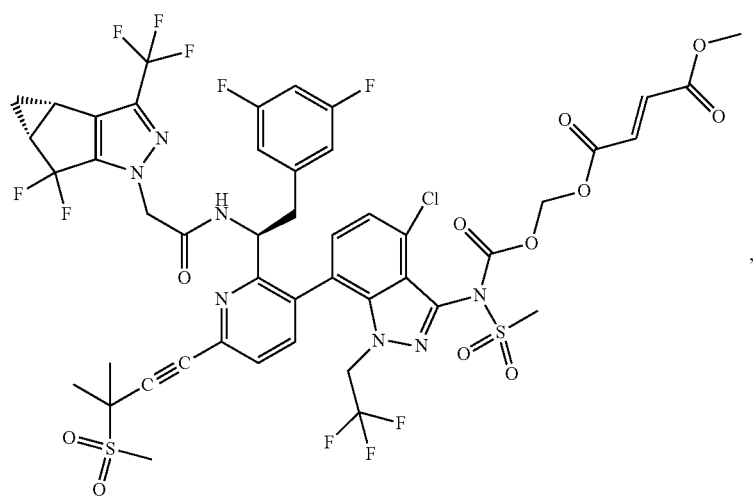
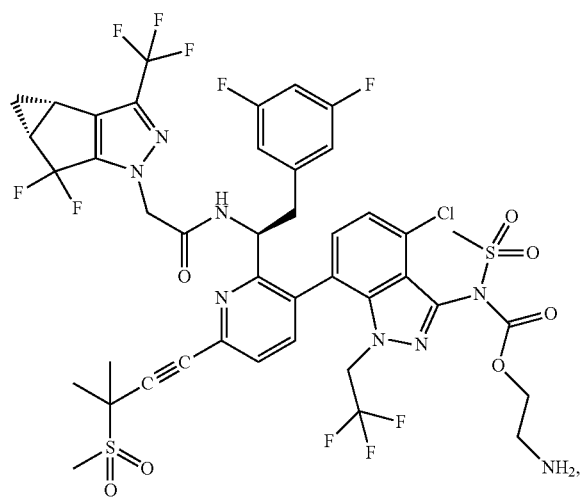

-continued
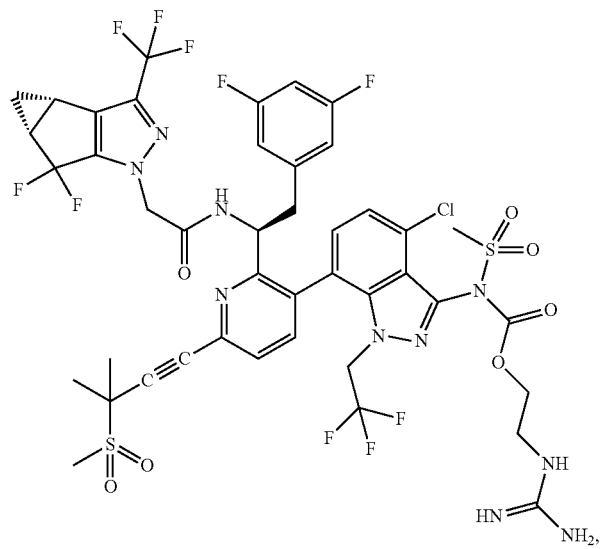
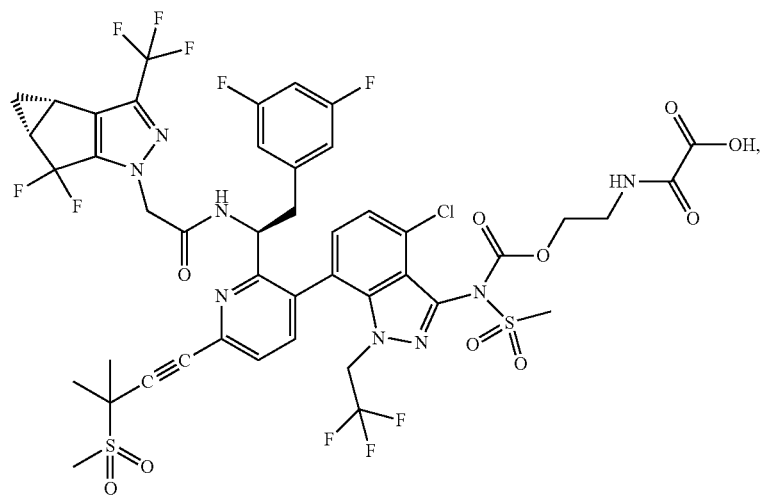
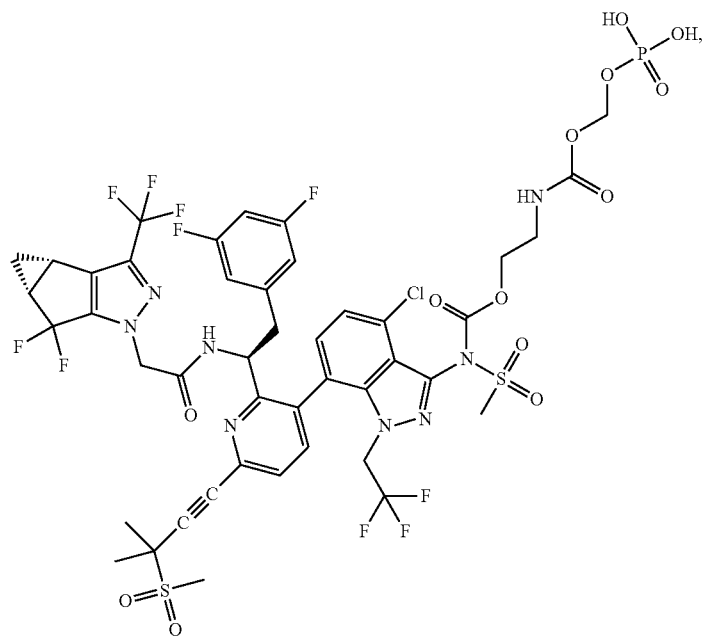

-continued
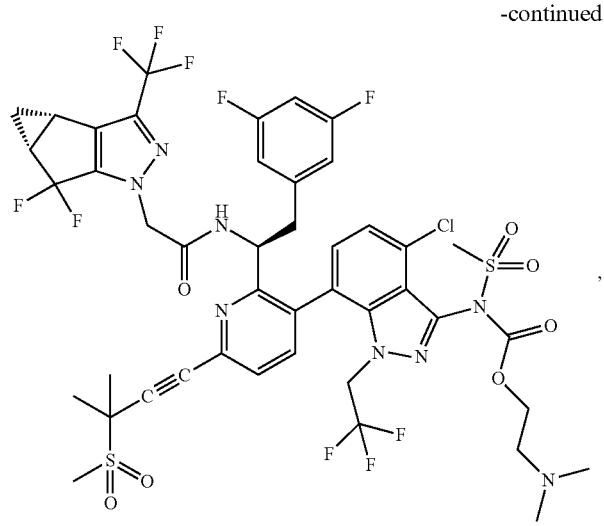
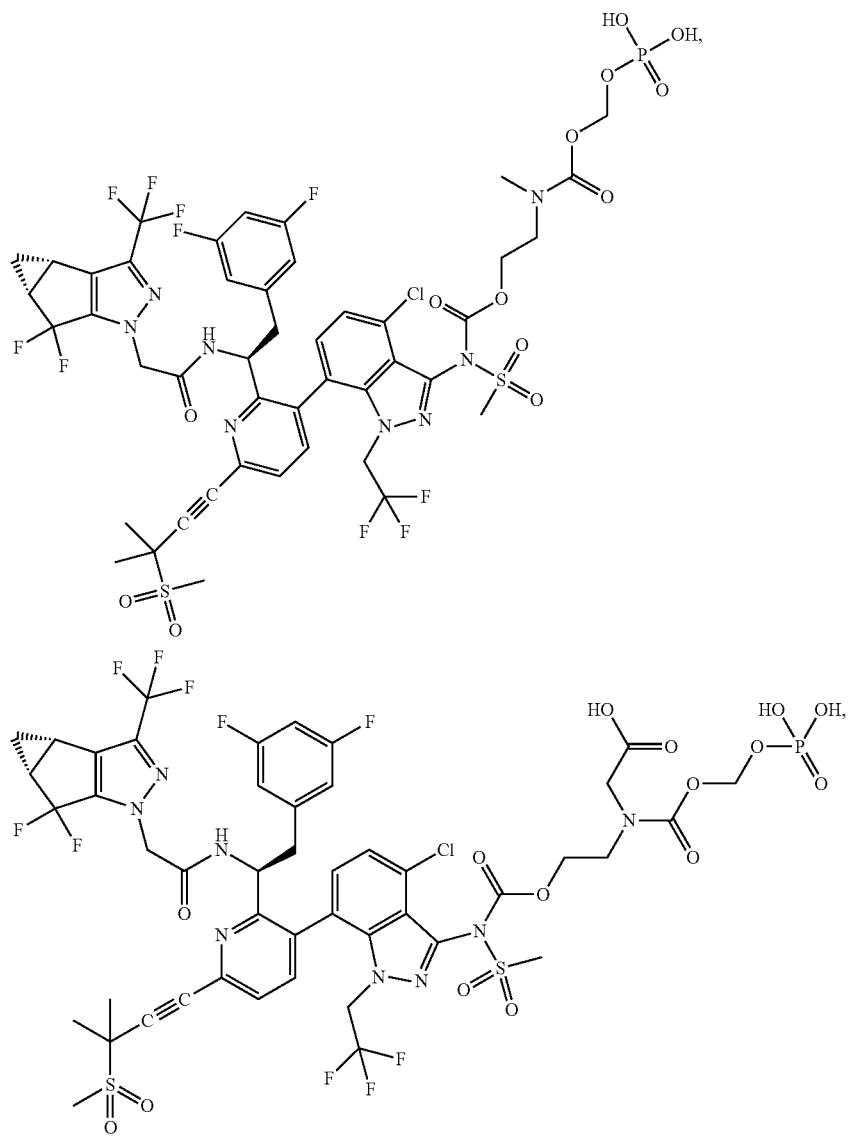

-continued
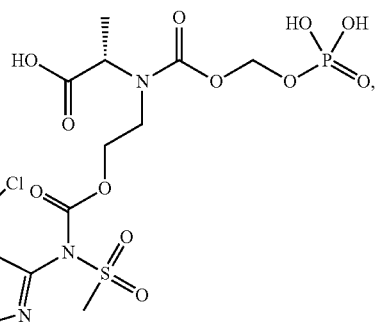
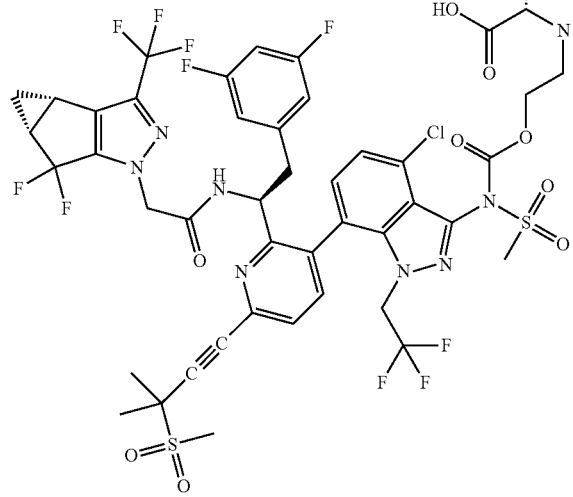
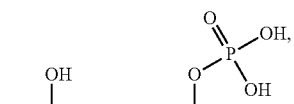
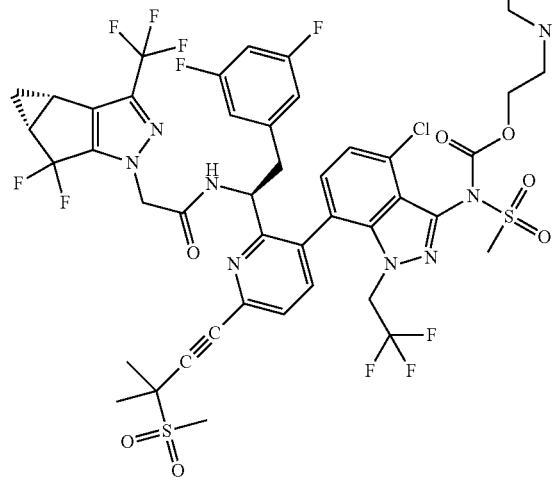
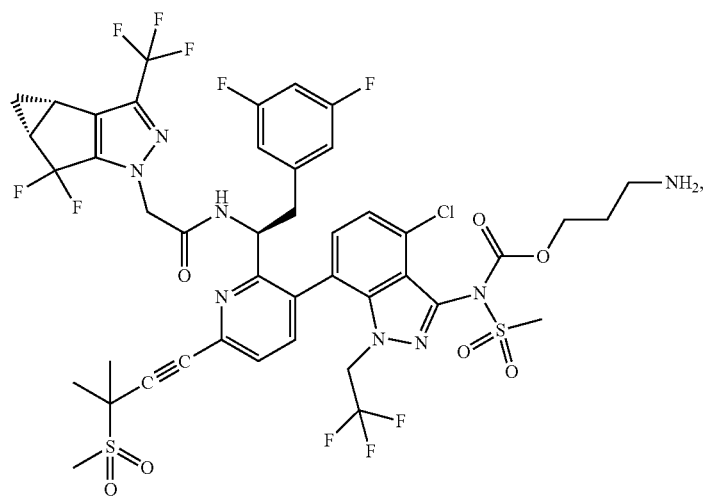

-continued
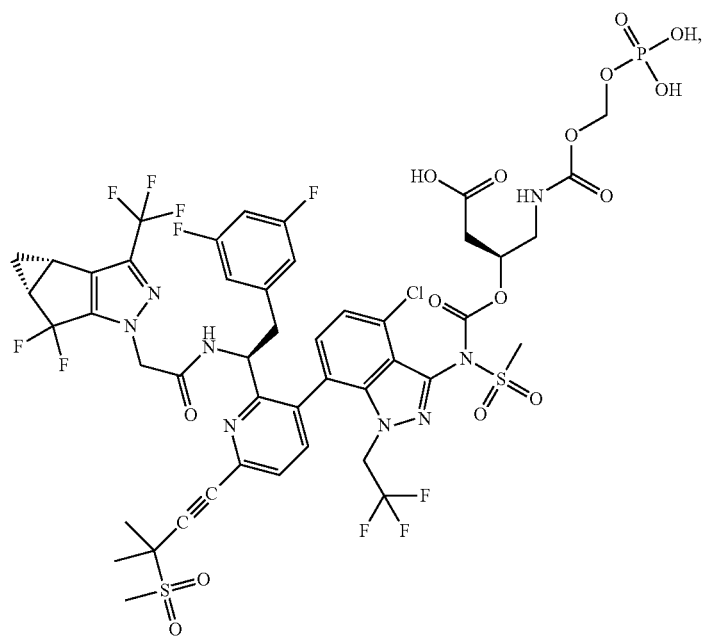
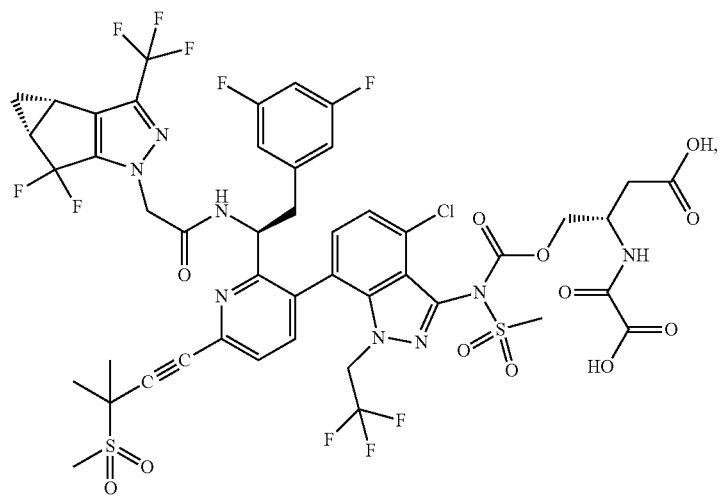
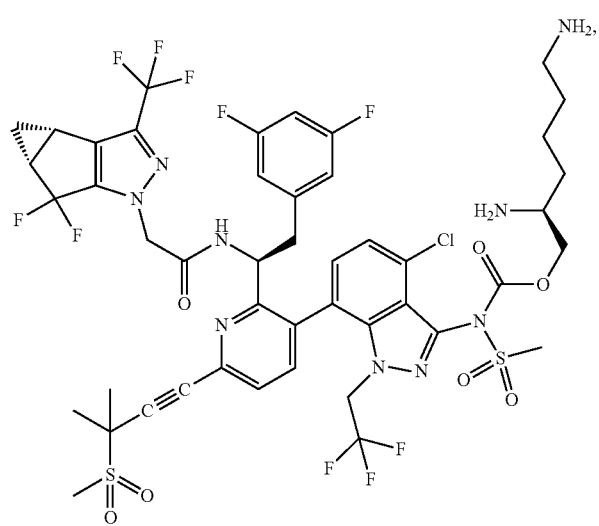

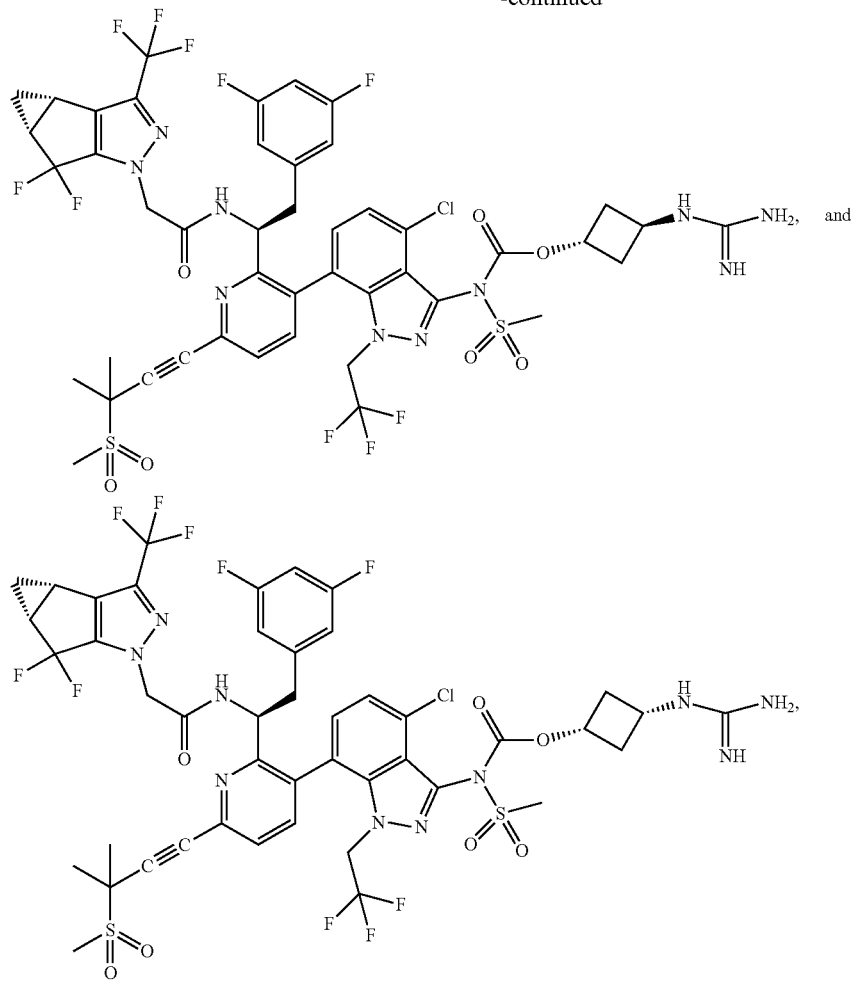
or a pharmaceutically acceptable salt thereof.
In some embodiments of the compound of Formula I, provided herein is a compound that is:
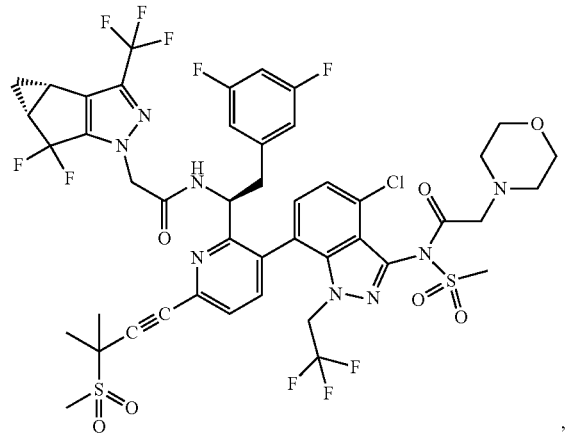 [SMILES: CC(C)(C#Cc1ccc(-c2ccc(Cl)c3c(N(C(=O)CN4CCOCC4)S(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]
or a pharmaceutically acceptable salt thereof.
In some embodiments of the compound of Formula I, provided herein is a compound that is:
or a pharmaceutically acceptable salt thereof.

In some embodiments of the compound of Formula I, provided herein is a compound that is:

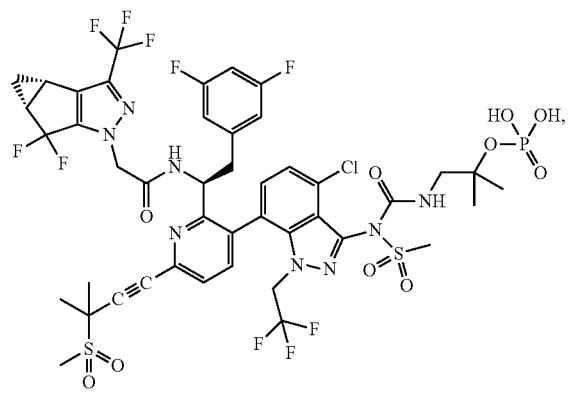 [SMILES: CC(C)(CNC(=O)N(c1nn(CC(F)(F)F)c2c(-c3ccc(C#CC(C)(C)S(C)(=O)=O)nc3[C@H](Cc3cc(F)cc(F)c3)NC(=O)Cn3nc(C(F)(F)F)c4c3C(F)(F)[C@@H]3C[C@H]43)ccc(Cl)c12)S(C)(=O)=O)OP(=O)(O)O]

or a pharmaceutically acceptable salt thereof.

In some embodiments of the compound of Formula I, provided herein is a compound that is:

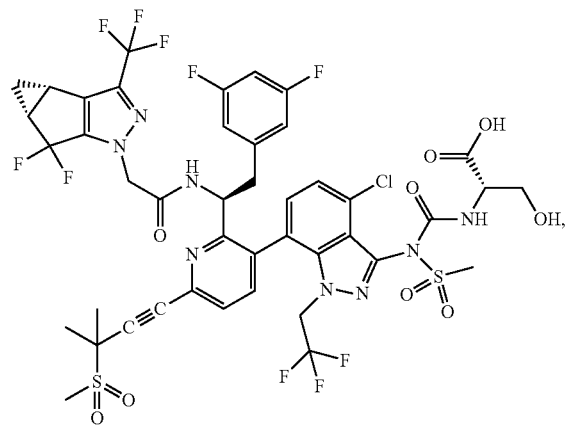 [SMILES: CC(C)(C#Cc1ccc(-c2ccc(Cl)c3c(N(C(=O)N[C@@H](CO)C(=O)O)S(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a pharmaceutically acceptable salt thereof.

In some embodiments of the compound of Formula I, provided herein is a compound that is:

In some embodiments of the compound of Formula I, provided herein is a compound that is:

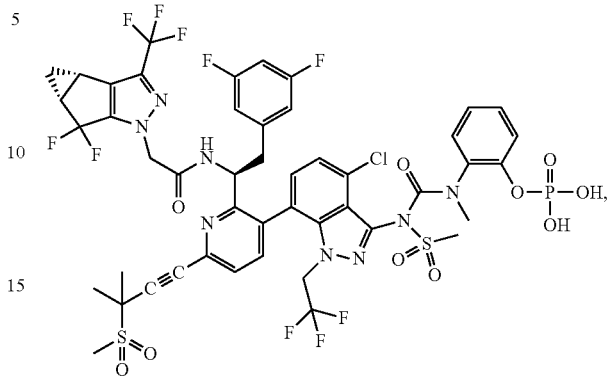

or a pharmaceutically acceptable salt thereof.

In some embodiments of the compound of Formula I, provided herein is a compound that is:

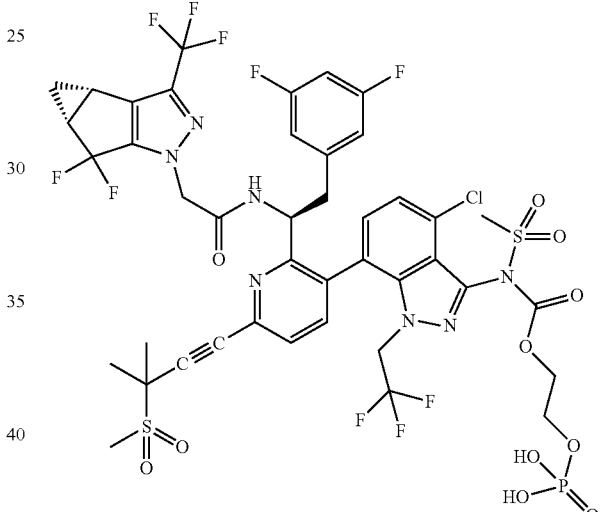

or a pharmaceutically acceptable salt thereof.

In one embodiment, provided herein is a compound selected from the group consisting of:

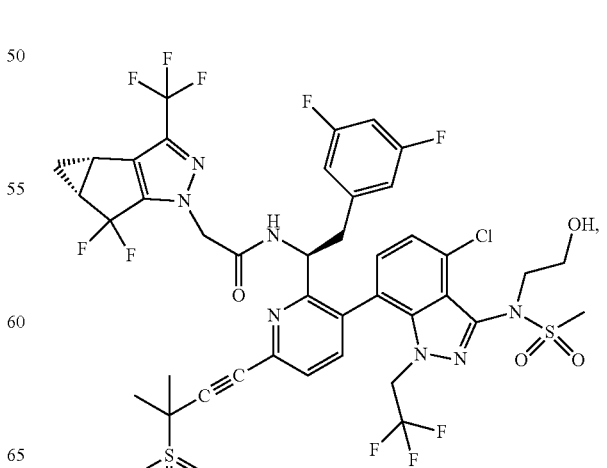

129
-continued
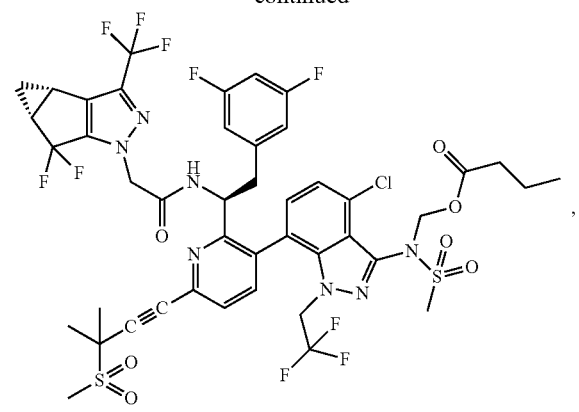
,
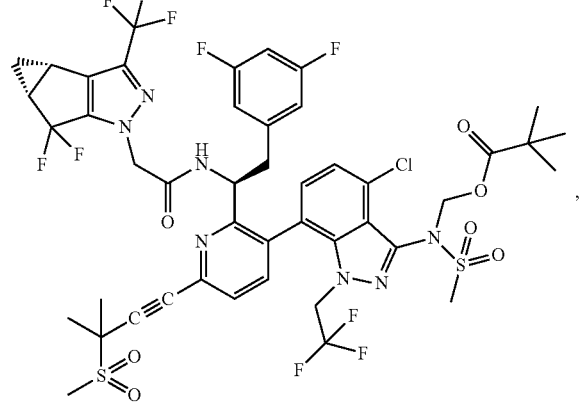
,
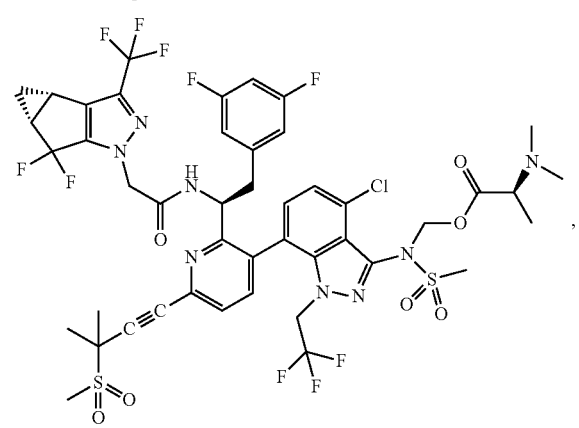
,
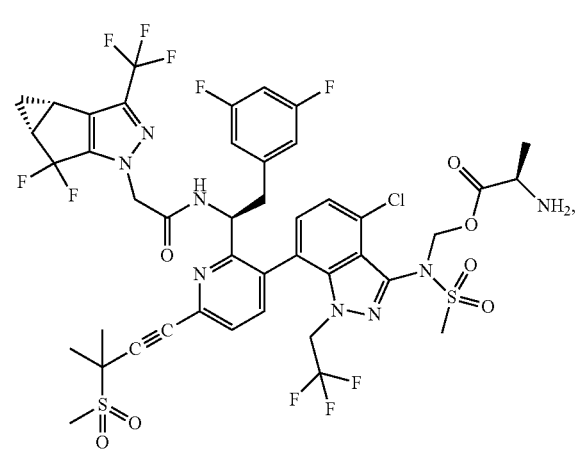
130
-continued
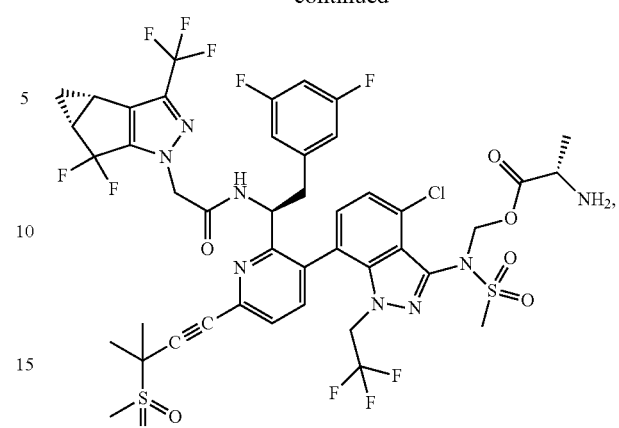
,

,
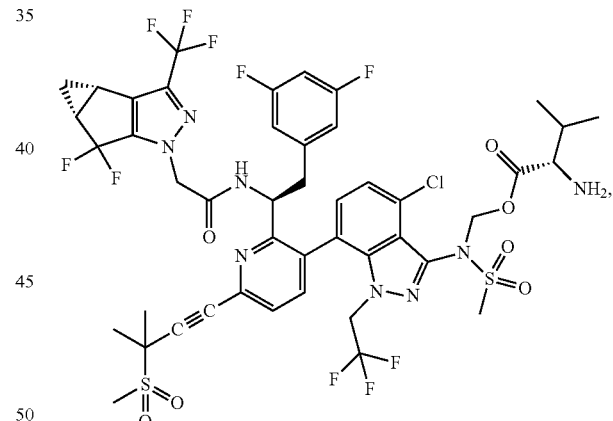
,
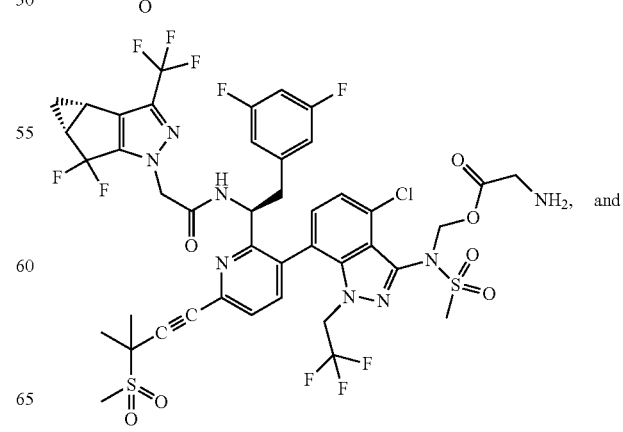 and -continued

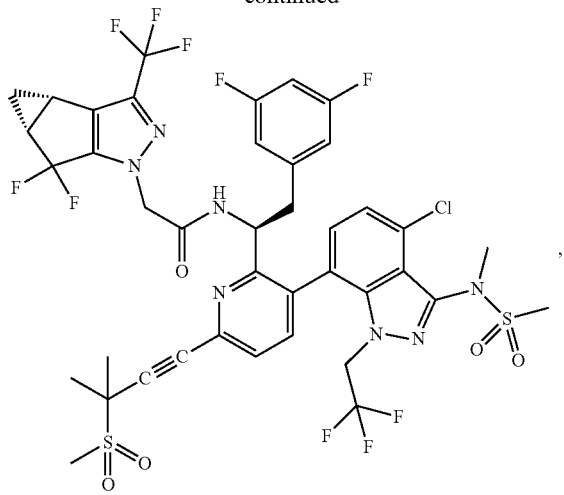

or a pharmaceutically acceptable salt thereof.

In some embodiments, the dosing of the compounds of Formula I results in the formation of lenacapavir, which is known to be active against HIV, as disclosed, for example, in U.S. Pat. No. 10,071,985. In some embodiments, the compounds of Formula I are converted to lenacapavir in the gastrointestinal tract. In some embodiments, the compounds of Formula I are more soluble than lenacapavir and thus are administered orally at a lower effective dose than the required oral effective dose for lenacapavir to achieve the same level of exposure of lenacapavir in vivo.

III. Compositions and Kits

Compounds provided herein, or pharmaceutically acceptable salts thereof, are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein, or pharmaceutically acceptable salts thereof, may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (i.e., a compound of Formula I), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (i.e., one, two, three, four; one or two; one to three; or one to four) additional therapeutic agents, or a pharmaceutically acceptable salt thereof. In some embodiments, the pharmaceutical compositions further comprise a therapeutically effective amount of the one or more (i.e., one, two, three, four; one or two; one to three; or one to four) additional therapeutic agents, or a pharmaceutically acceptable salt thereof.

In some embodiments, the one or more additional therapeutic agents include agents that are therapeutic for an HIV virus infection. In some embodiments, the one or more additional therapeutic agents is an anti-HIV agent. In some embodiments, the one or more additional therapeutic agents is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, anti-HIV peptides, and any combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and any combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and any combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and any combinations thereof.

In some embodiments, the additional therapeutic agent or agents are chosen from dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

In some embodiments, the additional therapeutic agent or agents are chosen from dolutegravir, cabotegravir, darunavir, bictegravir, elsulfavirine, rilpivirine, and any combinations thereof, or a pharmaceutically acceptable salt thereof.

Examples of combination drugs include, but are not limited to, ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY® (bictegravir+emtricitabine+tenofovir alafenamide), DOVATO® (dolutegravir+lamivudine), TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir +abacavir+lamivudine, lamivudine, cabotegravir+rilpivirine, 3-BNC117+albuvirtide, elpida (elsulfavirine, VM-1500), and VM-1500A, and dual-target HIV-1 reverse transcriptase/nucleocapsid protein 7 inhibitors.

In one embodiment, provided herein are pharmaceutical compositions comprising a therapeutically effective amount of a compound provided herein, or a pharmaceutically acceptable salt thereof, and a pharmaceutically acceptable excipient.

In some embodiments, the pharmaceutical compositions provided herein further comprise one, two, three, or four additional therapeutic agents.

In some embodiments, the pharmaceutical compositions provided herein further comprise one, two, three, or four additional therapeutic agents, wherein the additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

In some embodiments, the pharmaceutical compositions provided herein further comprise one, two, three, or four additional therapeutic agents, wherein the additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, "antibody-like" therapeutic proteins, or any combinations thereof.

In some embodiments, the pharmaceutical compositions provided herein further comprise one, two, three, or four additional therapeutic agents, wherein the additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. In some embodiments, the compounds, or pharmaceutically acceptable salts thereof, and pharmaceutical compositions disclosed herein are administered by subcutaneous injection.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments, the sterile injectable preparation disclosed herein may also be a sterile injectable solution or suspension prepared from a reconstituted lyophilized powder in a non-toxic parenterally acceptable diluent or solvent, such as a solution in 1,3-butane-diol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009. Examples of solubilizing excipients in a parenteral formulation (e.g., an SC or IM formulation) include, but are not limited to, polysorbates (such as polysorbate 20 or 80) and poloxamers (such as poloxamer 338, 188, or 207).

In some embodiments, the compounds, or pharmaceutically acceptable salts thereof, and pharmaceutical compositions disclosed herein are administered with implants.

Oral administration may be another route for administration of the compounds provided herein or pharmaceutically acceptable salts thereof. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds provided herein or pharmaceutically acceptable salts thereof may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one embodiment, provided herein are kits that comprise a compound provided herein, (i.e., a compound of Formula I), or a pharmaceutically acceptable salt, stereoisomer, prodrug, or solvate thereof, and suitable packaging. In some embodiments, the kit further comprises instructions for use. In some embodiments, the kit comprises a compound provided herein (i.e., a compound of Formula I), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (i.e., one, two, three, four; one or two; one to three; or one to four) additional therapeutic agents, or a pharmaceutically acceptable salt thereof.

In one embodiment, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

The methods provided herein may be applied to cell populations in vivo or ex vivo. "In vivo" means within a living individual, as within an animal or human. In this context, the methods provided herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the present disclosure may be used for a variety of purposes, including therapeutic and experimental purposes. For example, the present disclosure may be used ex vivo to determine the optimal schedule and/or dosing of administration of a compound as disclosed herein for a given cell type, individual, and other parameters. Information gleaned from such use may be used for experimental purposes or in the clinic to set protocols for in vivo treatment. Other ex vivo uses for which the present disclosure may be suited are described below or will become apparent to those skilled in the art. The selected compounds may be further characterized to examine the safety or tolerance dosage in human or non-human subjects. Such properties may be examined using commonly known methods to those skilled in the art.

In one embodiment, the present disclosure provides a method of treating or preventing a human immunodeficiency virus (HIV) infection in a patient in need thereof comprising administering to the patient a therapeutically effective amount of a compound provided herein, or a pharmaceutically acceptable salt thereof, or a pharmaceutical composition provided herein.

In one embodiment, the present disclosure provides a method of treating a human immunodeficiency virus (HIV) infection in a heavily treatment-experienced patient, the method comprising administering to the patient a therapeutically effective amount of a compound provided herein, or a pharmaceutically acceptable salt thereof, or a pharmaceutical composition provided herein.

In some embodiments, the methods provided herein further comprise administering a therapeutically effective amount of one, two, three, or four additional therapeutic agents, or a pharmaceutically acceptable salt thereof.

In some embodiments, the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

In some embodiments, the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and "antibody-like" therapeutic proteins, or any combinations thereof.

In some embodiments, the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

In some embodiments of the methods provided herein, the patient is a human.

In one embodiment, the present disclosure provides a therapeutically effective amount of a compound provided herein, or a pharmaceutically acceptable salt thereof, or a pharmaceutical composition provided herein for use in therapy.

In one embodiment, the present disclosure provides a compound provided herein, or a pharmaceutically acceptable salt, or a pharmaceutical composition provided herein for use in a method of treating or preventing a human immunodeficiency virus (HIV) infection in a patient in need thereof, the method comprising administering to the patient a therapeutically effective amount of the compound, or a pharmaceutically acceptable salt thereof, or the pharmaceutical composition.

In one embodiment, the present disclosure provides a compound provided herein, or a pharmaceutically acceptable salt thereof, or a pharmaceutical composition provided herein for use in a method of treating a human immunodeficiency virus (HIV) infection in a heavily treatment-experienced patient, the method comprising administering to the patient a therapeutically effective amount of the compound, or a pharmaceutically acceptable salt thereof, or the pharmaceutical composition.

In some embodiments, the uses provided herein further comprise administering a therapeutically effective amount of one, two, three, or four additional therapeutic agents, or a pharmaceutically acceptable salt thereof.

In some embodiments of the uses provided herein, the one, two, three, or four additional therapeutic agents are selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, and anti-HIV peptides, or any combinations thereof.

In some embodiments of the uses provided herein, the one, two, three, or four additional therapeutic agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, bispecific antibodies, and "antibody-like" therapeutic proteins, or any combinations thereof.

In some embodiments of the uses provided herein, the one, two, three, or four additional therapeutic agents are selected from the group consisting of dolutegravir, cabotegravir, darunavir, bictegravir, elsulfavirine, rilpivirine, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt thereof.

In some embodiments of the uses provided herein, the patient is a human.

V. Administration

The compounds of the present disclosure or pharmaceutically acceptable salts thereof (also referred to herein as the active ingredients) can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein, or pharmaceutically acceptable salts thereof, is that they are orally bioavailable and can be dosed orally.

A compound of the present disclosure, or a pharmaceutically acceptable salt thereof, may be administered to an individual in accordance with an effective dosing regimen for a desired period of time or duration, such as at least about one month, at least about 2 months, at least about 3 months, at least about 6 months, or at least about 12 months or longer. In some embodiments, the compound, or a pharmaceutically acceptable salt thereof, is administered on a daily or intermittent schedule for the duration of the individual's life.

The specific dose level of a compound of the present disclosure, or a pharmaceutically acceptable salt thereof, for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound provided herein, or a pharmaceutically acceptable salt thereof, per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The dosage may also be described as a total amount of a compound described herein, or a pharmaceutically acceptable salt thereof, administered per dose. The dosage or dosing frequency of a compound of the present disclosure, or a pharmaceutically acceptable salt thereof, may be adjusted over the course of the treatment, based on the judgment of the administering physician.

The compounds of the present disclosure, or pharmaceutically acceptable salts thereof, may be administered to an individual (e.g., a human) in a therapeutically effective amount. In some embodiments, the compound of Formula I, or a pharmaceutically acceptable salt thereof, is administered once daily, once weekly, once monthly, once every two months, once every three months, or once every six months. In some embodiments, the compound of Formula I, or a pharmaceutically acceptable salt thereof, is administered once daily. In some embodiments, the compound of Formula I, or a pharmaceutically acceptable salt thereof, is administered once weekly. In some embodiments, the compound of Formula I, or a pharmaceutically acceptable salt thereof, is administered once monthly. In some embodiments, the compound of Formula I, or a pharmaceutically acceptable salt thereof, is administered once every two months. In some embodiments, the compound of Formula I, or a pharmaceutically acceptable salt thereof, is administered once every three months. In some embodiments, the compound of Formula I, or a pharmaceutically acceptable salt thereof, is administered once every six months.

The compounds provided herein, or pharmaceutically acceptable salts thereof, can be administered by any useful route and means, such as by oral or parenteral (e.g., intravenous) administration. Therapeutically effective amounts of the compound, or a pharmaceutically acceptable salt thereof, may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein, or pharmaceutically acceptable salts thereof, include from about 0.3 mg to about 30 mg per day, or from about 30 mg to about 300 mg per day, or from about 0.3 µg to about 30 mg per day, or from about 30 µg to about 300 µg per day.

A compound of the present disclosure, or a pharmaceutically acceptable salt thereof, may be combined with one or more additional therapeutic agents in any dosage amount of the compound of the present disclosure or a pharmaceutically acceptable salt thereof (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, or a pharmaceutically acceptable salt thereof, are about 50, 100, 125, 150, 175, 200, 225, 250, 275, or 300 mg per dose. Other therapeutically effective amounts of the compound of Formula I, or pharmaceutically acceptable salts thereof, are about 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, a therapeutically effective amount of the compound of Formula I, or a pharmaceutically acceptable salt thereof, is about 1 mg to about 1000 mg. In some embodiments, a therapeutically effective amount of the compound of Formula I, or a pharmaceutically acceptable salt thereof, is about 1 mg to about 900 mg. In some embodiments, a therapeutically effective amount of the compound of Formula I, or a pharmaceutically acceptable salt thereof, is about 1 mg to about 800 mg. In some embodiments, a therapeutically effective amount of the compound of Formula I, or a pharmaceutically acceptable salt thereof, is about 1 mg to about 700 mg. In some embodiments, a therapeutically effective amount of the compound of Formula I, or a pharmaceutically acceptable salt thereof, is about 1 mg to about 600 mg. In some embodiments, a therapeutically effective amount of the compound of Formula I, or a pharmaceutically acceptable salt thereof, is about 1 mg to about 500 mg. In some embodiments, a therapeutically effective amount of the compound of Formula I, or a pharmaceutically acceptable salt thereof, is about 1 mg to about 400 mg. In some embodiments, a therapeutically effective amount of the compound of Formula I, or a pharmaceutically acceptable salt thereof, is about 1 mg to about 300 mg. In some embodiments, a therapeutically effective amount of the compound of Formula I, or a pharmaceutically acceptable salt thereof, is about 1 mg to about 200 mg. In some embodiments, a therapeutically effective amount of the compound of Formula I, or a pharmaceutically acceptable salt thereof, is about 1 mg to about 100 mg. In some embodiments, a therapeutically effective amount of the compound of Formula I, or a pharmaceutically acceptable salt thereof, is about 1 mg to about 75 mg. In some embodiments, a therapeutically effective amount of the compound of Formula I, or a pharmaceutically acceptable salt thereof, is about 1 mg to about 50 mg. In some embodiments, a therapeutically effective amount of the compound of Formula I, or a pharmaceutically acceptable salt thereof, is about 1 mg to about 25 mg. In some embodiments, a therapeutically effective amount of the compound of Formula I, or a pharmaceutically acceptable salt thereof, is about 1 mg to about 20 mg. In some embodiments, a therapeutically effective amount of the compound of Formula I, or a pharmaceutically acceptable salt thereof, is about 1 mg to about 15 mg. In some embodiments, a therapeutically effective amount of the compound of Formula I, or a pharmaceutically acceptable salt thereof, is about 1 mg to about 10 mg. In some embodiments, a therapeutically effective amount of the compound of Formula I, or a pharmaceutically acceptable salt thereof, is about 1 mg to about 5 mg.

In some embodiments, a therapeutically effective amount of the compound of Formula I, or a pharmaceutically acceptable salt thereof, is about 50 mg, about 75 mg, about 100 mg, about 125 mg, about 150 mg, about 175 mg, about 200 mg, about 225 mg, about 275 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, or about 1050 mg. In some embodiments, a therapeutically effective amount of the compound of Formula I, or a pharmaceutically acceptable salt thereof, is about 5 mg. In some embodiments, a therapeutically effective amount of the compound of Formula I, or a pharmaceutically acceptable salt thereof, is about 100 mg. In some embodiments, a therapeutically effective amount of the compound of Formula I, or a pharmaceutically acceptable salt thereof, is about 150 mg. In some embodiments, a therapeutically effective amount of the compound of Formula I, or a pharmaceutically acceptable salt thereof, is about 200 mg. In some embodiments, a therapeutically effective amount of the compound of Formula I, or a pharmaceutically acceptable salt thereof, is about 250 mg. In some embodiments, a therapeutically effective amount of the compound of Formula I, or a pharmaceutically acceptable salt thereof, is about 300 mg. In some embodiments, a therapeutically effective amount of the compound of Formula I, or a pharmaceutically acceptable salt thereof, is about 350 mg. In some embodiments, a therapeutically effective amount of the compound of Formula I, or a pharmaceutically acceptable salt thereof, is about 400 mg. In some embodiments, a therapeutically effective amount of the compound of Formula I, or a pharmaceutically acceptable salt thereof, is about 450 mg. In some embodiments, a therapeutically effective amount of the compound of Formula I, or a pharmaceutically acceptable salt thereof, is about 500 mg. In some embodiments, a therapeutically effective amount of the compound of Formula I, or a pharmaceutically acceptable salt thereof, is about 550 mg. In some embodiments, a therapeutically effective amount of the compound of Formula I, or a pharmaceutically acceptable salt thereof, is about 600 mg. In some embodiments, a therapeutically effective amount of the compound of Formula I, or a pharmaceutically acceptable salt thereof, is about 650 mg. In some embodiments, a therapeutically effective amount of the compound of Formula I, or a pharmaceutically acceptable salt thereof, is about 700 mg. In some embodiments, a therapeutically effective amount of the compound of Formula I, or a pharmaceutically acceptable salt thereof, is about 750 mg. In some embodiments, a therapeutically effective amount of the compound of Formula I, or a pharmaceutically acceptable salt thereof, is about 800 mg. In some embodiments, a therapeutically effective amount of the compound of Formula I, or a pharmaceutically acceptable salt thereof, is about 850 mg. In some embodiments, a therapeutically effective amount of the compound of Formula I, or a pharmaceutically acceptable salt thereof, is about 900 mg. In some embodiments, a therapeutically effective amount of the compound of Formula I, or a pharmaceutically acceptable salt thereof, is about 950 mg. In some embodiments, a therapeutically effective amount of the compound of Formula I, or a pharmaceutically acceptable salt thereof, is about 1000 mg. In some embodiments, a therapeutically effective amount of the compound of Formula I, or a pharmaceutically acceptable salt thereof, is about 1050 mg.

When administered orally, the total weekly dosage for a human subject may be between about 1 mg and 1,000 mg/week, between about 10-500 mg/week, between about 50-300 mg/week, between about 75-200 mg/week, or between about 100-150 mg/week. In some embodiments, the total weekly dosage for a human subject may be about 100, 200, 300, 400, 500, 600, 700, 800, 900, or 1000 mg/week administered in a single dose. In some embodiments, the total weekly dosage for a human subject of a compound of Formula I, or a pharmaceutically acceptable salt thereof, may be about 100 mg administered in a single dose. In some embodiments, the total weekly dosage for a human subject of a compound of Formula I, or a pharmaceutically acceptable salt thereof, may be about 150 mg administered in a single dose. In some embodiments, the total weekly dosage for a human subject of a compound of Formula I, or a pharmaceutically acceptable salt thereof, may be about 200 mg administered in a single dose. In some embodiments, the total weekly dosage for a human subject of a compound of Formula I, or a pharmaceutically acceptable salt thereof, may be about 250 mg administered in a single dose. In some embodiments, the total weekly dosage for a human subject of a compound of Formula I, or a pharmaceutically acceptable salt thereof, may be about 300 mg administered in a single dose. In some embodiments, the total weekly dosage for a human subject of a compound of Formula I, or a pharmaceutically acceptable salt thereof, may be about 350 mg administered in a single dose. In some embodiments, the total weekly dosage for a human subject of a compound of Formula I, or a pharmaceutically acceptable salt thereof, may be about 400 mg administered in a single dose. In some embodiments, the total weekly dosage for a human subject of a compound of Formula I, or a pharmaceutically acceptable salt thereof, may be about 450 mg administered in a single dose. In some embodiments, the total weekly dosage for a human subject of a compound of Formula I, or a pharmaceutically acceptable salt thereof, may be about 500 mg administered in a single dose.

When administered orally, the total monthly dosage for a human subject of a compound of Formula I, or a pharmaceutically acceptable salt thereof, may be between about 500 mg and 1,000 mg/month, between about 600-900 mg/month, or between about 700-800 mg/month. In some embodiments, the total weekly dosage for a human subject of a compound of Formula I, or a pharmaceutically acceptable salt thereof, may be about 100, 200, 300, 400, 500, 600, 700, 800, 900, or 1000 mg/week administered in a single dose. In some embodiments, the total monthly dosage for a human subject of a compound of Formula I, or a pharmaceutically acceptable salt thereof, may be about 500 mg administered in a single dose. In some embodiments, the total monthly dosage for a human subject may be about 550 mg administered in a single dose. In some embodiments, the total monthly dosage for a human subject of a compound of Formula I, or a pharmaceutically acceptable salt thereof, may be about 600 mg administered in a single dose. In some embodiments, the total monthly dosage for a human subject of a compound of Formula I, or a pharmaceutically acceptable salt thereof, may be about 650 mg administered in a single dose. In some embodiments, the total monthly dosage for a human subject of a compound of Formula I, or a pharmaceutically acceptable salt thereof, may be about 700 mg administered in a single dose. In some embodiments, the total monthly dosage for a human subject of a compound of Formula I, or a pharmaceutically acceptable salt thereof, may be about 750 mg administered in a single dose. In some embodiments, the total monthly dosage for a human subject of a compound of Formula I, or a pharmaceutically acceptable salt thereof, may be about 800 mg administered in a single dose. In some embodiments, the total monthly dosage for a human subject of a compound of Formula I, or a pharmaceutically acceptable salt thereof, may be about 850 mg administered in a single dose. In some embodiments, the total monthly dosage for a human subject of a compound of Formula I, or a pharmaceutically acceptable salt thereof, may be about 900 mg administered in a single dose. In some embodiments, the total monthly dosage for a human subject of a compound of Formula I, or a pharmaceutically acceptable salt thereof, may be about 950 mg administered in a single dose. In some embodiments, the total monthly dosage for a human subject of a compound of Formula I, or a pharmaceutically acceptable salt thereof, may be about 1000 mg administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound provided herein, or a pharmaceutically acceptable salt thereof, is administered once daily in a method disclosed herein. In some embodiments, a compound provided herein, or a pharmaceutically acceptable salt thereof, is administered twice daily in a method disclosed herein.

In some embodiments, a compound provided herein, or a pharmaceutically acceptable salt thereof, is administered once daily in a method disclosed herein. In some embodiments, a compound provided herein, or a pharmaceutically acceptable salt thereof, is administered once weekly in a method disclosed herein. In some embodiments, a compound provided herein, or a pharmaceutically acceptable salt thereof, is administered once monthly in a method disclosed herein. In some embodiments, a compound provided herein, or a pharmaceutically acceptable salt thereof, is administered once every two months in a method disclosed herein. In some embodiments, a compound provided herein, or a pharmaceutically acceptable salt thereof, is administered once every three months in a method disclosed herein. In some embodiments, a compound provided herein, or a pharmaceutically acceptable salt thereof, is administered once every six months in a method disclosed herein.

In some embodiments, a compound provided herein, or a pharmaceutically acceptable salt thereof, is administered orally in a single dose of about 100 mg once weekly. In some embodiments, a compound provided herein, or a pharmaceutically acceptable salt thereof, is administered orally in a single dose of about 150 mg once weekly. In some embodiments, a compound provided herein, or a pharmaceutically acceptable salt thereof, is administered orally in a single dose of about 200 mg once weekly. In some embodiments, a compound provided herein, or a pharmaceutically acceptable salt thereof, is administered orally in a single dose of about 250 mg once weekly. In some embodiments, a compound provided herein, or a pharmaceutically acceptable salt thereof, is administered orally in a single dose of about 300 mg once weekly. In some embodiments, a compound provided herein, or a pharmaceutically acceptable salt thereof, is administered orally in a single dose of about 350 mg once weekly. In some embodiments, a compound provided herein, or a pharmaceutically acceptable salt thereof, is administered orally in a single dose of about 400 mg once weekly. In some embodiments, a compound provided herein, or a pharmaceutically acceptable salt thereof, is administered orally in a single dose of about 450 mg once weekly. In some embodiments, a compound provided herein, or a pharmaceutically acceptable salt thereof, is administered orally in a single dose of about 500 mg once weekly.

In some embodiments, a compound provided herein, or a pharmaceutically acceptable salt thereof, is administered orally in a single dose of about 500 mg once monthly. In some embodiments, a compound provided herein, or a pharmaceutically acceptable salt thereof, is administered orally in a single dose of about 550 mg once monthly. In some embodiments, a compound provided herein, or a pharmaceutically acceptable salt thereof, is administered orally in a single dose of about 600 mg once monthly. In some embodiments, a compound provided herein, or a pharmaceutically acceptable salt thereof, is administered orally in a single dose of about 650 mg once monthly. In some embodiments, a compound provided herein, or a pharmaceutically acceptable salt thereof, is administered orally in a single dose of about 700 mg once monthly. In some embodiments, a compound provided herein, or a pharmaceutically acceptable salt thereof, is administered orally in a single dose of about 750 mg once monthly. In some embodiments, a compound provided herein, or a pharmaceutically acceptable salt thereof, is administered orally in a single dose of about 800 mg once monthly. In some embodiments, a compound provided herein, or a pharmaceutically acceptable salt thereof, is administered orally in a single dose of about 850 mg once monthly. In some embodiments, a compound provided herein, or a pharmaceutically acceptable salt thereof, is administered orally in a single dose of about 900 mg once monthly. In some embodiments, a compound provided herein, or a pharmaceutically acceptable salt thereof, is administered orally in a single dose of about 950 mg once monthly. In some embodiments, a compound provided herein, or a pharmaceutically acceptable salt thereof, is administered orally in a single dose of about 1000 mg once monthly.

The frequency of dosage of the compound of the present disclosure, or a pharmaceutically acceptable salt thereof, will be determined by the needs of the individual patient and can be, for example, once per day, once per week, once per month, once per every two months, once per every three months, or once per every six months. Administration of the compound, or a pharmaceutically acceptable salt thereof, continues for as long as necessary to treat the Retroviridae infection, including an HIV infection, or any other indication described herein. For example, a compound, or a pharmaceutically acceptable salt thereof, can be administered to a human suffering from a Retroviridae infection, including an HIV infection, for the duration of the human's life.

Administration can be intermittent, with a period of several or more days during which a patient receives a daily dose of the compound of the present disclosure, or a pharmaceutically acceptable salt thereof, followed by a period of several or more days during which a patient does not receive a daily dose of the compound or a pharmaceutically acceptable salt thereof. For example, a patient can receive a dose of the compound, or a pharmaceutically acceptable salt thereof, every other day, or three times per week. Again by way of example, a patient can receive a dose of the compound, or a pharmaceutically acceptable salt thereof, each day for a period of from 1 to 14 days, followed by a period of 7 to 21 days during which the patient does not receive a dose of the compound, or a pharmaceutically acceptable salt thereof, followed by a subsequent period (e.g., from 1 to 14 days) during which the patient again receives a daily dose of the compound, or a pharmaceutically acceptable salt thereof. Alternating periods of administration of the compound, or a pharmaceutically acceptable salt thereof, followed by non-administration of the compound, or a pharmaceutically acceptable salt thereof, can be repeated as clinically required to treat the patient.

The compounds of the present disclosure, or pharmaceutically acceptable salts thereof, or the pharmaceutical compositions of the present disclosure may be administered once, twice, three, or four times daily, using any suitable mode described above. Also, administration or treatment with the compounds, or pharmaceutically acceptable salts thereof, may be continued for a number of days; for example, commonly treatment would continue for at least 7 days, 14 days, or 28 days, for one cycle of treatment. Treatment cycles are well known for Retroviridae infections, including an HIV infection. In some embodiments, treatment cycles are frequently alternated with resting periods of about 1 to 28 days, commonly about 7 days or about 14 days, between cycles. The treatment cycles, in other embodiments, may also be continuous.

VI. Combination Therapy

Patients being treated by administration of the compounds provided herein, or pharmaceutically acceptable salts thereof, often exhibit diseases or conditions that benefit from treatment with other therapeutic agents, including agents that are therapeutic for Retroviridae infections, including an HIV infection. In some embodiments, the other therapeutic agent is an agent that is therapeutic for an HIV infection. Thus, one aspect of the disclosure is a method of treating an HIV infection comprising administering a compound of the present disclosure, or a pharmaceutically acceptable salt thereof, in combination with one or more compounds useful for the treatment of an HIV infection to a subject, particularly a human subject, in need thereof.

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure, or a pharmaceutically acceptable salt thereof, is combined with one or more additional therapeutic agents as described herein, the components of the composition are administered as a simultaneous or sequential regimen. When administered sequentially, the combination may be administered in two or more administrations.

In some embodiments, a compound of the present disclosure, or a pharmaceutically acceptable salt thereof, is combined with one or more additional therapeutic agents in a unitary dosage form for simultaneous administration to a patient, for example as a solid dosage form for oral administration.

In some embodiments, a compound of the present disclosure, or a pharmaceutically acceptable salt thereof, is co-administered with one or more additional therapeutic agents.

Co-administration includes administration of unit dosages of the compounds provided herein, or pharmaceutically acceptable salts thereof, before or after administration of unit dosages of one or more additional therapeutic agents. The compounds provided herein, or pharmaceutically acceptable salts thereof, may be administered within seconds, minutes, or hours of the administration of one or more additional therapeutic agents. For example, in some embodiments, a unit dose of a compound provided herein, or a pharmaceutically acceptable salt thereof, is administered first, followed within seconds or minutes by administration of a unit dose of one or more additional therapeutic agents. Alternatively, in other embodiments, a unit dose of one or more additional therapeutic agents is administered first, followed by administration of a unit dose of a compound provided herein, or a pharmaceutically acceptable salt thereof, within seconds or minutes. In some embodiments, a unit dose of a compound provided herein, or a pharmaceutically acceptable salt thereof, is administered first, followed, after a period of hours (i.e., 1-12 hours), by administration of a unit dose of one or more additional therapeutic agents. In other embodiments, a unit dose of one or more additional therapeutic agents is administered first, followed, after a period of hours (i.e., 1-12 hours), by administration of a unit dose of a compound provided herein or a pharmaceutically acceptable salt thereof.

In some embodiments, a compound of Formula I, or a pharmaceutically acceptable salt thereof, is formulated as a tablet, which may optionally contain one or more other compounds useful for treating the disease being treated. In certain embodiments, the tablet can contain another active ingredient for treating a Retroviridae infection, including an HIV infection. In some embodiments, such tablets are suitable for once daily dosing. In some embodiments, such tablets are suitable for once weekly dosing. In some embodiments, such tablets are suitable for once monthly dosing. In some embodiments, such tablets are suitable for once every two months dosing. In some embodiments, such tablets are suitable for once every three months dosing. In some embodiments, such tablets are suitable for once every six months dosing.

Also provided herein are methods of treatment in which a compound of Formula I, or a tautomer or pharmaceutically acceptable salt thereof, is given to a patient in combination with one or more additional therapeutic agents or therapy. In some embodiments, the total daily dosage of a compound of Formula I, or a tautomer, or a pharmaceutically acceptable salt thereof, may be about 1 to about 500 mg administered in a single dose for a human subject.

HIV Combination Therapy

In the above embodiments, the additional therapeutic agent or agents may be an anti-HIV agent. In some instances, the additional therapeutic agent can be HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolyl endopeptidase inhibitors, Phospholipase A2 inhibitors, pharmacokinetic enhancers, HIV gene therapy, HIV vaccines, anti-HIV peptides, and combinations thereof.

In some embodiments, the additional therapeutic agent or agents are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and combinations thereof.

In some embodiments, the additional therapeutic agent or agents any are chosen from dolutegravir, cabotegravir, darunavir, bictegravir, elsulfavirine, rilpivirine, and lenacapavir, and combinations thereof.

HIV Combination Drugs

Examples of combination drugs include, but are not limited to, ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+ FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY® (bictegravir+emtricitabine+tenofovir alafenamide), DOVATO® (dolutegravir+lamivudine), TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir +abacavir+ lamivudine, lamivudine, cabotegravir+rilpivirine, 3-BNC117+albuvirtide, elpida (elsulfavirine, VM-1500), and VM-1500A, and dual-target HIV-1 reverse transcriptase/nucleocapsid protein 7 inhibitors.

Other HIV Drugs

Examples of other drugs for treating HIV include, but are not limited to, aspernigrin C, acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, bevirimat derivatives, ABBV-382, ABX-464, AG-1105, APH-0812, APH0202, bryostatin-1, bryostatin analogs, BIT-225, BRII-732, BRII-778, CYT-107, CS-TATI-1, fluoro-beta-D-arabinose nucleic acid (FANA)-modified antisense oligonucleotides, FX-101, griffithsin, GSK-3739937, GSK-3739937 (long-acting), HGTV-43, HPH-116, HS-10234, hydroxychloroquine, IMB-10035, IMO-3100, IND-02, JL-18008, LADAVRU, MK-1376, MK-2048, MK-4250, MK-8507, MK-8558, NOV-205, OB-002H, ODE-Bn-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, xl-081, AVI-CO-004, rfhSP-D, [18F]-MC-225, URMC-099-C, RES-529, Verdinexor, IMC-M113V, IML-106, antiviral fc conjugate (AVC), WP-1096, WP-1097, Gammora, ISR-CO48, ISR-48, ISR-49, MK-8527, cannabinoids, ENOB-HV-32, HiviCide-I, T-1144, VIR-576, nipamovir, Covimro, and ABBV-1882.

HIV Protease Inhibitors

Examples of HIV protease inhibitors include, but are not limited to, amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, ASC-09+ritonavir, AEBL-2, DG-17, GS-1156, TMB-657 (PPL-100), T-169, BL-008, MK-8122, TMB-607, GRL-02031, and TMC-310911. Additional examples of HIV protease inhibitors are described, e.g., in U.S. Pat. No. 10,294,234, and U.S. Patent Application Publication Nos. US2020030327 and US2019210978.

HIV Gag Protein Inhibitors

Examples of HIV Gag protein inhibitors include, but are not limited to, HRF-10071.

HIV Ribonuclease H Inhibitors

Examples of HIV ribonuclease H inhibitors include, but are not limited to, NSC-727447.

HIV Nef Inhibitors

Examples of HIV Nef inhibitors include, but are not limited to, FP-1.

HIV Reverse Transcriptase Inhibitors

Examples of HIV non-nucleoside or non-nucleotide inhibitors of reverse transcriptase include, but are not limited to, dapivirine, delavirdine, delavirdine mesylate, doravirine, efavirenz, etravirine, lentinan, nevirapine, rilpivirine, ACC-007, ACC-008, AIC-292, F-18, KM-023, PC-1005, M1-TFV, M2-TFV, VM-1500A-LAI, PF-3450074, elsulfavirine (sustained release oral, HIV infection), elsulfavirine (long acting injectable nanosuspension, HIV infection), and elsulfavirine (VM-1500). Additional non-limiting examples of non-nucleoside or non-nucleotide inhibitors of reverse transcriptase include the compounds disclosed in U.S. Pat. No. 10,548,898.

Examples of HIV nucleoside or nucleotide inhibitors of reverse transcriptase include, but are not limited to, adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8583, VM-2500, and KP-1461.

Additional examples of HIV nucleoside or nucleotide inhibitors of reverse transcriptase include, but are not limited to, those described in patent publications US2007049754, US2016250215, US2016237062, US2016251347, US2002119443, US2013065856, US2013090473, US2014221356, and WO04096286.

HIV Integrase Inhibitors

Examples of HIV integrase inhibitors include, but are not limited to, elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T169, STP-0404, VM-3500, XVIR-110, and ACC-017. Additional non-limiting examples of HIV integrase inhibitors include the compounds disclosed in U.S. Pat. No. 11,084,832.

Examples of HIV non-catalytic site, or allosteric, integrase inhibitors (NCINI) include, but are not limited to, CX-05045, CX-05168, and CX-14442.

HIV Viral Infectivity Factor Inhibitors

Examples of HIV viral infectivity factor inhibitors include, but are not limited to, 2-amino-N-(2-methoxyphenyl)-6-((4-nitrophenyl)thio)benzamide derivatives, and Irino-L.

HIV Entry Inhibitors

Examples of HIV entry (fusion) inhibitors include, but are not limited to, AAR-501, LBT-5001, cenicriviroc, CCR5 inhibitors, gp41 inhibitors, CD4 attachment inhibitors, gp120 inhibitors, gp160 inhibitors, and CXCR4 inhibitors.

Examples of CCR5 inhibitors include, but are not limited to, aplaviroc, vicriviroc, maraviroc, maraviroc (long acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, thioraviroc and vMIP (Haimipu).

Examples of gp41 inhibitors include, but are not limited to, albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, Cl3hmAb, lipuvirtide, PIE-12 trimer and sifuvirtide.

Examples of CD4 attachment inhibitors include, but are not limited to, ibalizumab and CADA analogs.

Examples of gp120 inhibitors include, but are not limited to, anti-HIV microbicide, Radha-108 (receptol) 3B3-PE38, BMS818251, BanLec, bentonite-based nanomedicine, fostemsavir tromethamine, IQP-0831, VVX-004, and BMS-663068.

Examples of gp160 inhibitors include, but are not limited to, fangchinoline.

Examples of CXCR4 inhibitors include, but are not limited to, plerixafor, ALT-1188, N15 peptide, and vMIP (Haimipu).

HIV Maturation Inhibitors

Examples of HIV maturation inhibitors include, but are not limited to, BMS-955176, GSK-3640254 and GSK-2838232.

Latency Reversing Agents

Examples of latency reversing agents include, but are not limited to, toll-like receptor (TLR) agonists (including TLR7 agonists, e.g., GS-9620, TLR8 agonists, and TLR9 agonists), histone deacetylase (HDAC) inhibitors, proteasome inhibitors such as velcade, protein kinase C (PKC) activators, Smyd2 inhibitors, BET-bromodomain 4 (BRD4) inhibitors (such as ZL-0580, apabetalone), ionomycin, IAP antagonists (inhibitor of apoptosis proteins, such as APG-1387, LBW-242), SMAC mimetics (including TL32711, LCL161, GDC-0917, HGS1029, AT-406, Debio-1143), PMA, SAHA (suberanilohydroxamic acid, or suberoyl, anilide, and hydroxamic acid), NIZ-985, IL-15 modulating antibodies (including IL-15, IL-15 fusion proteins, and IL-15 receptor agonists), JQ1, disulfiram, amphotericin B, and ubiquitin inhibitors such as largazole analogs, APH-0812, and GSK-343. Examples of PKC activators include, but are not limited to, indolactam, prostratin, ingenol B, and DAG-lactones.

Additional examples of TLR7 agonists include, but are not limited to, those described in U.S. Patent Application Publication No. US2010143301.

Additional examples of TLR8 agonists include, but are not limited to, those described in U.S. Patent Application Publication No. US2017071944.

Histone Deacetylase (HDAC) Inhibitors

In some embodiments, the agents as described herein are combined with an inhibitor of a histone deacetylase, e.g., histone deacetylase 1, histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, and entinostat.

Capsid Inhibitors

Examples of capsid inhibitors include, but are not limited to, capsid polymerization inhibitors or capsid disrupting compounds, HIV nucleocapsid p7 (NCp7) inhibitors such as azodicarbonamide, HIV p24 capsid protein inhibitors, lenacapavir (GS-6207), GS-CA1, AVI-621, AVI-101, AVI-201, AVI-301, and AVI-CAN1-15 series, PF-3450074, HIV-1 capsid inhibitors (HIV-1 infection, Shandong University), and compounds described in (GSK WO2019/087016).

Additional examples of capsid inhibitors include, but not limited to, those described in U.S. Patent Application Publication Nos. US2018051005 and US2016108030.

Additional examples of HIV capsid inhibitors include, but are not limited to, those described in U.S. Patent Application Publication Nos. US2014221356 and US2016016973.

Cytochrome P450 3 Inhibitors

Examples of Cytochrome P450 3 inhibitors include, but are not limited to, those described in U.S. Pat. No. 7,939,553.

RNA Polymerase Modulators

Examples of RNA polymerase modulators include, but are not limited to, those described in U.S. Pat. Nos. 10,065,958 and 8,008,264.

Immune Checkpoint Modulators

In various embodiments, the agents as described herein, are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu et al., *J Exp Clin Cancer Res.* (2018) 37:110). In various embodiments, the immune checkpoint proteins or receptors regulate NK cell responses (e.g., reviewed in Davis et al., *Semin Immunol.* (2017) 31:64-75 and Chiossone et al., *Nat Rev Immunol.* (2018) 18(11):671-688).

Examples of immune checkpoint proteins or receptors include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAETiG; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); SLAM family member 7 (SLAMF7); and Hematopoietic Progenitor Kinase 1 (HPK1, MAP4K1).

In various embodiments, the agents described herein are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCDiLG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the agents, as described herein, are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu et al., *J Exp Clin Cancer Res.* (2018) 37:110.

In various embodiments, the agents as described herein, are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, the agents as described herein, are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis et al., *Semin Immunol.* (2017) 31: 64-75; Fang et al., *Semin Immunol.* (2017) 31:37-54; and Chiossone et al., *Nat Rev Immunol.* (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181(budigalimab), PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multi-specific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In various embodiments, the agents as described herein are combined with anti-TIGIT antibodies, such as BMS-986207, RG-6058, and AGEN-1307.

TNF Receptor Superfamily (TNFRSF) Member Agonists or Activators

In various embodiments, the agents as described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Examples of anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Examples of anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Examples of anti-TNFRSF9 (4-1BB, CD137) antibodies that can be co-administered include without limitation urelumab, utomilumab (PF-05082566), AGEN2373 and ADG-106.

Examples of anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Bi- and Tri-Specific Natural Killer (NK)-Cell Engagers

In various embodiments, the agents as described herein, are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (41BB). As appropriate, the anti-CD16 binding bi-specific molecules may or may not have an Fc. Illustrative bi-specific NK-cell engagers that can be co-administered target CD16 and one or more HIV-associated antigens as described herein. BiKEs and TriKEs are described, e.g., in Felices et al., Methods Mol Biol. (2016) 1441:333-346; Fang et al., Semin Immunol. (2017) 31:37-54. Examples of trispecific NK cell engagers (TRiKE) include, but are not limited to, OXS-3550, HIV-TriKE, and CD16-IL-15-B7H3 TriKe.

Indoleamine-Pyrrole-2,3-Dioxygenase (IDO1) Inhibitors

In various embodiments, the agents as described herein are combined with an inhibitor of indoleamine 2,3-dioxygenase 1 (IDO1; NCBI Gene ID: 3620). Examples of IDO1 inhibitors include without limitation, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, shIDO-ST, EOS-200271, KHK-2455, and LY-3381916.

Toll-Like Receptor (TLR) Agonists

In various embodiments, the agents as described herein are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered include without limitation AL-034, DSP-0509, GS-9620 (vesatolimod), vesatolimod analog, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR7/TLR8 agonists include without limitation NKTR-262, telratolimod and BDB-001. TLR8 agonists include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). TLR9 agonists include without limitation AST-008, cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. TLR4 agonists include, but are not limited to, G-100 and GSK-1795091.

CDK Inhibitors or Antagonists

In some embodiments, the agents described herein are combined with an inhibitor or antagonist of CDK. In some embodiments, the CDK inhibitor or antagonist is selected from the group consisting of VS2-370.

STING Agonists, RIG-1 and NOD2 Modulators

In some embodiments, the agents described herein are combined with a stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, STING agonist (latent HIV), 5,6-dimethylxanthenone-4-acetic acid (DMXAA), cyclic-GAMP (cGAMP) and cyclic-di-AMP. In some embodiments, the agents described herein are combined with a RIG-I modulator such as RGT-100, or NOD2 modulator, such as SB-9200, and IR-103.

LAG-3 and TIM-3 Inhibitors

In certain embodiments, the agents as described herein are combined with an anti-TIM-3 antibody, such as TSR-022, LY-3321367, MBG-453, INCAGN-2390.

In certain embodiments, the antibodies or antigen-binding fragments described herein are combined with an anti LAG-3 (Lymphocyte-activation) antibody, such as relatlimab (ONO-4482), LAG-525, MK-4280, REGN-3767, INCAGN2385.

Interleukin Agonists

In certain embodiments, the agents described herein are combined with an interleukin agonist, such as IL-2, IL-7, IL-15, IL-10, IL-12 agonists; examples of IL-2 agonists such as proleukin (aldesleukin, IL-2); BC-IL (Cel-Sci), pegylated IL-2 (e.g., NKTR-214); modified variants of IL-2 (e.g., THOR-707), bempegaldesleukin, AIC-284, ALKS-4230, CUI-101, Neo-2/15; examples of IL-15 agonists, such as ALT-803, NKTR-255, and hetIL-15, interleukin-15/Fc fusion protein, AM-0015, NIZ-985, SO-C101, IL-15 Synthorin (pegylated Il-15), P-22339, and a IL-15-PD-1 fusion protein N-809; examples of IL-7 include without limitation CYT-107.

Examples of additional immune-based therapies that can be combined with an agent of this disclosure include, but are not limited to, interferon alfa, interferon alfa-2b, interferon alfa-n3, pegylated interferon alfa, interferon gamma; FLT3 agonists such as CDX-301, GS-3583, gepon, normferon, peginterferon alfa-2a, peginterferon alfa-2b, and RPI-MN.

Phosphatidylinositol 3-kinase (PI3K) Inhibitors

Examples of PI3K inhibitors include, but are not limited to, idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include, but are not limited to, PTG-100, TRK-170, abrilumab, etrolizumab, carotegrast methyl, and vedolizumab.

HPK1 Inhibitors

Examples of HPK1 inhibitors include, but are not limited to, ZYF-0272, and ZYF-0057.

HIV Targeting Antibodies

Examples of HIV antibodies, bispecific antibodies, and "antibody-like" therapeutic proteins include, but are not limited to, DARTs®, DUOBODIES®, BITES®, XmAbs®, TandAbs®, Fab derivatives, bNAbs (broadly neutralizing HIV-1 antibodies), TMB-360, TMB-370, and those targeting HIV gp120 or gp41, antibody-Recruiting Molecules targeting HIV, anti-CD63 monoclonal antibodies, anti-GB virus C antibodies, anti-GP120/CD4, gp120 bispecific monoclonal antibody, CCR5 bispecific antibodies, anti-Nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT- 121), PGT121.414.LS, ibalizumab, ibalizumab (second generation), Immuglo, MB-66, clone 3 human monoclonal antibody targeting KLIC (HIV infection), GS-9721, BG-HIV, VRC-HIVMAB091-00-AB.

Various bNAbs may be used. Examples include, but are not limited to, those described in U.S. Pat. Nos. 8,673,307, 9,493,549, 9,783,594, 10,239,935, US2018371086, US2020223907, WO2014/063059, WO2012/158948, WO2015/117008, and PCT/US2015/41272, and WO2017/096221, including antibodies 12A12, 12A21, NIH45-46, bANC131, 8ANC134, 1B2530, INC9, 8ANC195, 8ANC196, 10-259, 10-303, 10-410, 10-847, 10-996, 10-1074, 10-1121, 10-1130, 10-1146, 10-1341, 10-1369, and 10-1074GM. Additional examples include those described in Klein et al., Nature, 492(7427): 118-22 (2012), Horwitz et al., Proc Natl Acad Sci USA, 110(41): 16538-43 (2013), Scheid et al., Science, 333: 1633-1637 (2011), Scheid et al., Nature, 458:636-640 (2009), Eroshkin et al, Nucleic Acids Res., 42 (Database issue):Dl 133-9 (2014), Mascola et al., Immunol Rev., 254(1):225-44 (2013), such as 2F5, 4E10, M66.6, CAP206-CH12, 10E81 (all of which bind the MPER of gp41); PG9, PG16, CH01-04 (all of which bind V1V2-glycan), 2G12 (which binds to outer domain glycan); b12, HJ16, CH103-106, VRC01-03, VRC-PG04, 04b, VRC-CH30-34, 3BNC62, 3BNC89, 3BNC91, 3BNC95, 3BNC104, 3BNC176, and 8ANC131 (all of which bind to the CD4 binding site).

Additional broadly neutralizing antibodies that can be used as a second therapeutic agent in a combination therapy are described, e.g., in U.S. Pat. Nos. 8,673,307; 9,493,549; 9,783,594; and WO 2012/154312; WO2012/158948; WO 2013/086533; WO 2013/142324; WO2014/063059; WO 2014/089152, WO 2015/048462; WO 2015/103549; WO 2015/117008; WO2016/014484; WO 2016/154003; WO 2016/196975; WO 2016/149710; WO2017/096221; WO 2017/133639; WO 2017/133640, which are hereby incorporated herein by reference in their entireties for all purposes. Additional examples include, but are not limited to, those described in Sajadi et al., Cell. (2018) 173(7):1783-1795; Sajadi et al., J Infect Dis. (2016) 213(1):156-64; Klein et al., Nature, 492(7427): 118-22 (2012), Horwitz et al., Proc Natl Acad Sci USA, 110(41): 16538-43 (2013), Scheid et al., Science, 333: 1633-1637 (2011), Scheid et al., Nature, 458:636-640 (2009), Eroshkin et al., Nucleic Acids Res., 42 (Database issue):Dl 133-9 (2014), Mascola et al., Immunol Rev., 254(1):225-44 (2013), such as 2F5, 4E10, M66.6, CAP206-CH12, 10E8, 10E8v4, 10E8-5R-100cF, DH511.11P, 7b2, 10-1074, and LN01 (all of which bind the MPER of gp41).

Examples of additional antibodies include, but are not limited to, bavituximab, UB-421, BF520.1, BiIA-SG, CH01, CH59, C2F5, C4E10, C2F5+C2G12+C4E10, CAP256V2LS, 3BNC117, 3BNC117-LS, 3BNC60, DH270.1, DH270.6, D1D2, 10-1074-LS, Cl3hmAb, GS-9722 (elipovimab), DH411-2, BG18, GS-9721, GS-9723, PGT145, PGT121, PGT-121.60, PGT-121.66, PGT122, PGT-123, PGT-124, PGT-125, PGT-126, PGT-151, PGT-130, PGT-133, PGT-134, PGT-135, PGT-128, PGT-136, PGT-137, PGT-138, PGT-139, MDX010 (ipilimumab), DH511, DH511-2, N6, N6LS, N49P6, N49P7, N49P7.1, N49P9, N49P11, N60P1.1, N60P25.1, N60P2.1, N60P31.1, N60P22, NIH 45-46, PGC14, PGG14, PGT-142, PGT-143, PGT-144, PGDM1400, PGDM12, PGDM21, PCDN-33A, 2Dm2m, 4Dm2m, 6Dm2m, PGDM1400, MDX010 (ipilimumab), VRC01, VRC-01-LS, A32, 7B2, 10E8, VRC-07-523, VRC07-523LS, VRC24, VRC41.01, 10E8VLS, 3810109, 10E8v4, IMC-HIV, iMabm36, eCD4-Ig, IOMA, CAP256-VRC26.25, DRVIA7, VRC-HIVMAB080-00-AB, VRC-HIVMAB060-00-AB, P2G12, VRC07, 354BG8, 354BG18, 354BG42, 354BG33, 354BG129, 354BG188, 354BG411, 354BG426, VRC29.03, CAP256, CAP256-VRC26.08, CAP256-VRC26.09, CAP256-VRC26.25, PCT64-24E and VRC38.01, PGT-151, CAP248-2B, 35022, ACS202, VRC34 and VRC34.01, 10E8, 10E8v4, 10E8-5R-100cF, 4E10, DH511.11P, 2F5, 7b2, and LN01.

Examples of HIV bispecific and trispecific antibodies include without limitation MGD014, B12BiTe, BiIA-SG, TMB-bispecific, SAR-441236, VRC-01/PGDM-1400/10E8v4, 10E8.4/iMab, 10E8v4/PGT121-VRC01.

Examples of in vivo delivered bNAbs include without limitation AAV8-VRC07; mRNA encoding anti-HIV antibody VRC01; and engineered B-cells encoding 3BNC117 (Hartweger et al., J. Exp. Med. 2019, 1301).

Pharmacokinetic Enhancers

Examples of pharmacokinetic enhancers include, but are not limited to, cobicistat and ritonavir.

Additional Therapeutic Agents

Examples of additional therapeutic agents include, but are not limited to, the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

HIV Vaccines

Examples of HIV vaccines include, but are not limited to, peptide vaccines, recombinant subunit protein vaccines, live vector vaccines, DNA vaccines, HIV MAG DNA vaccine, CD4-derived peptide vaccines, vaccine combinations, adenoviral vector vaccines (an adenoviral vector such as Ad5, Ad26 or Ad35), simian adenovirus (chimpanzee, gorilla, rhesus i.e. rhAd), adeno-associated virus vector vaccines, Chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, arenavirus vaccines (such as LCMV, Pichinde), bi-segmented or tri-segmented arenavirus based vaccine, trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as VSV and marabavirus; recombinant human CMV (rhCMV) based vaccine, alphavirus-based vaccines, such as semliki forest virus, venezuelan equine encephalitis virus and sindbis virus; (see Lauer, Clinical and Vaccine Immunology, 2017, DOI: 10.1128/CVI.00298-16); LNP formulated mRNA based therapeutic vaccines; LNP-formulated self-replicating RNA/self-amplifying RNA vaccines.

Examples of vaccines include: AAVLP-HIV vaccine, AE-298p, anti-CD40.Env-gp140 vaccine, Ad4-EnvC150, BG505 SOSIP.664 gp140 adjuvanted vaccine, BG505

SOSIP.GT1.1 gp140 adjuvanted vaccine, ChAdOx1.tHIVconsv1 vaccine, CMV-MVA triplex vaccine, ChAdOx1.HTI, Chimigen HIV vaccine, ConM SOSIP.v7 gp140, ALVAC HIV (vCP1521), AIDSVAX B/E (gp120), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), ChAdV63.HIVconsv, gp140 [delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-C55, TVI-HIV-1, Ad-4 (Ad4-env Clade C+Ad4-mGag), Paxvax, EN41-UGR7C, EN41-FPA2, ENOB-HV-11, ENOB-HV-12, PreVaxTat, AE-H, MYM-V101, CombiHIVvac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HI-VADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, arenavirus vector-based vaccines (Vaxwave, TheraT), MVA-BN HIV-1 vaccine regimen, mRNA based prophylactic vaccines, VPI-211, multimeric HIV gp120 vaccine (Fred Hutchinson cancer center), TBL-1203HI, CH505 TF chTrimer, CD40.HIVRI.Env vaccine, Drep-HIV-PT-1, mRNA-1644, and mRNA-1574.

Birth Control (Contraceptive) Combination Therapy

In certain embodiments, the agents described herein are combined with a birth control or contraceptive regimen. Therapeutic agents used for birth control (contraceptive) that can be combined with an agent of this disclosure include without limitation cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

In a particular embodiment, a compound disclosed herein, or a pharmaceutically acceptable salt thereof, is combined with one, two, three, or four additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir+emtricitabine+tenofovir alafenamide), adefovir; adefovir dipivoxil; cobicistat; emtricitabine; tenofovir; tenofovir alafenamide and elvitegravir; tenofovir alafenamide+elvitegravir (rectal formulation, HIV infection); tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; PEGylated raltegravir; raltegravir and lamivudine; lamivudine+lopinavir+ritonavir+abacavir; maraviroc; tenofovir+emtricitabine+maraviroc, enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, an agent disclosed herein, or a pharmaceutical composition thereof, is combined with an HIV nucleoside or nucleotide inhibitor of reverse transcriptase and an HIV non-nucleoside inhibitor of reverse transcriptase. In another specific embodiment, an agent disclosed herein, or a pharmaceutical composition thereof, is combined with an HIV nucleoside or nucleotide inhibitor of reverse transcriptase, and an HIV protease inhibiting compound. In an additional embodiment, an agent disclosed herein, or a pharmaceutical composition thereof, is combined with an HIV nucleoside or nucleotide inhibitor of reverse transcriptase, an HIV non-nucleoside inhibitor of reverse transcriptase, and a pharmacokinetic enhancer. In certain embodiments, an agent disclosed herein, or a pharmaceutical composition thereof, is combined with at least one HIV nucleoside inhibitor of reverse transcriptase, an integrase inhibitor, and a pharmacokinetic enhancer. In another embodiment, an agent disclosed herein, or a pharmaceutical composition thereof, is combined with two HIV nucleoside or nucleotide inhibitors of reverse transcriptase.

In another embodiment, an agent disclosed herein, or a pharmaceutical composition thereof, is combined with a first additional therapeutic agent chosen from dolutegravir, cabotegravir, darunavir, bictegravir, elsulfavirine, rilpivirine, and lenacapavir and a second additional therapeutic agent chosen from emtricitabine and lamivudine.

In some embodiments, an agent disclosed herein, or a pharmaceutical composition thereof, is combined with a first additional therapeutic agent (a contraceptive) selected from the group consisting of cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In certain embodiments, the agents described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of cell therapy include without limitation LB-1903, ENOB-HV-01, ENOB-HV-21, ENOB-HV-31, GOVX-B01, HSPCs overexpressing ALDH1 (LV-800, HIV infection), AGT103-T, and SupT1 cell based therapy. Examples of dendritic cell therapy include without limitation AGS-004. CCR5 gene editing agents include without limitation SB-728T, SB-728-HSPC. CCR5 gene inhibitors include without limitation Cal-1, and lentivirus vector CCR5 shRNA/TRIM5alpha/TAR decoy-transduced autologous CD34-positive hematopoietic progenitor cells (HIV infection/HIV-related lymphoma). In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Gene Editors

In certain embodiments, the agents described herein are combined with a gene editor, e.g., an HIV targeted gene editor. In various embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T Cell Therapy

In some embodiments, the agents described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include A-1801, A-1902, convertible CAR-T, VC-CAR-T, CMV-N6-CART, anti-HIV duoCAR-T, anti-CD4 CART-cell therapy, CD4 CAR+C34-CXCR4+CCR5 ZFN T-cells, dual anti-CD4 CART-T cell therapy (CD4 CAR+C34-CXCR4 T-cells), anti-CD4 MicAbody antibody+anti-MicAbody CAR T-cell therapy (iNKG2D CAR, HIV infection), GP-120 CAR-T therapy, autologous hematopoietic stem cells genetically engineered to express a CD4 CAR and the C46 peptide.

TCR T-Cell Therapy

In certain embodiments, the agents described herein are combined with a population of TCR-T-cells. TCR-T-cells are engineered to target HIV derived peptides present on the surface of virus-infected cells, for example, ImmTAV.

B-Cell Therapy

In certain embodiments, the antibodies or antigen-binding fragments described herein are combined with a population of B cells genetically modified to express broadly neutralizing antibodies, such as 3BNC117 (Hartweger et al., J. Exp. Med. 2019, 1301, Moffett et al., *Sci. Immunol.* 4, eaax0644 (2019) 17 May 2019.

A compound as disclosed herein (e.g., any compound of Formula I) may be combined with one, two, three, or four additional therapeutic agents in any dosage amount of the compound of Formula I (e.g., from 1 mg to 500 mg of compound).

In one embodiment, kits comprising a compound disclosed herein, or a pharmaceutically acceptable salt thereof, in combination with one or more (e.g., one, two, three, one or two, or one to three) additional therapeutic agents are provided.

In one embodiment, the additional therapeutic agent or agents of the kit is an anti-HIV agent, selected from HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T, autologous T cell therapies), compounds that target the HIV capsid, latency reversing agents, HIV bNAbs, immune-based therapies, phosphatidylinositol 3-kinase (PI3K) inhibitors, HIV antibodies, broadly neutralizing HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV viral infectivity factor inhibitors, TAT protein inhibitors, HIV Nef modulators, Hck tyrosine kinase modulators, mixed lineage kinase-3 (MLK-3) inhibitors, HIV splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and combinations thereof.

In some embodiments, the additional therapeutic agent or agents of the kit are selected from combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In a specific embodiment, the kit includes a compound disclosed herein, or a pharmaceutically acceptable salt thereof, and an HIV nucleoside or nucleotide inhibitor of reverse transcriptase. In a specific embodiment, the kit includes a compound disclosed herein, or a pharmaceutically acceptable salt thereof, and an HIV nucleoside or nucleotide inhibitor of reverse transcriptase and an HIV non-nucleoside inhibitor of reverse transcriptase. In another specific embodiment, the kit includes a compound disclosed herein, or a pharmaceutically acceptable salt thereof, and an HIV nucleoside or nucleotide inhibitor of reverse transcriptase, and an HIV protease inhibiting compound. In an additional embodiment, the kit includes a compound disclosed herein, or a pharmaceutically acceptable salt thereof, an HIV nucleoside or nucleotide inhibitor of reverse transcriptase, an HIV non-nucleoside inhibitor of reverse transcriptase, and a pharmacokinetic enhancer. In certain embodiments, the kit includes a compound disclosed herein, or a pharmaceutically acceptable salt thereof, at least one HIV nucleoside inhibitor of reverse transcriptase, an integrase inhibitor, and a pharmacokinetic enhancer. In another embodiment, the kit includes a compound disclosed herein, or a pharmaceutically acceptable salt thereof, and two HIV nucleoside or nucleotide inhibitors of reverse transcriptase. In a specific embodiment, the kit includes a compound disclosed herein, or a pharmaceutically acceptable salt thereof, an HIV nucleoside or nucleotide inhibitor of reverse transcriptase and an HIV capsid inhibitor. In a specific embodiment, the kit includes a compound disclosed herein, or a pharmaceutically acceptable salt thereof, an HIV nucleoside inhibitor of reverse transcriptase and an HIV capsid inhibitor. In a specific embodiment, the kit includes a compound disclosed herein, or a pharmaceutically acceptable salt thereof, and an HIV capsid inhibitor. In a specific embodiment, the kit includes a compound disclosed herein, or a pharmaceutically acceptable salt thereof, and one, two, three or four HIV bNAbs. In a specific embodiment, the kit includes a compound disclosed herein, or a pharmaceutically acceptable salt thereof, one, two, three or four HIV bNAbs and an HIV capsid inhibitor. In a specific embodiment, the kit includes a compound disclosed herein, or a pharmaceutically acceptable salt thereof, one, two, three or four HIV bNAbs, an HIV capsid inhibitor, and an HIV nucleoside inhibitor of reverse transcriptase.

HIV Long Acting Therapy

Examples of drugs that are being developed as long acting regimens include, but are not limited to, cabotegravir, rilpivirine, any integrase LA, VM-1500 LAI, maraviroc (LAI), tenofovir implant, doravirine, raltegravir, and long acting dolutegravir.

VII. Compound Preparation

Some embodiments of the present disclosure are directed to processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Isolation of final compounds can be performed by various methods known to those skilled in the art but is optimally reverse phase HPLC followed by lyophilization from various organic solvents. Repeated lyophilization can optionally be performed to reduce the amount of residual acidic modifiers resulting from the purification process. In some embodiments, the final compounds provided herein were isolated as mono- or bis-trifluoroacetic acid salts.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in the schemes below, and the particular examples that follow.

LIST OF ABBREVIATIONS AND ACRONYMS

| Abbreviation/Acronym | Meaning |
| --- | --- |
| 1,2-EDT | 1,2-ethanedithiol |
| Ac | Acetate |
| ACN or MeCN | Acetonitrile |

| Abbreviation/Acronym | Meaning |
| --- | --- |
| AcOH | Acetic acid |
| aq. | Aqueous |
| Ar | Argon |
| Bn | Benzyl |
| BnBr | Benzyl bromide |
| BnOH | Benzyl alcohol |
| Boc | Tert-butyloxycarbonyl |
| $Boc_2O$ | Di-tert-butyl dicarbonate |
| $Bu_4N$ | Tetrabutylammonium |
| C18 | Octadecyl bonded silica solid support |
| $CH_2N_4$ | 1-H-tetrazole |
| COMU | (1-Cyano-2-ethoxy-2-oxoethylidenaminooxy)dimethylamino-morpholino-carbenium hexafluorophosphate |
| DBDMH | 1,3-dibromo-5,5-dimethylhydantoin |
| DCE | 1,2-dichloroethane |
| DCM | Dichloromethane |
| DIEA or DIPEA | N,N-diisopropylethylamine |
| DMAc | N,N-dimethylacetamide |
| DMAP | 4-dimethylaminopyridine |
| DME | 1,2-dimethoxyethane |
| DMF | N,N-Dimethylformamide |
| DMSO | Dimethylsulfoxide |
| EDC | N-(3-Dimethylaminopropyl)-N'-ethylcarbodiimide hydrochloride |
| ESI | Electrospray ionization |
| Et | Ethyl |
| $Et_3N$ | Triethylamine |
| EtOAc | Ethyl acetate |
| h or hr(s) | Hour(s) |
| HATU | 1-[Bis(dimethylamino)methylene]-1H-1,2,3-triazolo[4,5-b]pyridiunium 3-oxide hexafluorophosphate |
| HPLC | High pressure liquid chromatography |
| i-Pr | Isopropyl |
| LCMS | Liquid chromatography mass spectrometry |
| Me | Methyl |
| MEK | Methyl ethyl ketone |
| MeOH | Methanol |
| $MeSO_3H$/MsOH | Methanesulfonic acid |
| MeTHF or 2-MeTHF | 2-methyltetrahydrofuran |
| Min | Minutes |
| MS | Mass spectrometry |
| MsCl | Methansulfonyl chloride |
| m/z | Mass to charge ratio |
| NaOAc | Sodium acetate |
| NMR | Nuclear magnetic resonance spectroscopy |
| NMM | 4-methylmorpholine |
| NMI | 1-methylimidazole |
| OMs | Methanesulfonate |
| OTs | para-toluenesulfonate |
| PhG | α-Phenylglycine |
| PhMe | Toluene |
| Ra-Ni | Raney nickel |
| RBF | Round-bottom flask |
| RT or rt | Room temperature |
| sat. or satd. | Saturated |
| T3P | Propylphosphonic anhydride |
| t-Bu or $^tBu$ | Tert-butyl |
| TBAI | Tetrabutylammonium iodide |
| TBSCl | Tert-butyldimethylsilyl chloride |
| TCFH | N'-tetramethylformamidinium hexafluorophosphate |
| TEA | Triethylamine |
| TEMPO | 2,2,6,6-tetramethylpiperidine 1-oxyl |
| $Tf_2O$ | Triflic anhydride |
| TFA | Trifluoroacetic acid |
| THF | Tetrahydrofuran |

General Synthetic Schemes

General Reaction Schemes 1-5 are provided as further embodiments of the present disclosure and illustrate general methods which were used to prepare certain compounds of the present disclosure and which can be used to prepare additional compounds of the present disclosure. Each of the variables (e.g. $R^1$, $R^2$, $R^3$, $R^4$) of the compounds disclosed in General Reaction Schemes 1-5 are as defined herein.

The compounds of the present disclosure may be prepared using the methods disclosed herein and routine modifications thereof, which will be apparent to a skilled artisan given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

Typical embodiments of compounds disclosed herein may be synthesized using the general reaction schemes described below. It will be apparent to a skilled artisan given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments disclosed in the present disclosure, inspection of the structure of the compound to be synthesized will provide the identity of each substituent group. The identity of the final product will generally render apparent the identity of the necessary starting materials by a simple process of inspection, given the examples herein.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present disclosure are inert organic solvents, and the reactions are carried out under an inert gas, preferably nitrogen or argon.

General Synthetic Scheme 1
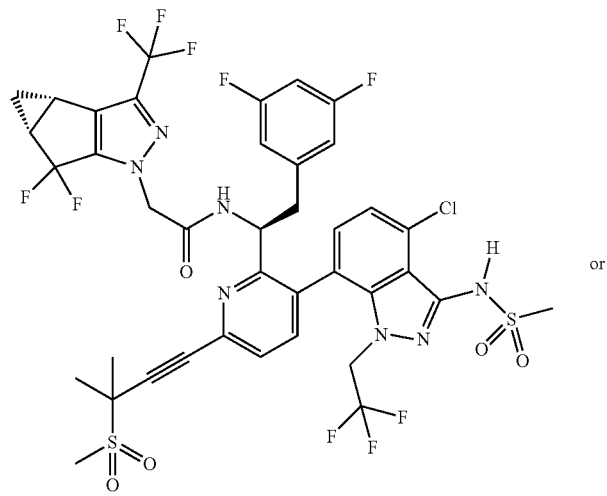
Intermediate 5
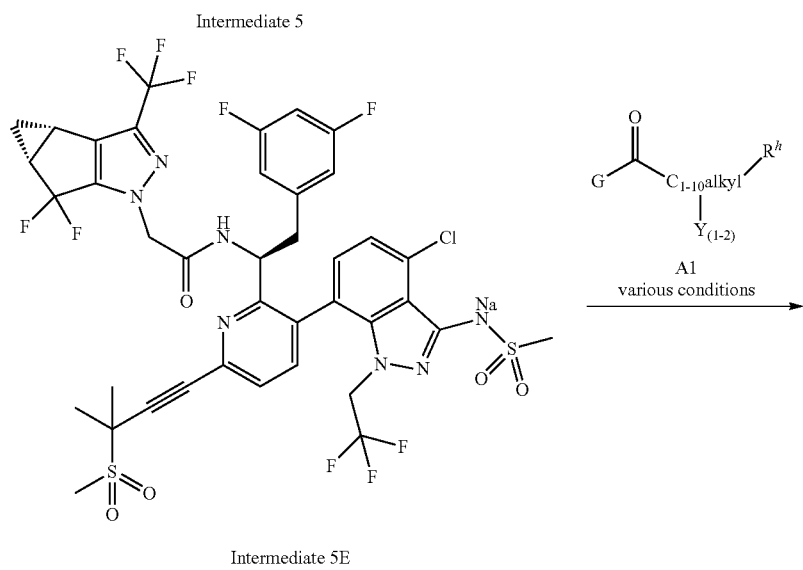
Intermediate 5E
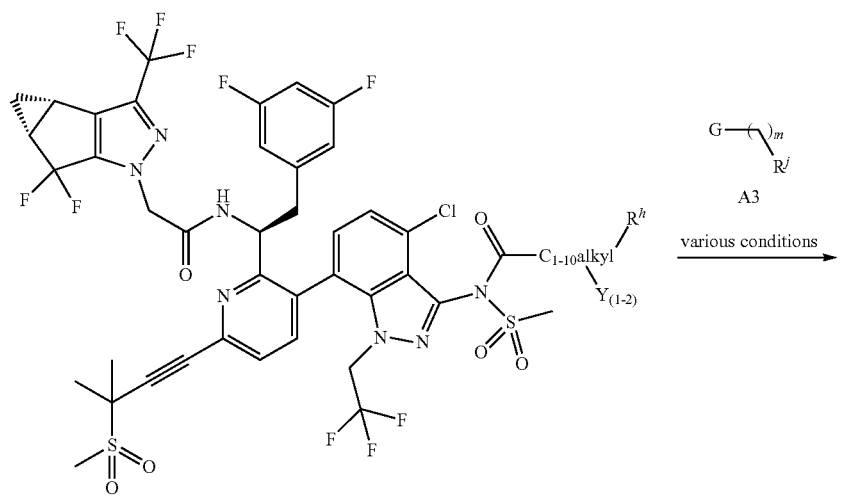
A2

-continued

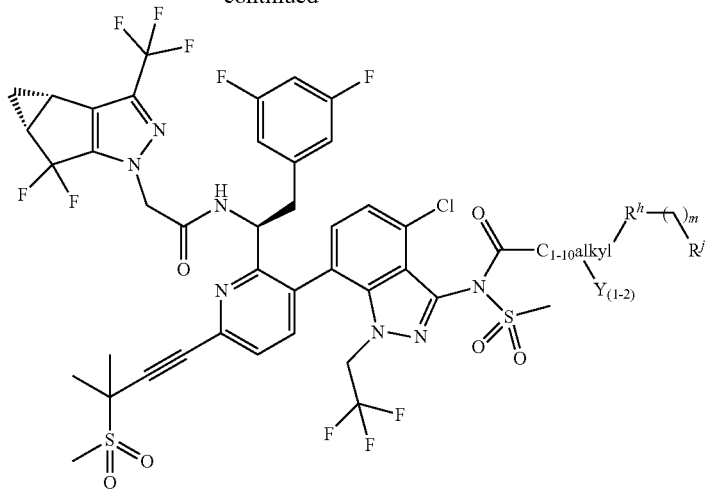

A4

Compounds of formula A2 and A4 can be prepared according to General Synthetic Scheme 1, wherein m is 0, 1, 2, 3, 4, 5, or 6; $R^h$ is H or 4-7 membered heterocyclyl, wherein the 4-7 membered heterocyclyl is optionally substituted with 1-3 groups independently selected from $R^a$, $R^b$, and $R^c$ as defined herein; $R^j$ is $R^b$ or $R^c$ as defined herein; and G is a general leaving group including but not limited to —Cl, —Br, —I, —F, —OTs, or —OH.

In accordance with General Synthetic Scheme 1, Intermediate 5 or Intermediate 5E can be reacted with a compound of formula A1 under various conditions to give a compound of formula A2. Non-limiting exemplary coupling conditions include the use of common coupling reagents such as HATU, COMU, TCFH, or EDC under appropriate solvent and temperature conditions in the presence of a base. A compound of formula A2, after optional deprotection of a protecting group, can be converted to a compound of formula A4 by employing various conditions known in the art for alkylation or acylation using a compound with a compound of formula A3. Compounds of formula A1 and A3 can be obtained commercially, or readily synthesized from known materials and reagents in one or more steps by those skilled in the art.

General Synthetic Scheme 2

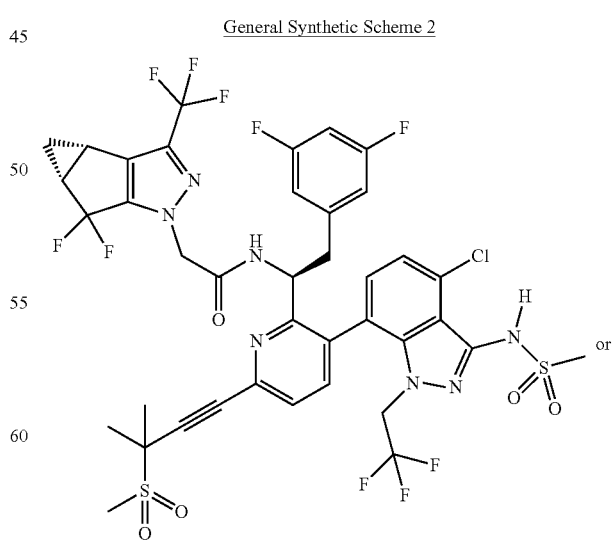

Intermediate 5

175
-continued

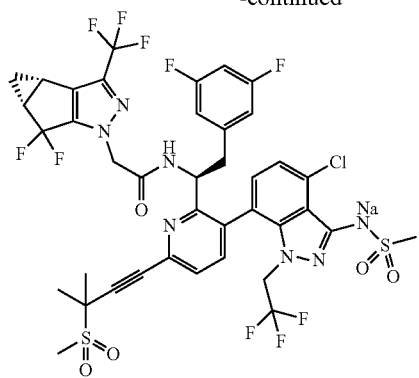

Intermediate 5E

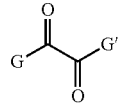

B1 various conditions →

176
-continued

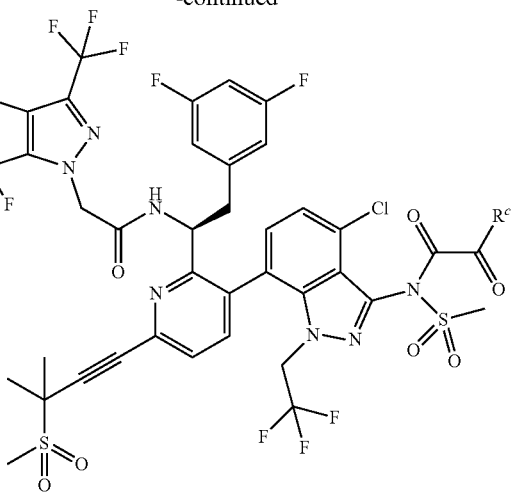

B3

Compounds of formulas B2 and B3 can be prepared according to General Synthetic Scheme 2, wherein $R^c$ is as defined herein; G is a general leaving group including but not limited to —Cl, —Br, —I, or —F; and G' is G, —OH, or —$OR^7$. In accordance with General Synthetic Scheme 2, a compound of formula B1 can be reacted with Intermediate 5 or Intermediate 5E under a variety of basic conditions to give a compound of formula B2. A compound of formula B2 can be converted to a compound of formula B3 through reaction with neutral or deprotonated H—$R^c$ with optional deprotection in cases where a protected functional group has been introduced. Compounds of formula B1 can be obtained commercially, or readily synthesized from known materials and reagents in one or more steps by those skilled in the art.

B2

H—$R^c$
various conditions →

General Synthetic Scheme 3.

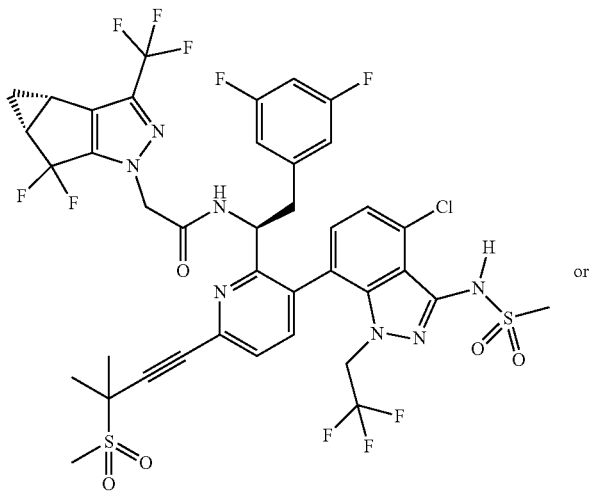

or

Intermediate 5

-continued

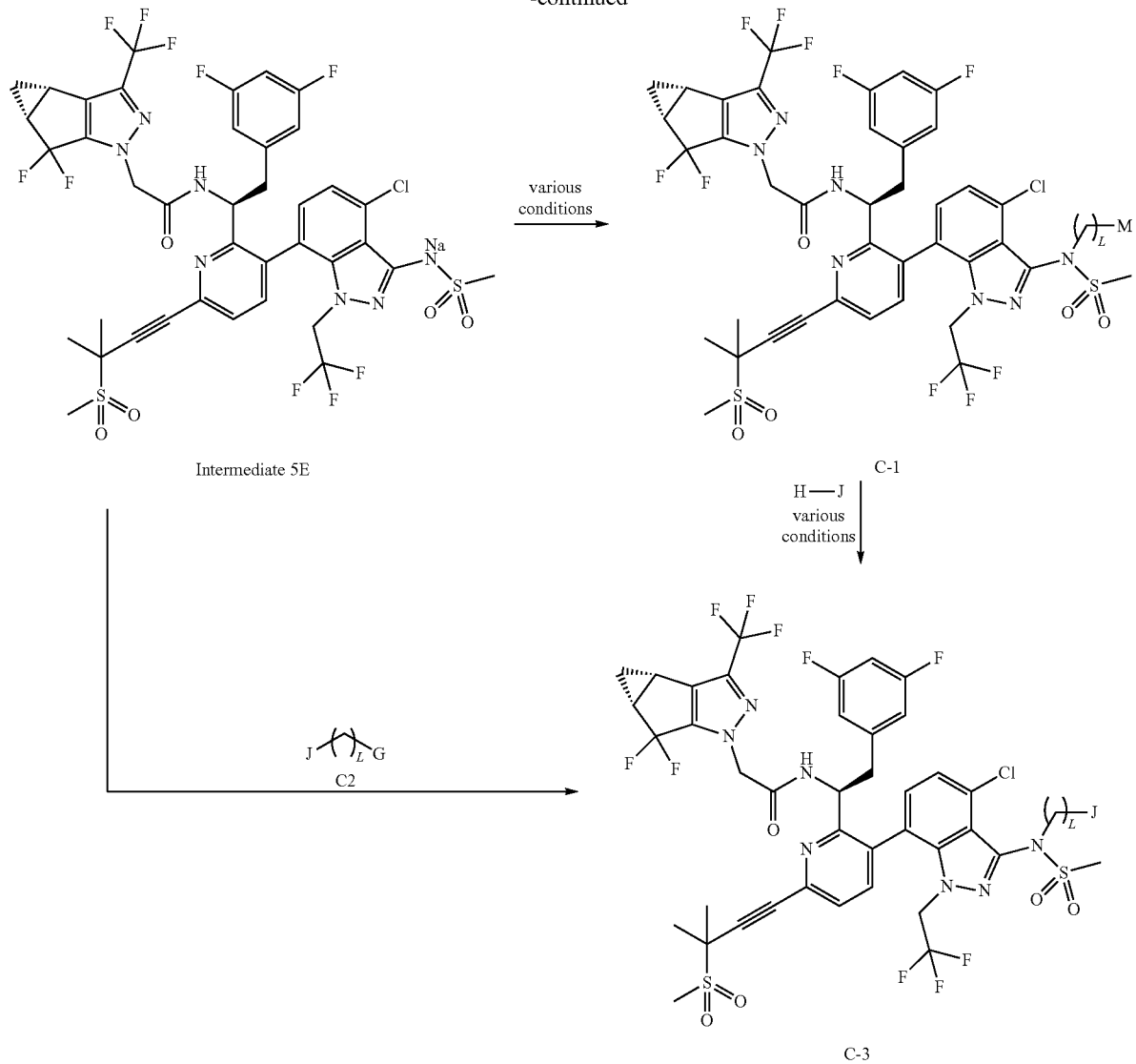

Intermediate 5E

C-1

C-3

Compounds of formulas C1 and C3 can be prepared according to General Synthetic Scheme 3, wherein M is $R^a$ as defined herein, —OH, or $C_{1-6}$ alkyl; G is a general leaving group including but not limited to —Cl, —Br, —I, or —F; J is —OC(O)$R^9$ or —OC(O)C(O)O$R^9$, wherein $R^9$ is as defined herein; and L is 1, 2, 3, 4, 5, or 6. In accordance with General Synthetic Scheme 3, Intermediate 5 or Intermediate 5E can be reacted under a variety of conditions to give a compound of formula C1. Non-limiting exemplary coupling conditions include di-tert-butyl chloromethyl phosphate, trimethylsilyl chloride and paraformaldehyde, or other electrophilic reagents. A compound of formula C1 can be reacted with neutral or deprotonated H-J under various basic conditions to provide a compound of formula C3 after optional deprotection in cases where H-J contains protected functionality. Alternatively, Intermediate 5 or Intemediate 5E can be converted directly to a compound of formula C3 through reaction with a compound of formula C2 under a variety of basic conditions. Compounds of formula C2 and H-J can be obtained commercially, or readily synthesized from known materials and reagents in one or more steps by those skilled in the art.

General Synthetic Scheme 4.

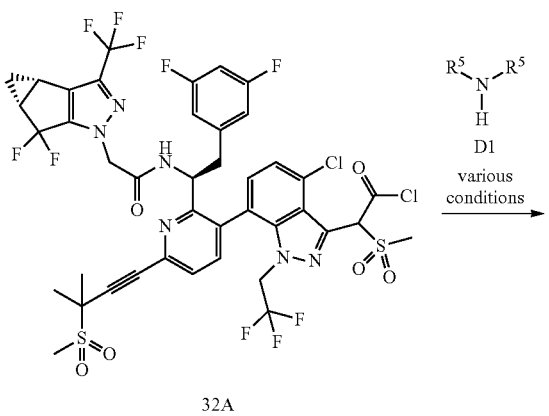

32A

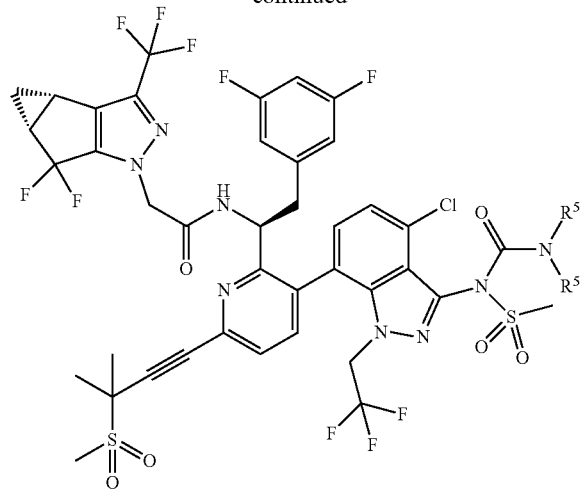

D2

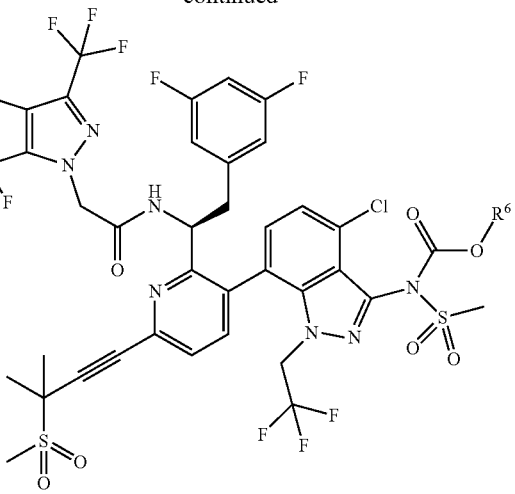

E2

Compounds of formula D2 can be prepared according to General Synthetic Scheme 4, wherein R⁵ is defined herein. In accordance with General Synthetic Scheme 4, a compound of formula D1 can be reacted with 32A under basic conditions to give a compound of formula D2 following optional deprotection and/or functionalization with various electrophilic reagents, including but not limited to di-tert-butyl N,N-diisopropylphosphoramidite, phosphoryl chloride, or N,N'-di-Boc-1H-pyrazole-1-carboxamidine with an optional second deprotection. Compounds of formula D1 can be obtained commercially, or readily synthesized from known materials and reagents in one or more steps by those skilled in the art.

Compounds of formula E2 can be prepared according to General Synthetic Scheme 5, wherein $R^5$ is as defined herein. In accordance with General Synthetic Scheme 5, a compound of formula E1 can be reacted with 32A under basic conditions to give a compound of formula E2 following optional deprotection and/or functionalization with various electrophilic reagents, including but not limited to di-tert-butyl N,N-diisopropylphosphoramidite, phosphoryl chloride, or N,N'-di-Boc-1H-pyrazole-1-carboxamidine with an optional second deprotection. Compounds of formula E1 can be obtained commercially, or readily synthesized from known materials and reagents in one or more steps by those skilled in the art.

VIII. Examples

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of General Synthetic Scheme 5.

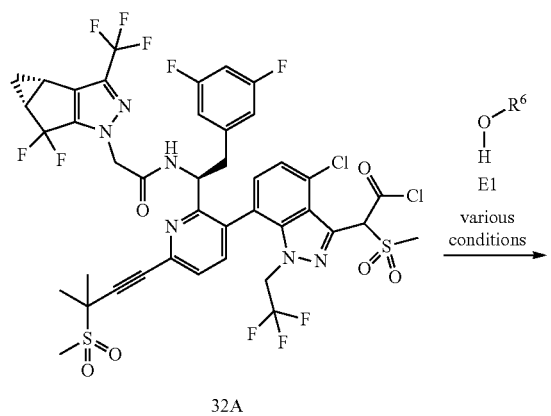

32A the disclosure. The following description is, therefore, not intended to limit the scope of the present disclosure.

INTERMEDIATES

Intermediate 1

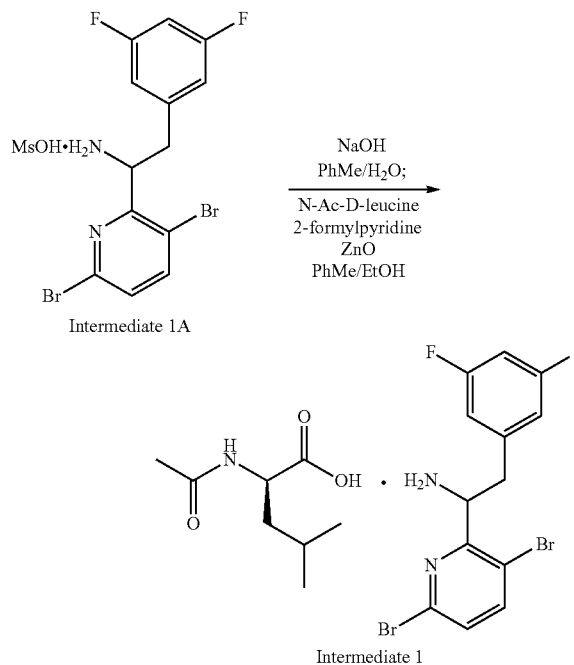

Intermediate 1

Synthesis of (S)-1-(3,6-dibromopyridin-2-yl)-2-(3,5-difluorophenyl)ethan-1-amine acetyl-D-leucinate (Intermediate 1): A mixture of Intermediate 1A (30.8 mmol, 1.00 equiv), 2-methyltetrahydrofuran (75 mL), water (45 g), and NaOH (37.9 mmol, 1.23 equiv) were agitated for 2 h. The aqueous phase was discarded and the organic phase was washed twice with water (45 mL). The organic phase was solvent exchanged into toluene, distilling to a final volume of 3 ml/g before diluting with toluene (224 mL). To the solution was added N-acetyl-D-leucine (43.3 mmol), zinc oxide (6.25 mmol), and 2-pyridinecarboxaldehyde (1.6 mmol). The mixture was agitated at 35° C. for 157 h prior to cooling to 20° C. The mixture was treated with a solution of NaOH (45 mmol) in water (75 mL) and then filtered through celite (7.5 g), rinsing forward toluene (30 mL). The aqueous phase was discarded and the organic phase was washed three times with water (75 mL). To the organic phase were added EtOH (15 mL), water (7.5 mL), toluene (76 mL), and N-acetyl-D-leucine (27.7 mmol). The mixture was cooled to 0° C. and filtered. The filter cake was washed with toluene (76 mL) and dried under vacuum to yield title compound Intermediate 1. $^1$H NMR (400 MHz, DMSO-$d_6$) δ 8.03 (d, J=8.0 Hz, 1H), 7.95 (d, J=8.3 Hz, 1H), 7.49 (d, J=8.3 Hz, 1H), 7.03 (tt, J=9.5, 2.4 Hz, 1H), 6.87 (dtd, J=8.4, 6.2, 2.2 Hz, 2H), 5.49 (s, 3H), 4.42 (dd, J=7.9, 5.9 Hz, 1H), 4.18 (q, J=7.8 Hz, 1H), 2.93 (dd, J=13.3, 5.9 Hz, 1H), 2.85 (dd, J=13.2, 8.0 Hz, 1H), 1.83 (s, 3H), 1.71-1.54 (m, 1H), 1.47 (dd, J=8.4, 6.2 Hz, 2H), 0.88 (d, J=6.6 Hz, 3H), 0.83 (d, J=6.5 Hz, 3H) ppm. $^{13}$C NMR (101 MHz, DMSO-$d_6$) δ 174.72, 169.03, 162.07 (dd, J=245.5, 13.3 Hz), 161.79, 143.51, 142.82 (t, J=9.4 Hz), 139.72, 128.39, 119.30, 113.36-111.39 (m), 101.73 (t, J=25.7 Hz), 55.19, 50.69, 41.74 (d, J=2.3 Hz), 40.51, 24.36, 22.91, 22.44, 21.46 ppm.

Intermediate 2

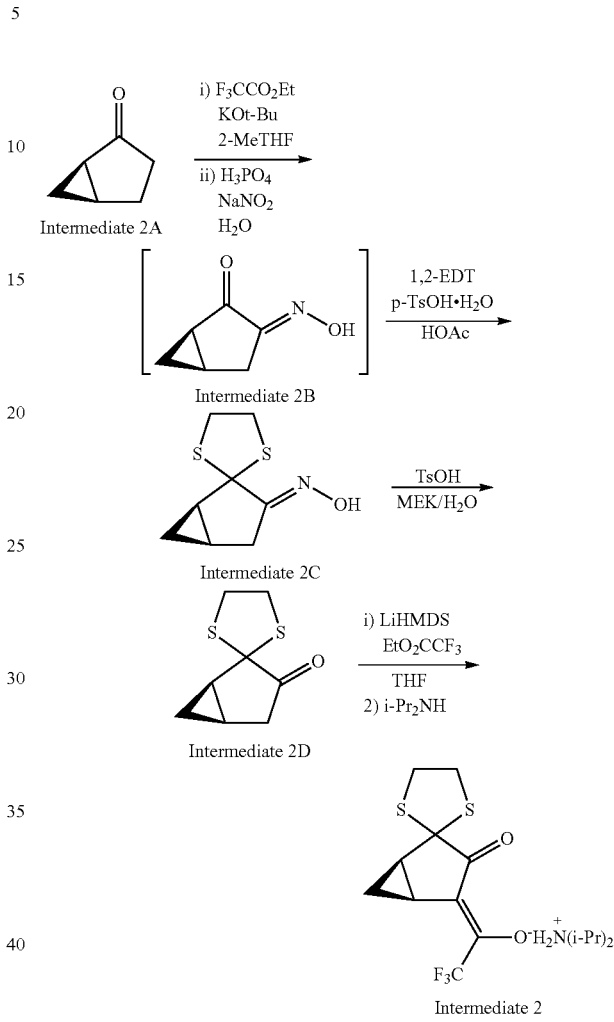

Synthesis of (1R,5R,E)-3-(hydroxyimino)bicyclo[3.1.0]hexan-2-one (Intermediate 2B): To a mixture of ketone Intermediate 2A (111 mmol) and ethyl trifluoroacetate (121 mmol) in 2-methyltetrahydrofuran (50 mL) at 5° C. was added 2 M potassium t-butoxide in 2-methyltetrahydrofuran (62.4 mL, 1.2 equiv). After 1 h, the solution was warmed to 20° C. and agitated for 3 h. The mixture was cooled to 5° C. and a solution of 86% phosphoric acid (133 mmol) in water (50 mL) was added. The mixture was warmed to 20° C. and sodium nitrite (122 mmol) was added. After 16 h, water (100 mL) was added and the aqueous phase was separated. The aqueous phase was back-extracted with 3 portions of 2-methyltetrahydrofuran (80 mL, 80 mL, and 50 mL). The combined organic phases were distilled to 3 mL/g and then exchanged into acetic acid, distilling to a total volume of 5 mL/g to afford a solution of the title compound Intermediate 2B. $^1$H NMR (400 MHz, DMSO-$d_6$) δ 12.26 (s, 1H), 2.73 (d, J=18.5 Hz, 1H), 2.63 (ddd, J=18.6, 5.3, 2.0 Hz, 1H), 2.17-2.01 (m, 2H), 1.34 (dddd, J=9.2, 7.1, 4.9, 2.0 Hz, 1H), 0.77 (td, J=4.6, 3.4 Hz, 1H) ppm.

Synthesis of (1R,5R,E)-spiro[bicyclo[3.1.0]hexane-2,2'-[1,3]dithiolan]-3-one oxime (Intermediate 2C): To a solution of Intermediate 2B (102 mmol) in acetic acid (55 mL total volume) at 20° C. was added 1,2-ethanedithiol (117 mmol) and p-toluenesulfonic acid (42 mmol). After 20 h, water (60 mL) was added and the mixture was cooled to 5° C. After 3 h, the reaction was filtered and then the filter cake was washed with 2 portions of a mixture of 2-propanol (24 mL) and water (6 mL) and dried under vacuum to afford title compound Intermediate 2C. $^1$H NMR (400 MHz, DMSO-$d_6$) δ 10.93 (s, 1H), 3.63-3.51 (m, 2H), 3.51-3.42 (m, 1H), 3.39-3.31 (m, 1H), 2.83 (d, J=17.4 Hz, 1H), 2.59-2.52 (m, 1H), 1.87 (ddd, J=8.0, 6.2, 3.7 Hz, 1H), 1.65 (dddd, J=7.7, 6.2, 5.2, 3.9 Hz, 1H), 0.93 (tdd, J=7.6, 5.5, 1.7 Hz, 1H), 0.02 (dt, J=5.5, 3.8 Hz, 1H) ppm.

Synthesis of (1R,5R)-Spiro[bicyclo[3.1.0]hexane-2,2'-[1,3]dithiolan]-3-one (Intermediate 2D): Para-toluenesulfonic acid (0.90 g) was charged to a vessel containing a suspension of Intermediate 2C (2.5 mmol) in methyl ethyl ketone (2.5 mL) and water (2.5 mL). The mixture was agitated at about 85° C. until the reaction was complete. The product was isolated from the reaction mixture by cooling to about 20° C., adding water (2.50 mL), and cooling to about 0° C. The slurry was filtered and the filter cake was washed with water, then deliquored thoroughly to afford title compound Intermediate 2D. $^1$H NMR (400 MHz, DMSO-$d_6$) δ 3.55-3.37 (m, 3H), 3.28-3.13 (m, 1H), 3.03 (ddd, J=18.5, 5.6, 2.2 Hz, 1H), 2.20 (d, J=18.5 Hz, 1H), 1.84 (ddd, J=8.0, 7.0, 3.8 Hz, 1H), 1.66 (tdd, J=7.2, 5.6, 4.1 Hz, 1H), 1.03 (tdd, J=7.9, 5.9, 2.1 Hz, 1H), 0.06 (dt, J=6.0, 4.0 Hz, 1H).

Synthesis of Diisopropylammonium (Z)-2,2,2-trifluoro-1-((1R,5S)-3-oxospiro[bicyclo[3.1.0]hexane-2,2'-[1,3]dithiolan]-4-ylidene)ethan-1-olate (Intermediate 2): Intermediate 2D (756 mg) was charged to a vessel and dissolved in 2-methyltetrahydrofuran (7.6 mL). To this mixture was charged ethyl trifluoroacetate (0.57 g) and the reaction was cooled to about 0° C. Lithium hexamethyldisilazide (1.0 M solution in THF, 4.5 g) was charged over about 60 minutes and the reaction was agitated until complete. A solution of sulfuric acid (2.0 g) in water (5.6 mL) was charged, then the reaction was warmed to about 20° C. and agitated for about 20 minutes. Layers were separated and the aqueous layer was extracted twice with 2-methyltetrahydrofuran (5.3 mL). The combined organic layers were concentrated and N,N-diisopropylamine (0.5 g) was charged. The product was crystallized by the addition of heptane (11 ml). The reaction was filtered and the filter cake was washed with heptane, then deliquored thoroughly, and dried to afford title compound Intermediate 2. $^1$H NMR (400 MHz, Acetonitrile-$d_3$) δ 7.84 (m, 2H), 3.58 (d, J=8.7 Hz, 2H), 3.47-3.27 (m, 4H), 2.20 (s, 1H), 1.81-1.68 (m, 1H), 1.24 (dd, J=6.5, 0.6 Hz, 12H), 0.99 (q, J=6.5 Hz, 1H), 0.13 (s, 1H).

Intermediate 3

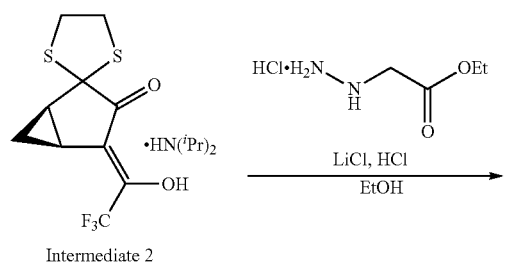

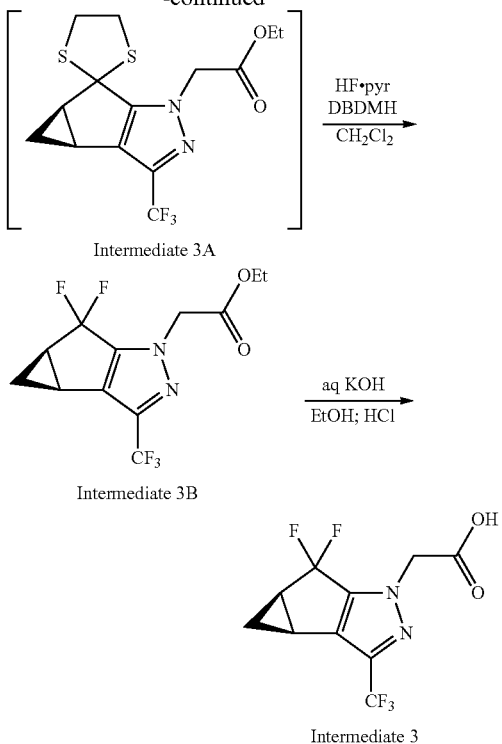

Synthesis of Ethyl 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetate (Intermediate 3B): Acetyl chloride (940 mmol) was added to EtOH (324 g) to produce a solution of anhydrous HCl in EtOH. To the solution were charged 2-ethyl hydrazinoacetate HCl (293 mmol), LiCl (850 mmol), Intermediate 2 (235 mmol), and EtOH (36 g). The mixture was stirred for 44 h and then concentrated to a volume of 2 mL/g prior to diluting with dichloromethane (1170 g). The mixture was washed with water (450 g) followed by solutions of sodium bicarbonate (428 mmol) in water (451 g) and NaCl (50.7 g) in water (452 g). The organic phase was treated with silica gel (45.1 g), filtered, and azeotropically distilled to a volume of 2 mL/g prior to dilution with dichloromethane (451 g). The crude Intermediate 3A was used in the following step.

To a mixture of dibromodimethylhydantoin (93.5 mmol) and dichloromethane (170 mL) at −13° C. was charged 70% w/w hydrogen fluoride pyridine (2652 mmol). To the resulting mixture was charged crude Intermediate 3A (27.4 mmol) in dichloromethane (50 mL). After 2.5 h, water (105 mL), a solution of sodium metabisulfite (109 mmol) in water (159 g), and a solution of 45% KOH (128 g) were added to the mixture in succession. The mixture was warmed to 20° C. and the aqueous phase was separated and discarded. The organic phase was washed with a solution of 35% HCl (113 mmol) in water (103 g) and a solution of NaCl (5.2 g) in water (105 g). The organic solution was exchanged to EtOH, distilling to a final volume of 8.2 mL/g. To the solution was added activated carbon (3.0 g) and stirred for 30 min. The mixture was filtered, rinsing forward additional EtOH (42 mL). The solution was distilled to a volume of 5.5 mL/g and water (50 mL) was added. The reaction was filtered and the filter cake was washed with a mixture of EtOH (20 mL) and water (20 L) and dried under vacuum to afford title compound Intermediate 3B. $^1$H NMR (400 MHz, DMSO-$d_6$) δ

5.31-5.04 (m, 2H), 4.17 (q, J=7.1 Hz, 2H), 2.78-2.57 (m, 2H), 1.47 (dddd, J=8.5, 7.1, 5.5, 1.4 Hz, 1H), 1.19 (t, J=7.1 Hz, 3H), 1.04 (tdt, J=5.3, 4.0, 1.8 Hz, 1H). $^{13}$C NMR (101 MHz, DMSO-d$_6$) δ 166.79, 143.15 (t, J=29.4 Hz), 134.65 (q, J=39.0 Hz), 132.99, 121.05 (q, J=268.4 Hz), 120.52 (t, J=243.3 Hz), 62.09, 52.49, 27.95 (dd, J=34.7, 29.0 Hz), 23.82 (d, J=2.6 Hz), 14.25, 12.14 (t, J=3.1 Hz). $^{19}$F NMR (376 MHz, DMSO-d$_6$) δ−60.47, −79.68 (dd, J=253.5, 13.2 Hz), −103.09 (dd, J=253.3, 9.8 Hz) ppm.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (Intermediate 3): To a mixture of Intermediate 3B (64.6 mmol) in EtOH (9.3 g) and water (80.3 g) was added 45% KOH (130 mmol) and the mixture was warmed to 50° C. After 17 h, the solution was added to a mixture of 35% HCl (170 mmol) in water (102 g). The reaction was filtered and the filter cake was washed with water (120 g) and dried under vacuum to afford title compound Intermediate 3. $^1$H NMR (400 MHz, DMSO-d$_6$) δ 13.50 (s, 1H), 5.14-4.81 (m, 2H), 2.82-2.56 (m, 2H), 1.46 (dddd, J=8.5, 7.1, 5.5, 1.4 Hz, 1H), 1.08-1.00 (m, 1H). $^{13}$C NMR (101 MHz, DMSO-d$_6$) δ 168.16, 143.05 (t, J=29.4 Hz), 134.40 (q, J=38.9 Hz), 132.80, 121.11 (q, J=268.4 Hz), 120.55 (t, J=243.3 Hz), 52.54, 27.97 (dd, J=34.7, 29.0 Hz), 23.81 (d, J=2.5 Hz), 12.13 (t, J=3.1 Hz). $^{19}$F NMR (376 MHz, DMSO-d$_6$) δ-60.39 (d, J=1.4 Hz), −79.83 (dd, J=253.2, 13.1 Hz), −102.97 (dd, J=253.2, 9.8 Hz).

Intermediate 4

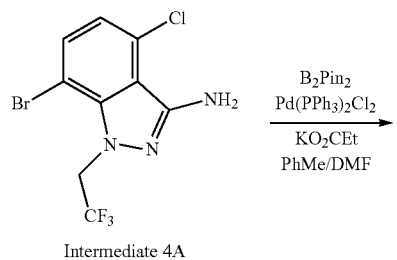

Intermediate 4A

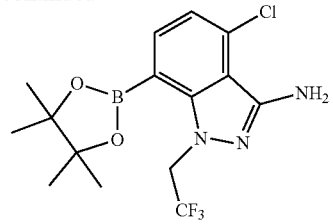

Intermediate 4

Synthesis of 4-chloro-7-(4,4,5,5-tetramethyl-1,3,2-dioxaborolan-2-yl)-1-(2,2,2-trifluoroethyl)-1H-indazol-3-amine (Intermediate 4): A mixture of bis(triphenylphosphine)palladium(II) dichloride (0.46 mmol), bis(pinacolato)diboron (33 mmol), Intermediate 4A (30.5 mmol), potassium propionate (89.3 mmol), toluene (44 g), and DMF (29 g) were degassed and then warmed to 107° C. After 7 h, the mixture was cooled to 60° C., treated with a solution of N-acetylcysteine (6.1 mmol) in water (20 g), and agitated for 18 h. The mixture was cooled to 20° C., diluted with EtOAc (50 g), and filtered through celite, rinsing forward additional EtOAc (40 g). The aqueous phase was discarded and the organic phase was washed 3 times with a solution of LiCl (6.0 g) in water (60 g). The organic phase was treated with activated carbon, rinsing forward additional EtOAc (80 g). The solution was exchanged into 2-propanol, distilling to a final volume of 4 mL/g. The mixture was diluted with n-heptane (41 g), warmed to 82° C., and then cooled to 15° C. The mixture was filtered and the filter cake was, washed with 2-propanol (32 g) and dried under vacuum to afford title compound Intermediate 4. $^1$H NMR (400 MHz, DMSO-d$_6$) δ 7.70 (dd, J=7.6, 1.0 Hz, 1H), 7.07 (dd, J=7.6, 1.0 Hz, 1H), 5.58 (s, 2H), 5.46 (q, J=9.1 Hz, 2H), 1.32 (s, 12h).

Intermediate 5

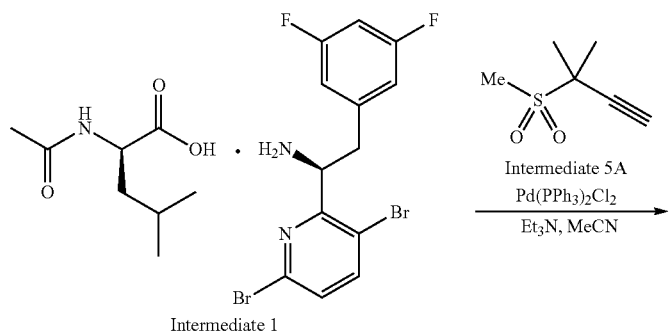

-continued
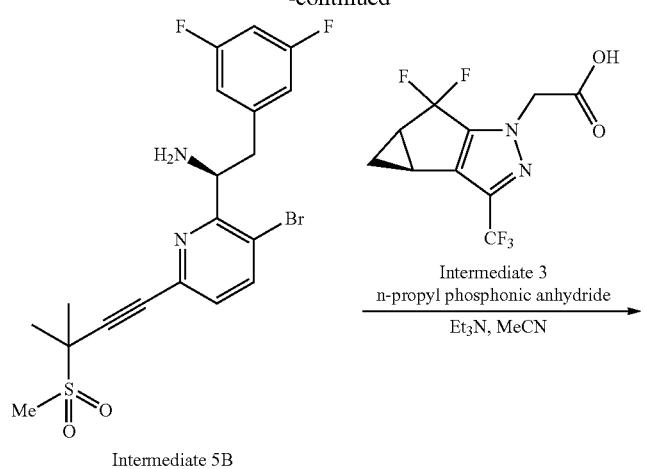
Intermediate 5B
Intermediate 3
n-propyl phosphonic anhydride
———————————————→
Et₃N, MeCN
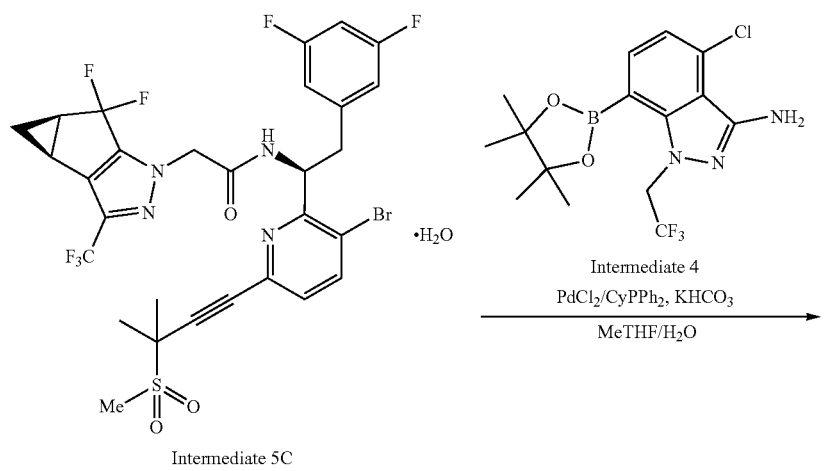
Intermediate 5C
Intermediate 4
PdCl₂/CyPPh₂, KHCO₃
————————————→
MeTHF/H₂O
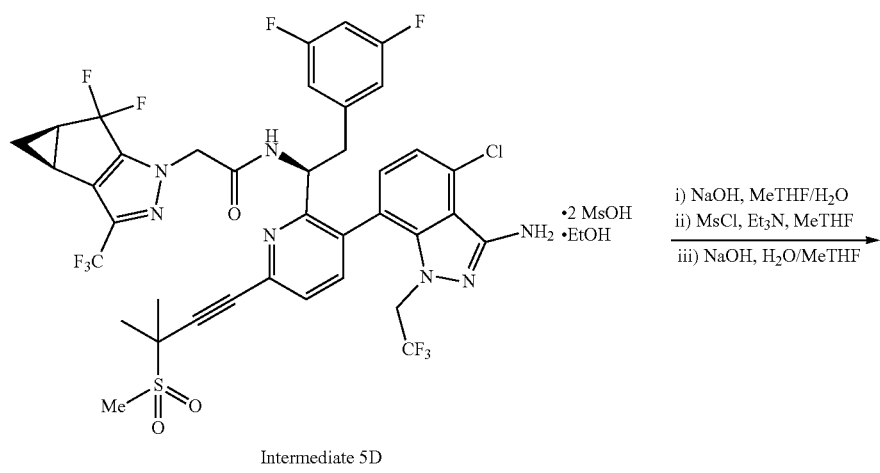
Intermediate 5D
i) NaOH, MeTHF/H₂O
ii) MsCl, Et₃N, MeTHF
iii) NaOH, H₂O/MeTHF

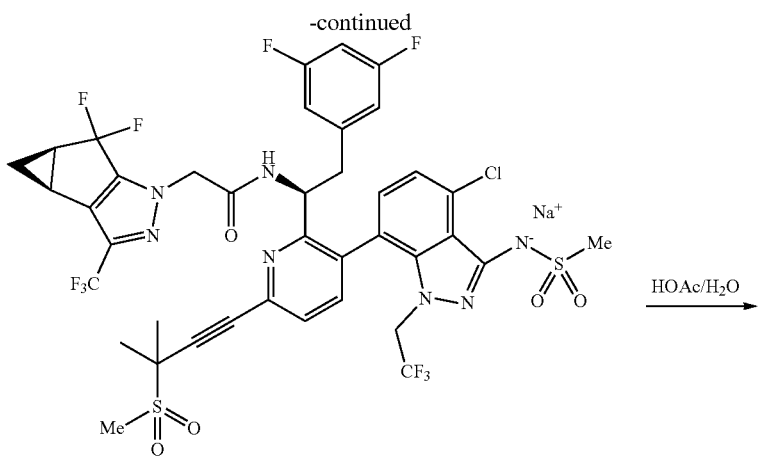

Intermediate 5E

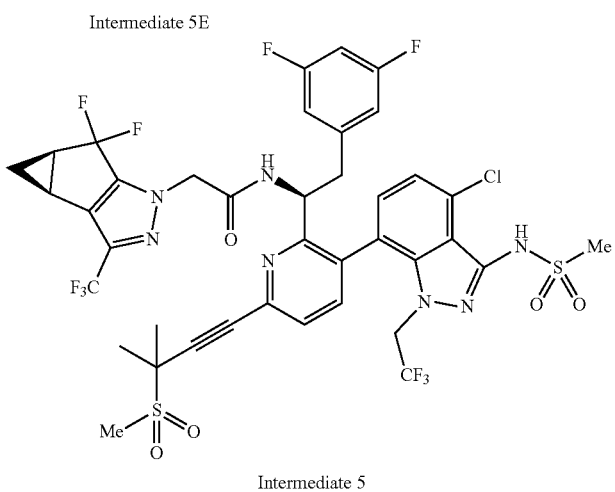

Intermediate 5

Synthesis of (S)-1-(3-bromo-6-(3-methyl-3-(methylsulfonyl)but-1-yn-1-yl)pyridin-2-yl)-2-(3,5-difluorophenyl)ethan-1-amine (Intermediate 5B): A mixture of Intermediate 1 (35.33 mmol, 1.00 equiv), Intermediate 5A (39.7 mmol, 1.12 equiv), bis(triphenylphosphine)palladium(II) dichloride (0.54 mmol, 0.015 equiv), and triethylamine (178.7 mmol, 5.06 equiv) in MeCN (64 g) was heated at 70° C. for 6 h. Water (10.1 g) was added and the mixture was cooled to 50° C. N-Acetyl-L-cysteine (0.60 g) was added and the mixture was cooled to RT. Water (150 g) was added and the reaction was filtered. The filter cake was washed with a mixture of MeCN (20 g) and water (52 g) and dried under vacuum to yield title compound Intermediate 5B. $^1$H NMR (400 MHz, DMSO-$d_6$) δ 8.05 (d, J=8.2 Hz, 1H), 7.42 (d, J=8.2 Hz, 1H), 7.01 (tt, J=9.5, 2.4 Hz, 1H), 6.97-6.84 (m, 2H), 4.41 (dd, J=8.5, 5.2 Hz, 1H), 3.20 (s, 3H), 2.93 (dd, J=13.3, 5.2 Hz, 1H), 2.79 (dd, J=13.3, 8.5 Hz, 1H), 1.99 (s, 2H), 1.68 (s, 6H). $^{13}$C NMR (101 MHz, DMSO-$d_6$) δ 162.25, 162.00 (dd, J=245.2, 13.4 Hz), 143.88 (t, J=9.4 Hz), 141.09, 139.72, 127.51, 120.08, 112.58-112.12 (m), 101.45 (t, J=25.7 Hz), 87.94, 84.25, 57.24, 55.90, 42.57, 34.99, 22.19.

Synthesis of N—((S)-1-(3-bromo-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Intermediate 5C): To a mixture of Intermediate 5B (43.8 mmol, 1.00 equiv), Intermediate 3 (48.1 mmol, 1.10 equiv), triethylamine (65.3 mmol, 1.49 equiv) in MeCN (100 g) was added a 50% (w/w) T3P/DMF solution (132 mmol, 1.5 equiv) and the mixture was stirred for 3 h. DMF (20.1 g) and water (50.1 g) were added followed by seed crystals of title compound Intermediate 5C (0.06 g). Water (90.0 g) was added and the reaction was filtered. The filter cake was washed with a mixture of MeCN (70.0 g) and water (90.1 g) and dried under vacuum to yield title compound Intermediate 5C. $^1$H NMR (400 MHz, DMSO-$d_6$) δ 9.19 (d, J=8.3 Hz, 1H), 8.12 (d, J=8.3 Hz, 1H), 7.50 (d, J=8.3 Hz, 1H), 7.07 (tt, J=9.4, 2.4 Hz, 1H), 6.96-6.87 (m, 2H), 5.52 (td, J=8.8, 5.3 Hz, 1H), 4.93-4.73 (m, 2H), 3.22 (s, 3H), 3.11-2.90 (m, 2H), 2.66-2.52 (m, 2H), 1.69 (s, 6H), 1.45-1.36 (m, 1H), 1.02-0.93 (m, 1H). $^{13}$C NMR (100 MHz, DMSO-$d_6$): δ 164.42, 163.62, 163.49, 161.17, 161.04, 158.19, 142.92, 142.20, 142.10, 142.01, 141.63, 140.23, 134.11, 133.73, 132.14, 128.66, 122.23, 120.49, 119.56, 112.49, 112.25, 104.75, 102.25, 88.62, 84.20, 57.44, 53.85, 53.03, 35.21, 23.41, 22.46, 22.40, 11.79.

Synthesis of N—((S)-1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Intermediate 5D): A mixture of Intermediate 5C (88.0 mmol, 1.00 equiv), Intermediate 4 (105 mmol, 1.19 equiv), potassium bicarbonate (266 mmol, 3.03 equiv), palladium(II) chloride (1.3 mmol, 0.015 equiv), and cyclohexyldiphenylphosphine (2.7 mmol, 0.030 equiv) in 2-methyltetrahydrofuran (449 g) and water (130 g) was heated at 70° C. for 15 h and then cooled to 40° C. N-Acetyl-L-cysteine (19.5 g), water (202 g), NaOH (6.5 g), and EtOH (48.7 g) were added and the mixture was stirred for 1 h. The aqueous phase was removed and the organic phase was washed with a mixture of N-acetyl-L-cysteine (19.5 g), water (429 g), NaOH (6.5 g), and EtOH (48.8 g) followed by a solution of water (293 g) and sodium dihydrogen phosphate (32.5 g). A portion of the organic phase (97.5 g) was azeotropically distilled with additional 2-methyltetrahydrofuran, followed by solvent exchange into EtOH and distillation to a volume of about 4 ml/g. Methanesulfonic acid (39.1 mmol) and seed crystals of title compound Intermediate 5D (0.06 g) were added followed by di-n-butyl ether (86.3 g). The reaction was filtered and the filter cake was washed with twice with a mixture of di-n-butyl ether (24 g) and ethanol (5.0 g) and dried under vacuum to yield title compound Intermediate 5D. $^1$H NMR (400 MHz, DMSO-$d_6$) δ 9.19 (d, J=8.3 Hz, 2H), 7.84-7.69 (m, 4H), 7.11 (d, J=7.7 Hz, 2H), 7.07-6.95 (m, 3H), 6.82 (d, J=7.7 Hz, 2H), 6.54-6.40 (m, 4H), 4.90 (d, J=16.4 Hz, 2H), 4.76-4.60 (m, 4H), 4.15 (dq, J=16.6, 8.4 Hz, 2H), 3.75 (dt, J=16.3, 8.7 Hz, 2H), 3.25 (s, 7H), 2.99-2.86 (m, 4H), 2.63-2.50 (m, 3H), 2.41 (s, 14H), 1.73 (d, J=2.1 Hz, 13H), 0.93 (dd, J=6.1, 3.9 Hz, 2H).

Synthesis of N—((S)-1-(3-(3-amino-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Intermediate 5E): A mixture of Intermediate 5D (17.8 mmol, 1.00 equiv) in 2-methyltetrahydrofuran (181 g) was washed with a solution of sodium carbonate (38 mmol, 2.1 equiv) in water (200 g). The aqueous phase was discarded and the organic phase was washed twice with a solution of sodium carbonate 38 mmol, 2.1 equiv) and sodium chloride (4.0 g) in water (200 g). The organic phase was azeotropically distilled with additional 2-methyltetrahydrofuran, followed by distillation to a volume of about 3 ml/g. Additional 2-methyltetrahydrofuran (240 g) was added, the temperature was adjusted to 10° C., and triethylamine (112 mmol, 6.3 equiv) and methanesulfonyl chloride (52 mmol, 2.9 equiv) were added. After 1.5 h, the mixture was washed with water (100 g). The organic phase was treated with a solution of sodium hydroxide (61 mmol, 3.4 equiv) in water (60 g) and warmed to 35° C. The aqueous phase was discarded and the organic phase was washed with water (60 g) and then azeotropically distilled with additional 2-methyltetrahydrofuran, followed by solvent exchange into EtOH and distillation to a volume of about 3 ml/g. Additional EtOH (32 g) was charged followed by n-heptane (69 g). The reaction was filtered and the filter cake was washed with a mixture of n-heptane (34 g) and ethanol (40 g) and dried under vacuum to yield title compound Intermediate 5E. $^1$H NMR (400 MHz, DMSO-$d_6$) δ 9.09 (d, J=8.0 Hz, 1H), 8.93* (d, J=8.5 Hz), 7.80-7.72* (m), 7.71 (s, 2H), 6.99 (tt, J=9.5, 2.4 Hz, 1H), 6.94 (d, J=7.6 Hz, 1H), 6.90* (d, J=6.3 Hz), 6.69 (d, J=7.6 Hz, 1H), 6.57-6.51* (m), 6.48-6.40 (m, 2H), 4.90 (d, J=16.5 Hz, 1H), 4.77 (d, J=16.4 Hz, 1H), 4.70 (td, J=8.3, 5.2 Hz, 1H), 4.63* (d, J=16.5 Hz), 4.22 (dq, J=16.7, 8.4 Hz, 1H), 3.90-3.75 (m, 1H), 3.26 (s, 3H), 2.92 (td, J=13.8, 8.5 Hz, 2H), 2.83* (s), 2.80 (s, 3H), 2.64-2.51 (m, 2H), 1.74 (d, J=2.2 Hz, 6H), 1.44-1.34 (m, 1H), 0.94 (dq, J=6.0, 3.7 Hz, 1H); $^{13}$C NMR (100 MHz, dmso) δ 164.39, 163.43, 163.39, 163.25, 160.94, 160.91, 160.81, 158.93, 158.22, 152.64, 151.94, 142.92, 142.72, 142.63, 142.43, 142.34, 142.19, 142.10, 142.00, 141.43, 141.14, 139.55, 139.36, 133.95, 133.56, 133.17, 132.12, 131.93, 131.68, 129.66, 129.56, 128.17, 127.91, 126.86, 126.76, 125.02, 122.35, 122.21, 122.08, 122.05, 119.93, 119.88, 119.38, 118.88, 118.18, 117.54, 117.21, 117.04, 112.18, 112.02, 111.95, 111.84, 111.78, 102.28, 102.03, 101.81, 88.14, 88.00, 84.69, 84.65, 57.33, 53.22, 52.96, 52.76, 52.44, 40.15, 39.94, 39.73, 39.52, 39.31, 39.10, 38.97, 38.89, 38.65, 35.10, 35.08, 27.86, 27.56, 27.52, 27.23, 23.19, 22.42, 22.41, 22.30, 22.28, 11.63. * Signals arising from minor atropisomer. $^{13}$C NMR data is reported for the mixture of atropisomers.

Synthesis of N—((S)-1-(3-(4-chloro-3-(methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (Intermediate 5): Intermediate 5E (1.0 g) and glacial acetic acid (2.1 g) were combined at about 20° C. and were agitated until dissolved. The resultant solution was transferred to a reactor containing water (15 g) over about 1 hour. The resultant slurry was further agitated for about one hour, and was filtered. The filter cake was washed with water (2×5 g), deliquored, and dried at about 60° C. under vacuum to provide title compound Intermediate 5, which is also known as lenacapavir. $^1$H NMR (400 MHz, $δ_6$-DMSO; 5:1 mixture of atropisomers) δ 10.11* (s), 10.00 (s, 1H), 9.25 (d, J=8.0 Hz, 1H), 8.92* (d, J=8.4 Hz), 7.90* (d, J=7.6 Hz), 7.81 (d, J=8.0 Hz, 1H), 7.76 (d, J=8.0 Hz, 1H), 7.32 (d, J=7.6 Hz, 1H), 7.23* (d, J=8.0 Hz), 7.19* (d, J=8.0 Hz), 7.02 (tt, J=9.4, 2.4 Hz, 1H), 6.94* (m), 6.86 (d, J=7.6 Hz, 1H), 6.54* (m), 6.48 (m, 2H), 4.92 (d, J=16.4 Hz, 1H), 4.77* (d, J=16.4 Hz), 4.71 (d, J=16.4 Hz, 1H), 4.68* (m), 4.51 (dq, J=16.4, 8.3 Hz, 1H), 4.19* (dq, J=16.4, 8.2 Hz), 3.96 (dq, J=16.8, 8.4 Hz, 1H), 3.27 (s, 3H), 3.24* (s), 3.17 (s, 3H), 3.11* (dd, J=13.0, 3.4 Hz), 3.02 (dd, J=13.6, 5.6 Hz, 1H), 2.95 (dd, J=13.8, 8.6 Hz, 1H), 2.92* (m), 2.60 (m, 1H), 2.55 (m, 1H), 1.74 (s, 6H), 1.40 (m, 1H), 0.96 (m, 1H); $^{13}$C NMR (100 MHz, $δ_6$-DMSO; 5:1 mixture of atropisomers) δ 164.5, 163.4*, 162.1 (dd, J=246.0, 13.4 Hz), 162.0* (dd, J=246.1, 13.4 Hz), 158.8, 158.1*, 142.7 (t, J=29.3 Hz), 142.3, 142.1* (m), 141.9 (t, J=9.5 Hz), 141.7*, 140.2*, 140.0*, 139.8*, 139.5, 139.3, 139.2, 133.8 (q, J=38.7 Hz), 132.0 (m), 131.7*, 131.1, 130.3*, 130.0, 126.8, 126.4, 126.2*, 123.0* (m), 122.9 (q, J=281.7 Hz), 122.7*, 122.1, 120.7 (q, J=268.3 Hz), 119.9 (t, J=243.4 Hz), 119.0, 118.7*, 117.5*, 117.4, 112.0 (m), 102.1 (t, J=25.6 Hz), 101.9* (m), 88.5*, 88.4, 84.5, 57.3, 52.8, 52.7, 52.4*, 50.2 (q, J=33.3 Hz), 50.0 (m), 41.4*, 41.2, 39.8, 38.7, 35.1, 27.5 (dd, J=35.1, 29.0 Hz), 23.2, 22.4, 22.3, 22.2*, 11.6. * Signals arising from the minor atropisomer.

FINAL EXAMPLES

Example 1

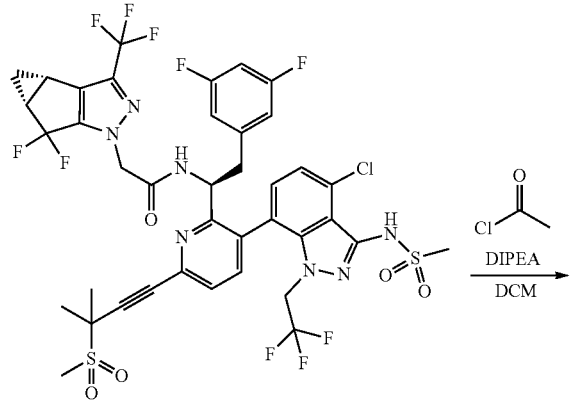

Intermediate 5

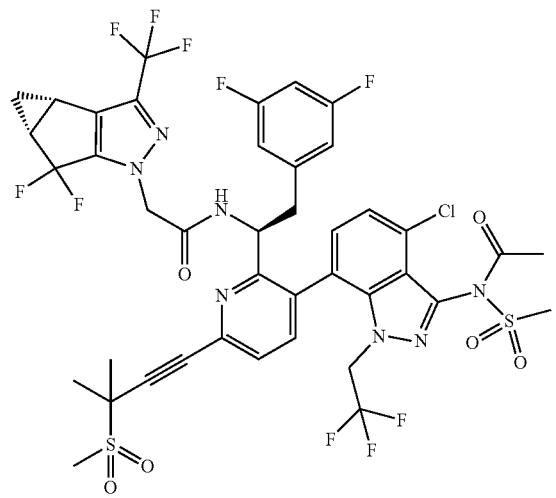

1

Synthesis of N—((S)-1-(3-(4-chloro-3-(N-(methylsulfonyl)acetamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (1): Intermediate 5 (0.0434 mmol) was dissolved in DCM (2 mL). Diisopropylethylamine (0.13 mmol) was added and the solution was cooled to 0° C. Acetyl chloride (0.065 mmol) was added and the mixture was stirred at 0° C. for 30 min. The solvent was then removed under reduced pressure and the residue was purified by reverse phase HPLC (5-95% acetonitrile/water with 0.1% TFA) to yield title compound 1 as a mixture of atropisomers. $^1$H NMR (400 MHz, DMSO-$d_6$) δ 9.12 (d), 7.92-7.70 (m), 7.47-7.23 (m), 7.09-6.93 (m), 6.85 (d), 6.55-6.36 (m), 4.97-4.48 (m), 3.95-3.85 (m), 3.58 (s), 3.53 (s), 3.24 (s), 3.15-2.87 (m), 2.62-2.50 (m), 2.00 (s), 1.43-1.34 (m), 0.99-0.92 (m) ppm. MS (m/z) 1010.1 [M+H]$^+$.

Example 2

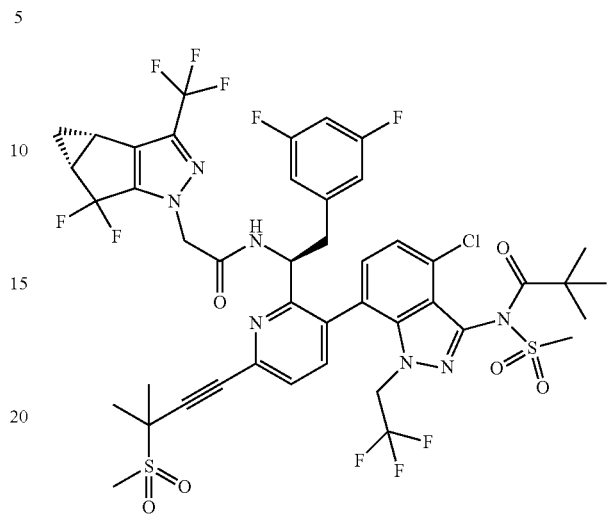

2

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-methyl-1H-indazol-3-yl)-N-(methylsulfonyl)octanamide (2): An atropisomeric mixture of the title compound was prepared according to the method presented for the synthesis of 1 of Example 1 utilizing pivaloyl chloride in the place of acetyl chloride. $^1$H NMR (400 MHz, Methanol-$d_4$) δ 8.84 (m), 7.91-7.71 (m), 7.74-7.65 (m), 7.41-7.25 (m), 6.80-6.70 (m), 6.59 (m), 6.27 (m), 4.72-4.56 (m), 3.94 (dq), 3.53 (m), 3.46 (s), 3.23 (m), 3.22 (m), 3.14-2.99 (m), 2.91 (dd), 2.48 (m), 2.23-2.09 (m), 2.06-1.97 (m), 1.82 (s), 1.81 (d), 1.55 (s), 1.56-1.47 (m), 1.48-1.28 (m), 1.27 (d), 1.19 (m), 0.91-0.80 (m). MS (m/z) 1054.24 [M+H]$^+$.

Example 3

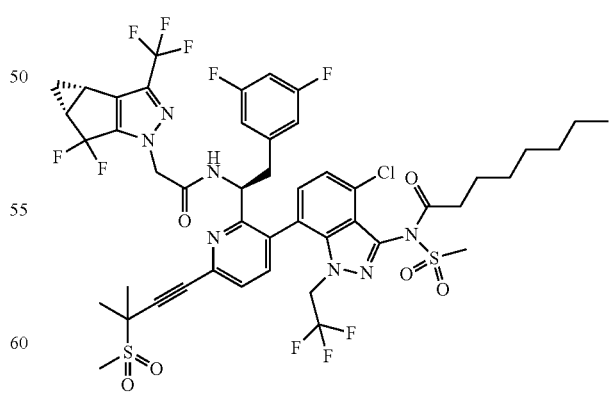

3

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)

but-1-yn-1-yl)pyridin-3-yl)-1-methyl-1H-indazol-3-yl)-N-(methylsulfonyl)pivalamide (3): An atropisomeric mixture of the title compound was prepared according to the method presented for the synthesis of 1 of Example 1 utilizing octanoyl chloride in the place of acetyl chloride. $^1$H NMR (400 MHz, Methanol-$d_4$) δ 8.86 (m), 7.90-7.65 (m), 7.40-7.23 (m), 6.75 (m), 6.48 (m), 6.28-6.18 (m), 4.79-4.58 (m), 3.98 (m), 3.46 (m), 3.39 (s), 3.24 (m), 3.13-2.83 (m), 2.55-2.44 (m), 1.82 (m), 1.81 (m), 1.06 (m), 0.95 (s) ppm. MS (m/z) 1052.16 [M+H]$^+$.

Example 4

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl)-2-morpholinoacetamide) (4): To a solution Intermediate 5 (0.156 mmol), 2-morpholineacetic acid (0.468 mmol, 3 equiv), and DMAP (0.468 mmol, 3 equiv) in DMF (2 mL) was added EDC (0.468 mmol, 3 equiv). When the reaction had reached completion, the mixture was filtered then purified by reverse phase HPLC. Fractions containing the product were pooled and lyophilized to give title compound 4 as a mixture of atro-

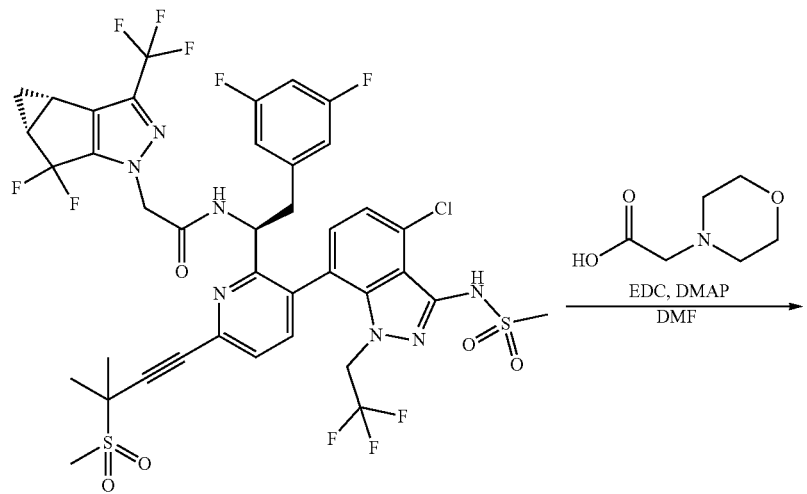

Intermediate 5

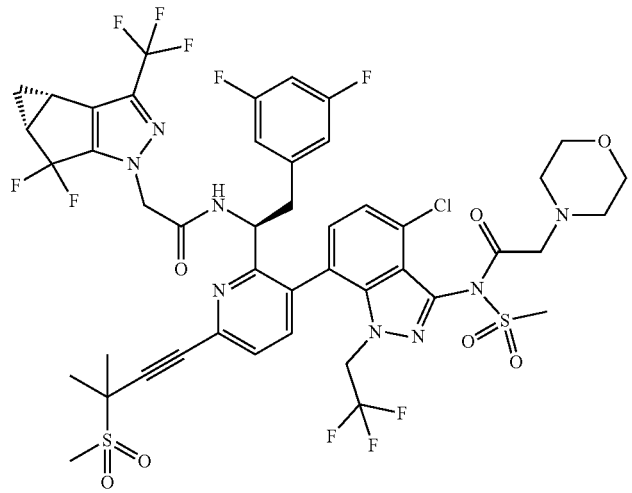

4 pisomers. ¹H NMR (400 MHz, Methanol-d₄) δ 9.06 (d), 8.00 (s), 7.93-7.81 (m), 7.82-7.71 (m), 7.45 (d), 7.36 (dd), 6.88-6.73 (m), 6.37-6.27 (m), 4.73 (s), 4.32 (s), 4.02 (dq), 3.82 (s), 3.69 (s), 3.69 (s), 3.60 (s), 3.54 (s), 3.25 (s), 3.15-3.05 (m), 3.02 (s), 2.88 (d), 2.62-2.51 (m), 1.84 (s), 1.84 (d), 1.48 (q), 1.13 (d) ppm. MS (m/z) 1095.21 [M+H]⁺.

Example 5

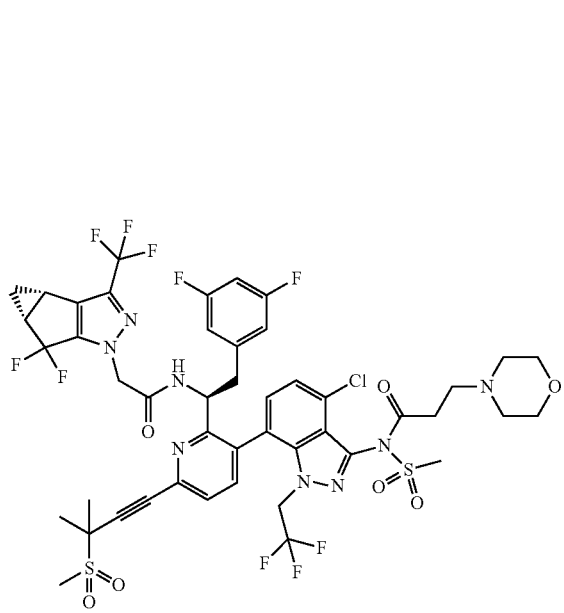 [SMILES: CC(C)(C#Cc1ccc(-c2ccc(Cl)c3c(N(C(=O)N[C@@H](CC(=O)O)C(=O)O)S(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

Example 6

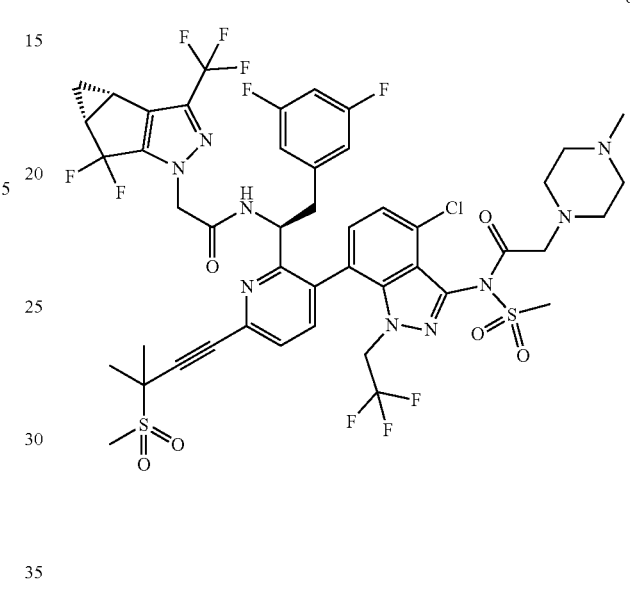

Synthesis of N-(4-chloro-7-(2-((S)-1-(2-((3bS,4aR)-5,5-difluoro-3-(trifluoromethyl)-3b,4,4a,5-tetrahydro-1H-cyclopropa [3,4] cyclopenta [1,2-c]pyrazol-1-yl) acetamido)-2-(3,5-difluorophenyl)ethyl)-6-(3-methyl-3-(methylsulfonyl) but-1-yn-1-yl) pyridin-3-yl)-1-(2,2,2-trifluoroethyl)-1H-indazol-3-yl)-N-(methylsulfonyl)-3-morpholinopropanamide (5): An atropisomeric mixture of the title compound was prepared according to the method presented for the synthesis of 4 of Example 4 utilizing 3-morpholinopropanoic acid in the place of 2-morpholinoacetic acid. 1H NMR (400 MHZ, Chloroform-d) δ 7.65 (d, J=8.1 Hz, 1H), 7.58 (d, J=7.9 Hz, 1H), 7.26-7.20 (m, 1H), 6.97 (d, J=13.9 Hz, 1H), 6.66 (q, J=12.7, 10.7 Hz, 1H), 6.34-6.15 (m, 4H), 4.74 (s, 3H), 3.94 (s, 6H), 3.55 (d, J=11.2 Hz, 6H), 3.41 (d, J=34.7 Hz, 4H), 3.20 (s, 5H), 3.03 (s, 2H), 2.95 (s, 4H), 2.90 (t, J=6.5 Hz, 5H), 2.52 (s, 4H), 1.89 (d, J=3.0 Hz, 9H), 1.47 (dd, J=15.0, 7.7 Hz, 2H), 1.18 (s, 2H) ppm. 19F NMR (375 MHz, Chloroform-d) δ -61.95--62.28 (m), -70.02, -70.71--71.19 (m), -76.31, -76.35, -80.67 (d), -81.04--81.49 (m), -103.48--103.91 (m), -104.28, -109.74 (dq), -110.11, -110.51 ppm. MS (m/z) 1110.31 [M+H]⁺.

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl) but-1-yn-1-yl)pyridin-3-yl)-1-(2,2,2-trifluoroethyl)-1H-indazol-3-yl)-2-(4-methylpiperazin-1-yl)-N-(methylsulfonyl)acetamide) (6): An atropisomeric mixture of the title compound was prepared according to the method presented for the synthesis of 4 of Example 4 utilizing 2-(4-methylpiperazin-1-yl)acetic acid in the place of 2-morpholinoacetic acid. ¹H NMR (400 MHz, Methanol-d₄) δ 9.03 (d), 8.00 (s), 7.94-7.81 (m), 7.80-7.68 (m), 7.37 (t), 6.90-6.73 (m), 6.72-6.59 (m), 6.38-6.30 (m), 4.94 (s), 4.71 (d), 4.36 (p), 3.99 (dq), 3.57 (d), 3.49 (s), 3.43-3.33 (m), 3.25 (d), 3.22-2.94 (m), 2.91-2.81 (m), 2.62-2.53 (m), 2.49-2.41 (m), 1.84 (d), 1.53-1.39 (m), 1.12-1.03 (m). MS (m/z) 1108.31 [M+H]⁺.

Example 7

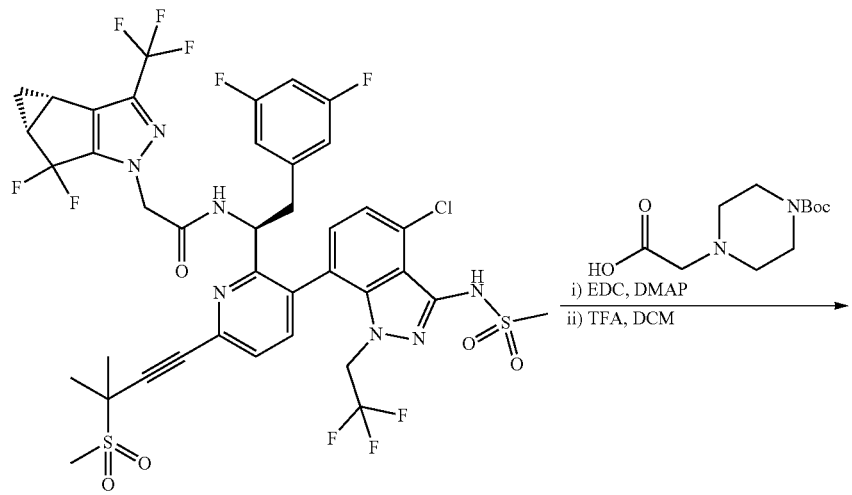

Intermediate 5

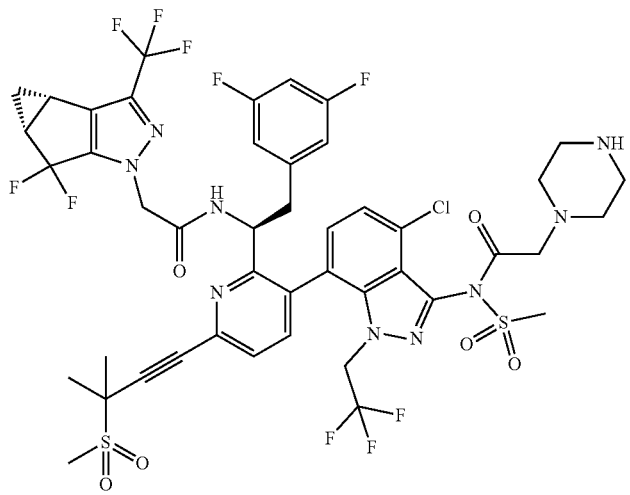

7

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl)-2-(piperazin-1-yl)acetamide) (7): To a solution of Intermediate 5 (0.156 mmol), 2-(4-tert-butoxycarbonylpiperazin-1-yl)acetic acid (0.468 mmol, 3 equiv), and DMAP (0.468 mmol, 3 equiv) in DMF (2 mL) was added EDC (0.468 mmol, 3 equiv). When the reaction had reached completion, the mixture was diluted with DCM (5 mL) and TFA (1 mL). The resulting mixture was then concentrated under reduced pressure, filtered, and purified by reverse phase HPLC. Fractions containing the product were pooled and lyophilized to obtain title compound 7. $^1$H NMR (400 MHz, Methanol-$d_4$) δ 9.02 (d), 8.00 (s), 7.94-7.81 (m), 7.80-7.70 (m), 7.40-7.32 (m), 6.83 (ddd), 6.62 (dd), 6.33 (d), 4.75-4.61 (m), 3.98 (dq), 3.58 (s), 3.48 (s), 3.26 (s), 3.24-3.08 (m), 3.09-2.95 (m), 2.88 (d), 2.82 (s), 2.70-2.50 (m), 1.84 (s), 1.83 (d), 1.48 (q), 1.08 (s) ppm. MS (m/z) 1094.31 [M+H]$^+$.

Example 8
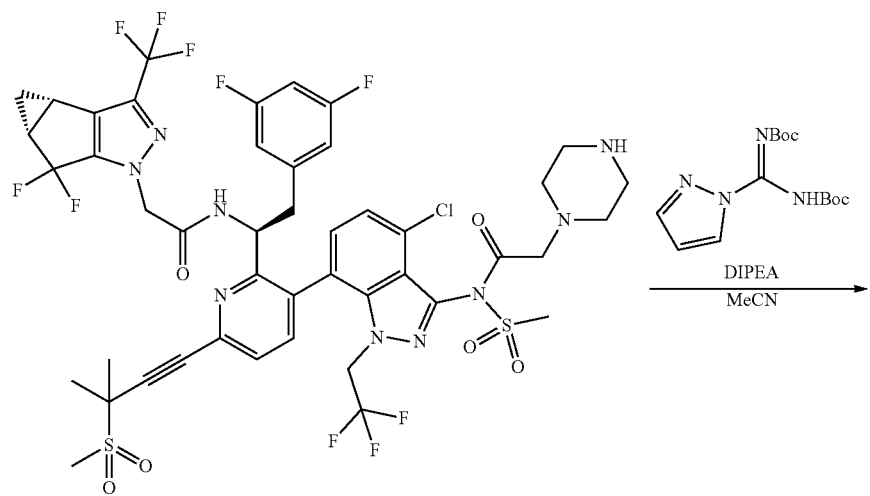
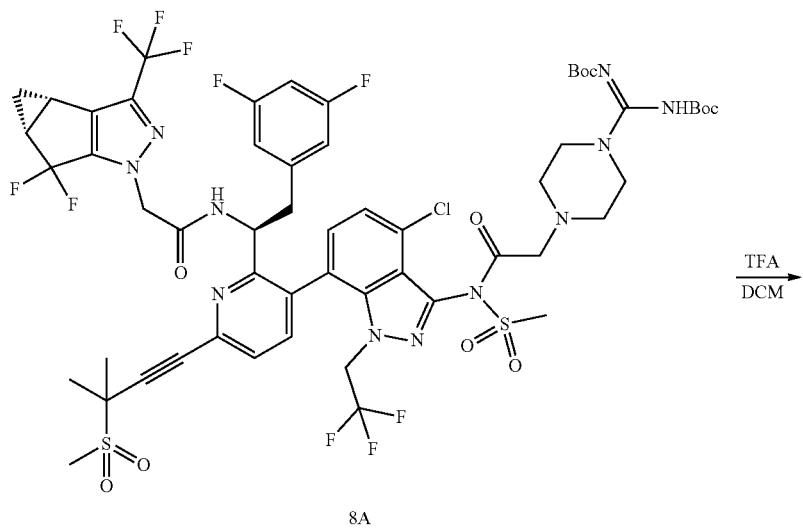
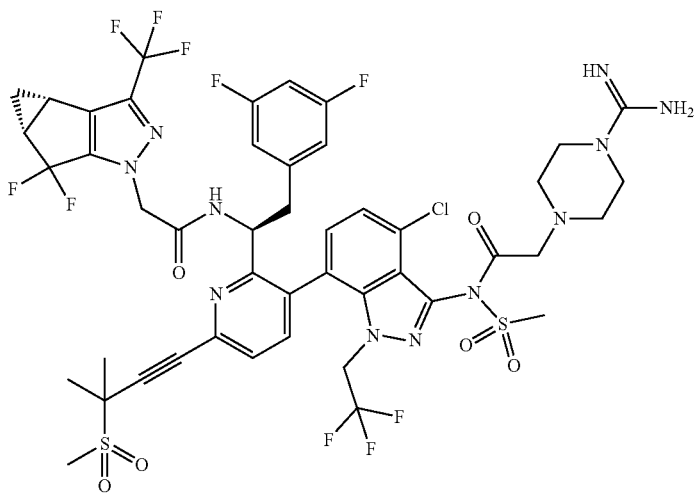

Synthesis of tert-butyl ((E)-((tert-butoxycarbonyl)amino)(4-(2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoethyl)piperazin-1-yl)methylene)carbamate (8A): To a solution of 7 (0.058 mmol) in MeCN (0.2 mL) were added sequentially N,N'-Di-Boc-1H-pyrazole-1-carboxamidine (0.116 mmol) and DIPEA (0.174 mmol) and the resulting mixture was stirred for 30 mins. Upon completion, the mixture was transferred to a separatory funnel using DCM (20 mL) and the organic layer was successively washed with 1M HCl (10 mL). The organic fraction was collected, dried over $Na_2SO_4$, and concentrated under reduced pressure to yield title compound 8A, which was carried forward without purification. MS (m/z) 1235.34 $[M+H]^+$.

Synthesis of 2-(4-carbamimidoylpiperazin-1-yl)-N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl)acetamide (8): To a solution of 8A (0.058 mmol) in DCM (2 mL) was added trifluoroacetic acid (3 mL). Upon completion, the reaction was concentrated under reduced pressure and purified using reverse phase HPLC. Fractions containing the product were pooled and lyophilized to give title compound 8 as a mixture of atropisomers. $^1$H NMR (400 MHz, Methanol-$d_4$) δ 9.05-8.91 (m), 7.95-7.83 (m), 7.76 (d), 7.43-7.32 (m), 7.24 (s), 6.85-6.65 (m), 6.41-6.27 (m), 4.71 (d), 4.05 (dq), 3.57 (s), 3.50 (s), 3.34 (s), 3.25 (s), 3.27-3.18 (m), 3.23-3.09 (m), 3.06 (d), 3.04-2.92 (m), 2.56 (s), 2.46-2.27 (m), 1.84 (s), 1.83 (d), 1.46 (p), 1.32 (d), 1.05 (s), -3.83 (s) ppm. MS (m/z) 1136.33 $[M+H]^+$.

Example 9

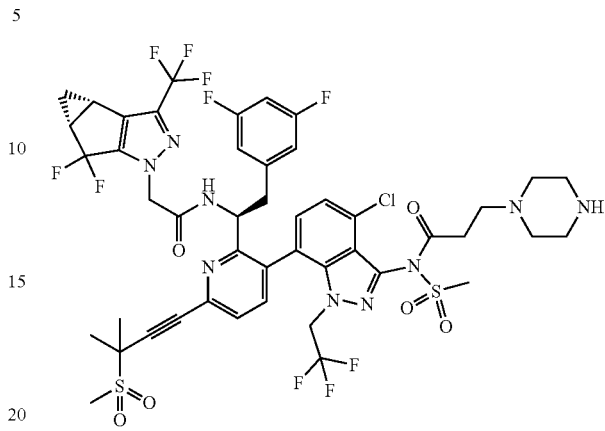

9

Synthesis of N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N-(methylsulfonyl)-3-(piperazin-1-yl)propanamide (9): An atropisomeric mixture of the title compound was prepared according to the two-step method presented for the synthesis of 7 of Example 7 utilizing 3-(4-tert-butoxycarbonylpiperazin-1-yl)propanoic acid in the place of 2-(4-tert-butoxycarbonylpiperazin-1-yl)acetic acid. $^1$H NMR (400 MHz, DMSO-$d_6$) δ 9.20 (dd, J=27.5, 8.3 Hz, 1H), 8.56 (s, 2H), 7.94 (d, J=8.0 Hz, 1H), 7.84 (dd, J=8.0, 2.4 Hz, 1H), 7.49 (dd, J=11.2, 7.7 Hz, 1H), 7.10-6.92 (m, 2H), 6.52-6.35 (m, 2H), 5.01 (d, J=16.5 Hz, 1H), 4.92-4.63 (m, 4H), 4.58 (dq, J=15.3, 7.7 Hz, 1H), 3.99 (dd, J=16.2, 8.3 Hz, 1H), 3.67-3.51 (m, 3H), 3.11 (s, 1H), 3.08-2.87 (m, 5H), 2.66-2.55 (m, 3H), 1.75 (d, J=2.3 Hz, 7H), 1.41 (dd, J=16.2, 9.5 Hz, 1H), 1.01 (s, 1H) ppm. $^{19}$F NMR (375 MHz, DMSO-$d_6$) δ-60.87 (d), -69.40 (dt), -69.98 (t), -74.92, -79.97 (d), -80.57 (dd), -102.80 (d), -103.48 (d), -110.51--110.64 (m), -110.67--110.81 (m) ppm. MS (m/z) 1108.45 $[M]^+$.

Example 10

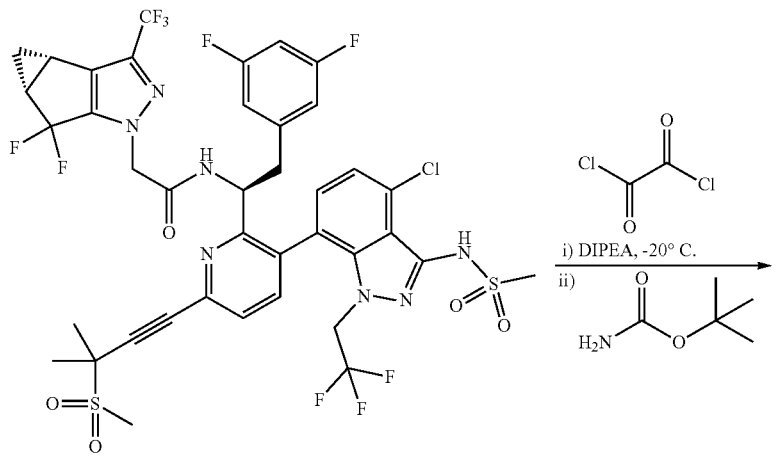

Intermediate 5

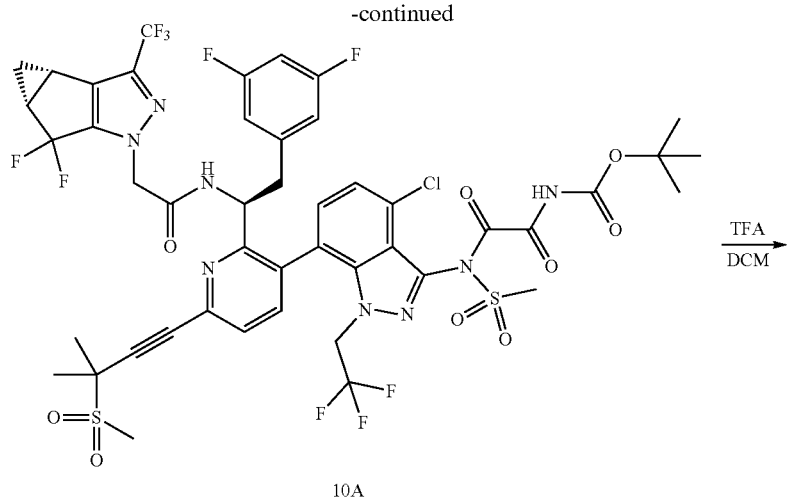

10A

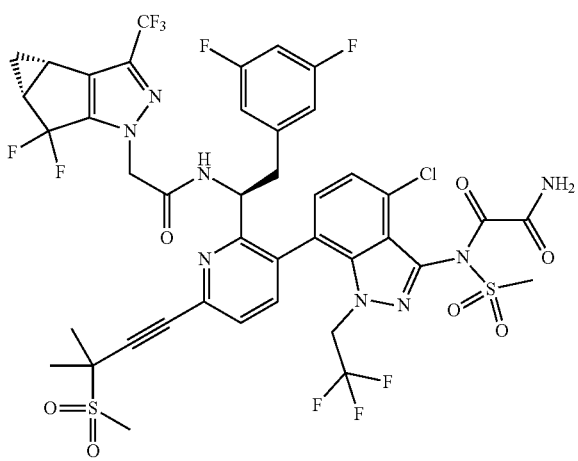

10

Synthesis of N1-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-N1-(methylsulfonyl)oxalamide (10): To a solution of Intermediate 5 (0.155 mmol) in 2 mL of DCM were added sequentially DIPEA (0.775 mmol, 5 equiv) and oxalyl chloride (0.310 mmol, 2 equiv) at −78° C. After 10 mins, tert-butyl carbamate (0.775 mmol, 5 equiv) was added as a single portion and the reaction allowed to warm to rt overnight. Upon completion of this time, the reaction contents were transferred to a separatory funnel using DCM (10 mL) and the organic layer was washed with sat. NaHCO$_3$(10 mL). The organic fraction was collected, dried over Na$_2$SO$_4$, concentrated under reduced pressure, and the resulting residue dissolved in 1 mL of a 5:1 DCM/TFA mixture. After 1 h, the reaction was concentrated under reduced pressure and purified by reverse phase HPLC. Fractions containing the product were pooled and lyophilized to give title compound 10 as a mixture of atropisomers. $^1$H NMR (400 MHz, DMSO-d$_6$) δ 9.23 (dd), 8.51 (d), 8.03 (d), 7.86-7.64 (m), 7.48-7.40 (m), 7.07-6.98 (m), 6.94 (d), 6.49 (ddd), 4.95-4.70 (m), 4.61 (qd), 4.34-4.01 (m), 3.27 (s), 2.99 (qt), 2.69-2.55 (m), 1.75 (d), 1.72-1.54 (m), 1.39 (p), 1.24 (d), 0.93-0.72 (m) ppm. $^{19}$F NMR (375 MHz, DMSO-d$_6$) δ-60.87 (d), −69.44 (t), −69.55, −69.76 (t), −74.98, −79.79 (dd), −80.47 (dd), −103.10--103.26 (m), −103.78--103.93 (m), −110.58 (td), −110.75 ppm. MS (m/z) 1038.93 [M]$^+$.

Example 11

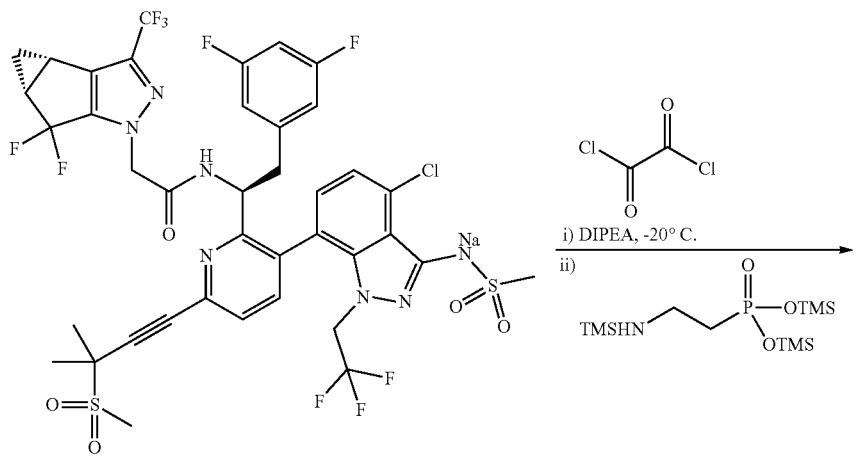

Intermediate 5E

11

Synthesis of (2-(2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoacetamido)ethyl)phosphonic acid (11): A suspension of 2-aminoethylphosphonic acid (0.25 mmol) in dichloromethane (2.5 mL) was treated with N,O-bis(trimethylsilyl)trifluoroacetamide (1 mmol) and diisopropylethylamine (1.0 mmol) at room temperature and the mixture was heated to 45° C. for 3 h. In a separate vial, oxalyl chloride (0.21 mmol) was dissolved in dichloromethane (1.0 mL) and cooled to 0° C. and treated with a solution of Intermediate 5E (0.10 mmol) in dichloromethane (1.0 mL) at 0° C. followed by diisopropylethylamine (0.12 mmol). The resulting reaction mixture was stirred at 0° C. for 30 min. Once oxamoyl chloride formation was observed by LCMS, the reaction was treated with freshly prepared bis(trimethylsilyl) (2-aminoethyl)phosphonate solution. Upon completion, the reaction mixture was concentrated under reduced pressure and purified by reverse phase HPLC. Fractions containing the product were combined and lyophilized to give title compound 11 as a mixture of atropisomers. $^1$H NMR (400 MHz, DMSO-$d_6$) δ 9.32-9.11 (m), 7.91-7.66 (m), 7.43 (d), 7.09-6.92 (m), 6.59-6.38 (m), 4.97-4.70 (m), 4.70-4.53 (m), 4.16-4.00 (m), 3.62 (d), 3.36-3.08 (m), 3.08-2.87 (m), 1.88-1.56 (m), 1.45-1.34 (m), 0.96 (s) ppm. 19F NMR (377 MHz, DMSO-$d_6$) δ-59.77--61.82 (m), -68.63--71.03 (m), -78.98--81.15 (m), -102.30--104.70 (m), -110.18--111.29 (m) ppm. MS (m/z) 1170.85 [M+Na]$^+$.

Example 12

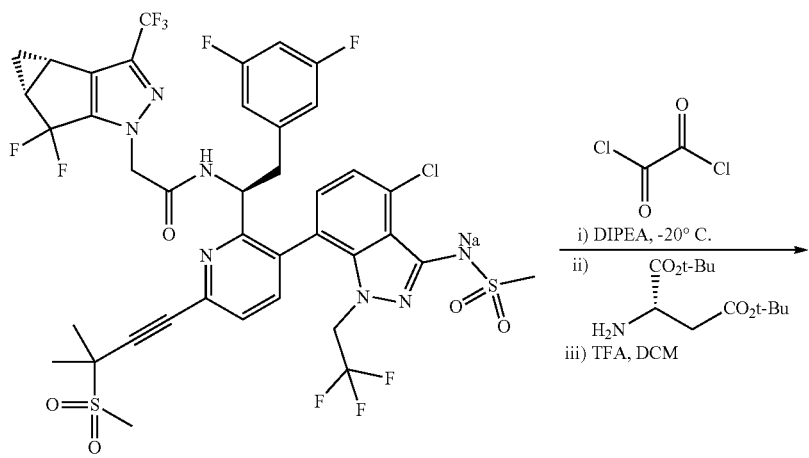

Intermediate 5E

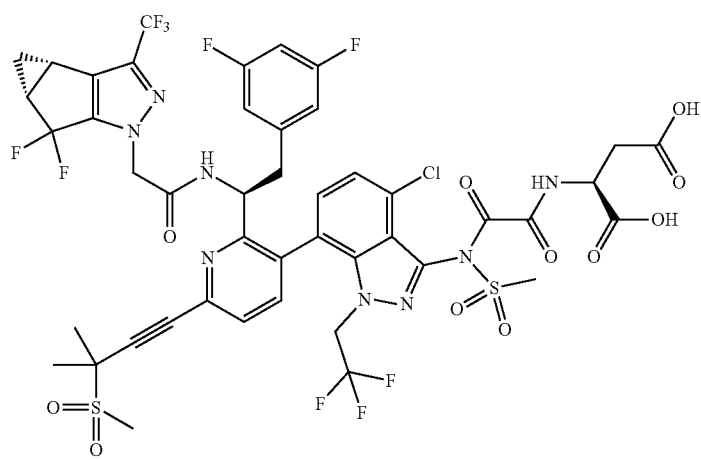

12

Synthesis of (2-(N-(4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoacetyl)-L-aspartic acid (12): An atropisomeric mixture of the title compound was prepared according to the method presented for the synthesis of 10 of Example 10 utilizing (S)-di-tert-butyl 2-aminosuccinate hydrochloride in the place of tert-butylcarbamate and Intermediate 5E in the place of Intermediate 5. $^1$H NMR (400 MHz, DMSO-$d_6$) δ 9.46 (d), 9.23 (dd), 8.22-7.70 (m), 7.42 (d), 7.16-6.89 (m), 6.68-6.32 (m), 5.02-4.68 (m), 4.66-4.37 (m), 4.17-4.06 (m), 3.72-3.52 (m), 3.27 (s), 3.09-2.93 (m), 1.75 (d), 1.48-1.31 (m), 1.31-1.20 (m), 0.96 (s) ppm. $^{19}$F NMR (376 MHz, DMSO-$d_6$) δ-60.37--61.29 (m), -69.53--70.03 (m), -79.35--81.28 (m), -102.63--104.44 (m), -110.07--111.19 (m) ppm. MS (m/z) 1155.88 [M+H]$^+$.

Example 13

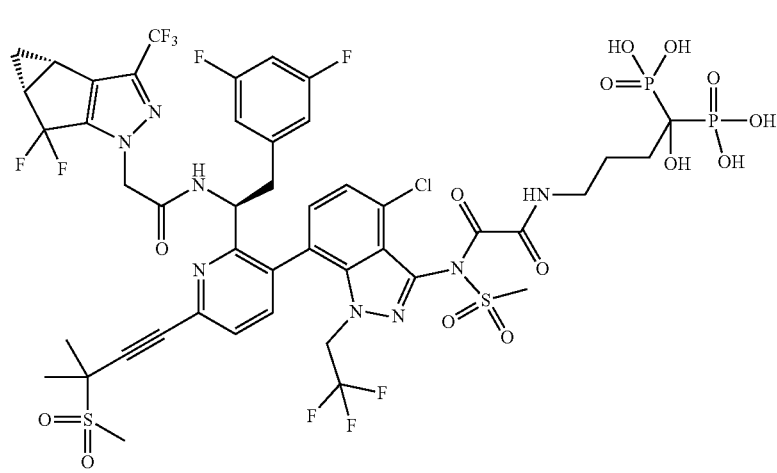

13

Synthesis of (4-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-1-hydroxybutane-1,1-diyl)bis(phosphonic acid) (13): An atropisomeric mixture of the title compound was prepared according to the method presented for the synthesis of 11 of Example 11 utilizing (4-amino-1-hydroxybutane-1,1-diyl)bis(phosphonic acid) in the place of 2-aminoethyl phosphonic acid. $^1$H NMR (400 MHz, DMSO-$d_6$) δ 9.29-9.11 (m), 7.94-7.66 (m), 7.52-7.36 (m), 7.13-6.88 (m), 6.71-6.42 (m), 4.96-4.60 (m), 3.58-3.42 (m), 3.18-2.90 (m), 1.92-1.58 (m), 1.45-1.33 (m), 0.97 (s). $^{19}$F NMR (376 MHz, DMSO-$d_6$) δ -60.85, -69.45 (d), -78.19--82.19 (m), -99.84--101.55 (m), -108.78--112.10 (m). MS (m/z) 1243.95 [M+H]$^+$.

Example 14

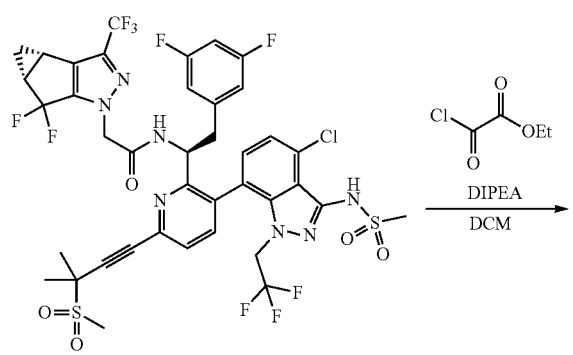

Intermediate 5

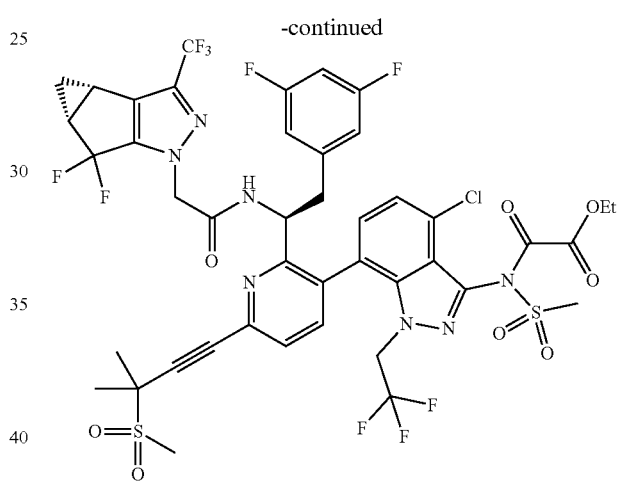

14

Synthesis of ethyl 2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoacetate (14): A solution of ethyl chlorooxoacetate (0.310 mmol) in DCM (0.3 ml) was cooled to 0° C. and to it was added a solution of Intermediate 5 (0.1 mmol) in DCM (2 ml) followed by addition of DIPEA (0.17 mmol). After stirring for 5 mins, the mixture was diluted with DCM and washed with 5% citric acid and brine. The organic layer was separated, dried over MgSO$_4$, filtered and concentrated. The residue was purified by reverse phase HPLC. Fractions containing the product were pooled and lyophilized to give title compound 14 as a mixture of atropisomers. $^1$H NMR (400 MHz, Chloroform-d) δ 7.74-7.49 (m), 7.18 (dd), 6.93 (t), 6.64 (qd), 6.30 (dd), 6.21-6.02 (m), 4.98-4.76 (m), 4.74-4.62 (m), 4.51 (dq), 4.21 (s), 3.96 (dp), 3.53 (d), 3.17 (d), 2.87 (dd), 2.72 (s), 2.48 (q), 1.85 (d), 1.43 (q), 1.34-0.90 (m) ppm. MS (m/z) 1068.12 [M+H]$^+$.

Example 15

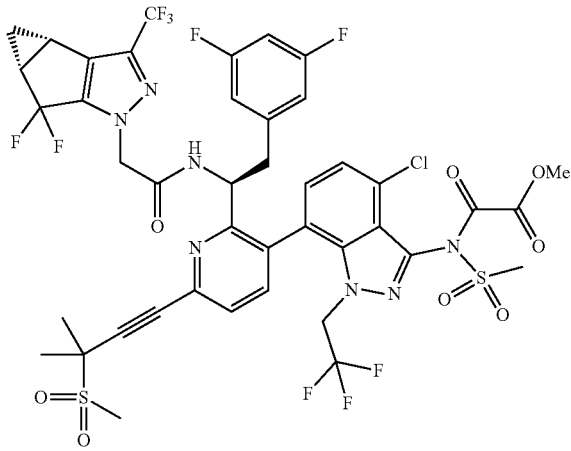

Synthesis of methyl 2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoacetate (15): An atropisomeric mixture of the title compound was prepared according to the method presented for the synthesis of 14 of Example 14 utilizing methyl chlorooxoacetate in the place of ethyl chlorooxoacetate. ¹H NMR (400 MHz, Methanol-d₄) δ 8.87 (d), 7.76 (d), 7.68 (d), 7.29 (dd), 6.86-6.69 (m), 6.62 (d), 6.53 (d), 6.43-6.16 (m), 4.79-4.52 (m), 4.13-3.87 (m), 3.77 (s), 3.50 (d), 3.22 (d), 3.12-2.80 (m), 2.51 (dd), 1.81 (s), 1.41 (q), 1.05 (d) ppm. MS (m/z) 1054.31 [M+H]⁺.

Example 16

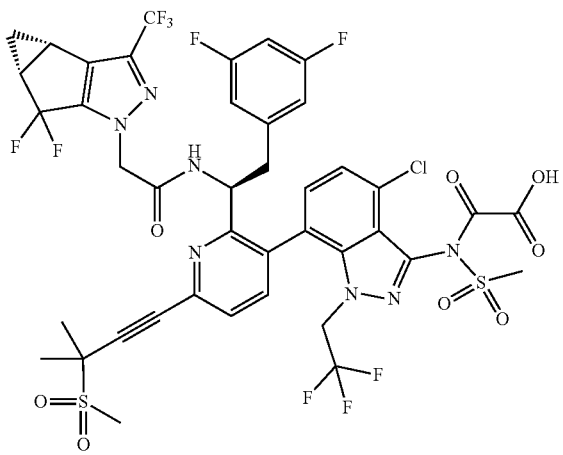

Synthesis of methyl 2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)-2-oxoacetate (16): An atropisomeric mixture of the title compound was prepared according to the method presented for the synthesis of 14 of Example 14 utilizing oxalyl chloride in the place of ethyl chlorooxoacetate. ¹H NMR (400 MHz, Methanol-d₄) δ 8.92 (dd), 7.78-7.72 (m), 7.68 (d), 7.30-7.23 (m), 6.81-6.72 (m), 6.57 (d), 6.53 (dd), 6.35-6.31 (m), 6.31-6.24 (m), 4.87-4.82 (m), 4.82-4.72 (m), 4.71-4.65 (m), 4.19-3.98 (m), 3.56 (s), 3.48 (s), 3.23 (d), 3.14-3.00 (m), 2.99-2.85 (m), 2.59-2.40 (m), 1.45-1.34 (m), 1.13-1.02 (m) ppm. MS (m/z) 1040.56 [M+H]⁺.

Example 17

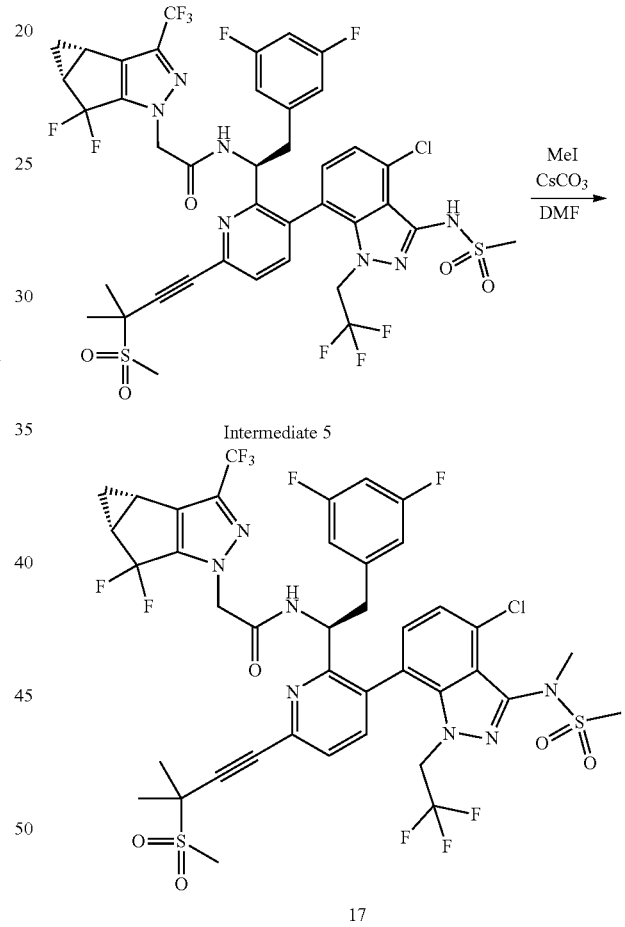

Synthesis of N—((S)-1-(3-(4-chloro-3-(N-methylmethylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (17): To a solution of Intermediate 5 (0.05 mmol) and cesium carbonate (0.258 mmol) in DMF (0.5 mL) was added iodomethane (0.052 mmol) and the reaction was stirred at rt. Upon completion, the reaction was filtered and purified by reverse phase HPLC. Fractions containing the product were pooled and lyophilized to give title compound 17 as a mixture of atropisomers. ¹H NMR (400 MHz, Chloroform-d) δ 7.53-7.48 (m), 7.12 (d), 7.07 (d), 6.64-6.54 (m), 6.18 (d), 6.10-6.03 (m), 4.81-4.73 (m), 4.69-4.63 (m), 4.46-4.31 (m), 4.11-4.01 (m), 3.91-3.78 ( ), 3.44 (s), 3.38 (s), 3.10 (s), 3.09 (s), 2.88 (dd), 2.79 (dd), 2.41 (d), 1.79 (s), 1.74 (d), 1.37 (q), 1.24-1.15 (m), 1.08 (s). MS (m/z) 981.96 [M+H]⁺.

Example 18

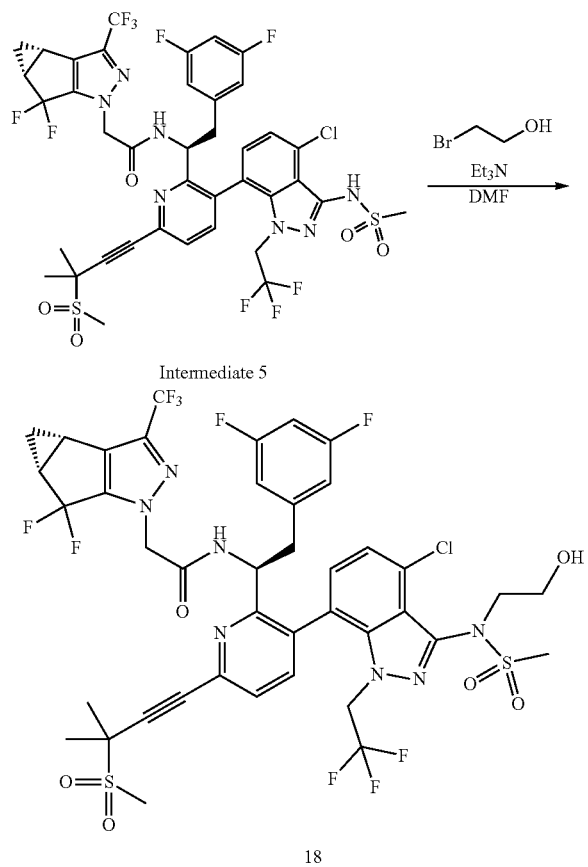

Intermediate 5

18

Synthesis of N—((S)-1-(3-(4-chloro-3-(N-(2-hydroxyethyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (18): Intermediate 5 (0.310 mmol) was dissolved in anhydrous DMF (5 mL). Triethylamine (1.55 mmol) was then added, followed by 2-bromoethanol (0.929 mmol). The vessel was sealed and the mixture was stirred at rt for 1 h then 45° C. for 1 day. Upon completion, the mixture was partitioned between ethyl acetate and water and the organic phase was separated and washed with 5% LiCl aqueous and brine, and the resulting organic fraction was dried over MgSO₄, filtered and concentrated under reduced pressure. The residue was purified by silica gel chromatography eluting with ethyl acetate/hexane to afford title compound 18 as a mixture of atropisomers. ¹H NMR (400 MHz, Methanol-d₄) δ 7.91-7.50 (m), 7.22 (d), 6.75 (dd), 6.51 (s), 6.26 (d), 4.87-4.49 (m), 4.04-3.58 (m), 3.30 (h), 3.20 (s), 3.17-3.00 (m), 2.98-2.74 (m), 2.64-2.27 (m), 1.81 (s), 1.41 (q), 1.13-0.95 (m). MS (m/z) 1012.26 [M+H]⁺.

Example 19

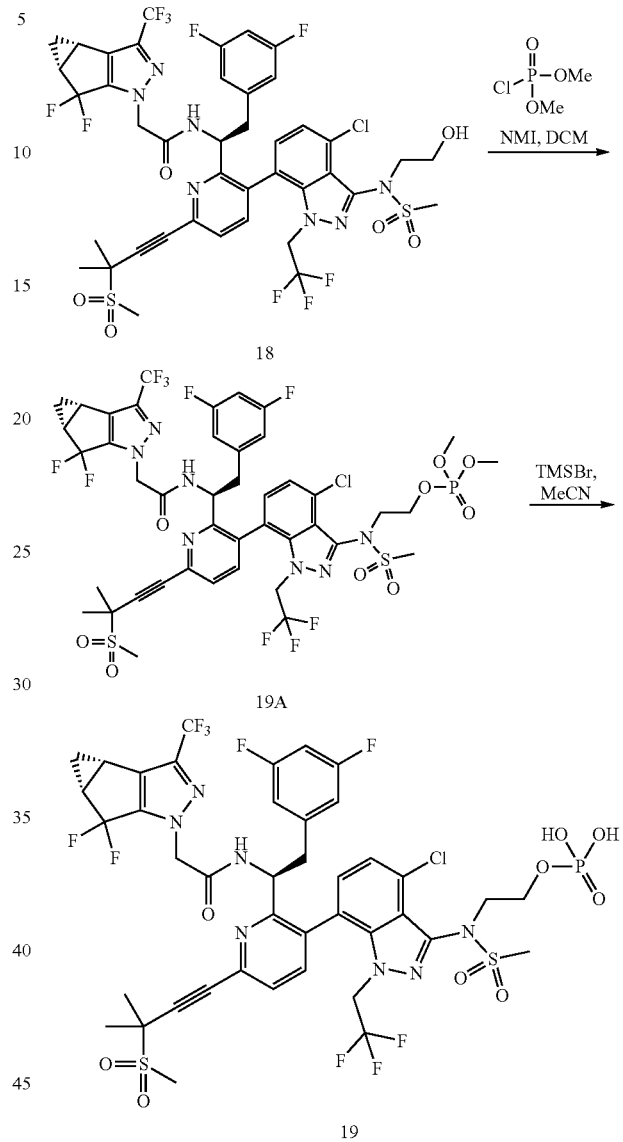

Synthesis of 2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)ethyl dimethyl phosphate (19A): A solution of 18 (0.0988 mmol) in CH₂Cl₂ (2 mL) at rt was treated successively with dimethylchlorophosphate (0.119 mmol) and N-methylimidazole (0.168 mmol). The reaction mixture was stirred at rt for 15 minutes and quenched by addition of saturated aqueous NH₄Cl solution and stirring for 5 minutes. The organic layer was next washed with brine and dried over Na₂SO₄. The solvent was evaporated under reduced pressure and the residue was purified by silica gel chromatography eluting with ethyl acetate in hexanes to afford an atropisomeric mixture of title compound 19A, which was used without further purification.

Synthesis of 2-(N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)ethyl dihydrogen phosphate (19): TMSBr (0.56 mmol) was added dropwise to a solution of 19A (0.056 mmol) in CH$_3$CN (6 mL). The reaction mixture was stirred at rt for 2 h and quenched with methanol and then partitioned between sat'd aq. NH$_4$Cl and ethyl acetate. The organic layer was separated, dried over MgSO$_4$, filtered and concentrated. The residue was purified by reverse phase HPLC. Fractions containing the product were pooled and lyophilized to give title compound 19 as a mixture of atropisomers. $^1$H NMR (400 MHz, Methanol-d$_4$) δ 7.91-7.58 (m), 7.23 (d, J=7.6 Hz), 6.88-6.67 (m), 6.62-6.38 (m), 6.35-6.17 (m,), 4.89-4.58 (m), 4.52-3.66 (m), 3.23 (s), 3.17-3.03 (m), 2.99-2.86 (m), 2.65-2.37 (m), 1.81 (s), 1.51-1.32 (m), 1.15-0.97 (m) ppm. MS (m/z) 1092.04 [M+H]$^+$.

Example 20

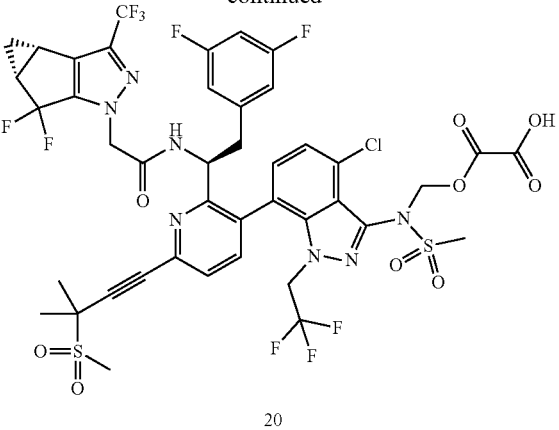

20

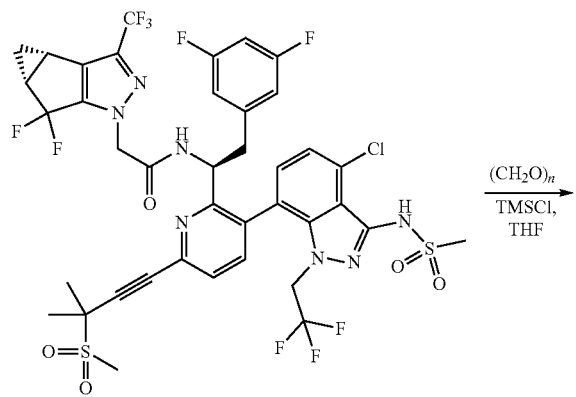

Intermediate 5

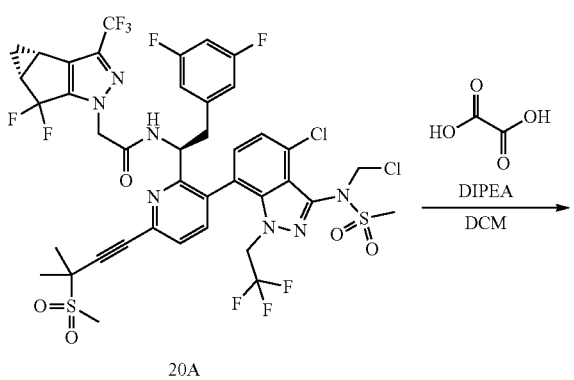

20A

Synthesis of N—((S)-1-(3-(4-chloro-3-(N-(chloromethyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (20A): To a vial containing Intermediate 5 (0.103 mmol) were added sequentially paraformaldehyde (15.5 mmol), chlorotrimethylsilane (8 mmol), and THF (0.2 mL). The vial was sealed and the resulting suspension was stirred at 60° C. overnight. Upon completion of this time, the reaction was filtered through Celite®, and concentrated under reduced pressure to yield title compound 20A, which was used without purification. MS (m/z) 1016.09 [M+H]$^+$.

Synthesis of 2-((N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methoxy)-2-oxoacetic acid (20): To a solution of 20A (0.039 mmol) in DCM (2.5 mL) were added sequentially oxalic acid (0.59 mmol) and DIPEA (0.787 mmol). The resulting suspension was heated to 45° C. overnight. Upon completion of this time, the reaction was filtered through Celite® and concentrated under reduced pressure. The resulting residue was purified by reverse phase HPLC. Fractions containing the product were pooled and lyophilized to give title compound 20 as a mixture of atropisomers. $^1$H NMR (400 MHz, Methanol-d$_4$) δ 8.92 (d), 7.79-7.67 (m), 7.42-7.22 (m), 6.80 (tt), 6.57 (d), 6.39-6.32 (m), 4.02 (dq), 3.74 (hept), 3.46 (s), 3.38 (s), 3.30-3.19 (m), 3.12 (d), 2.98 (dd), 1.83 (d), 1.39 (dd), 1.20 (t) ppm. $^{19}$F NMR (375 MHz, Methanol-d$_4$) δ-63.61, -63.62, -71.75, -72.23, -77.60, -82.46 (d), -83.06, -105.36 (d), -105.92, -112.21 (t), -112.33 ppm. MS (m/z) 1069.67 [M+H]$^+$.

Example 21

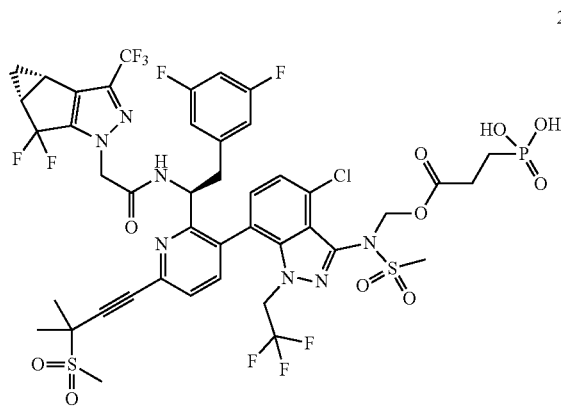

Synthesis of (3-((N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methoxy)-3-oxopropyl)phosphonic acid (21): An atropisomeric mixture of the title compound was prepared according to the method presented for the synthesis of 20 of Example 20 utilizing 3-phosphonopropanoic acid in the place of oxalic acid. $^1$H NMR (400 MHz, DMSO-d$_6$) δ 9.21 (d), 7.87-7.71 (m), 7.49-7.25 (m), 7.04 (td), 6.62-6.41 (m), 5.70 (s), 5.47-5.14 (m), 4.92-4.53 (m), 4.05 (s), 3.18-2.87 (m), 2.41-2.27 (m), 1.74 (d), 1.40 (d), 1.24 (s), 0.96 (s) ppm. $^{19}$F NMR (375 MHz, DMSO-d$_6$) δ-60.52--61.19 (m), -69.53, -74.73 (d), -79.76, -80.44, -103.13, -110.44--111.36 (m). MS (m/z) 1133.84 [M+H]$^+$.

Example 22

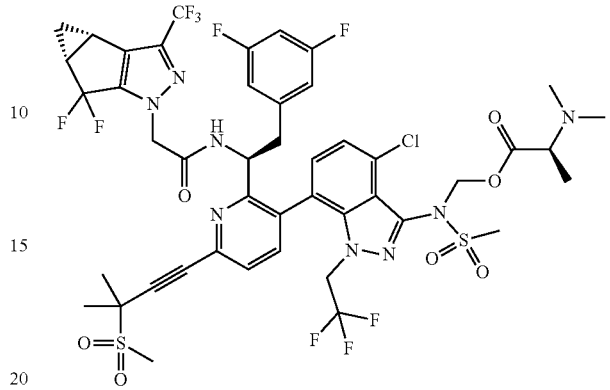

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl dimethyl-L-alaninate (22): An atropisomeric mixture of the title compound was prepared according to the method presented for the synthesis of 20 of Example 20 utilizing N,N-dimethyl-L-alanine in the place of oxalic acid. $^1$H NMR (400 MHz, Methanol-d$_4$) δ 8.00 (s), 7.82-7.67 (m), 7.37 (s), 6.82-6.72 (m), 6.28 (d), 6.05 (d), 4.09 (s), 3.66-3.55 (m), 3.39 (d), 3.25 (d), 3.14 (s), 3.01 (s), 2.97-2.86 (m), 2.87 (d), 2.72 (s), 2.55 (s), 1.98-1.85 (m), 1.84 (d), 1.80-1.58 (m), 1.57 (s), 1.52-1.43 (m), 1.46-1.34 (m), 1.25 (s), 1.09 (s), 1.03 (s), 0.95-0.83 (m) ppm. MS (m/z) 1097.04 [M+H]$^+$.

Example 23

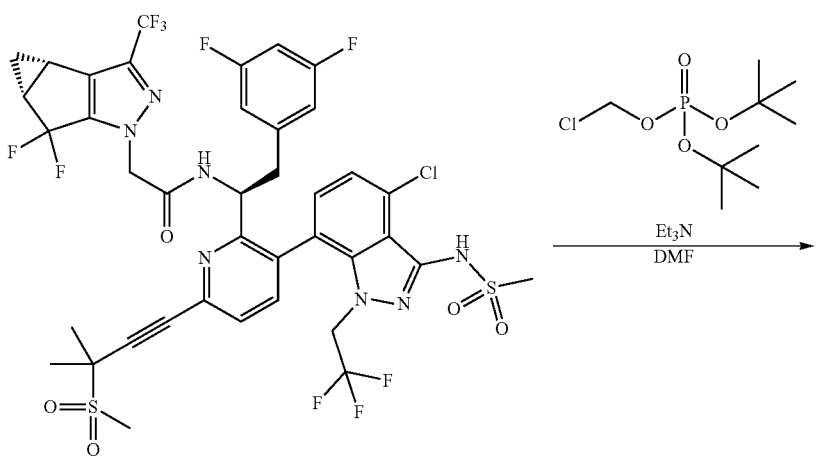

Intermediate 5

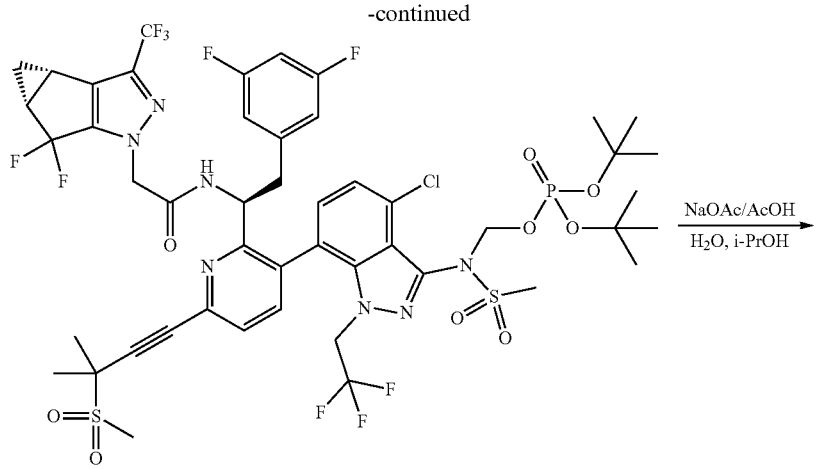

23A

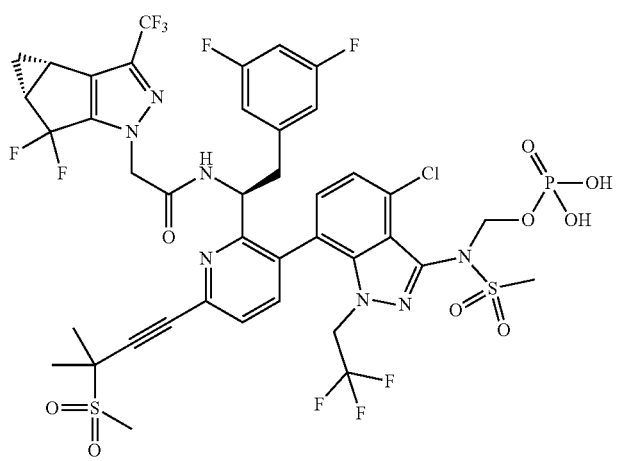

23

Synthesis of di-tert-butyl ((N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl) phosphate (23A): To a solution of Intermediate 5 (0.207 mmol) in 0.5 mL of DMF was added di-tert-butyl chloromethyl phosphate (1.03 mmol) and triethylamine (1.03 mmol). The reaction mixture was stirred at room temperature for 10 minutes then at 70° C. for 24 hours. Upon completion, the reaction was partitioned between 5% LiCl and ethyl acetate, and then the organic layer was separated, washed with brine, dried over MgSO$_4$, filtered and concentrated. The residue was purified by silica gel chromatography eluting with ethyl acetate/hexane to afford an atropisomeric mixture of title compound 23A. MS (m/z) 1189.51 [M+H]$^+$.

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl dihydrogen phosphate (23): 23A (0.06 mmol) was dissolved in isopropanol (3 mL) and to it was added 2 mL of pH 3.7 buffer (sodium acetate/acetic acid). The reaction was allowed to stir at 65° C. for overnight. Upon completion, the mixture was cooled to rt and extracted with ethyl acetate. The organic layer was washed with water and brine, dried over Na$_2$SO$_4$, filtered and concentrated under reduced pressure. The residue was dissolved in acetonitrile/water, passing through a pad of C18 and washed with acetonitrile. The filtrate was lyophilized to give title compound 23 as a mixture of atropisomers. $^1$H NMR (400 MHz, Methanol-d$_4$) δ 7.92-7.51 (m), 7.51-6.97 (m), 6.91-6.65 (m), 6.71-6.04 (m), 6.06-5.51 (m), 5.43-4.95 (m), 4.85-4.32 (m), 4.26-3.82 (m), 3.45 (d), 3.27-2.66 (m), 2.62-2.28 (m), 1.80 (s), 1.53-0.74 (m) ppm. MS (m/z): 1077.51 [M+H]$^+$.

Example 24

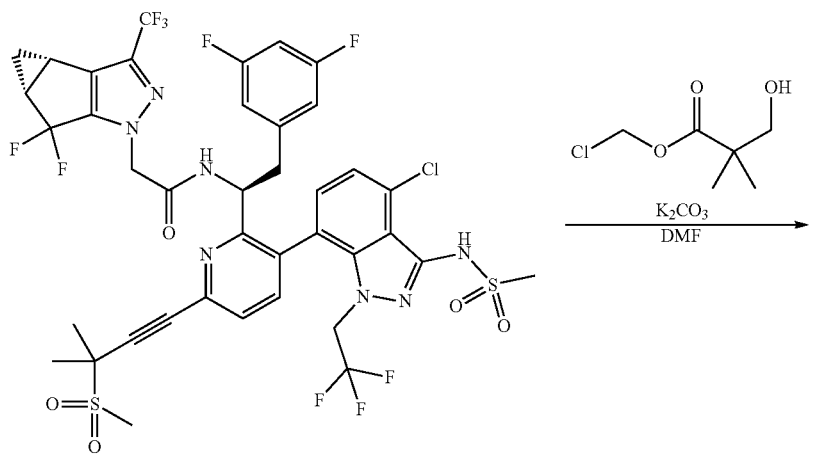

Intermediate 5

24

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl 3-hydroxy-2,2-dimethylpropanoate (24): To a solution of Intermediate 5 (0.207 mmol) in DMF (0.5 mL) was added potassium carbonate (0.620 mmol) and chloromethyl 3-hydroxy-2,2-dimethylpropanoate (0.413 mmol). The reaction mixture was stirred at rt overnight. Upon completion, the reaction was partitioned between ethyl acetate and water. The organic layer was separated, washed with 5% LiCl (aq.) and brine. The organic fraction was dried over $MgSO_4$, filtered and concentrated. The residue was dissolved in acetonitrile/water, passed through a pad of C18 and washed with acetonitrile, and the filtrate was lyophilized to give title compound 24 as a mixture of atropisomers. MS (m/z): 1098.01 [M+H]$^+$. $^1$H NMR (400 MHz, Methanol-$d_4$) δ 8.94 (s), 7.85-7.55 (m), 7.26 (d, J=7.6 Hz), 6.88-6.67 (m), 6.58 (s), 6.30 (d, J=7.2 Hz), 5.76 (s), 4.91-4.45 (m), 4.02 (dt, J=16.5, 8.3 Hz), 3.57-3.25 (m), 3.23 (s), 3.13-2.75 (m), 2.65-2.36 (m), 1.81 (s), 1.41 (q, J=7.0 Hz), 1.06 (s).

Example 25

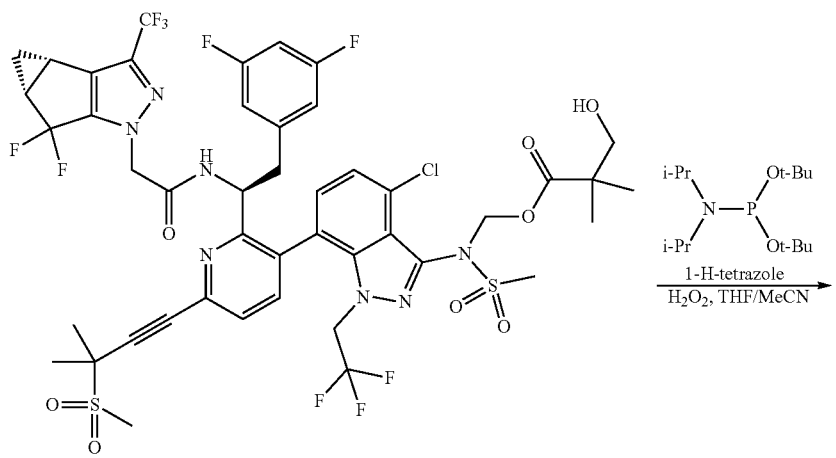

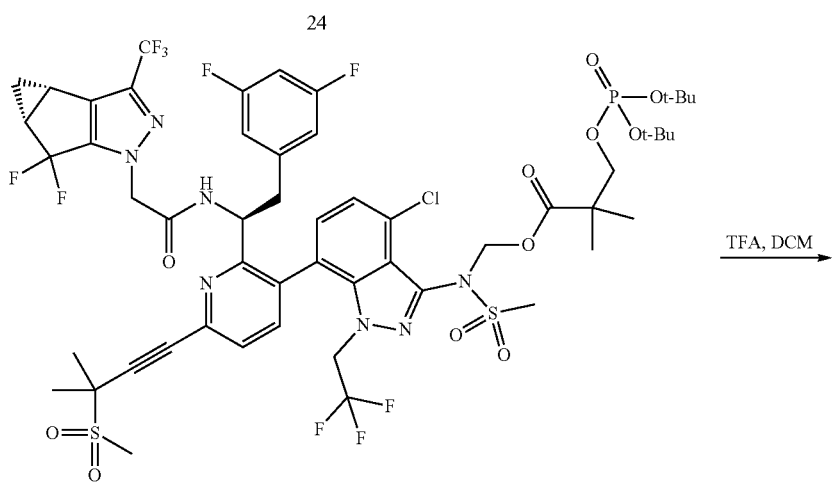

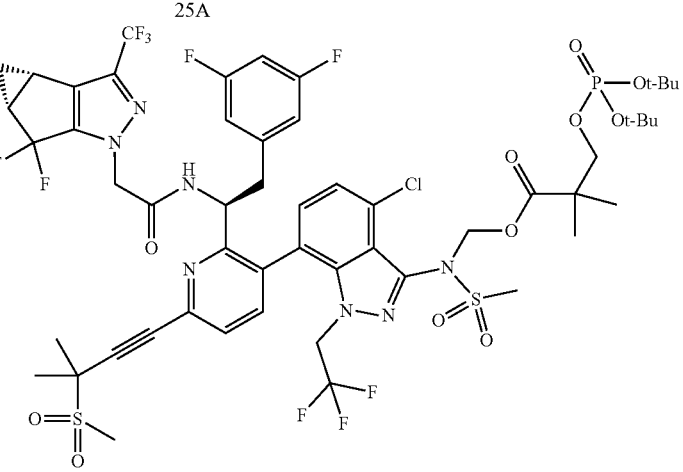

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl 3-((di-tert-butoxyphosphoryl)oxy)-2,2-dimethylpropanoate (25A): Tetrazole (0.182 mmol) and 24 (0.0910 mmol) in THF (1.6 mL) and acetonitrile (0.64 mL) were added to a flask. The mixture was stirred at room temperature for 16 h. The mixture was cooled to 0° C. and hydrogen peroxide (30% aqueous, 0.455 mmol) was added. After 15 min, the reaction was quenched with saturated aqueous sodium thiosulphate with a cooling water bath. After 25 min, the reaction was extracted with ethyl acetate. The combined extracts were washed with brine, dried, and evaporated. The crude product was purified by reverse phase HPLC. Fractions containing the product were pooled and lyophilized to give an atropisomeric mixture of title compound 25A.

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl 2,2-dimethyl-3-(phosphonooxy)propanoate (25): 25A was dissolved in DCM (3 mL) and cooled to 0° C. To it was added trifluoroacetic acid (0.018 mL) and the resulting reaction was stirred for 5 hours. Upon completion, the reaction was partitioned between saturated $NH_4Cl$ and ethyl acetate. The organic layer was separated, washed with brine, filtered and concentrated under reduced pressure and purified by reverse phase HPLC. Fractions containing the product were pooled and lyophilized to give title compound 25 as a mixture of atropisomers. $^1$H NMR (400 MHz, Methanol-$d_4$) δ 8.85 (d), 7.80-7.52 (m), 7.25 (d), 6.75 (t), 6.55 (brs), 6.29 (d), 5.81 (brs), 4.82-4.53 (m), 4.14-3.62 (m), 3.22 (s), 3.16-2.62 (m), 2.62-2.37 (m), 1.81 (s), 1.42 (q), 1.33-0.72 (m) ppm. MS (m/z) 1178.34 $[M+H]^+$.

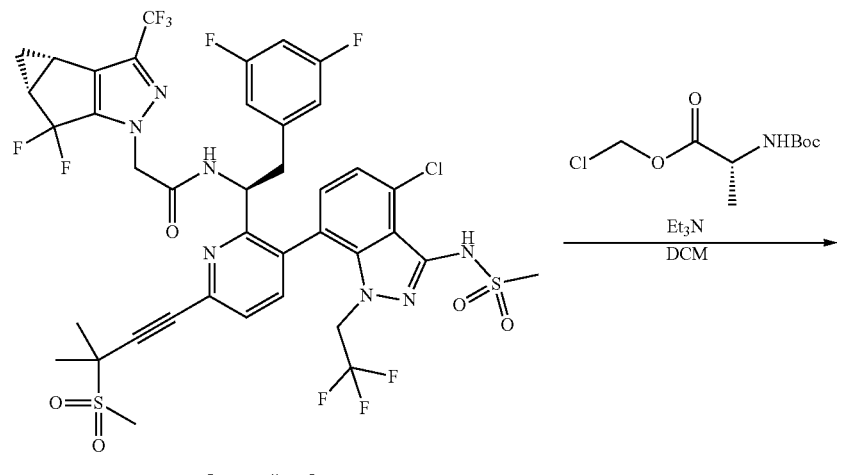

Intermediate 5

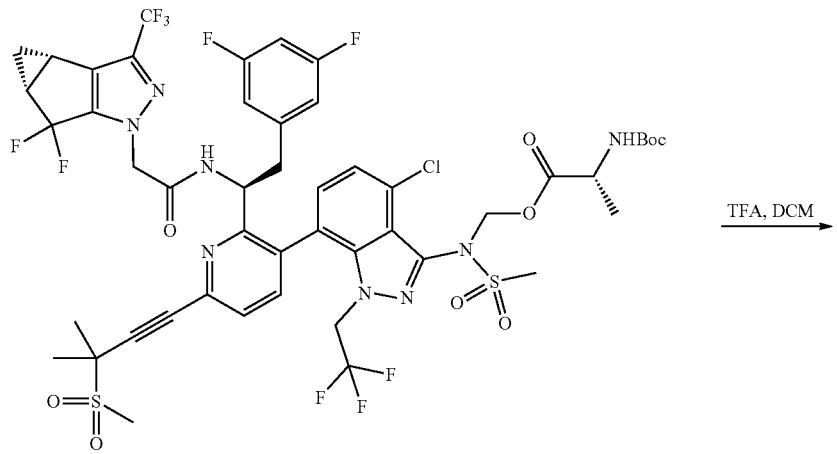

26A

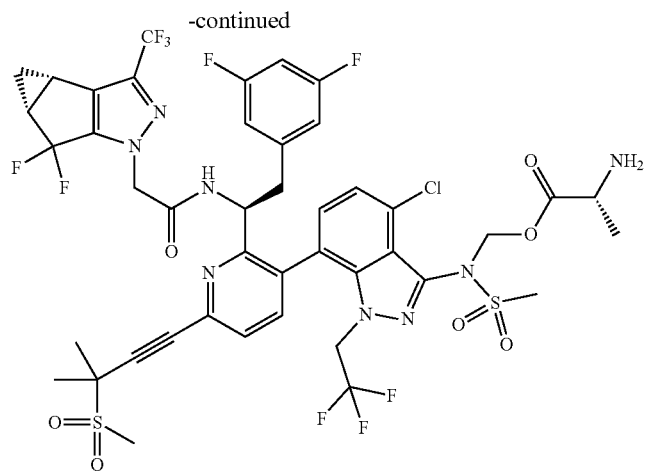

26

Example 26

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl (tert-butoxycarbonyl)-D-alaninate (26A): To a solution of Intermediate 5 (0.103 mmol) and chloromethyl (tert-butoxycarbonyl)-D-alaninate (0.310 mmol) in DCM (1 mL) was added triethylamine (0.516 mmol) and the reaction was stirred at rt. Upon completion, the reaction was partitioned between ethyl acetate and water. The organic layer was separated and washed with brine, dried over magnesium sulfate, filtered and concentrated to dryness to yield title compound 26A, which was used without further purification.

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl D-alaninate (26): 26A (0.103 mmol) was dissolved in DCM (3 mL) and cooled to 0° C. To it was added trifluoroacetic acid (2 mL) and the reaction was stirred at the same temperature. Upon completion, the reaction was concentrated under reduced pressure and purified by reverse phase HPLC. Fractions containing the product were pooled and lyophilized to give title compound 26A as a mixture of atropisomers. $^1$H NMR (400 MHz, Methanol-$d_4$) δ 8.04-7.52 (m), 7.25 (d), 6.90-6.67 (m), 6.67-6.37 (m), 6.36-5.71 (m), 5.12-4.51 (m), 4.09 (dd), 3.22 (d), 3.17-2.76 (m), 2.70-2.37 (m), 1.81 (d), 1.64-1.32 (m), 1.22-0.86 (m). MS (m/z) 1069.13 [M+H]$^+$.

Example 27

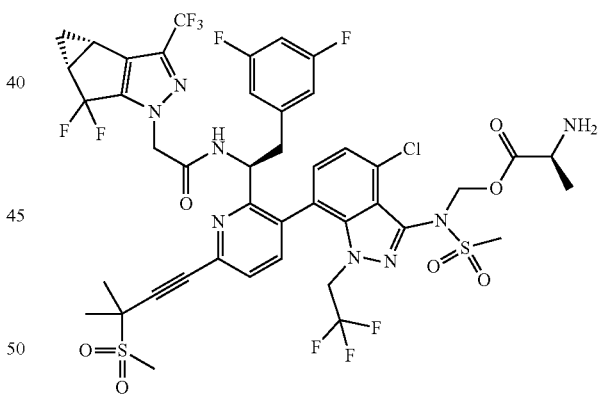

27

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl L-alaninate (27): An atropisomeric mixture of the title compound was prepared according to the method presented for the synthesis of 26 of Example 26 utilizing chloromethyl (tert-butoxycarbonyl)-L-alaninate in the place of chloromethyl (tert-butoxycarbonyl)-D-alaninate. $^1$H NMR (400 MHz, Methanol-$d_4$) δ 7.91-7.53 (m), 7.27 (dd), 6.92-6.34 (m), 6.25 (d), 6.13-5.71 (m), 5.06-4.44 (m), 4.05 (ddt), 3.22 (d), 3.16-2.80 (m), 2.67-2.25 (m), 1.81 (d), 1.53 (dd), 1.50-1.24 (m), 1.18-0.86 (m) ppm. MS (m/z) 1069.17 [M+H]$^+$.

Example 28

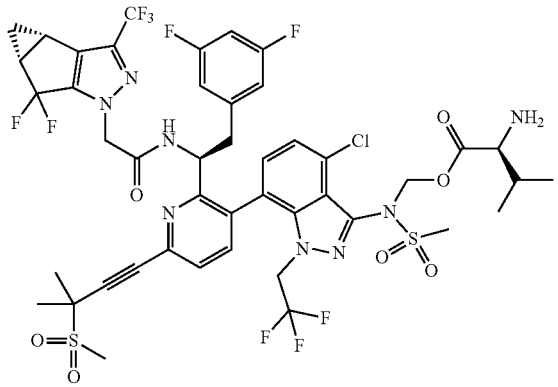

28

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl L-valinate (28): An atropisomeric mixture of the title compound was prepared according to the method presented for the synthesis of 26 of Example 26 utilizing chloromethyl (tert-butoxycarbonyl)-L-valinate in the place of chloromethyl (tert-butoxycarbonyl)-D-alaninate. $^1$H NMR (400 MHz, Methanol-$d_4$) δ 8.98 (s), 7.89-7.47 (m), 7.28 (dd), 6.89-6.40 (m), 6.36-6.20 (m), 5.95 (s), 5.10-4.42 (m), 4.20-3.74 (m), 3.22 (d), 3.15-2.78 (m), 2.68-2.39 (m), 2.42-2.10 (m), 1.81 (d), 1.43 (q), 1.16-0.91 (m) ppm. MS (m/z) 1097.04 [M+H]$^+$.

Example 29

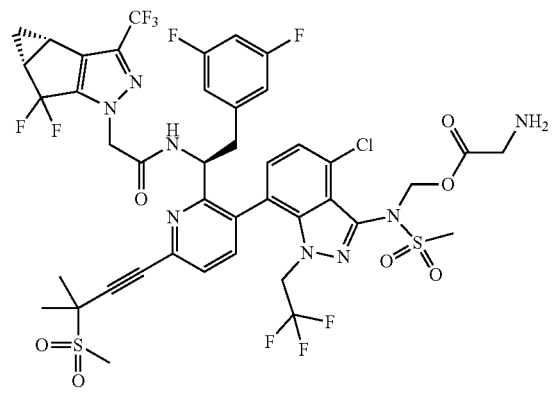

29

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl glycinate (29): An atropisomeric mixture of the title compound was prepared according to the method presented for the synthesis of 26 of Example 26 utilizing chloromethyl (tert-butoxycarbonyl) glycinate in the place of chloromethyl (tert-butoxycarbonyl)-D-alaninate. $^1$H NMR (400 MHz, Methanol-$d_4$) δ 7.87-7.54 (m), 7.28 (d), 6.92-6.46 (m), 6.23 (d), 6.05 (d), 6.01-5.76 (m), 5.08-4.86 (m), 4.67 (dt), 4.02 (dq), 3.86 (q), 3.22 (s), 3.12-2.76 (m), 2.67-2.35 (m), 1.81 (s), 1.44 (q), 1.16-0.85 (m) ppm. MS (m/z) 1054.96 [M+H]$^+$.

Example 30

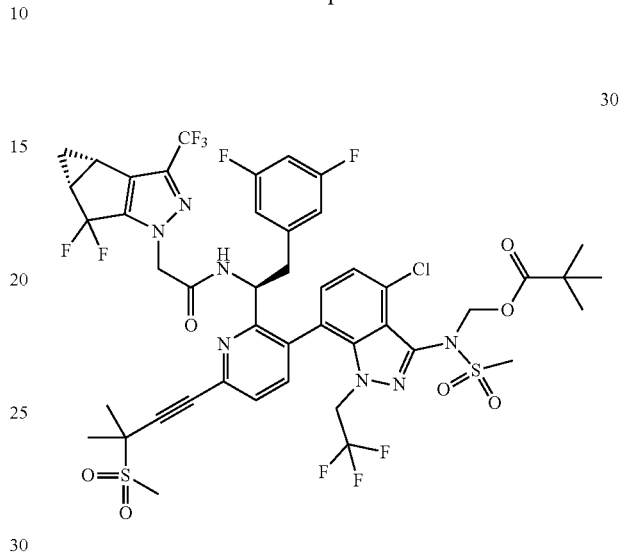

30

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl pivalate (30): An atropisomeric mixture of the title compound was prepared according to the method presented for the synthesis of 26A of Example 26 utilizing chloromethyl pivalate in the place of chloromethyl (tert-butoxycarbonyl)-D-alaninate. $^1$H NMR (400 MHz, Methanol-$d_4$) δ 8.83 (d), 7.81 (d), 7.76-7.61 (m), 7.39-7.17 (m), 6.81-6.38 (m), 6.38-6.21 (m), 5.79 (s), 4.78-4.52 (m), 4.04 (s), 3.22 (d), 3.17-2.89 (m), 2.58-2.41 (m), 1.81 (d), 1.42 (q), 1.14 (d). MS (m/z) 1182.58 [M+H]$^+$.

Example 31

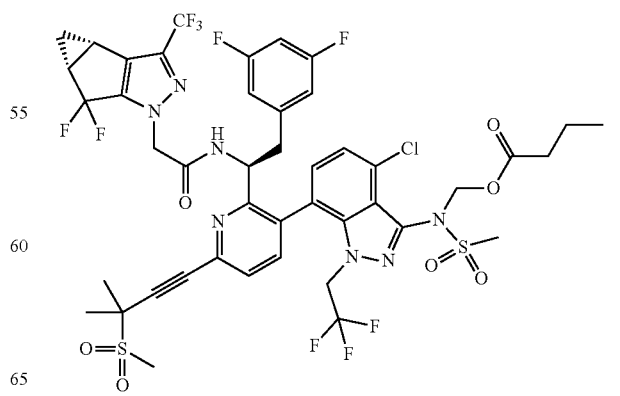

31

233

Synthesis of (N-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)methylsulfonamido)methyl butyrate (31): An atropisomeric mixture of the title compound was prepared according to the method presented for the synthesis of 26A of Example 26 utilizing chloromethyl butyrate in the place of chloromethyl (tert-butoxycarbonyl)-D-alaninate. $^1$H NMR (400 MHz, Methanol-$d_4$) δ 8.83 (d), 7.84-7.63 (m), 7.41-7.17 (m), 6.86-6.39 (m), 6.30 (d), 5.78 (s), 4.77-4.56 (m), 3.22 (d), 3.19-2.82 (m), 2.59-2.39 (m), 2.29 (dt), 1.81 (d), 1.66-1.32 (m), 1.15-0.79 (m) ppm. MS (m/z) 1067.94 [M+H]$^+$.

Example 32

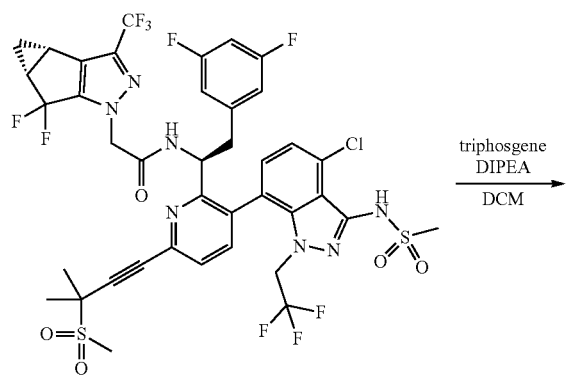

Intermediate 5

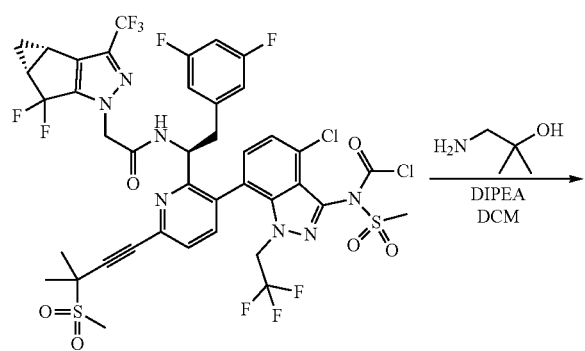

32A

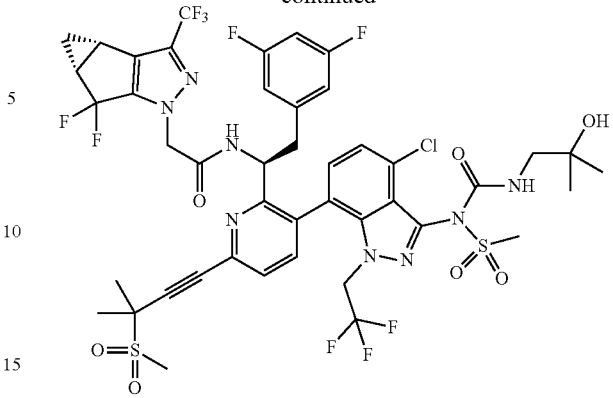

32

Synthesis of (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamic chloride (32A): To a vial containing Intermediate 5 (0.103 mmol) and triphosgene (0.309 mmol) was added DCM (2 mL) and the reaction was cooled to 0° C. in an ice bath. To the mixture was then added DIPEA (0.309 mmol) and the reaction was stirred for 15 minutes. Upon completion, the reaction was concentrated under reduced pressure to yield an atropisomeric mixture of title compound 32A which was used without further purification. MS (m/z) 1030.81 [M+H]$^+$.

Synthesis of N—((S)-1-(3-(4-chloro-3-(N-((2-hydroxy-2-methylpropyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (32): To a solution of 32A (0.103 mmol) in DCM (1.5 mL) was added 1-amino-2-methylpropan-2-ol (0.291 mmol, 3 equiv) followed by DIPEA (0.194 mmol, 2 equiv). Upon completion the reaction was partitioned between water and DCM (10 mL of each). The organic fraction was collected, dried over $Na_2SO_4$, concentrated under reduced pressure and purified by reverse phase HPLC. Fractions containing the product were pooled and lyophilized to yield title compound 32. $^1$H NMR (400 MHz, DMSO-$d_6$) δ 9.24 (s), 8.97 (s), 7.91 (s), 7.81 (s), 7.84-7.77 (m), 7.43-7.37 (m), 7.36-7.25 (m), 7.06-6.96 (m), 6.96-6.83 (m), 6.50 (s), 6.43 (s), 6.21 (s), 5.04-4.95 (m), 4.81-4.68 (m), 4.65-4.56 (m), 4.49 (s), 4.18 (s), 3.93 (s), 3.61-3.53 (m), 3.17 (s), 3.04 (s), 2.92 (s), 2.63-2.57 (m), 1.78-1.72 (m), 1.46-1.35 (m), 1.06 (s), 1.00 (s), 0.91 (s), 0.76 (s) ppm. 19F NMR (376 MHz, DMSO-$d_6$) δ -60.81, -60.90, -60.93, -69.13--70.11 (m), -74.04, -79.85, -80.53, -102.63--103.99 (m), -110.59--111.16 (m) ppm. MS (m/z) 1083.3 [M+H]$^+$.

Example 33

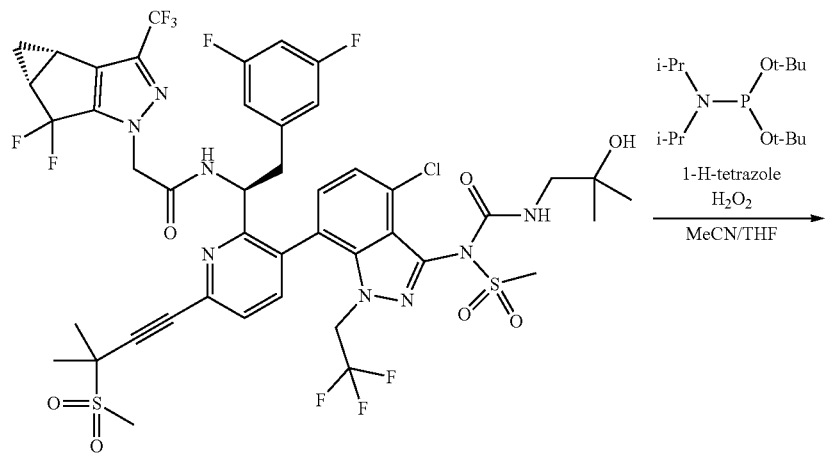

32

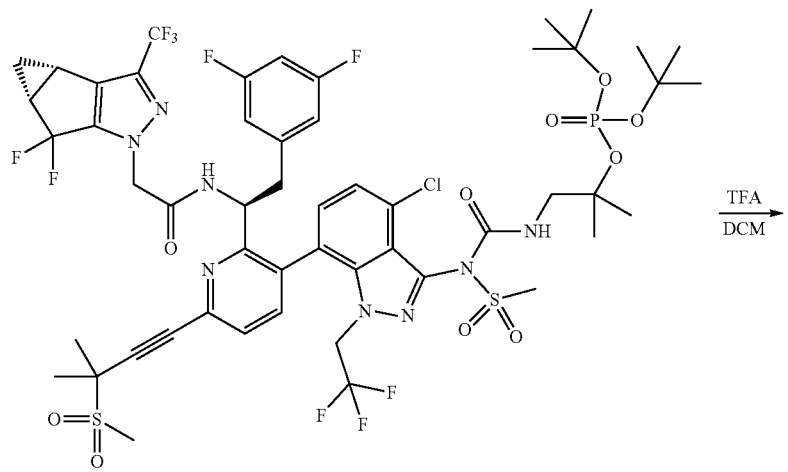

33A

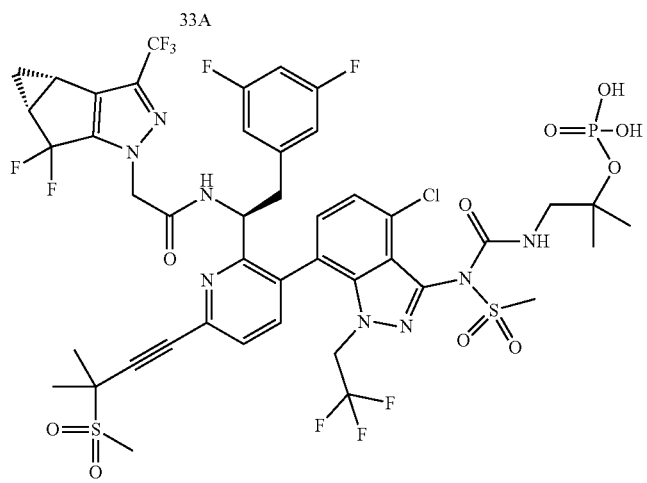

33

Synthesis of di-tert-butyl (1-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-2-methylpropan-2-yl) phosphate (33A): To a solution of 32 (0.069 mmol) in 3 mL of THF/MeCN (3:1 ratio) were added sequentially 1-H-tetrazole (0.257 mmol, 3.7 equiv), and di-tert-butyl N,N-diisopropylphosphoramidite (0.156 mmol, 2.25 equiv). Once the starting material was gone, the reaction was cooled to 0° C. in an ice bath and hydrogen peroxide was added (30% aqueous solution, 0.346 mmol, 5 equiv). Upon completion, the reaction was partitioned between water and DCM (10 mL of each). The organic fraction was collected, dried over Na₂SO₄, concentrated under reduced pressure and purified by reverse phase HPLC. Fractions containing the product were pooled and lyophilized to yield title compound 33A as a mixture of atropisomers. MS (m/z) 1275.71 [M+H]⁺.

Synthesis of 1-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-2-methylpropan-2-yl dihydrogen phosphate (33): To a solution of 33A (0.054 mmol) in DCM (3 mL) was added TFA (1 mL). Upon completion, the reaction was concentrated under reduced pressure, filtered, and purified by reverse phase HPLC. Fractions containing the product were pooled and lyophilized to yield title compound 33 as a mixture of atropisomers. ¹H NMR (400 MHz, DMSO-d₆) δ 9.24 (s), 8.20-8.10 (m), 7.89 (s), 7.47 (s), 7.43-7.36 (m), 7.02 (s), 6.91-6.83 (m), 6.58 (s), 6.43 (s), 5.05-4.96 (m), 4.88-4.78 (m), 4.76-4.67 (m), 4.49 (s), 3.96-3.90 (m), 3.61-3.53 (m), 3.55 (s), 3.51-3.42 (m), 3.40-3.28 (m), 2.93 (s), 2.66-2.53 (m), 1.84-1.72 (m), 1.54 (s), 1.49-1.36 (m), 1.33-1.18 (m), 1.21-1.12 (m), 1.16-1.09 (m), 1.09-0.99 (m), 1.00 (s) ppm. ¹⁹F NMR (376 MHz, DMSO-d₆) δ-60.60--61.04 (m), -69.09, -69.35--69.64 (m), -69.91, -74.72--74.95 (m), -74.99--75.27 (m), -75.13, -75.52, -79.79, -80.12, -80.47, -80.80, -102.54, -102.97--103.28 (m), -103.65--103.93 (m), -110.58--110.78 (m), -110.89--111.09 (m) ppm. MS (m/z) 1063.44.

Synthesis of N—((S)-1-(3-(4-chloro-3-(N—(((S)-2-hydroxypropyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (34): An atropisomeric mixture of the title compound was prepared according to the method presented for the synthesis of 32 of Example 32 utilizing (S)-1-aminopropan-2-ol in the place of 1-amino-2-methylpropan-2-ol. ¹H NMR (400 MHz, DMSO-d₆) δ 9.29-9.19 (m), 7.93 (s), 7.85-7.73 (m), 7.45-7.38 (m), 7.36-7.22 (m), 7.00 (s), 6.97-6.90 (m), 6.64 (s), 6.49 (s), 6.42 (s), 6.17 (s), 5.04-4.95 (m), 4.81 (s), 4.76-4.67 (m), 4.45 (s), 3.86 (s), 3.59-3.53 (m), 3.30-3.24 (m), 3.19-3.13 (m), 3.10-3.01 (m), 2.96-2.89 (m), 2.60 (d, J=13.2 Hz), 2.15 (s), 1.75 (s), 1.46-1.35 (m), 0.99 (s), 0.61 (s) ppm. ¹⁹F NMR (376 MHz, DMSO-d₆) δ-60.69--61.05 (m), -60.91, -69.15--69.53 (m), -69.54--69.81 (m), -69.90, -74.69, -79.86, -80.54, -102.82--103.21 (m), -103.68 (d, J=12632.8 Hz), -110.81 ppm. MS (m/z) 1069.41 [M+H]⁺.

Example 35

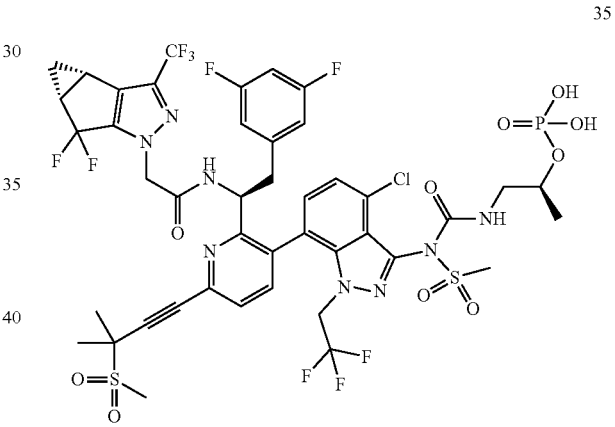

Synthesis of (S)-1-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido) propan-2-yl dihydrogen phosphate (35). An atropisomeric mixture of the title compound was prepared according to the method presented for the synthesis of 33 of Example 33 utilizing 34 in the place of 32. ¹H NMR (400 MHz, DMSO-d₆) δ 9.28-9.20 (m), 7.95 (d, J=7.6 Hz), 7.87-7.79 (m), 7.76 (s), 7.44 (d, J=7.8 Hz), 7.02-6.93 (m), 6.54 (s), 6.42 (s), 6.18 (s), 5.02 (d, J=15.9 Hz), 4.83 (s), 4.71 (d, J=16.6 Hz), 4.42 (s), 4.28 (s), 4.17 (s), 3.57 (s), 3.27 (d, J=2.8 Hz), 3.04 (s), 2.93 (s), 2.11 (s), 1.75 (s), 1.75 (d, J=6.7 Hz), 1.41 (d, J=7.3 Hz), 1.14 (s), 1.00 (s), 0.71 (d, J=5.9 Hz) ppm. ¹⁹F NMR (376 MHz, DMSO-ds) δ-60.90, -69.21, -69.43, -69.90, -74.29, -79.95, -80.63, -102.96, -110.84 ppm. MS (m/z) 1148.81 [M+H]⁺.

Example 34

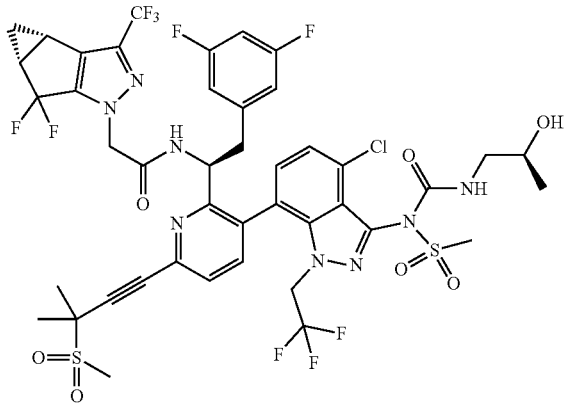

34

Example 36

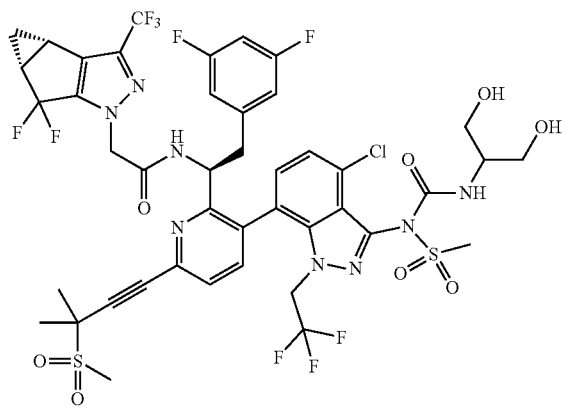

36

Synthesis of N—((S)-1-(3-(4-chloro-3-(N-((1,3-dihydroxypropan-2-yl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (36): An atropisomeric mixture of the title compound was prepared according to the method presented for the synthesis of 32 of Example 32 utilizing 2-amino-1,3-propanediol in the place of 1-amino-2-methyl-propan-2-ol. $^1$H NMR (400 MHz, DMSO-d$_6$) δ 7.96-7.69 (m), 7.57-7.19 (m), 7.19-6.80 (m), 6.51 (d), 4.75 (t), 1.75 (d), 1.40 (d), 0.99 (s, 2H) ppm. $^{19}$F NMR (375 MHz, DMSO-d$_6$) δ-60.70--61.05 (m), −69.38 (d), −69.92 (d), −74.21, −74.76, −79.79, −80.46, −110.73 (d) ppm. MS (m/z) 1084.890 [M]$^+$.

Example 37

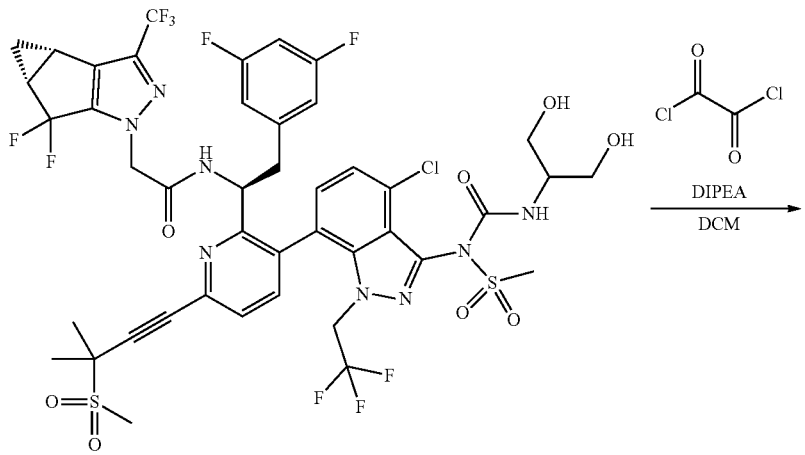

36

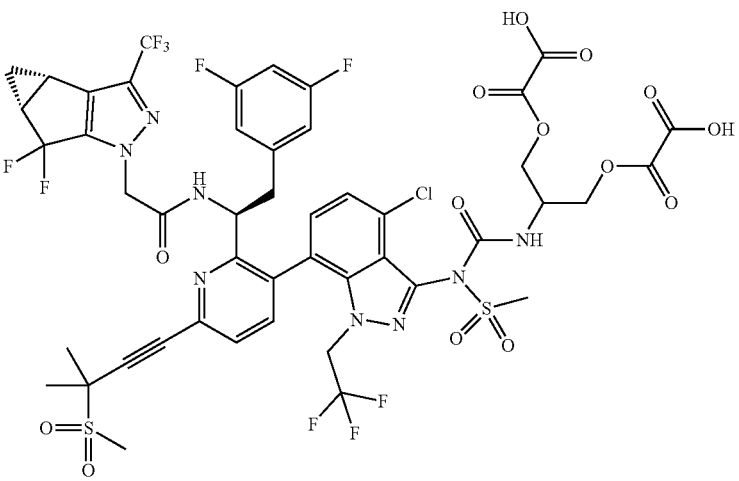

37

Synthesis of 2,2'-((2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)propane-1,3-diyl)bis(oxy))bis(2-oxoacetic acid) (37): To a solution of 36 (0.023 mmol) in DCM (1 mL) was added DIPEA (0.092 mmol) followed by tert-butyl-2-chloro-2-oxoacetate (0.182 mmol) and the resulting mixture was stirred for 10 mins. Trifluoroacetic acid (6.530 mmol) was then added with a further 10 mins stirring at which time the reaction was diluted with 1:1 H$_2$O:MeCN (1 mL). The reaction contents were then transferred to a separatory funnel with DCM (15 mL) and washed once with 1M HCl (20 mL). The organic fraction was collected, dried over Na$_2$SO$_4$, concentrated under reduced pressure, and purified by reverse phase HPLC. Fractions containing the product were pooled and lyophilized to give title compound 37 as a mixture of atropisomers. $^1$H NMR (400 MHz, DMSO-d$_6$) δ 9.19 (d), 7.91-7.67 (m), 7.38 (d), 7.27 (s), 7.10 (dd), 6.96 (d), 6.85 (dd), 6.52 (d), 5.15-4.68 (m), 4.60 (s), 4.47-4.13 (m), 4.13-3.90 (m), 3.27 (s), 3.00 (d), 1.75 (s), 1.44-1.31 (m), 1.31-1.18 (m), 1.02 (d), 0.81 (td) ppm. $^{19}$F NMR (375 MHz, DMSO-d$_6$) δ-60.69--61.03 (m), -69.46, -69.53 (d), -69.86, -74.74, -74.67--75.38 (m), -79.75, -80.42, -103.11 (d), -103.79 (d), -110.57--111.24 (m) ppm. MS (m/z) 1229.190 [M]$^+$.

Example 38

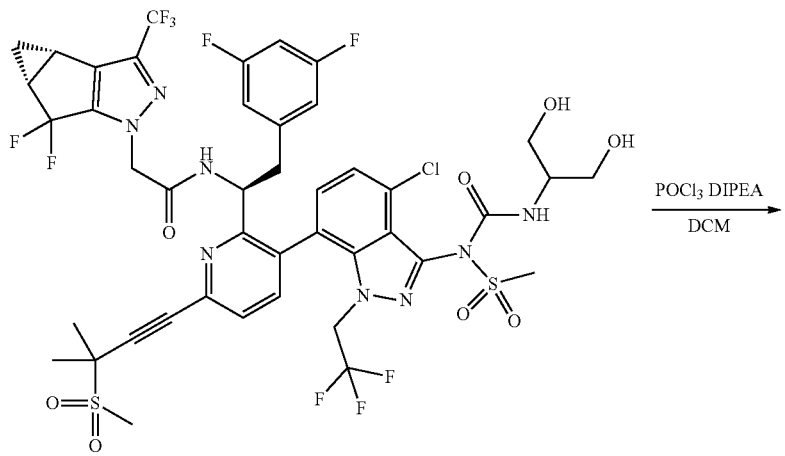

36

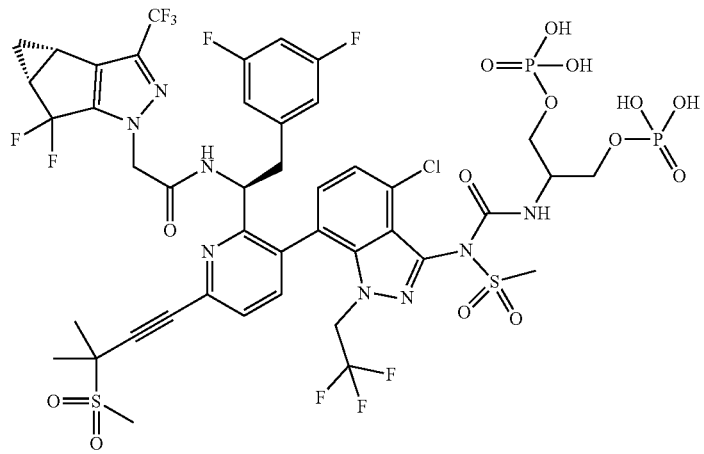

38

Synthesis of 2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)propane-1,3-diyl bis(dihydrogen phosphate) (38): To an ice-cold solution of 36 (0.023 mmol) in DCM (1 mL) were added sequentially $POCl_3$ (0.457 mmol, 20 equiv) and DIPEA (0.251 mmol, 11 equiv). After 10 mins, aqueous acetonitrile (1 mL of a 1:1 solution) was added to the mixture. The solvent was then removed under reduced pressure and the residue purified by reverse phase HPLC. Fractions containing the product were pooled and lyophilized to give title compound 38 as a mixture of atropisomers. $^1H$ NMR (400 MHz, DMSO-$d_6$) δ 9.24 (s), 9.15 (s), 9.04-8.97 (m), 7.90-7.71 (m), 7.52-7.45 (m), 7.43-7.36 (m), 7.33-7.22 (m), 7.09-6.98 (m), 6.98-6.89 (m), 6.55 (s), 4.87-4.75 (m), 4.77-4.60 (m), 4.10 (s), 4.02-3.86 (m), 3.60 (s), 3.54 (s), 3.10 (s), 3.05-2.97 (m), 1.79-1.72 (m), 1.40 (s), 1.27-1.18 (m), 1.02-0.93 (m) ppm. $^{19}F$ NMR (376 MHz, DMSO-$d_6$) δ-60.69--61.02 (m), -69.14--69.86 (m), -75.33, -75.34, -79.78, -80.46, -102.98--103.34 (m), -103.65--104.01 (m), -110.49--111.14 (m) ppm. MS (m/z) 1244.67 [M+H]$^+$.

Example 39

39

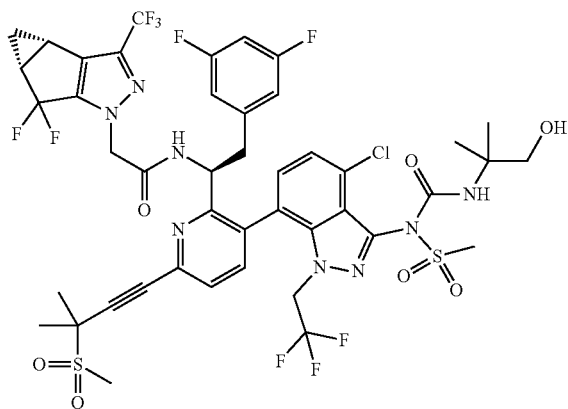

Synthesis of N—((S)-1-(3-(4-chloro-3-(N-((1-hydroxy-2-methylpropan-2-yl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (39): An atropisomeric mixture of the title compound was prepared according to the method presented for the synthesis of 32 of Example 32 utilizing tert-butyl (S)-3-amino-4-(trimethyl-14-azaneyl)butanoate in the place of 1-amino-2-methyl-propan-2-ol. $^1H$ NMR (400 MHz, DMSO-$d_6$) δ 9.30-9.21 (m), 9.22-9.12 (m), 8.01-7.73 (m), 7.50-7.24 (m), 7.09-6.97 (m), 7.01-6.83 (m), 6.52-6.39 (m), 5.01-4.92 (m), 4.87-4.71 (m), 4.72 (s), 4.68-4.53 (m), 3.30-3.25 (m), 3.24-3.14 (m), 2.96 (s), 2.64-2.57 (m), 1.78-1.72 (m), 1.44-1.35 (m), 1.29-1.18 (m), 1.12 (s), 1.02-0.94 (m) ppm. $^{19}F$ NMR (376 MHz, DMSO-$d_6$) δ -60.71--61.07 (m), -69.22--69.77 (m), -69.81--70.00 (m), -74.72--74.89 (m), -75.10, -79.80, -80.37--80.55 (m), -102.94, -103.16, -103.61, -103.74--103.91 (m), -110.70, -110.89 ppm. MS (m/z) 1154.13 [M]$^+$.

Example 40

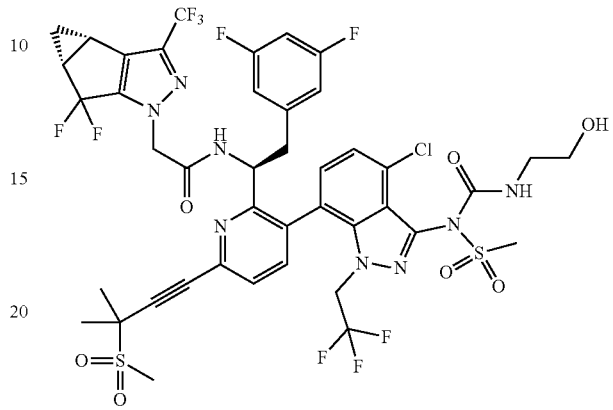

Synthesis of N—((S)-1-(3-(4-chloro-3-(N-((2-hydroxyethyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (40): An atropisomeric mixture of the title compound was prepared according to the method presented for the synthesis of 32 of Example 32 utilizing 2-aminoethanol in the place of 1-amino-2-methyl-propan-2-ol. $^1H$ NMR (400 MHz, Methanol-$d_4$) δ 9.01-8.94 (m), 7.86-7.79 (m), 7.78-7.69 (m), 7.37-7.30 (m), 6.83-6.73 (m), 6.63-6.56 (m), 6.26-6.18 (m), 4.03-3.88 (m), 3.48 (s), 3.44-3.32 (m), 3.26 (s), 3.08-2.98 (m), 2.95-2.85 (m), 2.61-2.50 (m), 1.84 (s), 1.50-1.40 (m). MS (m/z) 1055.20 [M+H]$^+$.

Example 41

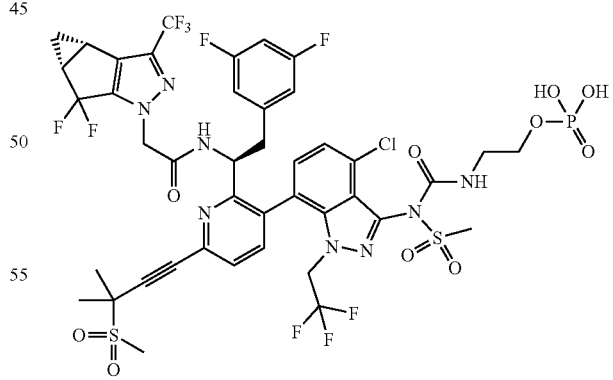

Synthesis of 2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)ethyl dihydrogen phosphate (41): An atropisomeric mixture of the title compound was prepared according to the method presented for the synthesis of 33 of Example 33 utilizing 40 in the place of 32. ¹H NMR (400 MHz, Methanol-d₄) δ 9.12 (s), 7.82 (s), 7.76-7.69 (m), 7.36-7.29 (m), 6.85-6.75 (m), 6.60-6.53 (m), 6.41-6.34 (m), 3.93 (s), 3.60-3.52 (m), 3.26 (s), 3.05-2.95 (m), 2.54 (s), 1.96 (s), 1.87-1.81 (m), 1.49-1.42 (m), 1.08 (s). MS (m/z) 1135.20 [M+H]⁺.

Example 42

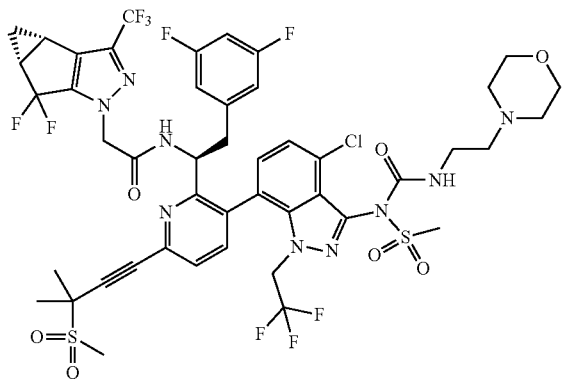

42

Synthesis of N—((S)-1-(3-(4-chloro-3-(N-((2-morpholinoethyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (42): An atropisomeric mixture of the title compound was prepared according to the method presented for the synthesis of 32 of Example 32 using 2-morpholinoethan-1-amine in the place of 1-amino-2-methyl-propan-2-ol. ¹H NMR (400 MHz, Methanol-d₄) δ 7.97 (s), 7.83 (d), 7.73 (d), 7.37 (d), 6.78 (d), 6.70 (d), 6.36 (d), 4.90 (d), 4.79-4.62 (m), 3.60-3.43 (m), 3.22 (d), 2.99 (s), 2.86 (d), 2.52 (s), 1.81 (d), 1.45-1.31 (m), 1.05 (s) ppm. MS (m/z) 1124.26 [M+H]⁺.

Example 43

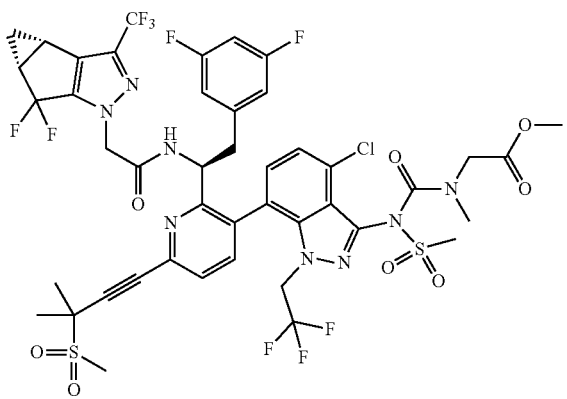

43

Synthesis of methyl N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-N-methylglycinate (43): An atropisomeric mixture of the title compound was prepared according to the method presented for the synthesis of 32 of Example 32 utilizing N-methylglycine methyl ester in the place of 1-amino-2-methyl-propan-2-ol. ¹H NMR (400 MHz, DMSO-d₆) δ 9.19 (d), 7.88 (s), 7.81 (d), 7.53-7.32 (m), 7.01 (tt), 6.33 (d), 4.97 (d), 4.72 (d), 4.52 (d), 4.08-3.77 (m), 3.28 (s), 2.95 (s), 2.87 (dd), 2.63-2.55 (m), 1.75 (s), 1.41 (dt), 1.05-0.86 (m) ppm. ¹⁹F NMR (375 MHz, DMSO-d₆) δ 19F NMR (376 MHz, DMSO-d₆) δ-60.85 (d), -60.95, -70.05, -75.12, -79.93, -80.61, -110.79 ppm. MS (m/z) 1096.90 [M+H]⁺.

Example 44

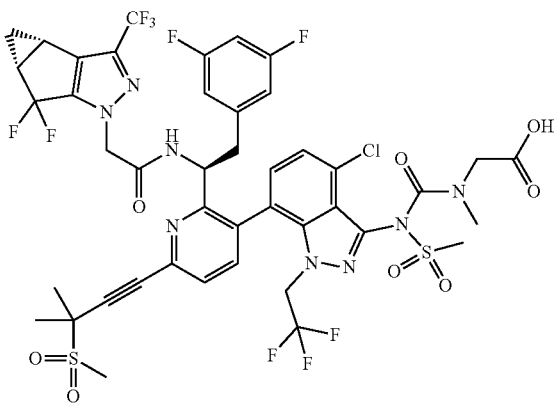

44

Synthesis of N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-N-methylglycine (44): An atropisomeric mixture of the title compound was prepared according to the method presented for the synthesis of 32 of Example 32 utilizing 2-(methylamino)acetic acid in the place of 1-amino-2-methyl-propan-2-ol. ¹H NMR (400 MHz, DMSO-d₆) δ 9.19 (d), 7.90 (d), 7.81 (d), 7.45 (d), 7.01 (tt), 6.88 (s), 6.38-6.26 (m), 4.97 (d), 4.89-4.75 (m), 4.71 (d), 4.54 (d), 4.02-3.80 (m), 3.28 (s), 2.96 (s), 2.87 (dd), 1.75 (s), 1.41 (q), 1.05-0.92 (m) ppm. 19F NMR (375 MHz, DMSO-d₆) δ-59.81--62.29 (m), -60.92, -70.10, -75.13 (d), -79.05--81.48 (m), -104.08, -110.91 ppm. MS (m/z) 1083.97 [M+H]⁺.

Example 45

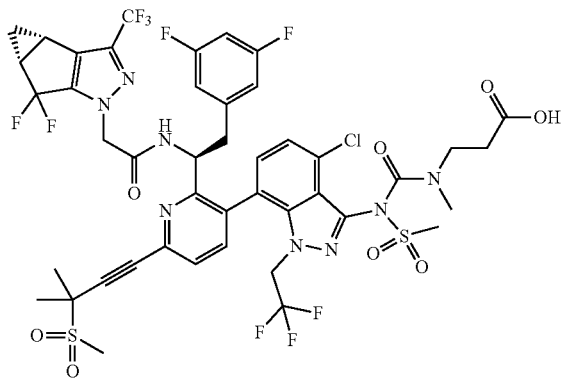

45

Synthesis of 3-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)propanoic acid (45): An atropisomeric mixture of the title compound was prepared according to the method presented for the synthesis of 32 of Example 32 utilizing 3-(methylamino)propanoic acid in the place of 1-amino-2-methyl-propan-2-ol. $^1$H NMR (400 MHz, DMSO-$d_6$) δ 9.18 (d), 7.94-7.74 (m), 7.44-7.35 (m), 7.01 (tt), 6.74 (s), 6.34 (h), 4.98 (d), 4.84-4.62 (m), 4.56 (q), 4.02-3.88 (m), 3.48-3.35 (m), 3.28 (d), 3.01-2.94 (m), 2.89 (dd), 2.66-2.53 (m), 2.26 (s), 1.75 (s), 1.44-1.33 (m), 1.00 (dtd) ppm. $^{19}$F NMR (375 MHz, DMSO-$d_6$) δ-60.80, -60.95, -69.60 (t), -70.09 (t), -75.39, -75.43, -79.94, -80.61, -103.10, -103.80 (d), -110.63--110.83 (m), -110.92 ppm. MS (m/z) 1097.84 [M+H]$^+$.

Example 46

46

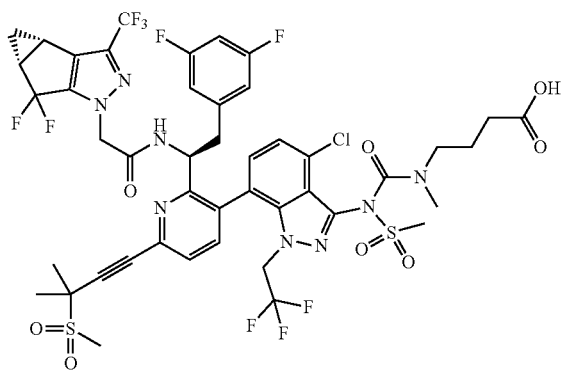

Synthesis of 4-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)butanoic acid (46): An atropisomeric mixture of the title compound was prepared according to the method presented for the synthesis of 32 of Example 32 utilizing 4-(methylamino)butanoic acid in the place of 1-amino-2-methyl-propan-2-ol. $^1$H NMR (400 MHz, DMSO-$d_6$) δ (375 MHz, DMSO-$d_6$) δ 9.20 (d), 7.89 (d), 7.80 (d), 7.43 (d), 7.00 (qt), 6.83 (s), 6.34 (p), 4.97 (d), 4.72 (td), 4.55 (q), 3.94 (dt), 3.29 (d), 3.24-3.14 (m), 3.14-3.01 (m), 2.97 (dd), 2.89 (dd), 2.00 (q), 1.90 (d), 1.75 (s), 1.50-1.35 (m), 0.99 (dq) ppm. $^{19}$F NMR δ -60.85 (d), -60.94, -69.44--69.82 (m), -70.05 (t), -75.22--75.91 (m), -75.48, -80.05, -80.72, -103.28, -103.97, -110.61--111.08 (m) ppm. MS (m/z) 1112.10 [M+H]$^+$.

Example 47

47

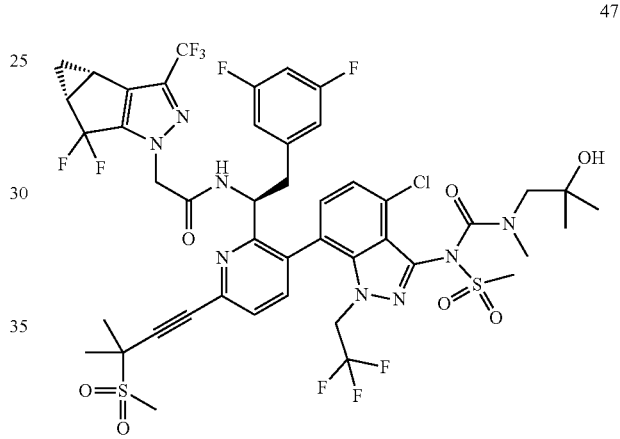

Synthesis of N—((S)-1-(3-(4-chloro-3-(N-((2-hydroxy-2-methylpropyl)(methyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (47): An atropisomeric mixture of the title compound was prepared according to the method presented for the synthesis of 32 of Example 32 utilizing 2-methyl-1-(methylamino)propan-2-ol in the place of 1-amino-2-methyl-propan-2-ol. $^1$H NMR (400 MHz, DMSO-$d_6$) δ 9.23-9.16 (m), 7.93-7.86 (m), 7.84-7.77 (m), 7.45-7.38 (m), 7.06-6.95 (m), 6.82 (s), 6.55-6.48 (m), 6.33-6.27 (m), 5.05-4.95 (m), 4.86-4.68 (m), 4.64-4.50 (m), 4.02-3.91 (m), 3.37 (s), 3.28 (s), 3.06 (s), 2.97-2.82 (m), 2.78 (s), 2.72 (s), 1.75 (s), 1.46-1.33 (m), 1.03-0.92 (m) ppm. $^{19}$F NMR (376 MHz, DMSO-$d_6$) δ-60.63--61.16 (m), -60.90, -69.96, -74.60, -79.93, -80.17--80.76 (m), -102.67--103.02 (m), -103.34--103.70 (m), -110.71 ppm. MS (m/z) 1096.84 [M+H]$^+$.

Example 48

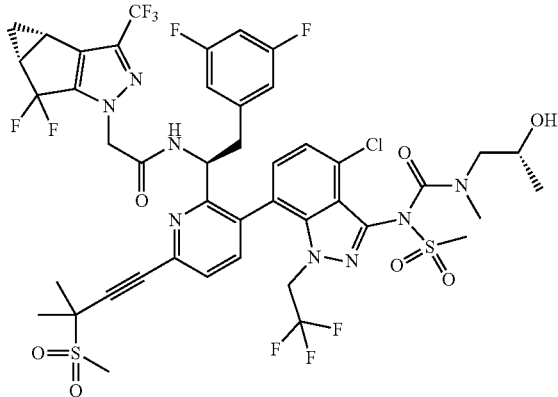
48

Synthesis of N—((S)-1-(3-(4-chloro-3-(N—(((R)-2-hydroxypropyl)(methyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (48): An atropisomeric mixture of the title compound was prepared according to the method presented for the synthesis of 32 of Example 32 utilizing (2R)-1-(methylamino)propan-2-ol in the place of 1-amino-2-methyl-propan-2-ol. $^1$H NMR (400 MHz, DMSO-d$_6$) δ 9.26-9.17 (m), 7.94-7.87 (m), 7.84-7.77 (m), 7.47-7.40 (m), 7.06-6.96 (m), 6.56-6.45 (m), 6.36-6.29 (m), 5.04-4.95 (m), 4.86-4.68 (m), 4.58-4.47 (m), 4.00-3.87 (m), 3.01-2.83 (m), 2.79-2.71 (m), 2.60 (s), 1.75 (s), 1.46-1.36 (m), 1.02 (s), 0.79 (s) ppm. $^{19}$F NMR (376 MHz, DMSO-d$_6$) δ-60.67--61.05 (m), -60.89, -69.44--69.82 (m), -70.06, -73.96, -79.95, -80.63, -103.89, -110.89 ppm. MS (m/z) 1083.29 [M+H]$^+$

Example 49

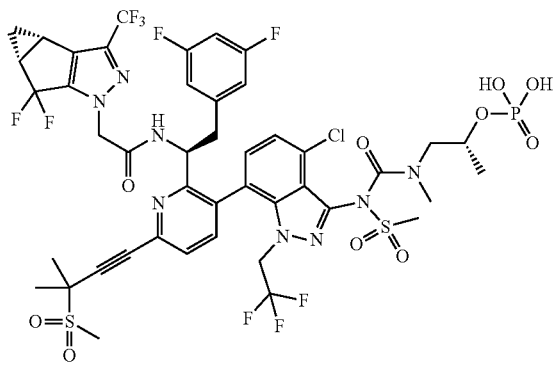
49

Synthesis of (R)-1-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)propan-2-yl dihydrogen phosphate (49): An atropisomeric mixture of the title compound was prepared according to the method presented for the synthesis of 33 of Example 33 utilizing 48 in the place of 32. $^1$H NMR (400 MHz, DMSO-d$_6$) δ 9.20-9.13 (m), 7.98-7.87 (m), 7.84-7.75 (m), 7.46-7.32 (m), 7.11-6.94 (m), 6.83 (s), 6.58-6.51 (m), 6.38-6.30 (m), 5.04-4.95 (m), 4.84-4.74 (m), 4.78-4.64 (m), 4.58-4.51 (m), 4.34 (s), 4.03-3.92 (m), 3.39 (s), 3.00-2.84 (m), 2.76-2.69 (m), 2.62-2.55 (m), 1.75 (s), 1.46-1.36 (m), 1.26-1.18 (m), 1.16-0.98 (m) ppm. $^{19}$F NMR (376 MHz, DMSO-d$_6$) δ-60.63--60.98 (m), -60.91, -69.41--69.83 (m), -70.08, -74.00, -79.96, -80.64, -103.09, -103.77, -110.63--111.09 (m) ppm. MS (m/z) 1163.69 [M+H]$^+$.

Example 50

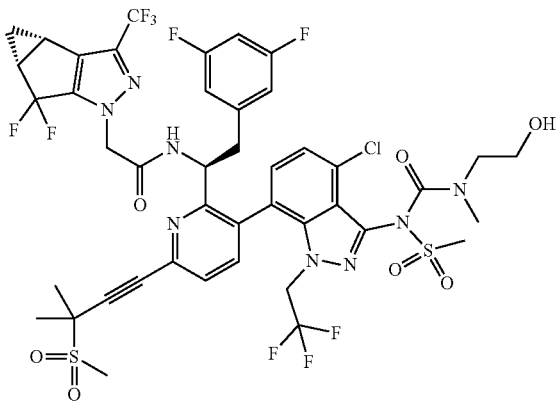 [SMILES: CC(C)(C#Cc1ccc(-c2ccc(Cl)c3c(N(C(=O)NCCO)S(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]
50

Synthesis of N—((S)-1-(3-(4-chloro-3-(N-((2-hydroxyethyl)(methyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (50): An atropisomeric mixture of the title compound was prepared according to the method presented for the synthesis of 32 of Example 32 utilizing 2-(methylamino)ethan-1-ol in the place of 1-amino-2-methyl-propan-2-ol. $^1$H NMR (400 MHz, Methanol-d$_4$) δ 9.01-8.93 (m), 7.86-7.79 (m), 7.78-7.71 (m), 7.37-7.30 (m), 6.83-6.73 (m), 6.63-6.56 (m), 6.26-6.18 (m), 4.03-3.88 (m), 3.48 (s), 3.44-3.32 (m), 3.26 (s), 3.08-2.98 (m), 2.95-2.85 (m), 2.75 (s), 2.64-2.50 (m), 1.96 (s), 1.84 (s), 1.50-1.40 (m), 1.13-1.07 (m) ppm. MS (m/z) 1069.22 [M+H]$^+$.

Example 51

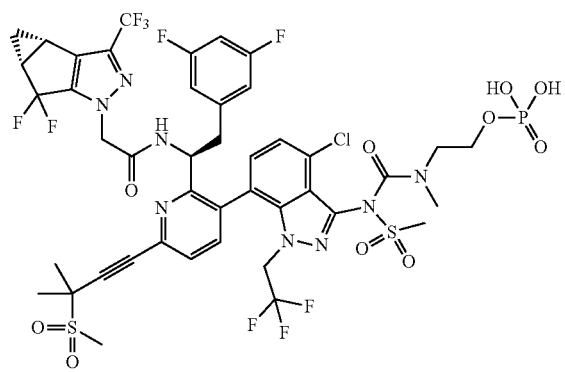 [SMILES: CC(C)(C#Cc1ccc(-c2ccc(Cl)c3c(N(C(=O)NCCOP(=O)(O)O)S(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

51

Synthesis of 2-(3-(4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)ethyl dihydrogen phosphate (51): An atropisomeric mixture of the title compound was prepared according to the method presented for the synthesis of 33 of Example 33 utilizing 50 in the place of 32. $^1$H NMR (400 MHz, Methanol-d$_4$) δ 9.15 (s), 7.82 (s), 7.79-7.69 (m), 7.38-7.22 (m), 6.88-6.74 (m), 6.60-6.51 (m), 6.48-6.31 (m), 3.97 (s), 3.66-3.57 (m), 3.26 (s), 3.01-2.81 (m), 2.51 (s), 1.99 (s), 1.96 (s) 1.89-1.80 (m), 1.47-1.44 (m), 1.01 (s). MS (m/z) 1149.20 [M+H]$^+$.

Example 52

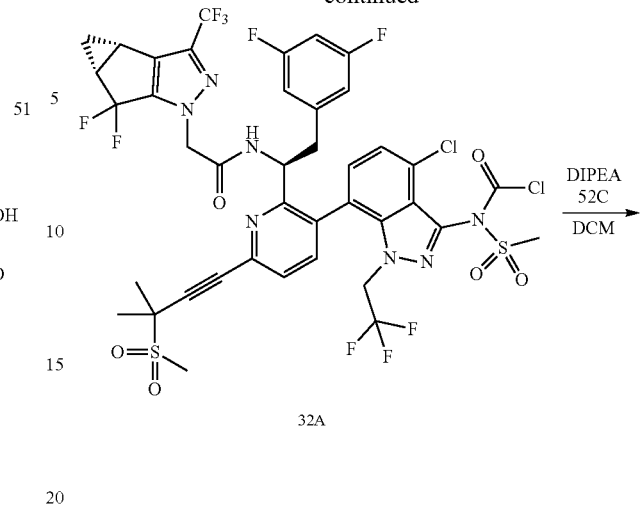

32A

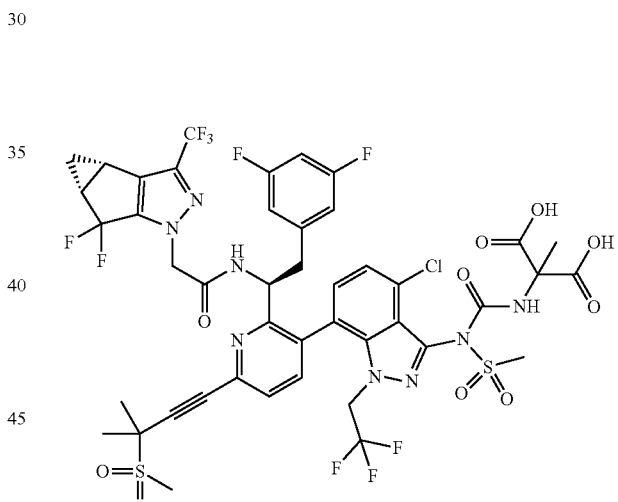

52

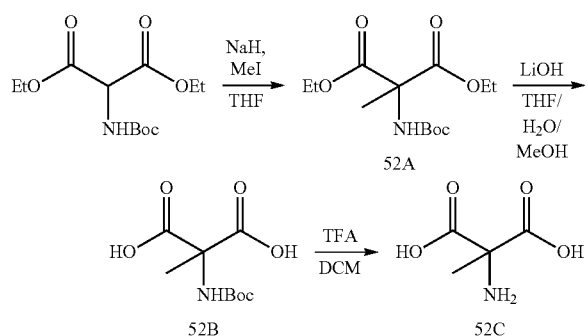

Synthesis of diethyl 2-((tert-butoxycarbonyl)amino)-2-methylmalonate (52A): To an ice-cold solution of diethyl 2-(tert-butoxycarbonylamino)propanedioate (2.91 mmol) in THF (4 mL) was carefully added sodium hydride (60% dispersion in mineral oil, 2.85 mmol, 0.98 equiv) in four portions. The resulting mixture was allowed to stir for 30 mins at 0° C. then 15 mins at RT at which time iodomethane (2.62 mmol, 0.9 equiv) was added. When the reaction had reached completion, the mixture was partitioned between DCM and water (30 mL of each), and the organic fraction was collected, dried over Na$_2$SO$_4$, concentrated under reduced pressure, and purified by silica gel chromatography to yield title compound 52A. $^1$H NMR (400 MHz, Chloroform-d) δ 5.97 (s, 1H), 4.37-4.12 (m, 4H), 1.45 (s, 9H), 1.28 (t, J=7.1 Hz, 6H) ppm.

Synthesis of 2-((tert-butoxycarbonyl)amino)-2-methylmalonic acid (52B): 52A (1.45 mmol) was added to a mixture of THF/MeOH/water (3 mL of 1:1:1) containing LiOH (5.81 mmol, 4 equiv). When the reaction had reached completion, the mixture was partitioned between DCM and water (30 mL of each), and the organic fraction was collected, dried over $Na_2SO_4$, and concentrated under reduced pressure to yield title compound 52B, which was used without further purification. $^1H$ NMR (400 MHz, Methanol-$d_4$) δ 1.69 (s, 3H), 1.46 (s, 9H) ppm.

Synthesis of 2-amino-2-methylmalonic acid (52C): To a solution of 52B (0.146 mmol) in DCM (1 mL) was added TFA (0.175 mmol, 12 equiv). When the reaction had reached completion, the solvent was removed under reduced pressure to yield title compound 52C, which was used without further purification. MS (m/z) 134.10 $[M+H]^+$.

Synthesis of 2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-2-methylmalonic acid (52): An atropisomeric mixture of the title compound was prepared according to the method presented for the synthesis of 32 of Example 32 utilizing 52C in the place of 1-amino-2-methyl-propan-2-ol. $^1H$ NMR (400 MHz, DMSO-$d_6$) δ 13.73-13.64 (m), 9.25 (d), 9.18 (d), 8.40 (s), 8.28 (s), 7.84-7.72 (m), 7.44-7.21 (m), 7.03 (ddt), 6.92 (d), 6.79 (d), 6.56-6.45 (m), 4.97-4.85 (m), 4.87-4.68 (m), 4.70-4.54 (m), 4.11 (dh), 3.65-3.51 (m), 3.27 (s), 3.00 (dtd), 1.75 (d), 1.66 (d), 1.64 (s), 1.32-1.17 (m), 1.03-0.95 (m) ppm. 19F NMR (375 MHz, DMSO-$d_6$) δ−60.86 (d), −69.31 (t), −69.45 (t), −69.64 (t), −69.78, −69.90 (t), −74.93, −79.76 (t), −80.18, −80.44 (t), −103.09 (dd), −103.76 (dd), −110.62 (dt), −110.87 (d) ppm. MS (m/z) 1127.63 $[M+H]^+$.

Example 53

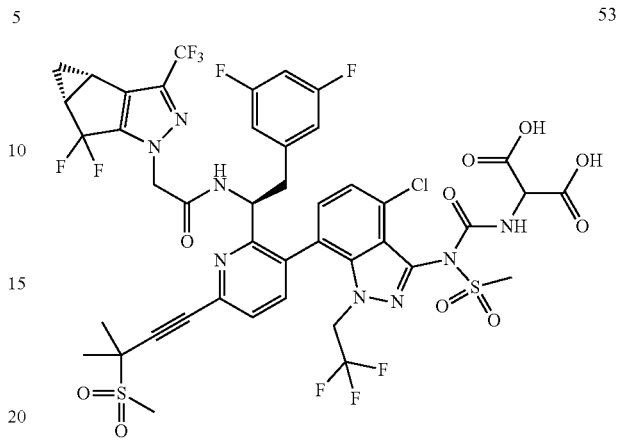

53

Synthesis of 2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)malonic acid (53): An atropisomeric mixture of the title compound was prepared according to the method presented for the synthesis of 32 of Example 32 utilizing aminomalonic acid in the place of 1-amino-2-methyl-propan-2-ol. $^1H$ NMR (400 MHz, DMSO-$d_6$) δ 9.29-9.10 (m, 1H), 7.79 (p, J=7.5, 6.4 Hz, 3H), 7.48-7.20 (m, 3H), 7.12-6.81 (m, 3H), 6.65-6.40 (m, 3H), 4.96-4.45 (m, 7H), 4.34-4.02 (m, 2H), 3.56 (d, J=10.3 Hz, 7H), 3.27 (s, 5H), 3.19-2.87 (m, 3H), 2.66-2.54 (m, 2H), 1.75 (d, J=1.7 Hz, 9H), 1.41 (t, J=7.7 Hz, 2H), 0.98 (s, 2H) ppm. 19F NMR (375 MHz, DMSO-$d_6$) −60.59-−61.05 (m), −69.09-−69.90 (m), −75.27, −79.54-−80.00 (m), −80.06-−80.71 (m), −102.99-−103.28 (m), −103.81 (d), −110.49-−111.22 (m) ppm. MS (m/z): 1113.861 $[M]^+$.

Example 54

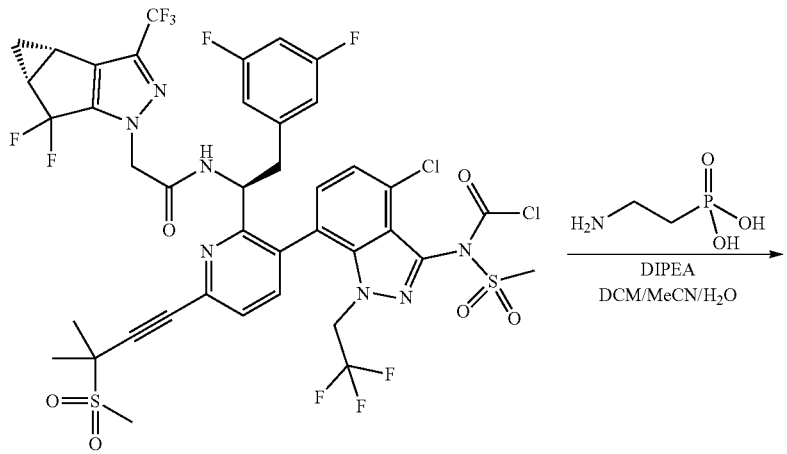

32A

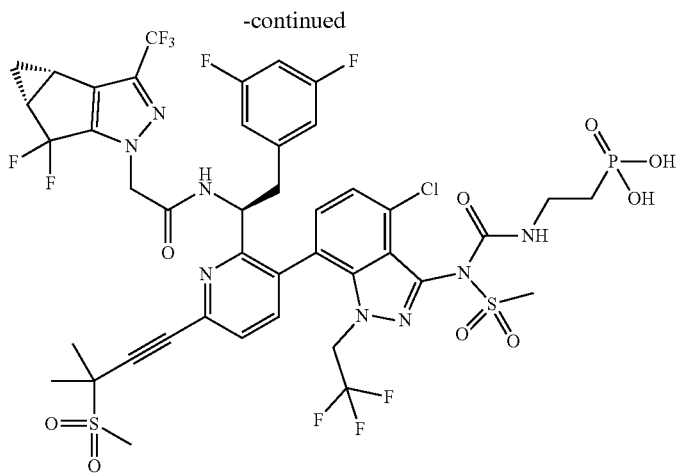

54

Synthesis of (2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)ethyl)phosphonic acid (2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)ethyl)phosphonic acid (54): To a solution of 32A (0.024 mmol) in MeCN (1.5 mL) and water (0.2 mL) was added (2-aminoethyl)phosphonic acid (0.096 mmol, 4 equiv) followed by DIPEA (0.045 mmol, 2 equiv). Upon completion the reaction was concentrated under reduced pressure, filtered, and purified by reverse phase HPLC. Fractions containing the product were pooled and lyophilized to yield title compound 54. $^1$H NMR (400 MHz, DMSO-$d_6$) δ 9.25 (s), 7.84-7.69 (m), 7.45-7.39 (m), 7.36-7.23 (m), 7.16 (s), 7.06-6.95 (m), 6.96 (s), 6.64 (s), 6.52 (s), 4.91 (s), 4.83 (s), 4.79-4.70 (m), 4.65 (s), 4.58 (s), 4.22 (s), 4.11 (s), 3.86 (s), 3.71 (s), 3.60-3.52 (m), 3.14-3.04 (m), 2.97 (s), 2.66-2.53 (m), 1.79-1.72 (m), 1.43-1.37 (m), 0.97 (s) ppm. $^{19}$F NMR (375 MHz, DMSO-$d_6$) δ −60.47-−61.10 (m), −69.25, −69.74, −74.89, −79.82, −80.49, −102.70-−104.08 (m), −110.47-−111.16 (m) ppm. MS (m/z) 1119.11 [M+H]$^+$.

Example 54-1

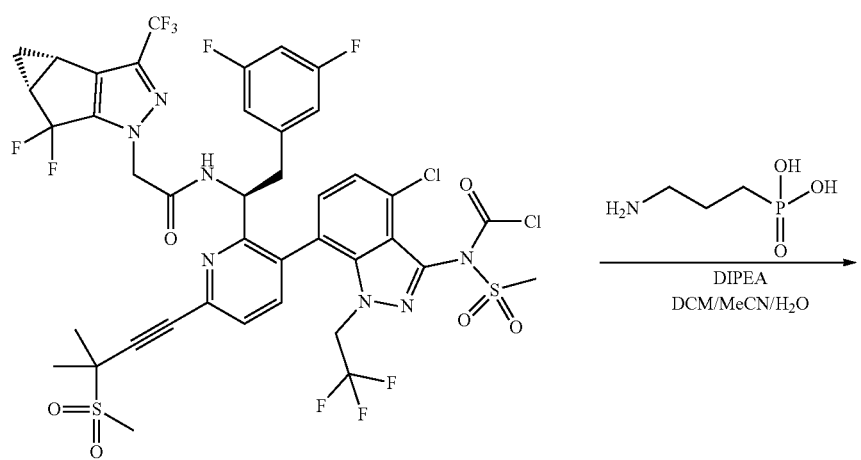

32A

-continued

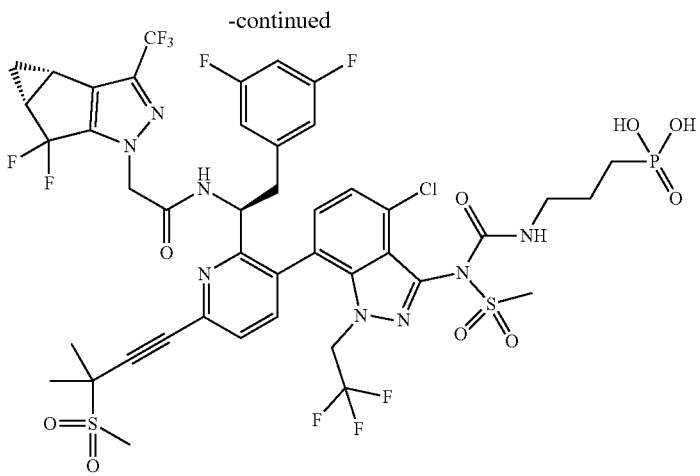

54-1

Synthesis of (3-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)propyl)phosphonic acid (54-1): An atropisomeric mixture of the title compound was prepared according to the method presented for the synthesis of 54 of Example 54 utilizing (3-aminopropyl)phosphonic acid in the place of (2-aminoethyl)phosphonic acid. $^1$H NMR (400 MHz, DMSO-$d_6$) δ 9.20 (s), 7.88 (s), 7.83-7.76 (m), 7.45-7.38 (m), 7.35-7.23 (m), 7.06-6.96 (m), 6.50 (s), 6.35 (s), 4.77-4.66 (m), 4.54 (s), 3.27 (s), 3.16-3.02 (m), 3.01-2.94 (m), 2.65-2.57 (m), 1.79-1.72 (m), 1.75 (s), 1.56 (s), 1.41 (s), 1.42-1.37 (m), 0.98 (s) ppm. $^{19}$F NMR (375 MHz, DMSO-$d_6$) δ −60.66−−61.06 (m), −60.91, −69.27, −69.10−−69.61 (m), −69.81, −74.99, −79.60−−79.91 (m), −80.28−−80.58 (m), −103.25, −103.60, −103.92, −110.76 ppm. MS (m/z) 1132.87 [M+H]$^+$.

Example 55

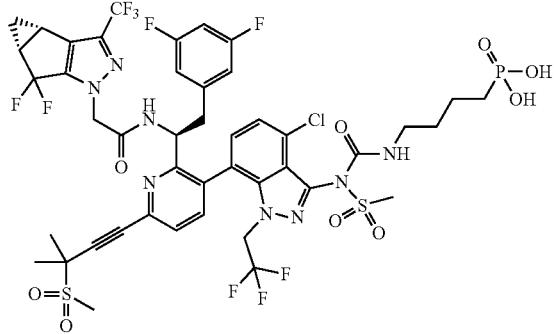

55

Synthesis of (4-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)butyl)phosphonic acid (55): An atropisomeric mixture of the title compound was prepared according to the method presented for the synthesis of 54 of Example 54 utilizing (4-aminobutyl)phosphonic acid in the place of (2-aminoethyl)phosphonic acid. $^1$H NMR (400 MHz, DMSO-$d_6$) δ 9.23-9.15 (m), 7.94 (s), 7.86-7.79 (m), 7.47-7.40 (m), 7.33-7.22 (m), 7.01-6.94 (m), 6.52 (s), 6.44 (s), 6.08 (s), 5.05-4.96 (m), 4.86-4.80 (m), 4.76-4.67 (m), 4.47 (s), 3.27 (s), 3.05 (s), 2.96-2.90 (m), 2.66-2.53 (m), 1.78-1.72 (m), 1.45-1.35 (m), 0.99 (s) ppm. $^{19}$F NMR (375 MHz, DMSO-$d_6$) δ−60.79, −60.92, −69.13−−69.64 (m), −69.88, −74.97, −79.92, −80.59, −102.78−−103.39 (m), −103.45−−104.10 (m), −110.53−−111.01 (m), −110.86, −111.23 ppm. MS (m/z) 1146.87 [M+H]$^+$.

Example 56

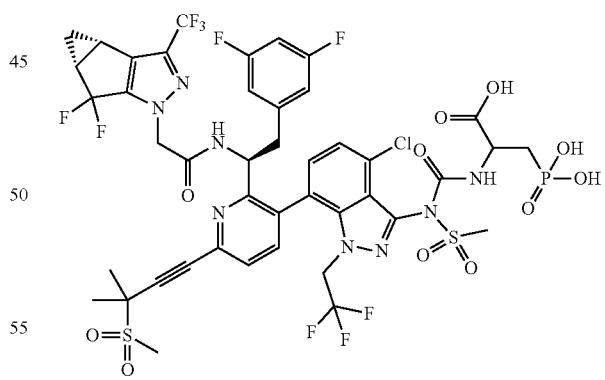

56

Synthesis of 2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-3-phosphonopropanoic acid (56): An atropisomeric mixture of the title compound was prepared according to the method presented for the synthesis of 54 of Example 54 utilizing (±)-2-amino-3-phosphonopropanoic acid in the place of (2-aminoethyl)phosphonic acid. $^1$H NMR (400 MHz, DMSO-d$_6$) δ 9.27-9.20 (m), 9.19-9.12 (m), 8.01-7.93 (m), 7.93-7.71 (m), 7.42-7.33 (m), 7.34-7.22 (m), 7.08-6.82 (m), 6.63-6.49 (m), 4.93-4.78 (m), 4.78-4.58 (m), 4.48-4.39 (m), 3.71-3.59 (m), 3.27 (s), 3.08 (s), 3.05-2.97 (m), 2.90 (s), 2.74 (s), 2.60 (s), 2.10 (s), 2.19-2.04 (m), 1.79-1.72 (m), 1.44-1.37 (m), 1.30-1.22 (m), 1.02-0.93 (m) ppm. $^{19}$F NMR (376 MHz, DMSO-d$_6$) δ −60.76−−60.94 (m), −69.12−−69.25 (m), −69.34−−69.46 (m), −69.70−−69.93 (m), −74.82, −79.71−−79.89 (m), −80.38−−80.57 (m), −102.95−−103.12 (m), −103.19, −103.61−−103.78 (m), −103.86, −110.50−−110.72 (m), −110.93 ppm. MS (m/z) 1163.64.

Example 57

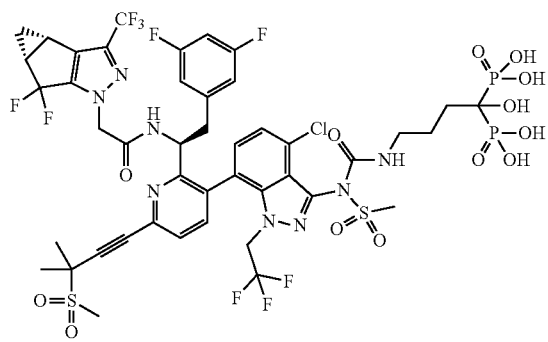

57

Synthesis of (4-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-1-hydroxybutane-1,1-diyl)bis(phosphonic acid) (57): An atropisomeric mixture of the title compound was prepared according to the method presented for the synthesis of 54 of Example 54 utilizing tetrakis(trimethylsilyl) (2,2,9,9-tetramethyl-8-oxa-3-aza-2,9-disiladecane-7,7-diyl)bis(phosphonate) (prepared as described in the synthesis of bis(trimethylsilyl) (2-aminoethyl)phosphonate of Example 11) in the place of 2-aminoethylphosphonic acid. $^1$H NMR (400 MHz, DMSO-d$_6$) δ 9.23 (s), 7.83-7.74 (m), 7.44-7.37 (m), 7.08-6.93 (m), 6.55 (s), 4.87 (s), 4.77 (s), 3.58-3.50 (m), 3.15-3.05 (m), 3.04 (s), 2.98 (s), 1.83-1.72 (m), 1.45-1.36 (m), 0.97 (s) ppm. MS (m/z) 1243.00 [M+H]$^+$.

Example 58

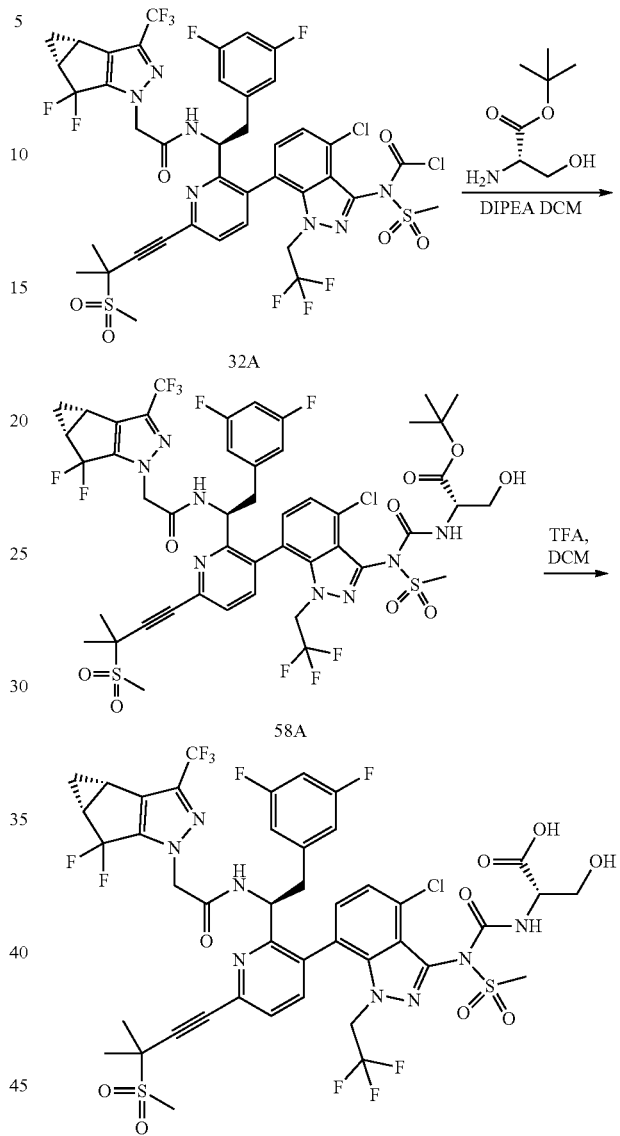

Synthesis of tert-butyl ((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-L-serinate (58A): To a solution of 32A (0.073 mmol) in DCM (1 mL) were added sequentially DIPEA (0.132 mmol 1.8 equiv) and tert-butyl-L-serinate (0.302 mmol, 4.1 equiv). Upon completion the reaction was partitioned between water and DCM (10 mL of each). The organic fraction was collected, dried over Na$_2$SO$_4$, concentrated under reduced pressure to yield title compound 58A, which was used without further purification. MS (m/z) 1155.64 [M+H]$^+$.

Synthesis of ((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-L-serine (58): To a solution of 58A (0.043 mmol) in DCM (1 mL) was added TFA (0.2 mL). Upon completion, the reaction was concentrated under reduced pressure, filtered, and purified by reverse phase HPLC. Fractions containing the product were pooled and lyophilized to yield title compound 58. $^1$H NMR (400 MHz, DMSO-d$_6$) δ 9.29-9.22 (m), 9.20-9.13 (m), 7.84-7.72 (m), 7.69-7.62 (m), 7.42-7.35 (m), 7.09-6.98 (m), 6.95-6.88 (m), 6.57-6.49 (m), 4.94-4.81 (m), 4.79-4.59 (m), 4.27 (s), 4.21-4.04 (m), 3.27 (s), 3.08-2.99 (m), 2.99 (s), 2.64-2.56 (m), 1.79-1.72 (m), 1.40 (s), 1.02-0.94 (m) ppm. $^{19}$F NMR (376 MHz, DMSO-d$_6$) δ-60.77--60.96 (m), −69.19--69.36 (m), −69.61, −69.71--69.88 (m), −74.93, −79.78, −80.35--80.52 (m), −102.99--103.19 (m), −103.67--103.87 (m), −110.53--110.73 (m) ppm. MS (m/z) 1099.04 [M+H]$^+$.

Example 59

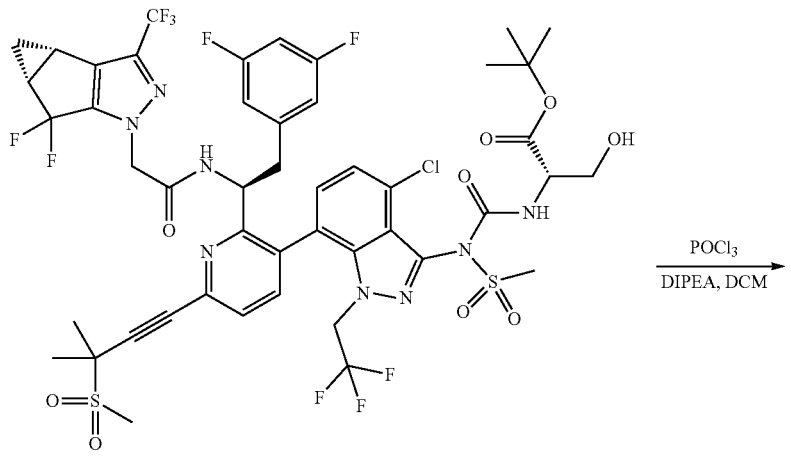

58A

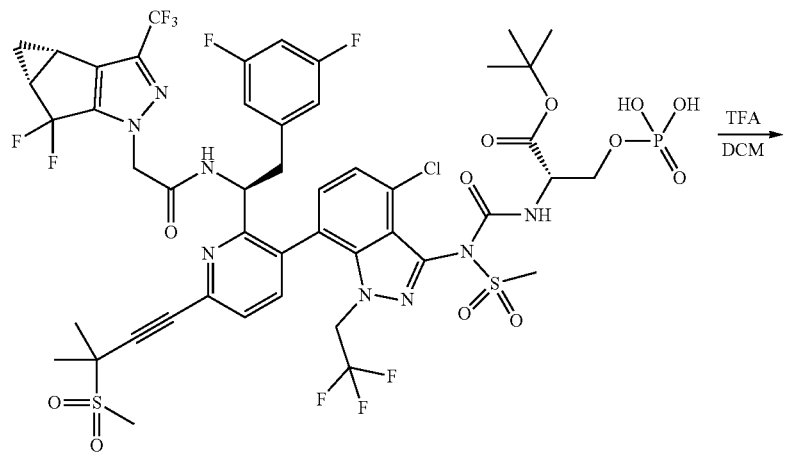

59A

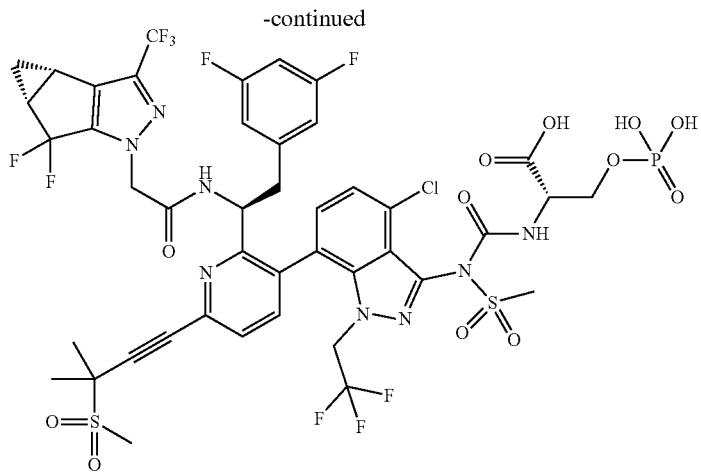

59

Synthesis of tert-butyl N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-O-phosphono-L-serinate (59A): To an ice-cold solution of 58A (0.022 mmol) in DCM (1 mL) were added sequentially POCl₃ (0.108 mmol, 5 equiv) and DIPEA (0.065 mmol, 3 equiv). After 1 h, the reaction was diluted with H₂O/MeCN (0.5 mL of 1:1 mixture). The volatiles were removed under reduced pressure to yield an atropisomeric mixture of title compound 59A, which was taken forward without purification.

Synthesis of N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-O-phosphono-L-serine (59): 59A (0.022 mmol) was diluted with DCM (1 mL) and TFA (0.3 mL). When the reaction had reached completion, the solvent was removed under reduced pressure and the residue was purified by reverse phase HPLC. Fractions containing the product were pooled and lyophilized to yield title compound 59. ¹H NMR (400 MHz, DMSO-d₆) δ 9.26 (s), 9.19-9.12 (m), 7.96-7.89 (m), 7.83-7.65 (m), 7.42-7.34 (m), 7.34-7.23 (m), 7.11-6.99 (m), 6.98-6.85 (m), 6.59-6.52 (m), 4.93-4.79 (m), 4.81-4.58 (m), 4.52 (s), 4.23 (s), 4.16 (s), 3.68-3.60 (m), 3.57 (s), 3.08 (s), 3.05-2.97 (m), 2.80 (s), 2.60 (s), 1.82-1.72 (m), 1.43-1.36 (m), 0.96 (s) ppm. ¹⁹F NMR (376 MHz, DMSO-d₆) δ −60.72−−60.99 (m), −69.10−−69.33 (m), −69.36−−69.87 (m), −74.12, −79.67−−79.90 (m), −80.35−−80.57 (m), −103.19, −103.87, −110.53−−110.74 (m), −110.70, −110.98 ppm. MS (m/z) 1178.89 [M+H]⁺.

Example 60

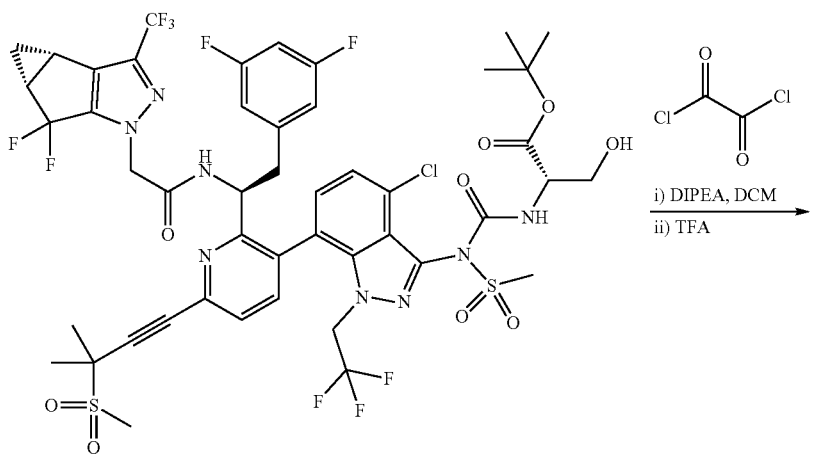

58A

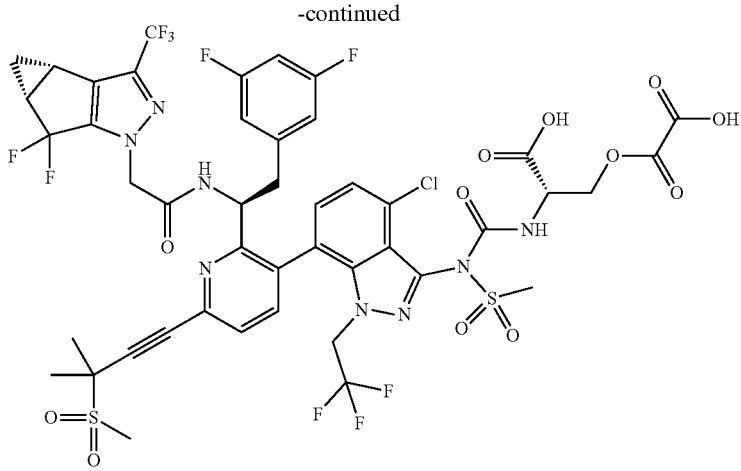

60

Synthesis of O-(carboxycarbonyl)-N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-L-serine (60): To a solution of 58A (0.043 mmol) in DCM (2 mL) was added DIPEA (0.130 mmol) followed by tert-butyl-2-chloro-2-oxoacetate (0.216 mmol) and the resulting mixture was stirred for 10 mins. Trifluoroacetic acid (6.530 mmol) was then added with a further 10 mins stirring at which time the reaction was diluted with 1:1 H$_2$O:MeCN (1 mL). The reaction contents were then transferred to a separatory funnel with DCM (15 mL) and washed once with 1M HCl (20 mL). The organic fraction was collected, dried over Na$_2$SO$_4$, concentrated under reduced pressure, and purified by reverse phase HPLC. Fractions containing the product were pooled and lyophilized to give title compound 60 as a mixture of atropisomers. $^1$H NMR (400 MHz, DMSO-d$_6$) δ 9.19 (dd), 7.78 (d), 7.66 (d), 7.37 (t), 7.02 (t), 6.94 (d), 6.52 (d), 4.99-4.49 (m), 4.44 (d), 4.24 (s), 3.27 (s), 3.01 (dd), 2.60 (s), 1.75 (s), 1.39 (q), 0.99 (s) ppm. $^{19}$F NMR (375 MHz, DMSO-d$_6$) δ−60.80 (d), −60.88, −68.09--70.40 (m), −75.08, −80.10 (dd), −103.44 (dd), −110.07--111.52 (m) ppm. MS (m/z) 1171.425 [M+H]$^+$.

Example 61

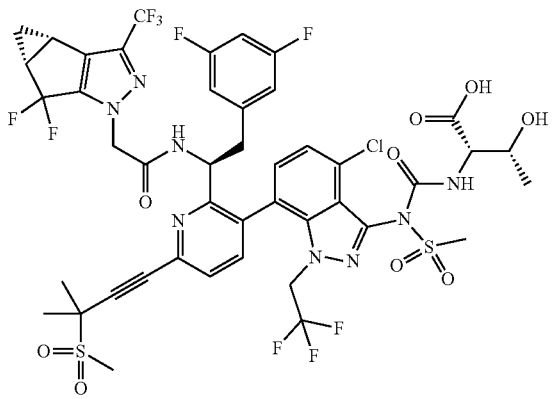

61

Synthesis of ((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H- indazol-3-yl)(methylsulfonyl)carbamoyl)-L-threonine (61): An atropisomeric mixture of the title compound was prepared according to the method presented for the synthesis of 58 of Example 58 utilizing L-threonine-tert-butyl ester in the place of tert-butyl-L-serinate. $^1$H NMR (400 MHz, DMSO-$d_6$) δ 9.28-9.21 (m), 9.21-9.14 (m), 7.85-7.72 (m), 7.66-7.59 (m), 7.42-7.26 (m), 7.08-6.98 (m), 6.97-6.86 (m), 6.57-6.50 (m), 5.20 (s), 4.93-4.81 (m), 4.80-4.68 (m), 4.62 (s), 4.66-4.57 (m), 4.22-4.04 (m), 3.67-3.60 (m), 3.55 (s), 3.27 (s), 3.07-2.93 (m), 1.77-1.72 (m), 1.45-1.39 (m), 1.17-1.05 (m), 0.98 (s) ppm. $^{19}$F NMR (376 MHz, DMSO-$d_6$) δ−60.76−−60.99 (m), −60.89, −69.24−−69.43 (m), −69.68−−69.85 (m), −74.09, −79.83 (d, J=13.8 Hz), −80.36−−80.58 (m), −102.99−−103.21 (m), −103.66−−103.89 (m), −110.58−−110.72 (m), −110.87 ppm. MS (m/z) 1113.06 [M+H]$^+$.

Example 62

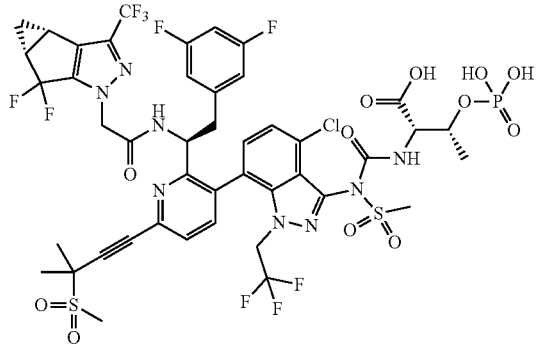

62

Synthesis of N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-O-phosphono-L-threonine (62): An atropisomeric mixture of the title compound was prepared according to the method presented for the synthesis of 59 of Example 59 utilizing 61 in the place of 58A. $^1$H NMR (400 MHz, DMSO-$d_6$) δ 9.29-9.22 (m), 9.21-9.14 (m), 9.02-8.93 (m), 7.96-7.89 (m), 7.85-7.72 (m), 7.44-7.24 (m), 7.08-6.98 (m), 6.99-6.87 (m), 6.56-6.47 (m), 4.93-4.79 (m), 4.81-4.69 (m), 4.68-4.57 (m), 4.30-4.19 (m), 4.22-4.15 (m), 4.19-4.05 (m), 3.67-3.60 (m), 3.27 (s), 3.16-2.93 (m), 1.77-1.72 (m), 1.47-1.33 (m), 1.18-1.07 (m), 0.99 (s) ppm. $^{19}$F NMR (376 MHz, DMSO-$d_6$) δ−60.76−−60.93 (m), −69.27−−69.43 (m), −69.55−−69.67 (m), −69.72−−69.84 (m), −74.97, −79.70−−79.88 (m), −80.11−−80.25 (m), −80.37−−80.56 (m), −80.75−−80.93 (m), −102.98−−103.14 (m), −103.65−−103.87 (m), −110.56−−110.70 (m), −110.75, −110.81−−110.91 (m) ppm. MS (m/z) 1192.85 [M+H]$^+$.

Example 63

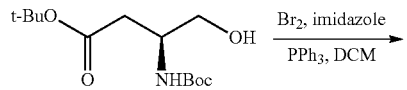

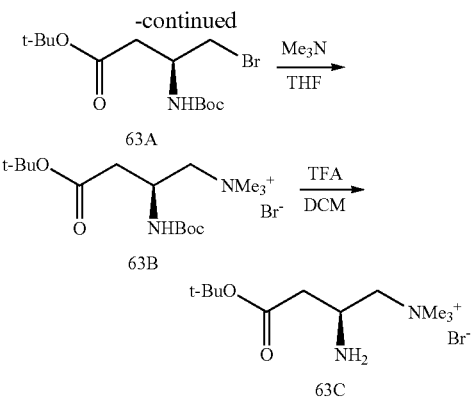

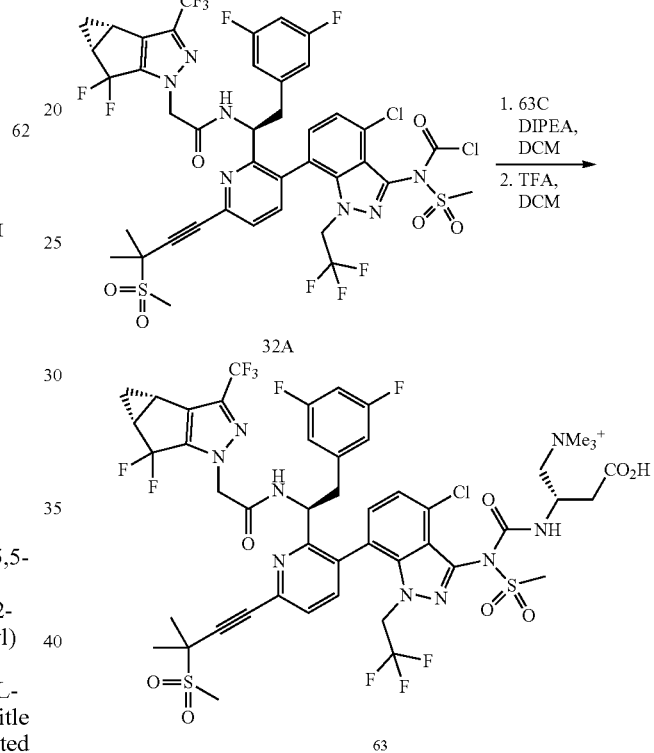

63

Synthesis of tert-butyl (S)-4-bromo-3-((tert-butoxycarbonyl)amino)butanoate (63A): To a solution of tert-butyl (S)-3-((tert-butoxycarbonyl)amino)-4-hydroxybutanoate (0.545 mmol), imidazole (0.599 mmol, 1.1 equiv), and triphenylphosphine (0.545 mmol, 1 equiv) in DCM (1 mL) at 0° C. was added bromine (0.599 mmol, 1.1 equiv). When the reaction had reached completion, it was partitioned between saturated $Na_2S_2O_3$ and DCM. The organic fraction was collected, dried over $Na_2SO_4$, and concentrated under reduced pressure to yield title compound 63A, which was used without further purification. $^1$H NMR (400 MHz, Chloroform-d) δ 4.31 (dd, J=5.2, 2.5 Hz, 1H), 3.05 (s, 2H), 2.56 (d, J=6.1 Hz, 1H), 1.47 (s, 9H) ppm.

Synthesis of tert-butyl (S)-4-bromo-3-((tert-butoxycarbonyl)amino)butanoate (63B): To a solution of 63A (0.443 mmol) in THF (1 mL) was added trimethylamine (13.3 mmol, 30 equiv). The resulting reaction was stirred at RT. Upon completion, the solvent was removed under reduced pressure to yield title compound 63B, which was used without further purification. MS (m/z) 317.42 [M+H]$^+$.

Synthesis of tert-butyl (S)-3-amino-4-(trimethyl-14-azaneyl)butanoate (63C): To a solution of 63B (0.315 mmol)

in DCM (1 mL) was added TFA (0.1 mL). Upon completion, the reaction was concentrated under reduced pressure to yield title compound 63C, which was used without further purification. MS (m/z) 217.21 [M+H]+.

Synthesis of (S)-3-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-4-(trimethyl-14-azaneyl)butanoic acid (63): An atropisomeric mixture of the title compound was prepared according to the method presented for the synthesis of 58 of Example 58 utilizing 63C in the place of tert-butyl-L-serinate. $^1$H NMR (400 MHz, DMSO-$d_6$) δ 9.28-9.21 (m), 8.96-8.87 (m), 7.85-7.73 (m), 7.35-7.28 (m), 7.09-6.98 (m), 6.90-6.83 (m), 6.63 (s), 6.54 (s), 6.52-6.44 (m), 4.97-4.88 (m), 4.78-4.67 (m), 4.65-4.54 (m), 4.56-4.43 (m), 4.32 (s), 4.02-3.90 (m), 3.19-3.07 (m), 3.04-2.90 (m), 2.78-2.67 (m), 2.65-2.55 (m), 1.77-1.72 (m), 1.46-1.36 (m), 1.01-0.93 (m) ppm. $^{19}$F NMR (376 MHz, DMSO-$d_6$) δ −60.78--−60.95 (m), −69.20--−69.30 (m), −69.62--−69.77 (m), −73.98, −79.78--−79.87 (m), −80.45--−80.54 (m), −103.19, −110.59--−110.67 (m) ppm. MS (m/z) 1154.13 [M+H]+.

Example 64 pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (64): Intermediate 5 (0.052 mmol) and methylcarbamic chloride (0.52 mmol) were suspended in DCM (1 mL) and treated with DIPEA (1.0 mmol). After stirring for 3 d, additional portions of methylcarbamic chloride (0.57 mmol) and DIPEA (1.0 mmol) were added. The reaction mixture was stirred for an additional 3 h, then quenched by addition of 2 mL MeOH. DCM was added and the organics were washed with saturated aqueous ammonium chloride. The aqueous layer was back extracted with DCM and the combined organics were dried over MgSO$_4$, filtered and concentrated under reduced pressure. The crude residue was purified by reverse phase HPLC. Fractions containing the product were pooled and lyophilized to give title compound 64 as a mixture of atropisomers. $^1$H NMR (400 MHz, Methanol-$d_4$) δ 9.18-9.11 (m), 7.88-7.81 (m), 7.76-7.67 (m), 7.35-7.29 (m), 6.82-6.72 (m), 6.66-6.59 (m), 6.39-6.28 (m), 6.13-6.08 (m), 4.86-4.81 (m), 4.75-4.58 (m), 3.89-3.84 (m), 3.54-3.49 (m), 3.31-3.26 (m), 3.26-3.21 (m), 3.22-3.12 (m), 3.00-2.90 (m), 2.55-2.50 (m), 2.60-2.47 (m), 1.85-1.79 (m), 1.48-1.38 (m), 1.32-1.27 (m), 1.06-1.01 (m), 0.96-0.86 (m). MS (m/z) 1025.25 [M+H]+.

Example 65

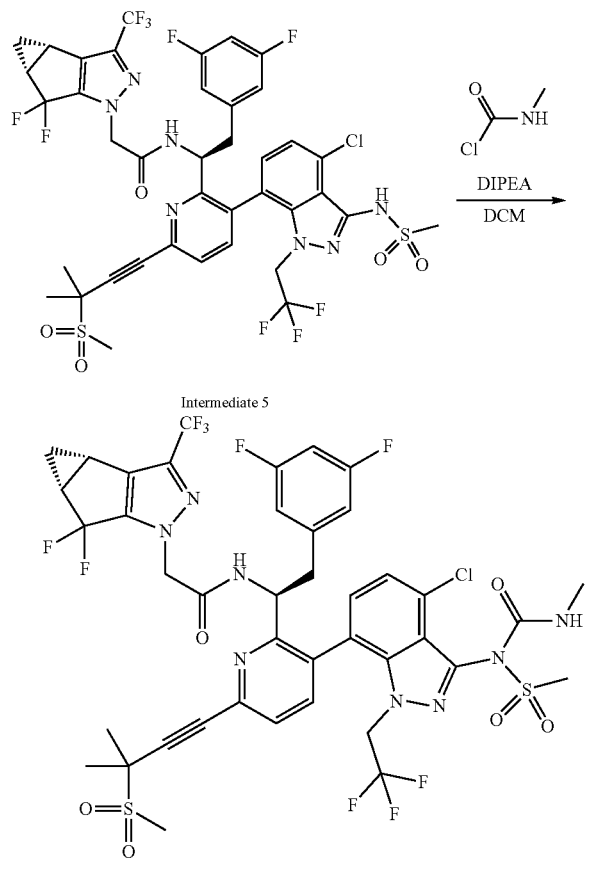

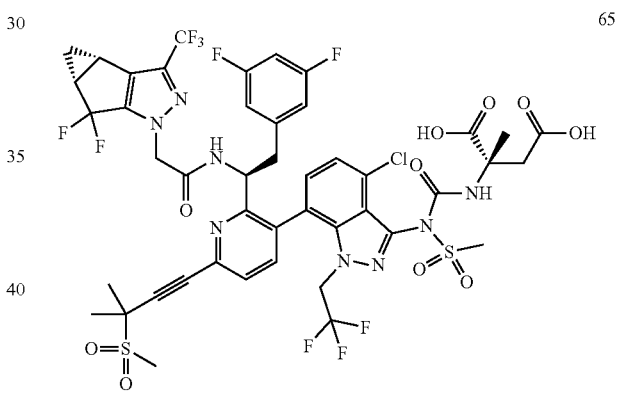

Synthesis of N—((S)-1-(3-(4-chloro-3-(N-(methylcarbamoyl)methylsulfonamido)-1-(2,2,2-trifluoroethyl)-1H-indazol-7-yl)-6-(3-methyl-3-(methylsulfonyl)but-1-yn-1-yl)

Synthesis of (S)-2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-2-methylsuccinic acid (65): An atropisomeric mixture of the title compound was prepared according to the method presented for the synthesis of 58 of Example 58 utilizing di-tert-butyl (S)-2-amino-2-methylsuccinate in the place of tert-butyl-L-serinate. $^1$H NMR (400 MHz, DMSO-$d_6$) δ 9.33-9.22 (m), 9.20-9.13 (m), 8.23-8.15 (m), 8.09 (s), 7.84-7.72 (m), 7.46-7.23 (m), 7.08-7.00 (m), 7.05-6.92 (m), 6.96-6.82 (m), 6.61-6.47 (m), 4.96-4.84 (m), 4.85-4.70 (m), 4.73-4.56 (m), 3.57 (s), 3.50 (s), 3.27 (s), 3.02-2.93 (m), 2.87-2.75 (m), 1.79-1.72 (m), 1.59-1.46 (m), 1.43-1.36 (m), 1.02-0.94 (m) ppm. $^{19}$F NMR (377 MHz, DMSO-$d_6$) δ−60.74--−60.96 (m), −69.20--−69.49 (m), −69.55--−69.69 (m), −69.77--−69.92 (m), −74.81, −79.71--−79.85 (m), −80.38--−80.52 (m), −103.20, −103.67--−103.80 (m), −103.87, −110.50--−110.74 (m), −110.79 ppm. MS (m/z) 1141.14 [M+H]+.

Example 66

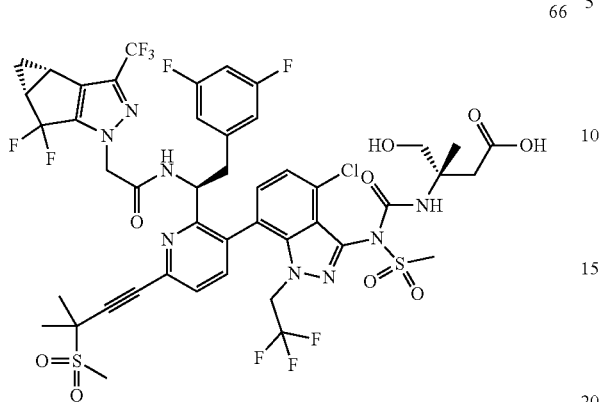

66

Synthesis of (S)-3-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)-4-hydroxy-3-methylbutanoic acid (66): An atropisomeric mixture of the title compound was prepared according to the method presented for the synthesis of 32 of Example 32 utilizing (S)-3-amino-4-hydroxy-3-methylbutanoic acid in the place of 1-amino-2-methyl-propan-2-ol. $^1$H NMR (400 MHz, DMSO-$d_6$) δ 13.22 (s), 12.89 (s), 9.30-9.23 (m), 9.21-9.14 (m), 9.05-8.93 (m), 8.15-8.09 (m), 7.99-7.87 (m), 7.85-7.67 (m), 7.40-7.22 (m), 7.09-6.82 (m), 6.58-6.45 (m), 4.97-4.52 (m), 4.19-4.04 (m), 3.91-3.83 (m), 3.67-3.54 (m), 3.27 (s), 3.13-3.04 (m), 3.05-2.93 (m), 2.61 (s), 1.79-1.72 (m), 1.48-1.31 (m), 1.03-0.93 (m) ppm. $^{19}$F NMR (376 MHz, DMSO-$d_6$) δ −60.78−−60.93 (m), −69.09−−69.21 (m), −69.36−−69.48 (m), −69.58−−69.69 (m), −69.80−−69.92 (m), −74.97, −79.70−−79.84 (m), −80.38−−80.52 (m), −80.82−−80.92 (m), −103.15, −103.70−−103.85 (m), −110.54−−110.77 (m), −110.87−−110.96 (m) ppm. MS (m/z) 1129.57 [M+H]$^+$.

Example 67

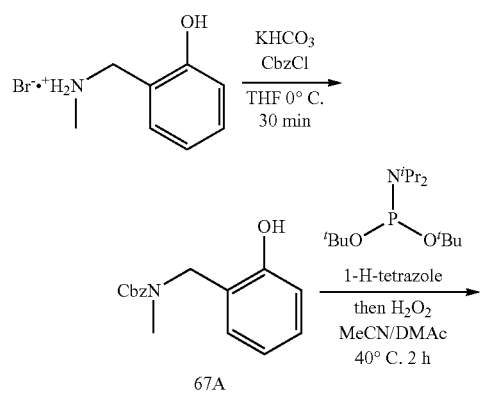

67A

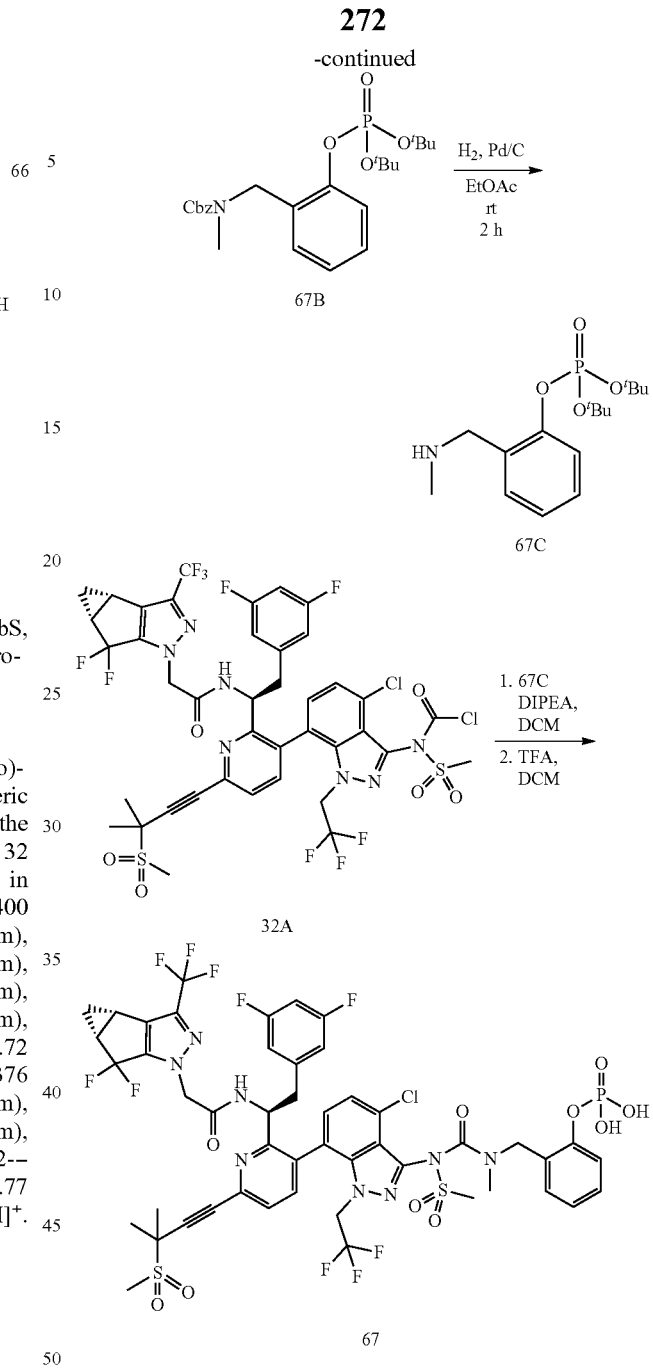

Synthesis of benzyl N-[(2-hydroxyphenyl)methyl]-N-methyl-carbamate (67A): To an ice-cold solution of (2-hydroxyphenyl)methyl-methyl-ammonium bromide (9.2 mmol) and KHCO$_3$ (19.3 mmol) in THF (46 mL) was added benzyl chloroformate (11 mmol). The reaction was sealed, cooled to 0° C., and stirred for 30 min. Upon completion, the reaction was transferred to a separatory funnel with 0.1M HCl (230 mL) and extracted 3× with EtOAc (115 mL). The organic fraction was collected, dried over Na$_2$SO$_4$, concentrated, and purified with silica chromatography. Fractions containing the product were pooled and concentrated to yield title compound 67A. MS (m/z): 272.20 [M+H]$^+$.

Synthesis of benzyl N-[(2-ditert-butoxyphosphoryloxyphenyl)methyl]-N-methyl-carbamate (67B): To a solution of 67A (2.2 mmol), 0.45M 1H-tetrazole in MeCN (6.6 mmol), and N,N-dimethylacetamide (4.4 mL) was added di-tertbutyl N,N-diisopropylphosphoramidite (5.5 mmol). The reaction was sealed, heated to 40° C., and stirred for 1 hour. Then 50% $H_2O_2$(11.1 mmol) was added to the reaction. The reaction was sealed, heated to 40° C., and stirred for 1 hour. Upon completion, the reaction was diluted with water (95 mL) and quenched with sat. $Na_2SO_3$ (1 mL). The solution was transferred to a separatory funnel and extracted 3× with 1:1 EtOAc/Hexanes (60 mL). The organic fraction was collected, washed with 0.1M HCl (120 mL), 5% LiCl (120 mL), sat. NaCl (60 mL), dried over $Na_2SO_4$, concentrated, and purified with silica chromatography. Fractions containing the product were pooled and concentrated to yield title compound 67B. MS (m/z): 486.20 [M+Na]$^+$.

Synthesis of di-tert-butyl [2-(methylaminomethyl)phenyl] phosphate (67C): To a solution of 67B (1.9 mmol) in EtOAc (6.3 mL) was added palladium on carbon (0.5 mmol) The reaction was sealed, purged with argon for 15 minutes, purged with $H_2$, and stirred under $H_2$ for 2 hours. Upon completion, the reaction was purged with argon for 15 minutes, diluted with Celite 545 (500 mg) and EtOAc (6 mL), and filtered. The solution was concentrated to yield title compound 67C, which was used without purification. MS (m/z): 352.10 [M+Na]$^+$.

Synthesis of 2-((3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)methyl) phenyl dihydrogen phosphate (67): An atropisomeric mixture of the title compound was prepared according to the method presented for the synthesis of 58 of Example 58 utilizing 67C in the place of tert-butyl-L-serinate. $^1$H NMR (400 MHz, CD3CN) δ 7.92 (s), 7.71 (d), 7.64 (d), 7.47 (d), 7.28 (d), 7.23 (d,), 7.16 (d), 7.00 (s), 6.69 (tq), 6.58-6.48 (m), 6.20 (d), 5.39 (s), 4.82-4.42 (m), 4.03 (h), 3.37 (s), 3.28 (s), 3.15 (d), 3.03-2.77 (m), 2.67 (s), 2.59 (s), 2.51-2.39 (m), 1.76 (s), 1.35 (q), 1.05-0.97 (m). $^{19}$F NMR (377 MHz, CD3CN) 6-62.61, −71.43, −77.38, −80.97--83.09 (m), −103.39--105.76 (m), −111.99. MS (m/z): 1211.20 [M+H]$^+$.

Example 68

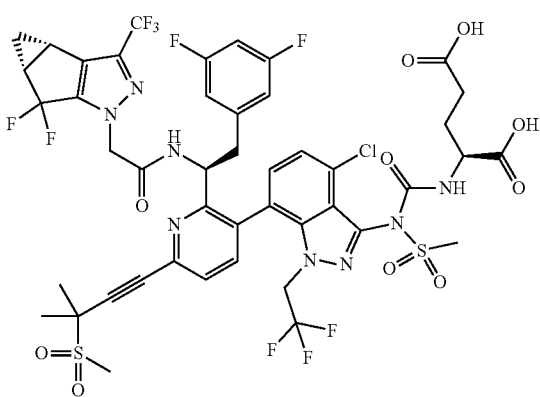

68

Synthesis of ((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-L-glutamic acid (68): An atropisomeric mixture of the title compound was prepared according to the method presented for the synthesis of 58 of Example 58 utilizing di-tert-butyl L-glutamate in the place of tert-butyl-L-serinate. $^1$H NMR (400 MHz, Methanol-d$_4$) δ 9.09-9.02 (m), 7.84-7.77 (m), 7.76-7.62 (m), 7.66-7.53 (m), 7.34-7.27 (m), 6.93-6.86 (m), 6.85-6.75 (m), 6.57-6.50 (m), 6.44-6.38 (m), 4.45 (s), 4.27 (s), 4.04-3.93 (m), 3.54 (s), 3.25 (s), 3.05-2.95 (m), 2.52 (s), 2.30-2.22 (m), 2.17-2.08 (m), 1.84 (s), 1.49-1.39 (m), 1.07 (s). MS (m/z) 1141.199 [M+H]$^+$.

Example 69

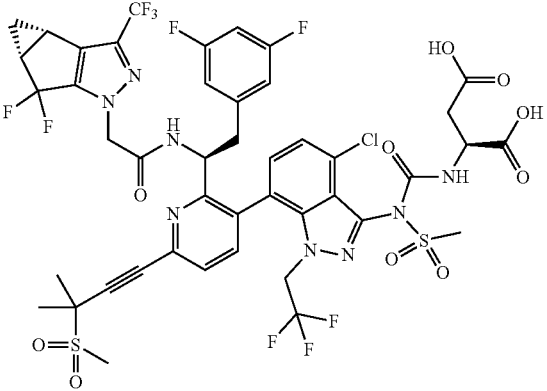

69

Synthesis of ((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-L-aspartic acid (69): An atropisomeric mixture of the title compound was prepared according to the method presented for the synthesis of 58 of Example 58 utilizing di-tert-butyl L-aspartic acid hydrochloride in the place of tert-butyl-L-serinate. $^1$H NMR (400 MHz, DMSO-d$_6$) δ 13.06 (s), 9.27-9.20 (m), 9.20-9.13 (m), 7.92-7.84 (m), 7.85-7.77 (m), 7.76 (s), 7.67-7.60 (m), 7.42-7.36 (m), 7.37-7.24 (m), 7.08-6.98 (m), 6.98-6.87 (m), 6.57-6.50 (m), 4.94-4.85 (m), 4.82 (s), 4.80-4.68 (m), 4.67-4.58 (m), 4.59-4.48 (m), 4.25-4.16 (m), 4.16 (s), 3.60 (s), 3.27 (s), 3.17-2.94 (m), 2.88-2.69 (m), 1.79-1.72 (m), 1.45-1.34 (m), 0.98 (s) ppm. 19F NMR (376 MHz, DMSO-d$_6$) δ−60.74--60.94 (m), −69.20--69.33 (m), −69.36--69.49 (m), −69.55, −69.71--69.84 (m), −74.81, −79.71--79.83 (m), −80.38--80.50 (m), −103.03, −103.16, −103.65--103.88 (m), −110.58--110.71 (m), −110.77--110.94 (m) ppm. MS (m/z) 1128.26 [M+H]$^+$.

Example 70

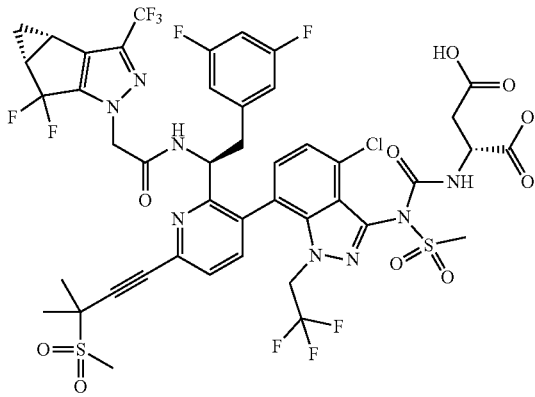

Synthesis of ((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-D-aspartic acid (70): An atropisomeric mixture of the title compound was prepared according to the method presented for the synthesis of 58 of Example 58 utilizing (R)-3-amino-4-(tert-butoxy)-4-oxobutanoic acid hydrochloride in the place of tert-butyl-L-serinate. $^1$H NMR (400 MHz, DMSO-d$_6$) δ 9.27-9.20 (m), 9.20-9.13 (m), 9.02-8.95 (m), 7.94-7.77 (m), 7.76 (s), 7.81-7.69 (m), 7.67-7.60 (m), 7.42-7.24 (m), 7.08-6.97 (m), 6.98-6.86 (m), 6.56-6.46 (m), 4.94-4.76 (m), 4.80-4.68 (m), 4.64 (s), 4.63-4.45 (m), 4.25-4.09 (m), 3.63-3.49 (m), 3.27 (s), 3.17-2.94 (m), 2.88-2.68 (m), 2.66-2.51 (m), 1.77-1.72 (m), 1.47-1.34 (m), 1.03-0.93 (m) ppm. $^{19}$F NMR (376 MHz, DMSO-d$_6$) δ−60.72--60.97 (m), −69.18--69.66 (m), −69.69--69.88 (m), −75.39, −75.42, −75.45, −79.69--79.87 (m), −79.99--80.28 (m), −80.36--80.54 (m), −80.67--80.96 (m), −102.98--103.27 (m), −103.63--103.94 (m), −110.56--110.81 (m), −110.92 ppm. MS (m/z) 1128.41 [M+H]$^+$.

Example 71

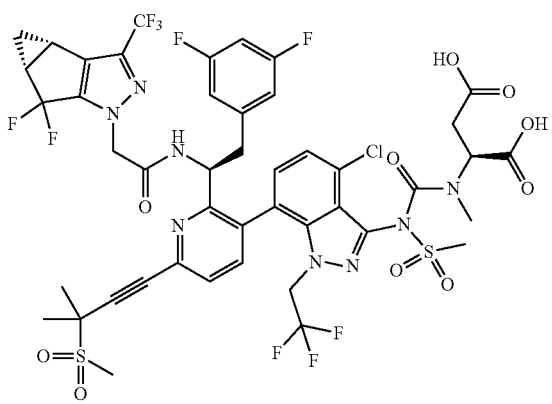

Synthesis of N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-N-methyl-L-aspartic acid (71): An atropisomeric mixture of the title compound was prepared according to the method presented for the synthesis of 58 of Example 58 utilizing (S)-3-methylamino-4-(tert-butoxy)-4-oxobutanoic acid hydrochloride in the place of tert-butyl-L-serinate. $^1$H NMR (400 MHz, DMSO-d$_6$) δ 9.21-9.14 (m), 7.83-7.76 (m), 7.39 (s), 7.06-6.92 (m), 6.67 (s), 6.52 (s), 6.40-6.33 (m), 4.94 (s), 4.79-4.68 (m), 4.64-4.54 (m), 3.97 (s), 3.40 (s), 3.27 (s), 2.96-2.85 (m), 2.65-2.58 (m), 1.75 (s), 1.45-1.36 (m), 1.00 (s) ppm. 19F NMR (376 MHz, DMSO-d$_6$) δ−60.60--61.11 (m), −69.25--69.86 (m), −69.92, −74.84, −79.80, −80.49, −103.00, −103.63, −110.67 ppm. MS (m/z) 1141.29 [M+H]$^+$.

Example 72

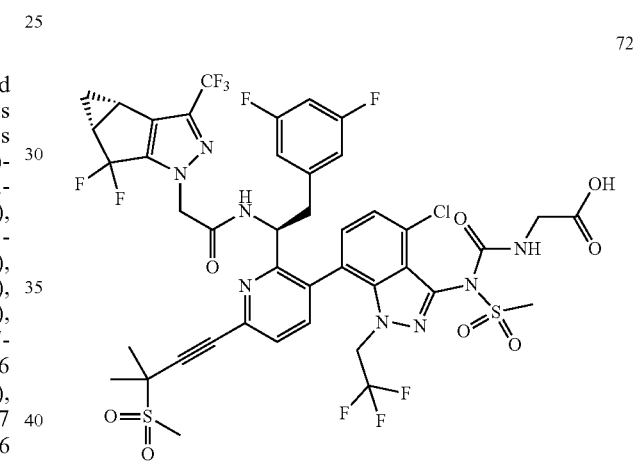

Synthesis of ((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)glycine (72): An atropisomeric mixture of the title compound was prepared according to the method presented for the synthesis of 58 of Example 58 utilizing glycine tert-butyl ester hydrochloride in the place of tert-butyl-L-serinate. $^1$H NMR (400 MHz, DMSO-d$_6$) δ 9.27-9.16 (m), 7.88-7.70 (m), 7.46-7.39 (m), 7.35-7.23 (m), 7.10 (s), 7.05-6.95 (m), 6.56 (s), 6.52-6.46 (m), 4.95-4.86 (m), 4.84-4.70 (m), 4.61-4.55 (m), 3.78 (s), 3.27 (s), 3.10-3.02 (m), 2.99-2.87 (m), 1.78-1.72 (m), 1.43-1.36 (m), 0.97 (s) ppm. $^{19}$F NMR (376 MHz, DMSO-d$_6$) δ−60.59--61.03 (m), −60.89, −69.19, −69.36--69.63 (m), −69.64--69.83 (m), −74.82, −79.57--79.84 (m), −80.21--80.49 (m), −103.09, −103.24, −103.76, −103.91, −110.61--110.87 (m), −110.82, −110.99, −111.16 ppm. MS (m/z) 1069.85 [M+H]$^+$.

Example 73

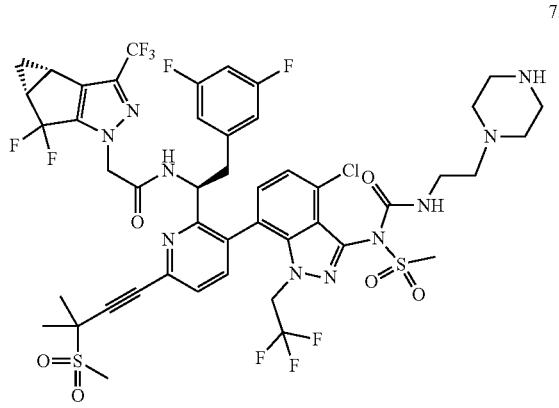

Synthesis of N—((S)-1-(3-(4-chloro-3-(N-((2-(piperazin-1-yl)ethyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (73): An atropisomeric mixture of the title compound was prepared according to the method presented for the synthesis of 58 of Example 58 utilizing tert-butyl 4-(2-aminoethyl)piperazine-1-carboxylate in the place of tert-butyl-L-serinate. $^1$H NMR (400 MHz, DMSO-d$_6$) δ 9.26 (s), 8.53 (s), 8.03-7.71 (m), 7.13-6.91 (m), 6.49 (s), 4.98 (d), 4.73 (d), 4.61 (s), 3.27 (s), 3.07 (d), 2.90 (s), 2.74 (s), 1.75 (d), 1.42 (t), 0.99 (s) ppm. $^{19}$F NMR (375 MHz, DMSO-d$_6$) δ−60.82 (d), −69.25, −69.76 (t), −74.76, −79.79 (d), −80.46 (d), −103.13, −103.79, −110.92 (d) ppm. MS (m/z) 1124.064 [M+H]$^+$.

Example 74

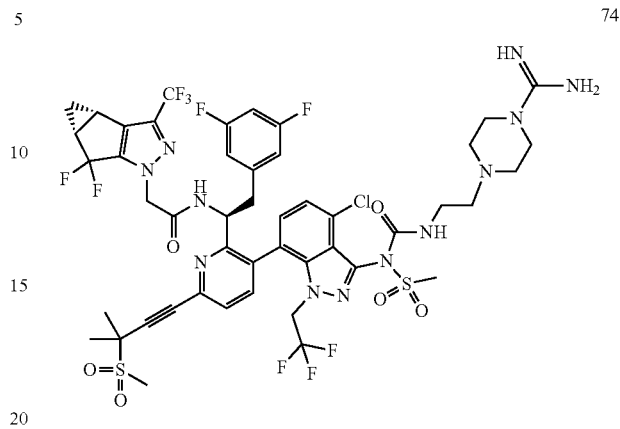

Synthesis of N—((S)-1-(3-(3-(N-((2-(4-carbamimidoylpiperazin-1-yl)ethyl)carbamoyl)methylsulfonamido)-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (74): An atropisomeric mixture of the title compound was prepared according to the method presented for the synthesis of 8 of Example 8 utilizing 73 in the place of 7. $^1$H NMR (400 MHz, DMSO-d$_6$) δ 9.25 (d, J=36.8 Hz, 1H), 8.00-7.71 (m, 3H), 7.71-7.37 (m, 5H), 7.17-6.97 (m, 2H), 6.51 (d, J=7.5 Hz, 3H), 4.95 (d, J=15.4 Hz, 1H), 4.88-4.69 (m, 3H), 4.60 (s, 2H), 3.27 (s, 5H), 3.06 (s, 4H), 2.97 (t, J=11.4 Hz, 3H), 1.75 (d, J=1.4 Hz, 7H), 1.41 (d, J=7.8 Hz, 1H), 0.97 (s, 1H) ppm. $^{19}$F NMR (375 MHz, DMSO-d$_6$) δ−60.44−−61.10 (m), −60.87, −69.26, −69.69, −74.58, −79.73 (d), −80.16−−80.69 (m), −103.19, −103.87, −110.43−−111.28 (m) ppm. MS (m/z) 1165.975 [M+H]$^+$.

Example 75

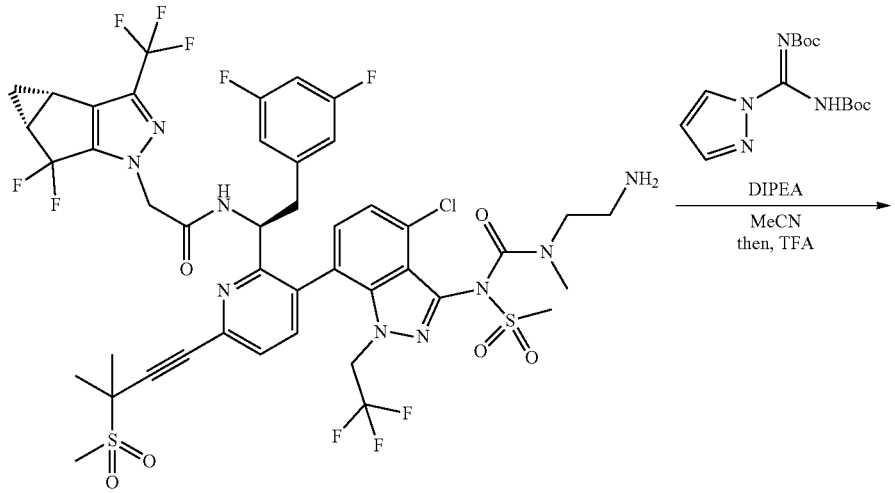

75A

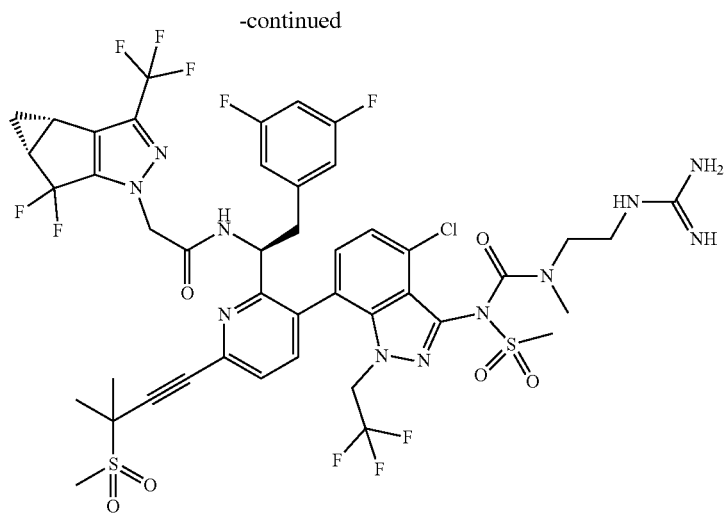

75

Synthesis of N—((S)-1-(3-(3-(N-((2-aminoethyl)(methyl)carbamoyl)methylsulfonamido)-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (75A): An atropisomeric mixture of the title compound was prepared according to the method presented for the synthesis of 58 of Example 58 utilizing N-Boc-N'-methylethylenediamine in the place of tert-butyl-L-serinate. MS (m/z) 1067.98 [M+H]⁺.

Synthesis of N—((S)-1-(3-(4-chloro-3-(N-((2-guanidinoethyl)(methyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (75): An atropisomeric mixture of the title compound was prepared according to the method presented for the synthesis of 8 of Example 8 utilizing 75A in the place of 7. ¹H NMR (400 MHz, Methanol-d₄) δ 9.17 (s), 7.91-7.84 (m), 7.81-7.74 (m), 7.44-7.35 (m), 6.81-6.73 (m), 6.21-6.14 (m), 5.02-4.93 (m), 4.81-4.72 (m), 4.04-3.93 (m), 3.55 (s), 3.44 (s), 3.36 (s), 3.25 (s), 3.28-3.20 (m), 3.04-2.94 (m), 2.92-2.82 (m), 2.76 (s), 2.68 (s), 2.52 (s), 1.84 (s), 1.52-1.41 (m), 1.07 (s) ppm. MS (m/z) 1130.39 [M+H]⁺.

Example 76

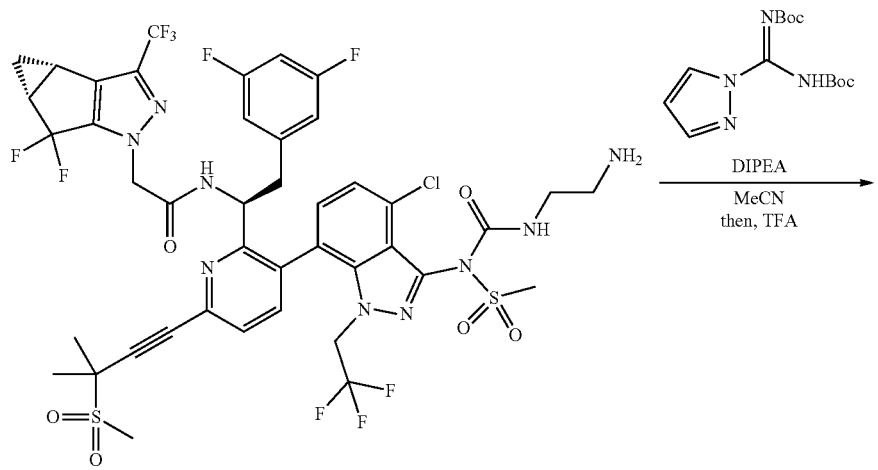

76A

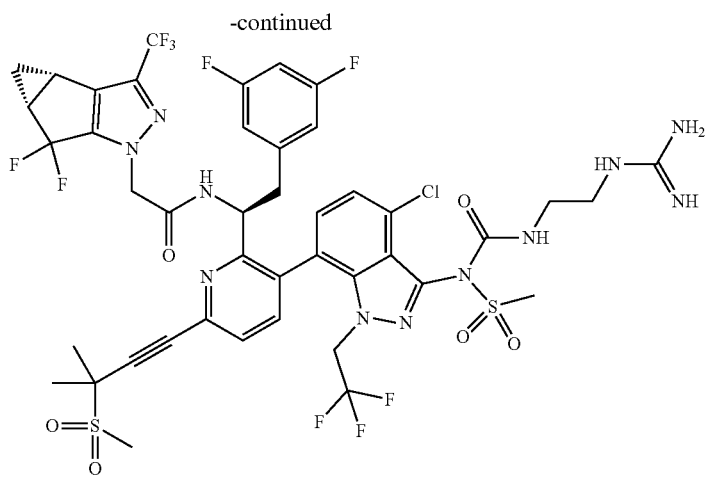

76

Synthesis of N—((S)-1-(3-(3-(N-((2-aminoethyl)carbamoyl)methylsulfonamido)-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (76A): An atropisomeric mixture of the title compound was prepared according to the method presented for the synthesis of 58 of Example 58 utilizing N-Boc-ethylenediamine in the place of tert-butyl-L-serinate. MS (m/z) 1054.41 [M+H]$^+$.

Synthesis Bis-boc-[N—((S)-1-(3-(4-chloro-3-(N-((2-guanidinoethyl)carbamoyl)methylsulfonamido)-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide] (76): An atropisomeric mixture of the title compound was prepared according to the method presented for the synthesis of 8 of Example 8 utilizing 76A in the place of 7. $^1$H NMR (400 MHz, DMSO-d$_6$) δ 9.25 (d), 7.97-7.68 (m), 7.44 (d), 7.29 (dt), 6.98 (dtt), 6.63-6.45 (m), 4.97-4.50 (m), 4.16 (s), 3.27 (s), 1.75 (d), 1.41 (q), 0.96 (d) ppm. $^{19}$F NMR (375 MHz, DMSO-d$_6$) δ −60.84 (d), −69.33 (d), −69.68, −74.60, −79.75, −80.32 (d), −103.15 (d), −103.82 (d), −110.73, −111.05 ppm. MS (m/z) 1096.95 [M+H]$^+$.

Example 77

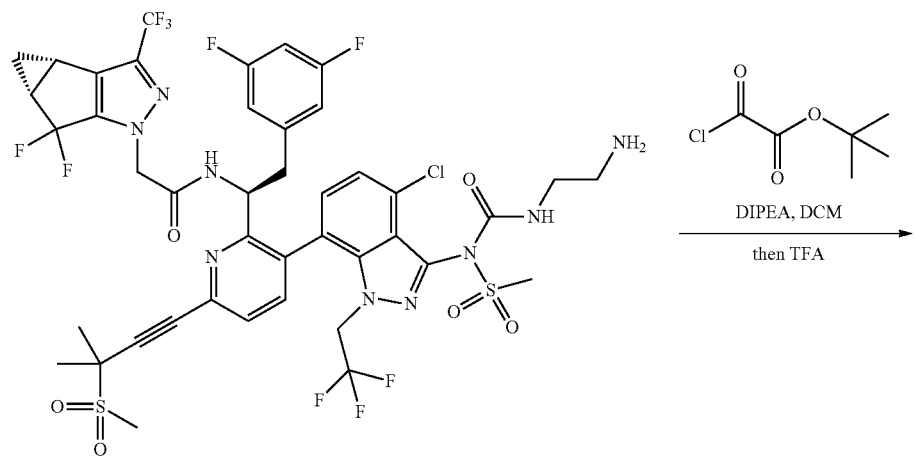

76A

283

-continued

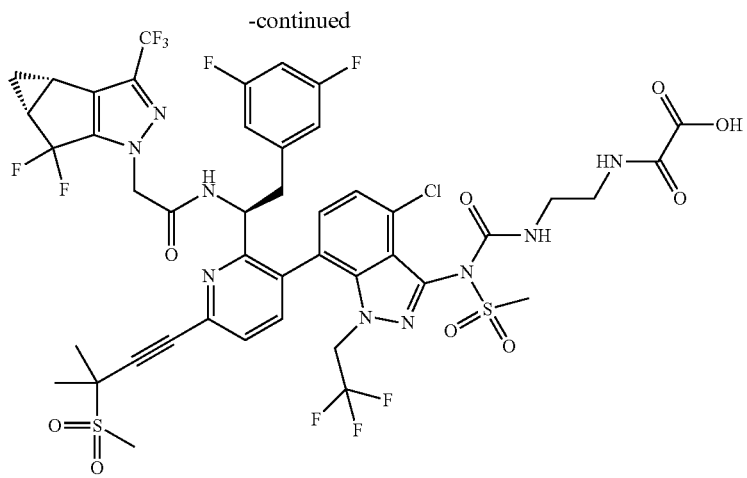

77

Synthesis of 2-((2-(3-(4-chloro-7-(2-((S)-1-(2-(((3bS, 4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)ureido)ethyl)amino)-2-oxoacetic acid (77): To a solution of 76A (0.029 mmol) in DCM (2 mL) was added DIPEA (0.085 mmol) followed by tert-butyl-2-chloro-2-oxoacetate (0.085 mmol) and the resulting mixture was stirred for 10 mins. Trifluoroacetic acid (6.530 mmol) was then added with a further 10 mins stirring at which time the reaction was diluted with 1:1 $H_2O$:MeCN (1 mL). The reaction contents were then transferred to a separatory funnel with DCM (15 mL) and washed once with 1M HCl (20 mL). The organic fraction was collected, dried over $Na_2SO_4$, concentrated under reduced pressure, and purified by reverse phase HPLC. Fractions containing the product were pooled and lyophilized to give the title compound 77 as a mixture of atropisomers. $^1$H NMR (400 MHz, DMSO-$d_6$) δ 9.22 (d), 7.82 (dd), 7.40 (d), 6.98 (d), 6.71-6.39 (m), 4.72 (dt), 4.02 (s), 3.55 (d), 3.00 (d), 1.75 (d), 1.40 (d), 0.97 (s) ppm. $^{19}$F NMR (375 MHz, DMSO-$d_6$) δ−60.86 (d, J=46.8 Hz), −69.38 (d), −69.78, −74.13, −79.70, −80.34, −102.89, −103.23, −103.57, −103.90, −110.79 (d) ppm. MS (m/z) 1126.21 [M+H]$^+$.

284

Example 78

78

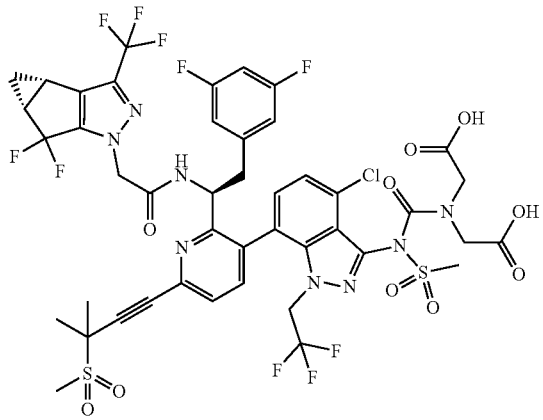

Synthesis of 2,2'-(((4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)

but-1-yn-1-yl)pyridin-3-yl)-1-(2,2,2-trifluoroethyl)-1H-indazol-3-yl)(methylsulfonyl)carbamoyl)azanediyl)diacetic acid (78): An atropisomeric mixture of the title compound was prepared according to the method presented for the synthesis of 58 of Example 58 utilizing di-tert-butyl 2,2'-azanediyldiacetatein the place of tert-butyl-L-serinate. $^1$H NMR (400 MHz, DMSO-d$_6$) δ 9.29-9.17 (m), 7.86-7.72 (m), 7.37 (s), 7.36-7.26 (m), 7.03 (tt, J=9.4, 2.2 Hz), 6.74 (s), 6.59-6.52 (m), 6.52-6.44 (m), 4.97-4.86 (m), 4.78-4.65 (m), 4.43 (s), 4.12-4.03 (m), 3.90 (s), 3.31-3.21 (m), 3.20-3.08 (m), 3.05-2.93 (m), 2.67-2.54 (m), 1.75 (s), 1.75 (s), 1.47-1.35 (m), 0.96 (s) ppm. $^{19}$F NMR (375 MHz, DMSO-d$_6$) δ −60.66–61.22 (m), −69.16–69.83 (m), −74.49, −79.71, −79.67–−80.22 (m), −80.39, −80.35–−80.90 (m), −103.05, −103.59–−103.88 (m), −110.68, −110.60–−111.15 (m) ppm. MS (m/z) 1127.68 [M+H]$^+$.

Example 79

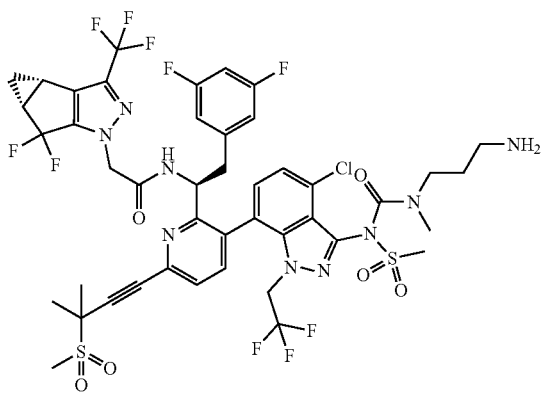

79

Synthesis of N—((S)-1-(3-(3-(N-((3-aminopropyl)(methyl)carbamoyl)methylsulfonamido)-4-chloro-1-(2,2,2-trifluoroethyl)-1H-indazol-7-yl)-6-(3-methyl-3-(methylsulfonyl)but-1-yn-1-yl)pyridin-2-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (79): An atropisomeric mixture of the title compound was prepared according to the method presented for the synthesis of 58 of Example 58 utilizing tert-butyl N-[3-(methylamino)propyl]carbamate in the place of tert-butyl-L-serinate. $^1$H NMR (400 MHz, DMSO-d$_6$) δ 1H NMR (400 MHz, DMSO-d$_6$) δ 9.25-9.18 (m), 7.98-7.87 (m), 7.85-7.78 (m), 7.70-7.62 (m), 7.51-7.44 (m), 7.06-6.96 (m), 7.00-6.90 (m), 6.34-6.26 (m), 6.11-6.06 (m), 5.49 (s), 5.03-4.94 (m), 4.89-4.76 (m), 4.78-4.69 (m), 4.58-4.47 (m), 4.29 (s), 4.03-3.88 (m), 3.34-3.23 (m), 2.99-2.81 (m), 2.77-2.67 (m), 2.66-2.52 (m), 2.57 (s), 2.49 (s), 1.75 (s), 1.74-1.61 (m), 1.46-1.36 (m), 1.05-0.97 (m) ppm. $^{19}$F NMR (375 MHz, DMSO-d$_6$) δ−60.84, −70.01–−70.29 (m), −74.72, −79.83–−80.10 (m), −80.51–−80.78 (m), −103.23, −103.91, −110.80 ppm. MS (m/z) 1082.10 [M+H]$^+$.

Example 80

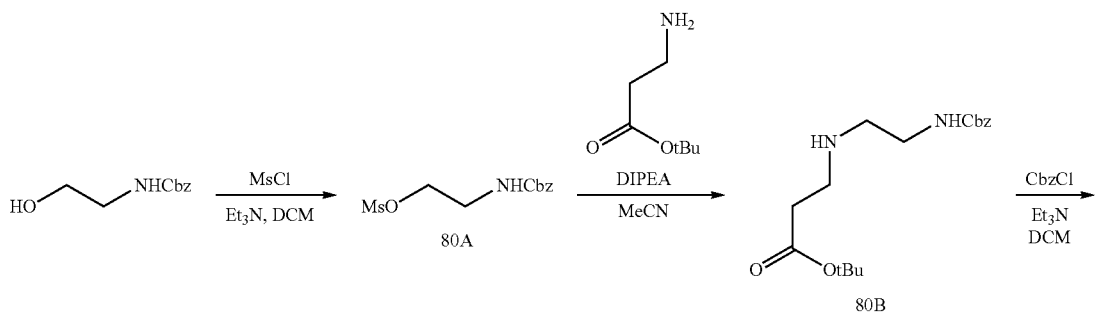

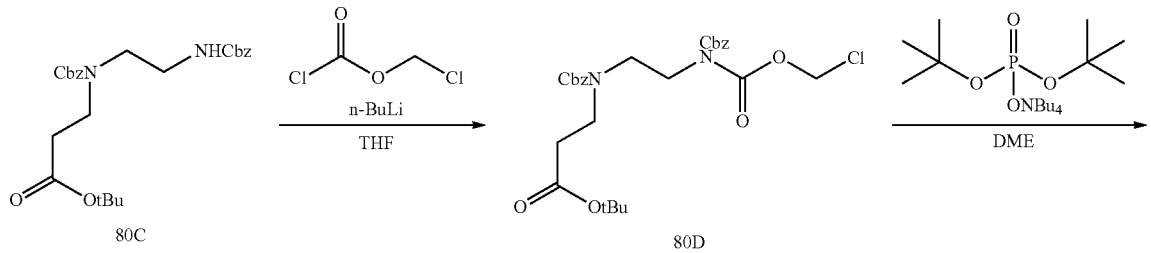

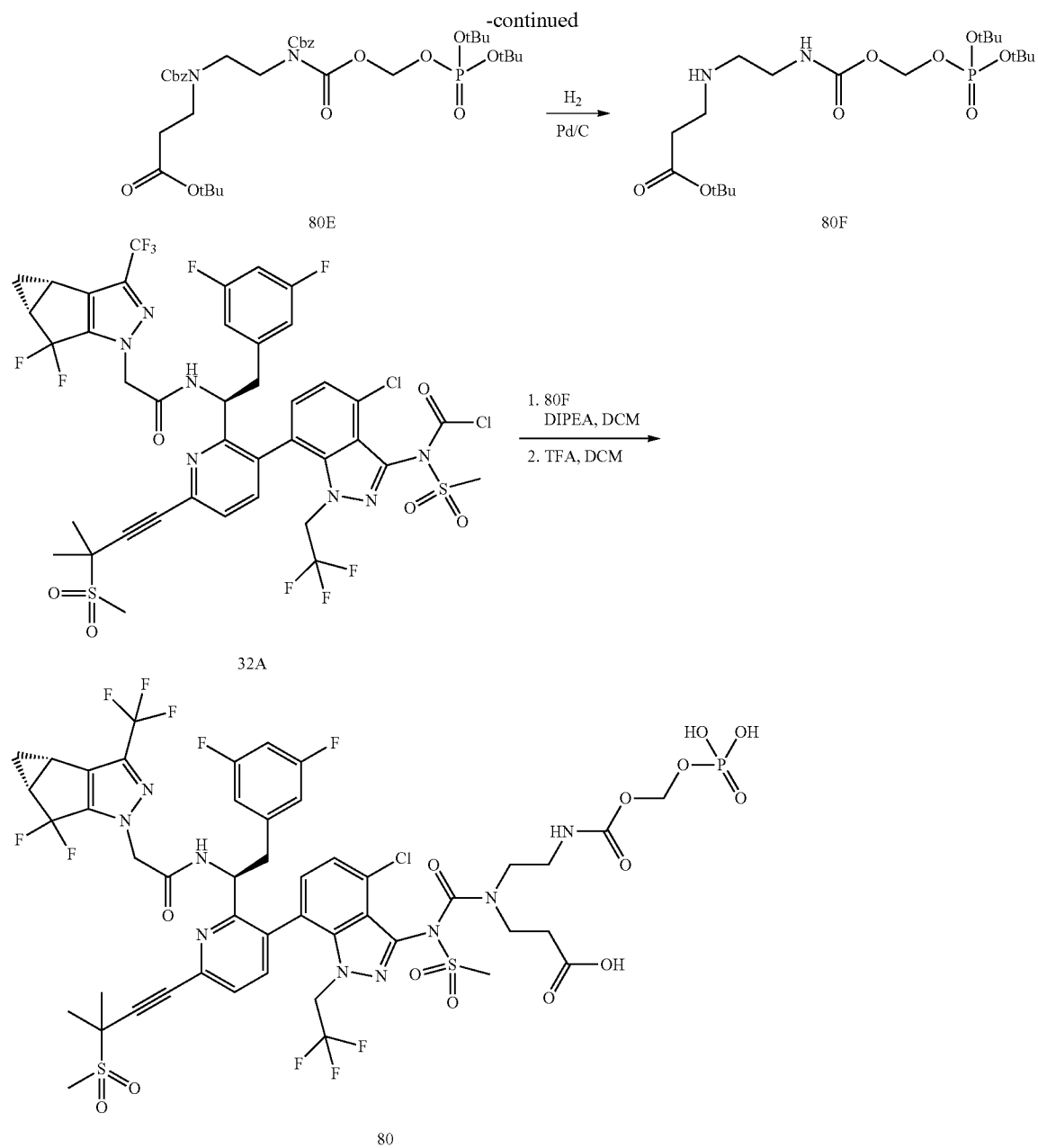

Synthesis of 2-(((Benzyloxy)carbonyl)amino)ethyl methanesulfonate (80A): To a solution of benzyl (2-hydroxyethyl)carbamate (51.2 mmol) and triethylamine (179 mmol) in DCM (400 mL) was added methanesulfonyl chloride (102 mmol) dropwise at 0° C. The reaction mixture was stirred for 18 hours, gradually warming up to RT. The organic layer was washed with 1N HCl (2×), sat. NaHCO$_{3(aq)}$, brine, dried over MgSO$_4$, filtered, concentrated and purified by silica gel chromatography to afford the title compound 80A. MS (m/z) 293.84 [M+Na]$^+$.

Synthesis of tert-butyl 3-((2-(((benzyloxy)carbonyl)amino)ethyl)amino)propanoate (80B): To a solution of 80A (50.2 mmol) in ACN (200 mL) was added tert-butyl 3-aminopropanoate hydrochloride (75.2 mmol) and DIPEA (125 mmol). The mixture was heated at 80° C. for 2 hours. The reaction was concentrated, diluted with water and extracted with EtOAc (3×). The combined organic layers were washed with brine, dried over MgSO$_4$, filtered and concentrated. The crude product was purified by silica gel chromatography to afford title compound 80B. MS (m/z) 322.89 [M+H]$^+$.

Synthesis of tert-butyl 3-(((benzyloxy)carbonyl)(2-(((benzyloxy)carbonyl)amino)ethyl)amino)propanoate (80C): To a solution of 80B (17.0 mmol) and triethylamine (42.6 mmol) in DCM (100 mL) at 0° C. was added benzyl chloroformate (32.3 mmol). The reaction was stirred at RT for 18 hours. The reaction was quenched with sat. NaHCO$_3$ $_{(aq)}$ and extracted with DCM (3×). The combined organic layers were washed with brine, dried over MgSO$_4$, filtered, concentrated and purified to afford title compound 80C. MS (m/z) 479.04 [M+Na]$^+$.

Synthesis of tert-butyl 3-(((benzyloxy)carbonyl)(2-(((benzyloxy)carbonyl)((chloromethoxy)carbonyl)amino)

ethyl)amino)propanoate (80D): A solution of 80C (10.1 mmol) in THF (50.0 mL) was cooled to −78° C. n-BuLi (1.6 M in hexanes, 15.2 mmol) was added dropwise and the reaction was stirred for 10 minutes, then chloromethyl chloroformate (15.2 mmol) was added dropwise. The reaction was stirred at RT for 30 minutes, quenched with sat. $NH_4Cl_{(aq)}$ and extracted with EtOAc (3×). The combined organic layers were washed with brine, dried over $MgSO_4$, filtered and concentrated to afford title compound 80D, which was used without purification. MS (m/z) 571.05 $[M+Na]^+$.

Synthesis of tert-butyl 3-(((benzyloxy)carbonyl)(2-(((benzyloxy)carbonyl)(((((di-tert-butoxyphosphoryl)oxy)methoxy)carbonyl)amino)ethyl)amino)propanoate (80E): To a solution of 80D (10.1 mmol) in DME (50.0 mL) was added tetra-n-butylammonium di-tert-butylphosphate (12.7 mmol). The mixture was heated at 80° C. for 6 hours, then concentrated and diluted with EtOAc. The organic layer was washed with water (2×), brine, dried over $MgSO_4$, filtered and concentrated. The crude product was purified by silica gel chromatography to afford title compound 80E. MS (m/z) 744.98 $[M+Na]^+$.

Synthesis of tert-butyl 3-((2-(((((di-tert-butoxyphosphoryl)oxy)methoxy)carbonyl)amino)ethyl)amino)propanoate (80F): A solution of 80E (4.15 mmol) in EtOH/AcOH (1:1, 24.0 mL) was purged with nitrogen/vacuum (3×). Palladium on carbon (10%, 0.830 mmol) was added and the reaction was purged with nitrogen/vacuum (3×). The flask was fitted with a hydrogen balloon, the reaction was purged with hydrogen/vacuum (3×) and was allowed to stir at RT under 1 atm of hydrogen for 3 hours. The reaction was purged with nitrogen, filtered over celite and concentrated. Toluene was added, the reaction was concentrated to afford title compound 80F, which was used without purification. MS (m/z) 454.97 $[M+H]^+$.

Synthesis of 3-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-3-(methylsulfonyl)-1-(2-(((((phosphonooxy)methoxy)carbonyl)amino)ethyl)ureido)propanoic acid (80): An atropisomeric mixture of the title compound was prepared according to the method presented for the synthesis of 58 of Example 58 utilizing 80F in the place of tert-butyl-L-serinate. $^1H$ NMR (400 MHz, DMSO-$d_6$) δ 11.13 (bs), 9.21 (d), 9.01 (d), 7.91-7.68 (m), 7.43 (bs), 7.37-7.23 (m), 7.03 (tt), 6.98-6.90 (m), 6.70-6.48 (m), 6.43 (d), 5.36 (d), 4.97 (d), 4.85-4.55 (m), 4.00-3.85 (m), 3.64-3.18 (m), 3.18-2.99 (m), 2.99-2.71 (m), 2.69-2.47 (m), 1.74 (s), 1.45-1.35 (m), 1.05-0.93 (m) ppm. $^{19}F$ NMR (376 MHz, DMSO-$d_6$) δ −60.79, −60.97, −69.32, −69.77, −79.75 (d), −80.18 (bs), −80.42 (d), −80.86 (bs), −102.95 (d), −103.09 (d), −103.62 (d), −103.76 (d), −110.62 (t), −110.84 (bs) ppm. $^{31}P$ NMR (162 MHz, DMSO-$d_6$) δ−2.85 (t) ppm. MS (m/z) 1279.96 $[M+H]^+$.

Example 81

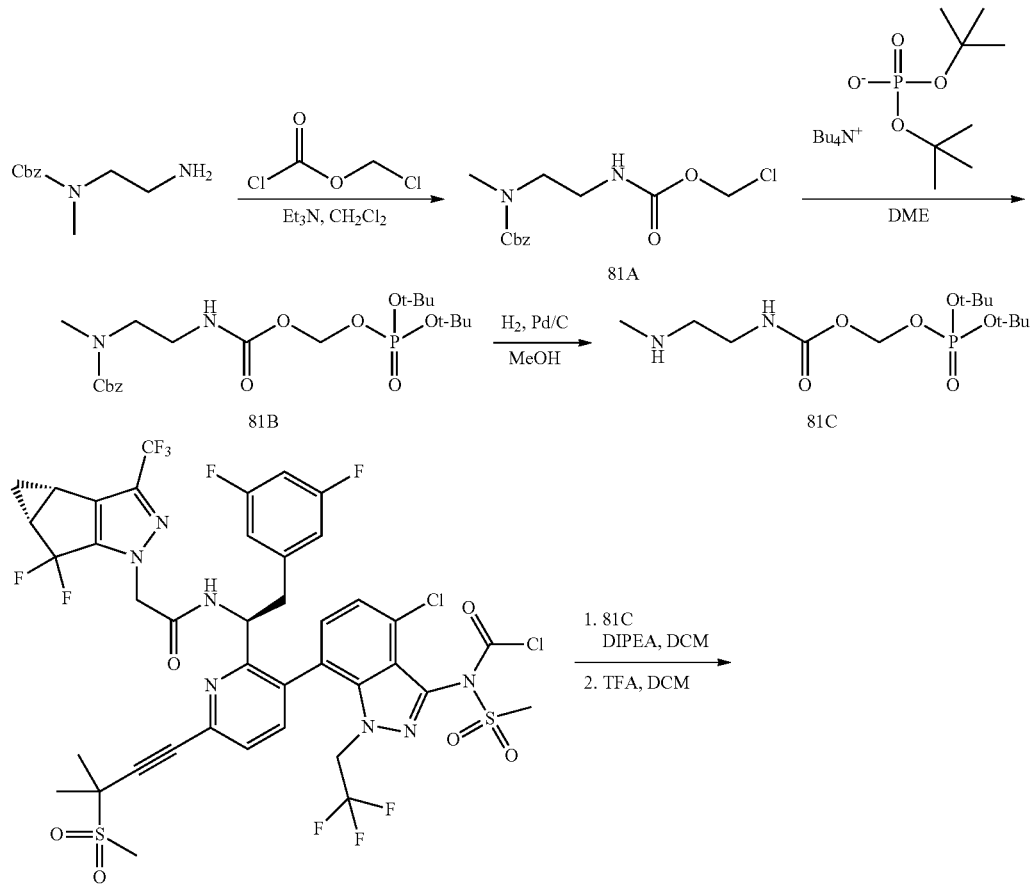

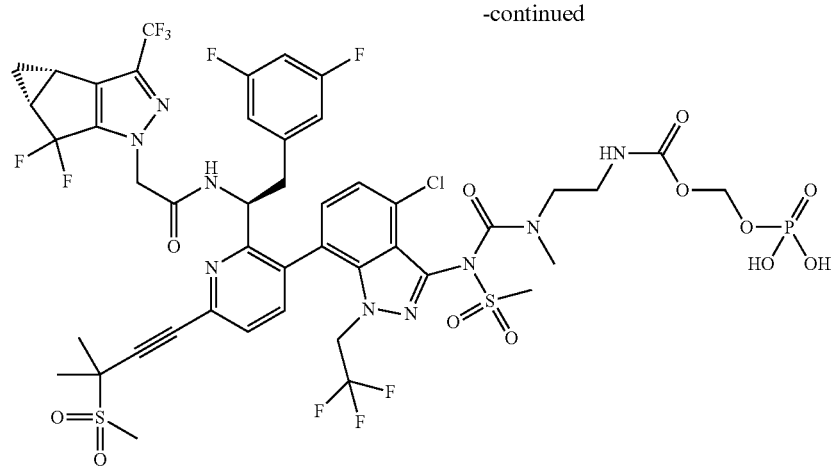

81

Synthesis of benzyl (2-(((chloromethoxy)carbonyl)amino)ethyl)(methyl)carbamate (81A): To a stirred solution of benzyl (2-aminoethyl)(methyl)carbamate (7.4 mmol) in CH$_2$Cl$_2$ (47 mL) at 0° C. was added triethylamine (3.6 mL, 25.7 mmol). Chloromethyl chloroformate (7.4 mmol) was then added and the reaction mixture was stirred at 0° C. and monitored by TLC and LCMS. After completion, the reaction mixture was washed with sat. aq. solutions of NH$_4$Cl and brine. The combined organic layers were dried over anhydrous Na$_2$SO$_4$, filtered, and concentrated. The crude mixture was purified by column chromatography (0% to 25% EtOAc in hexanes) to afford title compound 81A. MS (m/z) 301.1 [M+H]$^+$.

Synthesis of benzyl (2-(((((di-tert butoxyphosphoryl)oxy)methoxy)carbonyl)amino)ethyl) (methyl)carbamate (81B): To a solution of 81A (1.60 mmol) in dimethoxyethane (25 mL) was added di-t-butyl phosphate tetrabutylammonium salt (2.40 mmol) and the mixture was heated to 80° C. for 1 h. The mixture was cooled to room temperature and concentrated. The crude material was dissolved in EtOAc and washed with water (3×), brine, dried over Na$_2$SO$_4$, filtered, and concentrated. The crude mixture was then purified by column chromatography (20% to 100% EtOAc in hexanes) to afford title compound 81B. MS (m/z) 475.1 [M+H]$^+$.

Synthesis of ((di-tert-butoxyphosphoryl)oxy)methyl (2-(methylamino)ethyl)carbamate (81C): To a solution of 81B (0.25 mmol) in MeOH (3 mL) was added palladium on carbon (10% wt) and the mixture was stirred for 30 min under hydrogen gas (15 psi). The crude material was isolated after filtration over a pad of Celite. The residue was purified by column chromatography (0% to 10% MeOH in CH$_2$Cl$_2$) to afford title compound 81C. $^1$H NMR (400 MHz, CDCl$_3$) δ 5.58 (m, 2H), 3.31 (m, 2H), 2.76 (m, 2H), 2.43 (s, 3H), 1.48 (s, 18H) ppm.

Synthesis of ((di-tert-butoxyphosphoryl)oxy)methyl (2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)ethyl)carbamate (81): An atropisomeric mixture of the title compound was prepared according to the method presented for the synthesis of 58 of Example 58 utilizing 81C in the place of tert-butyl-L-serinate. $^1$H NMR (400 MHz, DMSO-d$_6$) δ 9.22-9.15 (m), 7.94-7.87 (m), 7.85-7.78 (m), 7.46-7.39 (m), 7.06-6.96 (m), 6.82 (s), 6.34-6.27 (m), 5.43-5.32 (m), 5.05-4.95 (m), 4.88-4.77 (m), 4.73-4.64 (m), 4.61-4.50 (m), 3.99-3.88 (m), 3.32-3.25 (m), 3.02 (s), 2.95 (s), 2.92-2.82 (m), 1.75 (s), 1.45-1.39 (m), 1.24 (s), 0.99 (s) ppm. $^{19}$F NMR (375 MHz, DMSO-d$_6$) δ −60.94, −70.19, −75.06, −110.75 ppm. MS (m/z): 1223.14 [M+H]$^+$.

Example 82

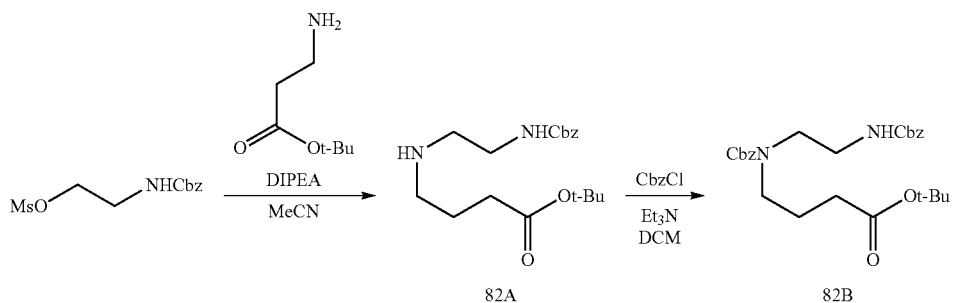

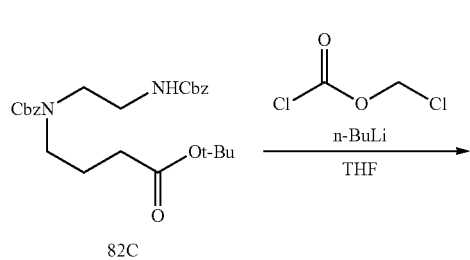
82C
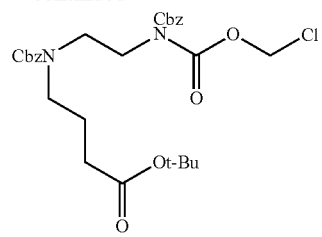
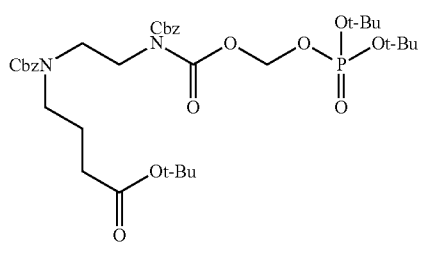
82D
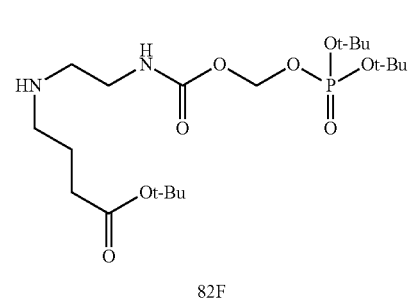
82E
82F
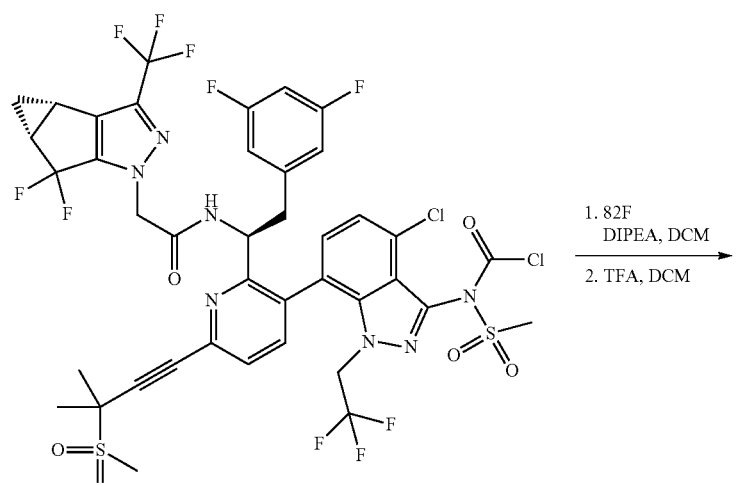
32A
1. 82F
   DIPEA, DCM
2. TFA, DCM
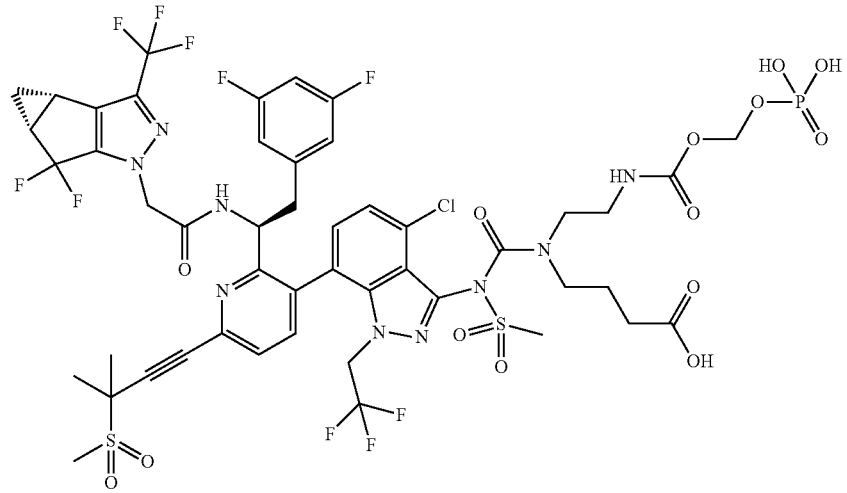
82
Synthesis of tert-butyl 4-((2-(((benzyloxy)carbonyl) amino)ethyl)amino)butanoate (82A): A mixture of 2-(((benzyloxy)carbonyl)amino)ethyl methanesulfonate (18.0 mmol), tert-butyl 4-aminobutanoate (19.9 mmol) and $K_2CO_3$ (36.1 mmol) in 20 mL of DMF was heated at 80° C. for 8 hours. The reaction was poured into water (200 mL), extracted with EtOAc (3×), washed with 5% LiCl$_{(aq)}$ (2×), dried over MgSO$_4$, filtered and concentrated. The crude material was purified by silica gel chromatography to yield the title compound 82A. MS (m/z): 336.94 [M+H]$^+$.

Synthesis of tert-butyl 4-(((benzyloxy)carbonyl)(2-(((benzyloxy)carbonyl)amino)ethyl)amino)butanoate (82B): The title compound was prepared according to the method presented for the synthesis of 80C of Example 80 utilizing 82A in the place of 80B. MS (m/z) 493.03 [M+Na]$^+$.

Synthesis of tert-butyl 4-(((benzyloxy)carbonyl)(2-(((benzyloxy)carbonyl)((chloromethoxy)carbonyl)amino)ethyl)amino)butanoate (82C): The title compound was prepared according to the method presented for the synthesis of 80D of Example 80 utilizing 82B in the place of 80C. MS (m/z) 585.11 [M+Na]$^+$.

Synthesis of tert-butyl 4-(((benzyloxy)carbonyl)(2-(((benzyloxy)carbonyl)(((((di-tert-butoxyphosphoryl)oxy)methoxy)carbonyl)amino)ethyl)amino)butanoate (82D): The title compound was prepared according to the method presented for the synthesis of 80E of Example 80 utilizing 82C in the place of 80D. MS (m/z) 758.95 [M+Na]$^+$.

Synthesis of tert-butyl 4-((2-(((((di-tert-butoxyphosphoryl)oxy)methoxy)carbonyl)amino)ethyl)amino)butanoate (82E): The title compound was prepared according to the method presented for the synthesis of 80F of Example 80 utilizing 82D in the place of 80E. MS (m/z): 468.99 [M+H]$^+$.

Synthesis of tert-butyl 4-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-(2-(((((di-tert-butoxyphosphoryl)oxy)methoxy)carbonyl)amino)ethyl)-3-(methylsulfonyl)ureido)butanoate (82): An atropisomeric mixture of the title compound was prepared according to the method presented for the synthesis of 58 of Example 58 utilizing 82E in the place of tert-butyl-L-serinate. $^1$H NMR (400 MHz, DMSO-d$_6$) δ 10.95 (bs), 9.22 (d), 9.03-8.94 (m), 7.98-7.86 (m), 7.85-7.78 (m), 7.76 (d), 7.50-7.40 (m), 7.38 (d), 7.29 (d), 7.08-6.98 (m), 6.98-6.90 (m), 6.64 (d), 6.54-6.48 (m), 6.44 (d), 5.51 (d), 5.36 (d), 4.95 (d), 4.77 (d), 4.73-4.53 (m), 3.98-3.82 (m), 3.41-2.75 (m), 2.65-2.42 (m), 1.74 (s), 1.57-1.22 (m), 0.97 (bs), 0.90-0.80 (m). $^{19}$F NMR (377 MHz, DMSO-d$_6$) δ−60.79, −60.97, −69.33, −69.74 (t), −79.81 (bs), −80.18 (bs), −80.49 (bs), −80.85 (bs), −102.96 (d), −103.10 (bs), −103.63 (d), −103.78 (bs), −110.59 (t), −110.81 (bs). $^{31}$P NMR (162 MHz, DMSO-d$_6$) δ−2.85 (t). MS (m/z) 1293.94 [M+H]$^+$.

Example 83

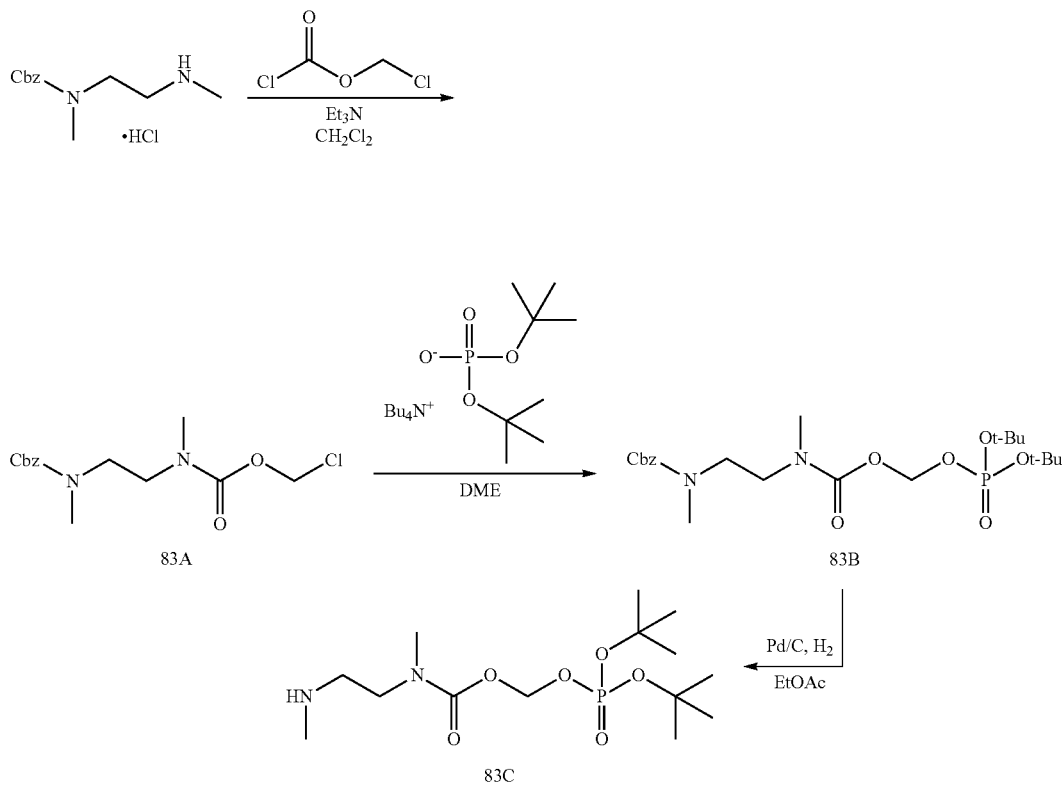

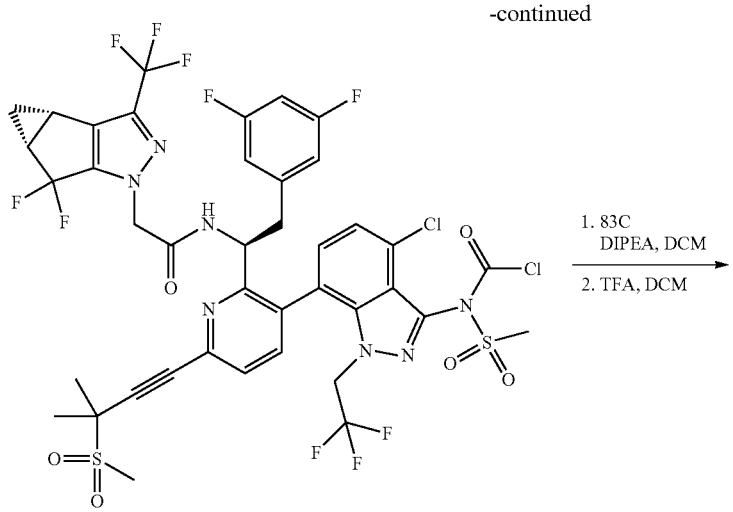

32A

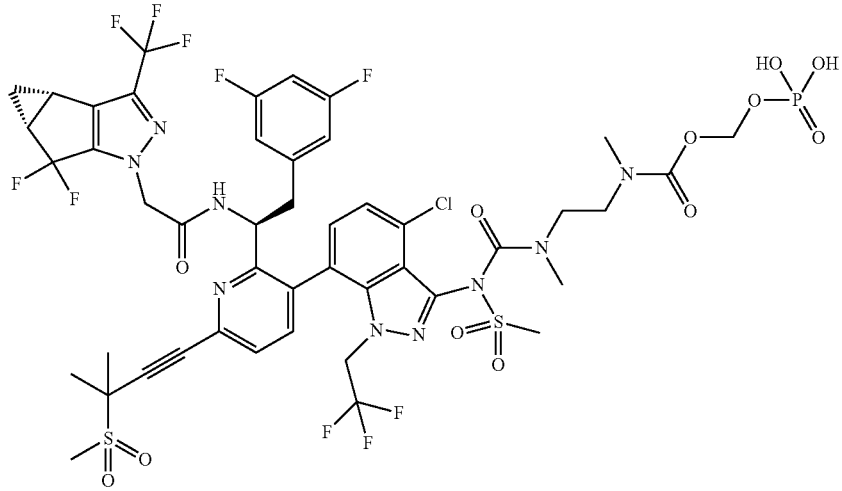

83

Synthesis of benzyl (chloromethyl) ethane-1,2-diylbis(methylcarbamate) (83A): To a stirred solution of the benzyl methyl(2-(methylamino)ethyl)carbamate hydrochloride (4.5 mmol) in $CH_2Cl_2$ (45 mL) at 0° C. was added triethylamine (11 mmol). Chloromethyl chloroformate (4.9 mmol) was then added and the reaction mixture was stirred at 0° C. and monitored by TLC and LCMS. After completion, the reaction mixture was washed with sat. aq. solutions of $NH_4Cl$ and brine. The combined organic layers were dried over anhydrous $Na_2SO_4$, filtered, and concentrated to afford title compound 83A, which was directly used in the subsequent reaction without purification. MS (m/z) 337.0 [M+Na]$^+$.

Synthesis of benzyl ((((di-tert-butoxyphosphoryl)oxy)methyl) ethane-1,2-diylbis(methylcarbamate) (83B): 83A (4.1 mmol) was dissolved in dimethoxyethane (20 mL) then di-t-butyl phosphate tetrabutylammonium salt (8.2 mmol) was added and the mixture was heated to 80° C. for 1 h. The mixture was cooled to room temperature and concentrated. The crude material was dissolved in EtOAc and washed with water (3×), brine, dried over $Na_2SO_4$, filtered, and concentrated. The crude mixture was then purified by column chromatography (55% to 100% EtOAc in hexanes) to afford title compound 83B. MS (m/z) 511.2 [M+Na]$^+$.

Synthesis of ((di-tert-butoxyphosphoryl)oxy)methyl methyl(2-(methylamino)ethyl)carbamate (83C): 83B (1.0 mmol) was dissolved in EtOAc (5 mL) and palladium on carbon (0.14 mmol) was added. After stirring for 0.5 h under hydrogen gas (1 atm), the reaction was filtered over a pad of Celite and concentrated under reduced pressure to afford the title compound 83C, which was used directly used in the subsequent reaction without purification. MS (m/z) 355.1 [M+Na]$^+$.

Synthesis of (phosphonooxy)methyl (2-(3-(4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)ethyl)(methyl)carbamate 83: An atropisomeric mixture of the title compound was prepared according to the method presented for the synthesis of 58 of Example 58 utilizing 83C in the place of tert-butyl-L-serinate. $^1$H NMR (400 MHz, DMSO) δ 9.21 (t), 8.05-7.70 (m), 7.54-7.21 (m), 7.02 (t), 6.87 (s), 6.71-6.21 (m), 5.49-5.34 (m), 5.00 (d), 4.89-4.63 (m), 4.55 (q), 4.09-3.84 (m), 3.52-3.21 (m), 3.20-3.04 (m), 3.02-2.86 (m), 2.82-2.65 (m), 1.75 (s), 1.53-1.34 (m), 0.99 (s). $^{19}$F NMR (376 MHz, DMSO) δ −59.58--−62.17 (m), −68.49--−72.06 (m), −80.45 (d), −103.43 (d), −110.76. MS (m/z): 1237.462 [M+H]$^+$.

Example 84

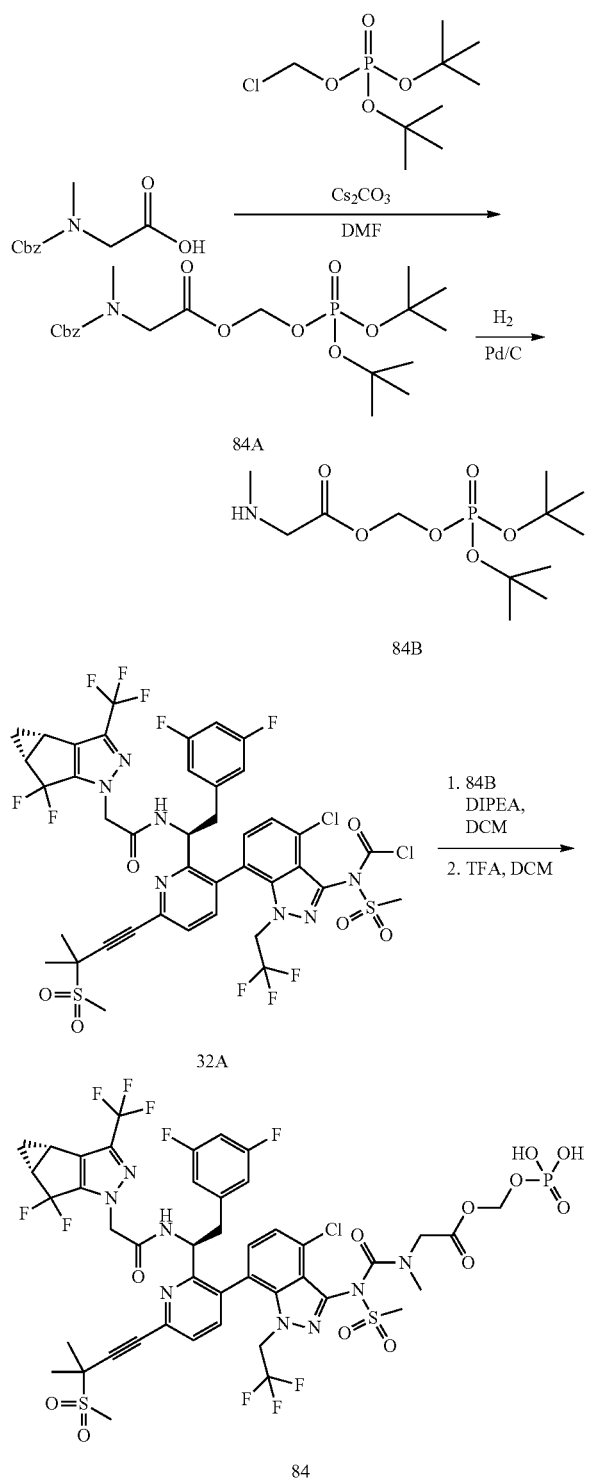

Synthesis of ((di-tert-butoxyphosphoryl)oxy)methyl N-((benzyloxy)carbonyl)-N-methylglycinate (84A): To a solution of N-((benzyloxy)carbonyl)-N-methylglycine (4.48 mmol) in 5 mL of dry DMF were added sequentially cesium carbonate (11.2 mmol, 2.5 equiv) and di-tert-butyl chloromethyl phosphate (4.93 mmol, 1.1 equiv). The reaction vessel was sealed and was allowed to stir for 20 h at rt. Upon completion of this time, the reaction contents were transferred to a separatory funnel using 50 mL of dichloromethane and 10 mL of H$_2$O. The organic layer was washed with 1M aqueous HCl (3×50 mL), dried over Na$_2$SO$_4$, concentrated under reduced pressure, and purified by silica gel chromatography. Fractions containing the product were pooled and concentrated under reduced pressure to yield title compound 84A. $^1$H NMR (400 MHz, CDCl$_3$) δ 7.26 (dt, J=18.6, 5.6 Hz, 5H), 5.55 (dd, J=21.5, 13.0 Hz, 2H), 5.07 (d, J=12.0 Hz, 2H), 4.09-3.98 (m, 3H), 2.95 (s, 3H), 1.96 (s, 1H), 1.42 (d, J=9.4 Hz, 18H), 1.18 (t, J=7.2 Hz, 1H) ppm.

Synthesis of ((di-tert-butoxyphosphoryl)oxy)methyl methylglycinate (84B): A solution of 84A (0.673 mmol) in 2 mL of EtOAc was sparged for 5 min with Ar. To the solution was then carefully added Pd/C (10% Pd on activated carbon, 0.067 mmol, 0.1 equiv). The reaction was then sparged with H$_2$ for 5 min, then stirred under 1 atm H$_2$ for 2 h until full conversion was seen by TLC. Upon completion, the reaction was diluted with 10 mL of EtOAc and sparged with Ar for 5 min before careful filtration over Celite®. The filter cake was washed carefully with 3×10 mL of EtOAc, and the organic filtrate concentrated under reduced pressure to yield title compound 84B, which was used without further purification.

Synthesis of (phosphonooxy)methyl N-((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)-N-methylglycinate (84): An atropisomeric mixture of the title compound was prepared according to the method presented for the synthesis of 58 of Example 58 utilizing 84B in the place of tert-butyl-L-serinate. $^1$H NMR (400 MHz, DMSO-d$_6$) δ 9.17 (d), 7.98-7.87 (m), 7.81 (d), 7.46 (d), 7.06-6.94 (m), 6.88 (s), 6.55 (s), 6.31 (d), 5.47 (s), 4.98 (dd), 4.83 (s), 4.70 (dd), 4.53 (s), 4.09-3.89 (m), 2.98-2.82 (m), 2.74 (s), 2.67-2.52 (m), 1.75 (s), 1.48-1.37 (m), 1.27-1.18 (m), 1.01 (s) ppm. $^{19}$F NMR (375 MHz, DMSO-d$_6$) δ −60.65--−61.08 (m), −69.67 (t), −70.14, −74.71, −79.89 (d), −80.57 (d), −103.19, −103.86, −110.84 ppm. MS (m/z) 1193.51 [M+H]$^+$.

Example 85

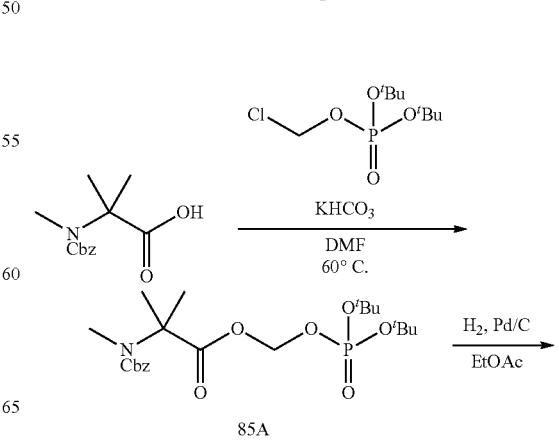

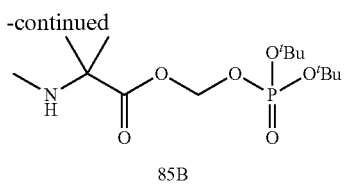

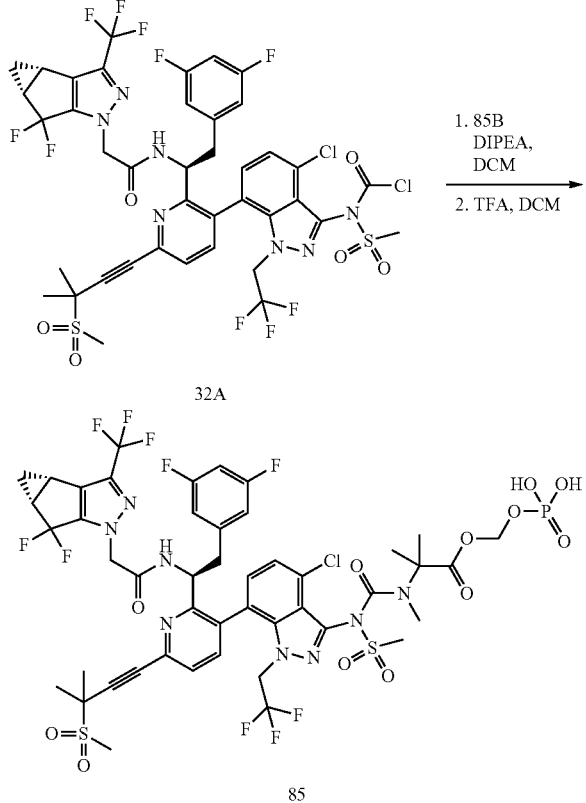

Synthesis of di-tert-butoxyphosphoryloxymethyl 2-[benzyloxycarbonyl(methyl)amino]-2-methyl-propanoate (85A): To a solution of 2-[benzyloxycarbonyl(methyl)amino]-2-methyl-propanoic acid (4.0 mmol) and potassium bicarbonate (4 mmol) in DMF (4.8 mL) was added di-tert-butyl chloromethyl phosphate (4.4 mmol). The reaction was sealed, heated to 60° C., and stirred for 1 hour. Upon completion, the reaction was diluted with hexanes (50 mL). The solution was transferred to a separatory funnel and washed 2× with 1M KOH (25 mL) and 1× with 5% LiCl (25 mL). The organic fraction was collected, dried over $Na_2SO_4$, concentrated, and purified with silica chromatography. Fractions containing the product were pooled and concentrated to yield title compound 85A. MS (m/z): 496.20 $[M+Na]^+$.

Synthesis of di-tert-butoxyphosphoryloxymethyl 2-methyl-2-(methylamino)propanoate (85B): To a solution of 85A (1.0 mmol) in EtOAc was added palladium on carbon (0.25 mmol). The reaction was sealed, purged with argon for 15 minutes, purged with $H_2$, and stirred under $H_2$ for 2 hours. Upon completion, the reaction was purged with argon for 15 minutes, diluted with Celite 545 (250 mg) and EtOAc (5 mL), and filtered. The mother liquor was concentrated to yield title compound 85B. MS (m/z): 340.20 $[M+H]^+$.

Synthesis of (phosphonooxy)methyl 2-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)-2-methylpropanoate 85: An atropisomeric mixture of the title compound was prepared according to the method presented for the synthesis of 58 of Example 58 utilizing 85B in the place of tert-butyl-L-serinate. $^1$H NMR (400 MHz, MeOD) δ 8.90 (d), 7.98 (s), 7.86 (d), 7.74 (d), 7.38 (d), 7.27 (s), 6.76 (tt), 6.38 (s), 6.17 (d), 5.83-5.45 (m), 4.81-4.63 (m), 3.97 (q), 3.24 (s), 3.20-3.10 (m), 3.00 (s), 2.93-2.80 (m), 2.78 (s), 2.63 (s), 2.53-2.48 (m), 1.82 (s), 1.49-1.39 (m), 1.28 (s), 1.15 (s), 1.05 (s). $^{19}$F NMR (376 MHz, MeOD) δ −63.56, −72.01−−73.02 (m), −77.91, −81.96−−83.40 (m), −105.53 (d), −112.32 (t). MS (m/z) 1221.20 $[M+H]^+$.

Example 86

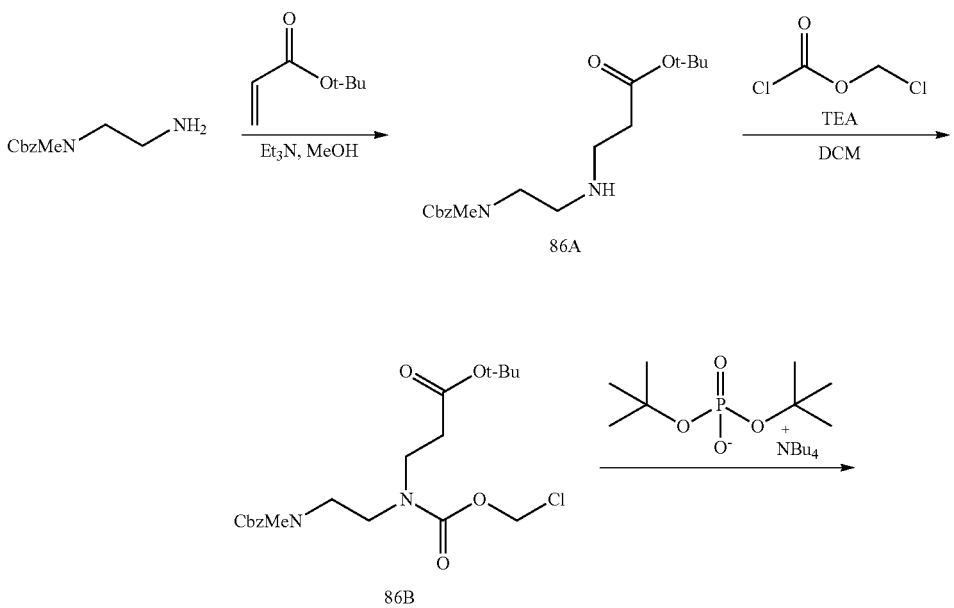

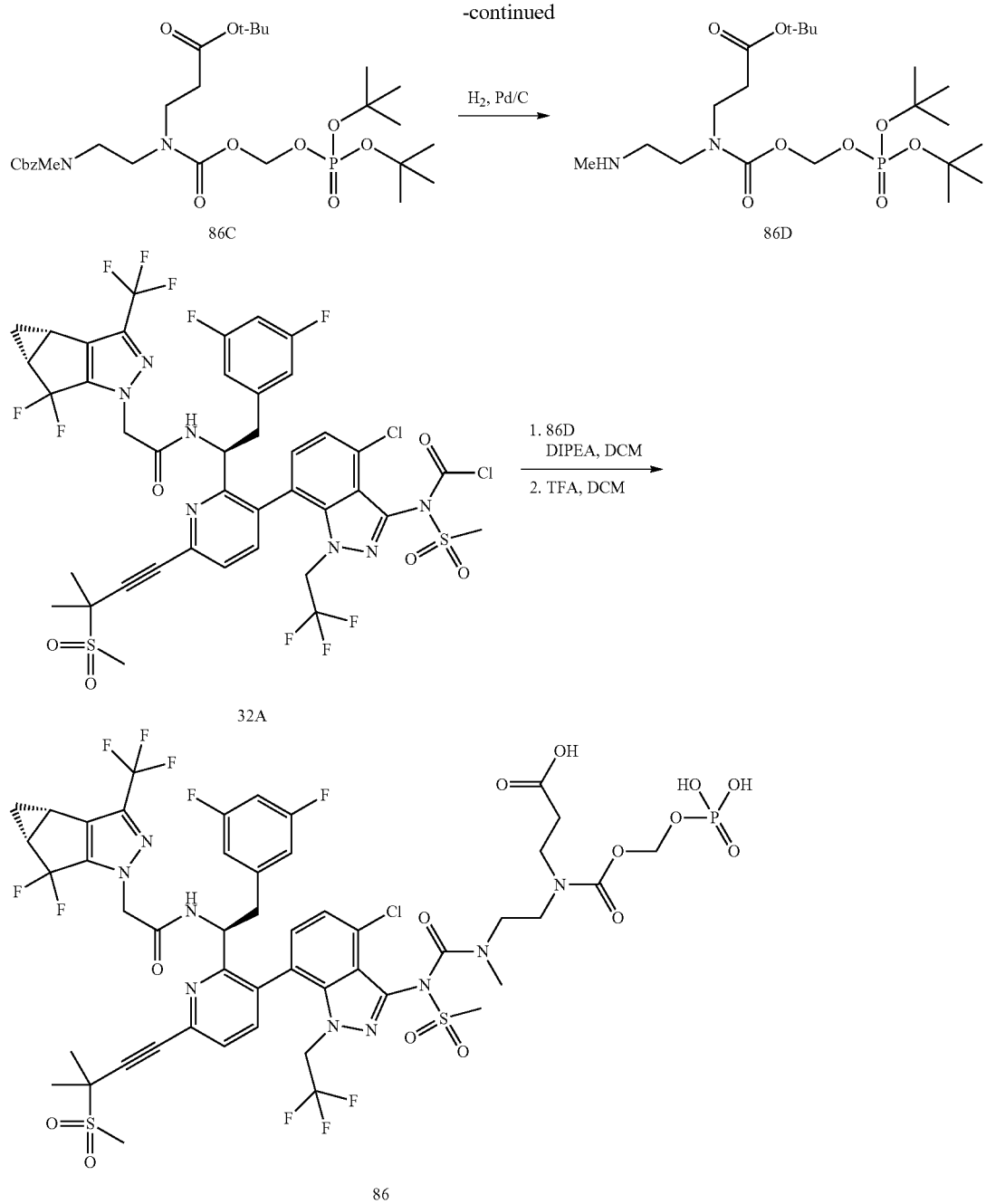

Synthesis of tert-butyl 3-((2-(((benzyloxy)carbonyl)(methyl)amino)ethyl)amino)propanoate (86A): To a solution of benzyl (2-aminoethyl)(methyl)carbamate (5.20 mmol) in MeOH (30 mL) was added triethylamine (5.20 mmol, 1 equiv) followed by tert-butyl acrylate (4.16 mmol, 0.8 equiv) dropwise. Upon completion of the reaction, the mixture was partitioned between ethyl acetate and water and the aqueous phase extracted 3× with EtOAc. The resulting organic fraction was dried over MgSO$_4$, filtered and concentrated under reduced pressure. The residue was purified by silica gel chromatography eluting with ethyl acetate/hexane to afford title compound 86A. MS (m/z) 336.44 [M+Na]$^+$.

Synthesis of tert-butyl 3-((2-(((benzyloxy)carbonyl)(methyl)amino)ethyl)((chloromethoxy)carbonyl)amino)propanoate (86B): The title compound was prepared according to the method presented for the synthesis of 83A of Example 83 utilizing 86A in the place of benzyl methyl(2-(methylamino)ethyl)carbamate hydrochloride. MS (m/z) 451.20 [M+Na]$^+$.

Synthesis of tert-butyl 3-((2-(((benzyloxy)carbonyl)(methyl)amino)ethyl)(((((di-tert-butoxyphosphoryl)oxy)methoxy)carbonyl)amino)propanoate (86C): The title compound was prepared according to the method presented for the synthesis of 83B of Example 83 utilizing 86B in the place of 83A. MS (m/z) 625.30 [M+Na]$^+$.

Synthesis of tert-butyl 3-((((((di-tert-butoxyphosphoryl)oxy)methoxy)carbonyl)(2-(methylamino)ethyl)amino)propanoate (86D): The title compound was prepared according to the method presented for the synthesis of 83C of Example 83 utilizing 86C in the place of 83B. MS (m/z) 469.31 [M+H]+.

Synthesis of 3-((2-(3-(4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)ethyl)(((phosphonooxy)methoxy)carbonyl)amino)propanoic acid (86): An atropisomeric mixture of the title compound was prepared according to the method presented for the synthesis of 58 of Example 58 utilizing 86D in the place of tert-butyl-L-serinate. $^1$H NMR (400 MHz, DMSO-$d_6$) δ 9.20-9.13 (m), 7.99-7.86 (m), 7.85-7.77 (m), 7.45-7.33 (m), 7.07-6.93 (m), 6.80 (s), 6.56-6.49 (m), 6.35-6.28 (m), 5.92 (s), 5.49-5.37 (m), 5.04-4.95 (m), 4.92-4.79 (m), 4.69 (m), 4.60-4.50 (m), 4.25 (s), 4.02-3.87 (m), 3.39-3.32 (m), 3.28 (s), 3.02-2.92 (m), 2.93-2.83 (m), 1.75 (s), 1.46-1.37 (m), 1.00 (s) ppm. 19F NMR (375 MHz, DMSO-$d_6$) δ−60.79, −60.95, −69.52--69.83 (m), −70.02--70.34 (m), −75.23--75.63 (m), −79.84--80.24 (m), −80.52--80.93 (m), −110.55--111.07 (m) ppm. MS (m/z) 1294.30 [M+H]+.

Example 87

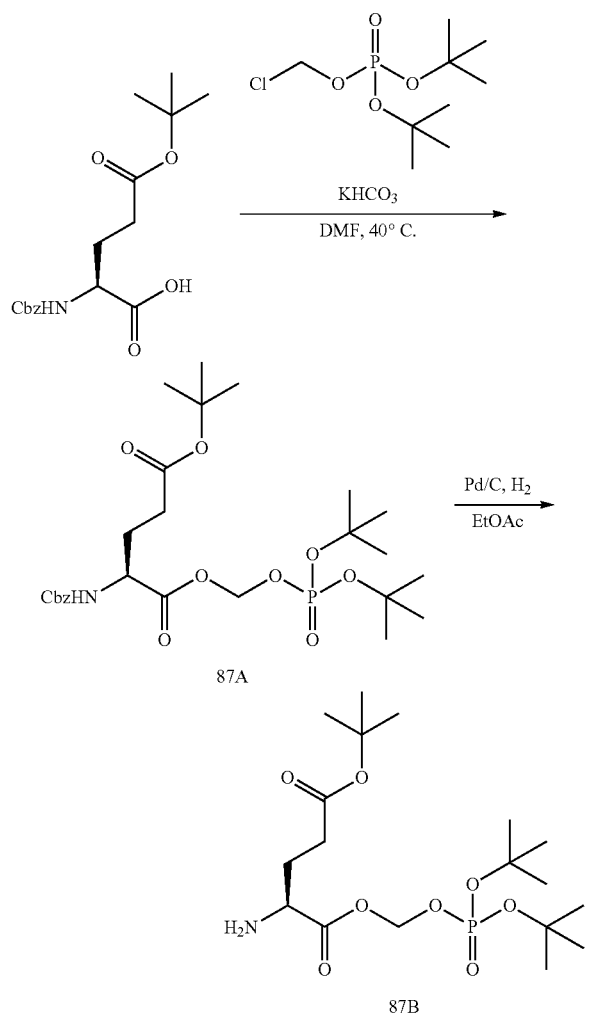

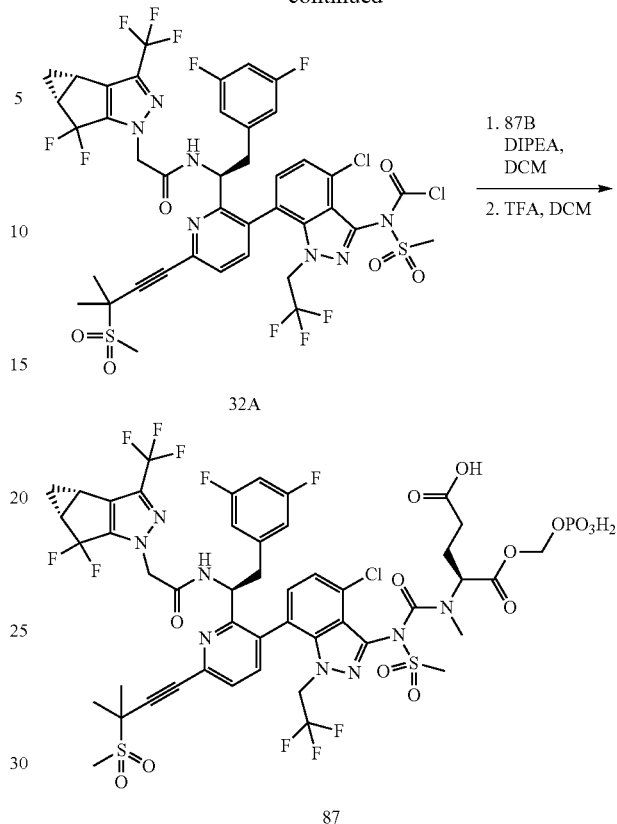

Synthesis of 5-(tert-butyl) 1-(((di-tert-butoxyphosphoryl)oxy)methyl) ((benzyloxy)carbonyl)-L-glutamate (87A): The title compound was prepared according to the method presented for the synthesis of 84A of Example 84 utilizing (S)-2-(((benzyloxy)carbonyl)amino)-5-(tert-butoxy)-5-oxopentanoic acid in the place of N-((benzyloxy)carbonyl)-N-methylglycine. MS (m/z) 596.3 [M+Na]+.

Synthesis of 5-(tert-butyl) 1-(((di-tert-butoxyphosphoryl)oxy)methyl) L-glutamate (87B): The title compound was prepared according to the method presented for the synthesis of 84B of Example 84 utilizing 87A in the place of 84A. MS (m/z) 440.26 [M+Na]+.

Synthesis of (S)-4-(3-(4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)-5-oxo-5-((phosphonooxy)methoxy)pentanoic acid (87): An atropisomeric mixture of the title compound was prepared according to the method presented for the synthesis of 58 of Example 58 utilizing 87B in the place of tert-butyl-L-serinate. $^1$H NMR (400 MHz, DMSO-$d_6$) δ 9.36 (s), 7.98 (s), 7.85-7.78 (m), 7.63 (s), 7.37 (s), 7.05-6.95 (m), 6.53 (s), 6.41 (s), 6.27 (s), 5.61-5.51 (m), 5.52-5.44 (m), 4.95 (d, J=16.5 Hz), 4.73-4.60 (m), 4.46 (s), 4.10-3.94 (m), 3.27 (s), 2.87-2.79 (m), 2.60 (s), 2.21 (s), 2.11 (s), 1.97-1.89 (m), 1.79-1.72 (m), 1.57-1.47 (m), 1.35 (s), 1.28 (s), 1.01-0.94 (m) ppm. $^{19}$F NMR (375 MHz, DMSO-$d_6$) δ−60.95, −69.31--69.59 (m), −69.89, −75.26, −81.31, −81.99 ppm. MS (m/z): 1265.20 [M+H]+.

Example 88

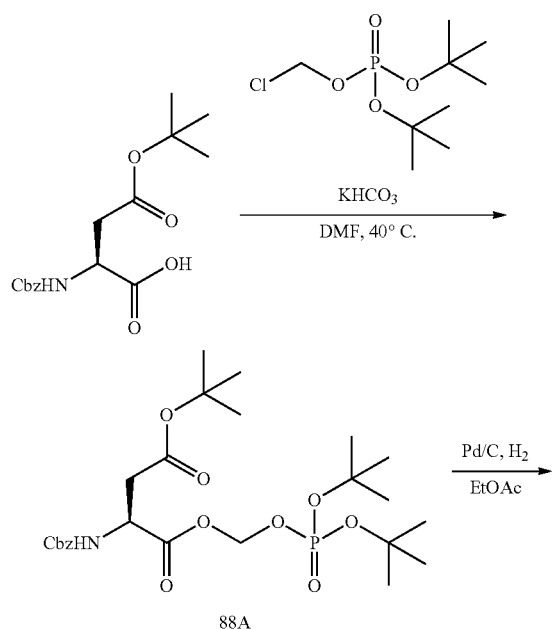

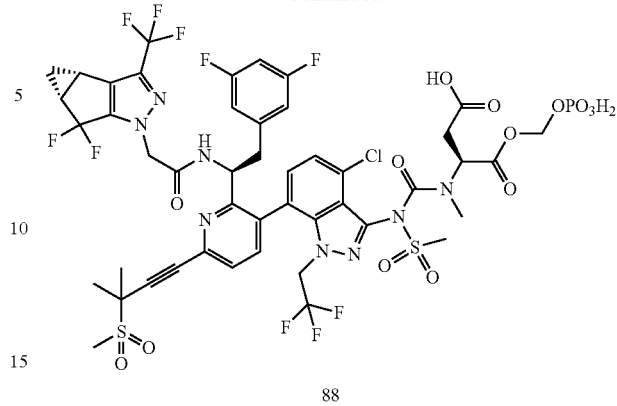

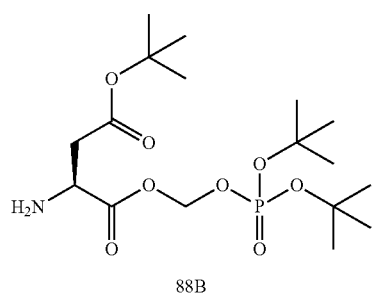

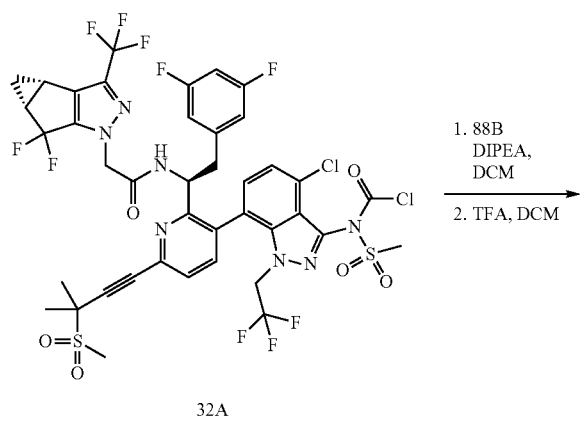

Synthesis of 4-(tert-butyl) 1-(((di-tert-butoxyphosphoryl)oxy)methyl) ((benzyloxy)carbonyl)-L-aspartate (88A): The title compound was prepared according to the method presented for the synthesis of 84A of Example 84 utilizing (S)-2-(((benzyloxy)carbonyl)amino)-4-(tert-butoxy)-4-oxobutanoic acid in the place of N-((benzyloxy)carbonyl)-N-methylglycine. MS (m/z) 582.20 [M+Na]+.

Synthesis of 4-(tert-butyl) 1-(((di-tert-butoxyphosphoryl)oxy)methyl) L-aspartate (88B): The title compound was prepared according to the method presented for the synthesis of 84B of Example 84 utilizing 88A in the place of 84A. MS (m/z) 426.17 [M+H]+.

Synthesis of (S)-3-(3-(4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)-1-methyl-3-(methylsulfonyl)ureido)-4-oxo-4-((phosphonooxy)methoxy)butanoic acid (88): An atropisomeric mixture of the title compound was prepared according to the method presented for the synthesis of 58 of Example 58 utilizing 88B in the place of tert-butyl-L-serinate. 1H NMR (400 MHz, DMSO-d6) δ 9.21-9.14 (m), 7.88-7.75 (m), 7.42-7.35 (m), 7.02 (s), 6.70 (s), 6.41-6.34 (m), 5.42 (s), 4.95 (s), 4.79-4.68 (m), 4.63-4.56 (m), 3.27 (s), 3.00 (s), 2.96-2.86 (m), 2.72 (s), 2.58 (s), 1.75 (s), 1.43-1.35 (m), 1.00 (s) ppm. 19F NMR (375 MHz, DMSO-d6) δ −60.56--61.22 (m), −60.93, −69.31--70.19 (m), −75.25, −75.26, −79.61--81.09 (m), −102.72--103.36 (m), −103.41--104.05 (m), −110.73 ppm. MS (m/z) 1250.98 [M+H]+.

Example 89

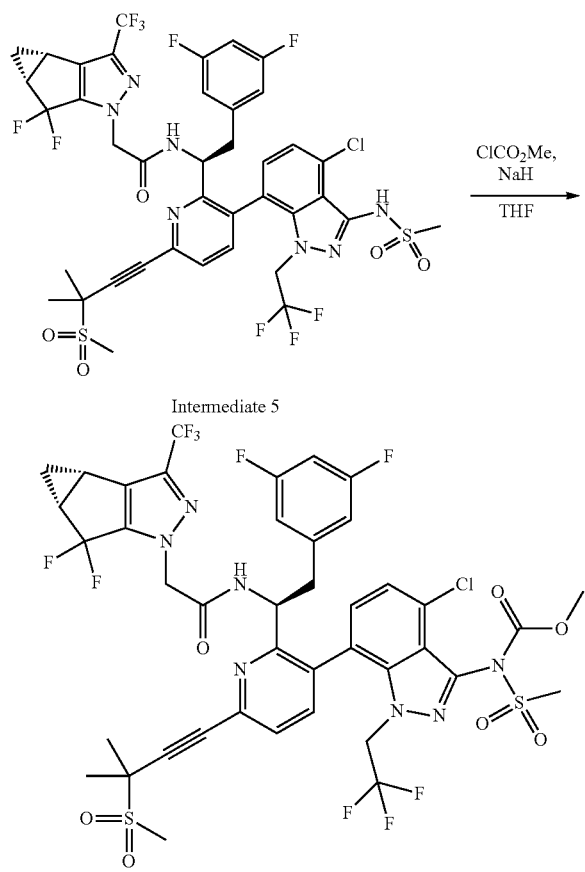

Synthesis of methyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (89): Intermediate 5 (0.052 mmol) was suspended in THF (2.5 mL) and treated with NaH (60% dispersion in mineral oil, 1.0 mmol). After stirring for 10 min at RT, methyl chloroformate (0.080 mL) was added. After another 1 h stirring, the reaction mixture was quenched with saturated aqueous ammonium chloride. The mixture was poured into water and extracted 2× with DCM. The combined organics were dried over MgSO$_4$, filtered and concentrated under reduced pressure. The crude residue was purified by reverse phase HPLC. Fractions containing the product were pooled and lyophilized to give title compound 89 as a mixture of atropisomers. $^1$H NMR (400 MHz, Methanol-d$_4$) δ 8.97-8.90 (m), 8.86-8.79 (m), 7.81-7.69 (m), 7.73-7.61 (m), 7.33-7.25 (m), 6.82-6.72 (m), 6.65-6.55 (m), 6.35-6.26 (m), 4.87-4.75 (m), 4.76-4.64 (m), 4.25-4.18 (m), 4.17-3.97 (m), 3.76 (d, J=27.0 Hz), 3.62-3.52 (m), 3.55-3.50 (m), 3.26-3.21 (m), 3.25-3.20 (m), 3.13-3.02 (m), 3.02-2.80 (m), 2.54-2.46 (m), 2.04-1.97 (m), 1.90-1.78 (m), 1.46-1.33 (m), 1.32-1.20 (m), 1.11-1.02 (m), 0.99-0.85 (m) ppm. MS (m/z) 1027.05 [M+H]$^+$.

Example 90

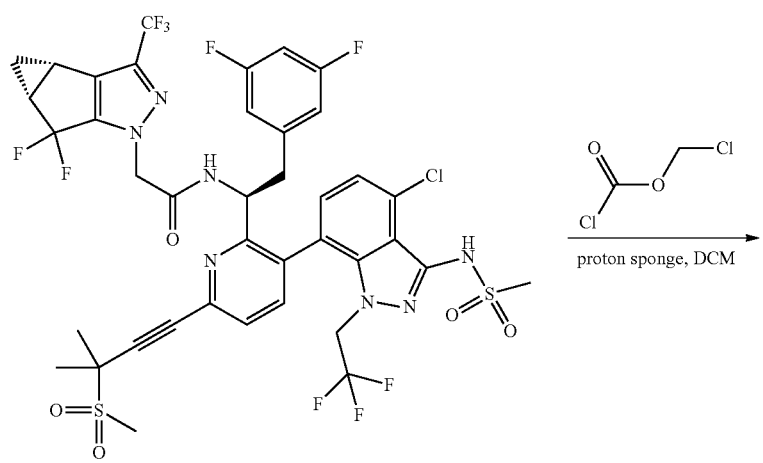

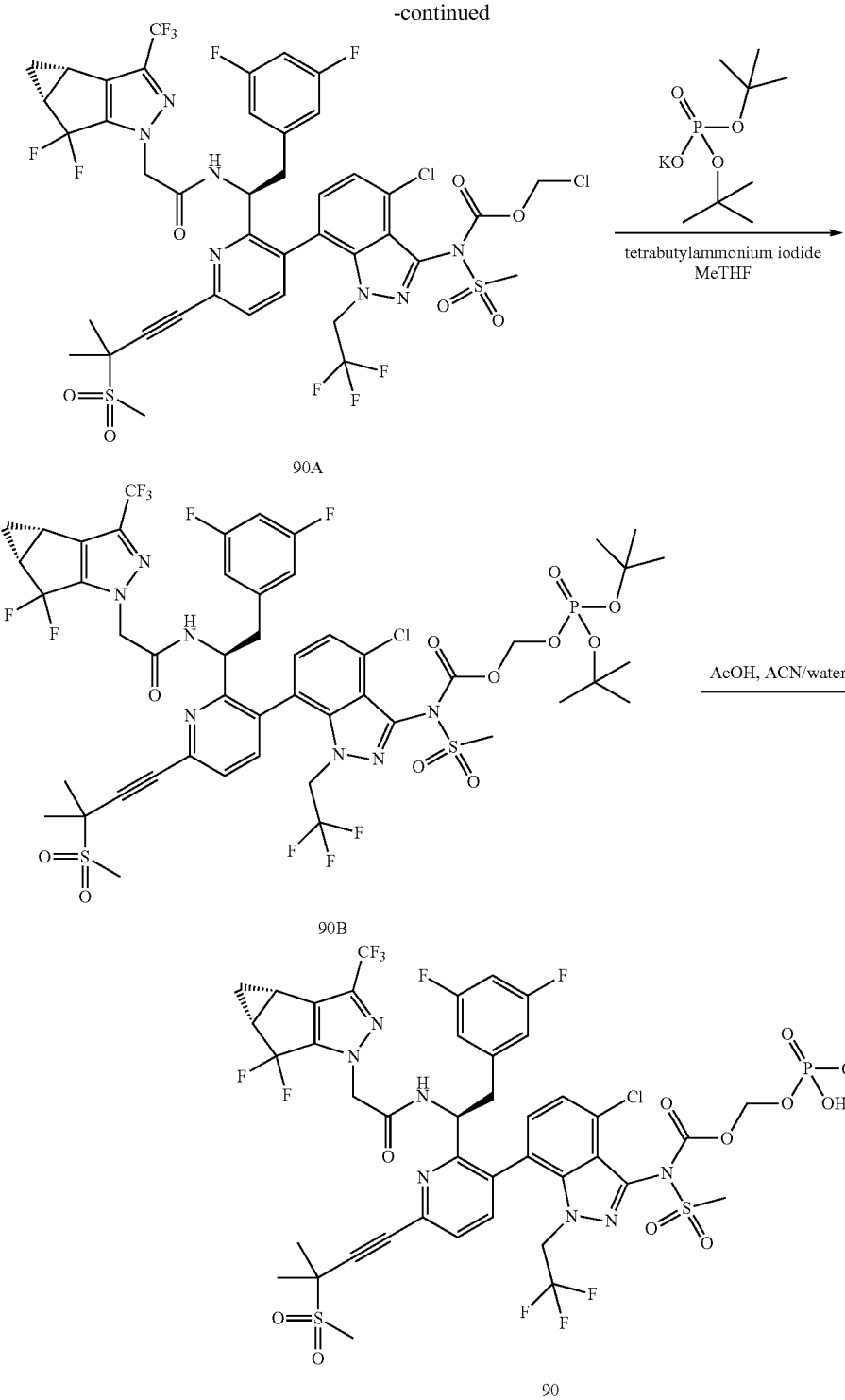

Synthesis of chloromethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (90A): To a solution of Intermediate 5 (, 0.103 mmol) in DCM (5 mL) was added chloromethyl chloroformate (0.207 mmol) and proton sponge (0.258 mmol) at room temperature. After stirring overnight and removal of the solvent, the residue was purified by silica gel chromatography to yield title compound 90A as a mixture of atropisomers. $^1$H NMR (400 MHz, Chloroform-d) δ 7.62-7.42 (m, 2H), 7.13 (t, J=8.0 Hz, 1H), 6.90 (dd, J=27.0, 8.5 Hz, 1H), 6.71-6.54 (m, 1H), 6.36-6.11 (m, 3H), 5.83-5.63 (m, 2H), 5.28 (s, 1H), 4.84 (d, J=6.5 Hz, 1H), 4.60-4.43 (m, 1H), 3.96 (d, J=7.9 Hz, 1H), 3.56 (d, J=9.2 Hz, 3H), 3.17 (d, J=1.1 Hz, 3H), 2.91 (dd, J=23.4, 7.4 Hz, 2H), 2.47 (d, J=2.7 Hz, 2H), 1.84 (d, J=1.4 Hz, 6H), 1.75-1.56 (m, 1H), 1.41 (s, 1H), 1.25 (dd, J=3.9, 1.6 Hz, 3H), 0.91-0.81 (m, 2H). MS (m/z) 1061.052 [M+H]+.

Synthesis of ((di-tert-butoxyphosphoryl)oxy)methyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (90B): To a solution of 90A (0.104 mmol) in MeTHF (10 mL) was added tetrabutylammonium iodide (0.0104 mmol) and potassium di-tert-butyl phosphate (0.156 mmol) at room temperature. The reaction mixture was heated to 65° C. for 3 hrs., after which the mixture was purified by silica gel chromatography. Fractions containing the product were pooled and concentrated to obtain title compound 90B as a mixture of atropisomers. MS (m/z) 1234.51 [M+H]+.

Synthesis of (phosphonooxy)methyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (90): A solution of 90B (0.035 mmol) in MeCN (1 ml), water (1 ml) and AcOH (1 ml) was heated to 45° C. for 3 hrs. The reaction mixture was concentrated under reduced pressure and purified by reverse phase HPLC. Fractions containing the product were pooled and lyophilized to give title compound 90 as a mixture of atropisomers. ¹H NMR (400 MHz, Methanol-d₄) δ 7.83 (t, J=8.5 Hz, 1H), 7.78-7.64 (m, 5H), 7.38-7.22 (m, 4H), 6.76 (dt, J=7.7, 2.1 Hz, 2H), 6.59 (d, J=7.7 Hz, 2H), 6.50 (d, J=7.7 Hz, 2H), 6.37-6.28 (m, 4H), 5.73-5.54 (m, 6H), 5.03 (s, 1H), 4.83-4.75 (m, 4H), 4.72-4.61 (m, 4H), 4.14 (s, 1H), 4.05 (dd, J=16.0, 8.0 Hz, 2H), 3.64-3.54 (m, 7H), 3.22 (d, J=0.8 Hz, 7H), 3.10 (d, J=7.8 Hz, 2H), 3.02-2.92 (m, 3H), 2.53-2.46 (m, 4H), 1.81 (d, J=1.3 Hz, 13H), 1.45-1.36 (m, 3H), 1.11-1.04 (m, 3H). MS (m/z) 1122.3 [M+H]+.

Example 91

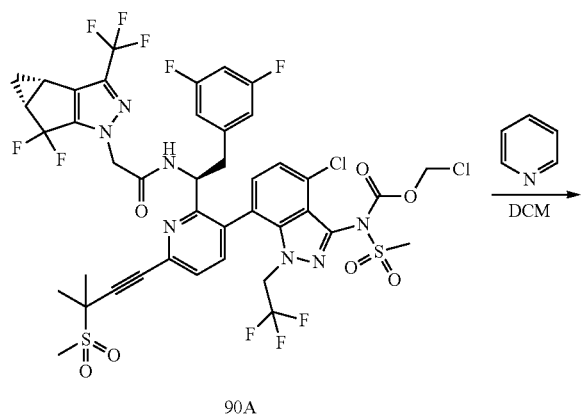

90A

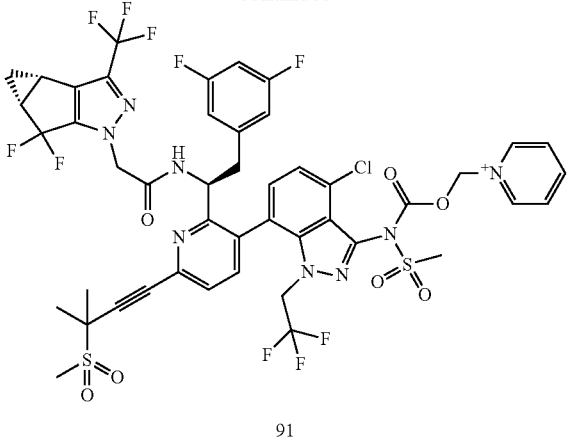

91

Synthesis of 1-(((((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)methyl)pyridin-1-ium (91): To a solution of 90A (0.094 mmol) in DCM (1 mL) was added pyridine (0.377 mmol, 4 equiv). Upon completion of the reaction, the solvent was removed under reduced pressure and the residue purified by reverse phase HPLC. Fractions containing the product were pooled and lyophilized to obtain title compound 91 as a mixture of atropisomers. ¹H NMR (400 MHz, Methanol-d₄) δ 9.18-9.10 (m), 9.09-9.00 (m), 8.98-8.86 (m), 8.85-8.74 (m), 8.29-8.09 (m), 7.89-7.69 (m), 7.33-7.25 (m), 6.87-6.72 (m), 6.72-6.65 (m), 6.64-6.54 (m), 6.44-6.22 (m), 4.90-4.81 (m), 4.82-4.71 (m), 4.69-4.61 (m), 4.11-3.98 (m), 3.64 (s), 3.60-3.54 (m), 3.29-3.22 (m), 3.21-2.89 (m), 2.60-2.48 (m), 1.87-1.81 (m), 1.50-1.43 (m) ppm. MS (m/z) 1103.20 [M+H]+.

Example 92

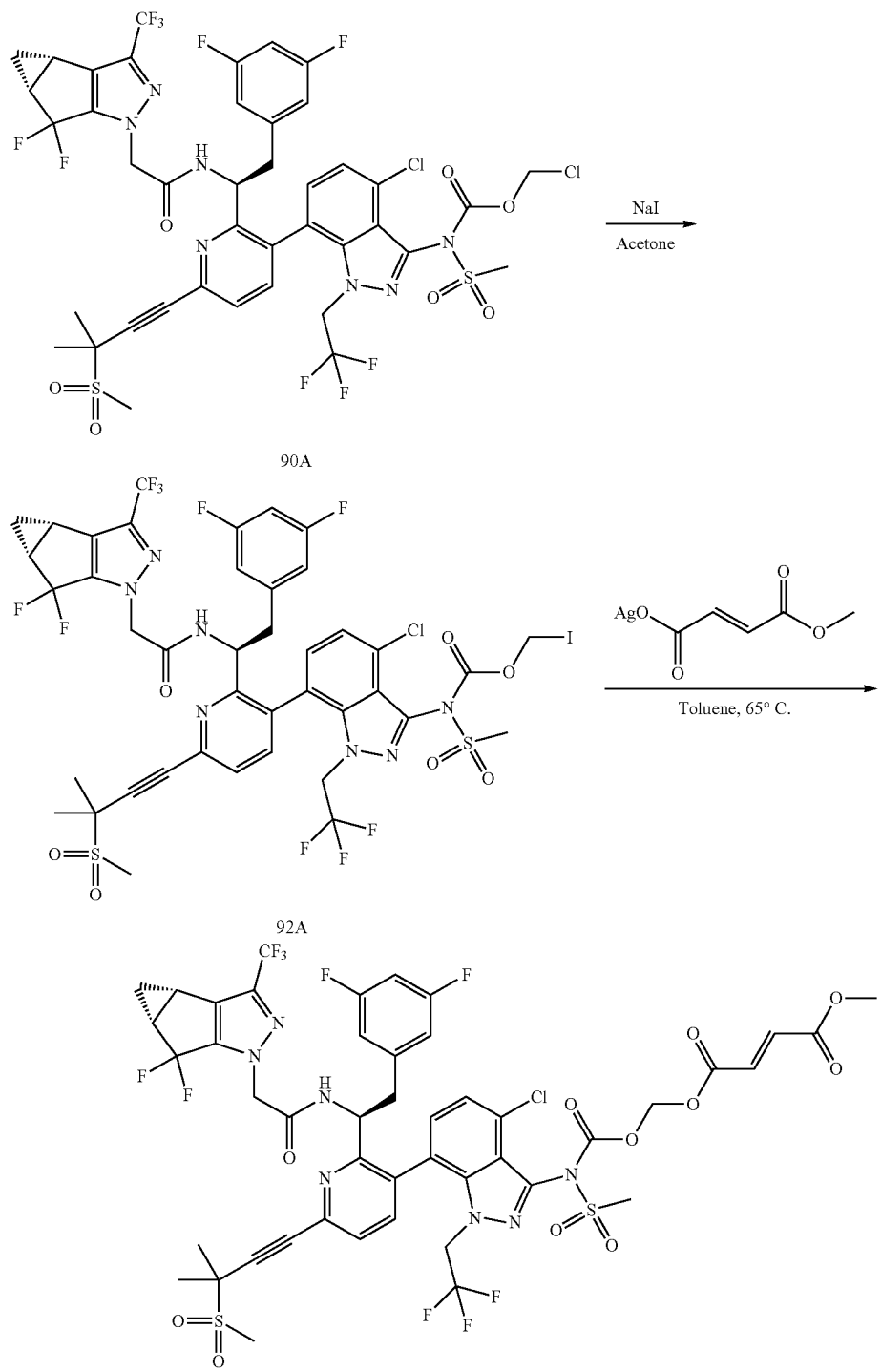

Synthesis of iodomethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (92A): To 90A (0.236 mmol) in acetone (0.5 mL) was added sodium iodide (0.943 mmol). The reaction mixture was stirred at room temperature for 2 hours, then filtered, concentrated in vacuo and purified by silica gel column chromatography (eluent: hexanes/ethyl acetate) to provide title compound 92A. MS (m/z) 1152.22 [M+H]$^+$.

Synthesis of (((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)methyl methyl fumarate (92): To a solution of 92A (0.017 mmol) in toluene (1 mL) was added (E)-((4-methoxy-4-oxobut-2-enoyl)oxy)silver (0.030 mmol). The reaction mixture was heated at 65° C. for 2 hours. The crude mixture was purified by silica gel column chromatography (eluent: hexanes/ethyl acetate) followed by reverse phase HPLC (eluent: water/acetonitrile containing 0.1% v/v TFA) to provide title compound 92 as a mixture of atropisomers. $^1$H NMR (400 MHz, Methanol-$d_4$) δ 7.80-7.73 (m), 7.74-7.65 (m), 7.30-7.20 (m), 6.91-6.70 (m), 6.58 (d), 6.55 (d), 6.42-6.27 (m), 5.96-5.86 (m), 5.78 (d), 4.76-4.61 (m), 4.17-3.95 (m), 3.81 (s), 3.81 (s), 3.57 (s), 3.55 (s), 3.24 (s), 3.23 (s), 3.11-3.02 (m), 2.93 (dd), 2.59-2.43 (m), 1.82 (s), 1.82 (s), 1.48-1.35 (m), 1.13-1.02 (m) ppm. MS (m/z) 1155.1 [M+H]$^+$.

Example 93

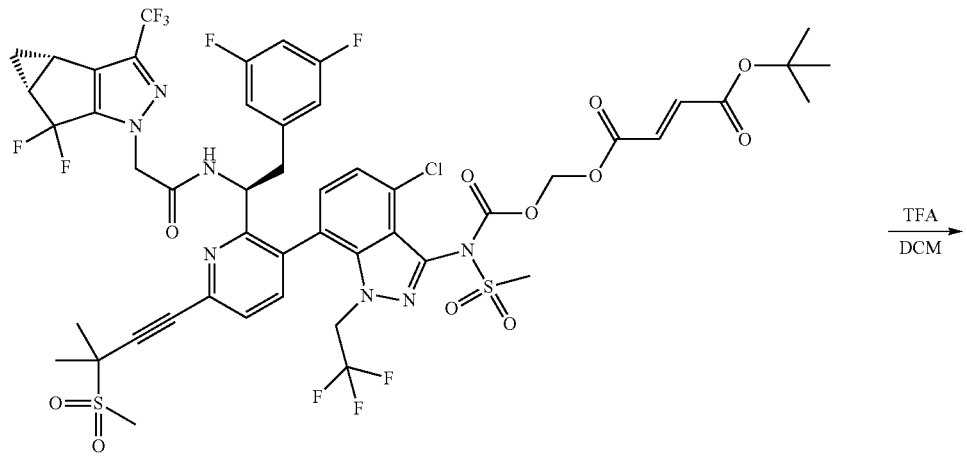

93A

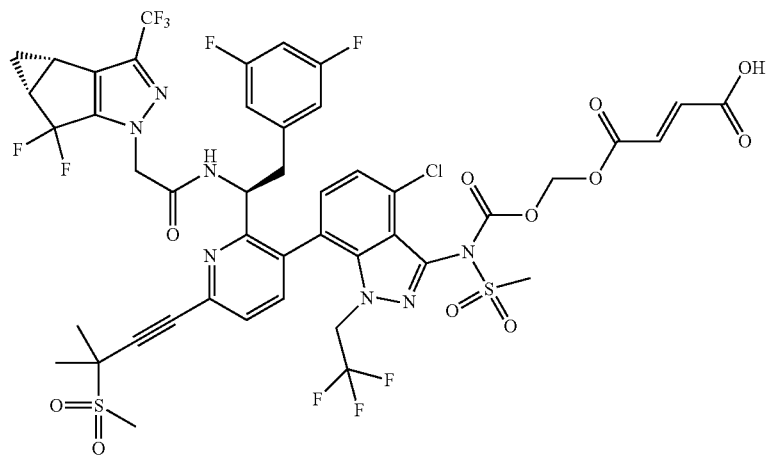

93

Synthesis of tert-butyl (((((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)methyl) fumarate (93A): An atropisomeric mixture of the title compound was prepared according to the method presented for the synthesis of 92 of Example 92 utilizing (E)-((4-(tert-butoxy)-4-oxobut-2-enoyl)oxy)silver in the place of (E)-((4-methoxy-4-oxobut-2-enoyl)oxy)silver. MS (m/z) 1196.21 [M+H]+.

Synthesis of (E)-4-(((((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)methoxy)-4-oxobut-2-enoic acid (93): 93A (0.018 mmol) was stirred in TFA (1.5 mL) until reaction completion. The reaction mixture was concentrated and purified by reverse phase HPLC (eluent: water/acetonitrile containing 0.1% v/v TFA) to provide title compound 93 as a mixture of atropisomers. $^1$H NMR (400 MHz, Chloroform-d) δ 7.75-7.55 (m), 7.13 (d), 6.93-6.92 (m), 6.90-6.88 (m), 6.71-6.62 (m), 6.50 (d), 6.28-6.23 (m), 6.23-6.16 (m), 6.04 (d), 5.99-5.86 (m), 5.75 (d), 4.91-4.82 (m), 4.77 (d), 4.76-4.72 (m), 4.64-4.46 (m), 3.97 (dp), 3.62 (s), 3.59 (s), 3.57 (s), 3.21-3.16 (m), 3.02-2.84 (m), 1.88 (s), 1.87 (s), 1.87 (s), 1.45 (p), 1.21-1.09 (m) ppm. MS (m/z) 1140.21 [M+H]+.

Example 94

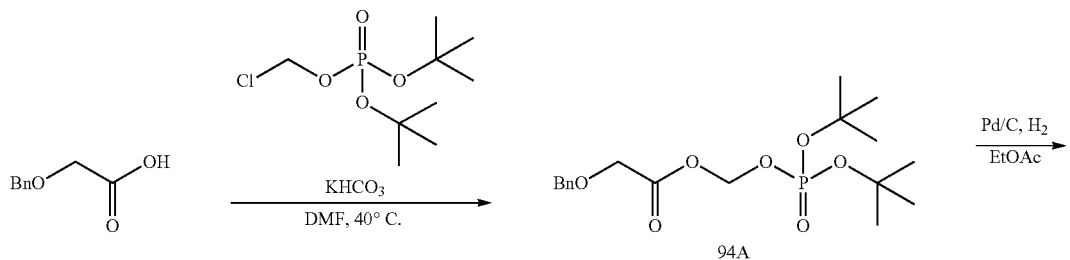

94A

94B

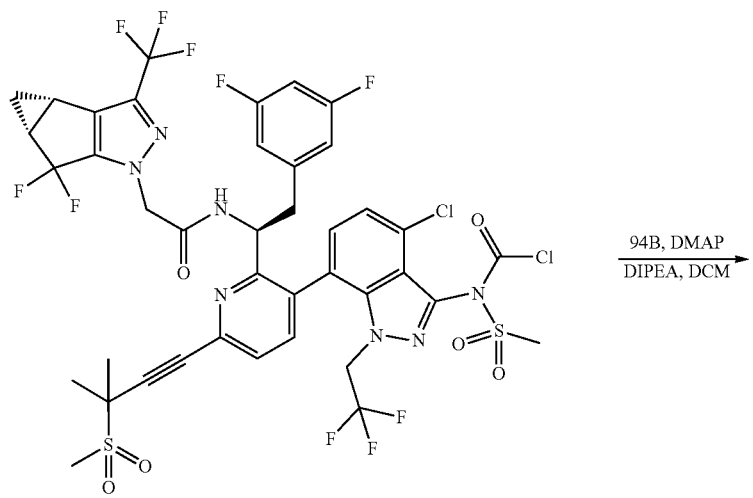

32A

-continued

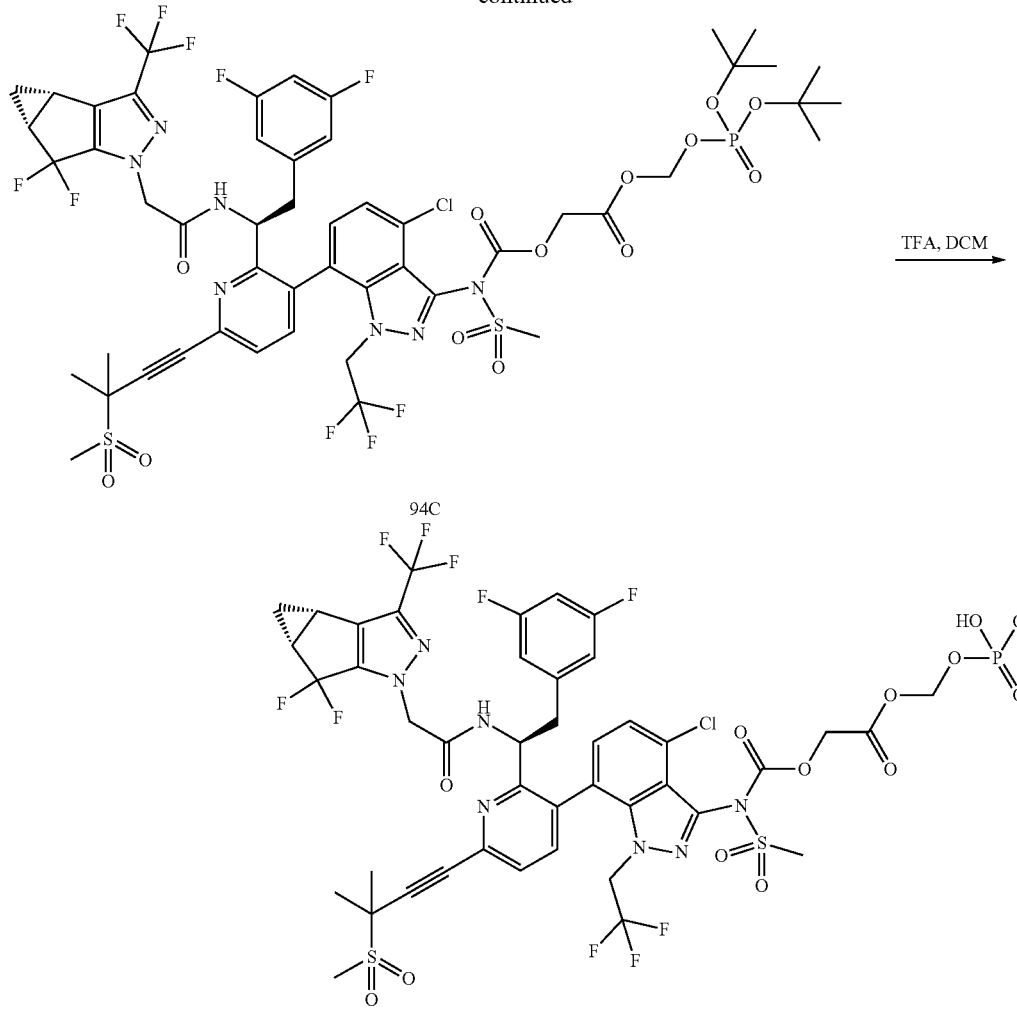

Synthesis of ((di-tert-butoxyphosphoryl)oxy)methyl 2-(benzyloxy)acetate (94A): The title compound was prepared according to the method presented for the synthesis of 84A of Example 84 utilizing glycolic acid benzyl ether in the place of N-((benzyloxy)carbonyl)-N-methylglycine. MS (m/z) 411.09 [M+Na]+.

Synthesis of ((di-tert-butoxyphosphoryl)oxy)methyl 2-hydroxyacetate (94B): The title compound was prepared according to the method presented for the synthesis of 84B of Example 84 utilizing 94A in the place of 84A. $^1$H NMR (400 MHz, CDCl$_3$) δ 5.71 (d, J=13.6 Hz, 2H), 4.26 (s, 2H), 1.51 (s, 18H) ppm.

Synthesis of ((di-tert-butoxyphosphoryl)oxy)methyl 2-(((4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)acetate (94C): To an ice-cold solution of 32A (0.582 mmol) in DCM (3 mL) was added 94B (1.16 mmol, 2 equiv) followed by DMAP (0.466 mmol, 0.8 equiv). DIPEA (1.42 mmol) was then added dropwise. When the reaction had reached completion, the mixture was partitioned between water (20 mL) and EtOAc (20 mL). The organic fraction was collected, and concentrated under reduced pressure to afford title compound 94C, which was used without purification.

Synthesis of (phosphonooxy)methyl 2-(((4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)acetate (94): 94C (0.582 mmol) was diluted with DCM (10 mL). To this solution was added TFA (1 mL). When reaction was complete, the mixture was concentrated under reduced pressure and purified by reverse phase HPLC. Fractions containing the product were pooled and lyophilized to obtain title compound 94. $^1$H NMR (400 MHz, DMSO-d$_6$) δ 9.30-9.16 (m), 7.86-7.79 (m), 7.82-7.71 (m), 7.51-7.42 (m), 7.36-7.22 (m), 7.10-6.97 (m), 6.56-6.44 (m), 5.59-5.47 (m), 5.01-4.90 (m), 4.87 (m), 4.82-4.69 (m), 4.64 (m), 4.29-4.08 (m), 3.66 (s), 3.27 (s), 3.09-2.92 (m), 2.63-2.52 (m), 1.79-1.72 (m), 1.39 (m), 1.02-0.94 (m) ppm. $^{19}$F NMR (375 MHz, DMSO-d$_6$) δ −60.60--61.03 (m), −69.18--69.76 (m), −75.51, −75.12--76.17 (m), −79.62--81.04 (m), −103.29, −103.96, −110.52--110.83 (m), −110.71, −111.00 ppm. MS (m/z) 1180.13 [M+H]+.

Example 95

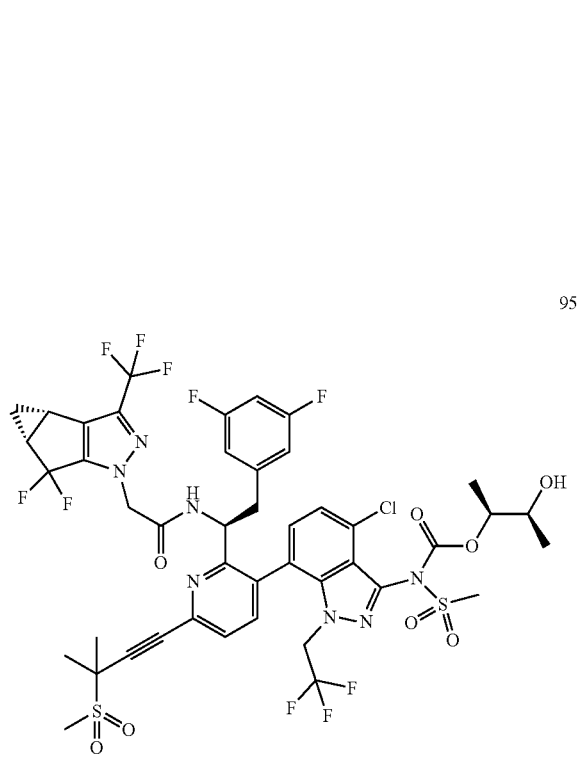 [SMILES: C[C@H](O)[C@H](C)OC(=O)N(c1nn(CC(F)(F)F)c2c(-c3ccc(C#CC(C)(C)S(C)(=O)=O)nc3[C@H](Cc3cc(F)cc(F)c3)NC(=O)Cn3nc(C(F)(F)F)c4c3C(F)(F)[C@@H]3C[C@H]43)ccc(Cl)c12)S(C)(=O)=O]

Synthesis of (2S,3S)-3-hydroxybutan-2-yl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (95): An atropisomeric mixture of the title compound was prepared according to the method presented for the synthesis of 94C of Example 94 utilizing (2S,3S)-butane-2,3-diol in the place of 94B. $^1$H NMR (400 MHz, DMSO-d$_6$) δ 9.24-9.17 (m), 8.01-7.71 (m), 7.50-7.37 (m), 7.36-7.24 (m), 7.08-6.85 (m), 6.52-6.41 (m), 4.99-4.79 (m), 4.83-4.50 (m), 4.24-4.08 (m), 4.10-3.94 (m), 3.70-3.51 (m), 3.30-3.24 (m), 3.20-3.07 (m), 3.09-2.90 (m), 2.64-2.53 (m), 1.78-1.72 (m), 1.45-1.33 (m), 1.17-1.09 (m), 1.09-0.93 (m), 0.94-0.81 (m), 0.81-0.70 (m), 0.58-0.51 (m) ppm. $^{19}$F NMR (376 MHz, DMSO-d$_6$) δ−60.75--60.95 (m), −69.41--69.73 (m), −69.74--69.84 (m), −75.08, −79.73--79.81 (m), −79.93--80.02 (m), −80.40--80.49 (m), −80.60--80.69 (m), −103.02--103.10 (m), −103.22--103.30 (m), −103.69--103.77 (m), −103.90--103.98 (m), −110.59--110.68 (m), −110.69--110.81 (m), −110.91--111.01 (m) ppm. MS (m/z) 1084.39 [M+H]$^+$.

Example 96

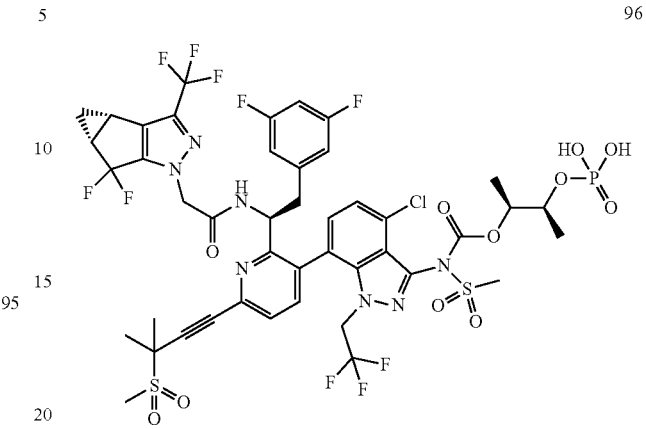

Synthesis of (2S,3S)-3-(phosphonooxy)butan-2-yl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (96): An atropisomeric mixture of the title compound was prepared according to the method presented for the synthesis of 33 of Example 33 utilizing 95 in the place of 32. $^1$H NMR (400 MHz, DMSO-d$_6$) δ 9.24-9.14 (m), 7.89-7.78 (m), 7.82-7.71 (m), 7.49-7.38 (m), 7.14-6.97 (m), 6.92-6.85 (m), 6.53 (s), 6.53-6.40 (m), 5.05-4.95 (m), 4.96-4.81 (m), 4.80-4.65 (m), 4.66-4.53 (m), 4.25 (s), 3.69-3.58 (m), 2.97 (s), 1.79-1.71 (m), 1.43-1.35 (m), 1.21-1.08 (m), 0.98 (s), 0.95-0.88 (m), 0.73-0.66 (m) ppm. 19F NMR (376 MHz, DMSO-d$_6$) δ−60.77--60.86 (m), −60.89--60.94 (m), −69.38--69.50 (m), −69.74--69.83 (m), −73.95, −80.06, −80.69--80.76 (m), −110.60--110.73 (m) ppm. MS (m/z) 1163.91 [M+H]$^+$.

Example 97

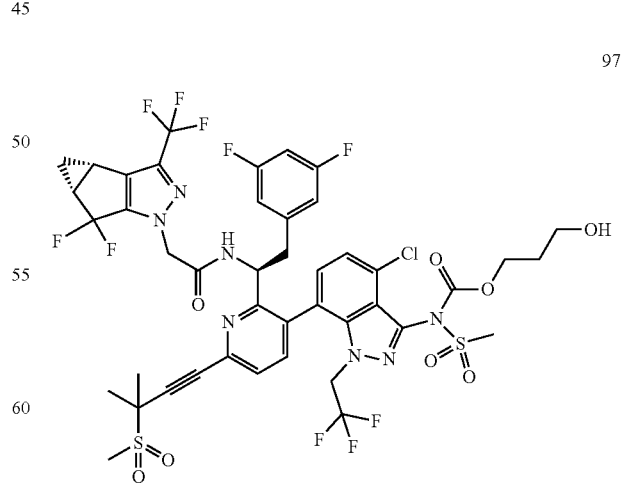

Synthesis of 3-hydroxypropyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)

acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (97): An atropisomeric mixture of the title compound was prepared according to the method presented for the synthesis of 94C of Example 94 utilizing propane-1,3-diol in the place of 94B. $^1$H NMR (400 MHz, CD$_3$OD) δ 8.98-8.90 (m, 1H), 7.90-7.67 (m, 4H), 7.45-7.17 (m, 2H), 6.85-6.71 (m, 1H), 6.65-6.46 (m, 2H), 6.32 (s, 3H), 6.36-6.28 (m, 1H), 4.94-4.56 (m, 6H), 4.40-3.89 (m, 3H), 3.62-3.52 (m, 3H), 3.49-3.38 (m, 1H), 3.32-3.19 (m, 8H), 3.16-3.03 (m, 2H), 3.02-2.90 (m, 1H), 2.57-2.48 (m, 1H), 1.96 (s), 1.87-1.71 (m, 12H), 1.74-1.58 (m, 1H), 1.49-1.39 (m, 2H), 1.12-1.05 (m) ppm. MS (m/z): 1070.11 [M+H]$^+$.

Example 98

98

Synthesis of 3-(phosphonooxy)propyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl) carbamate (98): An atropisomeric mixture of the title compound was prepared according to the method presented for the synthesis of 59A of Example 59 utilizing 97 in the place of 58A. $^1$H NMR (400 MHz, CD$_3$OD) δ 8.92-8.82 (m, 1H), 7.82-7.75 (m, 1H), 7.75-7.66 (m, 1H), 7.43-7.25 (m, 2H), 6.86-6.76 (m, 1H), 6.64-6.57 (m), 6.55-6.48 (m, 1H), 6.37-6.30 (m, 2H), 4.88-4.62 (m, 4H), 4.43-4.21 (m, 2H), 4.20-4.08 (m), 4.08-3.97 (m, 1H), 3.92-3.80 (m, 2H), 3.62-3.52 (m, 4H), 3.30-3.21 (m, 4H), 3.15-3.04 (m, 1H), 3.04-2.90 (m, 1H), 2.58-2.48 (m, 2H), 1.98-1.87 (m, 1H), 1.86-1.80 (m, 8H), 1.48-1.39 (m, 1H), 1.31 (s), 1.13-1.04 (m, 1H) ppm. MS (m/z) 1150.14 [M+H]$^+$.

Example 99

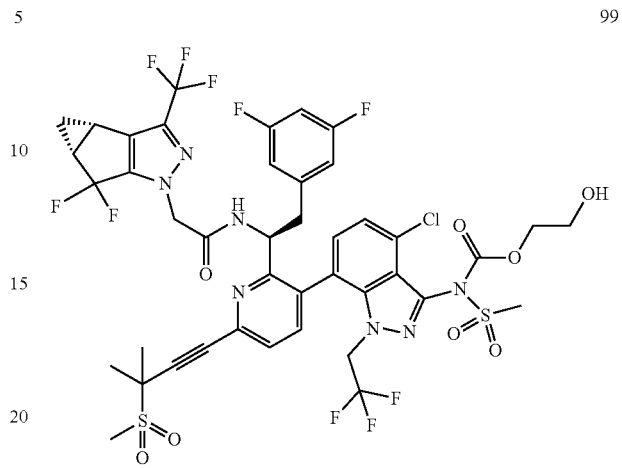

99

Synthesis of 2-hydroxyethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (99): An atropisomeric mixture of the title compound was prepared according to the method presented for the synthesis of 94C of Example 94 utilizing ethylene glycol in the place of 94B. $^1$H NMR (400 MHz, Methanol-d$_4$) δ 9.07-9.00 (m), 9.00-8.93 (m), 8.88-8.81 (m), 7.85-7.67 (m), 7.34-7.25 (m), 7.27-7.17 (m), 6.84-6.74 (m), 6.64-6.54 (m), 6.52-6.46 (m), 6.36-6.26 (m), 4.39-4.26 (m), 4.19-4.07 (m), 4.09-3.88 (m), 3.71-3.64 (m), 3.64-3.54 (m), 3.51-3.37 (m), 3.28-3.23 (m), 3.14-3.04 (m), 3.04-2.86 (m), 2.51 (s), 2.06 (s), 1.96 (s), 1.86-1.81 (m), 1.49-1.40 (m), 1.15-1.08 (m) ppm. MS (m/z) 1056.20 [M+H]$^+$.

Example 100

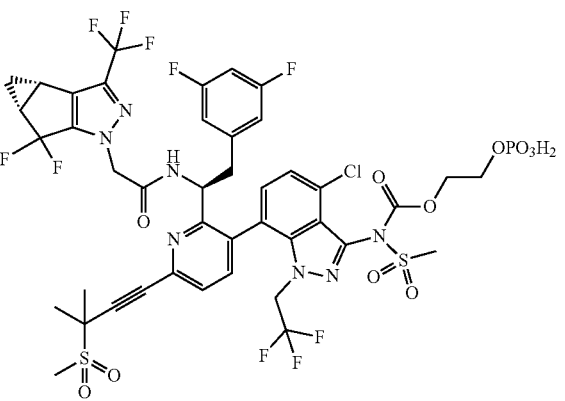

100

Synthesis of 2-(phosphonooxy)ethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (100): An atropisomeric mixture of the title compound was prepared according to the method presented for the synthesis of 59A of Example 59 utilizing 99 in the place of 58A. $^1$H NMR (400 MHz, Methanol-d$_4$) δ 7.80-7.74 (m, 1H), 7.76-7.67 (m, 1H), 7.35-7.24 (m, 1H), 6.85-6.74 (m), 6.78 (s, 1H), 6.64-6.57 (m), 6.57-6.47 (m, 1H), 6.34 (s, 2H), 4.50 (s, 2H), 4.51-4.44 (m), 4.42-4.34 (m), 4.21-4.01 (m, 1H), 3.65-3.54 (m, 3H), 3.33-3.22 (m, 4H), 3.16-3.04 (m, 1H), 3.03-2.91 (m, 1H), 2.57-2.49 (m, 3H), 2.06 (s, 4H), 1.97 (s, 1H), 1.94-1.75 (m, 8H), 1.48-1.39 (m, 1H), 1.30-1.22 (m), 1.09 (s, 1H) ppm. MS (m/z) 1136.21 [M+H]$^+$.

Example 101

Example 102

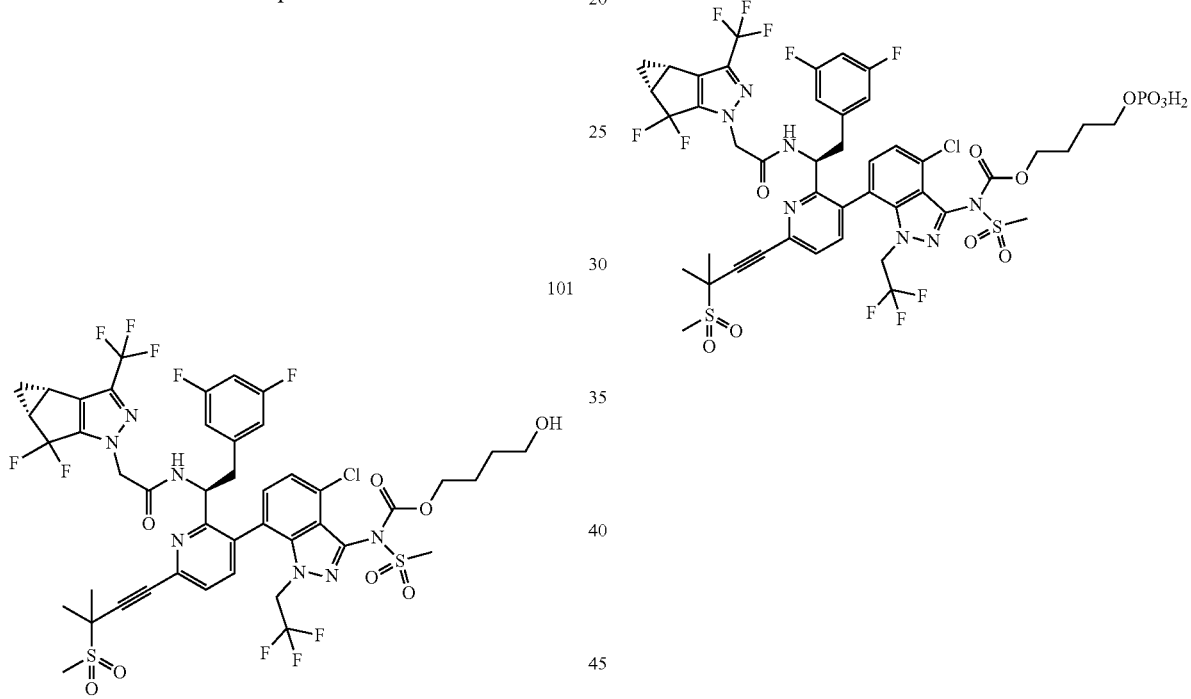

Synthesis of 4-hydroxybutyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c] pyrazol-1-yl) acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (101): An atropisomeric mixture of the title compound was prepared according to the method presented for the synthesis of 94C of Example 94 utilizing butane-1,4-diol in the place of 94B. $^1$H NMR (400 MHz, Methanol-d$_4$) δ 9.01-8.82 (m), 7.90-7.67 (m), 7.37-7.17 (m), 6.84-6.74 (m), 6.64-6.56 (m), 6.56-6.46 (m), 6.37-6.28 (m), 4.87-4.74 (m), 4.71-4.60 (m), 4.32-4.11 (m), 4.11-3.91 (m), 3.61-3.53 (m), 3.45-3.34 (m), 3.28-3.22 (m), 3.15-3.03 (m), 3.03-2.91 (m), 2.54-2.48 (m), 1.84 (s), 1.86-1.80 (m), 1.66-1.51 (m), 1.49-1.28 (m), 1.09 (s) ppm. MS (m/z) 1084.02 [M+H]$^+$.

Synthesis of 4-(phosphonooxy)butyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (102): An atropisomeric mixture of the title compound was prepared according to the method presented for the synthesis of 59A of Example 59 utilizing 101 in the place of 58A. $^1$H NMR (400 MHz, Methanol-d$_4$) δ 8.90-8.83 (m), 7.80-7.66 (m), 7.34-7.24 (m), 6.87-6.77 (m), 6.64-6.58 (m), 6.52-6.45 (m), 6.33 (d, J=7.6 Hz), 4.87-4.73 (m), 4.72-4.61 (m), 4.32-4.12 (m), 4.09-3.98 (m), 3.91-3.78 (m), 3.62-3.52 (m), 3.28-3.22 (m), 3.15-2.94 (m), 2.57-2.50 (m), 2.51 (s), 1.96 (s), 1.86-1.80 (m), 1.66 (d, J=7.8 Hz), 1.63 (s), 1.47 (s), 1.48-1.41 (m), 1.11 (s), 1.06 (s) ppm. MS (m/z): 1164.13 [M+H]$^+$.

Example 103

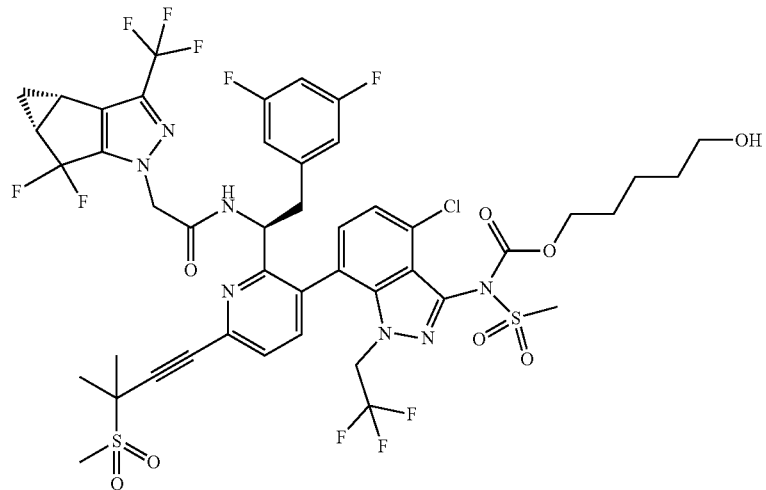

Synthesis of 5-hydroxypentyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (103): An atropisomeric mixture of the title compound was prepared according to the method presented for the synthesis of 94C of Example 94 utilizing pentane-1,5-diol in the place of 94B. $^1$H NMR (400 MHz, Methanol-$d_4$) δ (m), 8.91-8.80 (m), 7.81-7.67 (m), 7.43-7.17 (m), 6.84-6.76 (m), 6.65-6.53 (m), 6.53-6.46 (m), 6.37-6.28 (m), 4.83-4.69 (m), 4.27-4.20 (m), 4.15-3.93 (m), 3.62-3.52 (m), 3.46-3.35 (m), 3.25 (s), 3.15-3.05 (m), 3.03-2.92 (m), 2.51 (s), 1.84 (s), 1.86-1.80 (m), 1.56 (s), 1.47-1.35 (m), 1.19 (s), 1.08 (s) ppm. MS (m/z): 1098.03 [M+H]$^+$.

Example 104

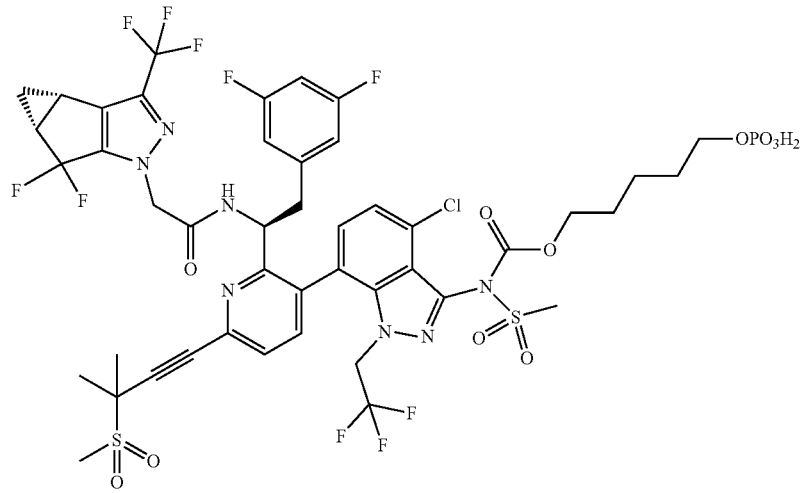

Synthesis of 5-(phosphonooxy)pentyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl) carbamate (104): An atropisomeric mixture of the title compound was prepared according to the method presented for the synthesis of 59A of Example 59 utilizing 103 in the place of 58A. $^1$H NMR (400 MHz, Methanol-$d_4$) δ 7.83-7.71 (m), 7.74-7.67 (m), 7.36-7.26 (m), 6.68-6.61 (m), 6.60-6.53 (m), 6.32 (s), 4.28-4.20 (m), 4.17-4.10 (m), 3.92-3.86 (m), 3.80-3.73 (m), 3.62-3.52 (m), 3.31 (s), 3.28-3.23 (m), 1.86-1.80 (m), 1.54 (s), 1.43 (s) ppm. MS (m/z): 1178.04 [M+H]$^+$.

Example 105

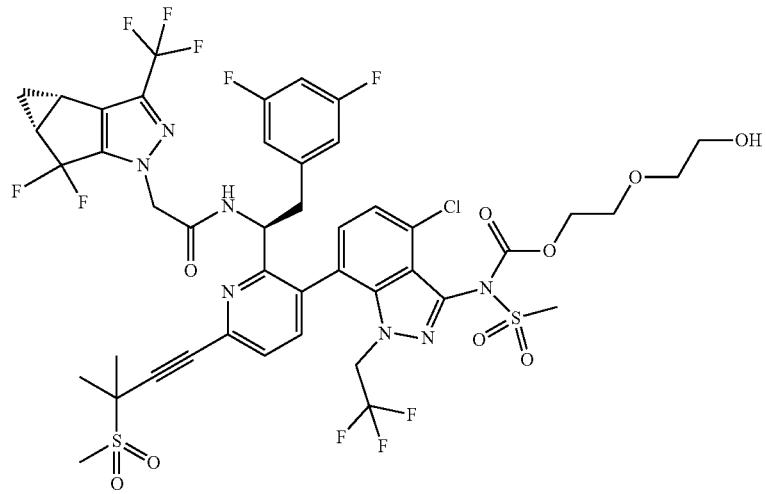

105

Synthesis of 2-(2-hydroxyethoxy)ethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl) carbamate (105): An atropisomeric mixture of the title compound was prepared according to the method presented for the synthesis of 94C of Example 94 utilizing 2,2'-oxybis(ethan-1-ol) in the place of 94B. $^1$H NMR (400 MHz, Methanol-$d_4$) δ 8.92-8.79 (m), 7.81-7.66 (m), 7.42-7.26 (m), 6.85-6.73 (m), 6.64-6.55 (m), 6.38-6.30 (m), 4.88-4.81 (m), 4.83-4.73 (m), 4.74-4.62 (m), 4.43-4.29 (m), 4.19-4.02 (m), 3.69-3.52 (m), 3.54-3.45 (m), 3.45-3.33 (m), 3.28-3.22 (m), 3.15-3.04 (m), 3.03-2.90 (m), 2.59-2.48 (m), 1.86-1.80 (m), 1.49-1.40 (m), 1.14-1.02 (m) ppm. MS (m/z) 1100.11 [M+H]$^+$.

Example 106

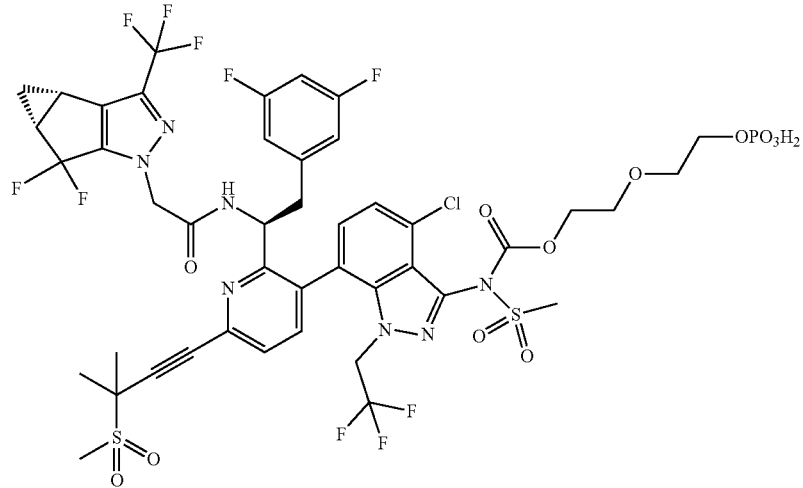

Synthesis of 2-(2-(phosphonooxy)ethoxy)ethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl) carbamate (106): An atropisomeric mixture of the title compound was prepared according to the method presented for the synthesis of 59A of Example 59 utilizing 105 in the place of 58A. $^1$H NMR (400 MHz, Methanol-$d_4$) δ 8.90-8.79 (m), 7.83-7.74 (m), 7.75-7.66 (m), 7.35-7.26 (m), 6.85-6.73 (m), 6.66-6.48 (m), 6.38-6.30 (m), 4.88-4.76 (m), 4.77-4.63 (m), 4.43-4.28 (m), 4.20-3.95 (m), 3.94-3.85 (m), 3.64 (s), 3.64-3.40 (m), 3.28-3.18 (m), 3.15-3.03 (m), 3.04-2.90 (m), 2.57-2.50 (m), 2.51 (s), 1.96 (s), 1.86-1.80 (m), 1.48-1.39 (m), 1.38-1.29 (m), 1.13-1.04 (m) ppm. MS (m/z): 1180.12 [M+H]$^+$.

Example 107

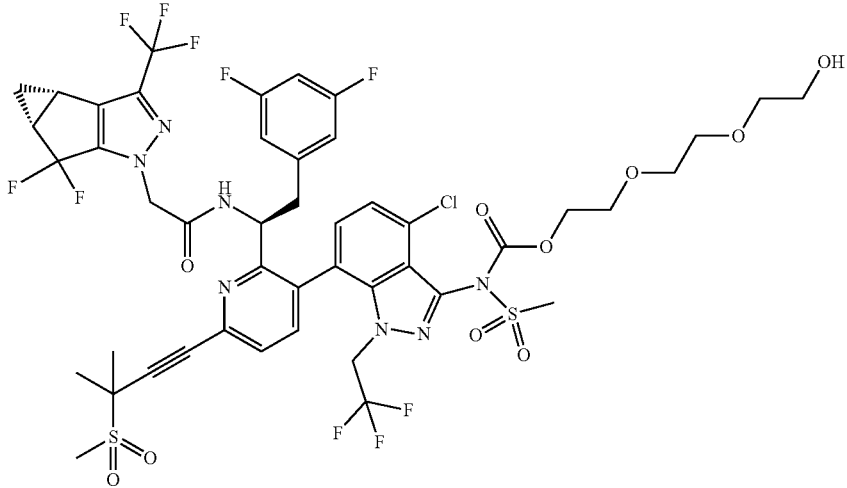

Synthesis of 2-(2-(2-hydroxyethoxy)ethoxy)ethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (107): An atropisomeric mixture of the title compound was prepared according to the method presented for the synthesis of 94C of Example 94 utilizing 2,2'-(ethane-1,2-diylbis(oxy))bis(ethan-1-ol) in the place of 94B. $^1$H NMR (400 MHz, Methanol-$d_4$) δ 8.92-8.81 (m), 7.82-7.67 (m), 7.42-7.27 (m), 6.86-6.74 (m), 6.65-6.48 (m), 6.38-6.30 (m), 4.88-4.81 (m), 4.83-4.62 (m), 4.45-4.35 (m), 4.38-4.25 (m), 4.20-3.97 (m), 3.69-3.39 (m), 3.42-3.35 (m), 3.28-3.22 (m), 3.16-3.04 (m), 3.03-2.90 (m), 2.56-2.48 (m), 2.05 (s), 1.86-1.80 (m), 1.47-1.39 (m), 1.11 (s), 1.06 (s) ppm. MS (m/z) 1166.30 [M+H]$^+$.

Example 108

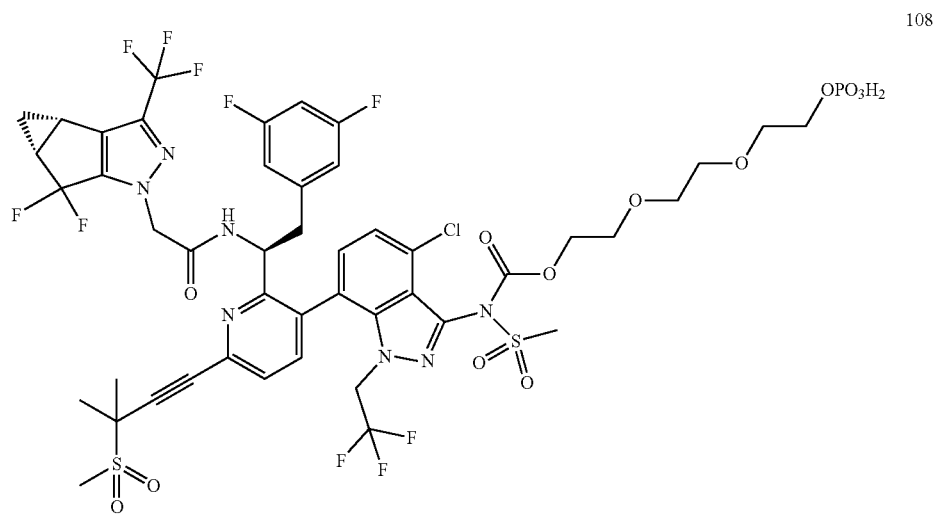

Synthesis of 2-(2-(2-(phosphonooxy)ethoxy)ethoxy)ethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (108): An atropisomeric mixture of the title compound was prepared according to the method presented for the synthesis of 59A of Example 59 utilizing 107 in the place of 58A. $^1$H NMR (400 MHz, Methanol-$d_4$) δ 7.77 (s), 7.74-7.67 (m), 7.34-7.27 (m), 6.34 (s), 3.67 (s), 3.64-3.54 (m), 3.25 (s), 1.96 (s), 1.86-1.81 (m) ppm. MS (m/z) 1224.17 [M+H]$^+$.

Example 109

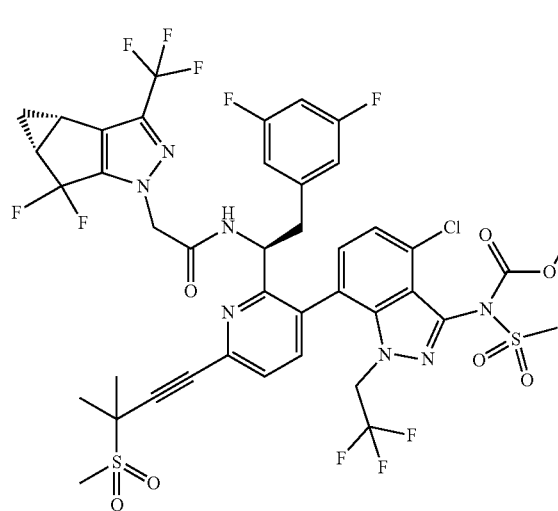

Synthesis of 2-(2-(2-(2-hydroxyethoxy)ethoxy)ethoxy)ethyl (4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (109): An atropisomeric mixture of the title compound was prepared according to the method presented for the synthesis of 94C of Example 94 utilizing 2,2'-((oxybis(ethane-2,1-diyl))bis(oxy))bis(ethan-1-ol) in the place of 94B. $^1$H NMR (400 MHz, Methanol-$d_4$) δ 8.92-8.81 (m), 7.82-7.67 (m), 7.45-7.27 (m), 6.86-6.74 (m), 6.66-6.48 (m), 6.38-6.30 (m), 4.88-4.62 (m), 4.55-4.48 (m), 4.44-4.24 (m), 4.20-3.99 (m), 3.70-3.57 (m), 3.62-3.52 (m), 3.57-3.40 (m), 3.43-3.33 (m), 3.28-3.22 (m), 3.15-3.04 (m), 3.03-2.90 (m), 2.56-2.49 (m), 2.50 (s), 1.86-1.80 (m), 1.49-1.37 (m), 1.11 (s), 1.06 (s) ppm. MS (m/z): 1188.18 [M+H]$^+$.

Example 110

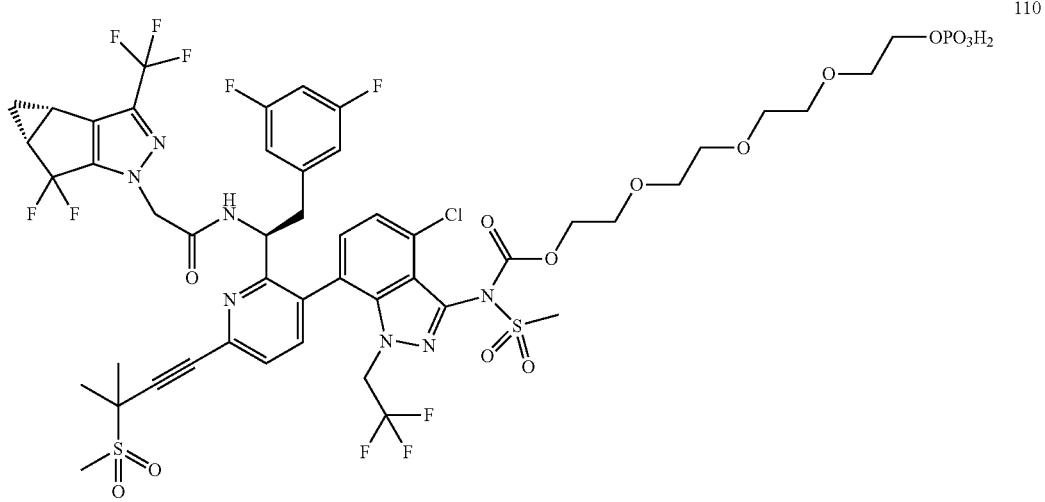

Synthesis of 2-(2-(2-(2-(phosphonooxy)ethoxy)ethoxy)ethoxy)ethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (110): An atropisomeric mixture of the title compound was prepared according to the method presented for the synthesis of 59A of Example 59 utilizing 109 in the place of 58A. $^1$H NMR (400 MHz, Methanol-$d_4$) δ 7.82-7.73 (m), 7.74-7.67 (m), 7.39-7.27 (m), 6.68-6.57 (m), 6.39-6.30 (m), 4.88-4.73 (m), 4.72-4.63 (m), 4.38 (s), 4.34-4.28 (m), 4.14-4.02 (m), 3.70 (s), 3.67-3.49 (m), 3.49 (s), 3.50-3.41 (m), 3.45-3.34 (m), 3.33-3.23 (m), 3.16-3.07 (m), 3.04-2.93 (m), 2.51 (s), 1.86-1.80 (m), 1.48-1.39 (m), 1.11 (s), 1.05 (s) ppm. MS (m/z): 1268.18 [M+H]$^+$.

Example 111

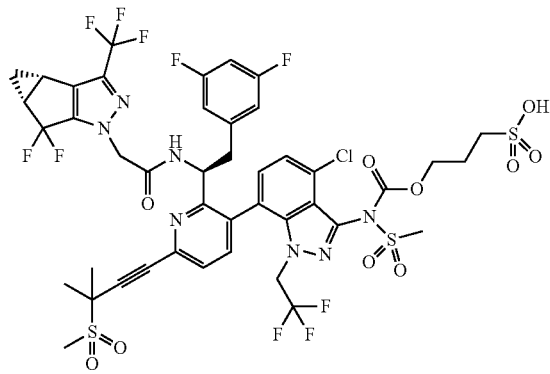

111

Synthesis of 3-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)propane-1-sulfonic acid (111): An atropisomeric mixture of the title compound was prepared according to the method presented for the synthesis of 94C of Example 94 utilizing 3-hydroxypropane-1-sulfonic acid in the place of 94B. $^1$H NMR (400 MHz, Methanol-$d_4$) δ 7.88-7.81 (m), 7.77-7.64 (m), 7.36-7.27 (m), 7.24-7.17 (m), 6.86-6.74 (m), 6.63-6.56 (m), 6.44-6.33 (m), 6.24-6.18 (m), 4.85-4.78 (m), 4.69-4.53 (m), 4.40-4.30 (m), 4.29-4.20 (m), 3.62-3.53 (m), 3.32-3.23 (m), 3.14-3.06 (m), 3.03-2.92 (m), 2.68 (s), 2.60-2.49 (m), 2.08-1.99 (m), 1.96 (s), 1.87-1.80 (m), 1.47-1.39 (m), 1.14-1.04 (m) ppm. MS (m/z) 1134.20 [M+H]$^+$.

Example 112

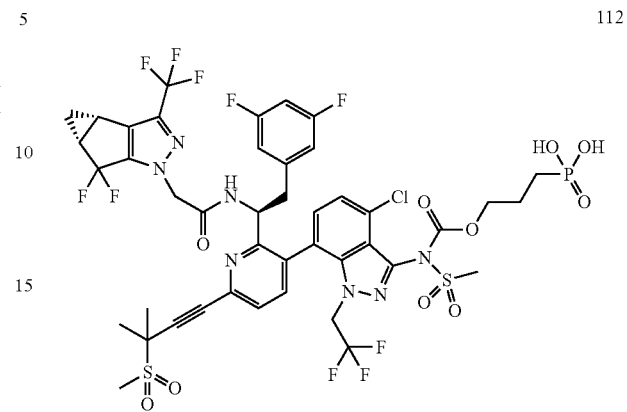

112

Synthesis of (3-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)propyl)phosphonic acid (112): An atropisomeric mixture of the title compound was prepared according to the method presented for the synthesis of 94 of Example 94 utilizing di-tert-butyl (3-hydroxypropyl)phosphonate in the place of 94B. $^1$H NMR (400 MHz, Methanol-$d_4$) δ 9.12 (s), 7.86-7.79 (m), 7.76-7.69 (m), 7.36-7.29 (m), 6.85-6.76 (m), 6.60-6.53 (m), 6.41-6.34 (m), 3.96-3.89 (m), 3.54 (s), 3.26 (s), 3.05-2.95 (m), 2.54 (s), 1.96 (s), 1.87-1.81 (m), 1.49-1.42 (m), 1.08 (s) ppm. MS (m/z) 1135.20 [M+H]$^+$.

Example 113

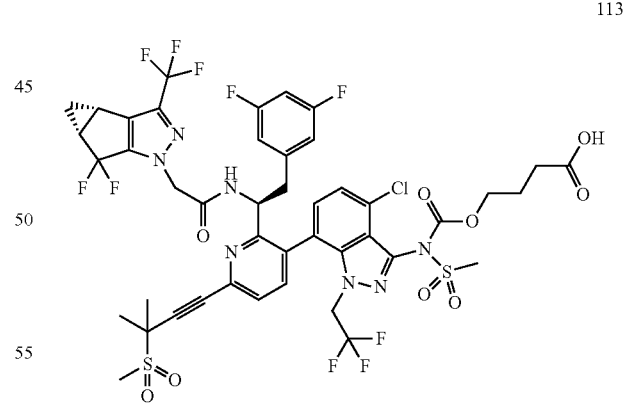

113

Synthesis of 3-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)propane-1-sulfonic acid (113): An atropisomeric mixture of the title compound was prepared according to the method presented for the synthesis of 94 of Example 94 utilizing tert-butyl 4-hydroxybutanoate in the place of 94B. $^1$H NMR (400 MHz, Methanol-d$_4$) δ 8.91-8.84 (m), 7.90-7.66 (m), 7.45-7.26 (m), 7.29-7.17 (m), 6.86-6.74 (m), 6.64-6.57 (m), 6.43-6.28 (m), 4.90-4.55 (m), 4.36-4.08 (m), 4.05-3.91 (m), 3.62-3.53 (m), 3.32-3.22 (m), 3.19-2.91 (m), 2.56-2.48 (m), 2.18-1.92 (m), 1.87-1.72 (m), 1.73 (s), 1.49-1.40 (m), 1.13-1.03 (m) ppm. MS (m/z) 1098.20 [M+H]$^+$.

Example 114

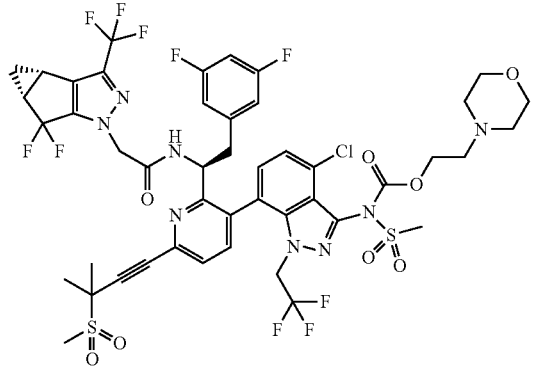

Synthesis of 2-morpholinoethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl) acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (114): An atropisomeric mixture of the title compound was prepared according to the method presented for the synthesis of 94C of Example 94 utilizing 2-morpholinoethan-1-ol in the place of 94B. $^1$H NMR (400 MHz, DMSO-d$_6$) δ 8.99 (s), 7.86-7.65 (m), 7.48-7.34 (m), 7.10-6.98 (m), 6.98-6.90 (m), 6.50 (s), 4.99-4.71 (m), 4.62 (s), 4.43 (s), 3.63 (s), 1.91 (s), 1.80-1.70 (m), 1.41 (s), 1.24 (s), 1.15 (s), 0.98 (s) ppm. MS (m/z) 1125.30 [M+H]$^+$.

Example 115

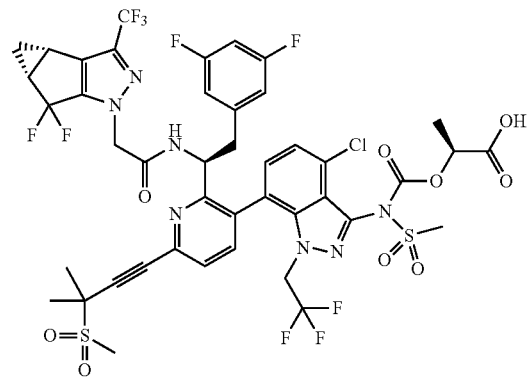

Synthesis of (S)-2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl) carbamoyl)oxy)propanoic acid (115): An atropisomeric mixture of the title compound was prepared according to the method presented for the synthesis of 94 of Example 94 utilizing tert-butyl-L-lactate in the place of 94B. $^1$H NMR δ (400 MHz, DMSO-d$_6$) 9.31-9.11 (m), 7.92-7.70 (m), 7.49-7.37 (m), 7.08-6.88 (m), 6.48 (ddd), 4.98-4.86 (m), 4.86-4.71 (m), 4.64 (ddt), 4.14-4.00 (m), 3.66 (d), 3.60 (s), 3.27 (d), 2.97 (dtt), 2.63-2.55 (m), 1.75 (d), 1.40 (p), 1.32 (d), 1.09 (s) ppm. $^{19}$F NMR (375 MHz, DMSO-d$_6$) δ −60.86 (q), −69.23--70.01 (m), −75.12, −79.90 (dd), −80.28--81.10 (m), −102.90--103.44 (m), −103.90 (dd), −110.48--111.11 (m) ppm. MS (m/z) 1085.06 [M+H]$^+$.

Example 116

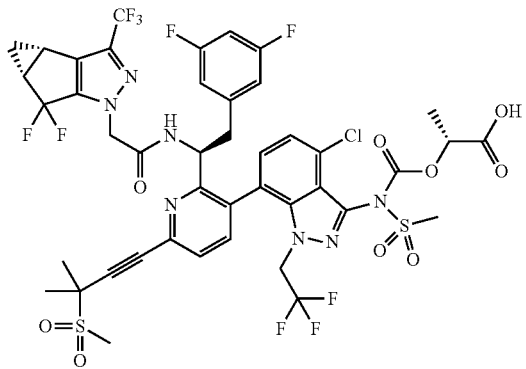

Synthesis of (R)-2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl) carbamoyl)oxy)propanoic acid (116): An atropisomeric mixture of the title compound was prepared according to the method presented for the synthesis of 94 of Example 94 utilizing tert-butyl-D-lactate in the place of 94B. $^1$H NMR (400 MHz, DMSO-d$_6$) δ 9.31-9.11 (m), 7.92-7.70 (m), 7.49-7.37 (m), 7.08-6.88 (m), 6.48 (ddd), 4.98-4.86 (m), 4.86-4.71 (m), 4.64 (ddt), 4.14-4.00 (m), 3.66 (d), 3.60 (s), 3.27 (d), 2.97 (dtt), 2.63-2.55 (m), 1.75 (d), 1.40 (p), 1.32 (d), 1.09 (d), 0.97 (q) ppm. $^{19}$F NMR (375 MHz, DMSO-d$_6$) δ −60.86 (q), −69.23--70.01 (m), −75.12, −79.90 (dd), −80.28--81.10 (m), −102.90--103.44 (m), −103.90 (dd), −110.48--111.11 (m) ppm. MS (m/z) 1085.06 [M+H]$^+$.

Example 117

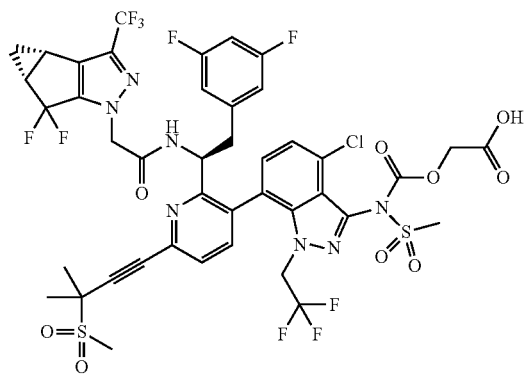

Synthesis of 2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)acetic acid (117): An atropisomeric mixture of the title compound was prepared according to the method presented for the synthesis of 94 of Example 94 utilizing tert-butyl-glycolate in the place of 94B. $^1$H NMR (400 MHz, DMSO-$d_6$) δ 13.28 (s), 9.22 (dd), 7.82 (d), 7.82-7.72 (m), 7.45 (dd), 7.08-6.97 (m), 6.56-6.44 (m), 4.93-4.55 (m), 4.16 (ddt), 3.70-3.62 (m), 3.50-3.45 (m), 3.04 (td), 2.94 (d), 2.74 (s), 2.58 (ddd), 2.54 (s), 1.75 (d), 1.46-1.34 (m), 0.98 (ddd) ppm. $^{19}$F NMR (375 MHz, DMSO-$d_6$) δ−60.49--61.09 (m), −69.18--69.84 (m), −74.78, −79.61--81.04 (m), −102.91--103.43 (m), −103.96, −110.70 (m) ppm. MS (m/z) 1071.03 [M+H]$^+$.

Example 118

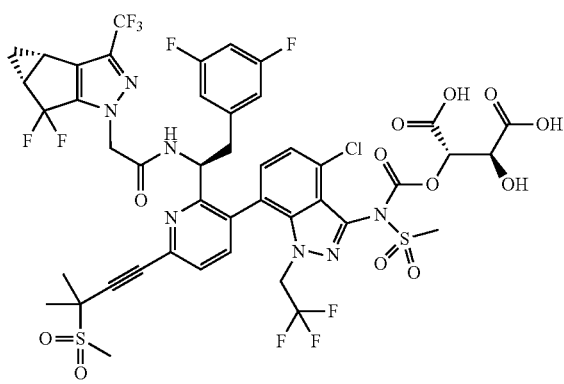

Synthesis of (2S,3S)-2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)-3-hydroxysuccinic acid (118): An atropisomeric mixture of the title compound was prepared according to the method presented for the synthesis of 94 of Example 94 utilizing di-tert-butyl D-tartrate in the place of 94B. $^1$H NMR (400 MHz, DMSO-$d_6$) δ 9.39-9.09 (m,), 7.84-7.71 (m), 7.47-7.36 (m), 7.02 (qt), 6.58-6.41 (m), 5.46-5.35 (m), 5.26-5.17 (m), 4.97-4.70 (m), 3.76-3.68 (m), 3.64 (s), 3.56 (d), 3.27 (s), 3.13-2.90 (m), 2.65-2.54 (m), 1.75 (t), 1.44-1.32 (m), 1.00 (s) ppm. $^{19}$F NMR (375 MHz, DMSO-$d_6$) δ−60.68--61.05 (m), −69.14--69.82 (m), −75.41, −75.43, −79.58--79.95 (m), −80.25--80.63 (m), −103.33, −103.62--104.12 (m), −110.46--111.08 (m) ppm. MS (m/z) 1144.293 [M+H]$^+$.

Example 119

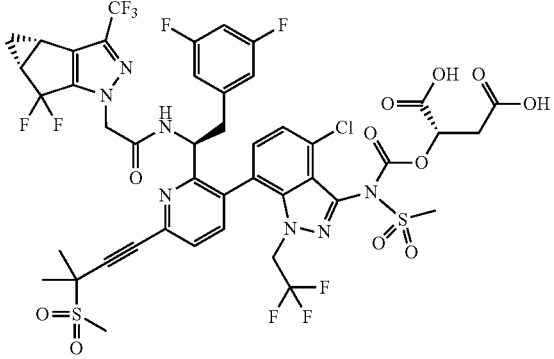

Synthesis of (S)-2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)succinic acid (119): An atropisomeric mixture of the title compound was prepared according to the method presented for the synthesis of 94 of Example 94 utilizing di-tert-butyl L-malate in the place of 94B. $^1$H NMR (400 MHz, DMSO-$d_6$) δ 9.23 (dd, J=28.3, 7.8 Hz, 1H), 7.86-7.71 (m, 2H), 7.42 (dd, J=7.7, 2.7 Hz, 1H), 7.02 (dd, J=10.6, 7.5 Hz, 2H), 6.94 (d, J=7.7 Hz, 1H), 6.50 (tdt, J=11.1, 7.9, 4.1 Hz, 3H), 5.45-5.30 (m, 1H), 4.97-4.49 (m, 6H), 3.71-3.53 (m, 6H), 3.27 (s, 4H), 3.01 (td, J=12.7, 11.6, 5.6 Hz, 2H), 2.89-2.75 (m, 2H), 1.74 (d, J=2.1 Hz, 8H), 1.52-1.27 (m, 1H), 1.00 (q, J=6.5, 6.0 Hz, 1H) ppm. $^{19}$F NMR (375 MHz, DMSO-$d_6$) δ−60.82 (dd), −69.30--69.49 (m), −69.65 (t), −75.28, −79.81 (dd), −80.48 (dd), −103.22 (dd), −103.90 (dd), −110.63 (dt), −110.81 (dd) ppm. MS (m/z) 1129.085 [M+H]$^+$.

Example 120

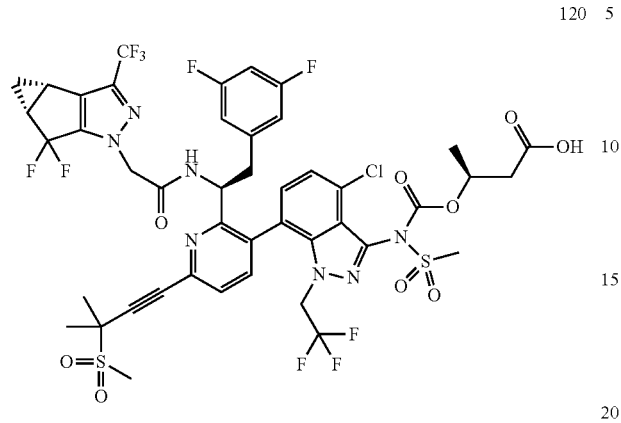

Synthesis of (S)-3-(((4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)butanoic acid (120): An atropisomeric mixture of the title compound was prepared according to the method presented for the synthesis of 94 of Example 94 utilizing (S)-3-hydroxybutanoic acid tert-butyl ester in the place of 94B. $^1$H NMR (400 MHz, DMSO-d$_6$) δ 9.24-9.12 (m, 1H), 7.87-7.72 (m, 2H), 7.53-7.26 (m, 1H), 7.08-6.99 (m, 2H), 6.54 (s, 2H), 6.51-6.44 (m, 3H), 6.45-6.34 (m, 1H), 5.12-5.05 (m, 1H), 4.94 (s, 1H), 4.92-4.79 (m, 1H), 4.80-4.66 (m, 2H), 4.66-4.57 (m, 2H), 3.96 (s, 1H), 3.65-3.51 (m, 3H), 3.28 (s, 2H), 3.05-2.90 (m, 4H), 1.78-1.72 (m, 14H), 1.44-1.31 (m, 2H), 1.28-1.21 (m, 1H), 1.23-1.06 (m, 1H), 1.10-0.94 (m, 4H), 0.70-0.64 (m, 1H) ppm. MS (m/z) 1098.10 [M+H]$^+$.

Example 121

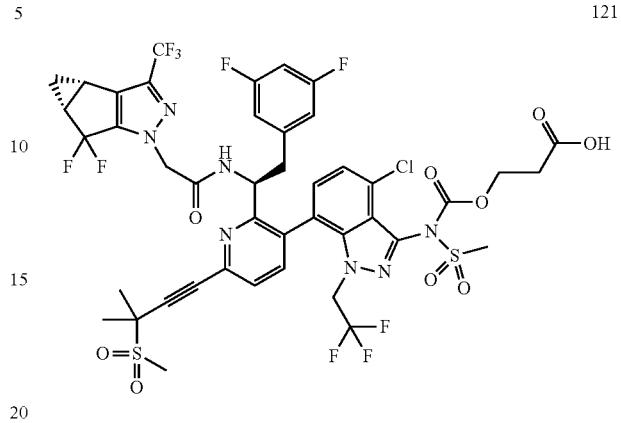

Synthesis of 3-(((4-chloro-7-(2-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)propanoic acid (121): An atropisomeric mixture of the title compound was prepared according to the method presented for the synthesis of 94 of Example 94 utilizing 3-hydroxypropanoic acid tert-butyl ester in the place of 94B. $^1$H NMR (400 MHz, DMSO-d$_6$) δ 9.24-9.12 (m), 7.87-7.72 (m), 7.53-7.26 (m), 7.08-6.99 (m), 6.54 (s), 6.51-6.44 (m), 6.45-6.34 (m), 5.12-5.05 (m), 4.94 (s), 4.92-4.79 (m), 4.80-4.66 (m), 4.66-4.57 (m), 3.96 (s), 3.65-3.51 (m), 3.28 (s), 3.05-2.90 (m), 1.78-1.72 (m), 1.44-1.31 (m), 1.28-1.21 (m), 1.23-1.06 (m), 1.10-0.94 (m), 0.70-0.64 (m) ppm. MS (m/z) 1084.44 [M+H]$^+$.

Example 122

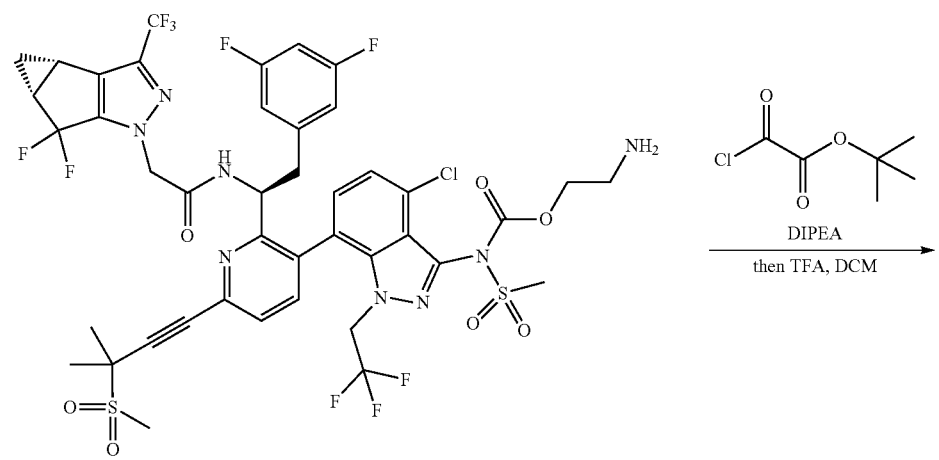

122A

-continued

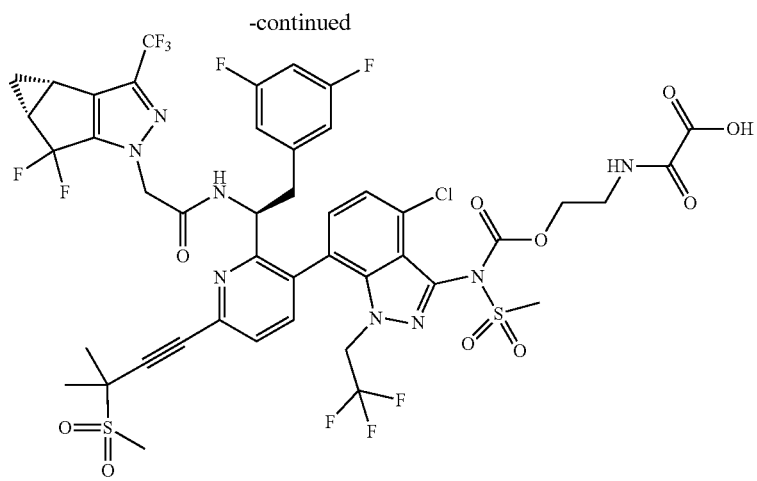

122

Synthesis of 2-aminoethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (122A): An atropisomeric mixture of the title compound was prepared according to the method presented for the synthesis of 94 of Example 94 utilizing N-Boc-ethanolamine in the place of 94B. MS (m/z) 1055.288 [M+H]⁺.

Synthesis of 2-((2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)ethyl)amino)-2-oxoacetic acid (122): To a solution of 122A (0.057 mmol) in DCM (0.5 mL) was added DIPEA (0.853 mmol) followed by tert-butyl-2-chloro-2-oxoacetate (0.513 mmol) and the resulting mixture was stirred for 10 mins. Trifluoroacetic acid (6.530 mmol) was then added with a further 10 mins stirring at which time the reaction was diluted with 1:1 H₂O:MeCN (1 mL). The reaction contents were then transferred to a separatory funnel with DCM (15 mL) and washed once with 1M HCl (20 mL). The organic fraction was collected, dried over Na₂SO₄, concentrated under reduced pressure, and purified by reverse phase HPLC. Fractions containing the product were pooled and lyophilized to give the title compound 122 as a mixture of atropisomers. ¹H NMR (400 MHz, Methanol-d₄) δ 9.05 (d), 7.81 (d), 7.76-7.53 (m), 7.30 (d), 6.90 (d), 6.80 (t), 6.53 (d), 6.41 (d), 4.45 (s), 4.27 (s), 4.04-3.93 (m), 3.54 (s), 3.25 (s), 3.05-2.95 (m), 2.51 (s), 2.26 (t), 2.17-2.08 (m), 1.84 (s), 1.44 (q), 1.07 (s) ppm. MS (m/z) 1127.046 [M+H]⁺.

Example 123

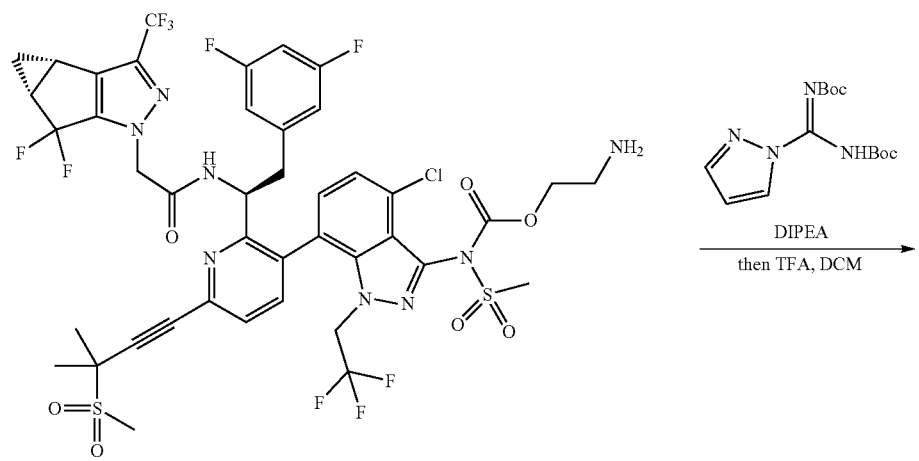

122A

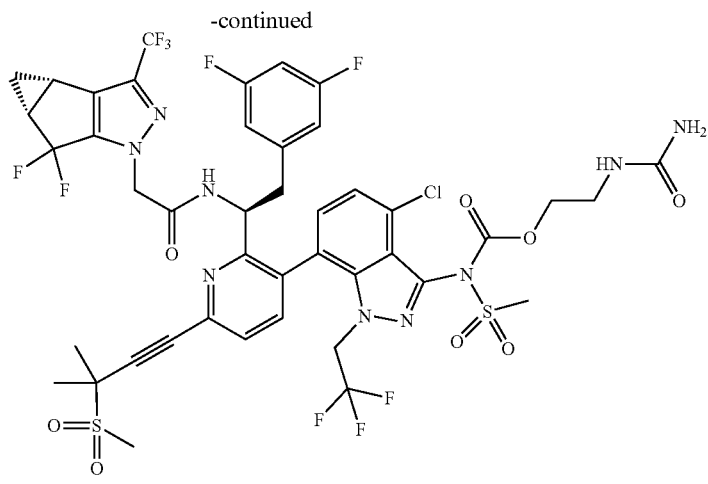

123

Synthesis of 2-guanidinoethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (123): An atropisomeric mixture of the title compound was prepared according to the method presented for the synthesis of 8 of Example 8 utilizing 122A in the place of 7. $^1$H NMR (400 MHz, Methanol-d$_4$) δ 9.38-9.31 (m, 1H), 7.95-7.84 (m, 1H), 7.81-7.69 (m, 1H), 7.45-7.38 (m, 1H), 7.35-7.26 (m), 6.95-6.88 (m, 1H), 6.84-6.74 (m, 1H), 6.69-6.60 (m), 6.37-6.29 (m, 3H), 4.99-4.89 (m, 1H), 4.83-4.67 (m, 2H), 4.67-4.58 (m), 4.52-4.38 (m, 1H), 4.19-3.98 (m, 2H), 3.64-3.54 (m, 4H), 3.51-3.43 (m), 3.33-3.22 (m), 3.25 (s, 4H), 3.19-2.89 (m, 3H), 2.58-2.48 (m, 1H), 1.84 (s, 7H), 1.86-1.81 (m, 2H), 1.51-1.39 (m, 1H), 1.13-1.03 (m) ppm. MS (m/z) 1097.30 [M+H]$^+$.

Example 124

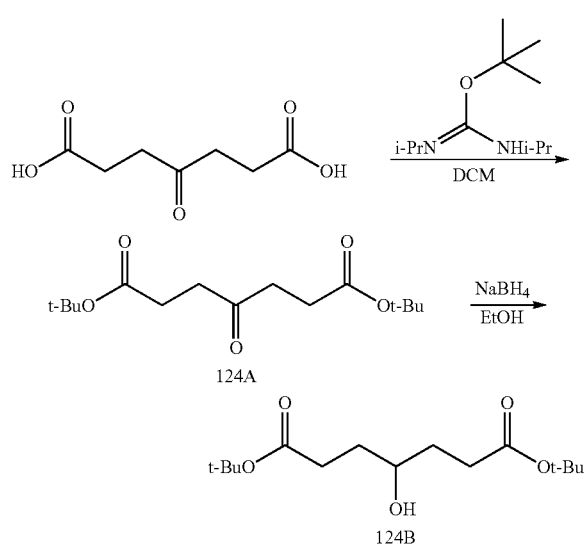

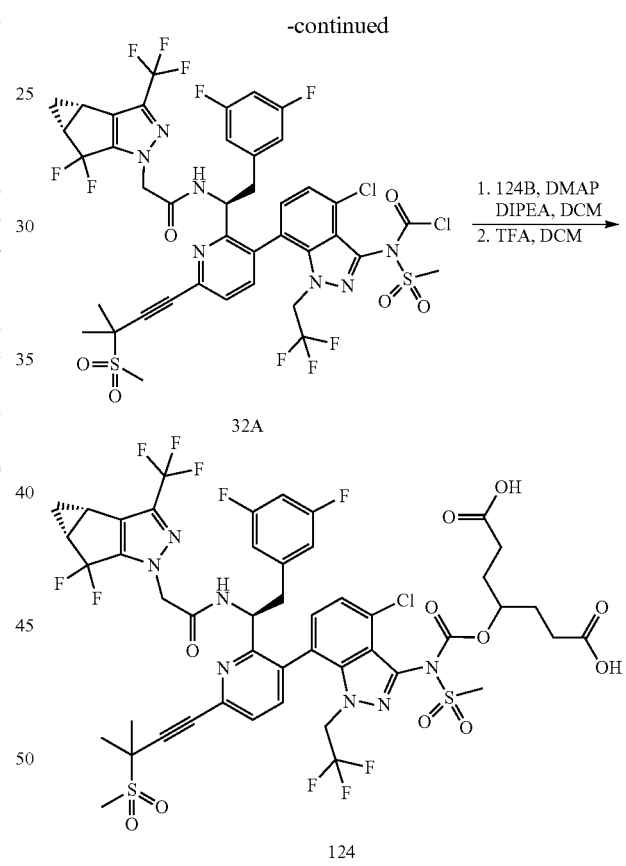

Synthesis of di-tert-butyl 4-oxoheptanedioate (124A): To a suspension of 4-oxoheptanedioic acid (2.87 mmol) in DCM (2 mL) was added 2-tert-butyl-1,3-diisopropylurea (14.4 mmol, 5 equiv). Upon completion of the reaction, the mixture was filtered and the filter cake rinsed with 20 mL of DCM. The mother liquor was concentrated under reduced pressure and purified via silica gel chromatography. Fractions containing the product were pooled and concentrated to give the title compound 124A. MS (m/z) 286.35 [M+H]$^+$.

Synthesis of di-tert-butyl 4-hydroxyheptanedioate (124B): To a solution of 124A (1.22 mmol) in EtOH (5 mL) at −10° C., was added portionwise sodium borohydride (3.67 mmol, 3 equiv). Upon completion, the reaction was concentrated under reduced pressure and the residue partitioned between 1M aqueous NaOH (5 mL) and EtOAc (50 mL). The organic fraction was collected, dried over $Na_2SO_4$, and concentrated under reduced pressure to yield the title compound 124B, which was used without purification. MS (m/z) 311.20 $[M+Na]^+$.

Synthesis of 4-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)heptanedioic acid (124): The title compound was prepared according to the method presented for the synthesis of 94 of Example 94 utilizing 124B in the place of 94B. $^1$H NMR (400 MHz, DMSO-$d_6$) δ 12.10 (s), 9.21 (d), 7.85-7.69 (m), 7.49-7.37 (m), 7.01 (t), 6.60-6.37 (m), 5.04-4.53 (m), 4.23-3.93 (m), 3.67-3.53 (m), 3.27 (s), 2.96 (s), 2.12 (q), 1.75 (q), 1.58 (d), 1.46-1.31 (m) ppm. $^{19}$F NMR (375 MHz, DMSO-$d_6$) δ 19F NMR (376 MHz, DMSO-$d_6$) δ −60.76−−60.87 (m), −60.91, −69.48 (d), −69.58 (t), −69.86 (t), −74.05, −110.63 (d) ppm. MS (m/z) 1169.93 $[M+H]^+$.

Example 125

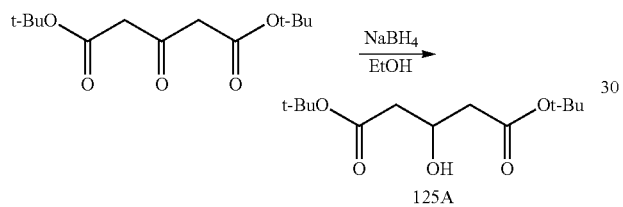

Synthesis of di-tert-butyl 3-hydroxypentanedioate (125A): To a solution of di-tert-butyl 3-oxopentanedioate (1.35 mmol) in EtOH (5 mL) at −10° C., was added portionwise sodium borohydride (2.03 mmol, 1.5 equiv). Upon completion, the reaction was concentrated under reduced pressure and the residue partitioned between 1M aqueous NaOH (5 mL) and EtOAc (50 mL). The organic fraction was collected, dried over $Na_2SO_4$, and concentrated under reduced pressure to yield the title compound 125A, which was used without purification. MS (m/z) 283.35 $[M+Na]^+$.

Synthesis of 3-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)pentanedioic acid (125): An atropisomeric mixture of the title compound was prepared according to the method presented for the synthesis of 94 of Example 94 utilizing 125A in the place of 94B. $^1$H NMR (400 MHz, DMSO-$d_6$) δ 9.23-9.13 (m), 7.97-7.90 (m), 7.84-7.71 (m), 7.46-7.23 (m), 7.05-6.95 (m), 6.89-6.82 (m), 6.46 (s), 5.43-5.36 (m), 4.96-4.83 (m), 4.84-4.68 (m), 4.65-4.56 (m), 1.91 (s), 1.77-1.71 (m), 1.43-1.35 (m), 1.24 (s), 1.19-1.13 (m), 0.98 (s), −0.06 (s). MS (m/z): 1142.04 $[M+H]^+$.

Example 126

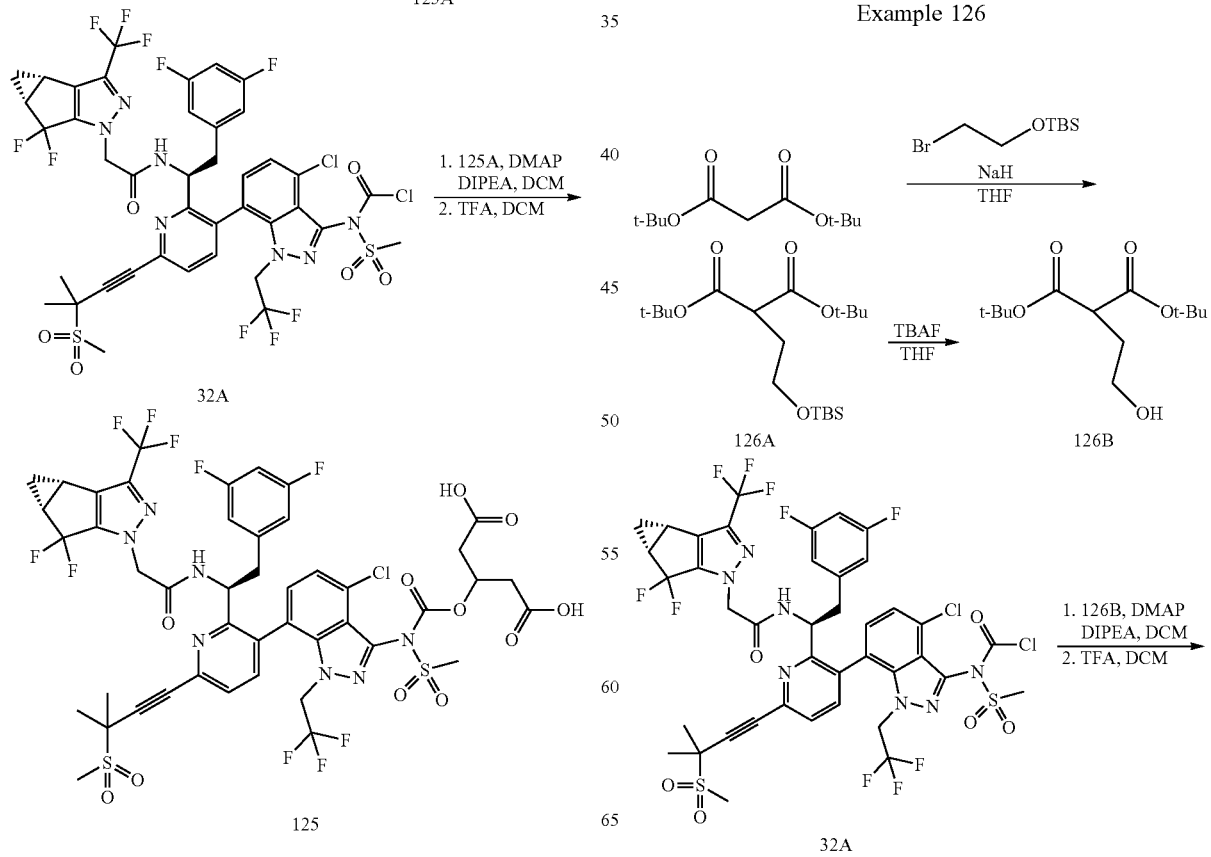

353

-continued

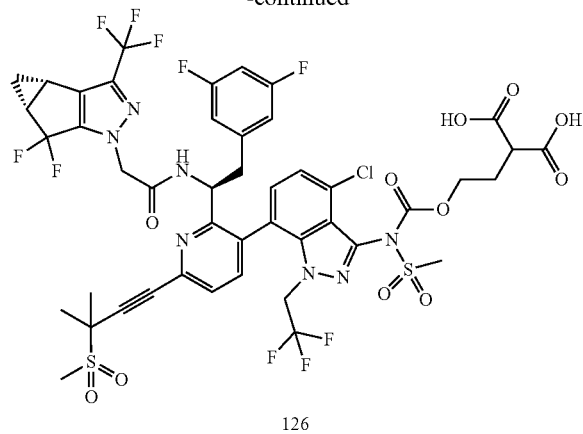

126

Synthesis of di-tert-butyl 2-(2-((tert-butyldimethylsilyl)oxy)ethyl)malonate (126A): To a solution of di-tert-butyl malonate (1.09 mmol) in THF (3 mL) at 0° C. was added NaH (60% dispersion in mineral oil, 0.684 mmol, 0.63 equiv) and the mixture was allowed to stir for 30 mins. At completion of this time, (2-bromoethoxy)-tert-butyldimethylsilane (1.19 mmol, 1.1 equiv) was added and the mixture was allowed to stir. When the reaction had reached completion, it was partitioned between EtOAc (15 mL) and water (15 mL). The organic fraction was dried over $Na_2SO_4$, concentrated under reduced pressure, and purified by silica gel chromatography. Fractions containing the product were pooled and concentrated to give the title compound 126A. MS (m/z) 411.61 [M+Na]$^+$.

354

Synthesis of di-tert-butyl 2-(2-hydroxyethyl)malonate (126B): To a solution of 126A (0.317 mmol) in THF (3 mL) was added TBAF (1M solution in THF, 0.475 mmol, 1.5 equiv). When the reaction had reached completion, the mixture was partitioned between EtOAc (15 mL) and water (15 mL). The organic fraction was dried over $Na_2SO_4$, concentrated under reduced pressure, and purified by silica gel chromatography. Fractions containing the product were pooled and concentrated to give the title compound 126B. MS (m/z) 274.35 [M+H]$^+$.

Synthesis of 2-(2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)ethyl)malonic acid (126): An atropisomeric mixture of the title compound was prepared according to the method presented for the synthesis of 94 of Example 94 utilizing 126B in the place of 94B. $^1$H NMR (400 MHz, DMSO-d$_6$) δ 12.82 (s), 9.21 (dd), 7.86-7.71 (m), 7.47-7.25 (m), 7.07-6.97 (m), 6.70 (d), 6.48 (ddd), 4.87 (dd), 4.84-4.70 (m), 4.71-4.52 (m), 4.31-4.21 (m), 4.25-4.10 (m), 4.04 (dd), 3.60 (d), 3.27 (s), 3.22 (d), 3.14-2.87 (m), 2.58 (dt), 2.07-1.94 (m), 1.92 (q), 1.75 (d), 1.40 (q), 0.98 (d) ppm. 19F NMR (375 MHz, DMSO-d$_6$) δ -60.56--61.20 (m), -60.94, -69.21--69.80 (m), -79.45--80.07 (m), -80.41 (d), -103.10, -103.18 (d), -103.52--104.20 (m), -110.33--111.10 (m) ppm. MS (m/z) 1142.09 [M+H]$^+$.

Example 127

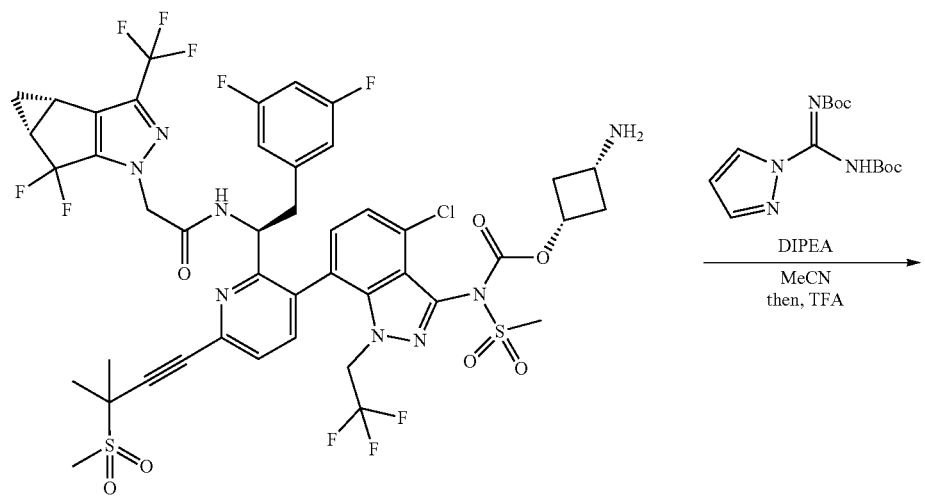

127A

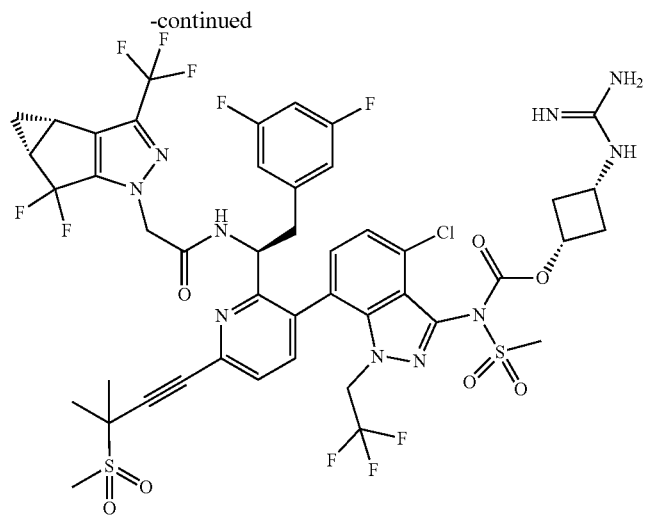

127

Synthesis of cis-3-aminocyclobutyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (127A): An atropisomeric mixture of the title compound was prepared according to the method presented for the synthesis of 94 of Example 94 utilizing tert-butyl (cis-3-hydroxycyclobutyl) carbamate in the place of 94B. MS (m/z) 1081.13 [M+H]⁺.

Synthesis of cis-3-guanidinocyclobutyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl) carbamate (127): An atropisomeric mixture of the title compound was prepared according to the method presented for the synthesis of 8 of Example 8 utilizing 127A in the place of 7. ¹H NMR (400 MHz, DMSO-d₆) δ 9.30-9.16 (m), 7.93-7.72 (m), 7.51-7.41 (m), 7.09-6.95 (m), 6.89 (s), 6.71 (s), 6.53 (s), 6.46 (s), 4.97-4.88 (m), 4.86-4.72 (m), 3.99 (s), 2.00-1.89 (m), 1.81 (s), 1.75 (s), 1.44-1.36 (m), 1.34 (s), 1.24 (s), 0.97 (s) ppm. MS (m/z): 1223.06 [M+H]⁺.

Example 128

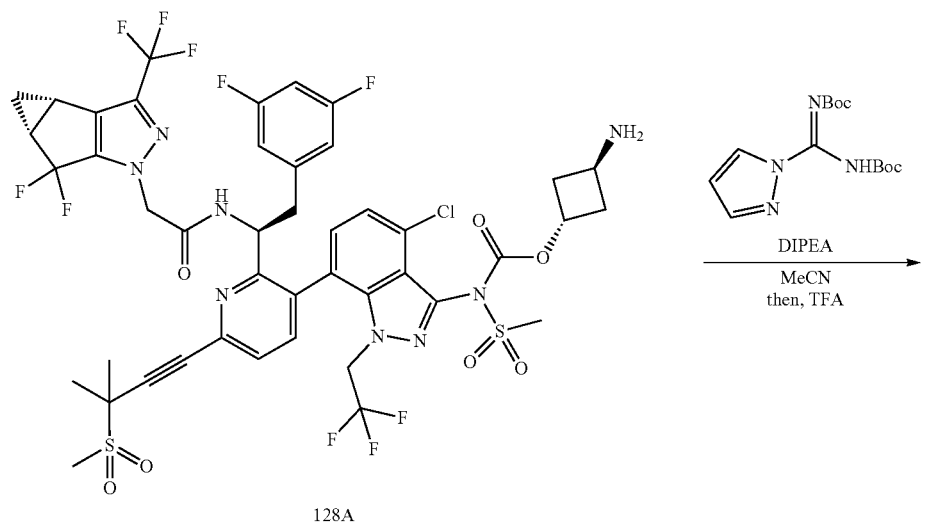

128A

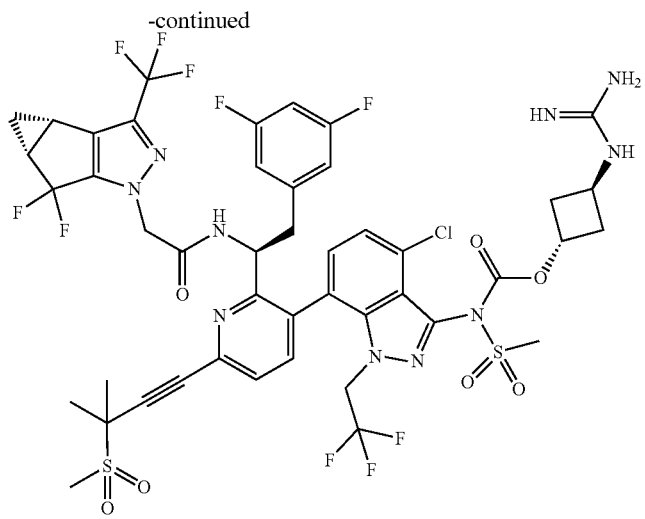

128

Synthesis of trans-3-aminocyclobutyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (128A): An atropisomeric mixture of the title compound was prepared according to the method presented for the synthesis of 94 of Example 94 utilizing tert-butyl (trans-3-hydroxycyclobutyl) carbamate in the place of 94B. MS (m/z) 1081.13 [M+H]$^+$.

Synthesis of trans-3-guanidinocyclobutyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (128): An atropisomeric mixture of the title compound was prepared according to the method presented for the synthesis of 8 of Example 8 utilizing 128A in the place of 7. $^1$H NMR (400 MHz, DMSO-d$_6$) δ 9.43-9.14 (m), 8.11-7.64 (m), 7.59-7.23 (m), 7.07-6.78 (m), 6.55-6.33 (m), 5.06-4.52 (m), 3.77-3.53 (m), 1.84-1.70 (m), 1.47-1.29 (m), 1.29-1.10 (m), 0.98 (s).MS (m/z) 1223.08 [M+H]$^+$.

Example 129

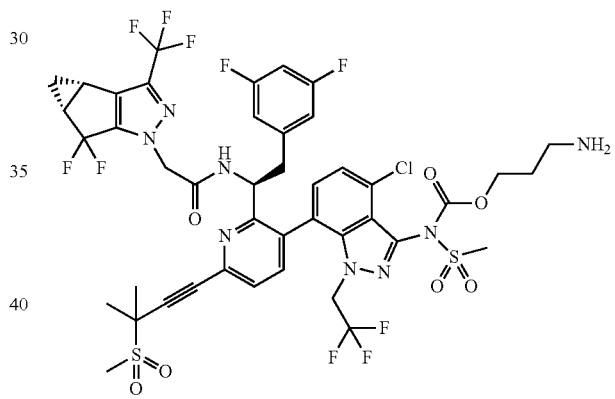

129

Synthesis of 3-aminopropyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (129): An atropisomeric mixture of the title compound was prepared according to the method presented for the synthesis of 94 of Example 94 utilizing tert-butyl N-(3-hydroxypropyl)carbamate in the place of 94B. $^1$H NMR (400 MHz, DMSO-d$_6$) δ 9.31-9.18 (m), 7.88-7.71 (m), 7.67 (s), 7.50-7.40 (m), 7.09-6.97 (m), 6.57-6.42 (m), 4.96-4.81 (m), 4.83-4.54 (m), 4.39-4.03 (m), 3.68-3.58 (m), 3.30-3.24 (m), 3.09-2.83 (m), 2.79-2.53 (m), 1.94-1.78 (m), 1.79-1.72 (m), 1.47-1.34 (m), 1.31-1.21 (m), 1.01-0.94 (m) ppm. $^{19}$F NMR (375 MHz, DMSO-d$_6$) δ −60.75--−61.00 (m), −69.29--−69.53 (m), −69.66--−69.81 (m), −74.53, −74.50--−74.62 (m), −79.76--−79.91 (m), −80.43--−80.59 (m), −103.08--−103.18 (m), −103.27, −103.76--−103.85 (m), −103.88--−103.98 (m), −110.57--−110.86 (m) ppm. MS (m/z) 1069.23 [M+H]$^+$.

Example 130

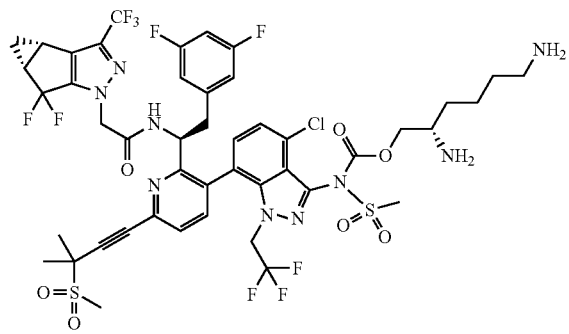

130

Synthesis of (S)-2,6-diaminohexyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (130): An atropisomeric mixture of the title compound was prepared according to the method presented for the synthesis of 94 of Example 94 utilizing di-tert-butyl (6-hydroxy-hexane-1,5-diyl)(S)-dicarbamate in the place of 94B. $^1$H NMR (400 MHz, DMSO-$d_6$) δ 8.17 (d), 7.93 (t), 7.88-7.69 (m), 7.47 (t), 7.09-6.94 (m), 6.48 (h), 4.88 (dd), 4.75 (d), 4.71-4.55 (m), 4.38 (ddd), 4.01 (dd), 3.64 (d), 3.26 (s), 3.11-2.91 (m), 2.83-2.69 (m), 2.59 (ddd), 1.75 (s), 1.61-1.42 (m), 1.30 (hept), 0.99-0.91 (m) ppm. $^{19}$F NMR (375 MHz, DMSO-$d_6$) δ −60.43−−61.20 (m), −69.56 (dt), −74.51, −79.27−−80.95 (m), −102.77−−104.15 (m), −110.25−−111.15 (m) ppm. MS (m/z) 1126.21 [M+H]$^+$.

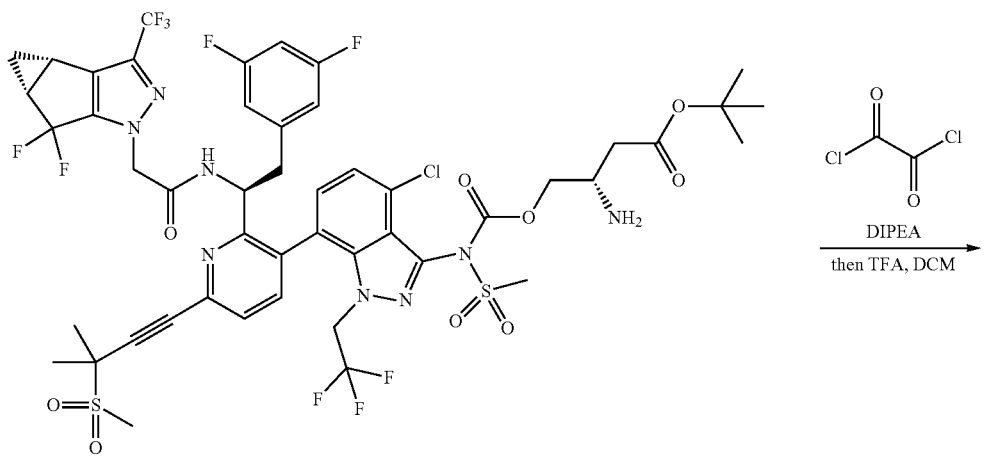

131A

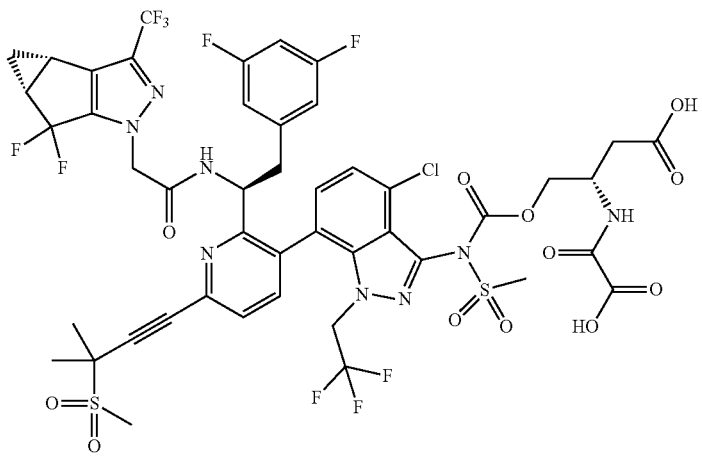

131

Synthesis of (S)-2,6-diaminohexyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (131A): An atropisomeric mixture of the title compound was prepared according to the method presented for the synthesis of 94 of Example 94 utilizing tert-butyl (S)-3-((tert-butoxycarbonyl)amino)-4-hydroxybutanoate in the place of 94B. MS (m/z) 1169.59 [M+H]$^+$.

Synthesis of (S)-2,6-diaminohexyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (131): To a solution of 131A (0.056 mmol) in DCM (3 mL) was added oxalyl chloride (0.117 mmol, 2.1 equiv) followed by DIPEA (0.222 mmol, 4 equiv). When the reaction had reached completion, aqueous MeCN was added (1 mL of 1:1 water:MeCN) followed by TFA (2 mL). When the reaction was complete, the reaction was concentrated under reduced pressure and purified by reverse phase HPLC. Fractions containing the product were pooled and lyophilized to give an atropisomeric mixture of the title compound 131. $^1$H NMR (400 MHz, DMSO-d$_6$) δ 9.25-9.14 (m), 9.05-8.97 (m), 8.78-8.59 (m), 7.98-7.87 (m), 7.85-7.69 (m), 7.45-7.32 (m), 7.32-7.18 (m), 7.14 (s), 7.08-6.98 (m), 6.98-6.86 (m), 6.80-6.73 (m), 6.70 (s), 6.62-6.47 (m), 4.91-4.62 (m), 4.67-4.49 (m), 4.40-4.33 (m), 4.31-4.14 (m), 3.27 (s), 3.13-2.95 (m), 2.65-2.55 (m), 2.44-2.34 (m), 1.79-1.72 (m), 1.46-1.33 (m), 1.03-0.91 (m), 0.86 (s) ppm. $^{19}$F NMR (376 MHz, DMSO-d$_6$) δ−60.80, −60.85--60.93 (m), −69.23--69.50 (m), −69.66--69.78 (m), −75.06, −79.72--79.86 (m), −80.39--80.54 (m), −103.28, −103.89--103.99 (m), −110.60--110.77 (m) ppm. MS (m/z) 1185.06 [M+H]$^+$.

Example 132

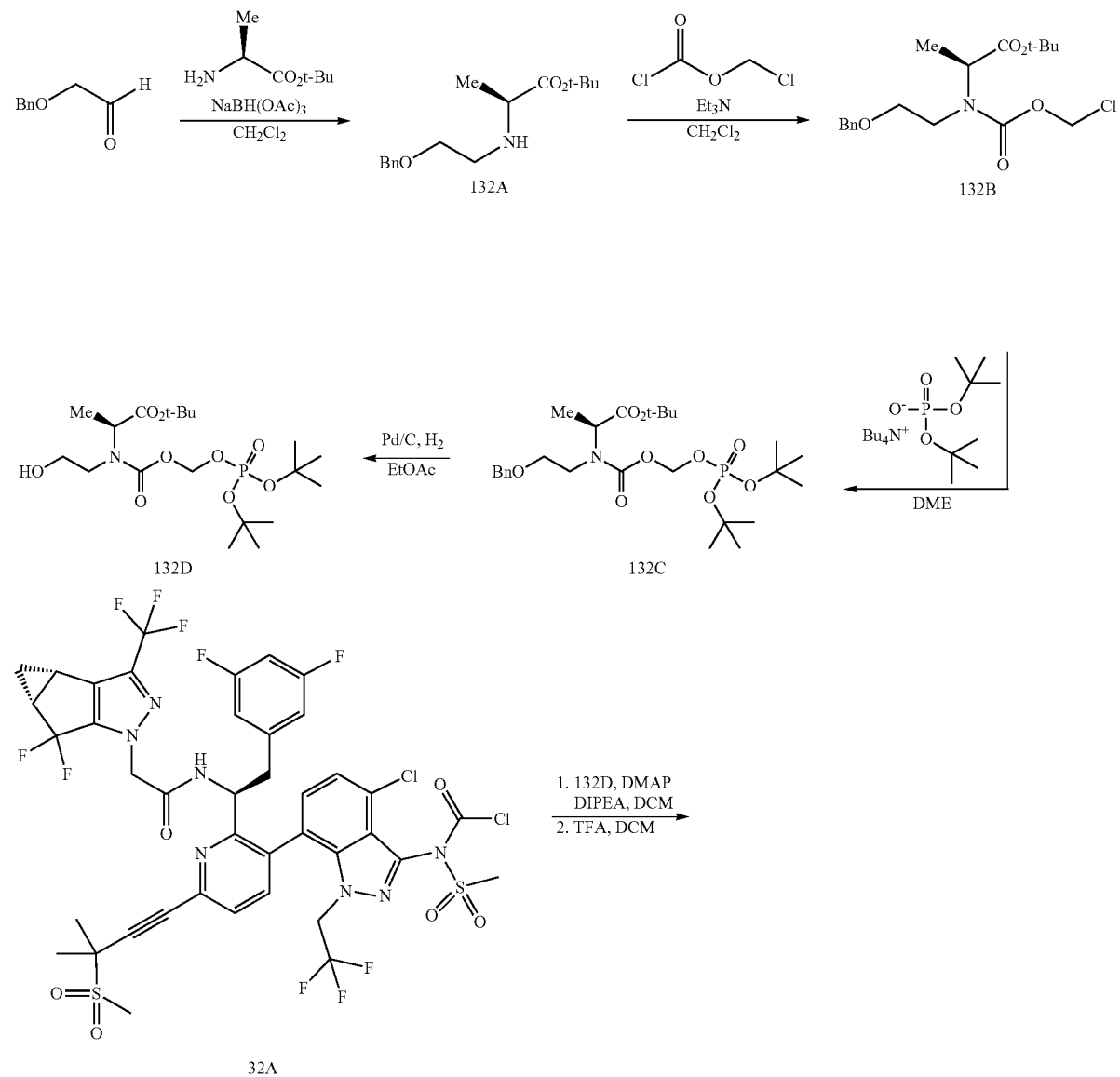

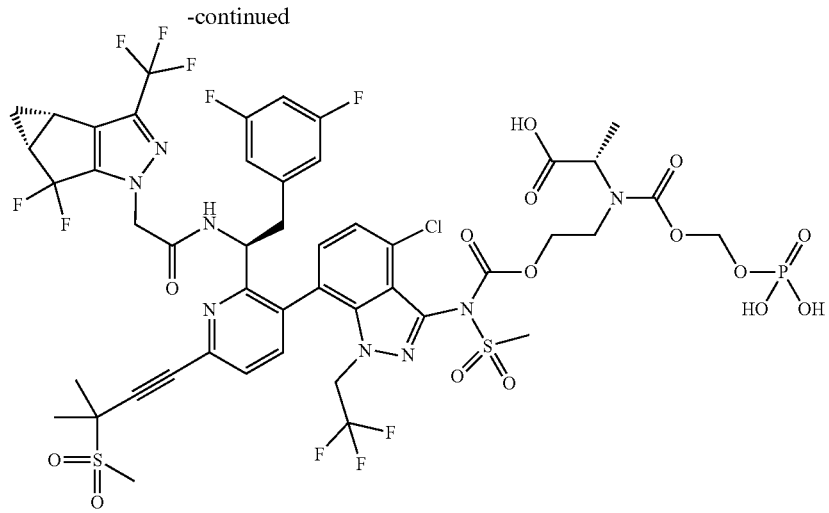

132

Synthesis of tert-butyl (2-(benzyloxy)ethyl)-L-alaninate (132A): To a solution of 2-benzyloxyacetaldehyde (13 mmol) in CH$_2$Cl$_2$ (44 mL) was added L-Alanine t-butyl ester hydrochloride (7.2 mmol) and the resulting mixture was stirred at room temperature before the addition of sodium triacetoxyborohydride (20 mmol). The resulting reaction mixture was stirred at room temperature for 16 h. After completion, the reaction mixture was poured into an ice-water mixture and treated with a sat. aq. solution of NaHCO$_3$ and extracted with CH$_2$Cl$_2$. The combined organic layers were dried over anhydrous Na$_2$SO$_4$, filtered, and concentrated. The crude mixture was purified by column chromatography (10% to 50% EtOAc in hexanes). Fractions containing the product were pooled and lyophilized to yield the title compound 132A. MS (m/z) 280.4 [M+H]$^+$.

Synthesis of tert-butyl N-(2-(benzyloxy)ethyl)-N-((chloromethoxy)carbonyl)-L-alaninate (132B): To a stirred solution of 132A (7.2 mmol) in CH$_2$Cl$_2$ (24 mL) at 0° C. was added triethylamine (18 mmol). Chloromethyl chloroformate (9.5 mmol) was then added and the reaction mixture was stirred at 0° C. and monitored by TLC and LCMS. After completion, the reaction mixture was washed with sat. aq. solutions of NH$_4$Cl and brine. The combined organic layers were dried over anhydrous Na$_2$SO$_4$, filtered, and concentrated to yield the title compound 132B, which was directly used in the subsequent reaction without purification. MS (m/z): 394.6 [M+Na]$^+$.

Synthesis of tert-butyl N-(2-(benzyloxy)ethyl)-N-((((di-tert-butoxyphosphoryl)oxy)methoxy)carbonyl)-L-alaninate (132C): 132B (7.2 mmol) was dissolved in dimethoxyethane (14 mL) then di-t-butyl phosphate tetrabutylammonium salt (9.4 mmol) was added and the mixture was heated to 80° C. for 1 h. The mixture was cooled to room temperature and concentrated. The crude material was dissolved in EtOAc and washed with water (3×), brine, dried over Na$_2$SO$_4$, filtered, and concentrated. The crude mixture was purified by column chromatography (50% to 100% EtOAc in hexanes) to afford the title compound 132C. $^1$H NMR (400 MHz, Chloroform-d) δ 7.39-7.29 (m, 5H), 5.67-5.55 (m, 2H), 4.53 (s, 2H), 4.44-4.35 (m, 1H), 3.72-3.58 (m, 3H), 3.50-3.38 (m, 1H), 1.51 (s, 18H), 1.45 (d, J=2.3 Hz, 9H) ppm.

Synthesis of tert-butyl N-((((di-tert-butoxyphosphoryl)oxy)methoxy)carbonyl)-N-(2-hydroxyethyl)-L-alaninate (132D): 132C (4.3 mmol) was dissolved in EtOAc (22 mL) then palladium on carbon (0.43 mmol) was added. After stirring for 24 h under hydrogen gas (1 atm), the crude product was isolated after filtration over a pad of Celite. Upon concentration, the crude was purified by column chromatography (50% to 100% EtOAc in hexanes) to afford the title compound 132D. $^1$H NMR (400 MHz, Chloroform-d) δ 5.70-5.57 (m, 2H), 4.45-4.26 (m, 1H), 3.82-3.75 (m, 2H), 3.63-3.55 (m, 1H), 3.48-3.37 (m, 1H), 1.53-1.46 (m, 30H) ppm. MS (m/z): 478.6 [M+Na]$^+$.

Synthesis of N-(2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)ethyl)-N-(((phosphonooxy)methoxy)carbonyl)-L-alanine (132): An atropisomeric mixture of the title compound was prepared according to the method presented for the synthesis of 94 of Example 94 utilizing 132D in the place of 94B. $^1$H NMR (400 MHz, DMSO) δ 9.44-8.93 (m), 8.06-7.65 (m), 7.45 (dd), 7.42-7.18 (m), 7.17-6.96 (m), 6.67-6.34 (m), 5.64-5.23 (m), 5.00-4.50 (m), 4.41-4.10 (m), 4.06-3.86 (m), 3.73 (d), 3.64 (s), 3.62-3.53 (m), 3.27 (d), 3.10-2.92 (m), 1.79-1.71 (m), 1.47-1.34 (m), 1.10 (d), 1.02-0.89 (m). $^{19}$F NMR (376 MHz, DMSO) δ -60.73--61.03 (m), -67.38--71.36 (m), -79.13--80.81 (m), -102.75--104.07 (m), -109.93--111.49 (m). MS (m/z) 1282.100 [M+H]$^+$.

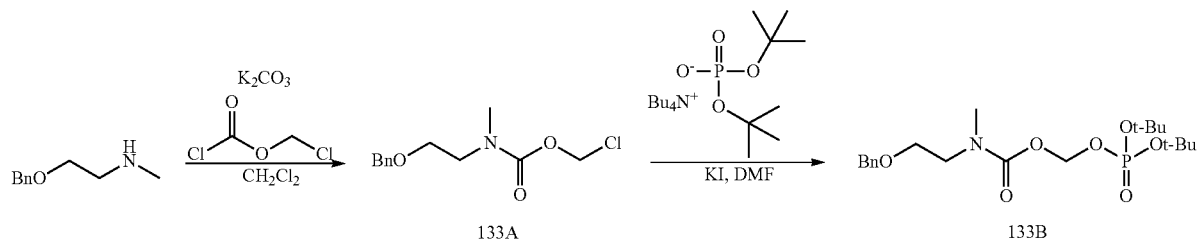
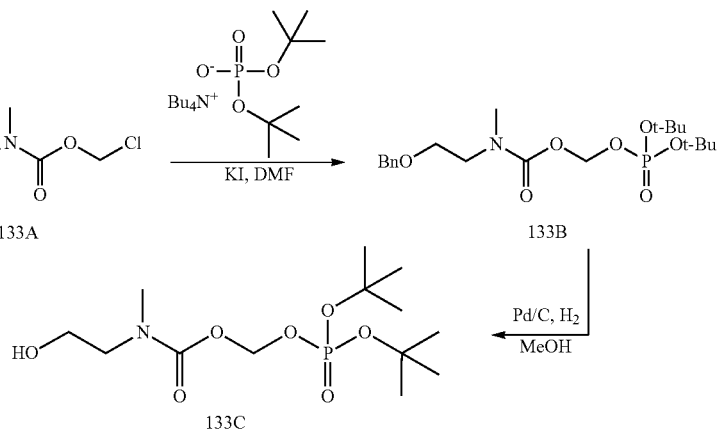

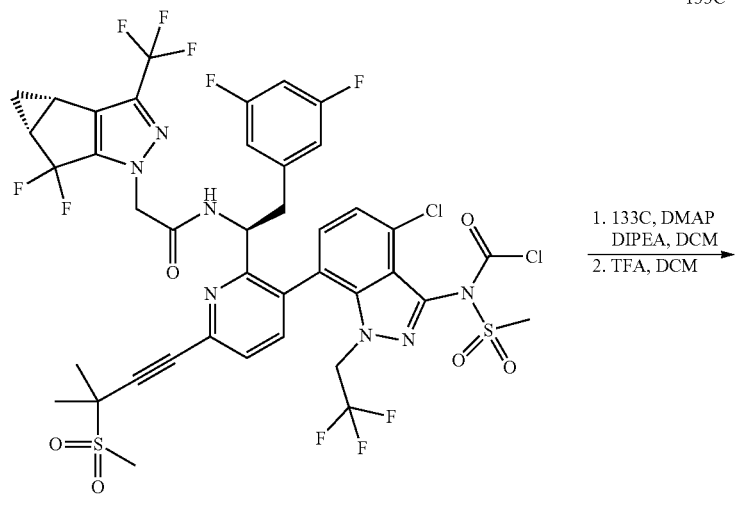

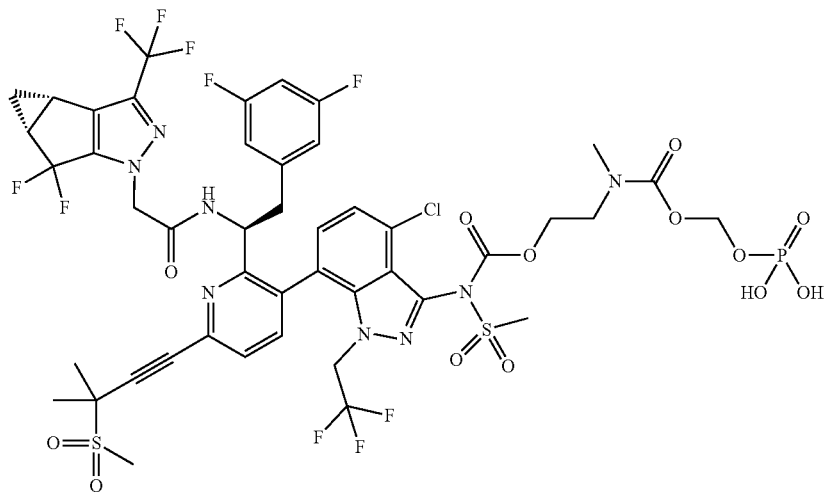

Synthesis of chloromethyl (2-(benzyloxy)ethyl)(methyl) carbamate (133A): To a stirred solution of 2-(benzyloxy)ethan-1-amine (36.3 mmol) in $CH_2Cl_2$ (36 mL) at 0° C. was added potassium carbonate (72.6 mmol) and chloromethyl chloroformate (36.3 mmol). The reaction mixture was stirred at 0° C. and monitored by TLC and LCMS. After completion, the reaction mixture was washed with sat. aq. solutions of $NH_4Cl$ and brine. The combined organic layers were dried over anhydrous $Na_2SO_4$, filtered, and concentrated. The crude mixture was purified by column chromatography (10% to 50% EtOAc in hexanes) to afford the title compound 133A. MS (m/z): 257.81 $[M+H]^+$.

Synthesis of ((di-tert-butoxyphosphoryl)oxy)methyl (2-(benzyloxy)ethyl)(methyl)carbamate (133B): 133A (23.2 mmol) was dissolved in DMF (60 mL) then di-tert-butyl phosphate tetrabutylammonium salt (25.6 mmol) and potassium iodide (27.9 mmol) were added and the mixture was heated to 50° C. for 12 h. The mixture was cooled to room temperature and diluted with dichloromethane. The organic layer was washed with water (3×), brine, dried over $Na_2SO_4$, filtered, and concentrated. The crude mixture was purified by column chromatography (10% to 100% EtOAc in hexanes) to afford the title compound 133B. MS (m/z): 454.47 [M+Na]$^+$.

Synthesis of ((di-tert-butoxyphosphoryl)oxy)methyl (2-hydroxyethyl)(methyl)carbamate (133C): 133B (32.8 mmol) was dissolved in MeOH (48 mL) and palladium on carbon (0.1 g, 20% wt) was added. After stirring for 4 h under hydrogen gas (50 psi) at 60° C., the crude material was isolated after filtration over a pad of Celite. The product was purified by column chromatography (0% to 10% MeOH in $CH_2Cl_2$) to afford title compound 133C. $^1$H NMR (CDCl$_3$ 400 MHz): δ 5.61 (br d, J=15.2 Hz, 2H), 3.70 (m, 2H), 3.47 (br d, J=4.41 Hz, 2H), 3.01 (q, J=14.19 Hz, 3H), 1.48 (18H). MS (m/z): 365.3 [M+Na]$^+$.

Synthesis of (phosphonooxy)methyl (2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)ethyl)(methyl)carbamate (133): An atropisomeric mixture of the title compound was prepared according to the method presented for the synthesis of 94 of Example 94 utilizing 133C in the place of 94B. $^1$H NMR (400 MHz, DMSO) δ 9.23 (q), 7.93-7.65 (m), 7.51-7.39 (m), 7.08-6.90 (m), 6.58-6.40 (m), 5.51-5.25 (m), 5.02-4.50 (m), 4.40-4.27 (m), 4.24-3.94 (m), 3.72-3.53 (m), 3.38 (d), 3.27 (d), 3.22-2.93 (m), 2.34 (d), 1.75 (s), 1.48-1.33 (m), 0.97 (s). $^{19}$F NMR (376 MHz, DMSO) δ-60.06--61.78 (m), -68.44--70.82 (m), -79.37--81.32 (m), -102.65--104.22 (m), -110.22--111.16 (m). MS (m/z): 1224.03 [M+H]$^+$.

Example 134

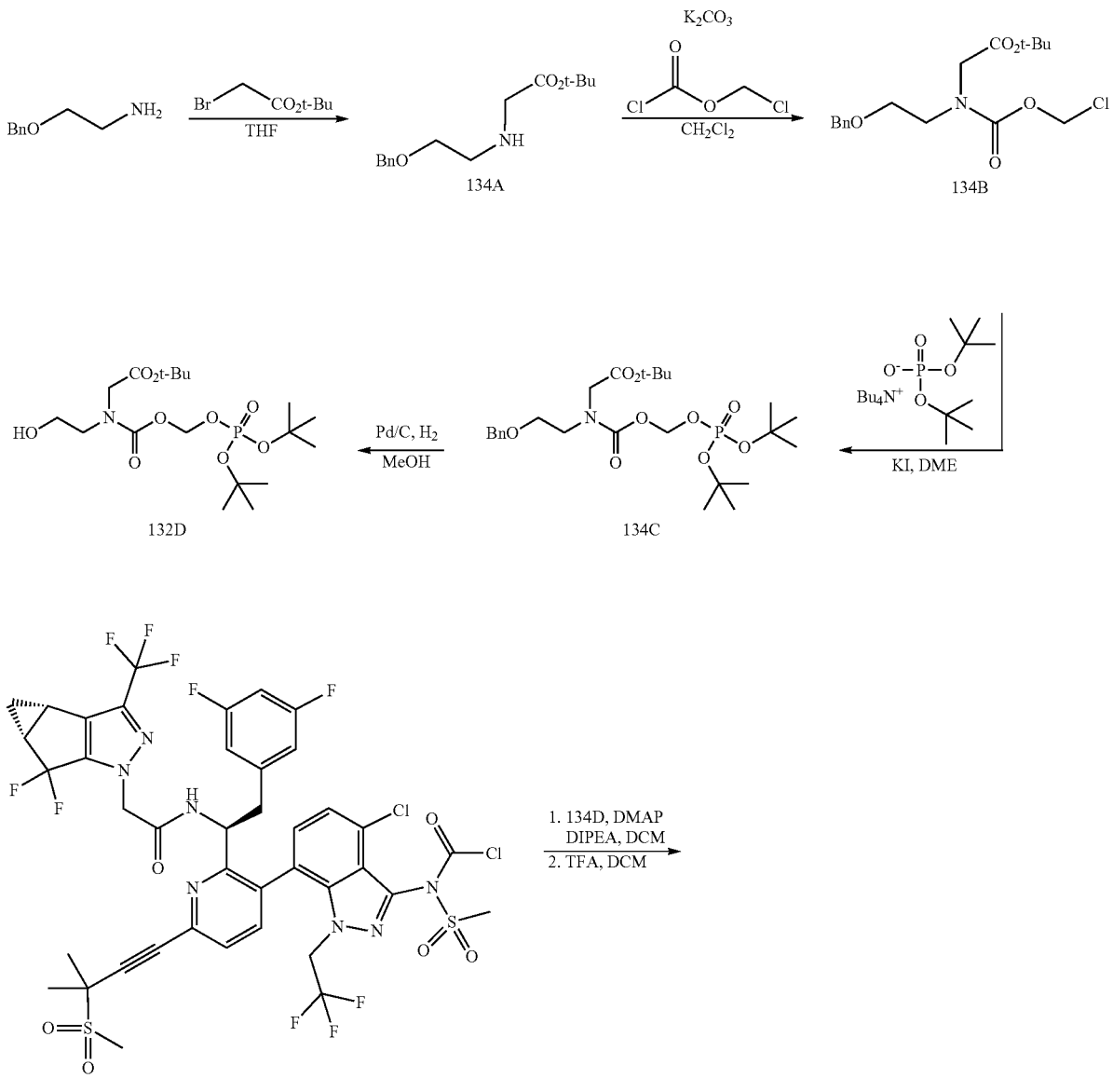

-continued

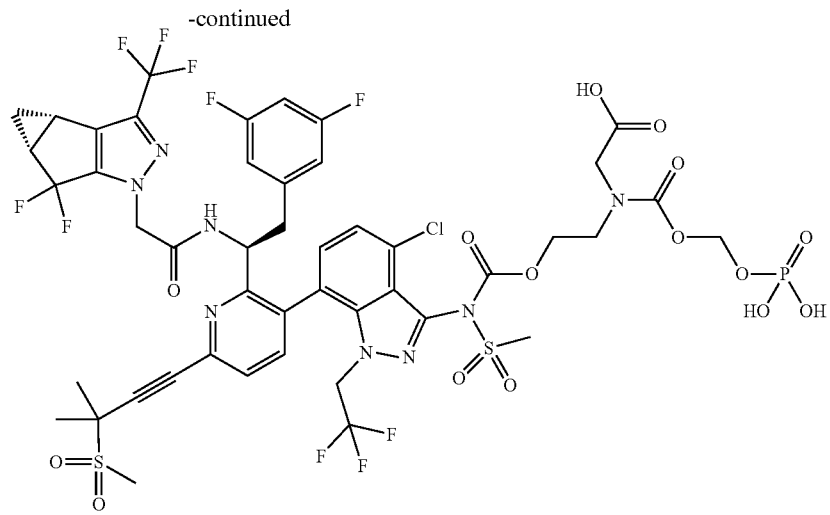

134

Synthesis of tert-butyl (2-(benzyloxy)ethyl)glycinate (134A): To a stirred solution of 2-(benzyloxy)ethan-1-amine (66.1 mmol) in THF (60 mL) was added tert-butyl bromoacetate (33.1 mmol) dropwise. The resulting reaction mixture was stirred at room temperature for 1 h. After completion, the reaction mixture was diluted with $CH_2Cl_2$ and extracted with water. The combined organic layers were dried over anhydrous $Na_2SO_4$, filtered, and concentrated. The crude mixture was purified by column chromatography (0% to 100% EtOAc in hexanes) to afford the title compound 134A.

Synthesis of tert-butyl N-(2-(benzyloxy)ethyl)-N-((chloromethoxy)carbonyl)glycinate (134B): To a stirred solution of 134A (15 mmol) in $CH_2Cl_2$ (24 mL) at 0° C. was added potassium carbonate (30 mmol) and chloromethyl chloroformate (15.0 mmol). The reaction mixture was stirred at 0° C. and monitored by TLC and LCMS. After completion, the reaction mixture was washed with sat. aq. solutions of $NH_4Cl$ and brine. The combined organic layers were dried over anhydrous $Na_2SO_4$, filtered, and concentrated. The crude mixture was purified by column chromatography (10% to 50% EtOAc in hexanes) to afford the title compound 134B.

Synthesis of tert-butyl N-(2-(benzyloxy)ethyl)-N-((((di-tert-butoxyphosphoryl)oxy)methoxy) carbonyl)glycinate (134C): To a solution of 134B (8.4 mmol) in DMF (30 mL) was added di-t-butyl phosphate tetrabutylammonium salt (9.2 mmol) and potassium iodide (10.1 mmol) and the mixture was heated to 50° C. for 12 h. The mixture was cooled to room temperature and diluted with $CH_2Cl_2$. The organic layer was washed with water (3×), brine, dried over $Na_2SO_4$, filtered, and concentrated. The crude mixture was purified by column chromatography (10% to 100% EtOAc in hexanes) to afford the title compound 134C.

Synthesis of tert-butyl N-((((di-tert-butoxyphosphoryl)oxy)methoxy)carbonyl)-N-(2-hydroxyethyl)glycinate (134D): To a solution of 134C in MeOH (30 mL), palladium on carbon (0.1 g, 20% wt) was added. After stirring for 4 hours under hydrogen gas (50 psi) at 60° C., the crude material was isolated after filtration over a pad of Celite. The product was purified by column chromatography (0% to 10% MeOH in $CH_2Cl_2$) to afford the title compound 134D. $^1H$ NMR ($CDCl_3$ 400 MHz): δ 5.61 (dd, J=16.1 Hz, 2H), 3.97 (d, J=7.28 Hz, 2H), 3.75 (br d, J=4.85 Hz, 2H), 3.54 (m, 2H), 1.48 (27H) ppm. MS (m/z): 464.2 [M+Na].

Synthesis of tert-butyl N-(2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)ethyl)-N-((((di-tert-butoxyphosphoryl)oxy)methoxy)carbonyl)glycinate (134): An atropisomeric mixture of the title compound was prepared according to the method presented for the synthesis of 94 of Example 94 utilizing 134D in the place of 94B. $^1H$ NMR (400 MHz, DMSO-$d_6$) δ 9.30-9.16 (m), 7.88-7.80 (m), 7.80-7.70 (m), 7.51-7.39 (m), 7.08-6.98 (m), 6.84-6.75 (m), 6.57-6.50 (m), 6.51-6.39 (m), 5.55-5.34 (m), 5.01-4.90 (m), 4.88-4.79 (m), 4.77 (s), 4.75-4.58 (m), 4.36-4.26 (m), 4.23 (s), 3.84-3.74 (m), 3.67-3.55 (m), 3.54-3.45 (m), 3.43 (s), 3.41-3.32 (m), 3.27 (s), 3.10-2.91 (m), 1.79-1.72 (m), 1.42-1.35 (m), 1.24 (s), 0.98 (s) ppm. 19F NMR (375 MHz, DMSO-$d_6$) δ−60.77--60.98 (m), −69.22--69.39 (m), −69.65--69.77 (m), −74.81, −79.79, −79.99, −80.40--80.51 (m), −103.30, −110.62--110.87 (m) ppm. MS (m/z) 1267.23 [M+H]$^+$.

Example 135

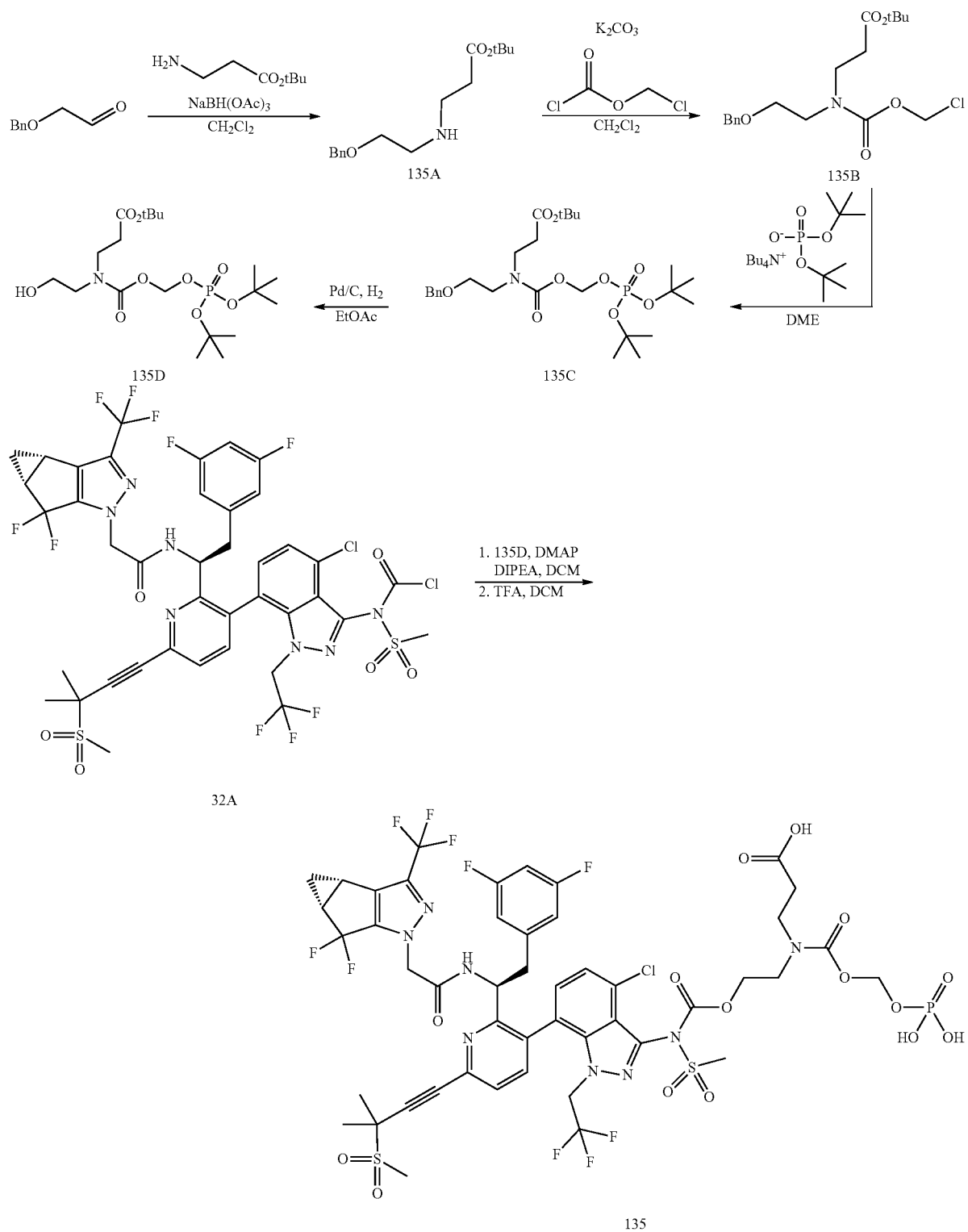

Synthesis of tert-butyl 3-((2-(benzyloxy)ethyl)amino)propanoate (135A): To a solution of 2-benzyloxyacetaldehyde (13 mmol) in CH$_2$Cl$_2$ (44 mL) was added t-butyl 3-aminopropanoate (13 mmol) and the resulting mixture was stirred at room temperature before adding sodium triacetoxyborohydride (20 mmol). The resulting reaction mixture was stirred at room temperature for 16 h. After completion, the reaction mixture was poured into an ice-water mixture and treated with a sat. aq. solution of NaHCO$_3$ and extracted with CH$_2$Cl$_2$. The combined organic layers were dried over anhydrous Na$_2$SO$_4$, filtered, and concentrated. The crude mixture was purified by column chromatography (10% to 50% EtOAc in hexanes) to afford the title compound 135A. MS (m/z): 280.24 [M+H]$^+$.

Synthesis of tert-butyl 3-((2-(benzyloxy)ethyl)((chloromethoxy)carbonyl)amino)propanoate (135B): To a stirred solution of 135A (6.3 mmol) in CH$_2$Cl$_2$ (63 mL) at 0° C. was added triethylamine (16 mmol). Chloromethyl chloroformate (8.3 mmol) was then added and the reaction mixture was stirred at 0° C. and monitored by TLC and LCMS. After completion, the reaction mixture was washed with sat. aq. solutions of NH$_4$Cl and brine. The combined organic layers were dried over anhydrous Na$_2$SO$_4$, filtered, and concentrated to give title compound 135B, which was directly used in the subsequent reaction without purification. MS (m/z): 394.01 [M+Na]$^+$.

Synthesis of tert-butyl 3-((2-(benzyloxy)ethyl)(((((di-tert-butoxyphosphoryl)oxy)methoxy)carbonyl)amino)propanoate (135C): 135B (6.3 mmol) was dissolved in dimethoxyethane (12 mL) then di-t-butyl phosphate tetrabutylammonium salt (13 mmol) was added and the mixture was heated to 80° C. for 1 h. The mixture was cooled to room temperature and concentrated. The crude material was dissolved in EtOAc and washed with water (3×), brine, dried over Na$_2$SO$_4$, filtered, and concentrated. The crude mixture was purified by column chromatography (50% to 100% EtOAc in hexanes). Fractions containing the product were pooled and concentrated under reduced pressure to afford title compound 135C. MS (m/z): 568.61 [M+Na]$^+$.

Synthesis of tert-butyl 3-(((((di-tert-butoxyphosphoryl)oxy)methoxy)carbonyl)(2-hydroxyethyl)amino)propanoate (135D): 135C (4.8 mmol) was dissolved in EtOAc (8 mL) then palladium on carbon (0.31 mmol) was added. After stirring for 1 h under hydrogen gas (1 atm), the crude product was isolated after filtration over a pad of Celite. Upon concentration, the crude was purified by column chromatography (50% to 100% EtOAc in hexanes) to afford title compound 135D. $^1$H NMR (400 MHz, Chloroform-d) δ 5.63 (dd, J=14.3, 7.5 Hz, 2H), 3.79 (dt, J=20.0, 5.2 Hz, 2H), 3.61 (q, J=7.0 Hz, 2H), 3.51 (t, J=5.2 Hz, 2H), 2.59 (dt, J=9.4, 7.0 Hz, 2H), 1.51 (s, 18H), 1.46 (s, 9H). MS (m/z): 478.5 [M+Na]$^+$.

Synthesis of 3-((2-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)ethyl)(((phosphonooxy)methoxy)carbonyl)amino)propanoic acid (135): An atropisomeric mixture of the title compound was prepared according to the method presented for the synthesis of 94 of Example 94 utilizing 135D in the place of 94B. $^1$H NMR (400 MHz, DMSO) δ 9.26-9.15 (m), 9.04-8.96 (m), 7.98-7.71 (m), 7.49-7.25 (m), 7.09-6.86 (m), 6.56-6.44 (m), 5.50-5.33 (m), 4.94-4.56 (m), 4.41-4.17 (m), 4.12-4.01 (m), 3.64-3.56 (m), 3.42 (d), 3.27 (s), 3.09-2.86 (m), 2.43-2.21 (m), 1.75 (s), 1.48-1.33 (m), 0.98 (s) ppm. $^{19}$F NMR (376 MHz, DMSO) δ-60.71--61.00 (m), −69.32--69.78 (m), −79.62--81.01 (m), −103.05--104.22 (m), −110.31--111.17 (m) ppm. MS (m/z): 1282.892 [M+H]$^+$.

Example 136

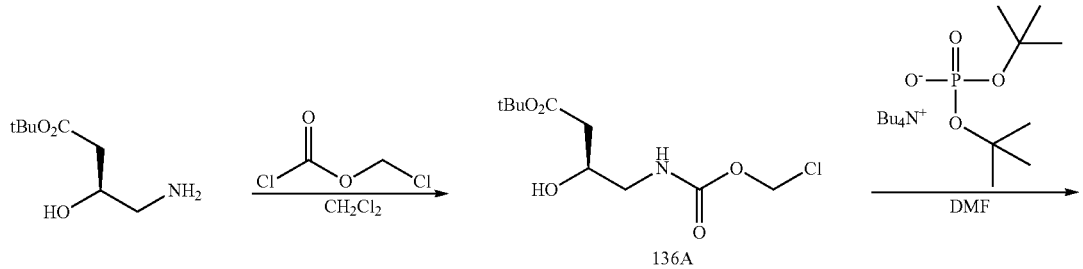

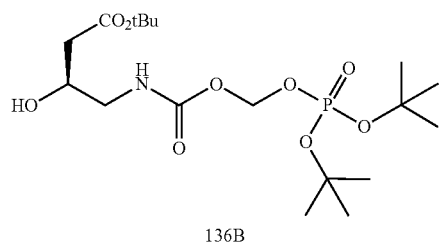

136B

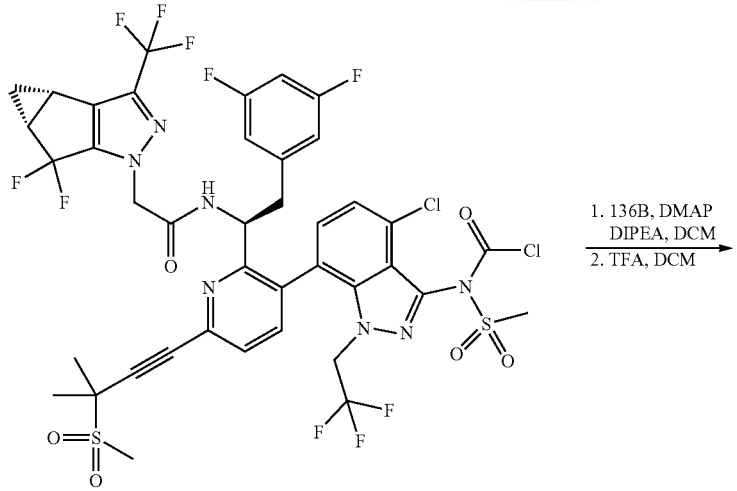

32A

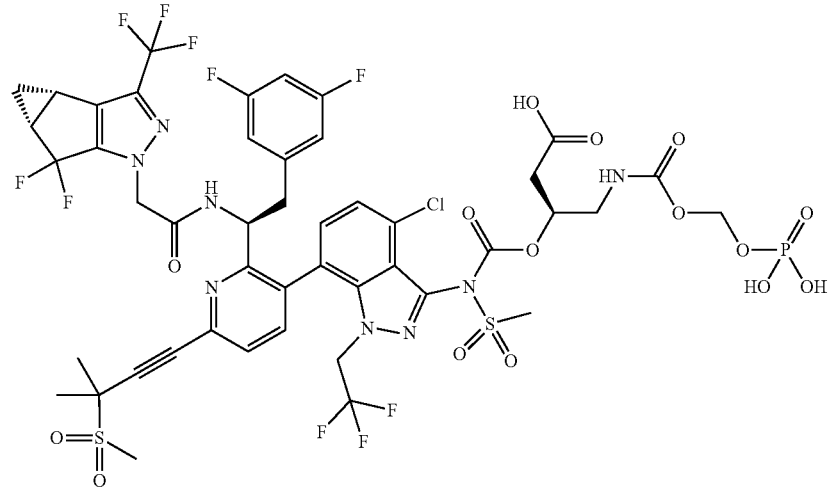

136

Synthesis of tert-butyl (S)-4-(((chloromethoxy)carbonyl)amino)-3-hydroxybutanoate (136A): To a stirred solution of tert-butyl (3S)-4-amino-3-hydroxybutanoate (28.5 mmol) in $CH_2Cl_2$ (50 mL) at room temperature was added proton-sponge (85.6 mmol). Chloromethyl chloroformate (31.3 mmol) was then added and the reaction mixture was stirred at 0° C. and monitored by TLC and LCMS. After completion, the reaction mixture was washed with sat. aq. solutions of $NH_4Cl$ and brine. The combined organic layers were dried over anhydrous $Na_2SO_4$, filtered, and concentrated. The crude mixture was then purified by column chromatography (10% to 50% EtOAc in hexanes) to afford title compound 136A. $^1H$ NMR (400 MHz, Chloroform-d) δ 5.74 (s, 2H), 5.58 (s, 1H), 4.10-4.07 (m, 1H), 3.43-3.38 (m, 1H), 3.21-3.16 (m, 1H), 2.42-2.39 (m, 2H), 1.45 (s, 9H) ppm.

Synthesis of tert-butyl (S)-4-(((((di-tert-butoxyphosphoryl)oxy)methoxy)carbonyl)amino)-3-hydroxybutanoate (136B): 136A (3.74 mmol) was dissolved in dimethoxyethane (50 mL) then di-t-butyl phosphate tetrabutylammonium salt (5.60 mmol) was added and the mixture was heated to 85° C. for 25 min. The mixture was cooled to room temperature and concentrated. The crude material was dissolved in EtOAc and washed with water (3×), brine, dried over $Na_2SO_4$, filtered, and concentrated. The crude mixture was purified by column chromatography (50% to 100% EtOAc in hexanes). Fractions containing the product were pooled and concentrated under reduced pressure to afford the title compound 136B. $^1H$ NMR (400 MHz, DMSO-$d_6$) δ 7.53-7.50 (m, 1H), 5.42 (d, J=12.4 Hz, 2H), 4.92 (d, J=5.6 Hz, 1H), 3.87-3.85 (m, 1H), 3.02-3.98 (m, 2H), 2.36-2.32 (m, 1H), 2.14-1.98 (m, 1H), 1.42-1.40 (m, 27H) ppm.

Synthesis of (S)-3-(((4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamoyl)oxy)-4-((((phosphonooxy)methoxy)carbonyl)amino)butanoic acid (136): An atropisomeric mixture of the title compound was prepared according to the method presented for the synthesis of 94 of Example 94 utilizing 136B in the place of 94B. $^1H$ NMR (400 MHz, DMSO) δ 9.34-9.10 (m), 7.93-7.68 (m), 7.66-7.55 (m), 7.42 (dd), 7.14-6.84 (m), 6.67-6.42 (m), 5.47-5.30 (m), 5.27-5.11 (m), 5.00-4.50 (m), 4.32-3.99 (m), 3.57 (d), 3.36-3.22 (m), 3.11-2.92 (m), 1.75 (s), 1.48-1.31 (m), 0.98 (s). $^{19}F$ NMR (376 MHz, DMSO) δ −59.77−−61.91 (m), −67.92−−70.69 (m), −79.35−−80.85 (m), −102.43−−104.37 (m), −110.10−−110.96 (m) ppm. MS (m/z): 1290.899 [M+Na]$^+$.

Example 137
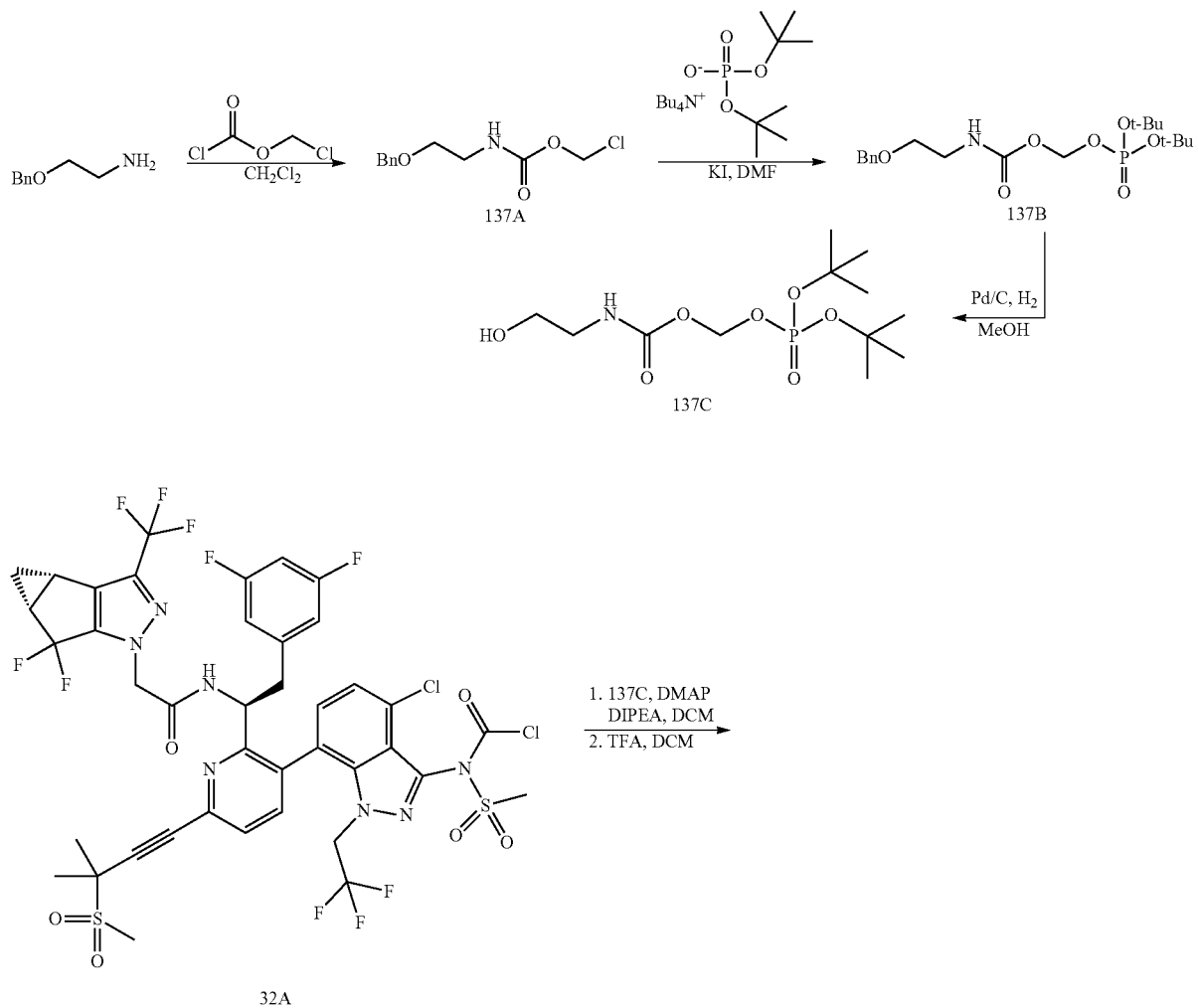

Synthesis of 2-(benzyloxy)ethan-1-amine (137A): To a stirred solution of 2-(benzyloxy)ethan-1-amine (66.1 mmol) in $CH_2Cl_2$ (60 mL) at 0° C. was added chloromethyl chloroformate (66.1 mmol). The reaction mixture was stirred at 0° C. and monitored by TLC and LCMS. After completion, the reaction mixture was washed with sat. aq. solutions of $NH_4Cl$ and brine. The combined organic layers were dried over anhydrous $Na_2SO_4$, filtered, and concentrated. The crude mixture was purified by column chromatography (10% to 50% EtOAc in hexanes) to afford title compound 137A.

Synthesis of chloromethyl (2-(benzyloxy)ethyl)carbamate (137B): 137A (32.8 mmol) was dissolved in DMF (80 mL) then di-tert-butyl phosphate tetrabutylammonium salt (39.4 mmol) and potassium iodide (36.1 mmol) were added and the mixture was heated to 50° C. for 12 h. The mixture was cooled to room temperature, then diluted with DCM. The organic layer was washed with water (3×), brine, dried over $Na_2SO_4$, filtered, and concentrated. The crude mixture was purified by column chromatography (10% to 100% EtOAc in hexanes) to afford title compound 137B.

Synthesis of ((di-tert-butoxyphosphoryl)oxy)methyl (2-hydroxyethyl)carbamate (137C): 137B (32.8 mmol) was dissolved in MeOH (48 mL) and palladium on carbon (1.0 g, 20% wt) was added. After stirring for 4 h under hydrogen gas (50 psi) at 60° C., the crude material was isolated after filtration over a pad of Celite. The product was purified by column chromatography (0% to 10% MeOH in $CH_2Cl_2$) to afford title compound 137C. $^1H$ NMR (DMSO-$d_6$ 400 MHz): δ 7.49 (t, J=5.66 Hz, 1H), 5.41 (d, J=11.92 Hz, 2H), 4.66 (t, J=5.54 Hz, 1H), 3.39 (q, J=6.16 Hz, 2H), 3.01 (m, 2H), 1.36-1.44 (18H). MS (m/z): 350.2 [M+Na].

Synthesis of 2-((((phosphonooxy)methoxy)carbonyl)amino)ethyl (4-chloro-7-(2-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-methyl-3-(methylsulfonyl)but-1-yn-1-yl)pyridin-3-yl)-1-(2,2,2-trifluoroethyl)-1H-indazol-3-yl)(methylsulfonyl)carbamate (137): An atropisomeric mixture of the title compound was prepared according to the method presented for the synthesis of 94 of Example 94 utilizing 137C in the place of 94B. $^1H$ NMR (400 MHz, DMSO) δ 9.21 (dd), 7.93-7.66 (m), 7.56-7.21 (m), 7.11-6.87 (m), 6.66-6.27 (m), 5.61-5.20 (m), 5.00-4.44 (m), 4.36-3.94 (m), 3.72-3.53 (m), 3.30-3.13 (m), 3.10-2.93 (m), 1.74 (d), 1.44-1.34 (m), 0.97 (s). $^{19}F$ NMR (376 MHz, DMSO) δ −59.94−−62.13 (m), −69.54 (dt), −79.16−−81.22 (m), −102.43−−104.68 (m), −110.09−−111.24 (m). MS (m/z): 1231.923 [M+Na]$^+$.

Biological Assays

1. Solubility in Simulated Intestinal Fluids

For the solubility assay, approximately 1 to 10 mg of the compound being tested was added to 1.7 mL polypropylene centrifuge tubes. A sufficient volume of fasted state simulated intestinal fluid (FaSSIF) or fed state simulated intestinal fluid (FeSSIF) was then added to each tube to achieve a final concentration of approximately 1 to 20 mg/mL. FaSSIF and FeSSIF were prepared according to manufacturer instruction (catalog #FFF02, Biorelevant, London, UK). Samples were first vortexed for approximately 10 seconds to suspend solids in solution and immediately placed in a bench top vial mixer set to 25° C. and 1400 rpm. After predetermined incubation times, samples were removed from the vial mixer and centrifuged at 15,000 g. A sample of the supernatant was then diluted in a UPLC vial and stored at −20° C. until analysis. After sampling, tubes were vortexed for approximately 10 seconds to re-suspend any solids and returned to the vial mixer at 25° C. and 1400 rpm until the next predetermined timepoint. At completion of the study, samples were removed from the freezer, equilibrated to ambient temperature, and analyzed by reversed-phase UPLC to determine the concentration of compound in the supernatant at each timepoint. Results are presented in the second column of Table 1 below.

2. Kinetic Solubility Analysis (CLND: Total Chemiluminescent Nitrogen Determination)

Kinetic Solubility from DMSO Stocks of each compound being tested: 100-fold dilutions of a 10 μM DMSO stock solution of each compound being tested were prepared in singleton by combining 3 μL of DMSO stock with 297 μL of the appropriate media (0.1N HCL (Alfa Aesar part number 35644-K2) and 1×PBS buffer (pH 7.4)) in a Millipore solubility filter plate with 0.45 M polycarbonate filter membrane using Hamilton Starlet liquid handling. The final DMSO Concentration is 1.0% and maximum theoretical compound concentration is 100 μM (assuming stock concentration of 10 mM). The filter plate was sealed. Following 24-hour incubation at ambient temperature (21.7-23.8° C.), the samples were vacuum filtered, and the filtrates were collected in a 96 well polypropylene plate for analysis. The collection plate was sealed for analysis.

Filtrates were injected into the nitrogen detector for quantification on Analiza's Automated Discovery Workstation. The results are reported in PM.

The equimolar nitrogen response of the detector was calibrated using standards which span the dynamic range of the instrument from 0.08 to 4500 μg/ml nitrogen. The filtrates were quantified with respect to this calibration curve. The calculated solubility values were corrected for background nitrogen present in the DMSO, and the media used to prepare the samples. The solubility results presented in the third column of Table 1 below assumed that the samples were free of nitrogen containing impurities and were stable under the assay conditions.

The 1×PBS buffer (pH 7.4) was prepared by adding 50 mL of phosphate buffered saline solution 10×, PBS (Fisher Bioreagent part number BP399-500) to approximately 450 mL HPLC grade $H_2O$. The volume of the solution was then adjusted to 500 mL for a total dilution factor of 1:10 and a final PBS concentration of 1×. The pH of the final solution was measured and found to be 7.4.

3. Oral Bioavailability PK Samples

Oral dose (suspension and solution vehicle) of the compound being tested was administered via gavage in rat (Sprague Dawley) and dog (Beagle). Serial blood samples were collected via jugular vein into pre-chilled $K_2EDTA$ with 2 mM dichlorvos (final concentration) for up to 168h. Whole blood was processed into plasma by centrifuge (3000 rpm for 10 minutes at 5C) within 30 minutes of collection.

Plasma samples were analyzed by direct protein precipitation with acetonitrile and further dilution with water before injecting onto Sciex API 5500 LC/MS/MS system for analysis. Unknown plasma samples concentration was calibrated using standard range of 5-10,000 nM for the compound being tested and 1-10,000 nM for Intermediate 5.

AUC was calculated as Area under the plasma concentration vs. time curve from 0 h to infinity.

Bioavailability (% F) was calculated by comparing plasma concentration via oral dose vs. plasma concentration via IV dose (intravenous). % F=[(PO AUCinf·IV Dose)/(IV AUCinf·PO Dose)]·100 and are reported in the fourth and fifth columns of Table 1 below. The plasma sample concentrations for the compounds being tested were below the limit of quantitation and are thus not reported in Table 1. The reported values in the fourth and fifth columns of Table 1 are based on observed exposure of Intermediate 5 in plasma.

The suspension vehicle was 0.5% hydroxypropyl methylcellulose, high viscosity and 99.5% water with final pH of 2.0. The solution vehicles used were 1) 5% ethanol, 20% propylene glycol, and 75% water and 2) 30% 10 mM HCl, 5% ethanol, 45% polyethylene glycol 300, and 20% propylene glycol.

TABLE 1

| Compound | FaSSIF/FeSSIF solubility[a] (µg/mL) | pH 2/pH 7 solubility (µM) | Dog F % (solution) | Dog F % (suspension) |
|---|---|---|---|---|
| Intermediate 5 | 4.0/4.2 | 0.11/0.32 | 24[b], 16[c] | 8 |
| 1 | — | 1/1 | — | — |
| 3 | — | 1/1 | — | — |
| 4 | — | 33/7 | — | — |
| 5 | — | 39/9 | — | — |
| 6 | — | 50/3 | — | — |
| 7 | — | 65/7 | — | — |
| 8 | — | 57/6 | — | — |
| 9 | — | 2/21 | — | — |
| 10 | — | 2/2 | — | — |
| 11 | — | 5/36 | — | — |
| 12 | — | 10/10 | — | — |
| 14 | — | 1/1 | — | — |
| 15 | — | 1/1 | — | — |
| 16 | 710/497 | 1/92 | 39[b] | — |
| 18 | — | 1/1 | — | — |
| 19 | — | 1/100 | — | — |
| 20 | 448/454 | 13/100 | — | — |
| 21 | — | 86/1 | — | — |
| 22 | — | 45/3 | — | — |
| 23 | — | 6/100 | — | — |
| 24 | — | 1/1 | — | — |
| 25 | — | 1/73 | — | — |
| 26 | 13/89 | 23/2 | — | — |
| 27 | — | 20/2 | — | — |
| 28 | — | 29/1 | — | — |
| 29 | 6/120 | 54/4 | — | — |
| 30 | — | 1/1 | — | — |
| 32 | — | 1/1 | — | — |
| 33 | — | 6/16 | — | — |
| 34 | — | 1/4 | — | — |
| 35 | — | 1/14 | — | — |
| 36 | — | 1/5 | — | — |
| 37 | — | 3/18 | — | — |
| 38 | — | 10/16 | — | — |
| 39 | — | 1/2 | — | — |
| 40 | — | 1/2 | — | — |
| 41 | — | 3/17 | — | — |
| 42 | — | 62/5 | — | — |
| 43 | — | 1/1 | — | — |
| 44 | 10/10 | 1/9 | — | — |
| 45 | 14/1 | 1/20 | — | — |
| 46 | 9/3 | 1/10 | — | — |
| 47 | — | 1/1 | — | — |
| 48 | — | 1/1 | — | — |
| 49 | — | 1/82 | — | — |
| 50 | — | 1/2 | — | — |
| 52 | — | 1/100 | — | — |
| 53 | 758/370 | 1/62 | — | — |
| 54 | 416/827 | 1/41 | — | — |
| 54-1 | — | 1/14 | — | — |
| 55 | — | 1/13 | — | — |
| 56 | 1082/1588 | 3/42 | — | — |
| 58 | 813/120 | 1/8 | — | — |
| 59 | 798/819 | 2/21 | — | — |
| 60 | 364/756 | 1/14 | — | — |
| 61 | — | 1/9 | — | — |
| 62 | — | 4/14 | — | — |
| 63 | ND/135 | — | — | — |
| 65 | — | 1/52 | — | — |
| 66 | 425/140 | 1/10 | — | — |
| 67 | 536/707 | 2/79 | — | — |
| 68 | 700/246 | 1/18 | 23[b] | — |
| 69 | 1583/247 | 1/81 | 24[b] | — |
| 70 | — | 1/58 | — | — |
| 71 | — | 1/15 | — | — |
| 72 | — | 1/9 | — | — |
| 73 | — | 72/16 | — | — |
| 74 | — | 72/24 | — | — |
| 75 | — | 16/13 | — | — |
| 76 | 7/68 | — | — | — |
| 77 | — | 21/1 | — | — |
| 78 | — | 14/22 | — | — |
| 79 | — | 59/14 | — | — |
| 80 | 7550/1724 | 6/100 | — | — |
| 81 | 490/660 | 1/83 | — | — |
| 82 | 2677/1800 | 2/100 | — | 15 |
| 83 | 1950/500 | 1/61 | 31[b] | — |
| 84 | 154/2 | 5/16 | — | — |
| 85 | — | 5/65 | — | — |
| 86 | 2025/1469 | 1/100 | — | 14 |
| 87 | >2480/299 | 1/18 | — | — |
| 88 | 841/589 | 1/15 | — | — |
| 89 | — | 3/3 | — | — |
| 90 | 2/3 | 1/48 | — | — |
| 91 | — | 50/10 | — | — |
| 93 | — | 1/22 | — | — |
| 94 | 481/189 | <1/1 | — | — |
| 95 | — | 1/3 | — | — |
| 96 | — | 1/99 | — | — |
| 97 | — | 1/2 | — | — |
| 98 | — | 1/100 | — | — |
| 99 | — | 1/1 | — | — |
| 100 | — | 2/100 | — | — |
| 102 | — | 1/100 | — | — |
| 103 | — | 1/1 | — | — |
| 104 | — | 1/89 | — | — |
| 106 | — | 4/100 | — | — |
| 107 | — | 4/1 | — | — |
| 108 | — | 1/100 | — | — |
| 110 | — | 1/100 | — | — |
| 111 | — | 33/42 | — | — |
| 112 | 778/1253 | 1/77 | — | — |
| 113 | 5/8 | 1/5 | — | — |
| 114 | — | 24/1 | — | — |
| 115 | — | 1/1 | — | — |
| 116 | — | 1/1 | — | — |
| 117 | — | 9/10 | — | — |
| 118 | — | 1/1 | — | — |
| 119 | — | 1/1 | — | — |
| 120 | — | 1/9 | — | — |
| 121 | — | 1/21 | — | — |
| 122 | 7/162 | 1/16 | — | — |
| 123 | 120/153 | 78/71 | 4[b] | — |
| 124 | — | 2/83 | — | — |
| 125 | 617/42 | 14/68 | — | — |
| 126 | 21/218 | 1/5 | — | — |
| 127 | — | 8/1 | — | — |
| 128 | — | 5/1 | — | — |
| 129 | — | 54/7 | — | — |
| 131 | 816/427 | 1/73 | — | — |
| 132 | 1626/1249 | 1/79 | — | — |
| 133 | 194/131 | 1/81 | 26[b] | — |
| 134 | 2640/7990 | 1/100 | 30[b] | — |
| 135 | 1290/1239 | 1/100 | — | — |
| 136 | 1490/2910 | 3/57 | — | — |
| 137 | 950/390 | 1/85 | 25[b] | — |

[a]FeSSIF = Fed-state simulated intestinal fluid; FaSSIF = Fasted-state simulated intestinal fluid.
[b]Vehicle is 30% 10 mM HCl, 5% ethanol, 45% polyethylene glycol 300, and 20% propylene glycol.
[c]Vehicle is 5% ethanol, 20% propylene glycol, and 75% water.

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be

What is claimed is:
1. A compound of Formula I,

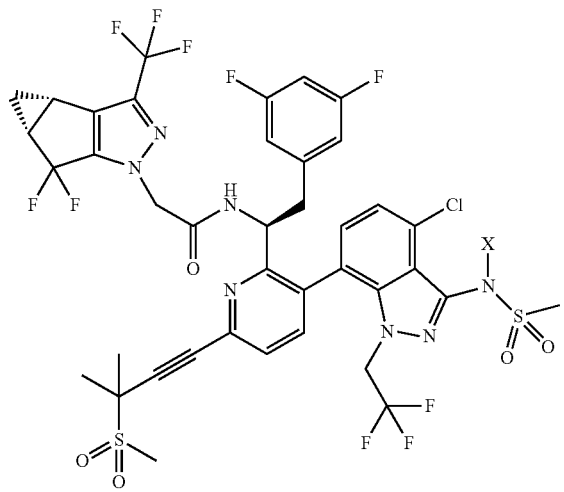

Formula I or a pharmaceutically acceptable salt thereof,
wherein
X is —C(O)C(O)NR$^1$R$^1$, —C(O)C(O)OR$^2$, —(C$_{1-6}$ alkyl)OR$^3$, —C(O)NR$^4$R$^5$, —C(O)OR$^6$, or —C(O)C$_{1-10}$ alkyl,
wherein the C$_{1-10}$ alkyl is optionally substituted with one 4-7 membered monocyclic heterocyclyl,
wherein the 4-7 membered monocyclic heterocyclyl is optionally substituted with 1-3 groups independently selected from —CN, halogen, R$^a$, R$^b$, and R$^c$;
each R$^1$ independently is H or C$_{1-6}$ alkyl, wherein the C$_{1-6}$ alkyl is optionally substituted with 1-3 groups independently selected from —CN, halogen, R$^a$, R$^b$, and R$^c$;
R$^2$ is H or C$_{1-6}$ alkyl, wherein the C$_{1-6}$ alkyl is optionally substituted with 1-3 groups independently selected from —CN, halogen, R$^a$, R$^b$, and R$^c$;
R$^3$ is —P(O)(OH)$_2$, —C(O)R$^{3a}$, —C(O)OR$^{3a}$, —C(O)NR$^{3b}$R$^{3b}$, —C(O)C(O)OR$^{3a}$, —S(O)$_2$R$^{3a}$, —S(O)$_2$NR$^{3b}$R$^{3b}$, or —S(O)$_2$OR$^{3a}$;
R$^{3a}$ is H or C$_{1-6}$ alkyl, wherein the C$_{1-6}$ alkyl is substituted with 1-3 groups independently selected from —CN, R$^a$, R$^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$;
each R$^{3b}$ independently is R$^d$ or C$_{1-6}$ alkyl, wherein the C$_{1-6}$ alkyl is substituted with 1-3 groups independently selected from —CN, R$^a$, R$^d$, —OC(O)R$^9$, —OC(O)C(O)OR$^9$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, and —NR$^{10}$S(O)$_2$R$^9$;
R$^4$ is H, or C$_{1-6}$ alkyl, wherein the C$_{1-6}$ alkyl is optionally substituted with 1-3 groups independently selected from —B(OH)$_2$, —CN, halogen, R$^a$, R$^b$, and R$^c$;
R$^5$ is H, C$_{1-6}$ alkyl, or 8-10 membered fused bicyclic heteroaryl,
wherein the C$_{1-6}$ alkyl is optionally substituted with 1-3 groups independently selected from —B(OH)$_2$, —CN, halogen, R$^a$, R$^b$, R$^c$, and R$^{5a}$,
wherein the 8-10 membered fused bicyclic heteroaryl is optionally substituted with 1-3 groups independently selected from —CN, halogen, R$^a$, Rb, R$^c$ and R$^{5b}$;
each R$^{5a}$ independently is 4-7 membered monocyclic heterocyclyl, phenyl, naphthalenyl, 5-6 membered monocyclic heteroaryl, or 8-10 membered fused bicyclic heteroaryl,
wherein the 4-7 membered monocyclic heterocyclyl, phenyl, naphthalenyl, 5-6 membered monocyclic heteroaryl, and 8-10 membered fused bicyclic heteroaryl are each independently optionally substituted with 1-3 groups independently selected from —CN, halogen, R$^a$, R$^b$, and R$^c$;
each R$^{5b}$ independently is C$_{1-6}$ alkyl, wherein the C$_{1-6}$ alkyl is optionally substituted with 1-3 groups independently selected from —CN, halogen, R$^a$, R$^b$, and R$^c$;
R$^6$ is C$_{1-10}$ alkyl or C$_{3-7}$ monocyclic cycloalkyl,
wherein the C$_{1-10}$ alkyl is optionally substituted with 1-3 groups independently selected from —CN, halogen, R$^a$, R$^b$, R$^c$, and —OC(O)(C$_{2-6}$ alkenylene)C(O)OR$^9$, 4-7 membered monocyclic heterocyclyl, phenyl, naphthalenyl, 5-6 membered monocyclic heteroaryl, and 8-10 membered fused bicyclic heteroaryl,
wherein the C$_{3-7}$ monocyclic cycloalkyl is optionally substituted with 1-3 groups independently selected from —CN, halogen, R$^a$, R$^b$, and R$^c$;
each R$^a$ independently is —P(O)(OH)$_2$ or —OP(O)(OH)$_2$;
each R$^b$ independently is —C(O)R$^7$, —C(O)OR$^7$, —C(O)NR$^8$R$^8$, —C(O)C(O)OR$^7$, —C(=NR$^{8a}$)(NR$^8$R$^8$), —S(O)$_2$R$^7$, —S(O)$_2$NR$^8$R$^8$, or —S(O)$_2$OR$^7$;
each R$^c$ independently is —OR$^7$, —OC(O)R$^7$, —OC(O)C(O)OR$^7$, —(O(C$_{1-4}$ alkyl))$_n$OR$^{7a}$, —NR$^8$R$^8$, —N$^+$R$^8$R$^8$R$^{8a}$, —NR$^8$C(O)R$^7$, —NR$^8$C(O)NR$^8$R$^8$, —NR$^8$C(O)OR$^7$, —NR$^8$C(O)C(O)OR$^7$, —NR$^8$C(=NR$^{8a}$)NR$^8$R$^8$, or —NR$^8$S(O)$_2$R$^7$;
each R$^7$ independently is H or C$_{1-6}$ alkyl, wherein the C$_{1-6}$ alkyl is optionally substituted with 1-3 groups independently selected from —CN, halogen, R$^a$, R$^d$, and R$^e$;
each R$^{7a}$ independently is H, —P(O)(OH)$_2$, or C$_{1-6}$ alkyl, wherein the C$_{1-6}$ alkyl is optionally substituted with 1-3 groups independently selected from —CN, halogen, R$^a$, R$^d$, and R$^e$;
each R$^8$ independently is H, R$^d$, or C$_{1-6}$ alkyl,
wherein the C$_{1-6}$ alkyl is optionally substituted with 1-3 groups selected from —CN, halogen, R$^a$, R$^d$, and R$^e$;
each R$^{8a}$ independently is H or C$_{1-3}$ alkyl;
each R$^d$ independently is —C(O)R$^9$, —C(O)OR$^9$, —C(O)NR$^{10}$R$^{10}$, —C(O)C(O)OR$^9$, —C(=NR$^{10a}$)(NR$^{10}$R$^{10}$), —S(O)$_2$R$^9$, —S(O)$_2$NR$^{10}$R$^{10}$, or —S(O)$_2$OR$^9$;
each R$^e$ independently is —OR$^9$, —OC(O)R$^9$, —OC(O)C(O)OR$^9$, —NR$^{10}$R$^{10}$, —N$^+$R$^{10}$R$^{10}$R$^{10a}$, —NR$^{10}$C(O)R$^9$, —NR$^{10}$C(O)NR$^{10}$R$^{10}$, —NR$^{10}$C(O)OR$^9$, —NR$^{10}$C(O)C(O)OR$^9$, —NR$^{10}$C(=NR$^{10a}$)NR$^{10}$R$^{10}$, or —NR$^{10}$S(O)$_2$R$^9$;
each R$^9$ independently is H or C$_{1-6}$ alkyl, wherein the C$_{1-6}$ alkyl is optionally substituted with 1-3 groups independently selected from CN, halogen, R$^a$, R$^f$, and R$^g$;
each R$^{10}$ independently is H, R$^f$ or C$_{1-6}$ alkyl, wherein the C$_{1-6}$ alkyl is optionally substituted with 1-3 groups independently selected from —CN, halogen, R$^a$, R$^f$, and R$^g$;

each $R^{10a}$ independently is H or $C_{1-3}$ alkyl;
each $R^f$ independently is —C(O)$R^{11}$, —C(O)O$R^{11}$, —C(O)N$R^{11}R^{11}$, —C(O)C(O)O$R^{11}$, —C(=N$R^{11a}$)(N$R^{11}R^{11}$), —S(O)$_2R^{11}$, —S(O)$_2$N$R^{11}R^{11}$, or —S(O)$_2$O$R^{11}$;
each $R^g$ independently is —O$R^{11}$, —OC(O)$R^{11}$, —OC(O)C(O)O$R^{11}$, —N$R^{11}R^{11}$, —N$^+R^{11}R^{11}R^{11a}$, —N$R^{11}$C(O)$R^{11}$, —N$R^{11}$C(O)N$R^{11}R^{11}$, —N$R^{11}$C(O)O$R^{11}$, —N$R^{11}$C(O)C(O)O$R^{11}$, —N$R^{11}$C(=N$R^{11a}$)N$R^{11}R^{11}$, or —N$R^{11}$S(O)$_2R^{11}$;
each $R^{11}$ independently is H or $C_{1-6}$ alkyl, wherein the $C_{1-6}$ alkyl is optionally substituted with 1-3 groups independently selected from —OH, CN, halogen, —COOH, and $R^a$;
each $R^{11a}$ independently is H or $C_{1-3}$ alkyl;
n is 1, 2, 3, 4, or 5;
wherein each 4 membered monocyclic heterocyclyl has 1 ring heteroatom selected from N, O, and S;
wherein each 5-7 membered monocyclic heterocyclyl has 1-2 ring heteroatoms independently selected from N, O, and S; and
wherein each 5-6 membered monocyclic heteroaryl and 8-10 membered fused bicyclic heteroaryl independently have 1-4 ring heteroatoms independently selected from N, O, and S.

2. The compound of claim 1, or a pharmaceutically acceptable salt thereof, wherein
X is —C(O)C(O)N$R^1R^1$, —C(O)C(O)O$R^2$, —($C_{1-6}$ alkyl)O$R^3$, —C(O)N$R^4R^5$, —C(O)O$R^6$, or —C(O)$C_{1-10}$ alkyl,
wherein the $C_{1-10}$ alkyl is optionally substituted with one 4-7 membered monocyclic heterocyclyl,
wherein the 4-7 membered monocyclic heterocyclyl is optionally substituted with 1-3 groups independently selected from —CN, halogen, $R^a$, $R^b$, and $R^c$;
each $R^1$ independently is H or $C_{1-6}$ alkyl, wherein the $C_{1-6}$ alkyl is optionally substituted with 1-3 groups independently selected from —OH, —CN, halogen, —C(O)OH, and $R^a$;
$R^2$ is H or $C_{1-6}$ alkyl, wherein the $C_{1-6}$ alkyl is optionally substituted with 1-3 groups independently selected from —OH, —CN, halogen, —C(O)OH, and $R^a$;
$R^3$ is —C(O)$R^{3a}$, —C(O)C(O)O$R^{3a}$, or —P(O)(OH)$_2$;
$R^{3a}$ is H or $C_{1-6}$ alkyl, wherein the $C_{1-6}$ alkyl is substituted with 1-3 groups independently selected from —CN, $R^a$, $R^d$, —OC(O)$R^9$, —OC(O)C(O)O$R^9$, —N$R^{10}$C(O)$R^9$, —N$R^{10}$C(O)N$R^{10}R^{10}$, —N$R^{10}$C(O)O$R^9$, —N$R^{10}$C(O)C(O)O$R^9$, —N$R^{10}$C(=N$R^{10a}$)N$R^{10}R^{10}$, and —N$R^{10}$S(O)$_2R^9$;
$R^4$ is H or $C_{1-6}$ alkyl, wherein the $C_{1-6}$ alkyl is optionally substituted with 1-3 groups independently selected from —B(OH)$_2$, —CN, halogen, $R^a$, $R^b$, and $R^c$;
$R^5$ is H, or $C_{1-6}$ alkyl, wherein the $C_{1-6}$ alkyl is optionally substituted with 1-3 groups independently selected from —CN, halogen, $R^a$, $R^b$, $R^c$, and $R^{5a}$;
each $R^{5a}$ independently is 4-7 membered monocyclic heterocyclyl or phenyl,
wherein the 4-7 membered monocyclic heterocyclyl and phenyl are each independently optionally substituted with 1-3 groups independently selected from —CN, halogen, $R^a$, $R^b$, and $R^c$;
$R^6$ is $C_{1-10}$ alkyl or $C_{3-7}$ monocyclic cycloalkyl,
wherein the $C_{1-10}$ alkyl is optionally substituted with 1-3 groups independently selected from —CN, halogen, $R^a$, $R^b$, $R^c$, and —OC(O)($C_{2-6}$ alkenylene)C(O)O$R^9$, 4-7 membered monocyclic heterocyclyl, and 5-6 membered monocyclic heteroaryl,
wherein the $C_{3-7}$ monocyclic cycloalkyl is optionally substituted with 1-3 groups independently selected from —OH, —CN, halogen, —C(O)OH, —N$R^8R^8$, and $R^a$;
each $R^a$ independently is —P(O)(OH)$_2$ or —OP(O)(OH)$_2$;
each $R^b$ independently is —C(O)$R^7$, —C(O)O$R^7$, —C(O)N$R^8R^8$, —C(O)C(O)O$R^7$, —C(=N$R^{8a}$)(N$R^8R^8$), —S(O)$_2R^7$, —S(O)$_2$N$R^8R^8$, or —S(O)$_2$O$R^7$;
each $R^c$ independently is —O$R^7$, —OC(O)$R^7$, —OC(O)C(O)O$R^7$, —(O($C_{1-4}$ alkyl))$_n$O$R^{7a}$, —N$R^8R^8$, —N$^+R^8R^8R^{8a}$, —N$R^8$C(O)$R^7$, —N$R^8$C(O)N$R^1R^1$, —N$R^8$C(O)O$R^7$, —N$R^8$C(O)C(O)O$R^8$, —N$R^8$C(=N$R^{8a}$)N$R^8R^8$, or —N$R^8$S(O)$_2R^7$;
each $R^7$ independently is H or $C_{1-6}$ alkyl, wherein the $C_{1-6}$ alkyl is optionally substituted with 1-3 groups independently selected from —CN, halogen, $R^a$, $R^d$, and $R^e$;
each $R^{7a}$ independently is H or —P(O)(OH)$_2$;
each $R^8$ independently is H or $C_{1-6}$ alkyl, wherein the $C_{1-6}$ alkyl is optionally substituted with 1-3 groups independently selected from —CN, halogen, $R^a$, $R^d$, and $R^e$;
each $R^{8a}$ independently is H or $C_{1-3}$ alkyl;
each $R^d$ independently is —C(O)$R^9$, —C(O)O$R^9$, —C(O)N$R^{10}R^{10}$, —C(O)C(O)O$R^9$, —C(=N$R^{10a}$)(N$R^{10}R^{10}$), —S(O)$_2R^9$, —S(O)$_2$N$R^{10}R^{10}$, or —S(O)$_2$O$R^9$;
each $R^e$ independently is —O$R^9$, —OC(O)$R^9$, —OC(O)C(O)O$R^9$, —N$R^{10}R^{10}$, —N$^+R^{10}R^{10}R^{10a}$, —N$R^{10}$C(O)$R^9$, —N$R^{10}$C(O)N$R^{10}R^{10}$, —N$R^{10}$C(O)O$R^9$, —N$R^{10}$C(O)C(O)O$R^9$, —N$R^{10}$C(=N$R^{10a}$)N$R^{10}R^{10}$, or —N$R^{10}$S(O)$_2R^9$;
each $R^9$ independently is H or $C_{1-6}$ alkyl, wherein the $C_{1-6}$ alkyl is optionally substituted with 1-3 groups independently selected from —OH, CN, halogen, —C(O)OH, and $R^a$;
each $R^{10}$ independently is H or $C_{1-6}$ alkyl, wherein the $C_{1-6}$ alkyl is optionally substituted with 1-3 groups independently selected from —OH, —CN, halogen, —C(O)OH, and $R^a$;
each $R^{10a}$ independently is H or $C_{1-3}$ alkyl;
n is 1, 2, 3, 4, or 5;
wherein each 4 membered monocyclic heterocyclyl has 1 ring heteroatom selected from N, O, and S;
wherein each 5-7 membered monocyclic heterocyclyl has 1-2 ring heteroatoms independently selected from N, O, and S; and
wherein each 5-6 membered monocyclic heteroaryl and 8-10 membered fused bicyclic heteroaryl independently have 1-4 ring heteroatoms independently selected from N, O, and S.

3. The compound of claim 1, or a pharmaceutically acceptable salt thereof,
wherein
X is —C(O)C(O)N$R^1R^1$, —C(O)C(O)O$R^2$, —($C_{1-6}$ alkyl)O$R^3$, —C(O)N$R^4R^5$, —C(O)O$R^6$, or —C(O)$C_{1-10}$ alkyl,
wherein the $C_{1-10}$ alkyl is optionally substituted with one 4-7 membered monocyclic heterocyclyl,
wherein the 4-7 membered monocyclic heterocyclyl is optionally substituted with 1-3 groups independently selected from —OH, —CN, halogen, —C(O)OH, —C(=N$R^8$a)(N$R^1R^1$), and $R^a$;
each $R^1$ independently is H or $C_{1-6}$ alkyl, wherein the $C_{1-6}$ alkyl is optionally substituted with 1-3 groups independently selected from —OH, —CN, halogen, —C(O)OH, and $R^a$;

387

R² is H or C$_{1-6}$ alkyl, wherein the C$_{1-6}$ alkyl is optionally substituted with 1-3 groups independently selected from —OH, —CN, halogen, —C(O)OH, and R$^a$;

R³ is —C(O)R$^{3a}$, —C(O)C(O)OR$^{3a}$, or —P(O)(OH)$_2$;

R$^{3a}$ is H or C$_{1-6}$ alkyl, wherein the C$_{1-6}$ alkyl is substituted with 1-3 groups independently selected from —CN, —C(O)OR$^9$, and R$^a$;

R⁴ is H or C$_{1-6}$ alkyl, wherein the C$_{1-6}$ alkyl is optionally substituted with 1-3 groups independently selected from —OH, —CN, halogen, —C(O)OH, and R$^a$;

R⁵ is H or C$_{1-6}$ alkyl, wherein the C$_{1-6}$ alkyl is optionally substituted with 1-3 groups independently selected from —OH, —CN, halogen, —C(O)OR⁷, —OC(O)C(O)OR⁷, —NR⁸R⁸, —N⁺R⁸R⁸R$^{8a}$, —NR⁸C(O)OR⁷, —NR⁸C(O)C(O)OR⁸, —NR⁸C(=NR$^{8a}$)NR⁸R⁸, R$^a$, and R$^{5a}$;

each R$^{5a}$ independently is 4-7 membered monocyclic heterocyclyl or phenyl, wherein the 4-7 membered monocyclic heterocyclyl and phenyl are each independently optionally substituted with 1-3 groups independently selected from —OH, —CN, halogen, —C(O)OH, —C(=NR$^{8a}$)(NR⁸R⁸), and R$^a$;

R⁶ is C$_{1-10}$ alkyl or C$_{3-5}$ monocyclic cycloalkyl,
wherein the C$_{1-10}$ alkyl is optionally substituted with 1-3 groups independently selected from —OH, —CN, halogen, —C(O)OR⁷, —S(O)$_2$OR⁷, —(O(C$_{1-4}$ alkyl))$_n$OR$^{7a}$, —NR⁸R⁸, R$^a$, —OC(O)(C$_{2-6}$ alkenylene)C(O)OR⁹, 4-7 membered monocyclic heterocyclyl, and 5-6 membered monocyclic heteroaryl,
wherein the C$_{3-5}$ monocyclic cycloalkyl is optionally substituted with 1-3 groups independently selected from —OH, —CN, halogen, —C(O)OH, —NR⁸R⁸, and R$^a$;

each R$^a$ independently is —P(O)(OH)$_2$ or —OP(O)(OH)$_2$;

each R⁷ independently is H or C$_{1-6}$ alkyl, wherein the C$_{1-6}$ alkyl is optionally substituted with 1-3 groups independently selected from —OH, —CN, halogen, —C(O)OR⁹, —NR¹⁰R¹⁰, and R$^a$;

each R$^{7a}$ independently is H or —P(O)(OH)$_2$;

each R⁸ independently is H, —C(O)OR⁹, —C(O)C(O)OR⁹, —C(=NR$^{10a}$)(NR¹⁰R¹⁰), or C$_{1-6}$ alkyl, wherein the C$_{1-6}$ alkyl is optionally substituted with 1-3 groups independently selected from —OH, —CN, halogen, —C(O)OR⁹, and R$^a$;

each R$^{8a}$ independently is H or C$_{1-3}$ alkyl;

each R⁹ independently is H or C$_{1-3}$ alkyl, wherein the C$_{1-3}$ alkyl is optionally substituted with 1-3 groups independently selected from —OH, CN, halogen, —C(O)OH, and R$^a$;

each R¹⁰ independently is H or C$_{1-4}$ alkyl, wherein the C$_{1-4}$ alkyl is optionally substituted with 1-3 groups independently selected from —OH, —CN, halogen, —C(O)OH, and R$^a$;

each R$^{10a}$ independently is H or C$_{1-3}$ alkyl;

n is 1, 2, 3, 4, or 5;

wherein each 4 membered monocyclic heterocyclyl has 1 ring heteroatom selected from N, O, and S;

wherein each 5-7 membered monocyclic heterocyclyl has 1-2 ring heteroatoms independently selected from N, O, and S; and wherein each 5-6 membered monocyclic heteroaryl and 8-10 membered fused bicyclic heteroaryl independently have 1-4 ring heteroatoms independently selected from N, O, and S.

388

4. The compound of claim 1, or a pharmaceutically acceptable salt thereof, wherein X is —C(O)C(O)NR¹R¹, and each R¹ independently is H or C$_{1-6}$ alkyl, wherein the C$_{1-6}$ alkyl is optionally substituted with 1-3 groups independently selected from —C(O)OH and R$^a$.

5. The compound of claim 1, or a pharmaceutically acceptable salt thereof, wherein X is —C(O)C(O)OR², and R² is H or C$_{1-3}$ alkyl, wherein the C$_{1-3}$ alkyl is optionally substituted with 1-3 groups independently selected from —C(O)OH and R$^a$.

6. The compound of claim 1, or a pharmaceutically acceptable salt thereof, wherein X is —(C$_{1-4}$ alkyl)OR³, and R³ is —P(O)(OH)$_2$, —C(O)R$^{3a}$ or —C(O)C(O)OR$^{3a}$.

7. The compound of claim 1, or a pharmaceutically acceptable salt thereof, wherein X is —C(O)NR⁴R⁵;
R⁴ is H or C$_{1-6}$ alkyl, wherein the C$_{1-6}$ alkyl is optionally substituted with 1-3 groups independently selected from —B(OH)$_2$, —C(O)OR⁷, —C(O)NR⁸R⁸, —S(O)$_2$R⁷, —S(O)$_2$NR⁸R⁸, —S(O)$_2$OR⁷, —NR⁸C(O)R⁷, —NR⁸C(O)NR⁸R⁸, —NR⁸S(O)$_2$R⁷, and R$^a$; and
R⁵ is H or C$_{1-6}$ alkyl, wherein the C$_{1-6}$ alkyl is optionally substituted with 1-3 groups independently selected from —B(OH)$_2$, —C(O)OR⁷, —C(O)NR⁸R⁸, —OC(O)C(O)OR⁷, —NR⁸R⁸, —N⁺R⁸R⁸R$^{8a}$, —NR⁸C(O)OR⁷, —NR⁸C(O)C(O)OR⁸, —NR⁸C(=NR$^{8a}$)NR⁸R⁸, —S(O)$_2$R⁷, —S(O)$_2$NR⁸R⁸, —S(O)$_2$OR⁷, —NR⁸C(O)R⁷, —NR⁸C(O)NR⁸R⁸, —NR'S(O)$_2$R⁷, R$^a$, and R$^{5a}$.

8. The compound of claim 1, or a pharmaceutically acceptable salt thereof, wherein X is —C(O)OR⁶, and R⁶ is C$_{1-10}$ alkyl, wherein the C$_{1-10}$ alkyl is optionally substituted with 1-3 groups independently selected from —OH, —CN, halogen, —C(O)OR⁷, —S(O)$_2$OR⁷, —(O(C$_{1-4}$ alkyl))$_n$OR$^{7a}$, —NR⁸R⁸, R$^a$, —OC(O)(C$_{2-6}$ alkenylene)C(O)OR⁹, 5-6 membered monocyclic heterocyclyl, and 6 membered monocyclic heteroaryl.

9. The compound of claim 1, or a pharmaceutically acceptable salt thereof, wherein X is —C(O)OR⁶ and R⁶ is C$_{1-5}$ alkyl, wherein the C$_{1-5}$ alkyl is substituted with one —(O(C$_{1-4}$ alkyl))$_n$OR$^{7a}$ and wherein n is 1, 2, or 3.

10. The compound of claim 1, or a pharmaceutically acceptable salt thereof, wherein X is —C(O)OR⁶ and R⁶ is C$_{1-4}$ alkyl, wherein the C$_{1-4}$ alkyl is substituted with pyridinyl or morpholinyl.

11. The compound of claim 1, or a pharmaceutically acceptable salt thereof, wherein X is —C(O)OR⁶ and R⁶ is C$_{3-5}$ monocyclic cycloalkyl, wherein the C$_{3-5}$ monocyclic cycloalkyl is substituted with 1-2 groups independently selected from —C(O)OH, —NR¹R¹, and R$^a$.

12. The compound of claim 1, or a pharmaceutically acceptable salt thereof, wherein X is —C(O) C$_{1-10}$ alkyl, wherein the C$_{1-10}$ alkyl is optionally substituted with one 4-7 membered monocyclic heterocyclyl, wherein the 4-7 membered monocyclic heterocyclyl is optionally substituted with 1-3 groups independently selected from —OH, —C(O)OH, —C(=NR$^{8a}$)(NR⁸R⁸), and R$^a$.

13. The compound of claim 1, or a pharmaceutically acceptable salt thereof, wherein each R⁷ independently is H or C$_{1-6}$ alkyl, wherein the C$_{1-6}$ alkyl is optionally substituted with 1-3 groups independently selected from —OH, —NR¹⁰R¹⁰, and R$^a$.

14. The compound of claim 1, or a pharmaceutically acceptable salt thereof, wherein each R⁸ independently is H, —C(O) OR⁹, —C(O)C(O)OH, —C(=NH)NH$_2$, or C$_{1-6}$ alkyl, wherein the C$_{1-6}$ alkyl is optionally substituted with 1-3 groups independently selected from —OH, C(O)OH, and R$^a$.

15. The compound of claim 1, which is selected from the group consisting of
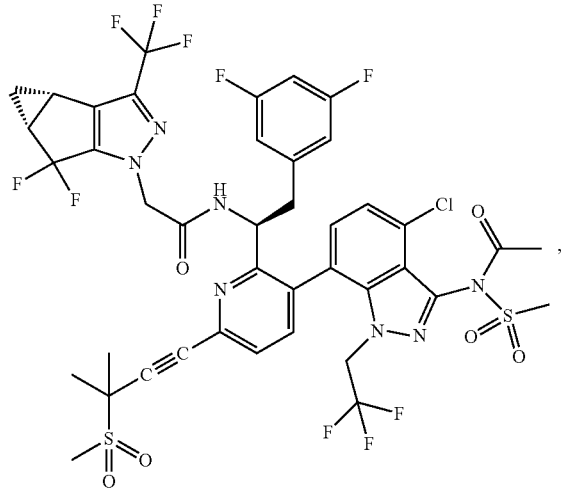
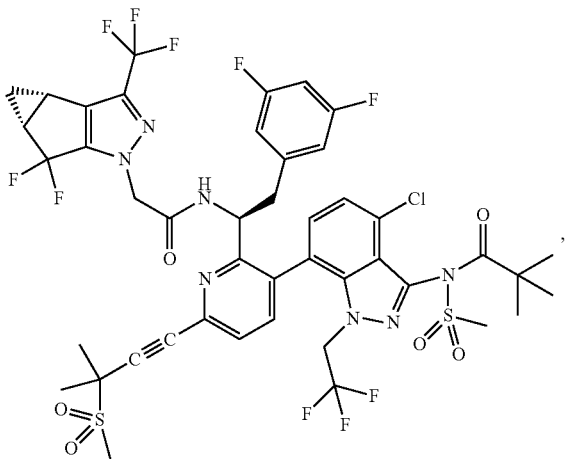
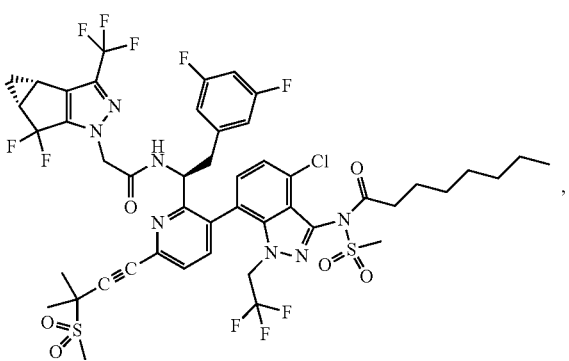
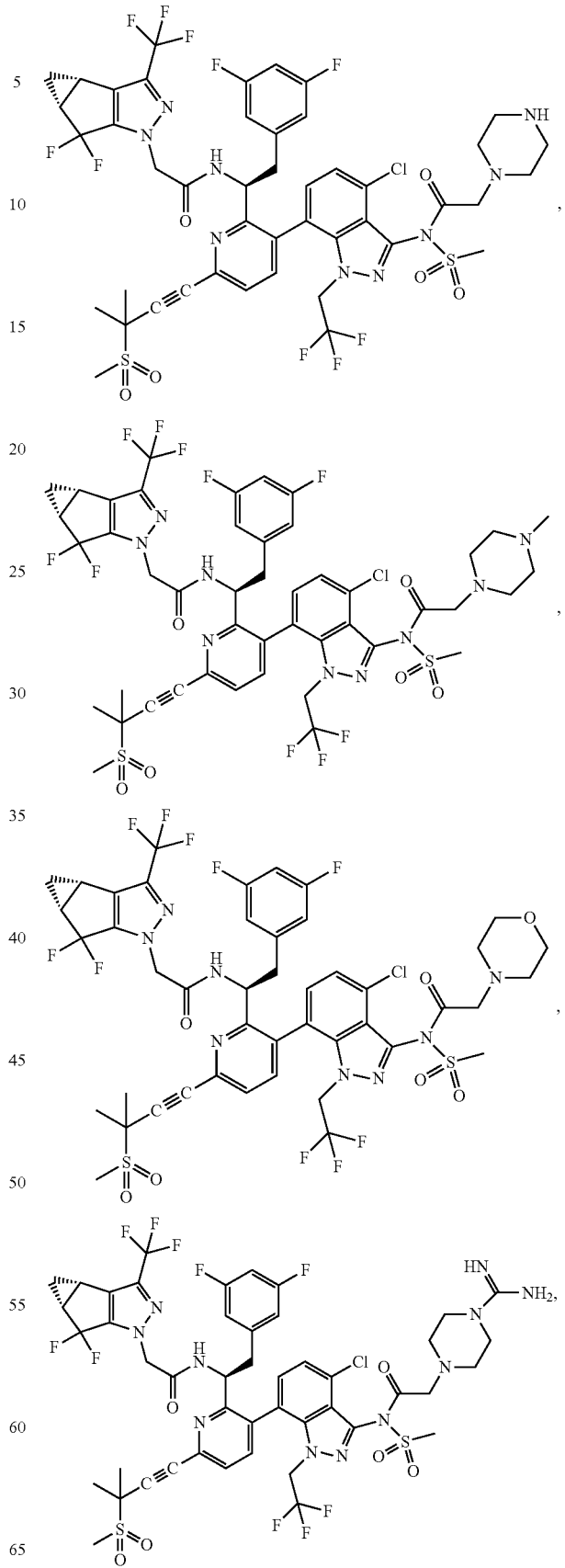

391
-continued
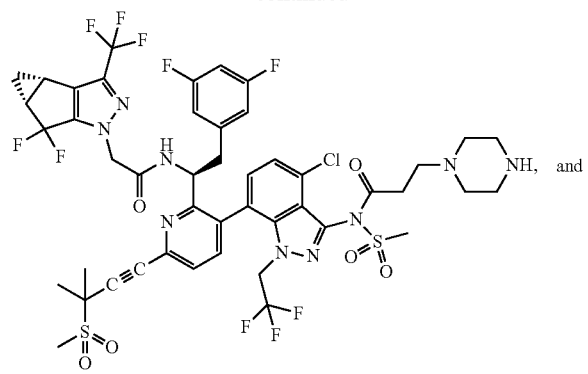
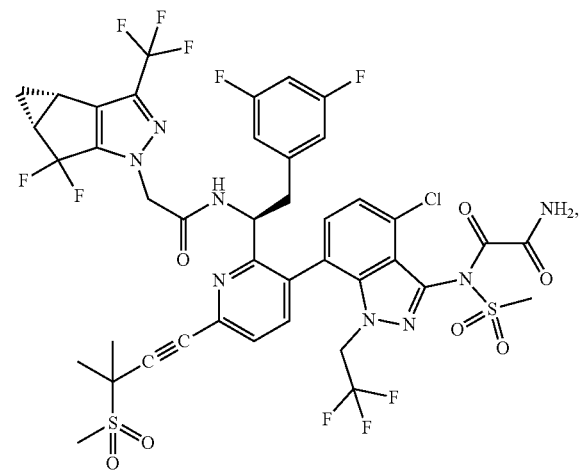
or a pharmaceutically acceptable salt thereof.
16. The compound of claim 1, which is selected from the group consisting of
392
-continued
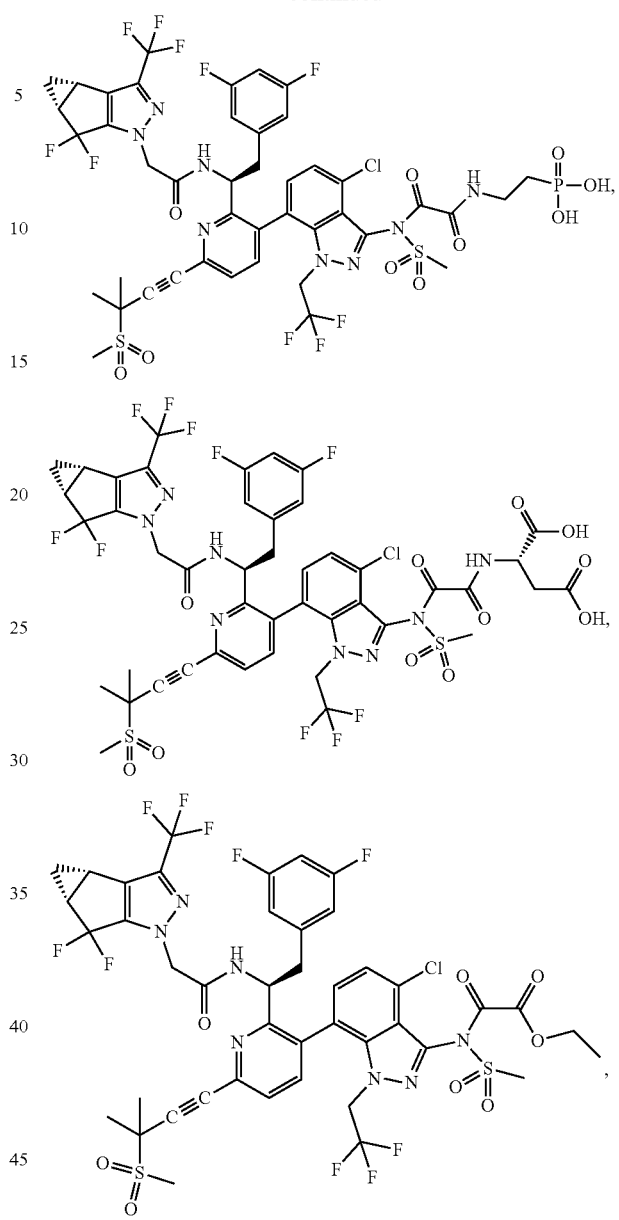
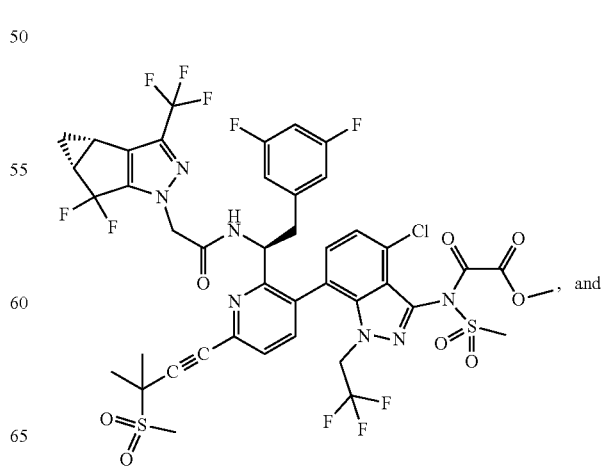

393
-continued
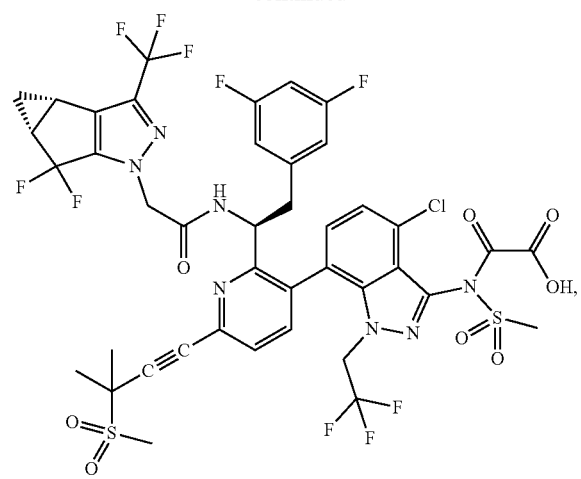
or a pharmaceutically acceptable salt thereof.
17. The compound of claim 1, which is selected from the group consisting of
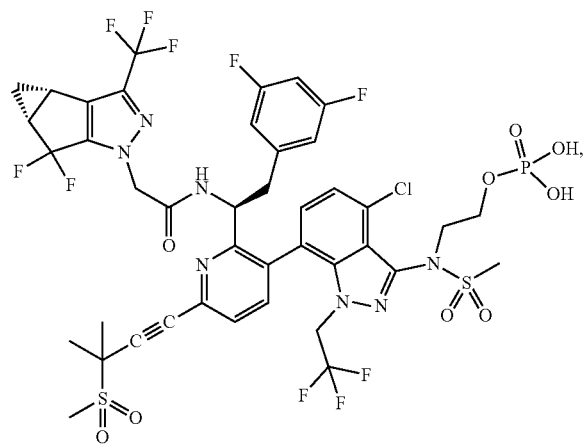
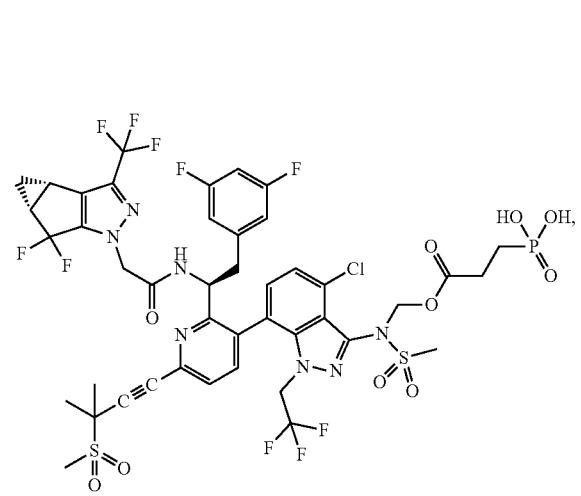
394
-continued
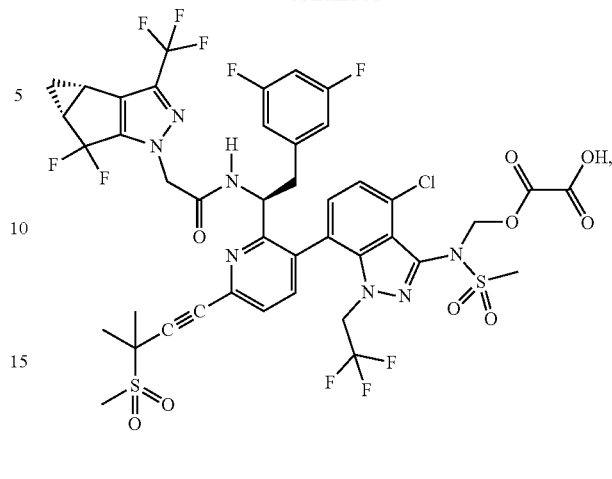
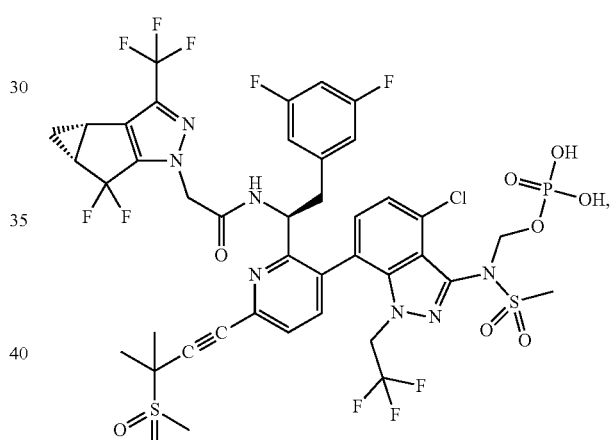
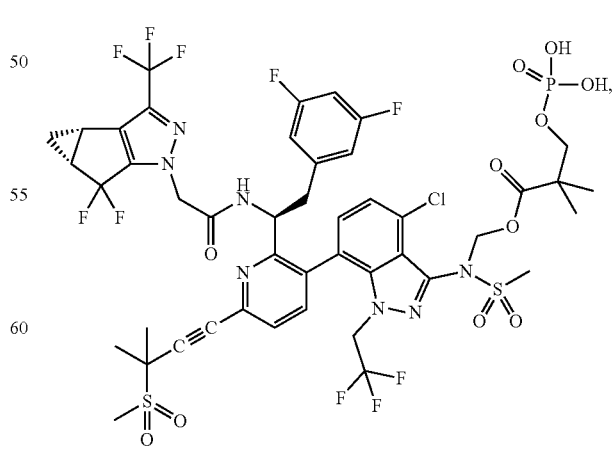
or a pharmaceutically acceptable salt thereof.

18. The compound of claim 1, which is selected from the group consisting of
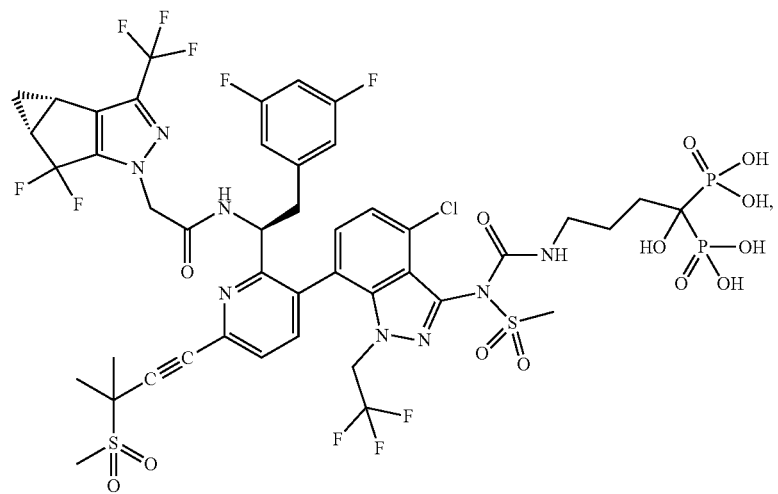
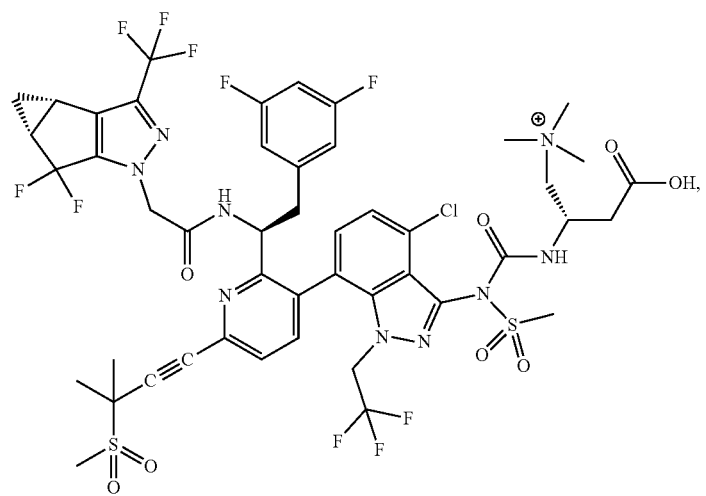
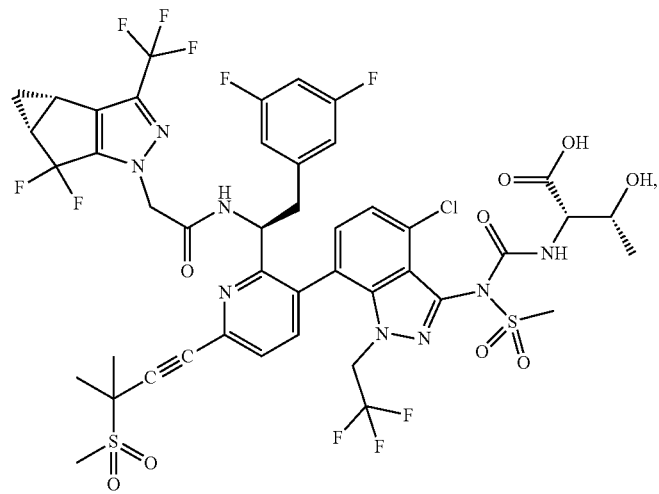

-continued
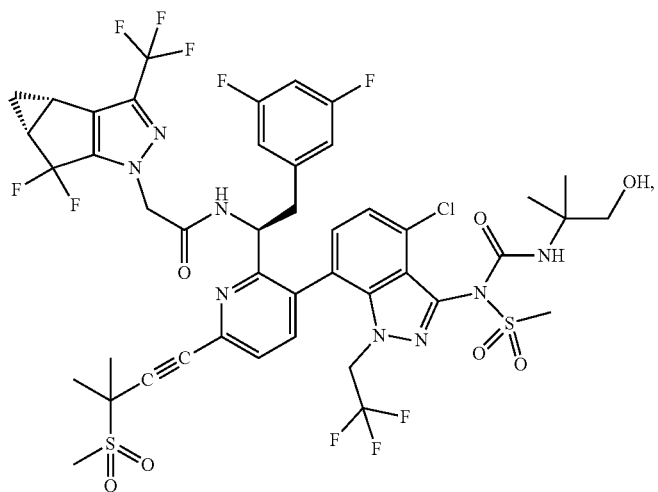
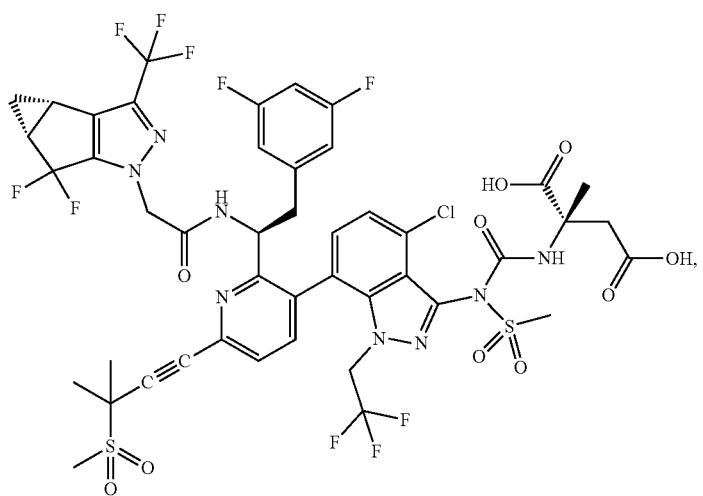
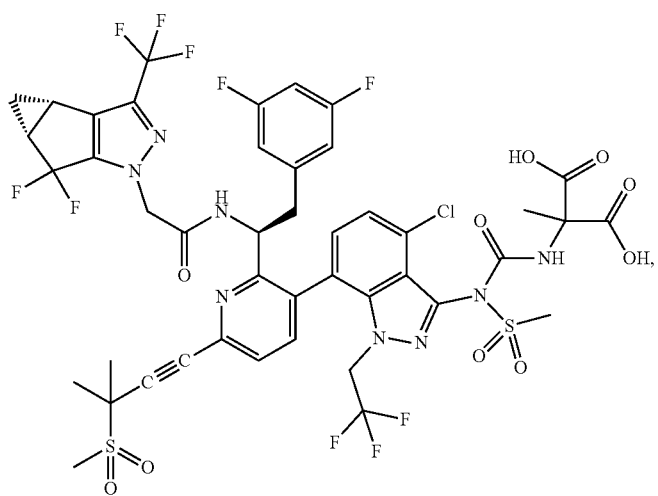

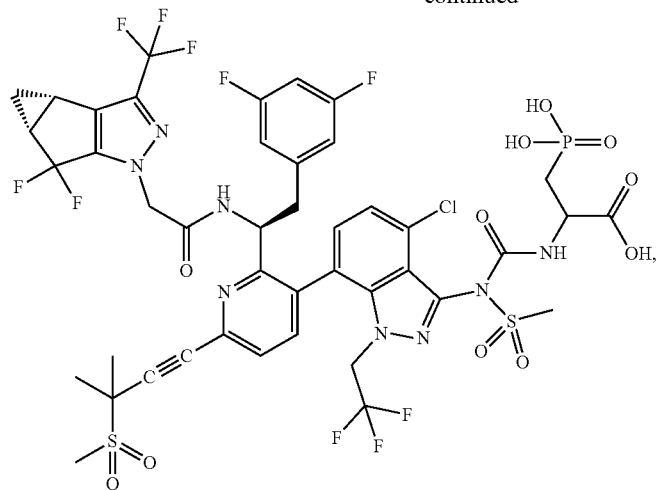
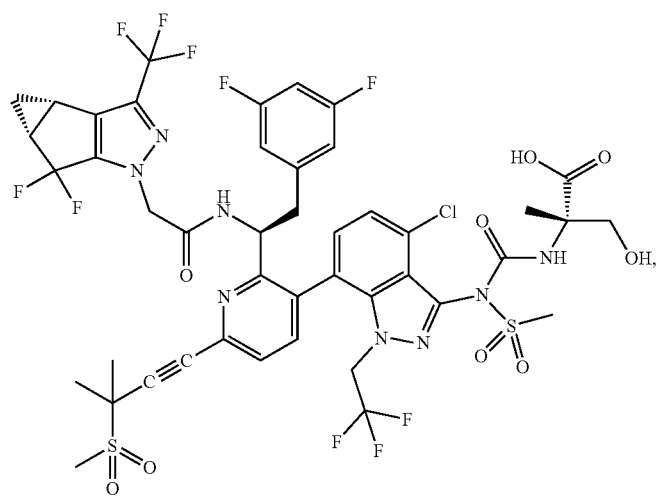
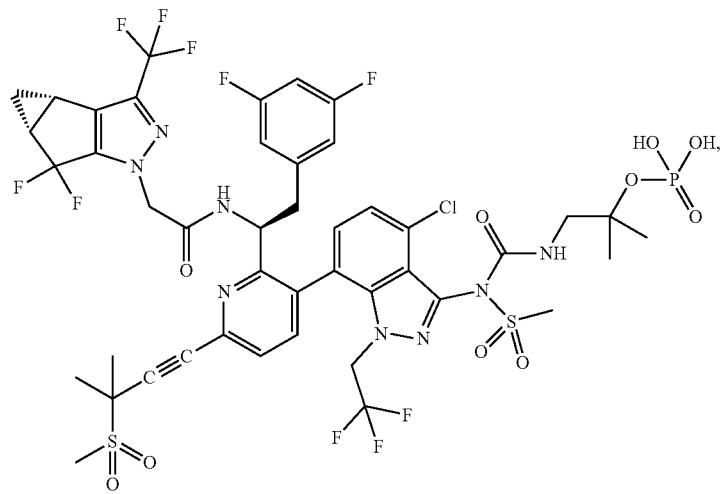

-continued
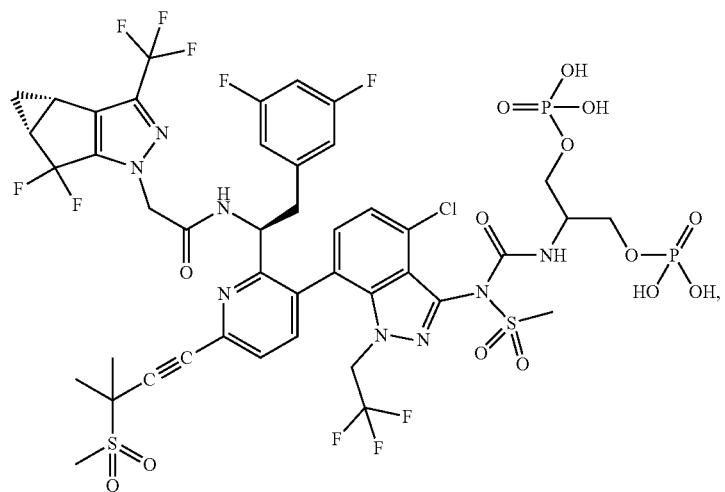
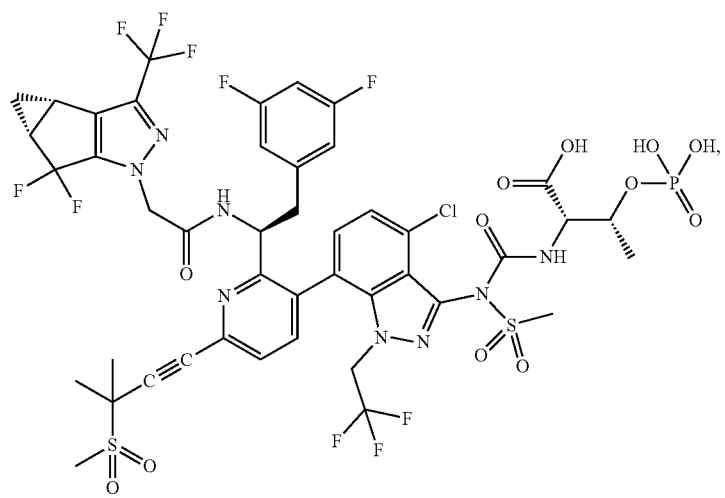
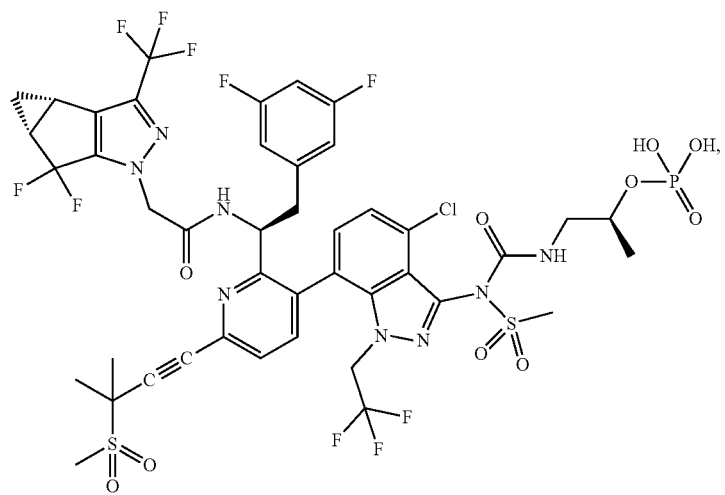

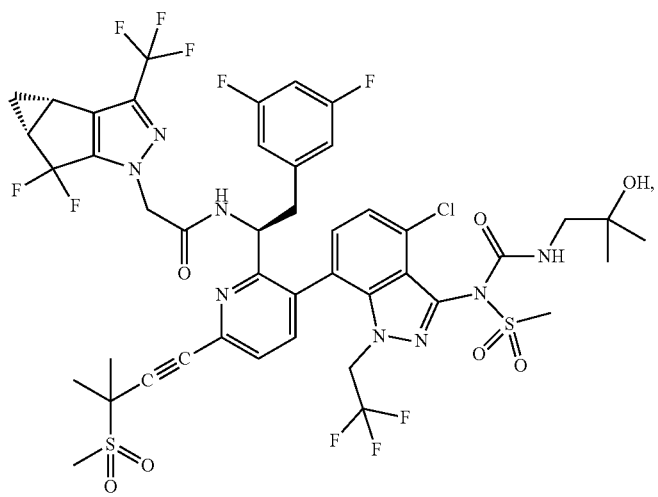
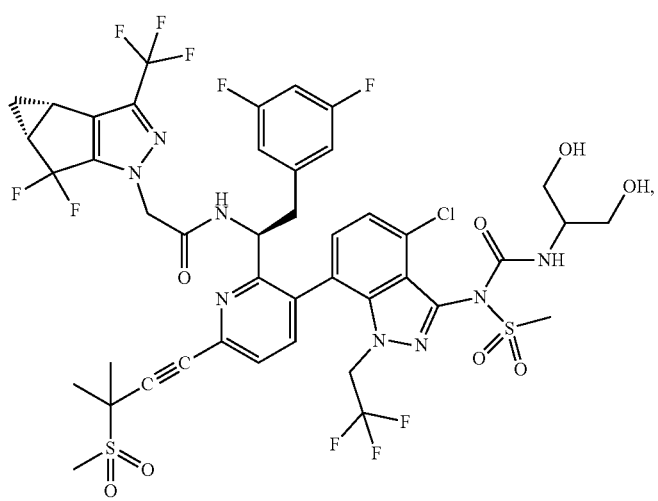
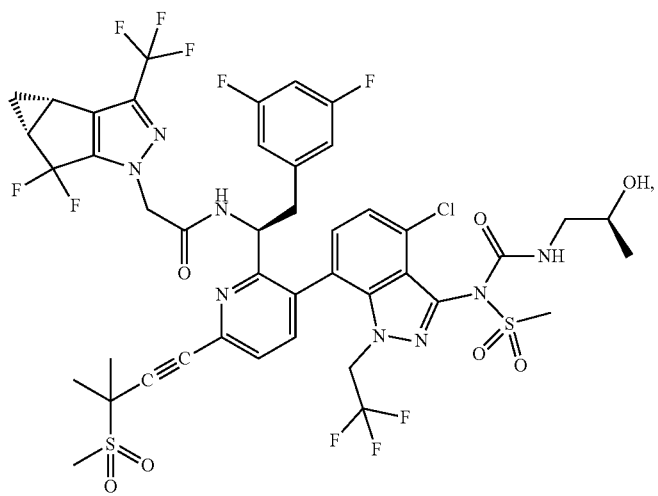

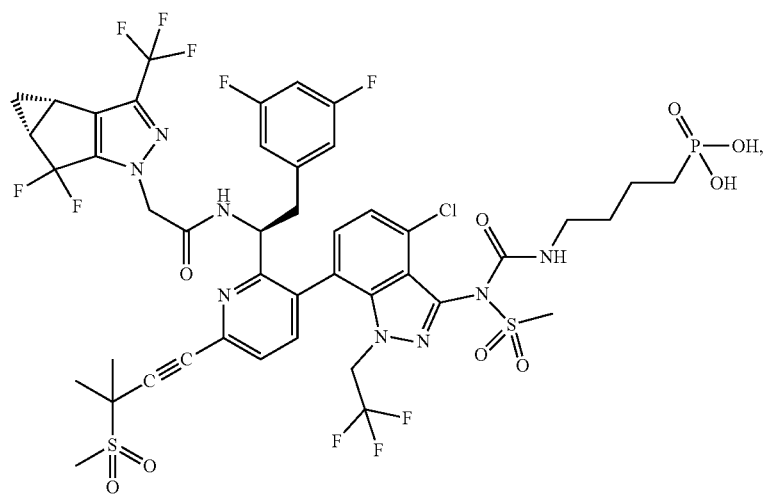
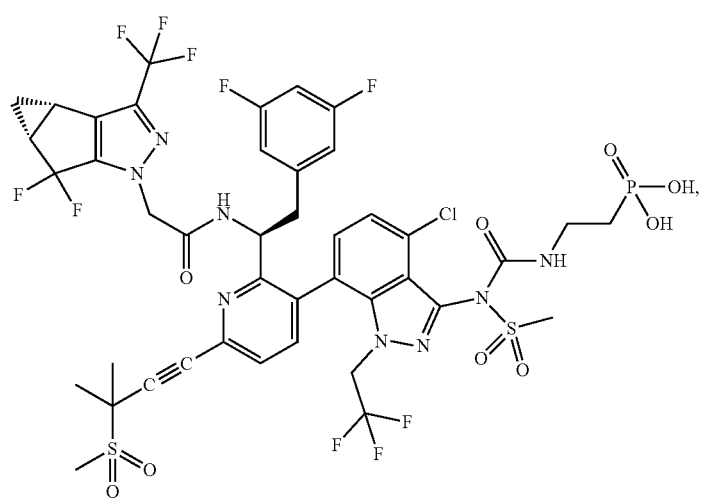
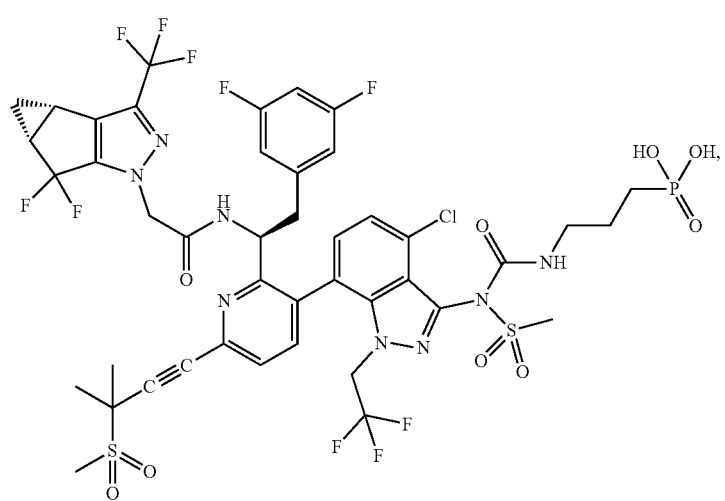

-continued
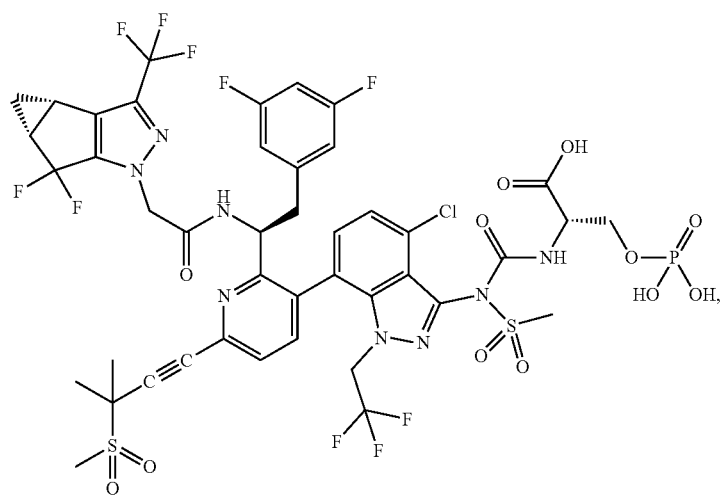
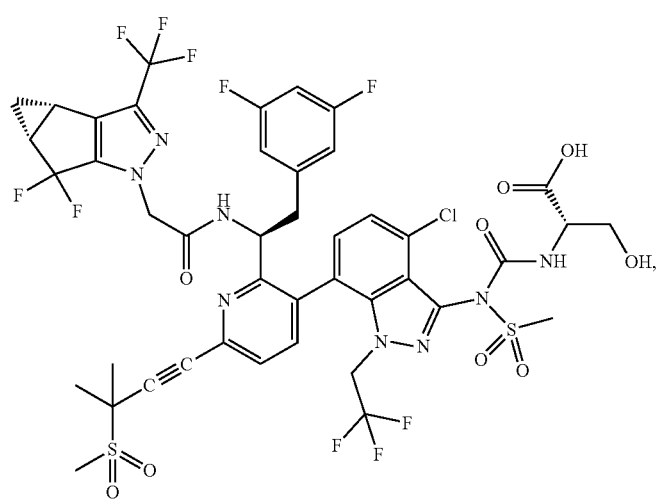
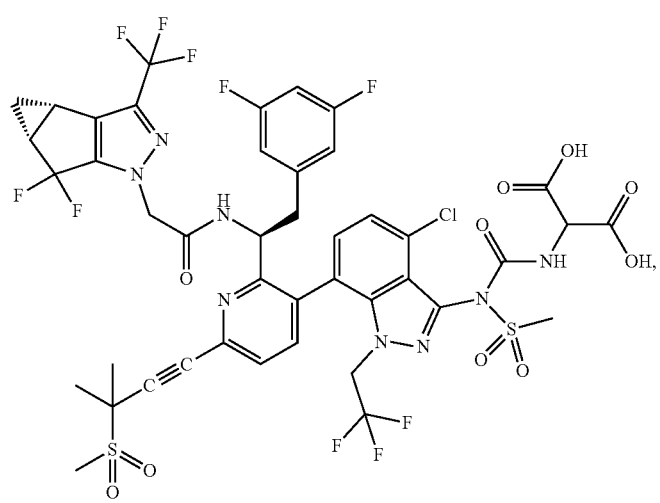

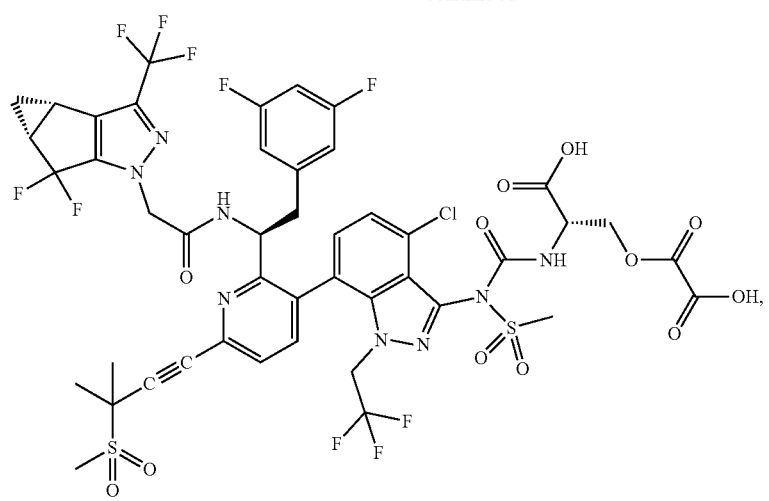
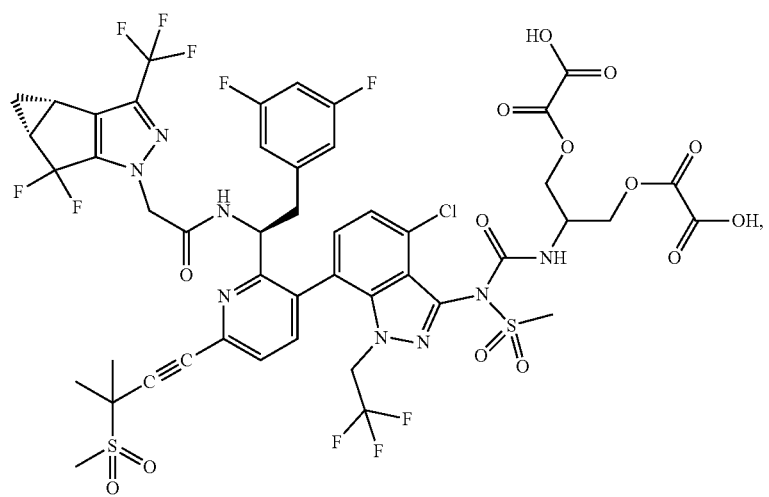
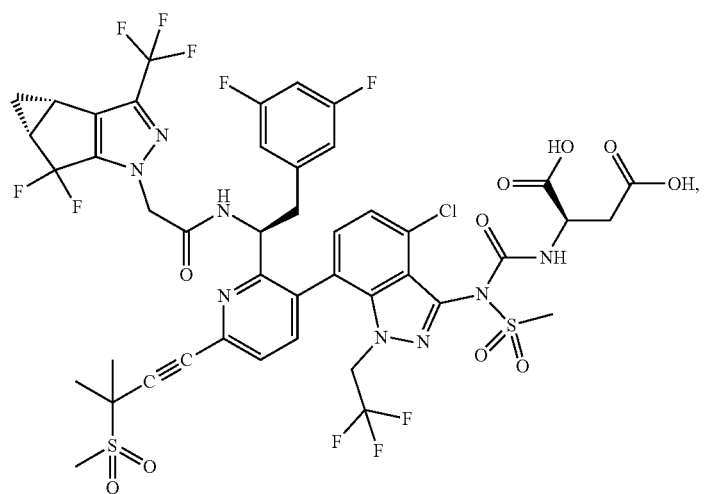

-continued
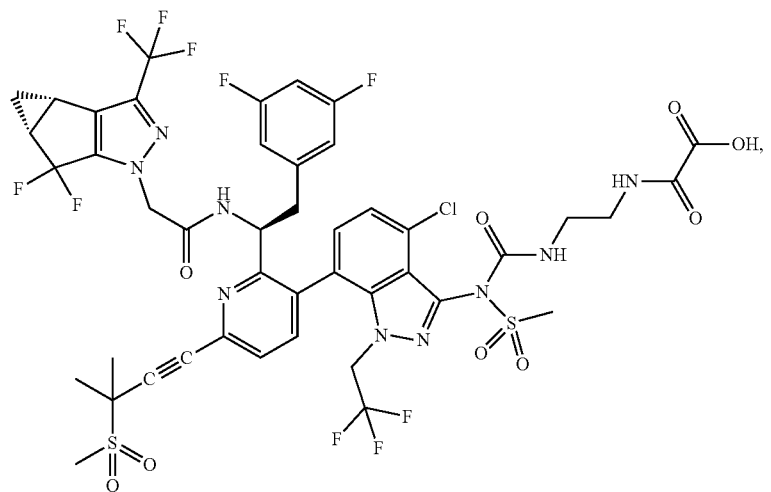
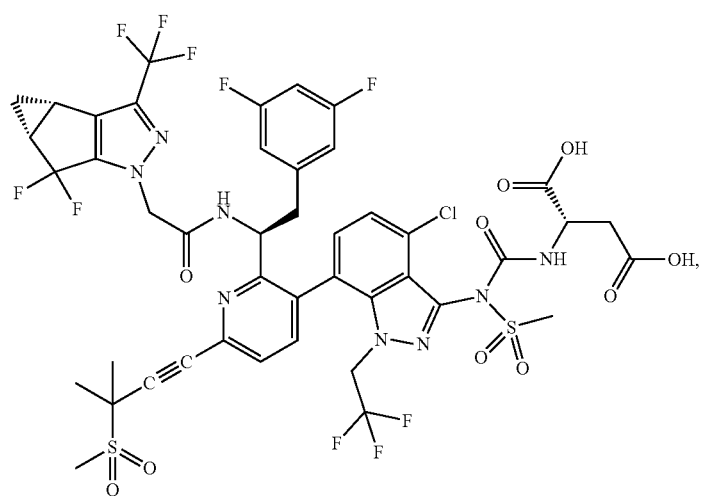
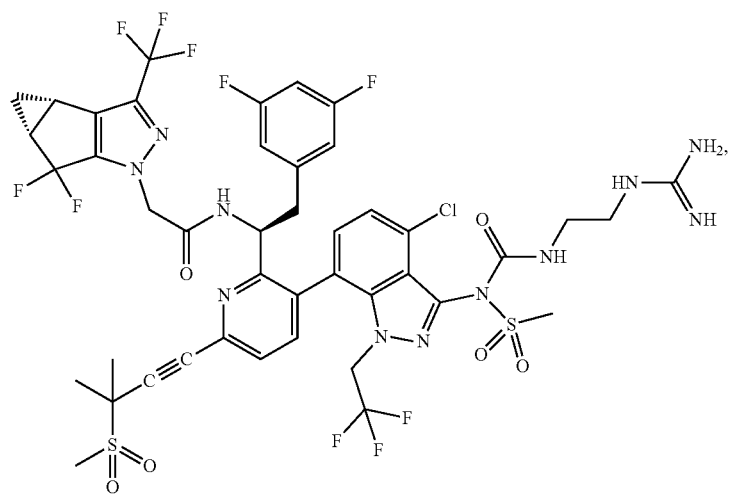

-continued
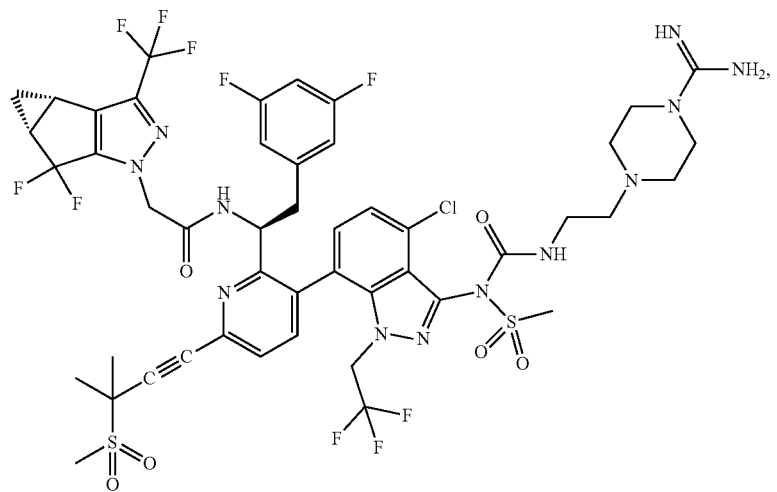
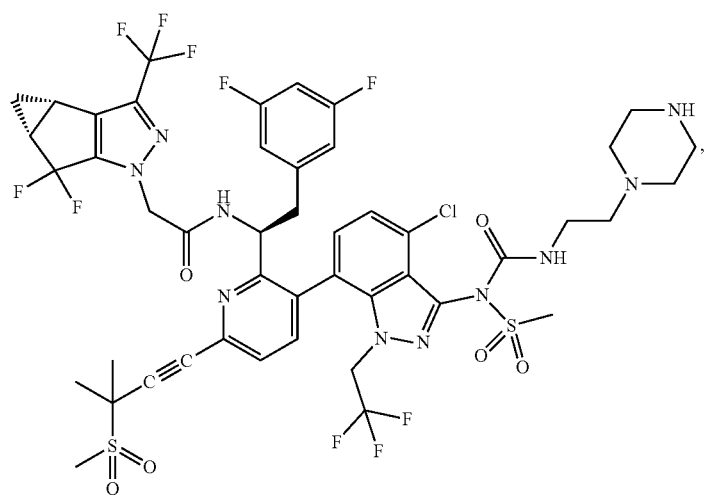
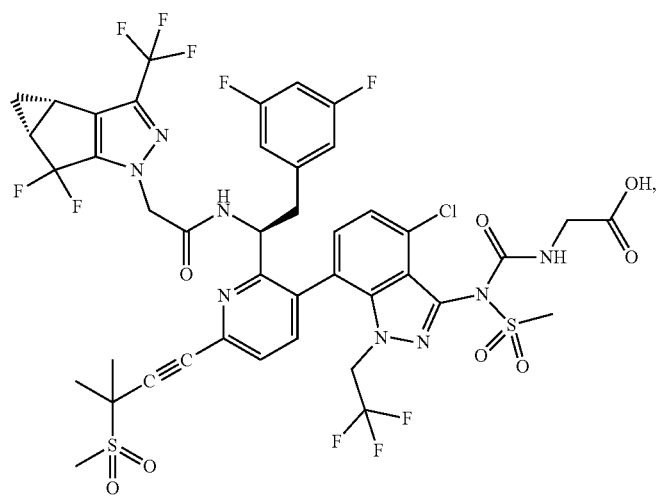

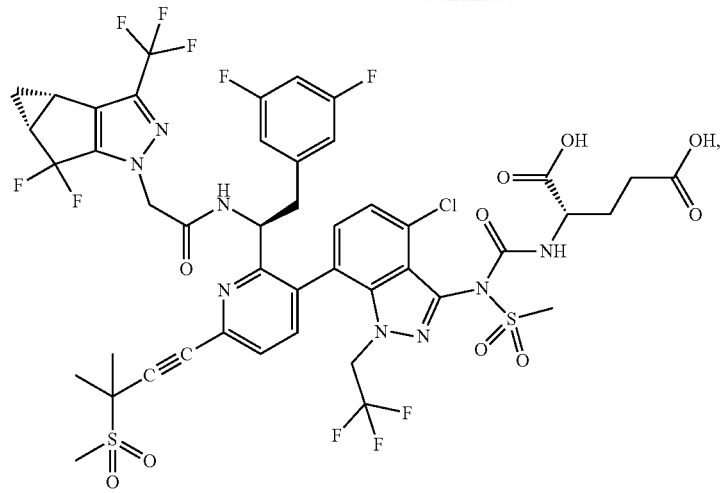
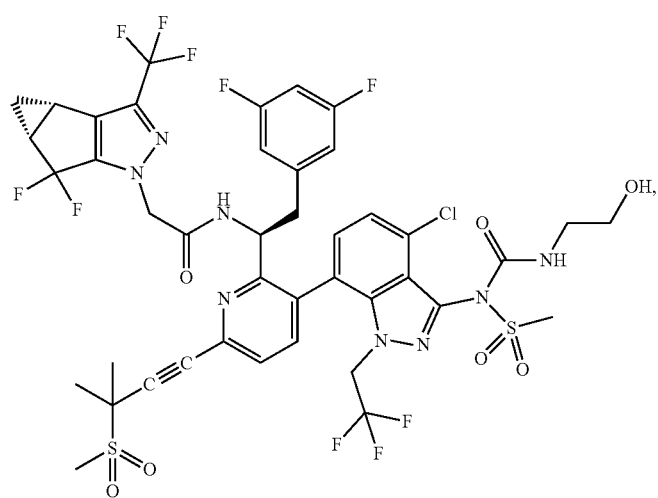
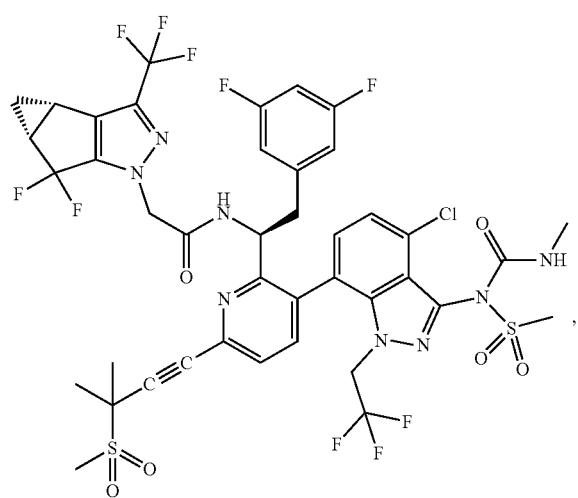

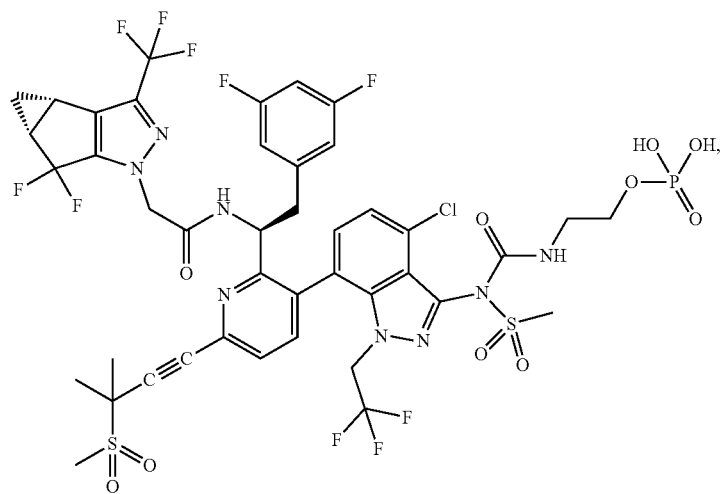
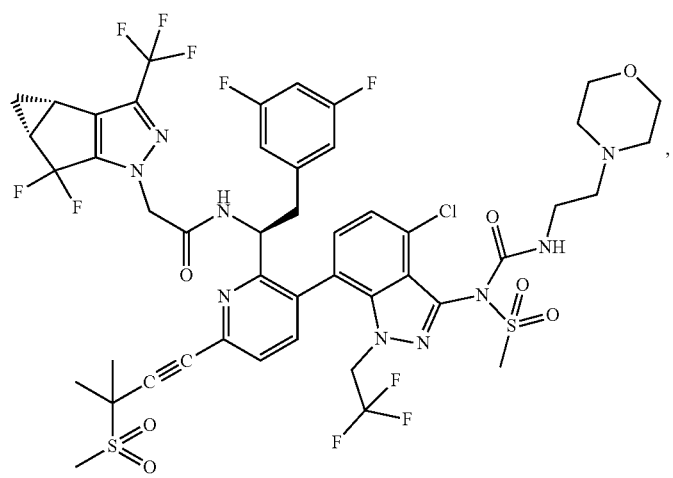
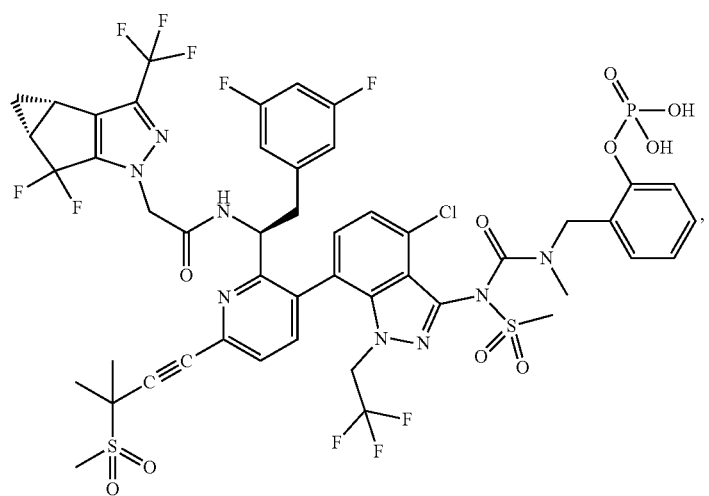

-continued
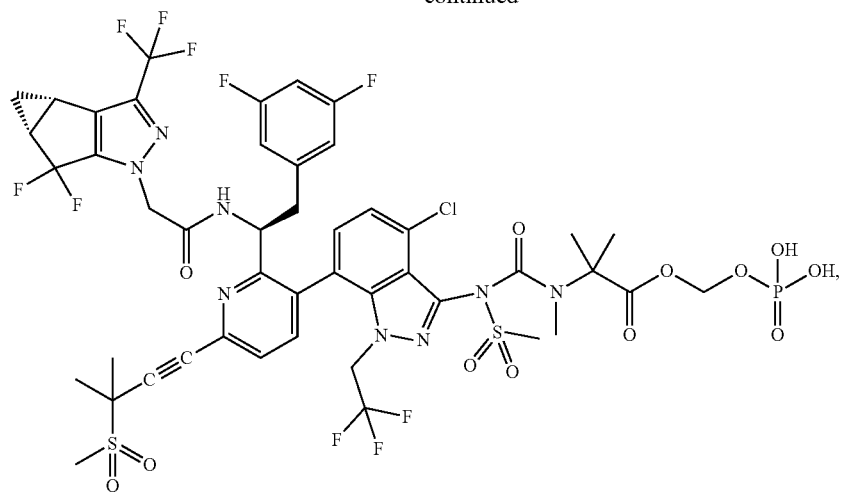
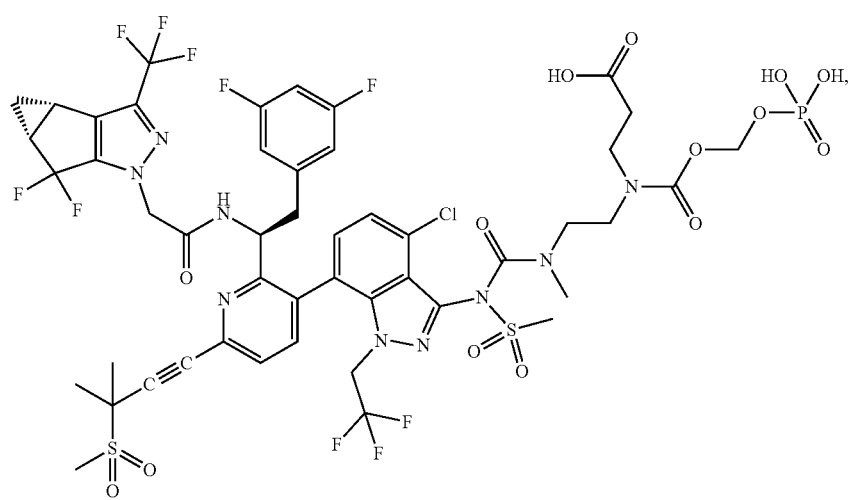
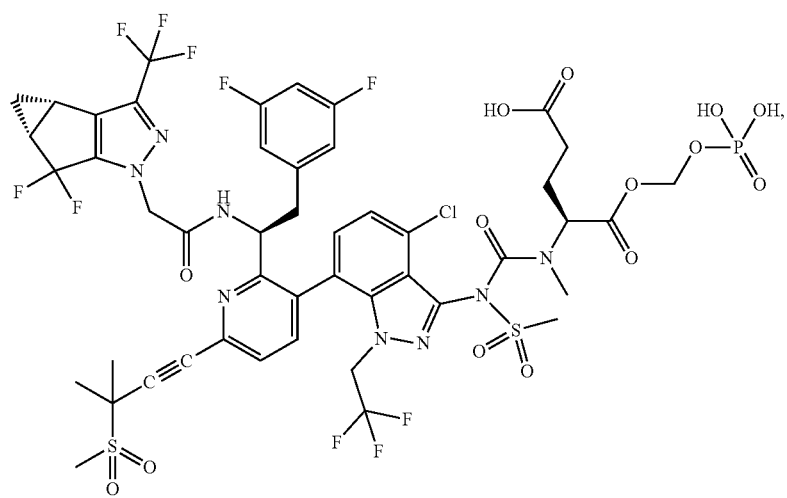

-continued
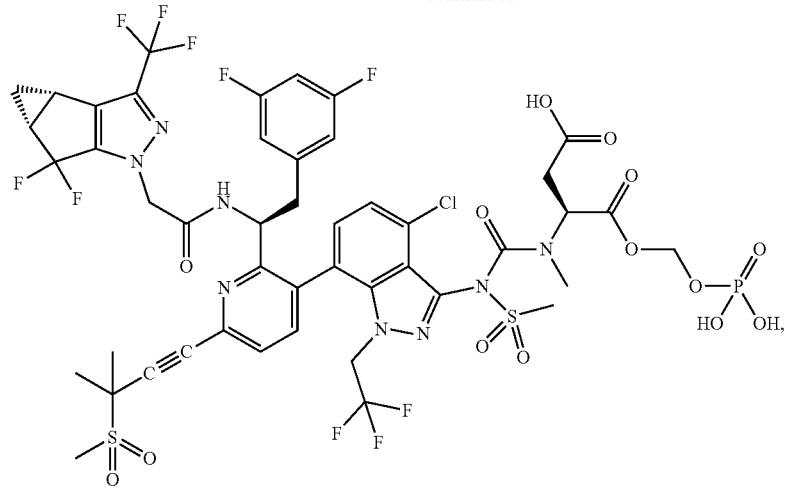
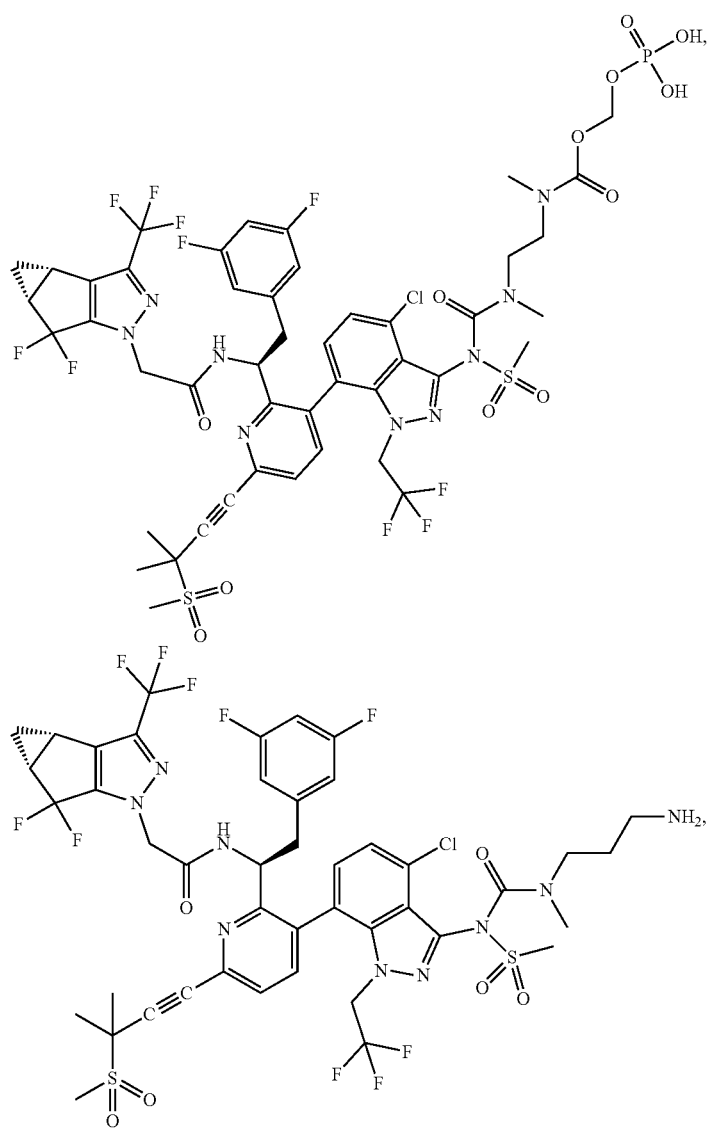

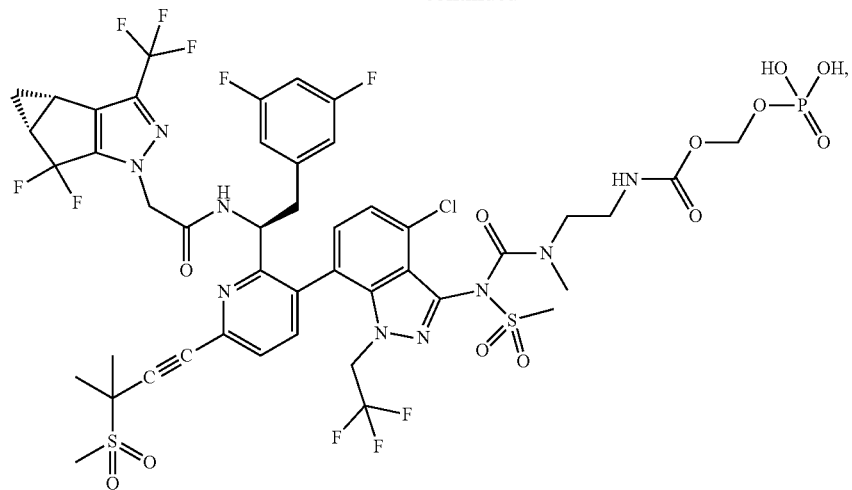
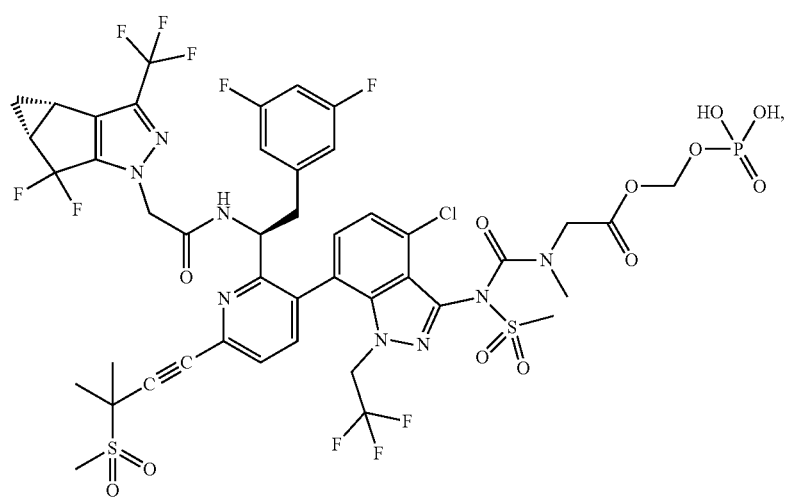
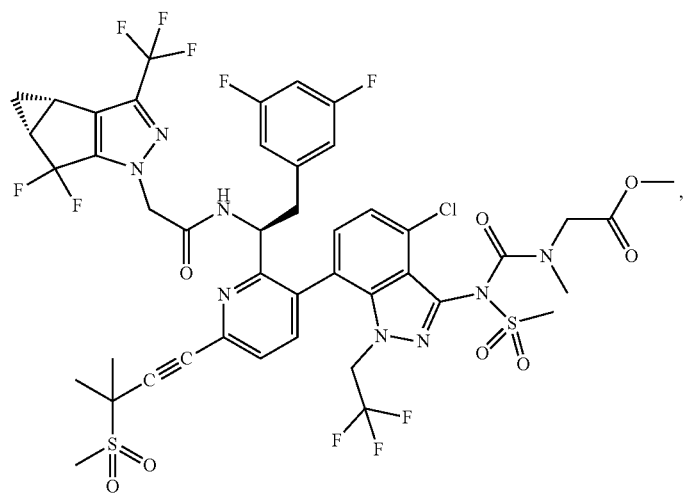

-continued
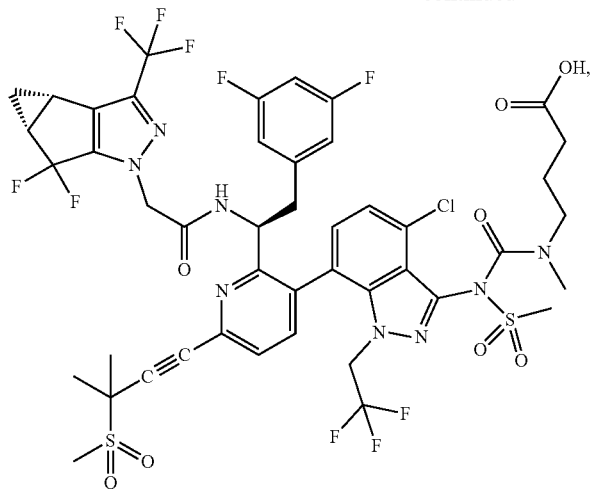
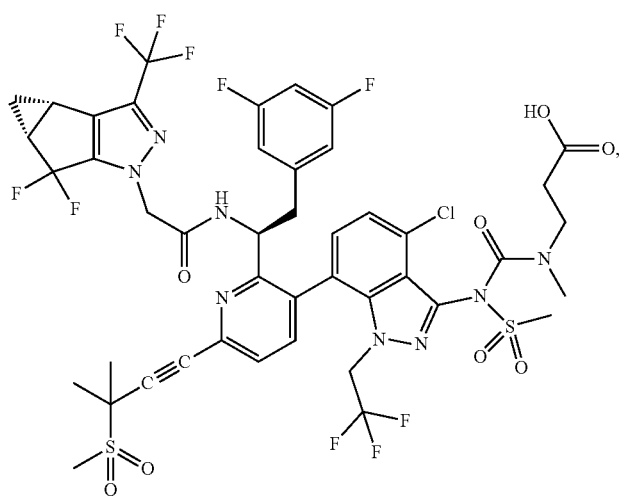
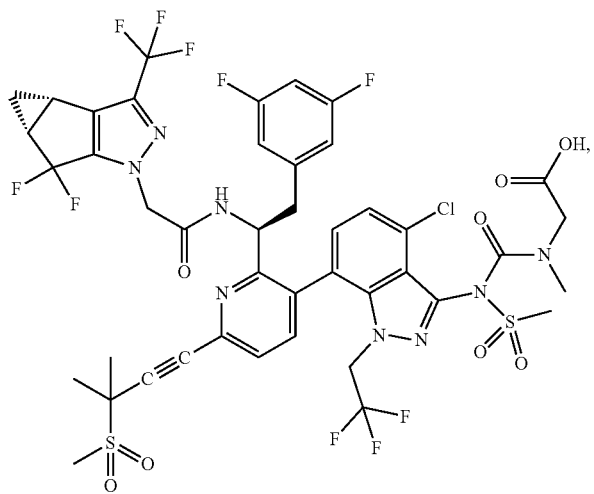

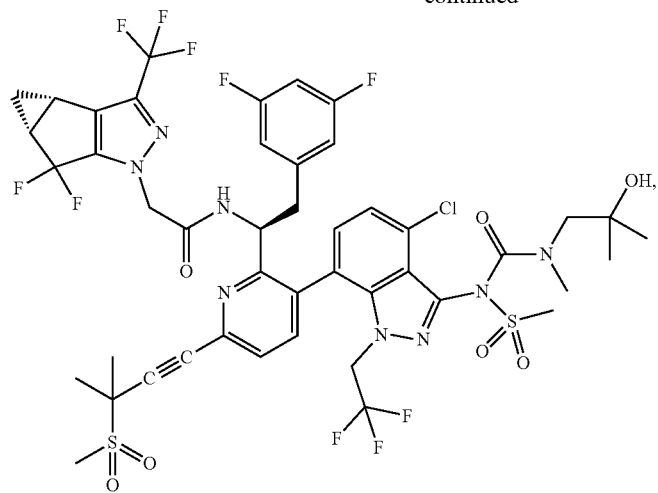
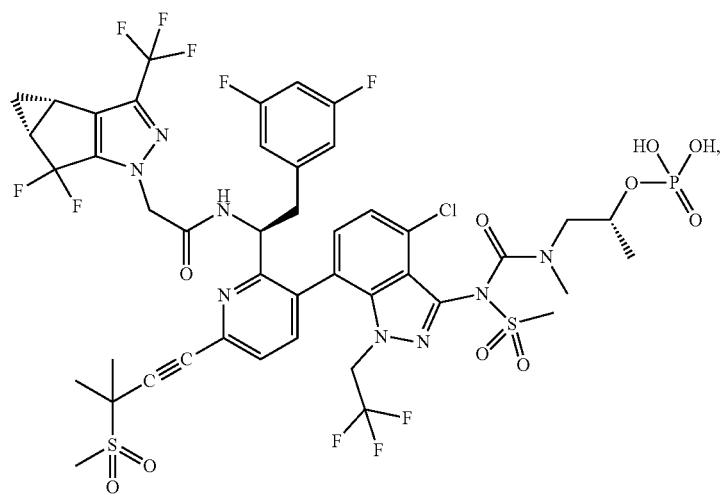
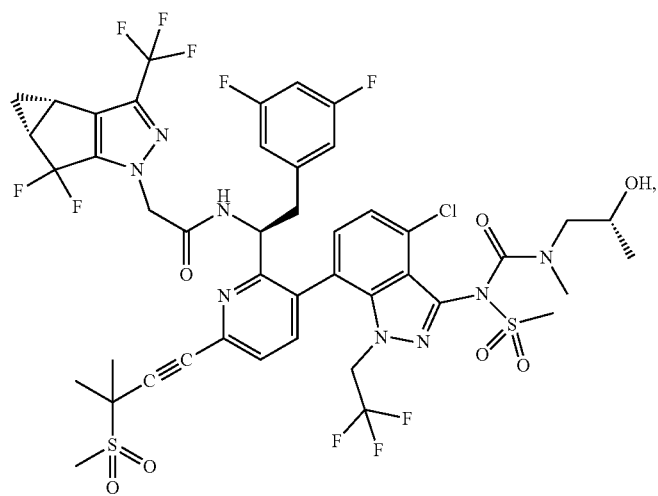

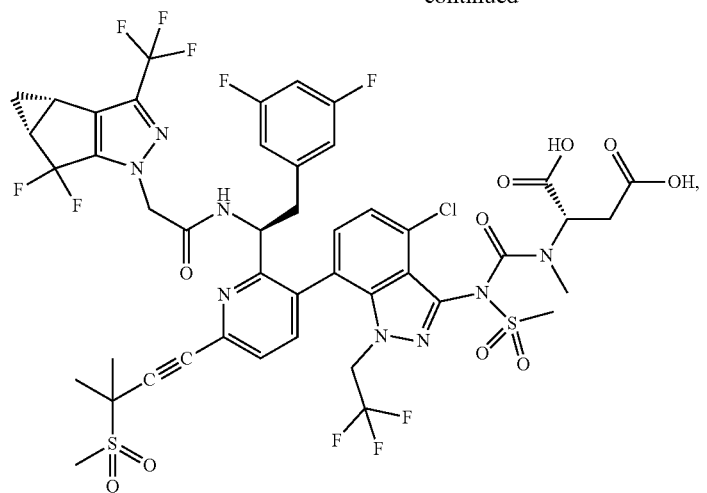
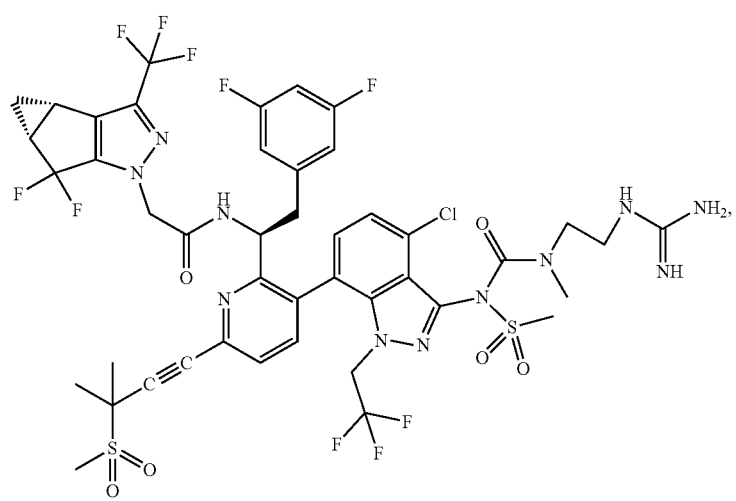
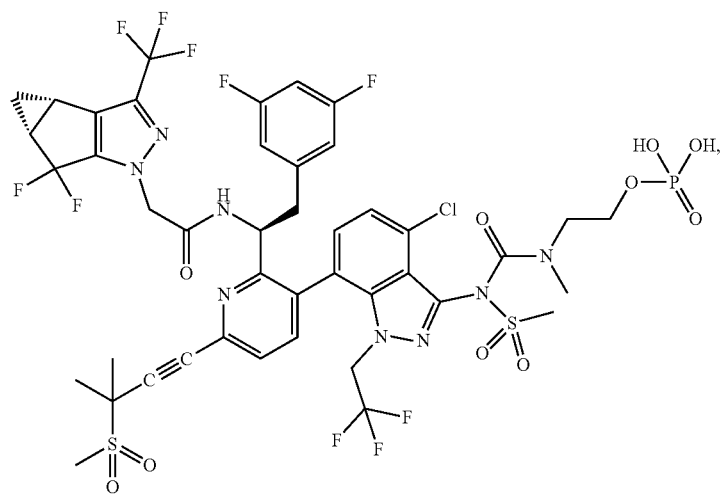

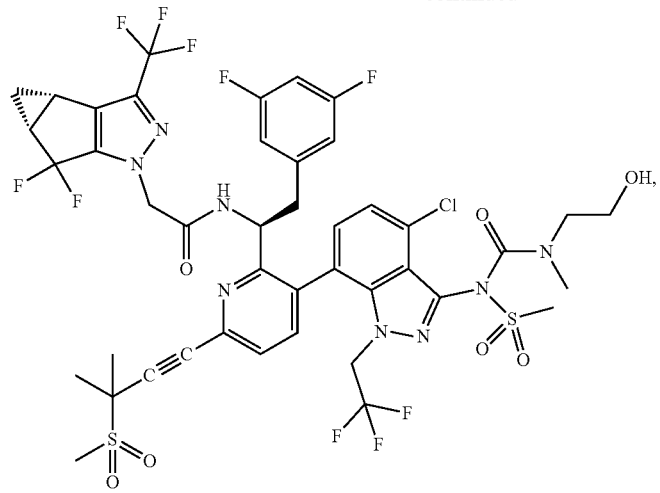
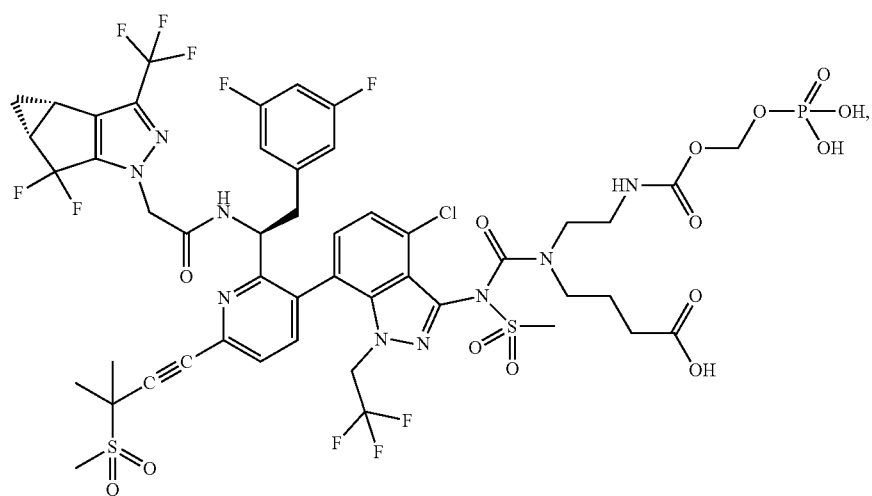
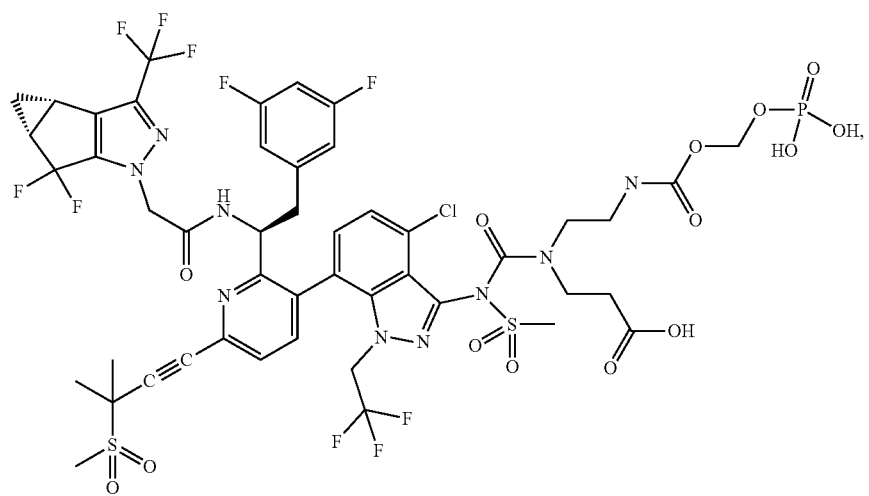

-continued
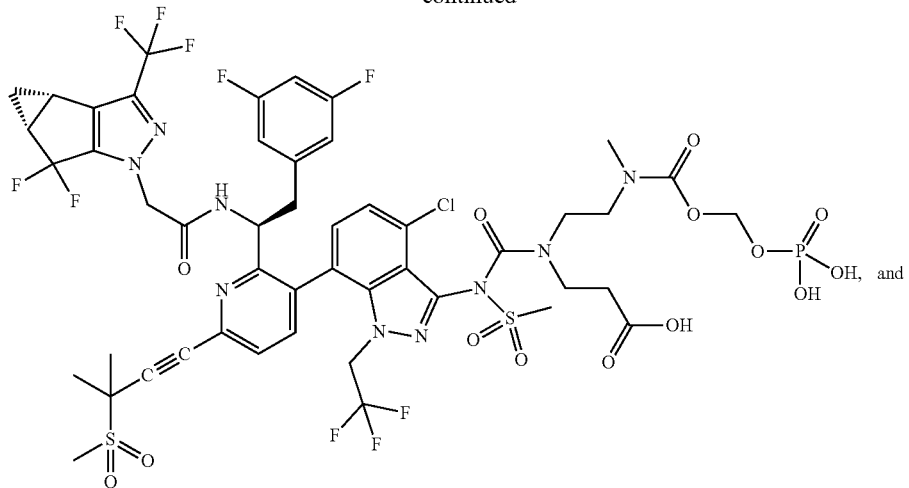
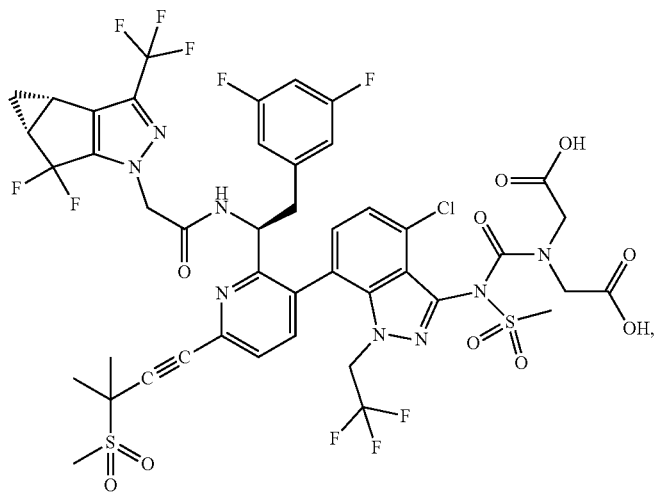
or a pharmaceutically acceptable salt thereof.
19. The compound of claim 1, which is selected from the group consisting of
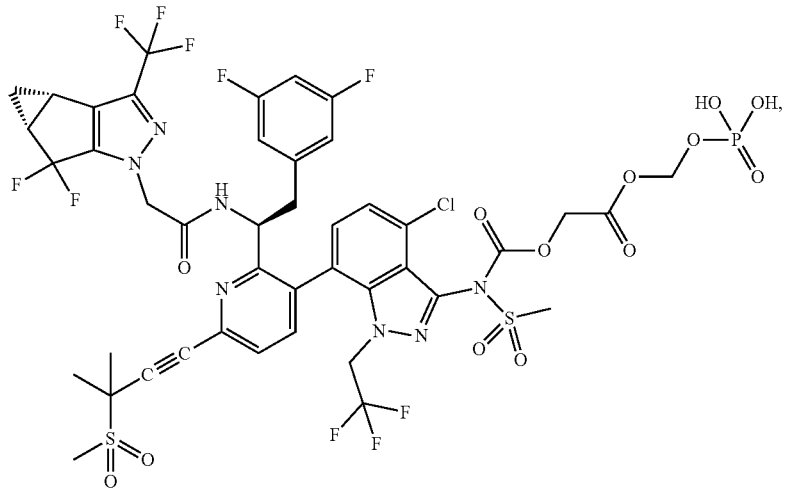

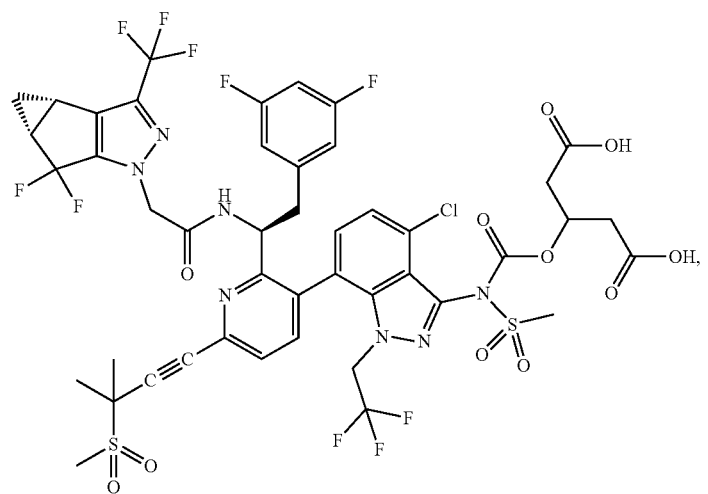
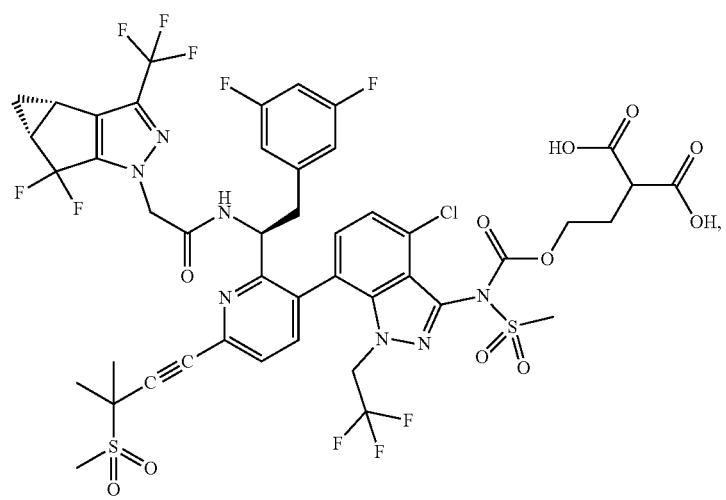
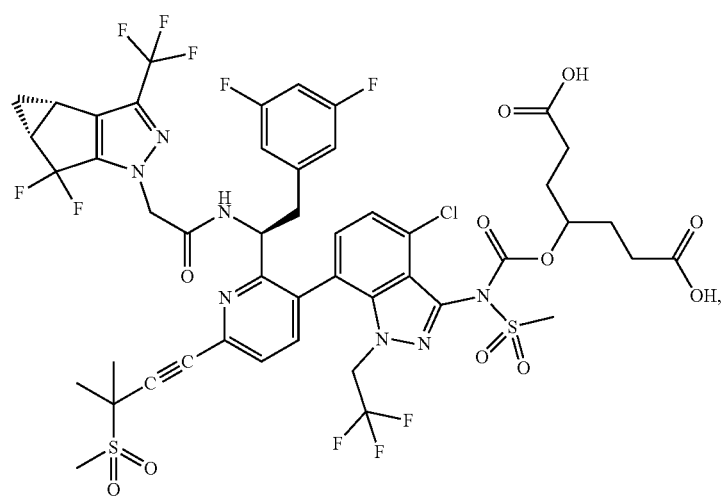

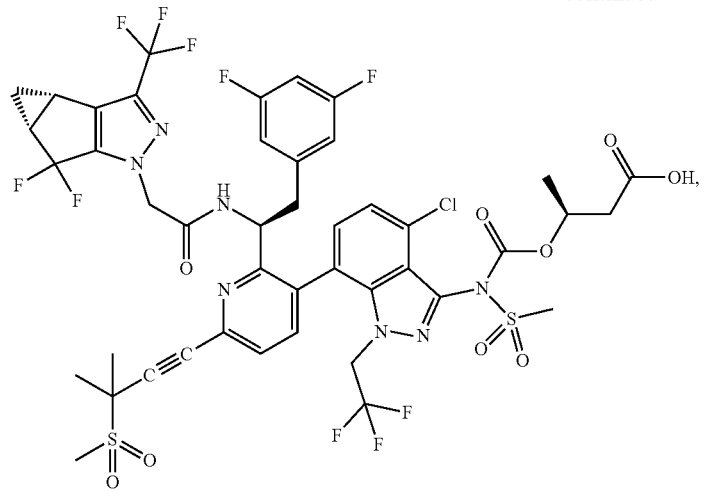
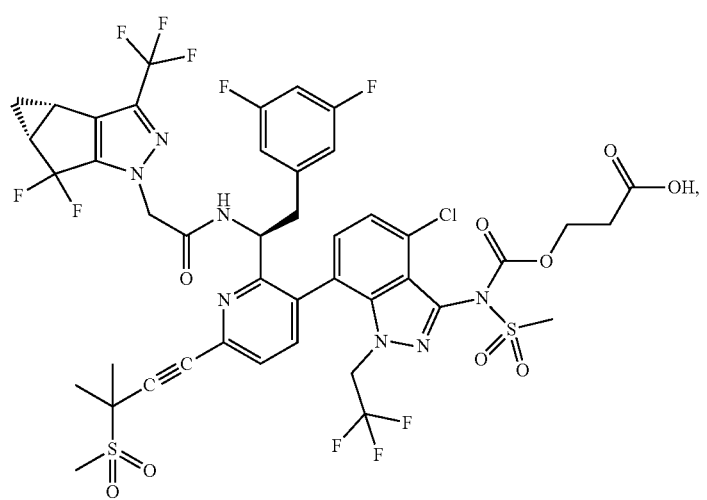
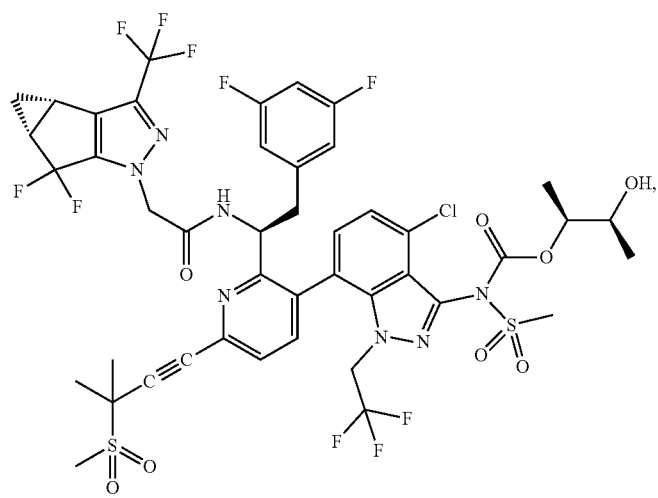

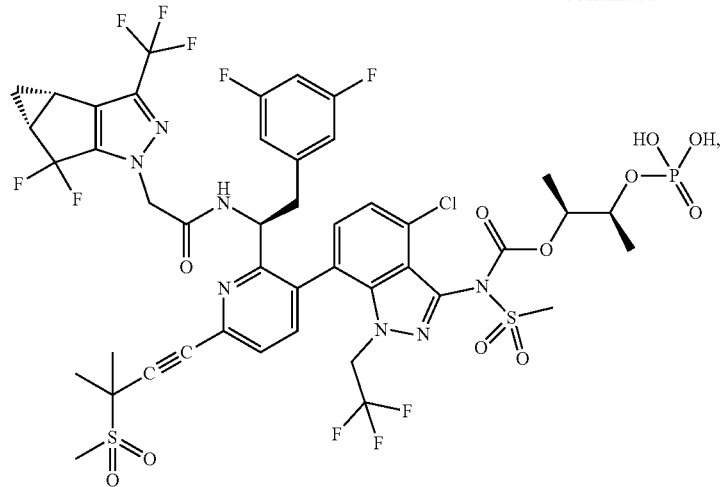
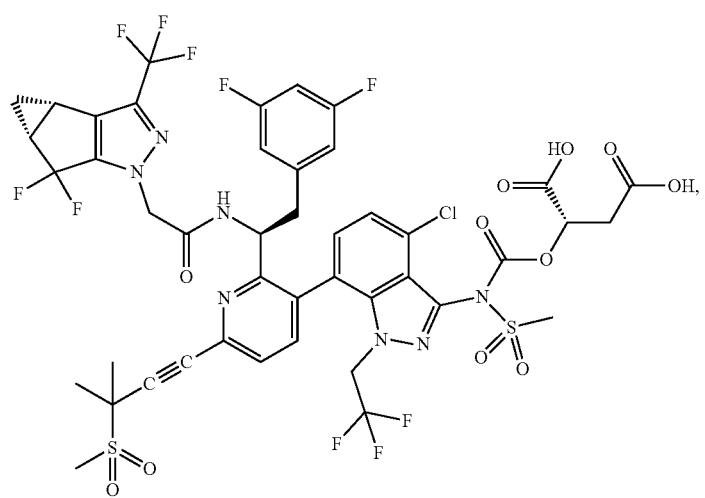
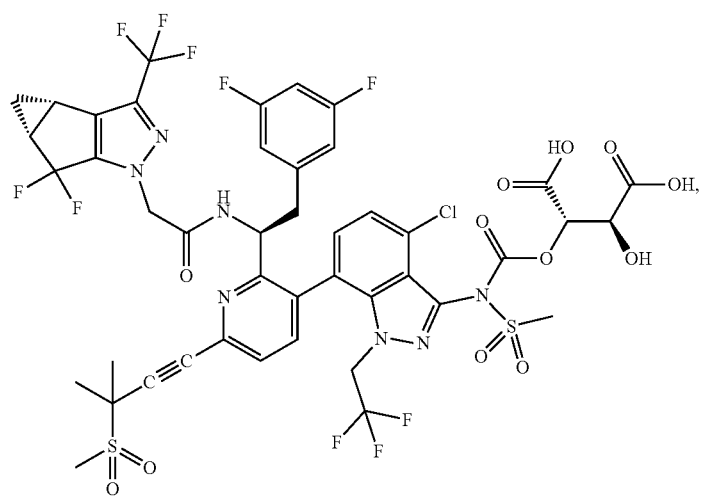

-continued
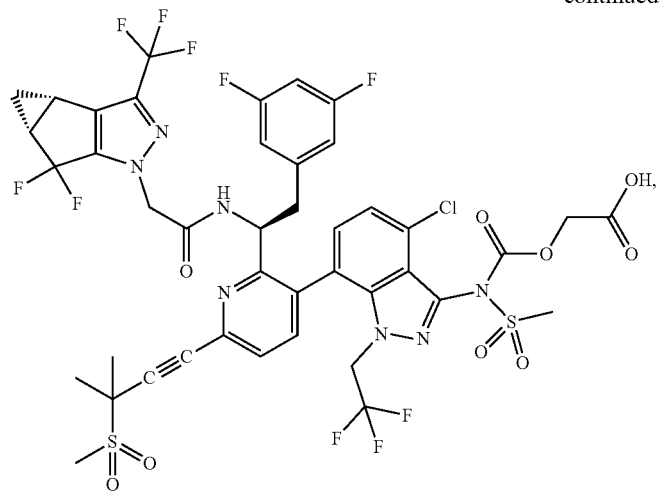
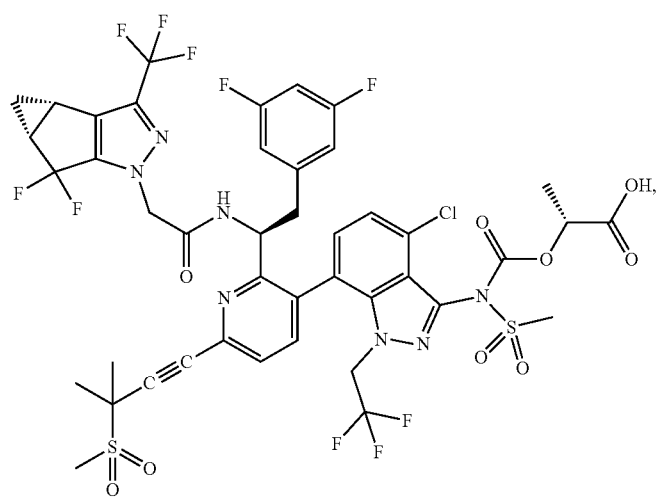
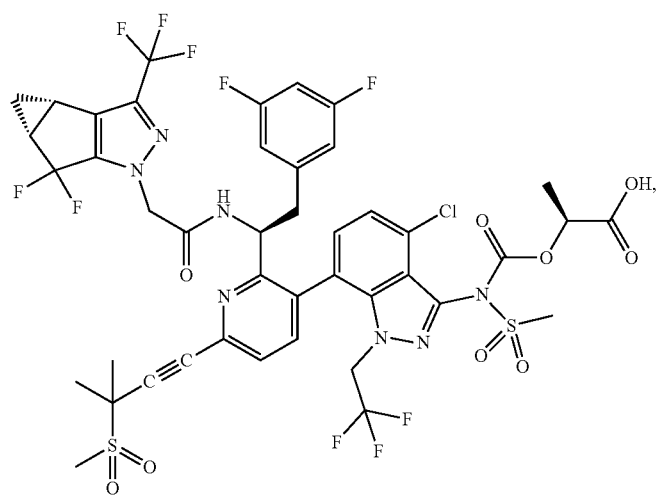

443
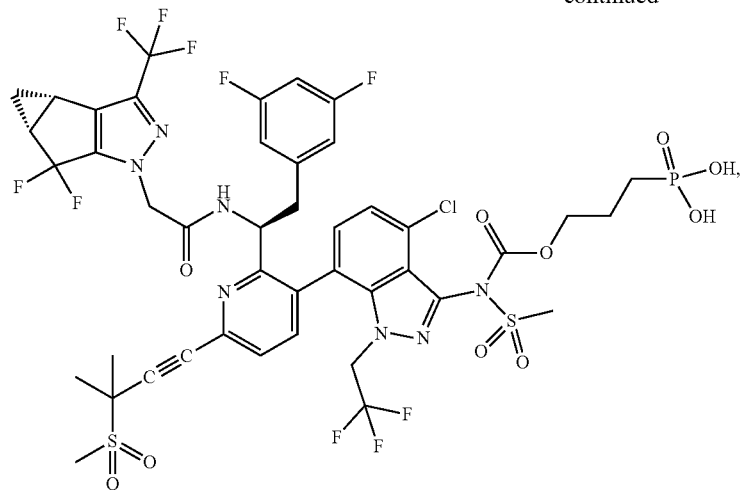
444
-continued
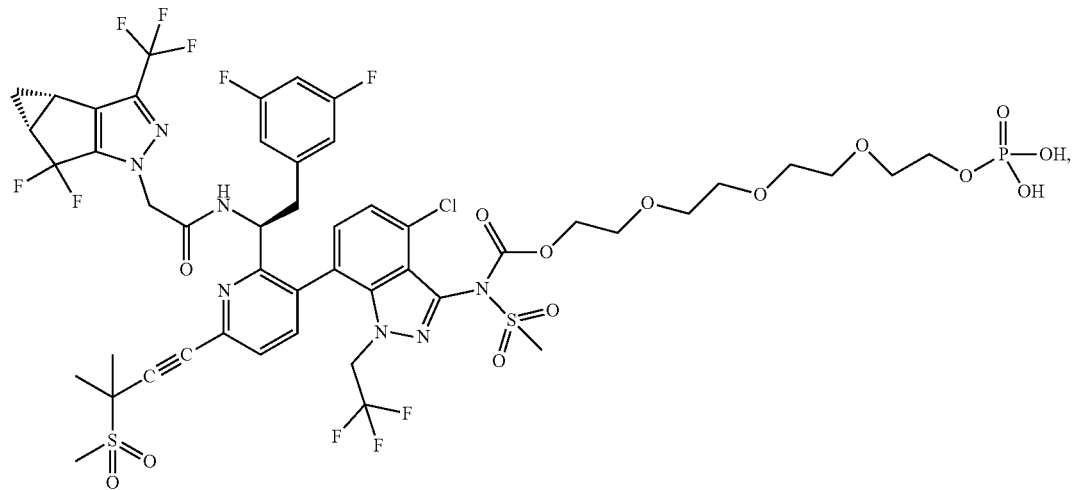
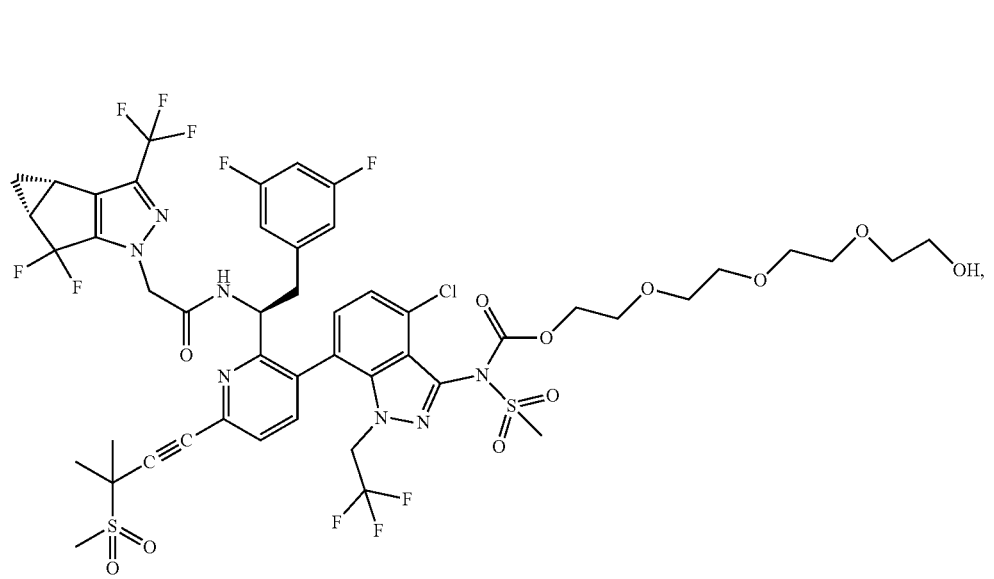

-continued
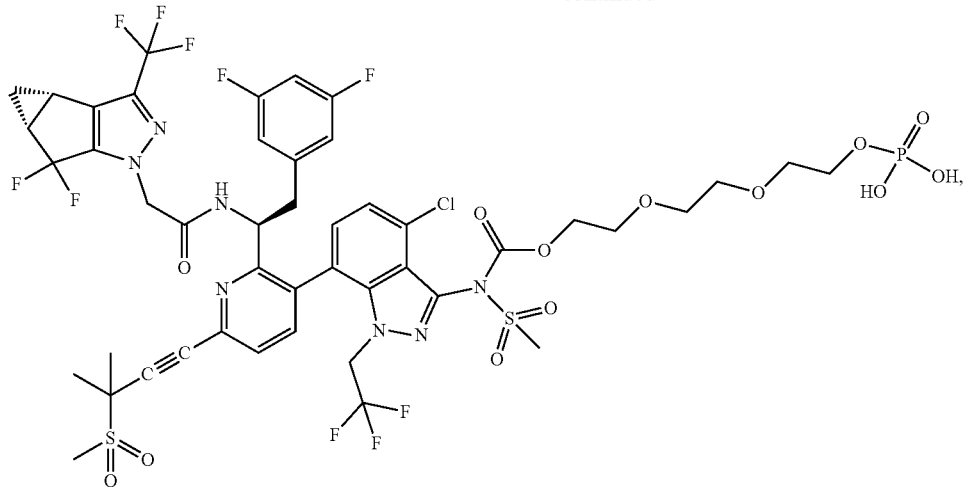
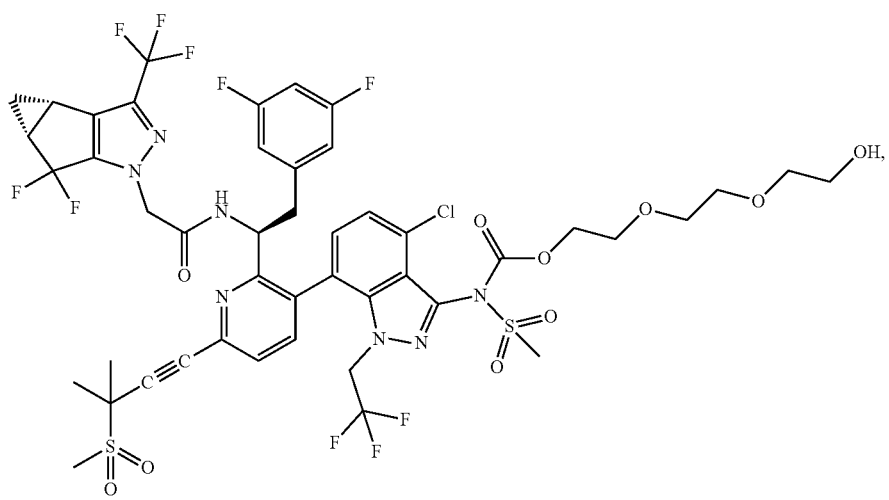
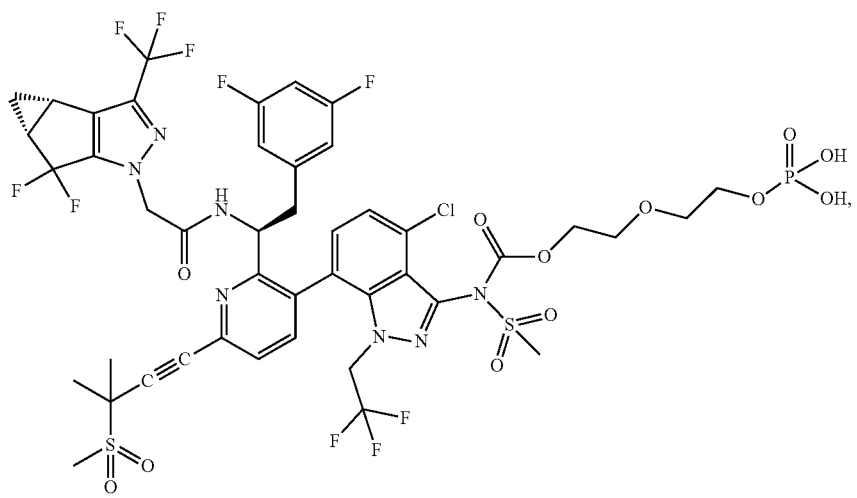

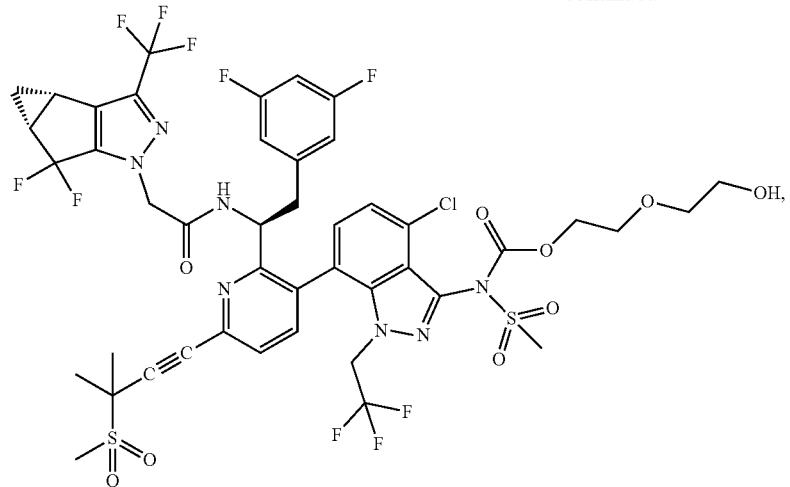
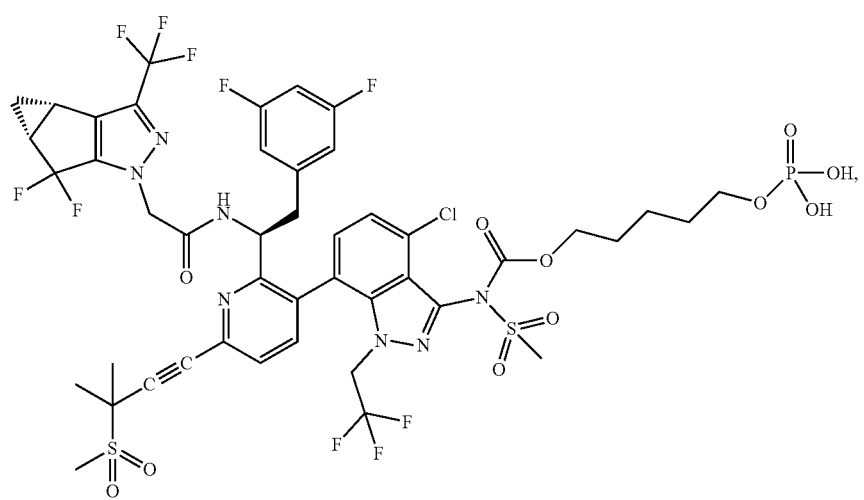
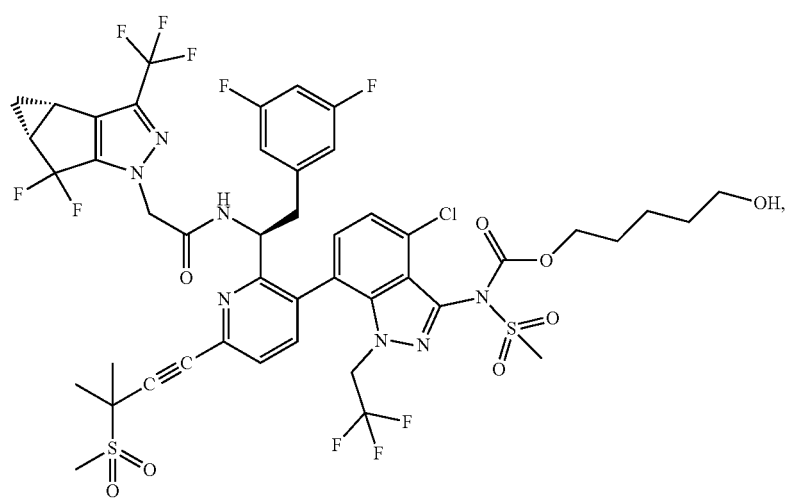

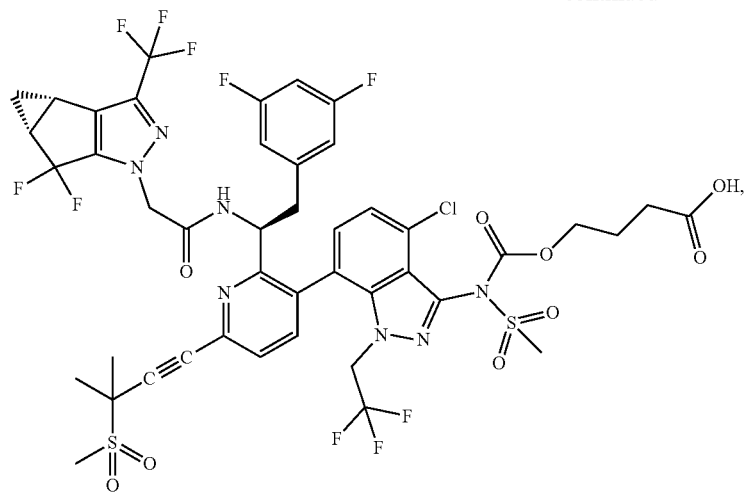
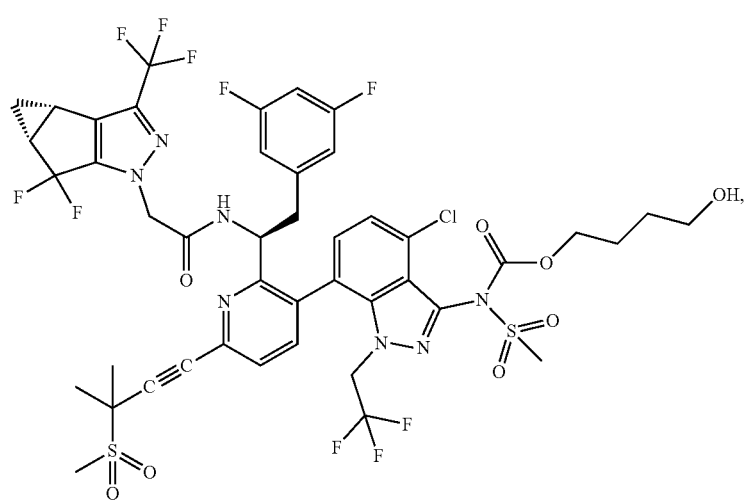
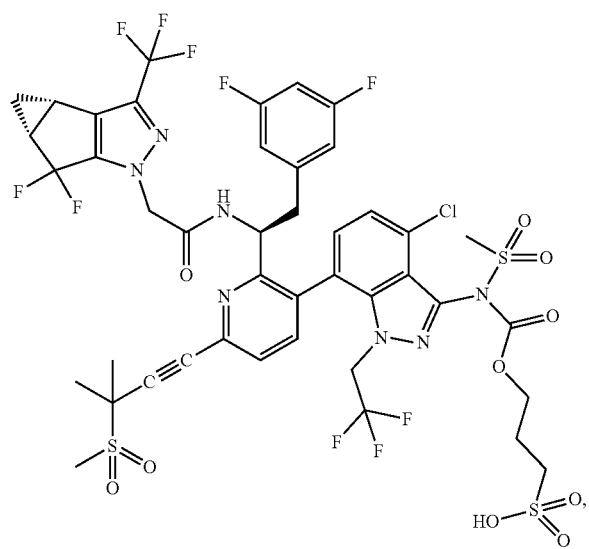

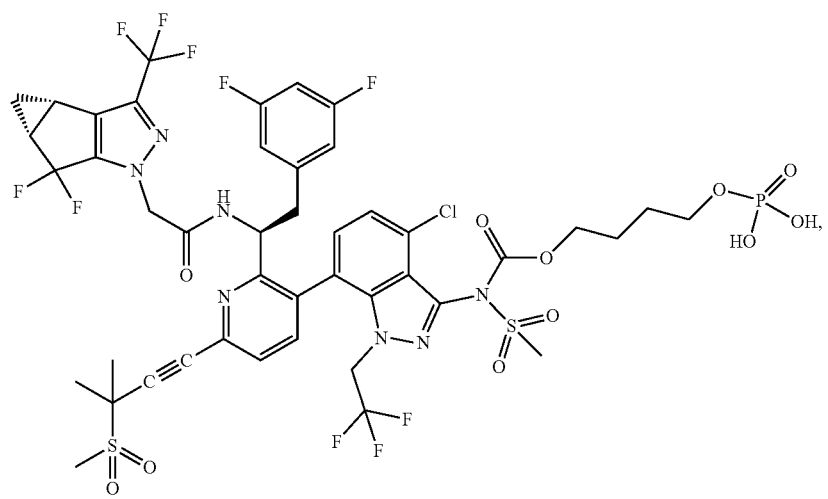
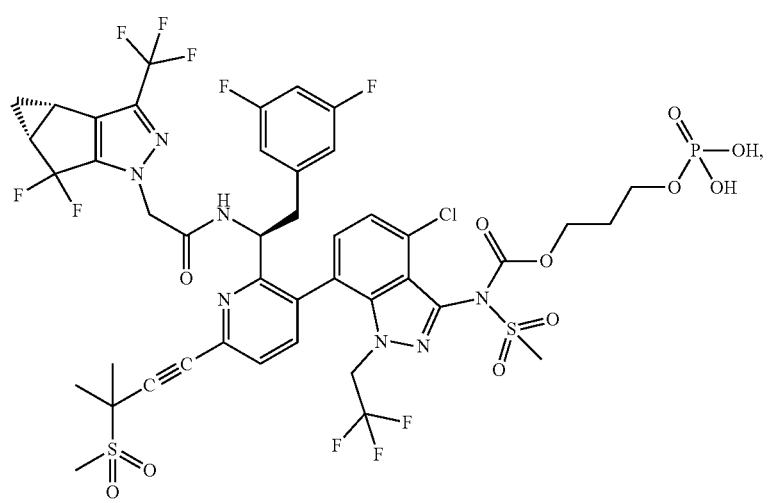
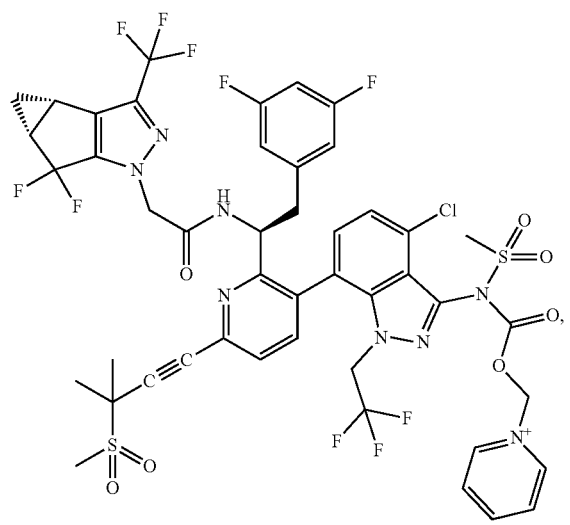

-continued
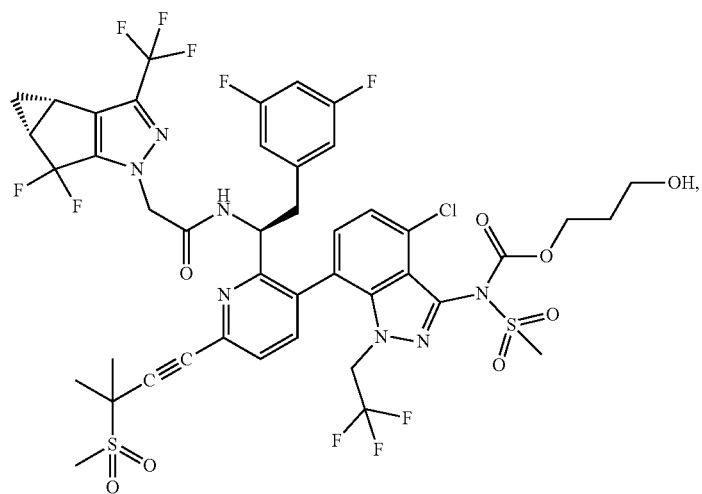
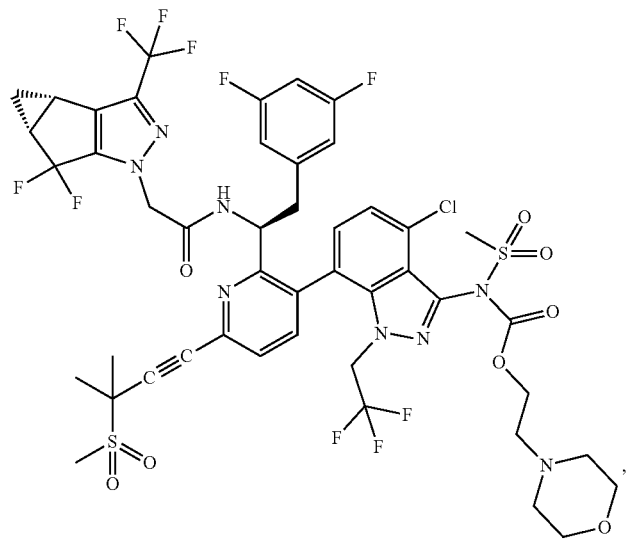
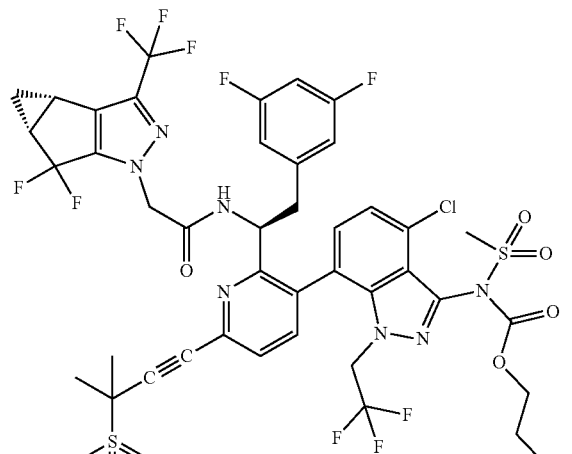
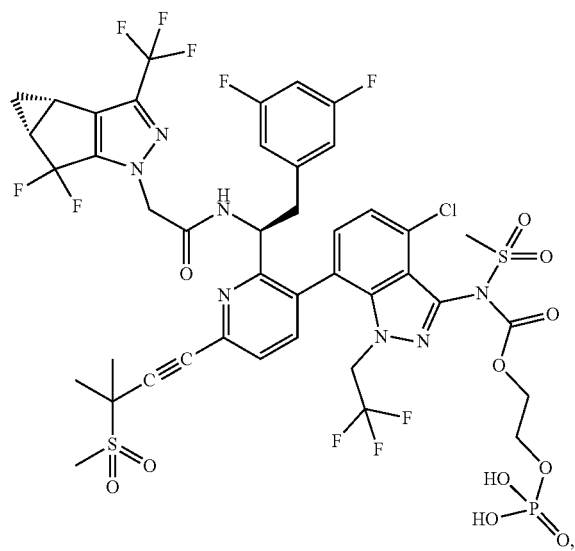
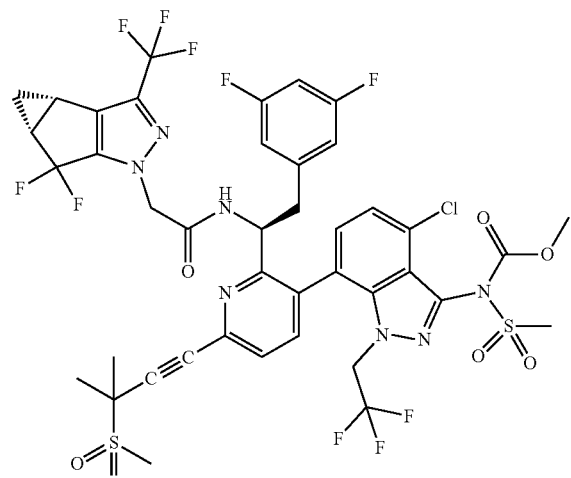

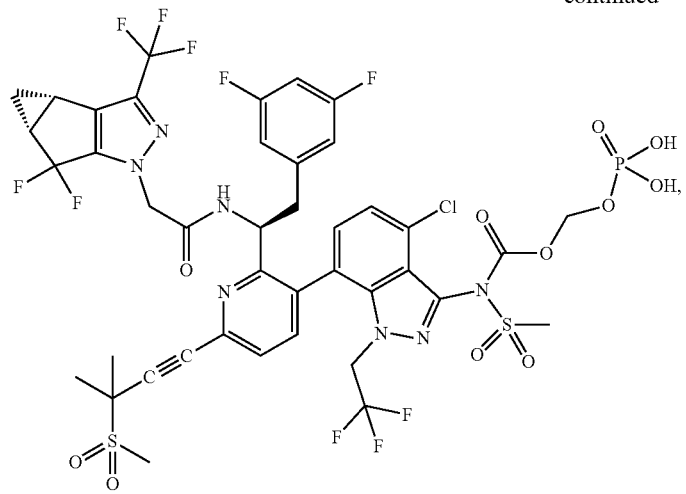
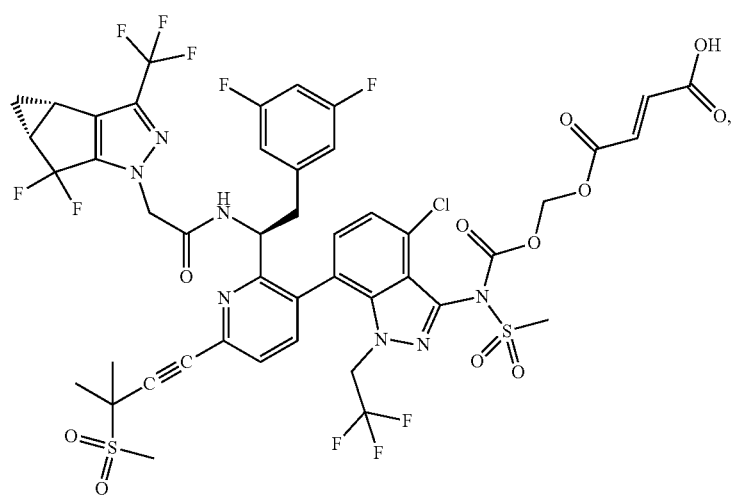
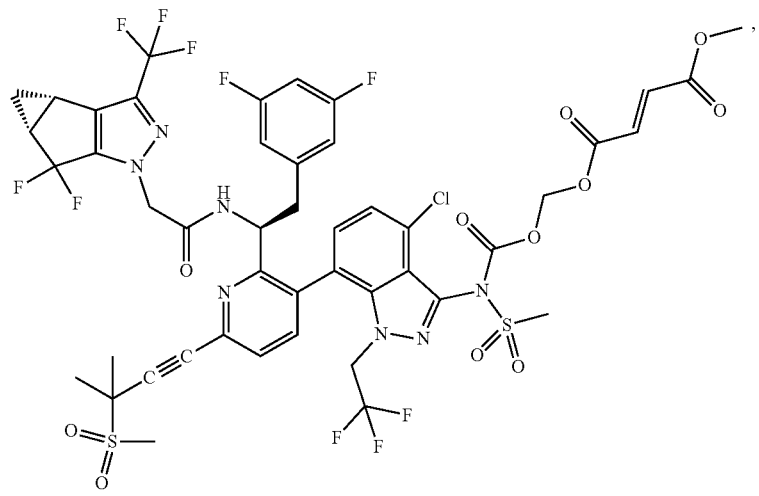

-continued
457
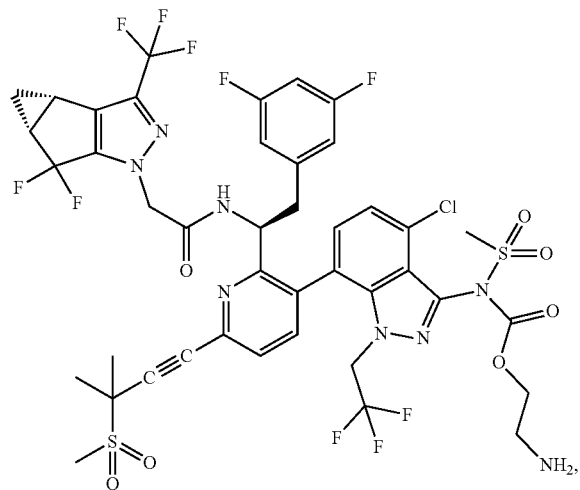
458
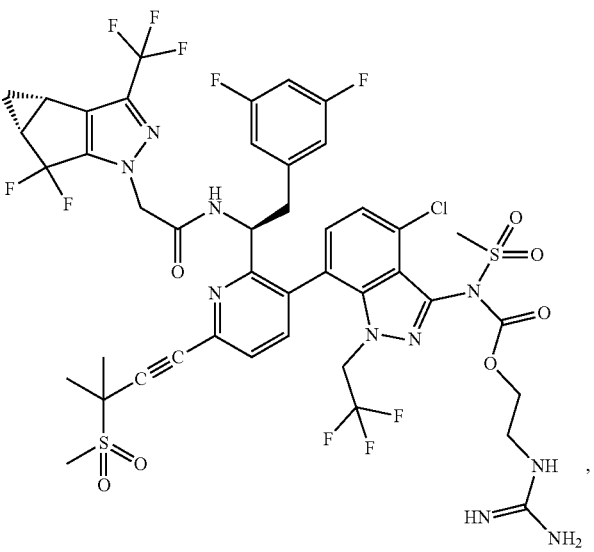
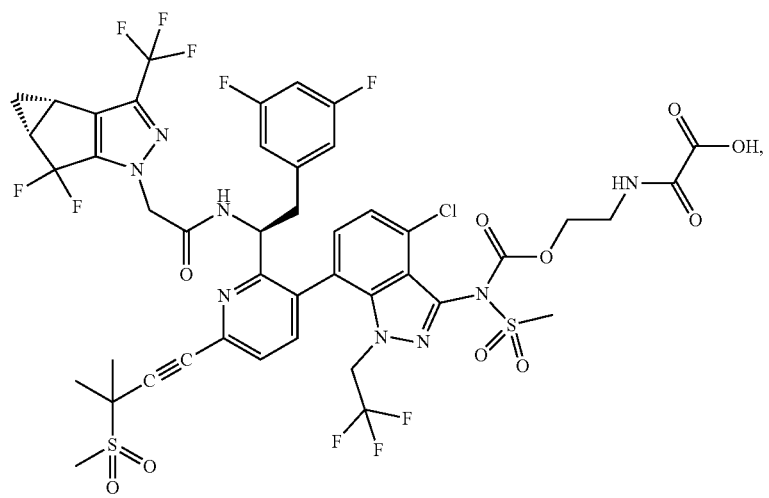
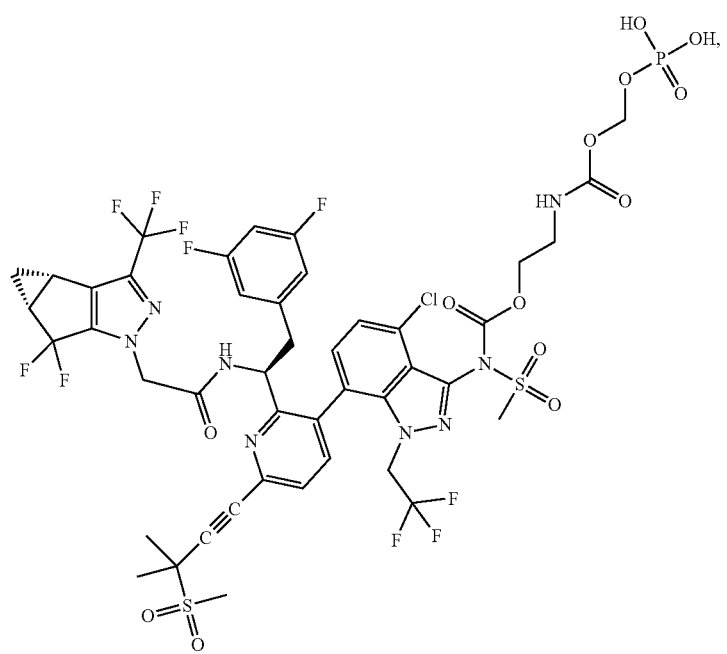

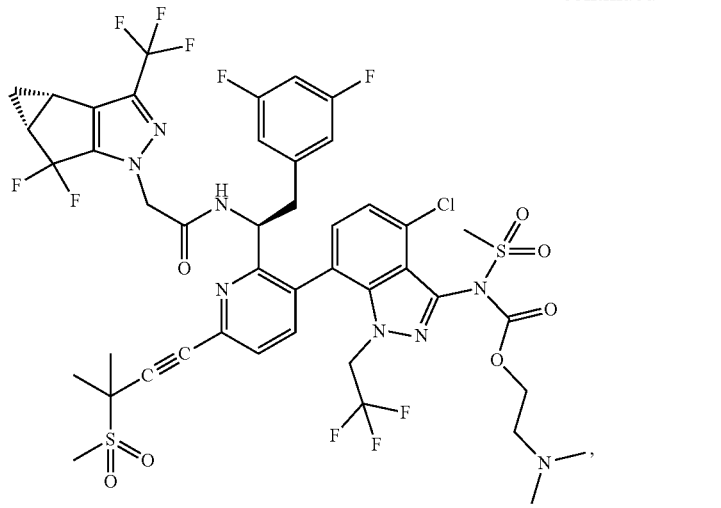
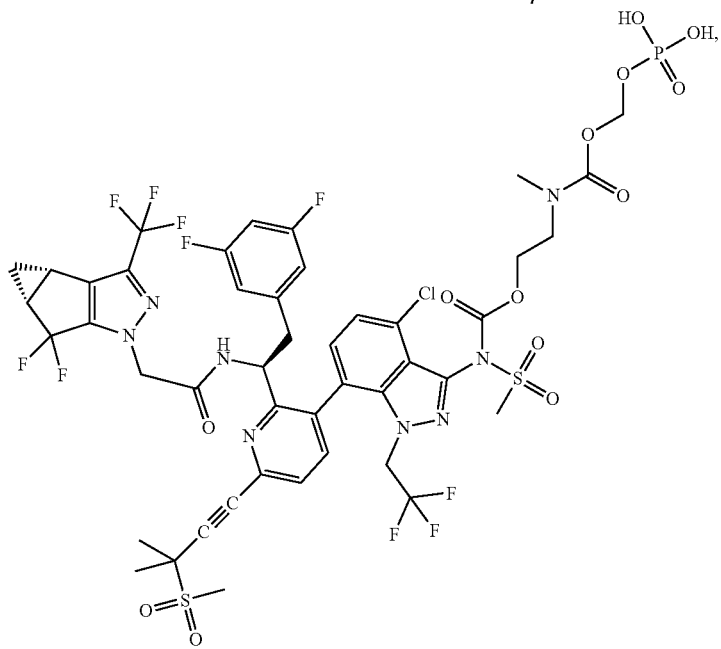
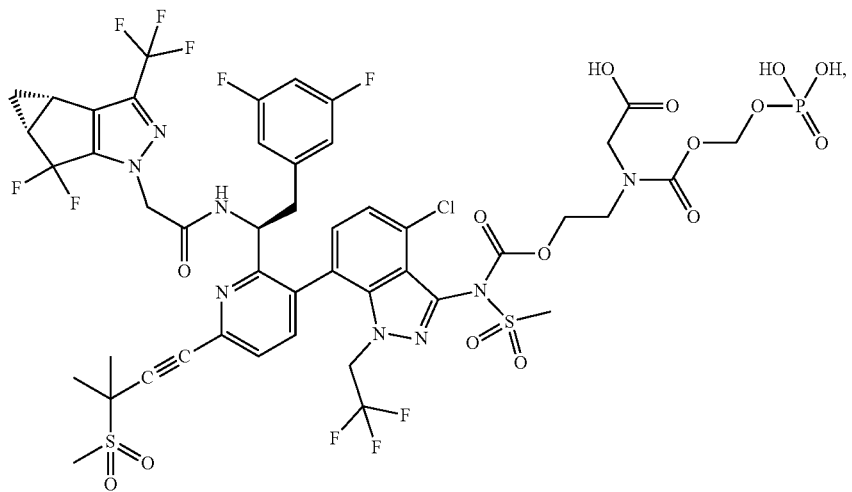

-continued
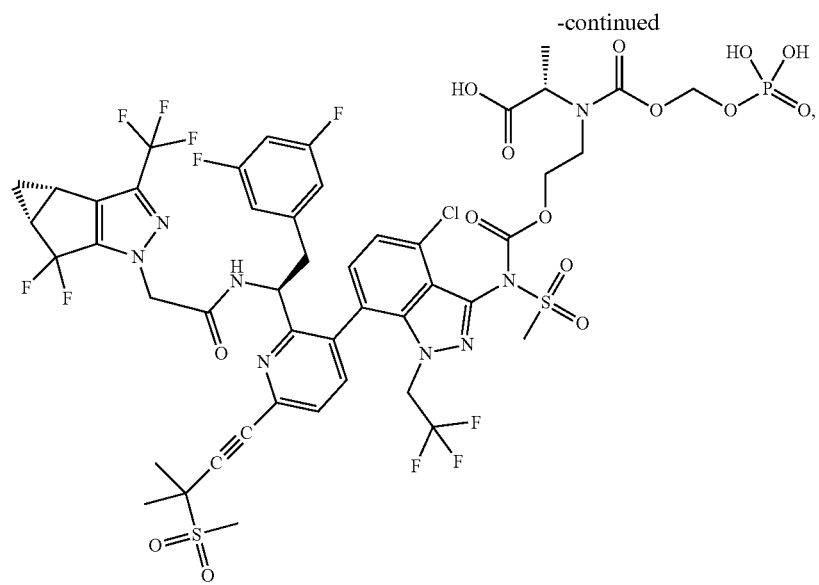
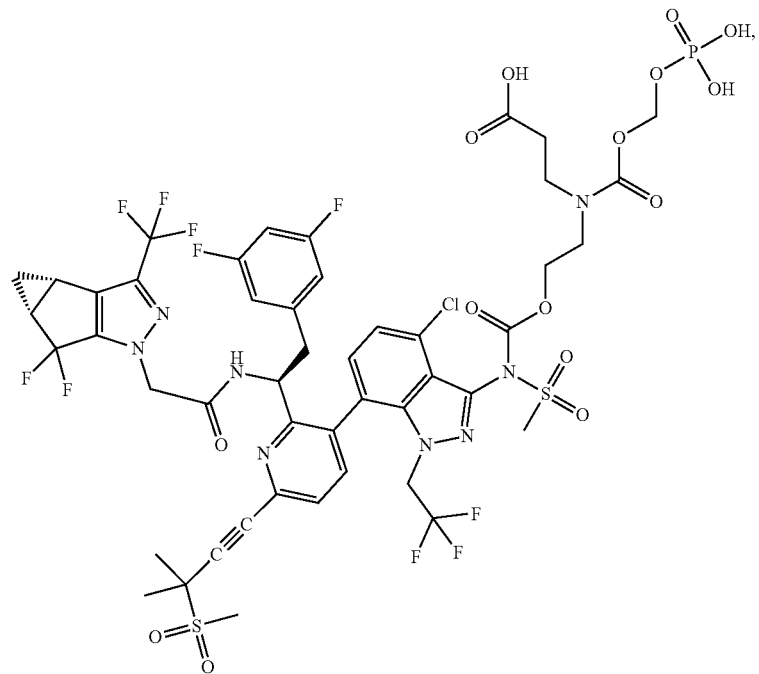
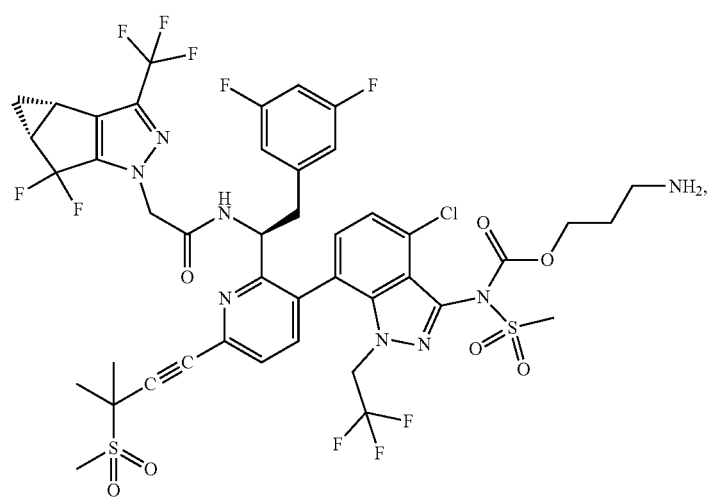

-continued
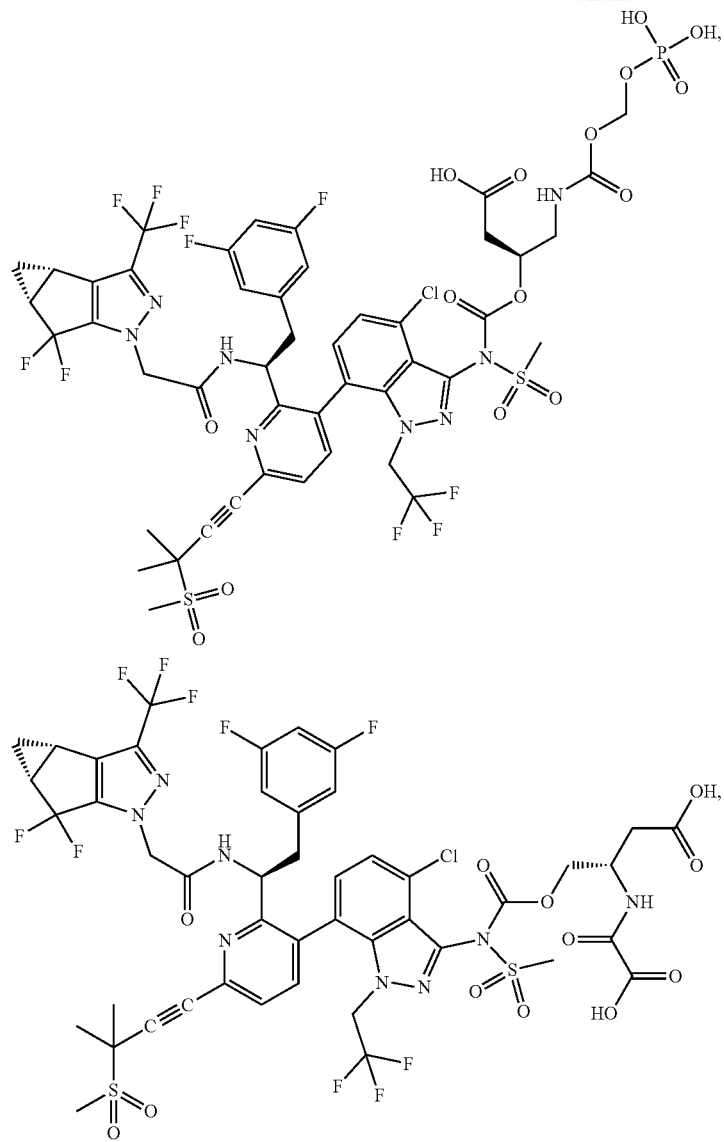
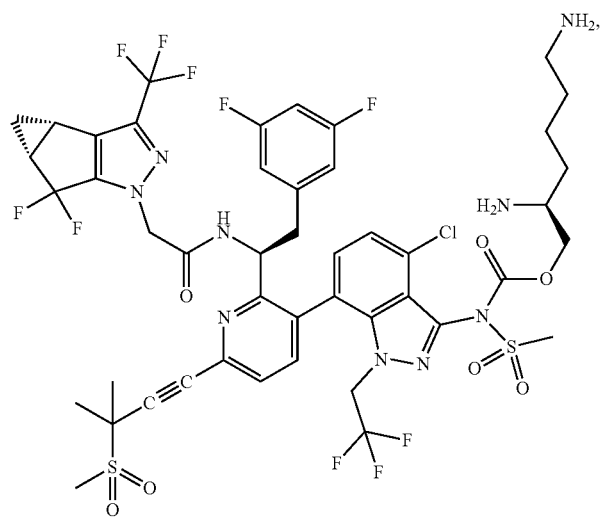

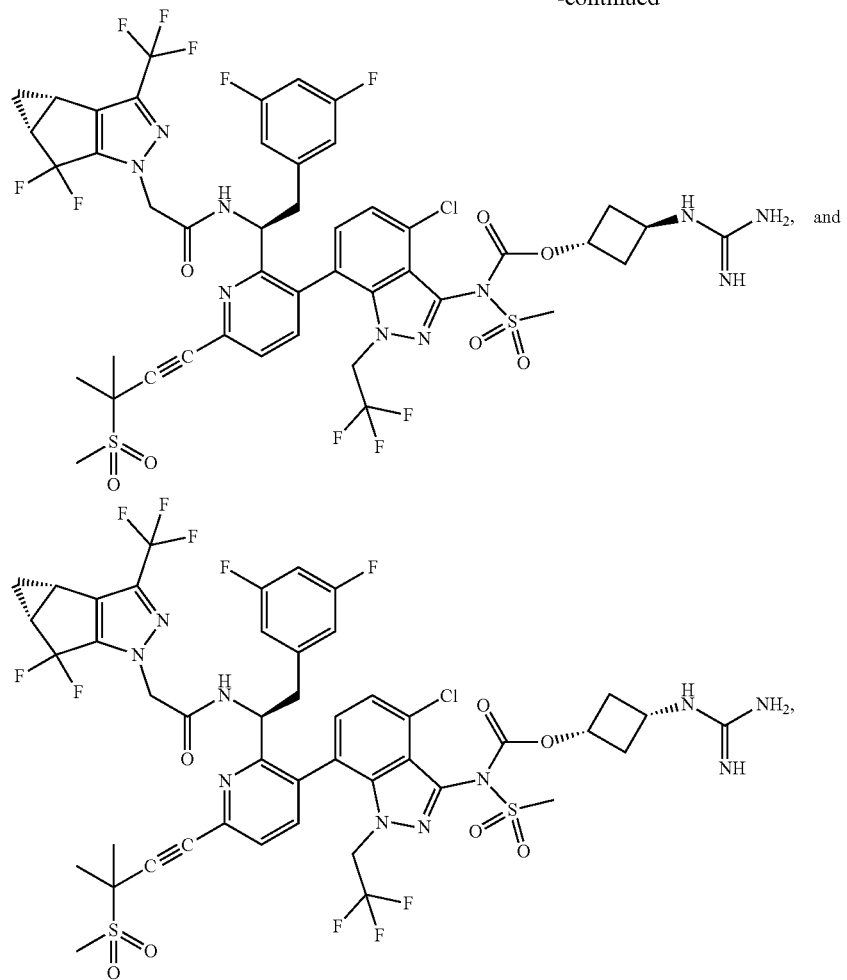
or a pharmaceutically acceptable salt thereof.
20. The compound of claim 1, which is selected from the group consisting of
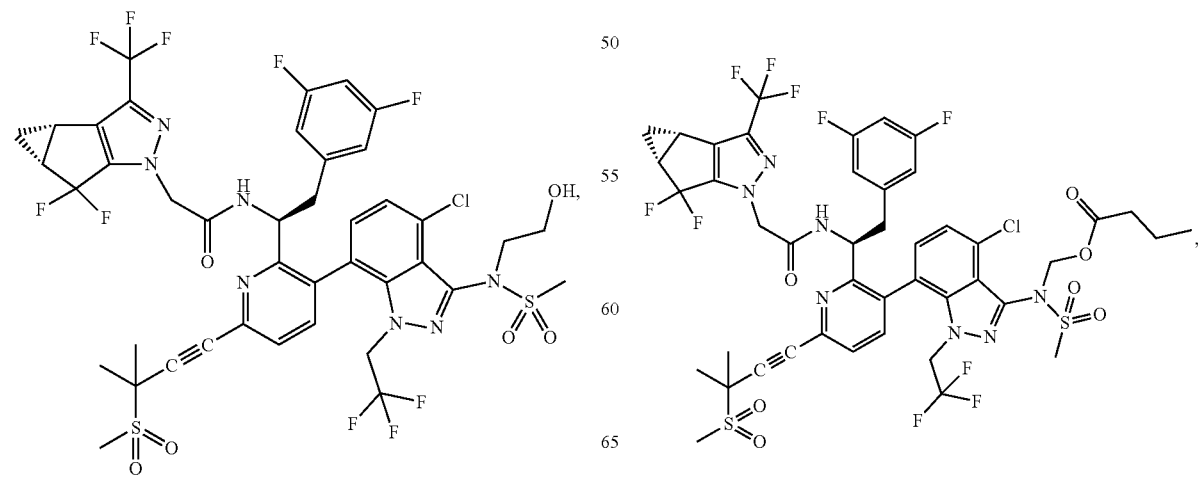

467
-continued
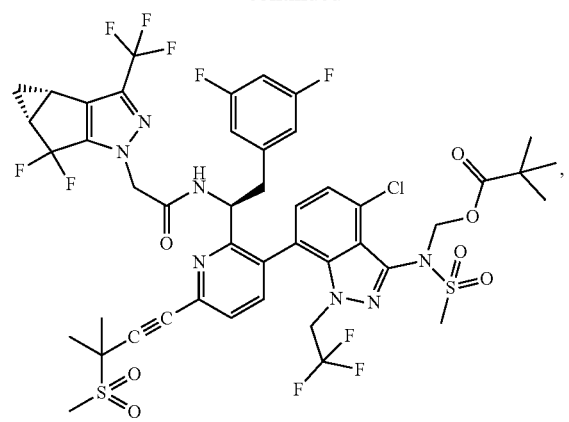
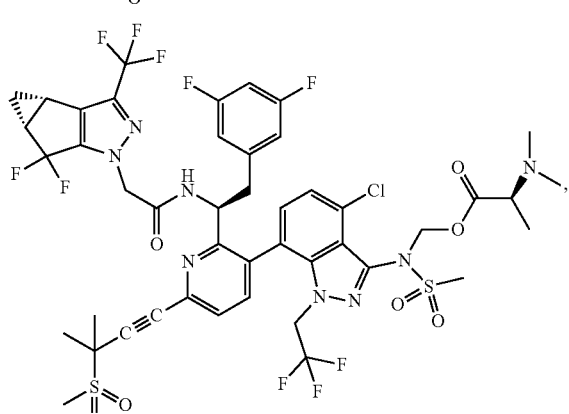
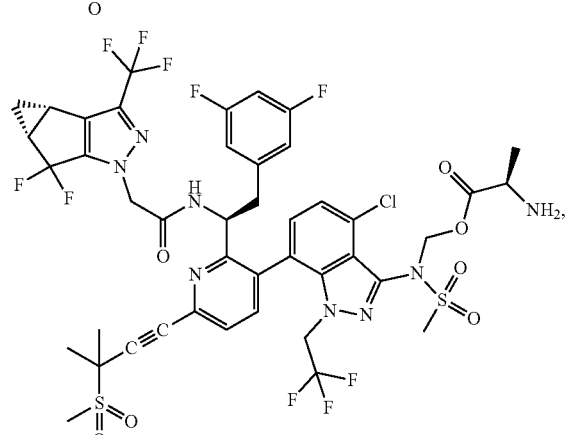
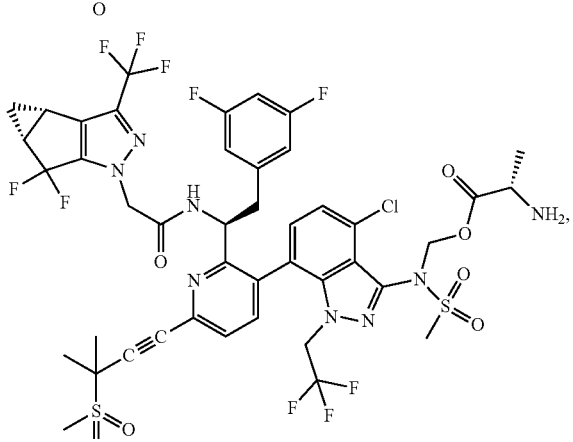
468
-continued
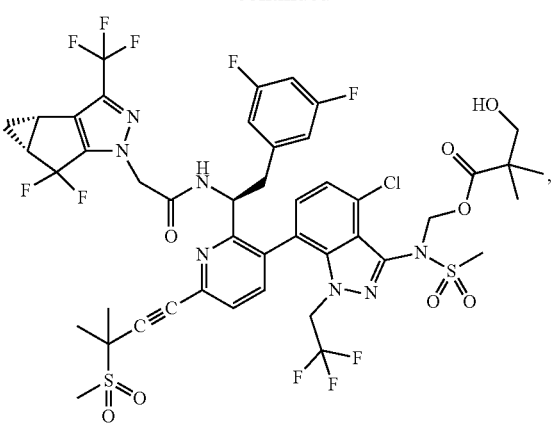
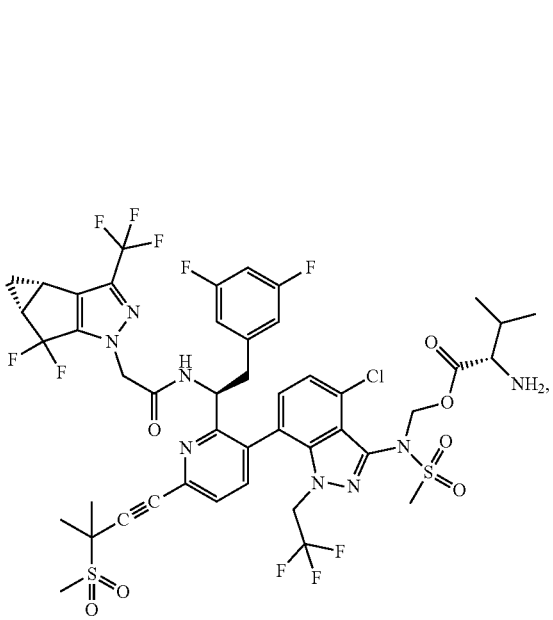
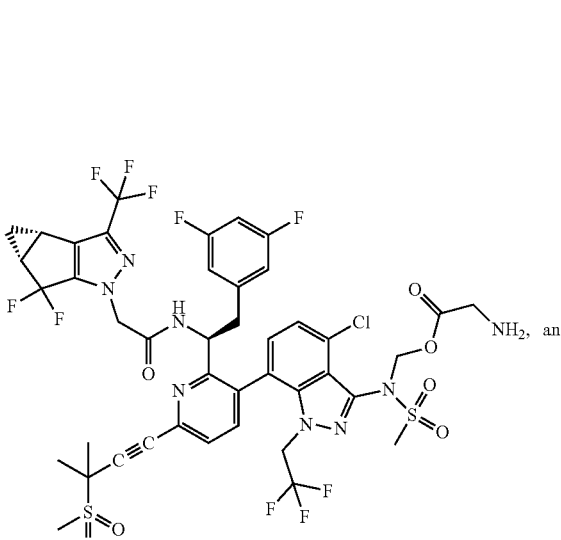

-continued

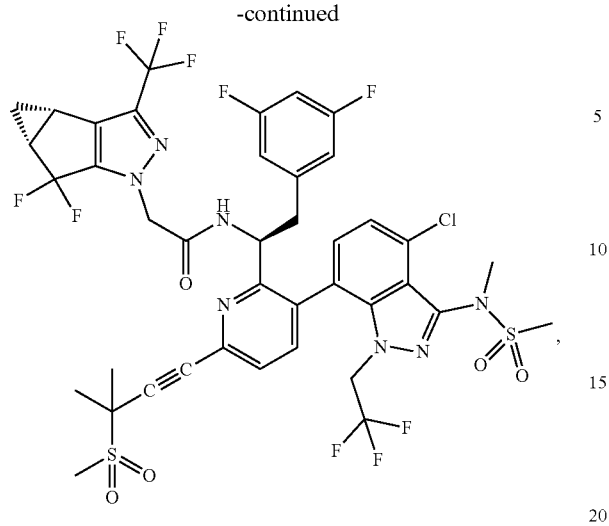

or a pharmaceutically acceptable salt thereof.

21. A pharmaceutical composition comprising a therapeutically effective amount of a compound of claim 1, or a pharmaceutically acceptable salt thereof, and a pharmaceutically acceptable excipient.

22. The pharmaceutical composition of claim 21, further comprising one, two, three, or four additional therapeutic agents.

* * * * *